US012467928B2

(12) United States Patent
Okerberg et al.

(10) Patent No.: US 12,467,928 B2
(45) Date of Patent: Nov. 11, 2025

(54) N-TERMINAL MODIFIER AGENTS AND BINDERS FOR TREATING AND ANALYZING PEPTIDES

(71) Applicant: Encodia, Inc., San Diego, CA (US)

(72) Inventors: Eric Okerberg, San Diego, CA (US); Stephen Verespy, III, San Diego, CA (US); Jason C. Klima, San Diego, CA (US); Soumya Ganguly, San Diego, CA (US); Zachary Miles, San Diego, CA (US); Jason Duarte Jacintho, San Diego, CA (US); Aaron Wise, San Diego, CA (US); Wadud Bhuiya, San Diego, CA (US)

( * ) Notice: Subject to any disclaimer, the term of this patent is extended or adjusted under 35 U.S.C. 154(b) by 0 days.

(21) Appl. No.: 18/764,943

(22) Filed: Jul. 5, 2024

(65) Prior Publication Data

US 2024/0377408 A1 Nov. 14, 2024

Related U.S. Application Data

(60) Provisional application No. 63/525,347, filed on Jul. 6, 2023.

(51) Int. Cl.
*C40B 70/00* (2006.01)
*C40B 40/10* (2006.01)
*G01N 33/68* (2006.01)

(52) U.S. Cl.
CPC ......... *G01N 33/6842* (2013.01); *C40B 40/10* (2013.01); *C40B 70/00* (2013.01); *G01N 33/6845* (2013.01)

(58) Field of Classification Search
None
See application file for complete search history.

(56) References Cited

U.S. PATENT DOCUMENTS

| | | | |
|---|---|---|---|
| 6,875,851 | B1 | 4/2005 | Travis et al. |
| 9,435,810 | B2 | 9/2016 | Havranek et al. |
| 9,528,984 | B2 | 12/2016 | Mitra |
| 10,473,654 | B1 | 11/2019 | Mallick |
| 10,852,305 | B2 | 12/2020 | Havranek et al. |
| 11,427,814 | B2 | 8/2022 | Desai et al. |
| 11,513,126 | B2 | 11/2022 | Chee et al. |
| 11,549,942 | B2 | 1/2023 | Mallick |
| 11,634,709 | B2 | 4/2023 | Chee et al. |
| 11,639,366 | B2 | 5/2023 | James et al. |
| 11,668,717 | B2 | 6/2023 | Mitra |
| 11,753,677 | B2 | 9/2023 | Chee et al. |
| 11,959,922 | B2 | 4/2024 | Chee et al. |
| 11,971,417 | B2 | 4/2024 | Estandian et al. |
| 12,000,835 | B2 | 6/2024 | Reed et al. |
| 12,019,078 | B2 | 6/2024 | Chee et al. |
| 2003/0118585 | A1 | 6/2003 | Muller et al. |
| 2005/0084927 | A1 | 4/2005 | Norioka et al. |
| 2006/0088908 | A1 | 4/2006 | Skerra et al. |
| 2006/0199279 | A1 | 9/2006 | Lopez-Avila et al. |
| 2006/0259995 | A1 | 11/2006 | Cayouette et al. |
| 2008/0305957 | A1 | 12/2008 | Thisted et al. |
| 2009/0264300 | A1 | 10/2009 | Franch et al. |
| 2011/0159573 | A1 | 6/2011 | Daigle et al. |
| 2014/0102915 | A1 | 4/2014 | Hu et al. |
| 2014/0273004 | A1* | 9/2014 | Havranek ........ C12Y 601/0102 435/68.1 |
| 2017/0052194 | A1 | 2/2017 | Havranek et al. |
| 2017/0190751 | A1 | 7/2017 | Barasch et al. |
| 2019/0145982 | A1 | 5/2019 | Chee et al. |
| 2020/0002710 | A1 | 1/2020 | Khalil et al. |
| 2020/0209255 | A1 | 7/2020 | Reed et al. |
| 2020/0348308 | A1 | 11/2020 | Chee et al. |
| 2021/0079398 | A1 | 3/2021 | Pawlosky et al. |
| 2021/0214701 | A1 | 7/2021 | Desai et al. |
| 2021/0355483 | A1 | 11/2021 | Chee et al. |
| 2022/0227889 | A1 | 7/2022 | Gunderson et al. |
| 2022/0283175 | A1 | 9/2022 | Okerberg et al. |
| 2023/0220589 | A1 | 7/2023 | Gunderson et al. |

FOREIGN PATENT DOCUMENTS

| | | |
|---|---|---|
| WO | WO 2000/057183 | 9/2000 |
| WO | WO 2010/065531 | 6/2010 |
| WO | WO 2015/073538 | 5/2015 |
| WO | WO 2016/164530 | 10/2016 |
| WO | WO 2019/089846 | 5/2019 |
| WO | WO 2020/198264 | 10/2020 |
| WO | WO 2020/252404 | 12/2020 |
| WO | WO 2022/147334 | 7/2022 |

OTHER PUBLICATIONS

Jin et al (FEBS 198:150-4) (Year: 1986).*
Mahon et al (Protein Science 24:1800-7). (Year: 2015).*
Dunn (BioMetals 18:295-303) (Year: 2005).*
Wilkinson et al (J. Chromatographic Science 16:547-51) (Year: 1978).*
Nair et al (JBC 271:1003-7) (Year: 1996).*
Nair et al (Biochemistry 34:3981-9) (Year: 1995).*
Buyukkidan, N. et al. (Apr. 2013). "Synthesis And Characterization of Metal Complexes of Heterocyclic Sulfonamide as Carbonic Anhydrase Inhibitors," Journal of Enzyme Inhibition Medicinal Chemistry 28(2):311-315.
Deng et al., "N-Terminal selective modification of peptides and proteins using 2-ethynylbenzaldehydes." Commun Chem. (2020) May 29;3(1):67.

(Continued)

*Primary Examiner* — Christopher M Gross
(74) *Attorney, Agent, or Firm* — DLA PIPER LLP (US); Dmitry Kryndushkin

(57) ABSTRACT

The present disclosure relates to a metalloprotein binder that specifically binds to a N-terminally modified peptide. Also provided herein is methods and related kits for treating or analyzing a peptide using the metalloprotein binder. The methods and compositions provided herein are useful for high-throughput peptide analysis and/or sequencing.

28 Claims, 33 Drawing Sheets

Specification includes a Sequence Listing.

(56) References Cited

OTHER PUBLICATIONS

Drag, M. et al. (Jan. 29, 2010). "Aminopeptidase Fingerprints, an Integrated Approach for Identification of Good Substrates and Optimal Inhibitors," J. Biol. Chem. 285(5):3310-3318.

Nair, S. K. et al. (Mar. 28, 1995). "Structural Basis of Inhibitor Affinity to Variants of Human Carbonic Anhydrase II," Biochemistry 34(12):3981-3989.

Poreba, M. et al. (Feb. 2012). "Fingerprinting the Substrate Specificity of M1 and M17 Aminopeptidases of Human Malaria, Plasmodium Falciparum," PLoS One 7(2):e31938, 8 pages.

Reetz, M. T. (Feb. 19, 2019). "Directed Evolution of Artificial Metalloenzymes: A Universal Means to Tune the Selectivity of Transition Metal Catalysts," Accounts of Chem Res. 52(2):336-344.

Rosati, M. et al. (Oct. 2017). "Two Cap Residues in the S1 Subsite of a Plasmodium Falciparum M1-Family Aminopeptidase Promote Broad Specificity and Enhance Catalysis," Mol Biochem Parasitol 217:7-12.

Scozzafava, A. et al. (Oct. 5, 2000). "Carbonic Anhydrase and Matrix Metalloproteinase Inhibitors: Sulfonylated Amino Acid Hydroxamates With MMP Inhibitory Properties Act as Efficient Inhibitors of CA Isozymes I, II, and IV, and N- Hydroxysulfonamides Inhibit Both These Zinc Enzymes," J. Med. Chem. 43(20):3677-3687.

Sigal, G. B. et al. (1996). "Benzenesulfonamide-Peptide Conjugates as Probes for Secondary Binding Sites Near the Active Site of Carbonic Anhydrase," Bioorganic and Medicinal Chemistry Letters 6(5):559-564.

Yang, J. et al. (Oct. 15, 2017). "Improved Molecular Recognition of Carbonic Anhydrase IX by Polypeptide Conjugation to Acetazolamide," Bioorg Med Chem. 25(20):5838-5848, 1 page, Abstract Only.

Ganji et al., "Structural basis for the inhibition of M1 family aminopeptidases by the natural product actinonin: Crystal structure in complex with *E. coli* aminopeptidase N," Protein Sci (2015) 24(5):823-31.

Rao, "Recent Developments in the Design of Specific Matrix Metalloproteinase Inhibitors aided by Structural and Computational Studies," Current Pharmaceutical Design (2005) 11(3):295-322.

Laura De Luca et al., "Structure-guided identification of a selective sulfonamide-based inhibitor targeting the human carbonic anhydraseVA isoform," Arch. Pharm. 356:e2200383, pp. 1-9, 2023.

Conor B. O'Herin et al., "Development of Human Carbonic Anhydrase II Heterobifunctional Degraders," Journal of Medical Chemistry, vol. 66, pp. 2789-2803, 2023.

Michael Kugler et al., "Identification of specific carbonic anhydrase inhibitors via in situ click chemistry, phage-display and synthetic peptide libraries: comparison of the methods and structural study," RSC Medicinal Chemistry, vol. 14, pp. 144-153, 2023.

Andrea Angeli et al., "Carbonio Anhydrase Inhibitors Targeting Metabolism and Tumor Microenvironment," Metabolites, vol. 10, No. 412, doi:10.3390/metabo10100412, pp. 1-21, 2020.

Jiayang Li et al., "New power of self-assembling carbonic anhydrase inhibitor: Short peptide-constructed nanofibers inspire hypoxic cancer therapy," Science Advances, vol. 5, eaax0937, pp. 1-15, 2019.

Hasan Küçükbay et al., "Synthesis and carbonic anhydrase inhibitory properties of novel 4-(2-aminoethyl benzenesulfonamide-dipeptideconjugates," Bioorganic Chemistry, vol. 83, pp. 414-423, Mar. 2019.

Nesrin Buğday et al., "Synthesis of novel dipeptide sulfonamide conjugates with effective carbonio anhydrasel, II, IX, and XII inhibitory properties," Bioorganic Chemistry, vol. 81, pp. 311-318, Dec. 2018.

Kazuya Matsuo et al., "One-step construction of caged carbonic anhydrase I using ligand-directed acyl imidazole-based protein labeling method," Chemical Science, vol. 4, pp. 2573-2580, 2013.

Gang Li et al., "Photoaffinity Labeling of Small-Molecule-Binding Proteins by DNA-Templated Chemistry," Ange. Chem. Int. Ed., vol. 52, pp. 9544-9549, DOI: 10.1002/anie.201302161, 2013.

* cited by examiner

Hydroxamic Acid, Hydrazide, N-Hydroxyurea, Squaric Acid, Carbamoylphosphonate

Oxazoline, Pyrimidinetrione, 1,2-HOPO, 1,2-HOPTO 1 2 3 4

5 6 7 8

9 10 11 12

13 14 15 16

M64

M65

M66

M67

M68

M69

M70

M71

M72

M73

M74

M75

M76

M81

M77

M82

M78

M83

M79

M84

M80

M85

M86

M87

M88

M89

M90

M91

M93

M94

M95

M96

M97

M98

P1 = A, F, E, S, L, or H

Formula (6)

Formula (7)

Formula (8)

Formula (9)

N-TERMINAL MODIFIER AGENTS AND BINDERS FOR TREATING AND ANALYZING PEPTIDES

CROSS-REFERENCE TO RELATED APPLICATIONS

This application claims benefit of priority to U.S. Provisional Application No. 63/525,347, filed Jul. 6, 2023, the entire contents of which application are incorporated herein by reference for all purposes.

STATEMENT REGARDING FEDERALLY SPONSORED RESEARCH

This invention was made with Government support awarded by National Institute of General Medical Sciences of the National Institutes of Health under Grant Number R44GM123836. The United States Government has certain rights in this invention pursuant to this grant.

REFERENCE TO AN ELECTRONIC SEQUENCE LISTING

The contents of the electronic sequence listing (776532005300SUBSEQLIST.xml; Size: 226,597 bytes; and Date of Creation: Jan. 21, 2025) is herein incorporated by reference in its entirety.

TECHNICAL FIELD

The present disclosure generally relates to biotechnology, in particular to methods for analysis or sequencing of peptides employing N-terminal modifying reagents and N-terminal binders engineered from metalloenzymes. The disclosure finds utility at least in a variety of methods and related kits for high-throughput peptide sequencing.

BACKGROUND

High-throughput nucleic acid sequencing has transformed life science research through improved sensitivity and lower costs, and consequently has found multiple applications in medicine and personal genomics. Similar high-throughput approaches to protein sequencing are not currently available, yet knowledge about protein identity in a sample can be crucial for better understanding of proteome dynamics in health and disease. This information can enable precision medicine and can be used in multiple diagnostic applications. Despite advances in mass spectroscopy (MS), corresponding innovation in proteomics is needed to have a similar broad-ranging impact on biomedical research. MS suffers from several drawbacks including high instrument cost, requirement for a sophisticated user, poor quantification ability, and limited ability to make measurements spanning the dynamic range of the proteome. For example, since proteins ionize at different levels of efficiencies, absolute quantitation and even relative quantitation between sample is challenging. Also, MS typically only analyzes the more abundant species, making characterization of low abundance proteins challenging. There remains a need in the art for improved techniques relating to macromolecule recognition and/or analysis. There is a need for proteomics technology that is highly-parallelized, accurate, sensitive, and high-throughput.

BRIEF SUMMARY

Several approaches to high-throughput protein sequencing have been published, including U.S. Pat. No. 9,435,810

B2, WO2010/065531A1, US 2019/0145982 A1, US 2020/0348308 A1, which utilize N-terminal amino acid (NTAA) recognition as a critical step during a protein sequencing assay. A number of methods to evolve specific NTAA binders from different scaffolds have been disclosed, including directed evolution approaches to derive variant amino acyl tRNA synthetases, N-recognins such as ClpS and ClpS2, anticalins, and aminopeptidases (disclosed in US 2019/0145982 A1, U.S. Pat. No. 9,435,810 B2). However, identifying binders that afford amino acid specificity with sufficiently strong affinity has proven challenging.

The present disclosure describes the development of peptide sequencing reagents including specific NTAA binders, and methods that fulfill this and other needs. These and other embodiments of the invention will be apparent upon reference to the following detailed description. To this end, various references are set forth herein which describe in more detail certain background information, procedures, compounds and/or compositions, and are each hereby incorporated by reference in their entireties.

The summary is not intended to be used to limit the scope of the claimed subject matter. Other features, details, utilities, and advantages of the claimed subject matter will be apparent from the detailed description including those embodiments disclosed in the accompanying drawings and in the appended claims.

The present disclosure relates to an engineered binder that specifically binds to an N-terminally modified peptide via interaction with modified N-terminal amino acid (NTAA) residue of the peptide. Also provided herein is a method and related kits for treating a peptide using or comprising the binder and/or the cleavase reagent. In some embodiments, also provided herein is a method and related kits for transferring information using a plurality of enzymes, including for performing a ligation, extension, and cleavage reaction with nucleic acid molecules associated with the peptide for analysis.

In one embodiment, provided herein is a method for modifying the plurality of peptides with an N-terminal modifier agent, thereby generating a modified N-terminal amino acid (NTAA) residue on each peptide of the plurality of peptides, wherein each peptide of the plurality of peptides is attached to a solid support, each modified NTAA residue is capable of coordinating or chelating a metal cation, and wherein the N-terminal modifier agent is selected from the group consisting of:

(6)

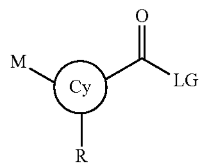

, (7)

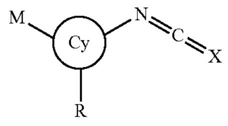

, (8)

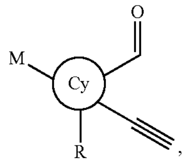

,

-continued and (9)

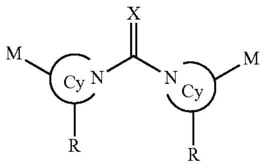

, wherein M is a metal cation binding group that comprises sulfonamide, hydroxamic acid, sulfamate, or sulfamide; the group

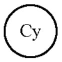

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, ORQ, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH.

In another embodiment, provided herein is a method of analyzing a plurality of peptides, the method comprising:

(a) modifying the plurality of peptides with an N-terminal modifier agent, thereby generating a modified N-terminal amino acid (NTAA) residue on each peptide of the plurality of peptides, wherein each peptide of the plurality of peptides is attached to a solid support, each modified NTAA residue is capable of coordinating or chelating a metal cation, and wherein the N-terminal modifier agent is selected from the group consisting of:

(6)

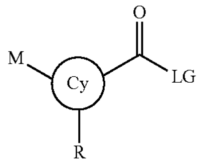

, (7)

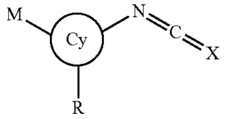

, (8)

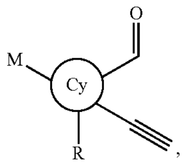

,

-continued and (9)

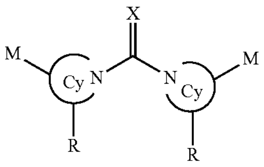

, wherein M is a metal cation binding group that comprises sulfonamide, hydroxamic acid, sulfamate, or sulfamide; the group

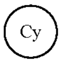

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, ORQ, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH;

(b) contacting one or more peptides of the plurality of peptides with a set of engineered metalloprotein binders, wherein one or more engineered metalloprotein binders of the set specifically bind to a particular modified NTAA residue of the one or more peptides, wherein each engineered metalloprotein binder of the set comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp), and E (Glu); X1, X2, X3 and X4 are each any amino acid sequence independently comprising between 0 and 500 amino acid residues in length, and wherein the amino acid sequence X1-C/H/D/E-X2-C/H/D/E-X3-C/H/D/E-X4 chelates the metal cation; and (c) generating a signal indicative of the binding of the one or more engineered metalloprotein binders to the modified NTAA residue(s) of the one or more peptides, thereby analyzing the plurality of peptides.

In yet another embodiment, provided herein is a kit for treating a target peptide, the kit comprising:

(a) an N-terminal modifier agent selected from the group consisting of:

(6)

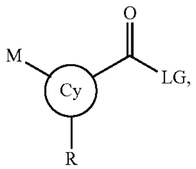

,

-continued (7)

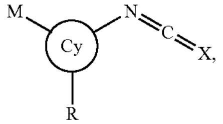

(8)

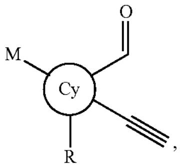

, and (9)

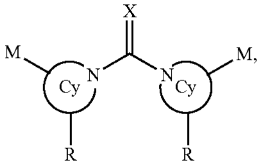

wherein M is a metal cation binding group that comprises sulfonamide, hydroxamic acid, sulfamate, or sulfamide; the group

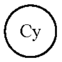

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, ORQ, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH; and (b) an engineered metalloprotein binder that specifically binds to a modified N-terminal amino acid (NTAA) residue in a target peptide, wherein the modified NTAA residue is generated by modifying the target peptide with the N-terminal modifier agent, wherein the engineered metalloprotein binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates the metal cation; and (c) a solid support which is configured for attachment of the target peptide.

In yet another embodiment, provided herein is a composition comprising:

(a) a solid support, wherein the solid support comprises a plurality of peptide molecules attached to the solid support, wherein each of the plurality of peptide molecules comprise a modified N-terminal amino acid (NTAA) residue generated by modifying a peptide molecule with an N-terminal modifier agent, wherein the modified NTAA residue is capable of coordinating or chelating a metal cation, and the N-terminal modifier agent is selected from the group consisting of:

(6)

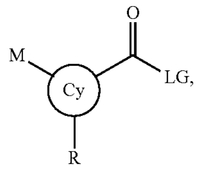

(7)

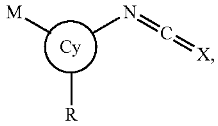

(8)

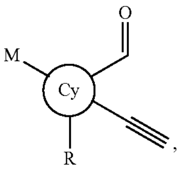

, and (9)

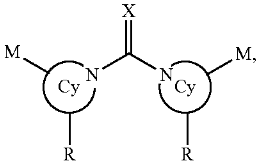

wherein M is a metal cation binding group that comprises sulfonamide, hydroxamic acid, sulfamate, or sulfamide; the group

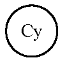

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, ORQ, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH; and (b) an engineered metalloprotein binder that specifically binds to a peptide molecule of the plurality of peptide molecules, wherein the engineered metalloprotein binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates the metal cation.

In yet another embodiment, provided herein is an engineered metalloprotein binder that specifically binds to an N-terminally modified target peptide modified by an N-terminal modifier agent, wherein:

(a) the N-terminally modified target peptide has a formula: Z-P1-P2-peptide, wherein Z is an N-terminal modification capable of coordinating or chelating a metal cation, P1-P2-peptide is a target peptide before modification with the N-terminal modifier agent, Z-P1 is a modified N-terminal amino acid (NTAA) residue of the target peptide, and P2 is a penultimate terminal amino acid residue of the target peptide;

(b) the engineered metalloprotein binder specifically binds to the N-terminally modified target peptide through interaction between the engineered metalloprotein binder and the Z-P1 of the N-terminally modified target peptide; and (c) the engineered metalloprotein binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates a metal cation. In preferred embodiments, X1, X2, X3 and X4 together comprise at least 30 amino acid residues in length. In preferred embodiments, the amino acid sequence X1-C/H/D/E-X2-C/H/D/E-X3-C/H/D/E-X4 chelates a metal cation with a thermodynamic dissociation constant of 1000 nM or less.

In yet another embodiment, provided herein is an isolated nucleic acid molecule comprising a polynucleotide having a sequence encoding the engineered metalloprotein binder described in the previous paragraph.

In yet another embodiment, provided herein is a kit for treating a target peptide, the kit comprising:

(a) an engineered binder that specifically binds to an N-terminally modified target peptide modified by an N-terminal modifier agent, wherein:

(i) the N-terminally modified target peptide has a formula: Z-P1-P2-peptide, wherein Z is an N-terminal modification capable of coordinating or chelating a metal cation, P1-P2-peptide is a target peptide before modification with the N-terminal modifier agent, Z-P1 is a modified N-terminal amino acid (NTAA) residue of the target peptide, and P2 is a penultimate terminal amino acid residue of the target peptide;

(ii) the engineered binder specifically binds to the N-terminally modified target peptide through interaction between the engineered binder and the Z-P1 of the N-terminally modified target peptide; and (iii) the engineered binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates a metal cation; and (b) the N-terminal modifier agent selected from the group consisting of compounds of the following Formula (6)-(9):

(6)

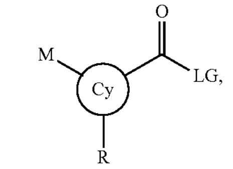

(7)

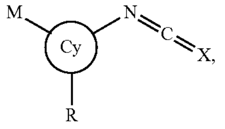

(8)

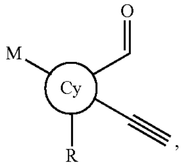

, and (9)

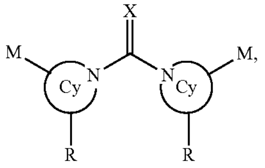

wherein M is a metal cation binding group that comprises sulfonamide, hydroxamic acid, sulfamate, or sulfamide; the group

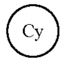

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, ORQ, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH. In preferred embodiments, the metal cation binding group is a Zn cation binding group.

In yet another embodiment, provided herein is a kit for treating a target peptide, the kit comprising:

(a) an engineered metalloprotein binder that specifically binds to an N-terminally modified target peptide modified by an N-terminal modifier agent, wherein:

(i) the N-terminally modified target peptide has a formula: Z-P1-P2-peptide, wherein Z is an N-terminal modification capable of coordinating or chelating a metal cation, P1-P2-peptide is a target peptide before modification with the N-terminal modifier agent, Z-P1 is a modified N-terminal amino acid (NTAA) residue of the target peptide, and P2 is a penultimate terminal amino acid residue of the target peptide;

(ii) the engineered metalloprotein binder specifically binds to the N-terminally modified target peptide through interaction between the engineered metalloprotein binder and the Z-P1 of the N-terminally modified target peptide; and (iii) the engineered metalloprotein binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between O and 500 amino acid residues in length, and wherein the amino acid sequence X1-C/H/D/E-X2-C/H/D/E-X3-C/H/D/E-X4 chelates a metal cation; and (b) an agent configured for removing the modified NTAA residue from the N-terminally modified target peptide, thereby exposing a new NTAA residue.

In yet another embodiment, provided herein is a method of treating a target peptide, the method comprises:

(a) contacting a peptide of the plurality of peptides with an N-terminal modifier agent to form an N-terminally modified peptide having a formula: Z-P1-P2-peptide, wherein Z is an N-terminal modification capable of coordinating or chelating a metal cation, P1-P2-peptide is the peptide before modification with the N-terminal modifier agent, Z-P1 is a modified N-terminal amino acid (NTAA) residue of the peptide, and P2 is a penultimate terminal amino acid residue of the peptide;

(b) contacting the N-terminally modified peptide with a set of engineered metalloprotein binders, wherein at least one engineered metalloprotein binder of the set specifically binds to the modified NTAA residue of the N-terminally modified peptide, wherein each engineered metalloprotein binder of the set comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp), and E (Glu); X1, X2, X3 and X4 are each any amino acid sequence independently comprising between 0 and 500 amino acid residues in length, and wherein the amino acid sequence X1-C/H/D/E-X2-C/H/D/E-X3-C/H/D/E-X4 chelates the metal cation; and (c) detecting a signal indicative of the binding of the at least one engineered metalloprotein binder to the N-terminally modified peptide;

(d) optionally, dissociating the at least one engineered metalloprotein binder from the N-terminally modified peptide;

(e) removing the modified NTAA residue from the N-terminally modified peptide by an agent configured for removing the modified NTAA residue, thereby exposing a new NTAA residue; and (f) optionally, repeating steps (a)-(e) one or more times for peptides of the plurality of peptides. In some embodiments, the method further comprises the following step: determining one or more characteristics of each peptide for which the signal was detected in (c), thereby analyzing the plurality of peptides.

BRIEF DESCRIPTION OF THE DRAWINGS

Non-limiting embodiments of the present invention will be described by way of example with reference to the accompanying figures, which are schematic and are not intended to be drawn to scale. For purposes of illustration, not every component is labeled in every figure, nor is every component of each embodiment of the invention shown where illustration is not necessary to allow those of ordinary skill in the art to understand the invention.

FIG. 8A. Structure of a bipartite NTM (NTMa) comprised of "binding" region ("N") and a separate metal-binding group (MBG) connected with an amide bond. N could be a natural amino acid residue. NTMb has a composite metal-binding region (both groups involve in metal binding). FIG. 8B. The NTMs are activated using standard methods (activated ester)

and are coupled to the N-terminal amine on the P1 residue. FIG. 8C. An engineered metalloprotein binder binds to the modified NTAA of the peptide by interacting with the P1 residue and the NTM. Metal ion located in the metalloprotein binding pocket interacts with the MBG. "N" can interact with amino acid residues distant from the metal-coordinating residues. FIG. 8D. An engineered metalloprotein binder binds to the modified NTAA of the peptide by interacting with P1 and NTMb. Metal ion located in the metalloprotein binding pocket interacts with both groups of NTMb.

FIG. 9A. Derivatives of NTM M64 were evaluated using colorimetric IC50 assay to determine relative binding affinity of NTMs to wild-type hCAII protein based on NTM inhibition capacity. The slopes versus the concentration of NTM were put into a non-linear regression equation to determine the IC50 of the selected NTMs to the wild-type hCAII.

FIG. 9B. Derivatives of NTM M64 were installed on the N-terminus of a model peptide AAEIR. The N-terminally modified peptides were then evaluated using colorimetric IC50 assay to determine relative binding affinity of NTM-AAEIR to wild-type hCAII protein based on NTM-AAEIR inhibition capacity. The slopes versus the concentration of NTM-AAEIR were put into a non-linear regression equation to determine the IC50 of the selected NTM-AAEIR peptides to the wild-type hCAII.

FIG. 15A shows generalized scheme of the installation reaction comprising modifying the N-terminal modifier agent (left) with the catalyst, creating the catalytic intermediate (middle), which reacts with the peptide generating the peptide modified with the NTM. FIG. 15B shows a particular installation reaction comprising modifying the N-terminal modifier agent (left) with L-proline, creating the catalytic intermediate (middle), which reacts with the peptide generating the peptide modified with M103 NTM (Example 12).

FIG. 15C shows comparison of conversion rates of starting material peptide to the product peptide (M103-peptide) in the reaction of FIG. 15B without and with the catalyst (1% proline) performed by monitoring the 216 nm absorbance. Details of the installation reaction are described in Example 12.

FIG. 15D shows exemplary synthesis of compounds having Formula (8).

FIG. 15E shows exemplary synthesis of 3-H-ethynyl-4-formylbenzenesulfonamide for N-terminal modification of peptides.

FIG. 15F shows exemplary compounds of Formula (8).

FIG. 21A shows exemplary data on binding affinities of the designed binding agents (S222_1601-S222_1645, which have sequences set forth in SEQ ID NO: 128-135) with the calculated ~35-40% sequence identity to parent proteins (parents were S222_1333, S222_1519, and S222_1581, which have sequences set forth in SEQ ID NO: 125-127) towards M103-modified peptides immobilized on beads. See Example 14 for further details. FIG. 21B is the same as FIG. 21A, but "zoomed in", with net MFI>250 cropped.

DETAILED DESCRIPTION

Figure 1:
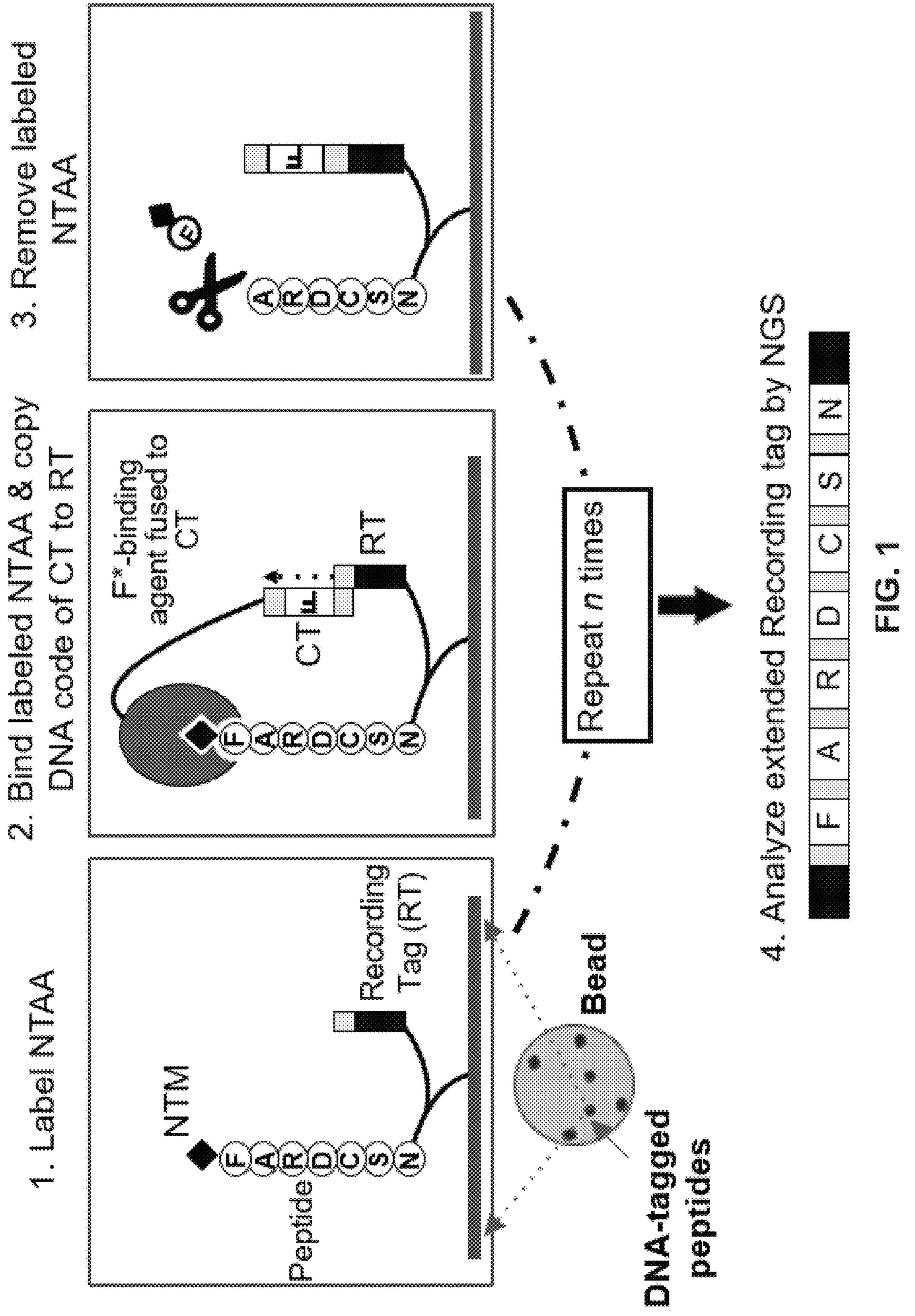
FIG. 1 depicts an exemplary design of the NGPS peptide sequencing assay utilizing N-terminal amino acid (NTAA)-specific binding agents (binders). (1) Peptide molecules are each associated with a DNA recording tag (RT) and attached to beads at a low molecular density, a sparsity that permits only intramolecular information transfer to occur. The N-terminal amino acid (NTAA) residue (F) of the peptide (FARDCSN (SEQ ID NO: 140)) is labeled with an N-terminal modification (NTM). (2) Next, immobilized and labeled peptides are contacted with binders specific for labeled NTAA (labeled F (F*)-specific binder is shown). Each binder comprises a DNA coding tag (CT) that comprises identifying information regarding the binder. After binding and washing, the coding tag identifying information is transferred enzymatically to the recording tag (via extension or ligation), generating an extended RT. (3) The labeled NTAA is removed by using mild Edman-like elimination chemistry or by a Cleavase enzyme, generating ARDCSN (SEQ ID NO: 141). The cycle 1-2-3 is repeated n times. After n cycles, the extended RT representing the n amino acids of the peptide sequence is formed and can be sequenced by NGS. A representative structure of the extended RT after 7 cycles is shown.

The present disclosure relates to a metalloprotein binder that specifically binds to an N-terminally modified amino acid residue of a peptide. Also provided herein is a method and related kits for modifying N-terminal amino acid residue of a peptide with a N-terminal modifier agent, as well as for treating a peptide using the metalloprotein binder. In some embodiments, also provided herein is a method and related kits for transferring information regarding the metalloprotein binder that specifically binds to the N-terminally modified amino acid residue of a peptide and identifying the N-terminal amino acid residue of the peptide based on this information. Transferring information involves one or more enzymes, including for performing a nucleic acid ligation, nucleic acid extension and/or a N-terminal amino acid cleavage reaction. In some embodiments, a plurality of peptides obtained from a sample is analyzed. In some embodiments, the sample is obtained from a subject. In some embodiments, the peptide sequencing or analysis method includes using a plurality of binders associated with coding tags to detect a plurality of peptides to be analyzed. Also provided are kits containing components and/or reagents for performing the provided methods for peptide sequencing and/or analysis. In some embodiments, the kits also include instructions for using the kit to perform any of the methods provided herein.

Highly-parallel characterization and recognition of macromolecules such as peptides remains a challenge. In proteomics, one goal is to identify and quantitate numerous proteins in a sample, which is a formidable task to accomplish in a high-throughput way. One approach for peptide sequencing disclosed in, for example, U.S. Pat. No. 9,435,810 B2, US 2019/0145982 A1, US 2020/0348308 A1, comprises contacting a peptide immobilized on a support with one or more N-terminal amino acid (NTAA) binders, obtaining and/or transferring information regarding the NTAA binder bound to the NTAA of the peptide, and identifying the NTAA of the peptide based on the obtained information. To identify penultimate terminal amino acid residue of the peptide, the NTAA of the peptide is removed after obtaining and/or transferring information step, thus exposing the penultimate terminal amino acid residue of the peptide as a new NTAA of the peptide. After that, the described above steps of contacting the peptide with one or more NTAA binders and obtaining and/or transferring information regarding the NTAA binder bound to the NTAA of the peptide are repeated (see, for example, FIG. 1). The information regarding specific NTAA binders for each cycle are collected and either processed immediately or stored until later or the end of the cycles (when all or most amino acid residues of the peptide are cleaved). The described method requires a set of specific binding agents (binders), wherein each binder from the set binds with high affinity to a particular NTAA and does not bind to other NTAAs. U.S. Pat. No. 9,435,810 B2 discloses an approach to make specific NTAA binders by introducing mutations into *E. coli* methionine aminopeptidase and different tRNA synthetases, since these enzymes have intrinsic specificity for free amino acids and can be utilized as a scaffold for specific binders. However, this approach resulted in binders with μM or higher affinity constants, and approximately 2:1 ratio of specific to non-specific binding (U.S. Pat. No. 9,435,810, Examples 1 and 10). Accordingly, there remains a need for more accurate, sensitive and high-throughput techniques relating to protein sequencing and/or analysis, as well as to products, methods and kits for accomplishing the same.

The disclosure provided herein is aimed to obtain specific binders to NTAAs with a high binding affinity (preferably, equilibrium dissociation constant $K_d$ is less than 500 nM). Weak binding affinity ($K_d$>500 nM) imparts some constraints on utility for methods (material production, high protein concentration, etc.). Chemical modification of N-terminus of a peptide can be used to improve binder affinity through additional hydrogen bonding and hydrophobic interactions. One approach to impart NTAA/binder affinity is to modify N-termini with established small molecule inhibitors of specific macromolecule targets (such as metalloenzymes) and employ those targets as binders. Medicinal chemistry programs have provided countless high affinity N-terminal modification (NTM)/binder pairs as starting points. However, synthetic tractability, facile installation, and prediction of appropriate binder/NTAA interactions make identification of ideal NTM/binder pairs a complicated proposition. Once appropriate reagents are identified, the P1, P2, etc. specificity must be evaluated and potentially tuned through genetic modification of the binder protein sequence (herein, P1 is a N-terminal amino acid residue and P2 is a penultimate terminal amino acid residue of the peptide to be analyzed). The capacity for altered NTAA specificity is strongly dependent on the tertiary structure of the initial protein scaffold and the NTM binding site, as well as the NTM chemical structure(s). Preferably, a single N-terminal modifier agent can be used for all NTAAs during binding, and also can be utilized for removal of the NTAA after binding and collecting information regarding the binder during multi-cycle approach for peptide sequencing.

Disclosed herein are metal chelating pharmacophores as high affinity, universal N-terminal modifications (NTMs) recognized by structurally diverse metalloenzymes that serve as binder scaffolds. Disclosed herein are N-terminal modifier agents that interact with and modify (or functionalize)N-terminal amino acid residues (P1 residues) of peptides to be analyzed. Such an N-terminal modifier agent modifies a peptide to form NTM-P1 group at the N-terminus of the peptide, wherein NTM is a chemical group that incorporate a metal cation binding group (MBG) in order to coordinate or chelate a metal ion. This approach employs metal ions as dual action affinity reagents, simultaneously recognized by both the binder scaffold and the NTM. This facilitates high affinity binder/NTM interactions and is used as a mechanism for protein tertiary structure to impart NTAA specificity. Metalloenzymes offer nM or sub-nM affinity towards their substrates, and an enhanced affinity in the disclosed methods is derived from an ability of the NTAA modification to coordinate an active site metal ion. Common structural elements in metal binding proteins (such as the conserved HEXGHXXGXXH (SEQ ID NO: 142) zinc binding sequence) enable multiple orthogonal protein scaffolds to serve as binders, with the aim of attaining the NTAA specificity required for the disclosed protein sequencing assay. Numerous high affinity metal chelating pharmacophores identified in medicinal chemistry programs provide a wealth of potential metal binding NTM's. The scope of known metal binding NTMs include those with simple installation and potential compatibility with both chemical and enzymatic N-terminal elimination (NTE) of peptide's NTAA. The approach described herein provides the opportunity to derive multiple binders, with varied NTAA specificity, against a single, high affinity metal binding NTM.

Figure 2A:
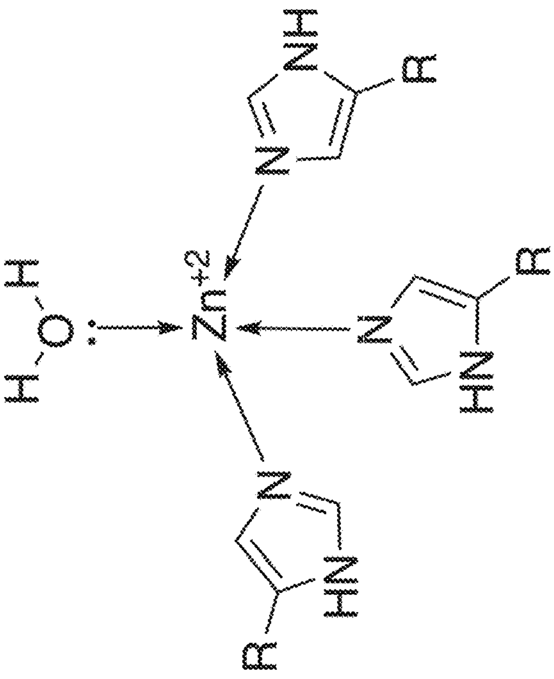
FIG. 2A. Exemplary active site architecture common in zinc binding metalloenzymes.

In metalloenzymes, active site histidines (and/or cysteines, glutamates, aspartates) coordinate metal ions in a multidentate fashion to yield a high affinity metal binding site. An "activated" water molecule is often coordinated to the protein bound metal ion to affect catalysis (FIG. 2A). This water molecule is generally displaced by metal binding pharmacophores, resulting in high affinity but non-target specific interactions. Medicinal chemistry efforts therefore focus on defining additional substituents to impart selectivity for a particular target. Common metal binding pharmacophores include sulfonamides, hydroxamates, carboxylates, thiols, phosphonates, pyrazoles, etc. with typical $K_d$ values ranging from pM to nM (see, for example, FIG. 2-FIG. 5). The fact that many metalloprotease inhibitors are derived from peptide substrates supports the notion that NTM-peptides can serve as effective ligands.

Several metal cation binding groups are evaluated as metal binding NTMs. Preferred NTMs are those that can be installed on NTAA of a peptide, provide high affinity and specificity during binding reactions with metalloprotein binders that recognize NTM-modified NTAAs (including a proper size of NTMs that fit a binding pocket of the binding metalloprotein binder), and also are compatible with removal of the NTM-modified NTAAs after binding. Removal of a modified terminal amino acid can be accomplished by a number of known techniques, including chemical cleavage and enzymatic cleavage. Agents configured for removing modified NTAA residues from the N-terminally modified target peptide are known in the art. Agents for chemical cleavage, such as mild Edman-like degradation, are disclosed in, for example, in US 2020/0348307 A1 or US 2022/0227889 A1, incorporated by reference herein. In some embodiments, mild conditions are preferably used during cleavage, since they are compatible with transferring information regarding the binder during the encoding assay (see, e.g., Example 7 below). In some embodiments, utilized mild conditions are compatible with DNA (do not compromise integrity of DNA or DNA-related assays). In other embodiments, instead of chemical cleavage, an engineered enzyme (cleavase) is used as the agent configured for removing modified NTAA residue(s) from the N-terminally modified target peptide. Enzymatic cleavage can be accomplished by an engineered cleavase, such as aminopeptidase, a carboxypeptidase, dipeptidyl peptidase, dipeptidyl aminopeptidase, or variant thereof. Exemplary engineered cleavases are disclosed in the published patents and patent applications U.S. Pat. No. 9,435,810 B2, U.S. Pat. No. 11,427,814 B2 or US 2023/0021091 A1, incorporated by reference herein.

In some embodiments, the agent configured for removing modified NTAA residue(s) from the N-terminally modified target peptide is a modified cleavase enzyme, which: (i) is configured to cleave a peptide bond between a terminally labeled amino acid residue and a penultimate terminal amino acid residue of a polypeptide; (ii) is derived from a dipeptidyl aminopeptidase, which removes an unlabeled terminal dipeptide from a polypeptide; (iii) comprises two or more amino acid substitutions in the dipeptidyl aminopeptidase in the residues corresponding to positions N214, W215, R219, N329, D673 and G674 of SEQ ID NO: 3, and comprises an amino acid sequence that exhibits at least 20%, at least 30%, at least 40%, at least 50%, or more sequence identity to SEQ ID NO: 67 (see also U.S. Pat. No. 11,427,814, incorporated herein by reference).

In some embodiments, a set of modified cleavases, comprising at least two different modified cleavases is used (e.g., as disclosed in U.S. Pat. No. 11,427,814), wherein: (i) each of the modified cleavases from the set of modified cleavases is configured to cleave a peptide bond between a terminally labeled amino acid residue and a penultimate terminal amino acid residue of a polypeptide, wherein the modified cleavase is derived from a dipeptidyl aminopeptidase, which removes an unlabeled terminal dipeptide from a polypeptide, wherein the dipeptide aminopeptidase comprises an amino acid sequence having at least 20% sequence identity to the amino acid sequence of SEQ ID NO: 4 and also comprising an asparagine residue at a position corresponding to position 191 of SEQ ID NO: 4, a tryptophan residue or phenylalanine residue at a position corresponding to position 192 of SEQ ID NO: 4, an arginine residue at a position corresponding to position 196 of SEQ ID NO: 4, an asparagine residue at a position corresponding to position 306 of SEQ ID NO: 4, and an aspartate residue at a position corresponding to position 650 of SEQ ID NO: 4; and wherein the modified cleavase comprises two or more amino acid substitutions in the residues corresponding to positions N191, W/F192, R196, N306, and D650 of SEQ ID NO: 4; and (ii) the modified cleavases from the set of modified cleavases have different specificities for terminally labeled amino acids, which the modified cleavases are configured to remove.

Figure 3:
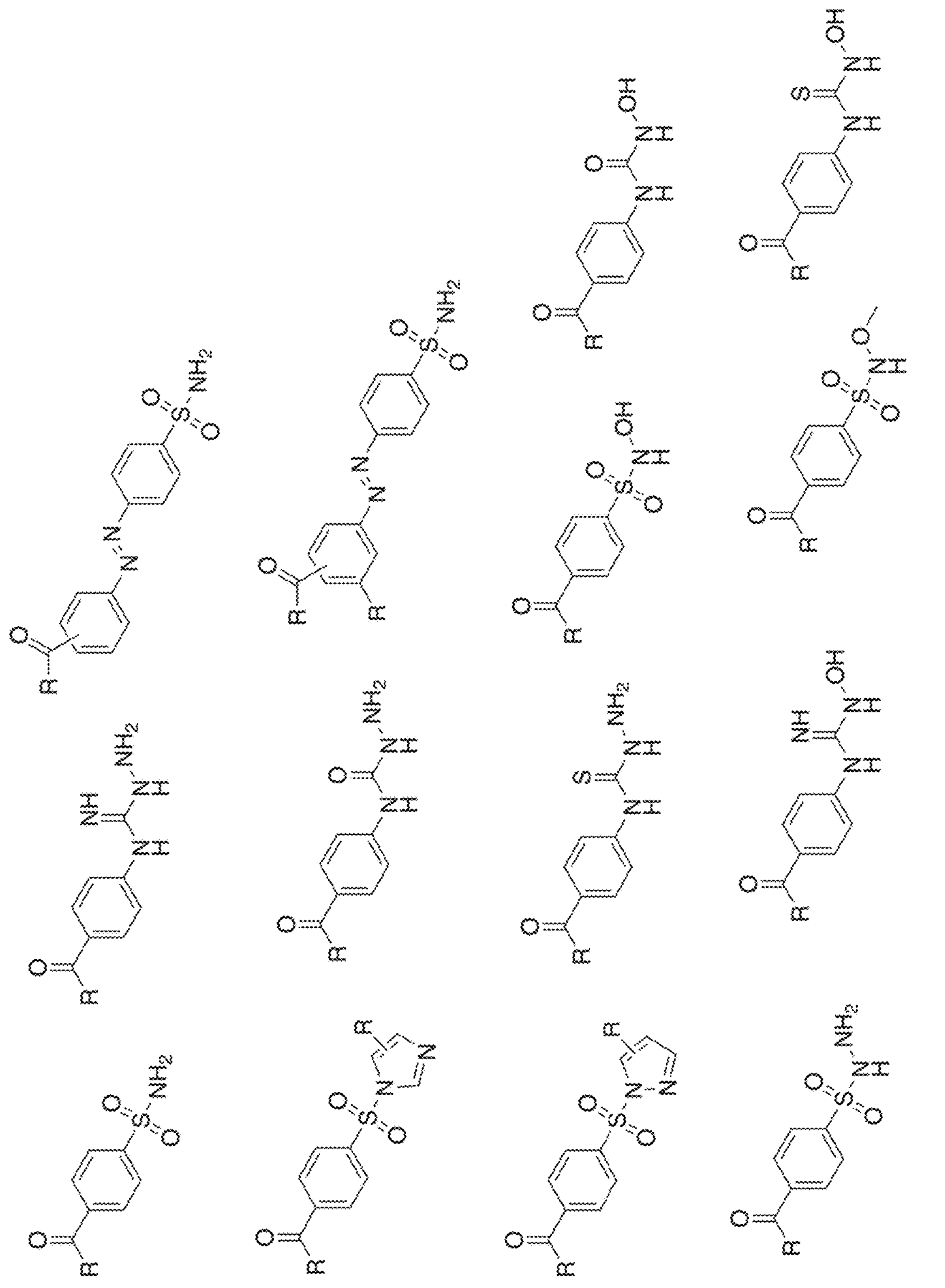
FIG. 3. Examples of zinc-binding N-terminal modifications (NTMs).
Figure 4:
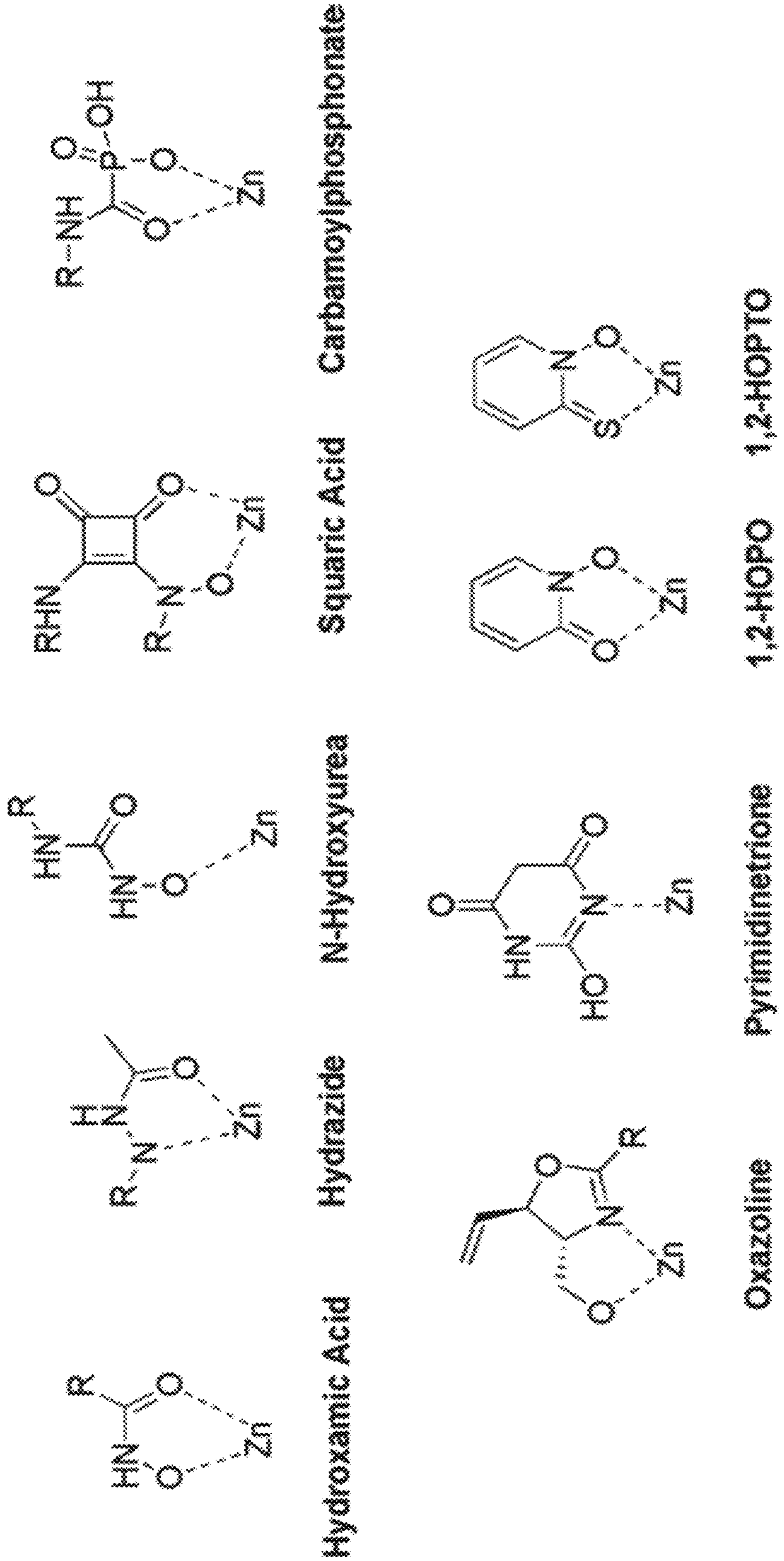
FIG. 4. Examples of zinc-binding NTMs.
Figure 5:
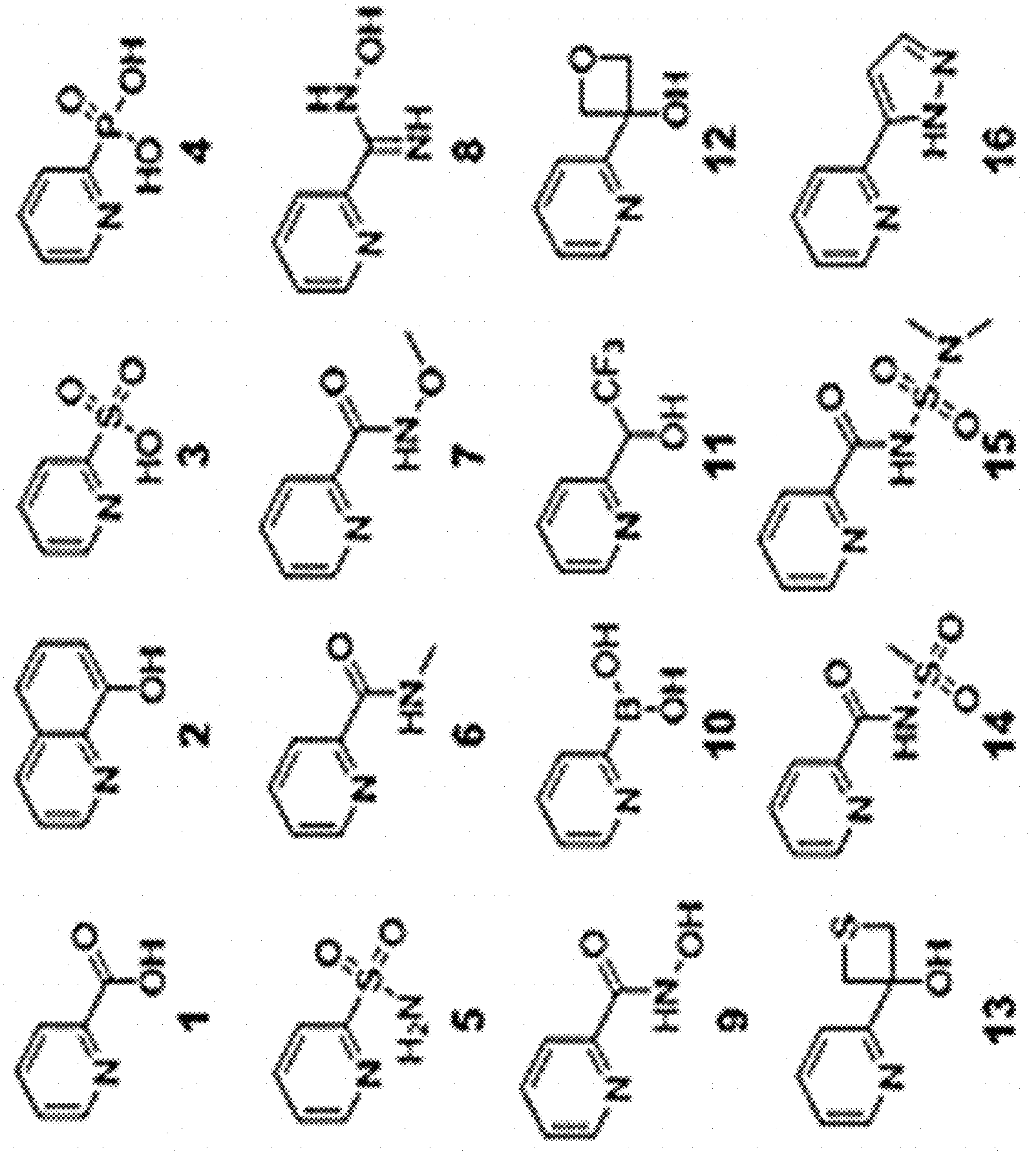
FIG. 5. Exemplary metal-binding isosteres of picolinic acid (1) for use as NTMs.

In some embodiments, the provided N-terminal modifier agents and/or NTMs comprise chemical moieties that are known functional inhibitors of metalloenzymes, or structural variants thereof. Some examples of NTMs include phenylsulfonamide substituents that afford strong affinity, ease of installation, broad specificity, and structural similarity to cleavase substrates. Some variants of sulfonamides include aryl (benzene, pyrazole, imidazole), amino acid, alkyl sulfonamides. Terminal sulfonamides and N-substituted sulfonamides can be utilized. Arylsulfonamides are well-established inhibitors of carbonic anhydrase (CA). Other derivatives of sulfonamides can also impart high affinity metal binding. Further, isothiocyanate activated phenylsulfonamides enable efficient N-terminal installation and Edman-like degradation of NTM-NTAAs. Alternatively, hydrazides, semicarbazides, imidazoles, and pyrrazoles are established metal cation binding groups and are structurally related to reagents implemented in mild chemical cleavage of modified NTAAs described in WO2020/223133 A1. For example, aryl-4,5-dihydro-1H-pyrazole-1-carboxamide derivatives bearing a sulfonamide moiety show nanomolar inhibition constants against carbonic anhydrases (Hargunani P, et al., Aryl-4,5-dihydro-1H-pyrazole-1-carboxamide Derivatives Bearing a Sulfonamide Moiety Show Single-digit Nanomolar-to-Subnanomolar Inhibition Constants against the Tumor-associated Human Carbonic Anhydrases IX and XII Int J Mol Sci. 2020 Apr. 9; 21(7):2621). In other embodiments, hydroxamates, compounds bearing the functional group RC(O)N(OH)R', with R and R' are organic residues and CO is a carbonyl group can be utilized in NTMs. Many hydroxamates are used as metal chelators and display nanomolar affinities against metalloenzymes (established as inhibitors for matrix metalloenzymeases (MMPs), aminopeptidases, histone deacetylases (HDACs), peptide deformylases, carboxypeptidases, and carbonic anhydrases). In other embodiments, thiol groups or carboxylates can be included in NTMs, since these groups are common in $Fe^{2+}$ and in $Mg^{2+}$ binding motifs, respectively. In other embodiments, benzoxaborole derivatives can be utilized in NTMs as they were shown to potently inhibit carbonic anhydrases (Langella E, et al, Exploring benzoxaborole derivatives as carbonic anhydrase inhibitors: a structural and computational analysis reveals their conformational variability as a tool to increase enzyme selectivity. J Enzyme Inhib Med Chem. 2019 December; 34(1):1498-1505). In other embodiments, NTMs as shown in FIGS. 3-5 are provided and utilized in the methods disclosed herein.

In some aspects, this application relates to U.S. patent application Ser. No. 17/727,677 filed Apr. 22, 2022, entitled "METALLOENZYMES FOR BIOMOLECULAR RECOGNITION OF N-TERMINAL MODIFIED PEPTIDES," the publication of which is US 2022/0283175 A1, which is herein incorporated by reference in its entirety for all purposes.

In some embodiments, N-terminal modifier agent or an NTM group comprises a compound of Formula (1):

(1)

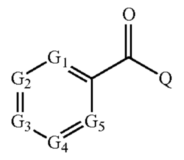

wherein Q is OH, $OR^Q$ or OM, each $R^Q$ is independently aryl, heteroaryl, or heterocycloalkyl each of which is optionally substituted with one or more groups selected from halo, nitro, cyano, sulfonate, carboxylate, alkylsulfonyl, and N of heteroaryl is optionally oxidized; or $R^Q$ can be —C(═O)R or —C(═O)—OR; M is a cationic counterion;

$G^1$-$G^5$ are each independently selected from CH, CJ, and N, provided not more than 3 of $G^1$-$G^5$ are N; J at each occurrence is independently selected from H, $C_1$-$C_2$ alkyl, $NO_2$, $C_1$-$C_2$ haloalkyl, $C_1$-$C_2$ haloalkoxy, halo, —$OR^1$, —$N(R^1)_2$, —$SR^1$, —$S(O)_nR^1$, —$NR^1SO_2R^1$, —$SO_2N(R^1)_2$, —$SO_3R^1$, —$B(OR^1)_2$, —C(═O)$R^1$, —CN, —N═N—$R^1$, —C(N)$R^1$, —CON$(R^1)_2$, —CSN$(R^1)_2$ —COO$R^1$, —C(O)Ar, and tetrazole, where Ar represents a phenyl or 5-6 membered heteroaryl ring that is optionally substituted with one or two groups selected from halo, CN, $R^1$ and $OR^1$;

$R^1$ is independently selected at each occurrence from H, $OR^2$, $N(R^2)_2$, $C_1$-$C_2$ alkyl, $C_1$-$C_2$ haloalkyl, aryl, heteroaryl, that is optionally substituted with one or two groups selected from halo, $N(R^2)_n$, COOH, —$S(O)_nR^2$, —$S(O)_2N(R^2)_n$;

$R^2$ is independently selected from H, OH, $NH_2$ or $C_1$-$C_2$ alkyl; and n at each occurrence is independently 1 or 2.

In some embodiments, N-terminal modifier agent or an NTM group comprises a compound of the following Formulas:

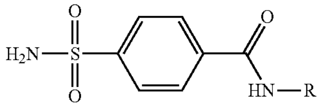 or

-continued

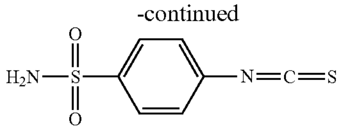 or

2

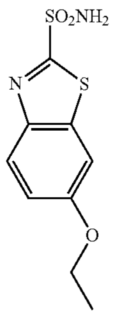 or (EZA)

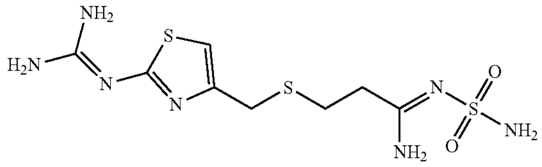

In some embodiments, N-terminal modifier agent comprises:

either (b1) a metal-binding compound of Formula (5):

(5)

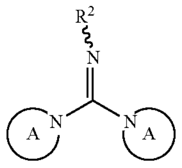

wherein:

$R^2$ is H or $R^4$;

$R^4$ is $C_{1-6}$ alkyl, which is optionally substituted with one or two members selected from halo, $C_{1-3}$ alkyl, $C_{1-3}$ alkoxy, $C_{1-3}$ haloalkyl, phenyl, 5-membered heteroaryl, and 6-membered heteroaryl, wherein the phenyl, 5-membered heteroaryl, and 6-membered heteroaryl are optionally substituted with one or two members selected from halo, —OH, $C_{1-3}$ alkyl, $C_{1-3}$ alkoxy, $C_{1-3}$ haloalkyl, $NO_2$, CN, COOR", and CON(R")$_2$, where each R" is independently H or $C_{1-3}$ alkyl;

each ring A is a 5-membered heteroaryl ring containing up to three N atoms as ring members and is optionally fused to an additional phenyl or a 5-6 membered heteroaryl ring, and wherein the 5-membered heteroaryl ring and optional fused phenyl or 5-6 membered heteroaryl ring are each optionally substituted with one or two groups selected from $C_{1-4}$ alkyl, $C_{1-4}$ alkoxy, —OH, halo, $C_{1-4}$haloalkyl, $NO_2$, COOR, $CONR_2$, —$SO_2R^*$, —$NR_2$, phenyl, and 5-6 membered heteroaryl;

wherein each R is independently selected from H and $C_{1-3}$ alkyl optionally substituted with OH, OR*, —$NH_2$, —NHR*, or —$NR^*_2$; and each R* is $C_{1-3}$ alkyl, optionally substituted with OH, oxo, $C_{1-2}$ alkoxy, or CN;

wherein two R, or two R", or two R* on the same N can optionally be taken together to form a 4-7 membered heterocyclic ring, optionally containing an additional heteroatom selected from N, O and S as a ring member, and optionally substituted with one or two groups selected from halo, $C_{1-2}$ alkyl, OH, oxo, $C_{1-2}$ alkoxy, or CN;

or (b2) a metal-binding compound of the formula $R^3$—NCS;

wherein $R^3$ is H or an optionally substituted group selected from phenyl, 5-membered heteroaryl, 6-membered heteroaryl, $C_{1-3}$ haloalkyl, and $C_{1-6}$ alkyl, wherein the optional substituents are one to three members selected from halo, —OH, $C_{1-3}$ alkyl, $C_{1-3}$ alkoxy, $C_{1-3}$ haloalkyl, $NO_2$, CN, $COOR^1$, —$N(R')_2$, $CON(R')_2$, phenyl, 5-membered heteroaryl, 6-membered heteroaryl, and $C_{1-6}$ alkyl, wherein the phenyl, 5-membered heteroaryl, 6-membered heteroaryl, and $C_{1-6}$ alkyl are each optionally substituted with one or two members selected from halo, —OH, $C_{1-3}$ alkyl, $C_{1-3}$ alkoxy, $C_{1-3}$ haloalkyl, $NO_2$, CN, $COOR^1$, —$N(R')_2$, and $CON(R')_2$;

where each R' is independently H or $C_{1-3}$ alkyl;

wherein two R' on the same N can optionally be taken together to form a 4-7 membered heterocyclic ring, optionally containing an additional heteroatom selected from N, O and S as a ring member, and optionally substituted with one or two groups selected from halo, $C_{1-2}$ alkyl, OH, oxo, $C_{1-2}$ alkoxy, or CN.

In some embodiments, the N-terminal modifier agent comprises a compound of Formula (2):

(2)

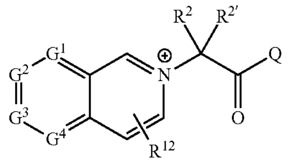

wherein Q is OH, $OR^Q$, or OM, each $R^Q$ is independently aryl or heteroaryl, each of which is optionally substituted with one or more groups selected from halo, nitro, cyano, sulfonate, carboxylate, alkylsulfonyl, and N of heteroaryl is optionally oxidized; or $R^Q$ can be —C(═O)R or —C(═O)—OR;

M is a cationic counterion;

$G^1$-$G^5$ are each independently selected from CH, CJ, BN, BO, and N, provided not more than 3 of $G^1$-$G^5$ are N;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —$N(R^8)_2$, —$SR^8$, —$S(O)_nR^8$, —$NR^8SO_2R^8$, —$SO_2N(R^8)_2$, $SO_3R^8$, —$B(OR^8)_2$, $C(═O)R^8$, CN, $CON(R^8)_2$, —$COOR^8$, —C(—O)Ar, and tetrazole, where Ar represents a phenyl or 5-6 membered heteroaryl ring that is optionally substituted with one or two groups selected from halo, CN, $R^8$ and $OR^8$;

$R^2$ and $R^{2'}$ can each be the side chain of an amino acid, e.g. one of the side chains of the 20 common amino acid side chains, optionally protected amino acid side chains, post-translationally modified amino acid side chains, unnatural amino acid sidechains;

or $R^2$ and $R^{2'}$ can each be H or a group selected from aryl, heteroaryl, bicyclic aryl, bicyclic heteroaryl, and heterocyclyl, each of which is optionally substituted with one to six groups (or with one to four groups when $R^2$ or $R^{2'}$ is aromatic) selected from halo, CN, $NH_2$, $NH(CH_3)$, $N(CH_3)_2$, protected amine (e.g., N3, $NO_2$, NHFmoc, NHBoc), $C(O)NR_2$, NHC(O)R, $B(OR)_2$, aryl, heteroaryl, $C_1$—C2 alkyl, $C_1$-$C_2$ haloalkyl, $C_1$-$C_2$ haloalkoxy, and —$OR^4$;

each R, $R^4$ and $R^8$ is independently selected at each occurrence from H, $C_1$-$C_2$ alkyl, and $C_1$-$C_2$ haloalkyl;

n at each occurrence is independently 1 or 2; and $R^{12}$ represents one or two optional substituents on the pyridinium ring, which are independently selected from $C_1$-$C_2$ alkyl, $C_1$-$C_2$ alkoxy, $C_1$-$C_2$ haloalkyl, $C_1$-$C_2$ haloalkoxy, and halo.

Compounds of Formula (2) also comprise an anionic counterion, typically an unreactive anionic counterion, such as halo, tetrafluoroborate, hexafluorophosphate, fluorosulfonate, trifluoromethylsulfonate, and the like.

In some embodiments, the N-terminal modifier agent comprises a compound of Formula (3):

(3)

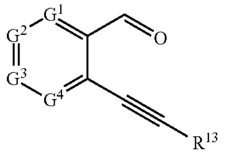

wherein:

$G^1$-G4 are each independently selected from CH, CJ, and N, provided not more than 3 of G1-G4 are N;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —$N(R^8)_2$, —$SR^8$, —$S(O)_nR^8$, —$NR^8SO_2R^8$, —$SO_2N(R^8)_2$, $SO_3R^8$, —$B(OR^8)_2$, $C(═O)R^8$, CN, $CON(R^8)_2$, —$COOR^8$, —C(—O)Ar, and tetrazole, where Ar represents a phenyl or 5-6 membered heteroaryl ring that is optionally substituted with one or two groups selected from halo, CN, $R^8$ and $OR^8$;

each $R^8$ is independently selected from H, $C_1$—C2 alkyl, and $C_1$-$C_2$ haloalkyl;

n at each occurrence is independently 1 or 2; and $R^{13}$ is selected from H, $C_1$-$C_2$ alkyl, C1-C2 alkoxy, $C_1$-$C_2$ haloalkyl, and $C_1$-$C_2$ haloalkoxy. In preferred embodiments, $R^{13}$ is H.

In some embodiments, the N-terminal modifier agent comprises a compound selected from the group consisting of compounds of the following formula:

(A)

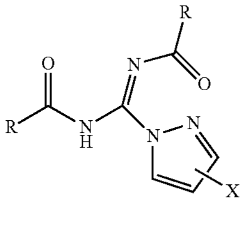

wherein R is $CH_3$, $CF_3$, $OC(CH_3)_3$, or $OCH_2C_6H_5$, and X is H, $CH_3$, $CF_3$, $CF_2H$, or $OCH_3$;

(B)

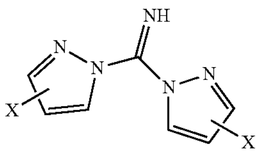

wherein X is H, $CH_3$, $CF_3$, $CF_2H$, $OCH_3$, or $SO_2NH_2$;

(C)

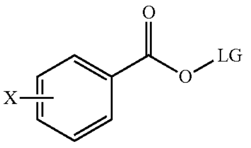

wherein X is H, F, Cl, $OCH_3$, $OCF_3$, CN, or $SO_2NH_2$, and LG is succinimide, pentafluorophenyl, or tetrafluorophenyl;

and (D)

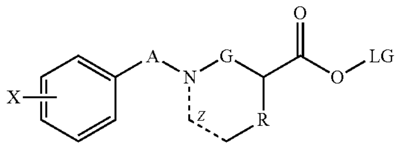

wherein X is H, F, Cl, $NH_2$, $OCH_3$, $OCF_3$, CN, or $SO_2NH_2$, A=CONH or $SO_2$, G=0 or 1 $CH_2$, R is any amino acid or unnatural amino acid, and Z ring=0 (not there), 1, 2, or 3 $CH_2$.

A compound of Formula (3) can be used to generate a modified target polypeptide by contacting the target polypeptide with a 2-ethynyl benzaldehyde derivative of Formula (3) in a polar aprotic solvent such as DMSO, DMF, DMA and the like in 10-500 mM buffer (e.g., PBST, MES, acetate, etc., where the PBST buffer is 1× phosphate-buffered saline having 0.1% Tween 20 detergent) at pH 6-9 and a reaction temperature of about 20-80° C., preferably 25-60° C. Typically, a concentration of 1-100 mM of the compound of Formula (3) is used. See also Example 12 below for exemplary installation conditions.

When a compound of Formula (3) reacts with a target polypeptide, it forms a bicyclic group of Formula (4):

(4)

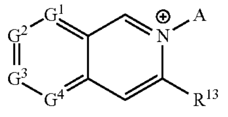

wherein A represents the point of attachment of the group to P1 of a target polypeptide;

$G^1$-$G^4$ are each independently selected from CH, CJ, and N, provided not more than 3 of $G^1$-$G^4$ are N;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —$N(R^8)_2$, —$SR^8$, —$S(O)_nR^8$, —$NR^8SO_2R^8$, —$SO_2N(R^8)_2$, $SO_3R^8$, —$B(OR^8)_2$, $C(=O)R^8$, CN, $CON(R^8)_2$, —$COOR^8$, —C(—O)Ar, and tetrazole, where Ar represents a phenyl or 5-6 membered heteroaryl ring that is optionally substituted with one or two groups selected from halo, CN, $R^9$ and $OR^9$;

each $R^8$ and each $R^9$ is independently selected from H, $C_1$-$C_2$ alkyl, and $C_1$-$C_2$ haloalkyl;

n at each occurrence is independently 1 or 2; and $R^{13}$ is selected from H, $C_1$-$C_2$ alkyl, $C_1$-$C_2$ alkoxy, $C_1$-$C_2$ haloalkyl, and $C_1$-$C_2$ haloalkoxy.

Therefore, in some embodiments, the modified target polypeptide is of Formula M-P1-P2-polypeptide, wherein M is the moiety of Formula (4). In some particular embodiments, the reagent of Formula (3) used to attach M to the target polypeptide's NTAA is 4-(sulfamoyl)-2-ethynylbenzaldehyde, and the group M in the modified target polypeptides of the Formula M-P1-P2-polypeptide is an 6-(sulfamoyl)isoquinolinium of Formula (4), where $G^1$, $G^2$, and $G^4$ are CH, $G^3$ is CJ, where J is comprised of —$SO_2(R^8)_2$ where $R^8$ is H.

Compounds of Formula (4) also comprise an anionic counterion, typically an unreactive anionic counterion, such as halo, tetrafluoroborate, hexafluorophosphate, fluorosulfonate, trifluoromethylsulfonate, and the like.

Unlike compounds of Formulas (1)-(2) where Q is OH or OM, which require a peptide coupling agent, when the NTM is a compound of Formula (3), no coupling agent is needed, as the ethynyl arylaldehyde reacts directly with the free amine of the NTAA.

$R^2$ for compounds of Formulas (1)-(2) can in particular be a side chain of an amino acid selected from Alanine, aspartic acid, asparagine, glutamic acid, glutamine, glycine, (2-, 3-, or 4-pyridyl-)alanine, phenylglycine, 4-fluorophenylglycine, leucine, norleucine, isoleucine, cycloleucine, valine, dimethylglycine, methionine, methionine sulfoxide, phenylalanine, halophenylalanine, haloalkylphenylalanine, cyclopropylalanine, (2-thienyl)alanine, cyclopropylglycine, serine, phosphoserine, threonine, phosphothreonine, cysteine, carbamidomethylcysteine, trifluoromethylcysteine, tyrosine, phosphotyrosine, tryptophan, histidine, acetyllysine, proline, (2- or 3-)azetidine carboxylic acid, piperidine carboxylic acid, methylated lysine, citrulline, nitroarginine, and norvaline. In some embodiments, $R^{2'}$ is H.

Where Q is —$OR^Q$ in any of Formulas (1)-(2), $R^Q$ is typically an electron-deficient aryl or heteroaryl group. Suitable options include benzotriazolyl, halobenzotriazolyl, pyridinotriazolyl, benzotriazolyl-N-oxide, pyridinotriazolyl-N-oxide, —N-succinimide, 1-cyano-2-ethoxy-2-oxoethylideneamino, —N-phthalimide, 4-nitrophenyl, 2,4-dinitrophenyl, 4-fluorophenyl, 2,4-difluorophenyl, 2,3,4,5,6-pentafluorophenyl, 2,3,5,6-tetrafluorophenyl, and 4-sulfo-2,3,5,6,tetrafluorophenyl.

In compounds of Formula (3), each of $G^1$-$G^5$ is typically N or CJ, and preferably no more than two of them in any compound is N. In some embodiments, each J is selected from H, amino, halo, hydroxy, $CF_3$, $OCF_3$ $NO_2$, $SO_2Me$, $SO_2NR_2$, methoxy, methyl, phenyl, and —$B(OR)_2$ where each R is independently H or $C_{1-2}$ alkyl.

In preferred embodiments, the N-terminal modifier agent comprises a compound selected from the group consisting of compounds of the following Formula (6)-(9):

(6)

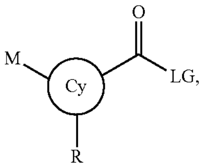

(7)

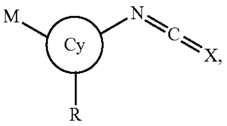

(8)

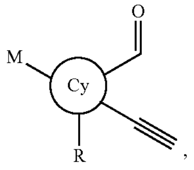

(9)

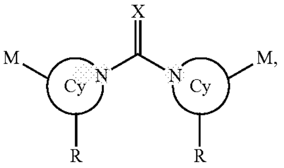

wherein M is a metal cation binding group that comprises sulfonamide, hydroxamic acid, sulfamate, or sulfamide; the group

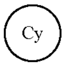

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, $OR^Q$, or OCC, wherein each $R^Q$ is independently aryl or heteroaryl, each of which is optionally substituted with one or more groups selected from halo, nitro, cyano, sulfonate, carboxylate, alkylsulfonyl, and N of heteroaryl is optionally oxidized; or $R^Q$ can be —C(═O)R or —C(═O)—OR; CC is a cationic counterion; X is one of the following: O, S, Se, or NH. In preferred embodiments, the metal cation binding group is a Zn cation binding group.

Figure 14:
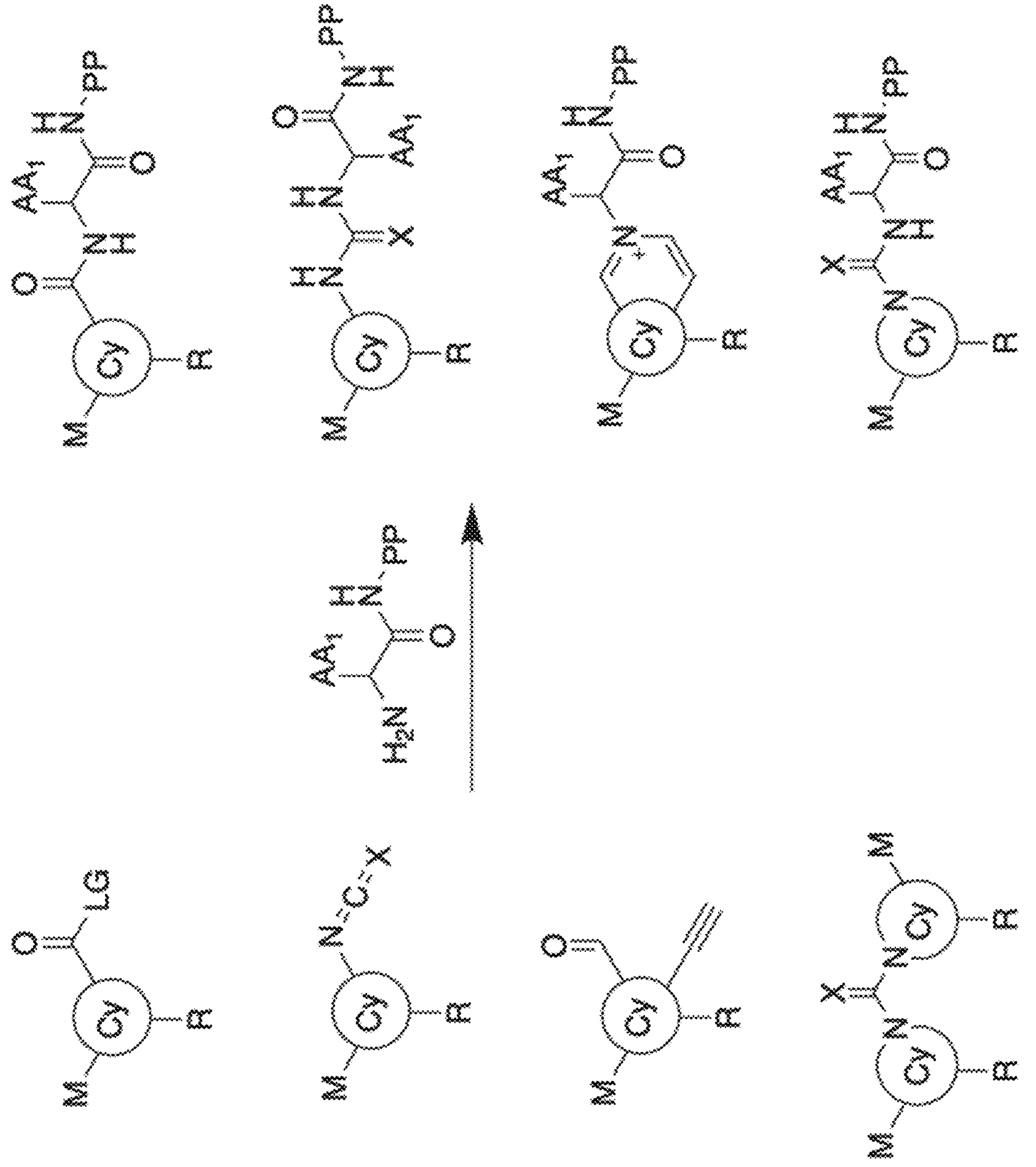
FIG. 14 shows exemplary structures of N-terminal modifier agents of Formula (6)-(9), as well as corresponding installation reactions on NTAA residues of peptides.
Figure 15A:
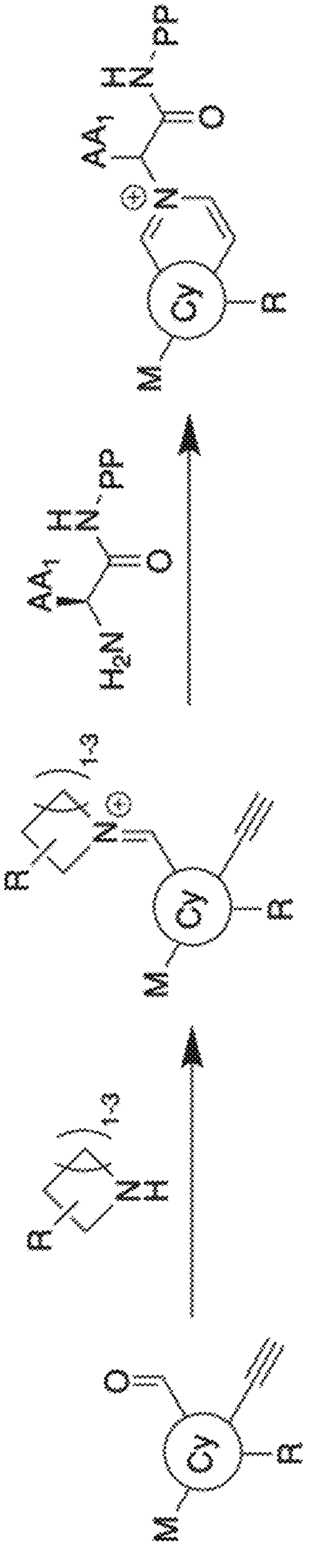
FIG. 15A-FIG. 15F illustrate exemplary installation of a particular class of NTMs having Formula (8) on the N-terminus of a peptide.

Exemplary structures of N-terminal modifier agents as well as corresponding installation reactions on NTAA residues of peptides are shown in FIG. 14 and FIG. 15A.

Figure 15B:
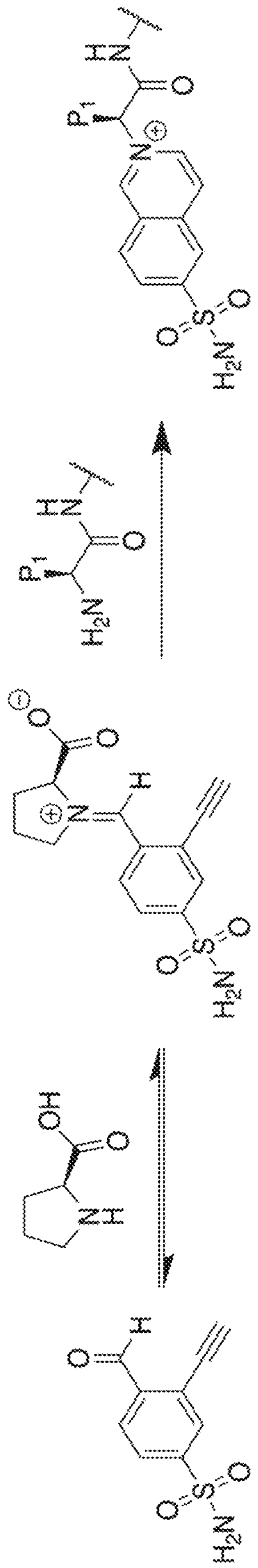
Figure 15C:
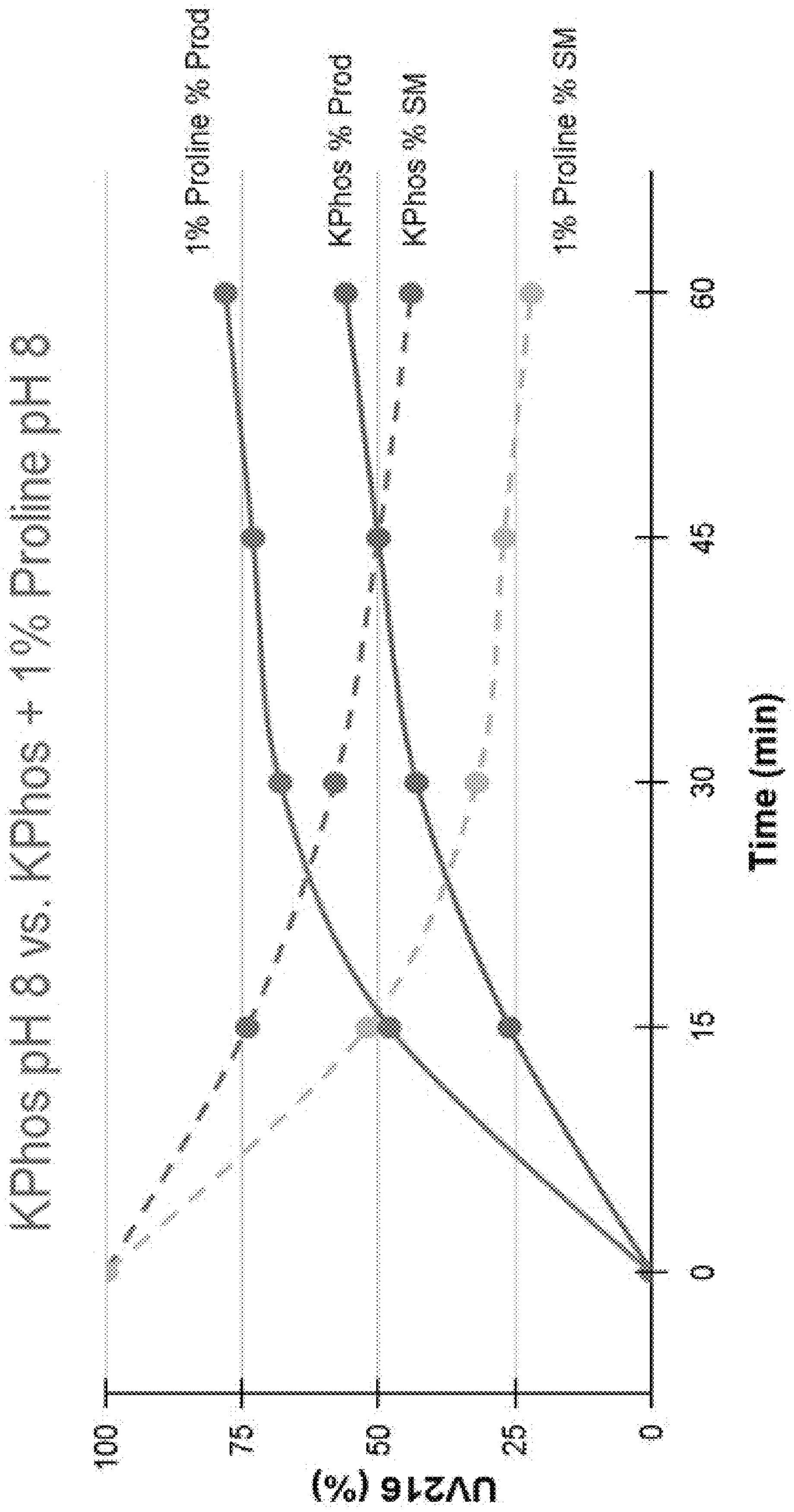
Figure 15D:
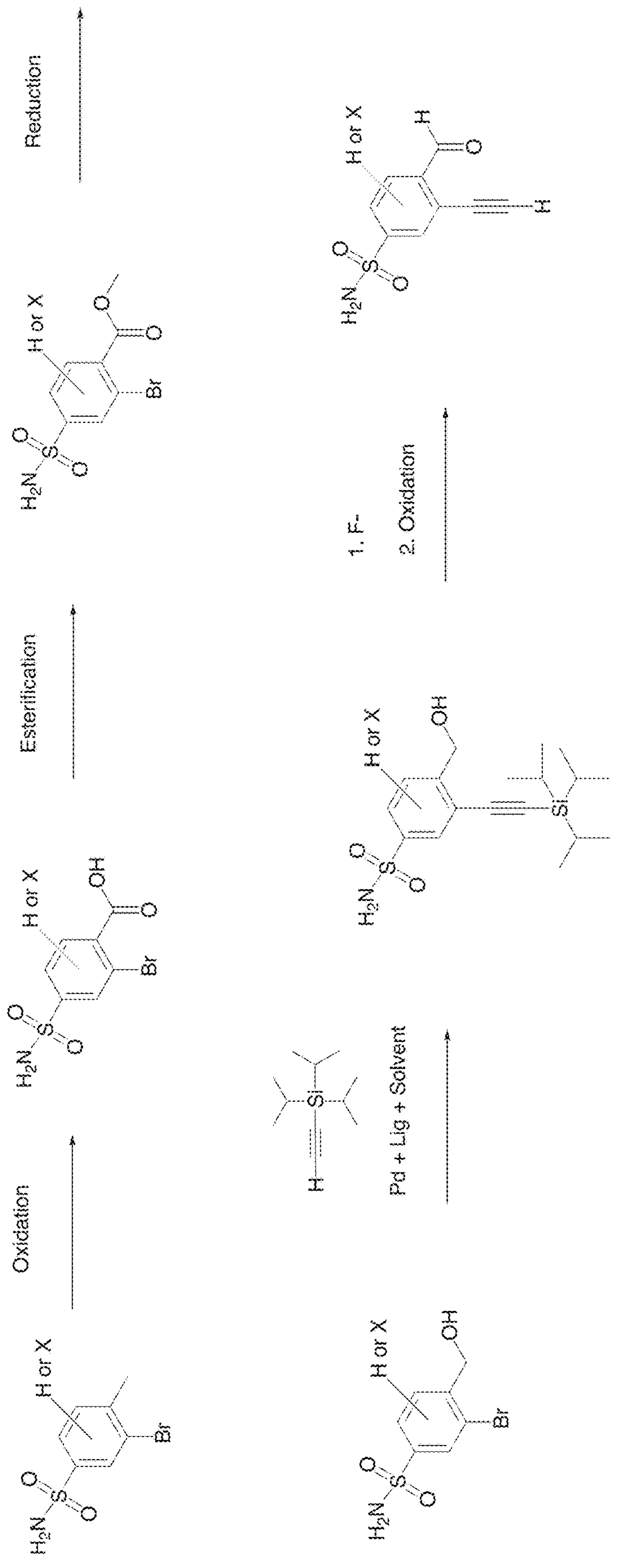
Figure 15E:
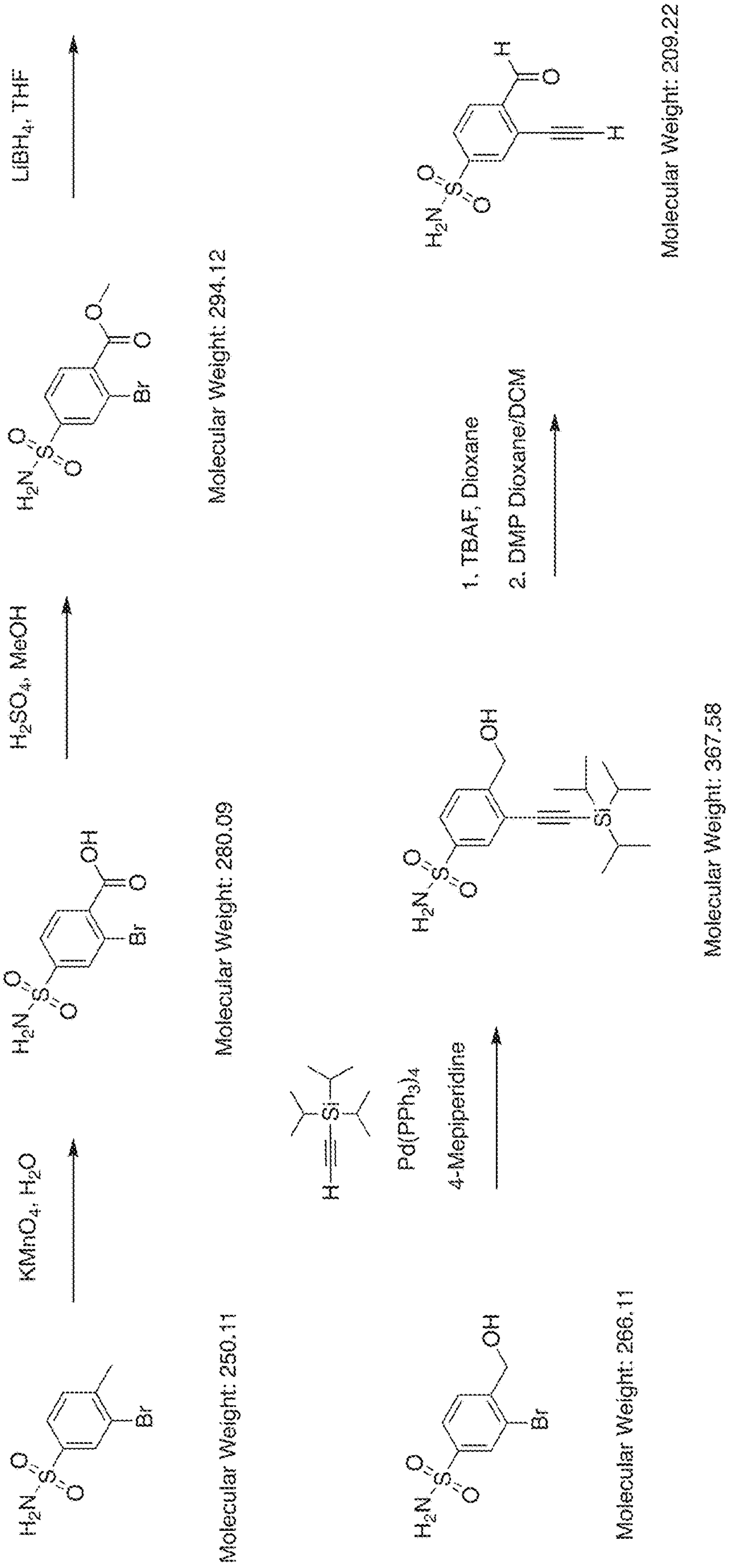
Figure 15F:
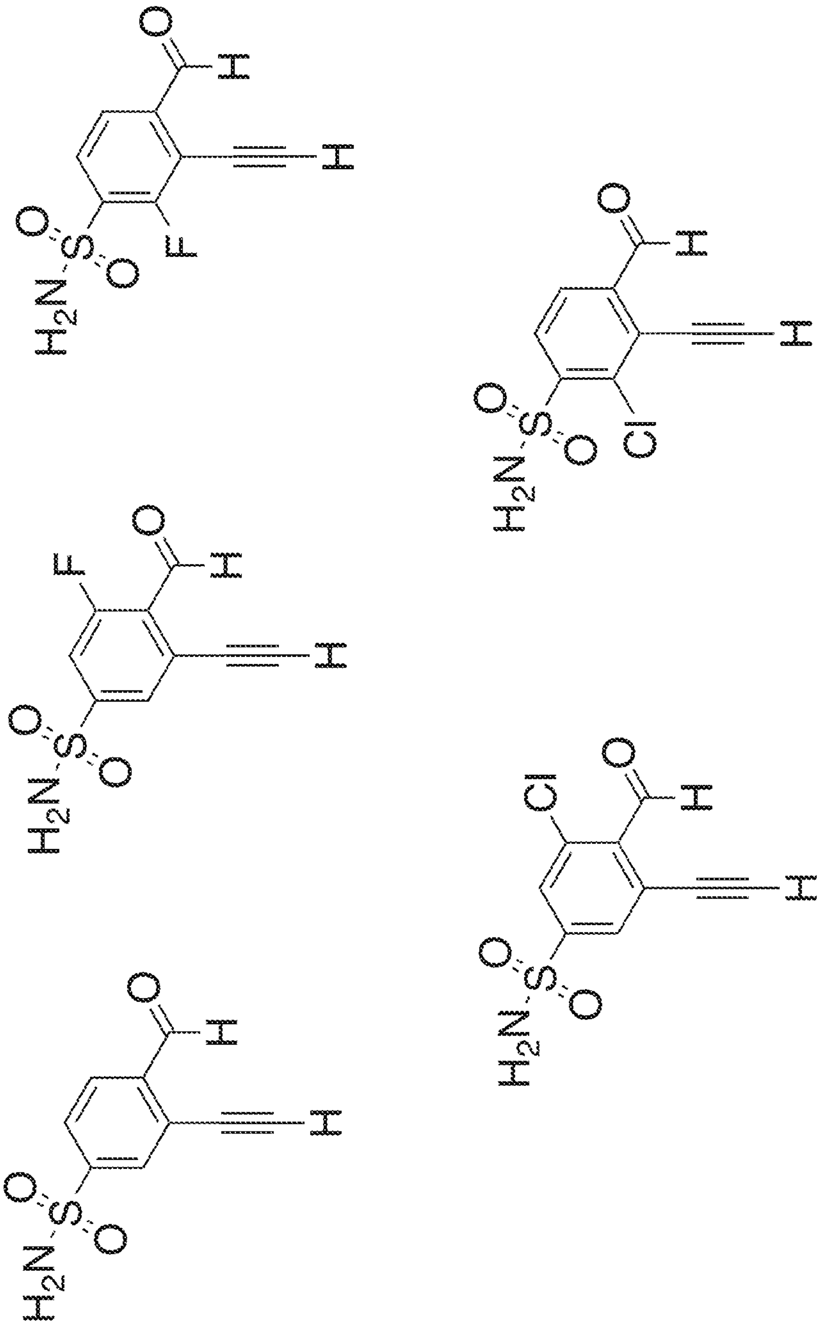

In some embodiments, N-terminal modifier agents used in the described methods and compositions have structures as shown in FIG. 15B and FIG. 15F (all within Formula (8)).

Figure 15G:
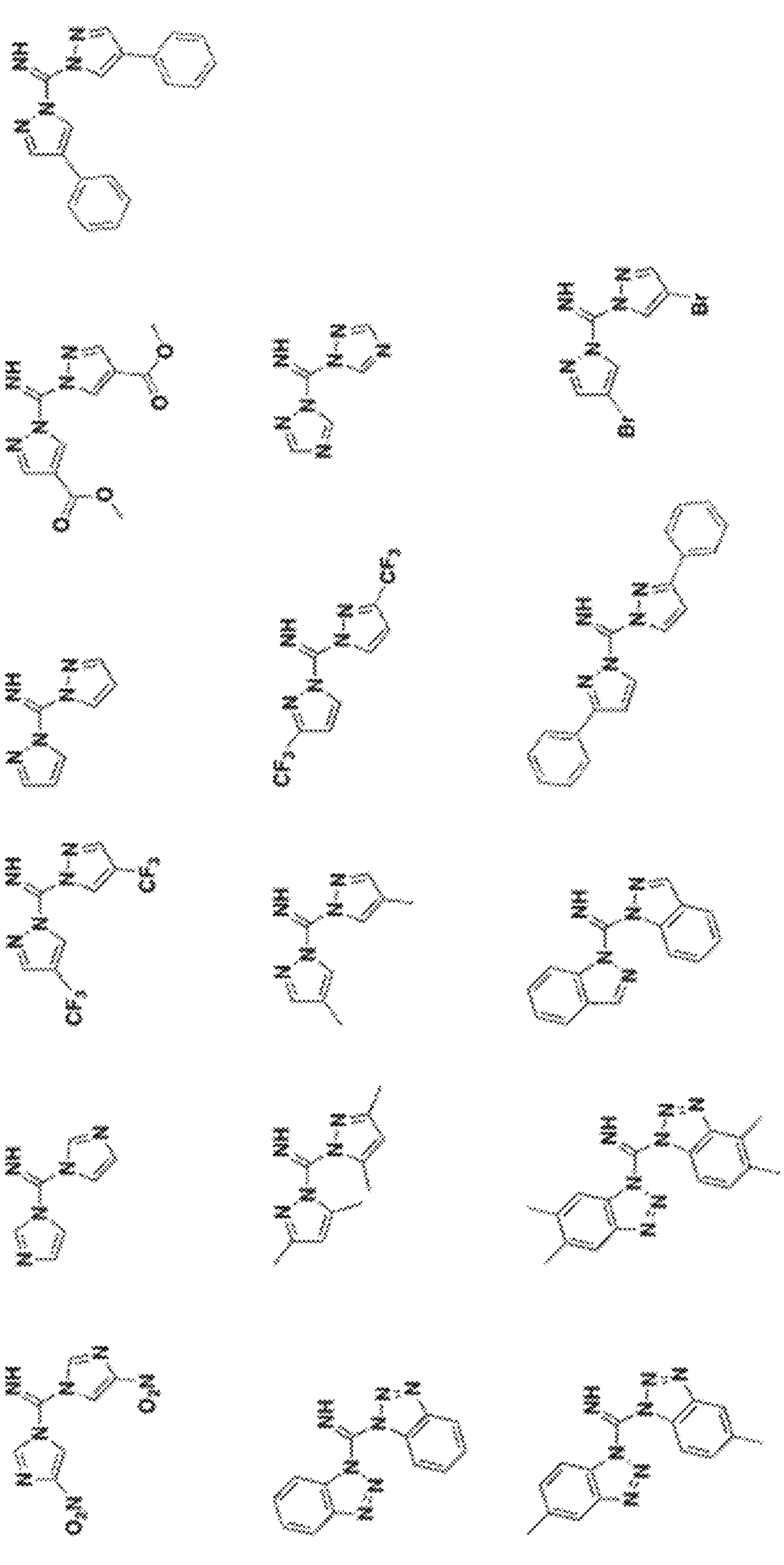
FIG. 15G shows exemplary compounds of Formula (9).

In some embodiments, N-terminal modifier agents used in the described methods and compositions have structures as shown in FIG. 15G (all within Formula (9)). In some embodiments, each 5-6 membered aromatic ring is independently selected and contains 1 or 2 heteroatoms selected from N, O and S as ring members. In these embodiments, each 5-membered aromatic group present can be a 5-membered ring comprising one or two heteroatoms selected from N, O and S as ring members, and the 6-membered aromatic group can be a 6-membered ring comprising one to two nitrogen atoms as ring members.

In some embodiments, N-terminal modifier agents used in the described methods and compositions have structures within Formula (7) as disclosed in US 2020/0348307 A1, incorporated herein by reference. N-terminal modifier agents within Formula (7) comprise standard isocyanates and thioisocyanates, which are efficient at Edman degradation reactions.

In some embodiments, N-terminal modifier agents used in the described methods and compositions have structures as shown below:

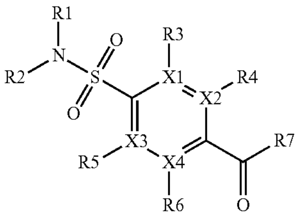

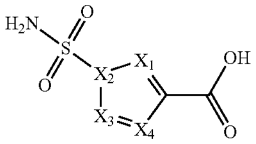

wherein R1-$R^6$ represents one or two optional substituents selected from the group consisting of H, F, Cl, $CH_3$, $CF_2H$, $CF_3$, OH, $OCH_3$, $OCF_3$, $NH_2$, $N(CH_3)_2$, $NO_2$, CCH, $SCH_3$, $SO_2CH_3$, $CH_2OH$, CN, $CONH_2$, $CO_2H$, and $CONHCH_3$; X1-X4 represents one to three optional substituents selected from the group consisting of C, O, S, Se, N; R7 is H or a leaving group (LG), which is OH, $OR^Q$, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion. In some embodiments, R6=CCH (ethynyl) and R7=H.

In some embodiments, the N-terminal modifier agent of Formula (3) or Formula (8) can be installed onto the N-terminus of a peptide using a catalyst (see, e.g., FIG. 15A for the example of the installation reaction). In some embodiments, the catalyst for installation of the N-terminal modifier agent of Formula (3) or Formula (8) comprises a compound of Formula (10), Formula (11), or Formula (12):

(10)

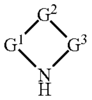

(11)

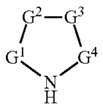

(12)

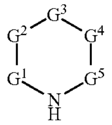

wherein:

$G^1$-$G^5$ are each independently selected from $CJ_2$, NH, S, and O provided not more than 1 of $G^1$-$G^5$ are NH, S, or O;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —$N(R^8)_2$, —$S(O)_nR^8$, —$NR^8SO_2R^8$, —$SO_2N(R^8)_2$, $SO_3R^8$, —$B(OR^8)_2$, $C(=O)R^8$, CN, $CON(R^8)_2$, —$COOR^8$, —C(—O)Ar, and tetrazole, where Ar represents a phenyl or 5-6 membered heteroaryl ring that is optionally substituted with one or two groups selected from halo, CN, $R^9$ and $OR^9$;

each $R^8$ and each $R^9$ is independently selected from H, $C_1$-$C_2$ alkyl, and $C_1$-$C_2$ haloalkyl; n at each occurrence is independently 1 or 2.

Potential advantages of the N-terminal modifier agents of Formula (3) and/or Formula (8) include their increased specificity towards primary amine groups present in peptide backbones (in the N-terminus and side chains of Lys residues) in comparison with other N-terminal modifier agents, which may also react with hydroxyl groups (such as side chains of Ser or Thr residues).

Figure 2B:
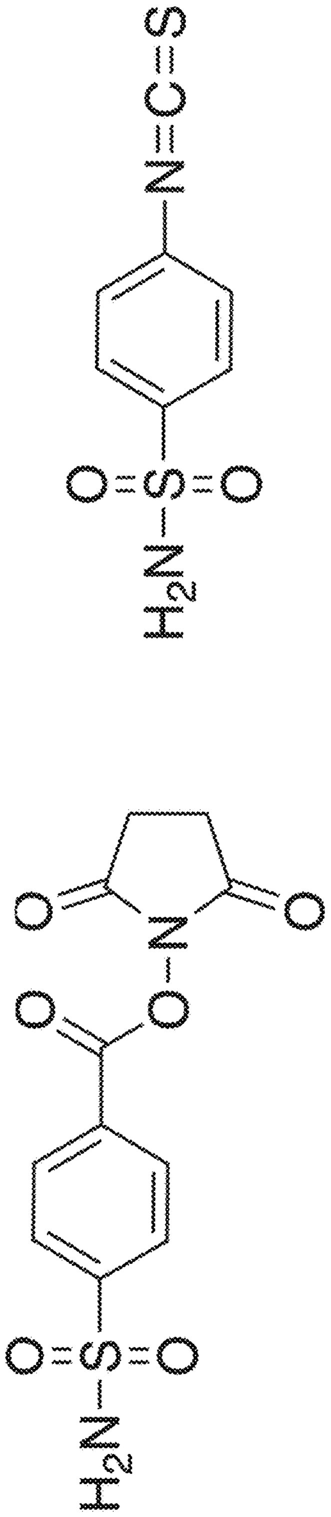
FIG. 2B. Potential zinc binding N-terminal modifications: sulfamoylbenzene-NHS ester and -isothiocyanate.
Figure 2C:
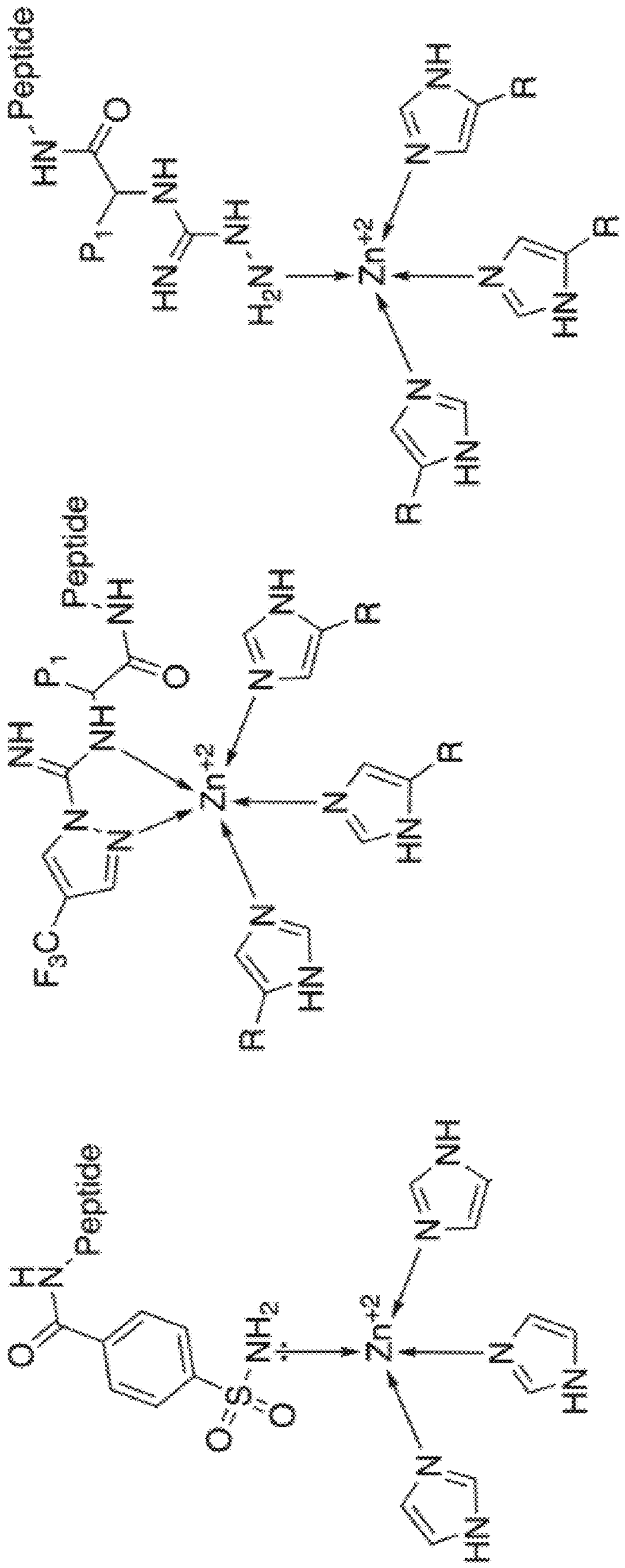
FIG. 2C. Proposed sulfamoylbenzene, "PMI" and aminoguanidine zinc coordination by the modified N-termini of a peptide.

In some embodiments, examples of metal-binding NTMs include structures shown in FIGS. 2-4, as well as metal-binding isosteres of picolinic acid as provided in Dick B L, Cohen S M. Metal-Binding Isosteres as New Scaffolds for Metalloenzyme Inhibitors. Inorg Chem. 2018 Aug. 6; 57(15):9538-9543 (see FIG. 5), and derivatives of Famotidine, potent inhibitor of carbonic anhydrase II (Angeli A, Ferraroni M, Supuran C T. Famotidine, an Antiulcer Agent, Strongly Inhibits *Helicobacter pylori* and Human Carbonic Anhydrases. ACS Med Chem Lett. 2018 Sep. 4; 9(10):1035-1038).

In some embodiments, an N-terminal modifier agent used to modify the NTAA of a peptide, or an NTM group, comprises a chemical moiety that is a potent inhibitor of a metalloenzyme used as a binder that specifically binds to the modified NTAA of the peptide. In other embodiments, the N-terminal modifier agent or the NTM group comprises a chemical moiety that is a derivative of the metalloenzyme inhibitor. A metalloprotein binder provided herein would preferably have several of the following characteristics. In a preferred embodiment, it recognizes and binds to the modified NTAA residue (NTM-P1 residue) with a high affinity and specificity. In some embodiments, instead of binding to a single specific amino acid residue, a metalloprotein binder specifically binds independently to structurally similar modified NTAA residues, for example, to small hydrophobic amino acid residues modified with a N-terminal modifier agent or to negatively charged residues modified with a N-terminal modifier agent. At the same time, interaction with P2 amino acid of the peptide is limited, so that the binding affinity of the binder to the NTM-P1 residue does not depend significantly on P2 residue. In some embodiments, binding affinity and/or specificity between a metalloprotein binder and a NTM-P1 residue of the peptide is predominantly or substantially determined by interaction between the metalloprotein binder and the NTM-P1 residue of the peptide. In some embodiments, binding affinity and/or specificity between a metalloprotein binder and a NTM-P1 residue of the peptide differs no more than 3 fold, no more than 2 fold or no more than 1.5 fold depending on identity of the P2 residue of the peptide. In some preferred embodiments, a metalloprotein binder possesses additional characteristics, such as monomeric structure, ease of production, limited number of cysteines (preferably less than two Cys residues), high stability (thermal or in the presence of a detergent), limited post-translational modifications (e.g., glycosylation, phosphorylation), stable tertiary structure upon genetic manipulation, and compatibility with phage display or other protein engineering platforms that enable selection of preferred variants. Many classes of metalloenzymes can be evolved to be utilized in the methods disclosed herein. Importantly, high affinity and specificity towards NTM-P1 residue of the peptide are to be achieved by selecting a combination of a metalloenzyme and specific NTM.

Several high-throughput screening methods known in the art can be used to select metalloenzyme variants with desired specificity by utilizing a panel of metalloenzyme mutants and, optionally, a panel of structurally-related NTMs. To start the maturation process, an appropriate metalloenzyme scaffold may be chosen based on size of the binding pocket that should accommodate NTM-P1. Another important consideration is knowledge about potential evolvability of P1/P2 specificity based on natural substrates or known inhibitors of metalloenzymes. Based on the knowledge about natural substrates or known inhibitors, several classes of metalloenzymes can be considered as desired candidates for specific binders. First, metalloproteases, such as dipeptidyl peptidases or aminopeptidases, are good candidates, since they are known to have peptides as substrates, possess substrates specificity, but at the same time structurally-related variants of these enzymes have diverse specificity for substrates. Aminopeptidases catalyze the cleavage of specific amino acids from the N-terminus of peptides, so their binding pocket can be evolved to recognize specific NTM-P1 groups. Dipeptidyl peptidases catalyze the cleavage of specific dipeptides from the N-terminus of peptides, so they can also be evolved to recognize specific NTM-P1 groups if the size of NTM is similar to the size of an amino acid. Examples of suitable aminopeptidase scaffolds include M1 aminopeptidases, such as aminopeptidase N, leucyl-, arginine-, methionyl-, aspartyl-, alanyl-, glutamyl-, prolyl-, and cystinyl-aminopeptidases. Some of the suitable dipeptidyl peptidase scaffolds include Cathepsin C (dipeptidyl peptidase-1), Dipeptidyl-peptidase II, dipeptidyl peptidase-3, dipeptidyl peptidase-4, dipeptidyl peptidase-6, dipeptidyl peptidase-7, dipeptidyl peptidase-8, dipeptidyl peptidase-9, dipeptidyl peptidase-10. Other suitable metalloprotease scaffolds include metzincins (astacins, serralysins, snapalysins, leishmanolysins, pappalysins, archaemetzincins, fragilysins, cholerilysins, toxilysins, igalysins, matrix metalloproteases (MMPs), collagenases, stromelysins, gelatinases, ADAM proteases), gluzincins, thermolysins, minigluzincins, cowrins, M48/M56 integral membrane MMPs, leukotriene A-4 hydrolases, anthrax lethal factor, clostridial neurotoxins, neprilysins, inverzincins, aspzincins, funnelins, carboxypeptidases. Other suitable metalloenzyme scaffolds include peptide deformylases (zinc, nickel, cobalt, and iron), histone deacetylases, carbonic anhydrases, phospholipases, oxidoreductases (iron), cytochromes, prostaglandin-endoperoxide synthases (COX½), alcohol dehydrogenases, sorbitol dehydrogenases, transcription factors with zinc finger domains or ring finger domains, metal responsive transcription factor-1, metal transporters (such as ZnuA-Syn, PsaA, TroA, ZinT, MntC), metallo-beta lactamase.

In some embodiments, suitable scaffolds include synthetic or artificial metalloenzymes, where known metal-binding motifs are introduced into "naive" scaffolds. There are numerous known metal binding motifs that can be used for incorporation into "naive" scaffolds, such as HEXXH or HEXGHXXGXXH for zinc ion. Other non-limiting examples include $Zn^{2+}$ binding motifs provided in Andreini C, et al., Zinc through the three domains of life. J Proteome Res. 2006 November; 5(11):3173-8. Several public databases are known in the art that provide information on metal-binding sites detected in the three-dimensional (3D) structures of biological macromolecules. Examples include the MetalPDB database presented in Putignano V, et al., MetalPDB in 2018: a database of metal sites in biological macromolecular structures. Nucleic Acids Res. 2018 Jan. 4; 46(D1):D459-D464, or the MetalMine database (Kensuke Nakamura et al., MetalMine: a database of functional metal-binding sites in proteins; Plant Biotechnology 26, 517-521 (2009)). There are a number of approaches known in the art for making artificial metalloenzymes, for example, Schwizer F, Okamoto Y, Heinisch T, Gu Y, Pellizzoni M M, Lebrun V, Reuter R, Köhler V, Lewis J C, Ward T R. Artificial Metalloenzymes: Reaction Scope and Optimization Strategies. Chem Rev. 2018 Jan. 10; 118(1):142-231; Reetz M T. Directed Evolution of Artificial Metalloenzymes: A Universal Means to Tune the Selectivity of Transition Metal Catalysts? Acc Chem Res. 2019 Feb. 19; 52(2):336-344; Liang A D, Serrano-Plana J, Peterson R L, Ward T R. Artificial Metalloenzymes Based on the Biotin-Streptavidin Technology: Enzymatic Cascades and Directed Evolution. Acc Chem Res. 2019 Mar. 19; 52(3):585-595, incorporated by reference herein. For example, lipocalins or streptavidin can be used as scaffolds for artificial metalloenzymes. In some embodiments, DNA/RNA scaffolds can be used for metalloenzymes, such as zinc binding ribozymes or zinc/peptide binding aptamers.

Various metal ions can be utilized in the methods disclosed herein. In some embodiments, one of divalent metal ions, such as Mn(II), Fe(II), Co(II), Ni(II) or Zn(II) is used together with engineered metalloenzymes and NTMs that bind such divalent metal ion with a high affinity. Numerous examples of natural metalloenzymes with intrinsic specificity to these divalent metal ions are described in the art. For some metalloenzyme scaffolds, for example for metalloaminopeptidases, several different divalent metal ions can be used interchangeably, because such metalloenzymes were shown to be active when reconstituted with any of these different divalent metal ions (Rouffet M, Cohen S M. Emerging trends in metalloenzyme inhibition. Dalton Trans. 2011 Apr. 14; 40(14):3445-54).

During binding reaction between a metalloprotein binder and an NTM-P1 group of a peptide to be analyzed, the corresponding metal ion can be added to the reaction or can be comprised in the metalloprotein binder (as a part of the metalloenzyme holoprotein).

Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications, including patent documents, scientific articles and databases, referred to in this application are incorporated by reference in their entireties for all purposes to the same extent as if each individual publication were individually incorporated by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

Definitions

Unless defined otherwise, all technical and scientific terms used herein have the same meaning as is commonly understood by one of ordinary skill in the art to which the present disclosure belongs. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a," "an" and "the" include plural referents unless the context clearly dictates otherwise. Thus, for example, reference to "a peptide" includes one or more peptides, or mixtures of peptides. Also, and unless specifically stated or obvious from context, as used herein, the term "or" is understood to be inclusive and covers both "or" and "and".

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X.

As used herein, the term "sample" refers to anything which may contain an analyte for which an analyte assay is desired. As used herein, a "sample" can be a solution, a suspension, liquid, powder, a paste, aqueous, non-aqueous or any combination thereof. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

In some embodiments, the sample is a biological sample. A biological sample of the present disclosure encompasses a sample in the form of a solution, a suspension, a liquid, a powder, a paste, an aqueous sample, or a non-aqueous sample. As used herein, a "biological sample" includes any sample obtained from a living or viral (or prion) source or other source of macromolecules and biomolecules, and includes any cell type or tissue of a subject from which nucleic acid, protein and/or other macromolecule can be obtained. The term "subject" includes a mammal. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom. In some embodiments, the sample can be derived from a tissue or a body fluid, for example, a connective, epithelium, muscle or nerve tissue; a tissue selected from the group consisting of brain, lung, liver, spleen, bone marrow, thymus, heart, lymph, blood, bone, cartilage, pancreas, kidney, gall bladder, stomach, intestine, testis, ovary, uterus, rectum, nervous system, gland, and internal blood vessels; or a body fluid selected from the group consisting of blood, urine, saliva, bone marrow, sperm, an ascitic fluid, and subfractions thereof, e.g., serum or plasma.

The terms “level” or “levels” are used to refer to the presence and/or amount of a target, e.g., a substance or an organism that is part of the etiology of a disease or disorder, and can be determined qualitatively or quantitatively. A “qualitative” change in the target level refers to the appearance or disappearance of a target that is not detectable or is present in samples obtained from normal controls. A “quantitative” change in the levels of one or more targets refers to a measurable increase or decrease in the target levels when compared to a healthy control.

As used herein, the term “macromolecule” encompasses large molecules composed of smaller subunits. Examples of macromolecules include, but are not limited to peptides, nucleic acids, carbohydrates, lipids, macrocycles, or a combination or complex thereof. A macromolecule also includes a chimeric macromolecule composed of a combination of two or more types of macromolecules, covalently linked together (e.g., a peptide linked to a nucleic acid). A macromolecule assembly may be composed of the same type of macromolecule (e.g., protein-protein) or of two or more different types of macromolecules (e.g., protein-DNA).

The term “peptide” is used interchangeably with the term “polypeptide”, and encompasses peptides and proteins, and refers to a molecule comprising a chain of three or more amino acids joined by peptide bonds. In some embodiments, a peptide comprises 3 to 50 amino acid residues. In some embodiments, a peptide does not comprise a secondary, tertiary, or higher structure. In some embodiments, the peptide is a protein. In some embodiments, a protein comprises 30 or more amino acids. In some embodiments, in addition to a primary structure, a protein comprises a secondary, tertiary, or higher structure. The amino acids of the peptides are most typically L-amino acids, but may also be D-amino acids, modified amino acids, amino acid analogs, amino acid mimetics, or any combination thereof. Peptides may be naturally occurring, synthetically produced, or recombinantly expressed. Peptides may be synthetically produced, isolated, recombinantly expressed, or be produced by a combination of methodologies as described above. Peptides may also comprise additional groups modifying the amino acid chain, for example, functional groups added via post-translational modification. The polymer may be linear or branched, it may comprise modified amino acids, and it may be interrupted by non-amino acids. The term also encompasses an amino acid polymer that has been modified naturally or by intervention; for example, disulfide bond formation, glycosylation, lipidation, acetylation, phosphorylation, or any other manipulation or modification, such as conjugation with a labeling component.

As used herein, the term “amino acid” refers to an organic compound, which serves as a monomeric subunit of a peptide. An amino acid includes the 20 standard, naturally occurring or canonical amino acids as well as non-standard amino acids. The standard, naturally-occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). An amino acid may be an L-amino acid or a D-amino acid. Non-standard amino acids may be modified amino acids, amino acid analogs, amino acid mimetics, non-standard proteinogenic amino acids, or non-proteinogenic amino acids that occur naturally or are chemically synthesized.

As used herein, the term “metalloenzyme” refers to a macromolecule containing a binding pocket that incorporates a metal ion, which plays a crucial role in recognition of a metalloenzyme’s substrate and is directly bound to the macromolecule or to a macromolecule-bound prosthetic group. Non-limiting examples of macromolecular scaffolds for metalloenzymes include peptides or polynucleotides. There are natural metalloenzymes (such as various metalloproteins, including metalloproteases), or artificial metalloenzymes. Artificial metalloenzymes result from anchoring a metal-containing moiety within a macromolecular scaffold (preferably, peptide or polynucleotide). Metal ions in metalloenzymes are usually coordinated by nitrogen, oxygen or sulfur centers with very high association constants ($K_a>10^{10}$ $M^{-1}$, and often $K_a>10^{15}$ $M^{-1}$).

As used herein, the term “N-terminal modifier agent” refers to a small molecule that interacts with a peptide to be analyzed and modifies (or functionalizes) the N-terminal amino acid residue (P1 residue) of the peptide. The interaction between N-terminal modifier agent and peptide creates an N-terminal modification (NTM) of the P1 residue, forming NTM-P1 group at the N-terminus of the peptide. The disclosed herein N-terminal modifier agents and/or NTMs incorporate at least one metal cation binding group in order to coordinate a metal ion.

As used herein, the term “post-translational modification” refers to modifications that occur on a peptide after its translation, e.g., translation by ribosomes, is complete. A post-translational modification may be a covalent chemical modification or enzymatic modification. A post-translational modification includes modifications of the amino terminus and/or the carboxyl terminus of a peptide. Modifications of the terminal amino group include, but are not limited to, des-amino, N-lower alkyl, N-di-lower alkyl, and N-acyl modifications. The term post-translational modification can also include peptide modifications that include one or more detectable labels.

As used herein, the term “engineered metalloprotein binder”, “engineered binder”, “binding agent”, or “binder” refers to an engineered polypeptide or an engineered protein that binds to, associates, unites with, recognizes, or combines with a binding target, e.g., a peptide or a component or feature of a peptide, such as an modified N-terminal amino acid (NTAA) residue of the peptide. In preferred embodiments, “engineered metalloprotein binder” refers to an engineered (non-natural) polypeptide-based binder derived from a metalloenzyme by mutating one or more amino acid residues in a substrate-binding pocket of the metalloenzyme to accommodate a modified N-terminal amino acid of a peptide substrate (e.g., Z-P1). A binder may form a covalent association or non-covalent association with the peptide or component or feature of a peptide. A binder may be a naturally occurring, synthetically produced, or recombinantly expressed molecule. A binder may bind to a single monomer or subunit of a peptide (e.g., a single amino acid of a peptide) or bind to a plurality of linked subunits of a peptide (e.g., a di-peptide, tri-peptide, or higher order peptide of a longer peptide, peptide, or protein molecule). A binder may preferably bind to a chemically modified or labeled amino acid (e.g., an amino acid that has been labeled by a N-terminal modifier agent) over a non-modified or unlabeled amino acid residue. For example, a binder may preferably bind to an N-terminal amino acid (NTAA) residue of a peptide that has been labeled or modified over the NTAA residue that is unlabeled or unmodified. A binder may exhibit selective binding to a component or feature of a peptide (e.g., a binder may selectively bind to one of the 20 possible NTAA residues and bind with very low affinity or not at all to the other 19 NTAA residues). A binder may exhibit less selective binding, where the binder is capable of binding or configured to bind to a plurality of components or features of a peptide (e.g., a binder may bind with similar affinity to two or more different NTAA residues). A binder may comprise a coding tag, which may be joined to the binder by a linker.

As used herein, the term "linker" refers to one or more of a nucleotide, a nucleotide analog, an amino acid, a peptide, a peptide, a polymer, or a non-nucleotide chemical moiety that is used to join two molecules. A linker may be used to join a binder with a coding tag, a recording tag with a peptide, a peptide with a support, a recording tag with a solid support, etc. In certain embodiments, a linker joins two molecules via enzymatic reaction or chemistry reaction (e.g., click chemistry).

The term "ligand" as used herein refers to any molecule or moiety connected to the compounds described herein. "Ligand" may refer to one or more ligands attached to a compound. In some embodiments, the ligand is a pendant group or binding site (e.g., the site to which the binder binds).

The terminal amino acid at one end of a peptide or peptide chain that has a free amino group is referred to herein as the "N-terminal amino acid" (NTAA). The terminal amino acid at the other end of the chain that has a free carboxyl group is referred to herein as the "C-terminal amino acid" (CTAA). The amino acids making up a peptide may be numbered in order, with the peptide being "n" amino acids in length. As used herein, NTAA is considered the $n^{th}$ amino acid (also referred to herein as the "n NTAA"). Using this nomenclature, the next amino acid is the n-1 amino acid, then the n-2 amino acid, and so on down the length of the peptide from the N-terminal end to C-terminal end. In certain embodiments, an NTAA, CTAA, or both may be modified or labeled with a chemical moiety.

As used herein, the term "barcode" refers to a nucleic acid molecule of about 2 to about 30 bases (e.g., 2, 3, 4, 5, 6, 7, 8, 9, 10, 11, 12, 13, 14, 15, 16, 17, 18, 19, 20, 21, 22, 23, 24, 25, 26, 27, 28, 29 or 30 bases) providing a unique identifier tag or origin information for a peptide, a binder, a set of binders from a binding cycle, a sample peptides, a set of samples, peptides within a compartment (e.g., droplet, bead, or separated location), peptides within a set of compartments, a fraction of peptides, a library of peptides, or a library of binders. A barcode can be an artificial sequence or a naturally occurring sequence. In certain embodiments, each barcode within a population of barcodes is different. In other embodiments, a portion of barcodes in a population of barcodes is different, e.g., at least about 10%, 15%, 20%, 25%, 30%, 35%, 40%, 45%, 50%, 55%, 60%, 65%, 70%, 75%, 80%, 85%, 90%, 95%, 97%, or 99% of the barcodes in a population of barcodes is different. A population of barcodes may be randomly generated or non-randomly generated. In certain embodiments, a population of barcodes are error-correcting or error-tolerant barcodes. Barcodes can be used to computationally deconvolute the multiplexed sequencing data and identify sequence reads derived from an individual peptide, sample, library, etc. A barcode can also be used for deconvolution of a collection of peptides that have been distributed into small compartments for enhanced mapping. For example, rather than mapping a peptide back to the proteome, the peptide is mapped back to its originating protein molecule or protein complex.

As used herein, the term "coding tag" refers to a polynucleotide with any suitable length, e.g., a nucleic acid molecule of about 2 bases to about 100 bases, including any integer including 2 and 100 and in between, that comprises identifying information for its associated binder. A "coding tag" may also be made from a "sequenceable polymer" (see, e.g., Niu et al., 2013, Nat. Chem. 5:282-292; Roy et al., 2015, Nat. Commun. 6:7237). A coding tag may comprise a barcode sequence, which is optionally flanked by one spacer on one side or optionally flanked by a spacer on each side. A coding tag may also be comprised of an optional UMI and/or an optional binding cycle-specific barcode. A coding tag may be single stranded or double stranded. A double stranded coding tag may comprise blunt ends, overhanging ends, or both. A coding tag may refer to the coding tag that is directly attached to a binder, to a complementary sequence hybridized to the coding tag directly attached to a binder (e.g., for double stranded coding tags), or to coding tag information present in an extended recording tag. In certain embodiments, a coding tag may further comprise a binding cycle specific spacer or barcode, a unique molecular identifier, a universal priming site, or any combination thereof.

As used herein, the term "spacer" (Sp) refers to a nucleic acid molecule of about 1 base to about 20 bases (e.g., 1, 2, 3, 4, 5, 6, 7, 8, 9, 10, 11, 12, 13, 14, 15, 16, 17, 18, 19, or 20 bases) in length that is present on a terminus of a recording tag or coding tag. In certain embodiments, a spacer sequence flanks a barcode sequence of a coding tag on one end or both ends. Following binding of a binder to a peptide, annealing between complementary spacer sequences on their associated coding tag and recording tag, respectively, allows transfer of binding information through a primer extension reaction or ligation to the recording tag. Sp' refers to spacer sequence complementary to Sp. Preferably, spacer sequences within a library of binders possess the same number of bases. A common (shared or identical) spacer may be used in a library of binders. A spacer sequence may have a "cycle specific" sequence in order to track binders used in a particular binding cycle. The spacer sequence (Sp) can be constant across all binding cycles, be specific for a particular class of peptides, or be binding cycle number specific. In some embodiments, only the sequential binding of correct cognate pairs results in interacting spacer elements and effective primer extension. A spacer sequence may comprise sufficient number of bases to anneal to a complementary spacer sequence in a recording tag to initiate a primer extension (also referred to as polymerase extension) reaction, or provide a "splint" for a ligation reaction, or mediate a "sticky end" ligation reaction.

As used herein, the term "recording tag" refers to a nucleic acid molecule, or a sequenceable polymer molecule (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety) to which identifying information of a coding tag can be transferred. Identifying information can comprise any information characterizing a molecule such as information pertaining to sample, fraction, partition, spatial location, interacting neighboring molecule(s), cycle number, etc. Additionally, the presence of UMI information can also be classified as identifying information. In certain embodiments, after a binder binds to a peptide, information from a coding tag linked to a binder can be transferred to the recording tag associated with the peptide while the binder is bound to the peptide. In other embodiments, after a binder binds to a peptide, information from a recording tag associated with the peptide can be transferred to the coding tag linked to the binder while the binder is bound to the peptide. A recording tag may be directly linked to a peptide, linked to a peptide via a multifunctional linker, or associated with a peptide by virtue of its proximity (or co-localization) on a support. A recording tag may be linked via its 5' end or 3' end or at an internal site, as long as the linkage is compatible with the method used to transfer coding tag information to the recording tag or vice versa. A recording tag may further comprise other functional components, e.g., a universal priming site, unique molecular identifier, a barcode (e.g., a sample barcode, a fraction barcode, spatial barcode, a compartment tag, etc.), a spacer sequence that is complementary to a spacer sequence of a coding tag, or any combination thereof. The spacer sequence of a recording tag is preferably at the 3'-end of the recording tag in embodiments where polymerase extension is used to transfer coding tag information to the recording tag.

As used herein, the term "primer extension", also referred to as "polymerase extension", refers to a reaction catalyzed by a nucleic acid polymerase (e.g., DNA polymerase) whereby a nucleic acid molecule (e.g., oligonucleotide primer, spacer sequence) that anneals to a complementary strand is extended by the polymerase, using the complementary strand as template.

As used herein, the term "unique molecular identifier" or "UMI" refers to a nucleic acid molecule of about 3 to about 40 bases (3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases) in length providing a unique identifier tag for each macromolecule, peptide or binder to which the UMI is linked. A peptide UMI can be used to computationally deconvolute sequencing data from a plurality of extended recording tags to identify extended recording tags that originated from an individual peptide. A peptide UMI can be used to accurately count originating peptide molecules by collapsing NGS reads to unique UMIs. A binder UMI can be used to identify each individual molecular binder that binds to a particular peptide.

As used herein, the term "universal priming site" or "universal primer" or "universal priming sequence" refers to a nucleic acid molecule, which may be used for library amplification and/or for sequencing reactions. A universal priming site may include, but is not limited to, a priming site (primer sequence) for PCR amplification, flow cell adaptor sequences that anneal to complementary oligonucleotides on flow cell surfaces enabling bridge amplification in some next generation sequencing platforms, a sequencing priming site, or a combination thereof. The term "forward" when used in context with a "priming site" or "primer" may also be referred to as "5'" or "sense". The term "reverse" when used in context with a "priming site" or "primer" may also be referred to as "3'" or "antisense".

As used herein, the term "extended recording tag" refers to a recording tag to which information of at least one binder's coding tag (or its complementary sequence) has been transferred following binding of the binder to a peptide. Information of the coding tag may be transferred to the recording tag directly (e.g., ligation) or indirectly (e.g., primer extension). Information of a coding tag may be transferred to the recording tag enzymatically or chemically. An extended recording tag may comprise binder information of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more coding tags. The base sequence of an extended recording tag may reflect the temporal and sequential order of binding of the binders identified by their coding tags, may reflect a partial sequential order of binding of the binders identified by the coding tags, or may not reflect any order of binding of the binders identified by the coding tags. In certain embodiments where the extended recording tag does not represent the peptide sequence being analyzed with 100% identity, errors may be due to off-target binding by a binder, or to a "missed" binding cycle.

As used herein, the term "solid support", "solid surface", or "solid substrate", or "support" refers to any solid material, including porous and non-porous materials, to which a peptide can be associated directly or indirectly, by any means known in the art, including covalent and non-covalent interactions, or any combination thereof. A solid support may be two-dimensional (e.g., planar surface) or three-dimensional (e.g., gel matrix or bead). A solid support can be any support surface including, but not limited to, a bead, a microbead, an array, a glass surface, a silicon surface, a plastic surface, a filter, a membrane, a PTFE membrane, a PTFE membrane, a nitrocellulose membrane, a nitrocellulose-based polymer surface, nylon, a silicon wafer chip, a flow through chip, a flow cell, a biochip including signal transducing electronics, a channel, a microtiter well, an ELISA plate, a spinning interferometry disc, a nitrocellulose membrane, a nitrocellulose-based polymer surface, a polymer matrix, a nanoparticle, or a microsphere. Materials for a solid support include but are not limited to acrylamide, agarose, cellulose, dextran, nitrocellulose, glass, gold, quartz, polystyrene, polyethylene vinyl acetate, polypropylene, polyester, polymethacrylate, polyacrylate, polyethylene, polyethylene oxide, polysilicates, polycarbonates, poly vinyl alcohol (PVA), Teflon, fluorocarbons, nylon, silicon rubber, polyanhydrides, polyglycolic acid, polyvinylchloride, polylactic acid, polyorthoesters, functionalized silane, polypropylfumerate, collagen, glycosaminoglycans, polyamino acids, dextran, or any combination thereof. Solid supports further include thin film, membrane, fibers, shaped polymers such as tubes, particles, beads, microspheres, microparticles, or any combination thereof. For example, when solid surface is a bead, the bead can include, but is not limited to, a ceramic bead, a polystyrene bead, a polymer bead, a polyacrylate bead, a methylstyrene bead, an agarose bead, a cellulose bead, a dextran bead, an acrylamide bead, a solid core bead, a porous bead, a paramagnetic bead, a glass bead, a controlled pore bead, a silica-based bead, or any combinations thereof. A bead may be spherical or an irregularly shaped. A bead or support may be porous. In certain embodiments, beads range in size from about 0.2 micron to about 200 microns, or from about 0.5 micron to about 5 micron. In some embodiments, beads can be about 1, 1.5, 2, 2.5, 5, 7, 10, 15, or 20 μm in diameter. In certain embodiments, "a bead" solid support may refer to an individual bead or a plurality of beads. In some embodiments, the solid surface is a nanoparticle. In certain embodiments, the nanoparticles range in size from about 1 nm to about 500 nm in diameter, for example, between about 1 nm and about 50 nm, between about 10 nm and about 50 nm, between about 10 nm and about 200 nm, between about 50 nm and about 100 nm, between about 50 nm and about 200 nm, between about 100 nm and about 200 nm, or between about 200 nm and about 500 nm in diameter.

As used herein, the term "nucleic acid molecule" or "polynucleotide" refers to a single- or double-stranded polynucleotide containing deoxyribonucleotides or ribonucleotides that are linked by 3'-5' phosphodiester bonds, as well as polynucleotide analogs. A nucleic acid molecule includes, but is not limited to, DNA, RNA, and cDNA. A polynucleotide analog may possess a backbone other than a standard phosphodiester linkage found in natural polynucleotides and, optionally, a modified sugar moiety or moieties other than ribose or deoxyribose. Polynucleotide analogs contain bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide. Examples of polynucleotide analogs include, but are not limited to xeno nucleic acid (XNA), bridged nucleic acid (BNA), glycol nucleic acid (GNA), peptide nucleic acids (PNAs), γPNAs, morpholino polynucleotides, locked nucleic acids (LNAs), threose nucleic acid (TNA), 2'—O-Methyl polynucleotides, and boronophosphate polynucleotides. A polynucleotide analog may possess purine or pyrimidine analogs, including for example, 7-deaza purine analogs, 8-halopurine analogs, 5-halopyrimidine analogs, or universal base analogs that can pair with any base, including hypoxanthine, nitroazoles, isocarbostyril analogues, azole carboxamides, and aromatic triazole analogues, or base analogs with additional functionality, such as a biotin moiety for affinity binding. In some embodiments, the nucleic acid molecule or oligonucleotide is a modified oligonucleotide. In some embodiments, the nucleic acid molecule or oligonucleotide is a DNA with pseudo-complementary bases, a DNA with protected bases, an RNA molecule, a BNA molecule, an XNA molecule, a LNA molecule, a PNA molecule, a γPNA molecule, or a morpholino DNA, or a combination thereof. In some embodiments, the nucleic acid molecule or oligonucleotide is backbone modified, sugar modified, or nucleobase modified. In some embodiments, the nucleic acid molecule or oligonucleotide has nucleobase protecting groups such as Alloc, electrophilic protecting groups such as thiranes, acetyl protecting groups, nitrobenzyl protecting groups, sulfonate protecting groups, or traditional base-labile protecting groups.

As used herein, "nucleic acid sequencing" means the determination of the order of nucleotides in a nucleic acid molecule or a sample of nucleic acid molecules, and "peptide sequencing" refers to the determination of the order of amino acids in a peptide molecule or a sample of peptide molecules.

As used herein, "next generation sequencing" refers to high-throughput sequencing methods that allow the sequencing of millions to billions of molecules in parallel. Examples of next generation sequencing methods include sequencing by synthesis, sequencing by ligation, sequencing by hybridization, polony sequencing, ion semiconductor sequencing, and pyrosequencing. By attaching primers to a solid substrate and a complementary sequence to a nucleic acid molecule, a nucleic acid molecule can be hybridized to the solid substrate via the primer and then multiple copies can be generated in a discrete area on the solid substrate by using polymerase to amplify (these groupings are sometimes referred to as polymerase colonies or polonies). Consequently, during the sequencing process, a nucleotide at a particular position can be sequenced multiple times (e.g., hundreds or thousands of times)—this depth of coverage is referred to as "deep sequencing." Examples of high throughput nucleic acid sequencing technology include platforms provided by Illumina, BGI, Qiagen, Thermo-Fisher, and Roche, including formats such as parallel bead arrays, sequencing by synthesis, sequencing by ligation, capillary electrophoresis, electronic microchips, "biochips," microarrays, parallel microchips, and single-molecule arrays (See e.g., Service, Science (2006) 311:1544-1546).

As used herein, "analyzing" the peptide means to identify, detect, quantify, characterize, distinguish, or a combination thereof, all or a portion of the components of the peptide. For example, analyzing a peptide includes determining all or a portion of the amino acid sequence (contiguous or non-continuous) of the peptide. Analyzing a peptide also includes partial identification of a component of the peptide. Analyzing the peptide also includes obtaining an information regarding at least one amino acid residue of the peptide. As used herein, "obtaining an information regarding at least one amino acid residue" refers to identifying, detecting, quantifying, characterizing, distinguishing, or a combination thereof, at least one amino acid residue of the peptide. Obtaining an information regarding at least one amino acid residue also includes partial identification of the amino acid residue of the peptide. For example, partial identification of amino acids in the peptide sequence can identify an amino acid in the peptide sequence as belonging to a subset of possible amino acids. Analysis typically begins with analysis of the n NTAA, and then proceeds to the next amino acid of the peptide (e.g., n-1, n-2, n-3, and so forth). This is accomplished by elimination of the n NTAA, thereby converting the n-1 amino acid of the peptide to an N-terminal amino acid (referred to herein as the "n-1 NTAA"). Analyzing the peptide may include combining different types of analysis, for example obtaining epitope information, amino acid sequence information, post-translational modification information, or any combination thereof.

As used herein, the term "detectable label" refers to a substance which can indicate the presence of another substance when associated with it. The detectable label can be a substance that is linked to or incorporated into the substance to be detected. In some embodiments, a detectable label is suitable for allowing for detection and also quantification, for example, a detectable label that emitting a detectable and measurable signal. Detectable labels include any labels that can be utilized and are compatible with the provided peptide analysis assay format and include, but not limited to, a bioluminescent label, a biotin/avidin label, a chemiluminescent label, a chromophore, a coenzyme, a dye, an electro-active group, an electrochemiluminescent label, an enzymatic label (e.g. alkaline phosphatase, luciferase or horseradish peroxidase), a fluorescent label, a latex particle, a magnetic particle, a metal, a metal chelate, a phosphorescent dye, a protein label, a radioactive element or moiety, and a stable radical. When attached to a engineered binder, a detectable label may indicate a binding event between the engineered binder and a polypeptide.

The term "unmodified" (also "wild-type" or "native") as used herein is used in connection with biological materials such as nucleic acid molecules and proteins (e.g., metalloprotein binders), refers to those which are found in nature and not modified by human intervention.

The term "modified" or "engineered" (or "variant", or "mutant") as used in reference to nucleic acid molecules and protein molecules, e.g., an engineered metalloprotein binder, implies that such molecules are created by human intervention and/or they are non-naturally occurring. The variant, mutant or engineered metalloprotein binder is a polypeptide or peptide having an altered amino acid sequence, relative to an unmodified or wild-type protein, such as starting metalloenzyme scaffold, or a portion thereof. An engineered metalloprotein binder is a polypeptide or peptide which differs from a wild-type metalloenzyme scaffold sequence, or a portion thereof, by one or more amino acid substitutions, deletions, additions, or combinations thereof. Sequence of an engineered metalloprotein binder can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid differences (e.g., mutations) compared to the sequence of starting metalloenzyme scaffold. An engineered metalloprotein binder generally exhibits at least 70%, 80%, 85%, 86%, 87%, 88%, 89%, 90%, 91%, 92%, 93%, 94%, 95%, 96%, 97%, 98%, 99% or more sequence identity to a corresponding wild-type starting metalloenzyme scaffold. An engineered metalloprotein binder can exhibit at least 70%, 80%, 85%, 86%, 87%, 88%, 89%, 90%, 91%, 92%, 93%, 94%, 95%, 96%, 97%, 98%, 99% or more sequence homology to a corresponding wild-type starting metalloenzyme scaffold. Non-naturally occurring amino acids as well as naturally occurring amino acids are included within the scope of permissible substitutions or additions. An engineered metalloprotein binder is not limited to any engineered binders made or generated by a particular method of making and includes, for example, an engineered metalloprotein binder made or generated by genetic selection, protein engineering, directed evolution, de novo recombinant DNA techniques, or combinations thereof. The term "variant" in the context of variant or engineered metalloprotein binder is not to be construed as imposing any condition for any particular starting composition or method by which the variant or engineered metalloprotein binder is created. Thus, variant or engineered metalloprotein binder denotes a composition and not necessarily a product produced by any given process. A variety of techniques including genetic selection, protein engineering, recombinant methods, chemical synthesis, or combinations thereof, may be employed.

In some embodiments, variants of a metalloprotein binder displaying only non-substantial or negligible differences in structure can be generated by making conservative amino acid substitutions in the engineered metalloprotein binder. By doing this, engineered metalloprotein binder variants that comprise a sequence having at least 90% (90%, 91%, 92%, 93%, 94%, 95%, 96%, 97%, 98%, and 99%) sequence identity with the engineered metalloprotein binder sequences can be generated, retaining at least one functional activity of the engineered metalloprotein binder, e.g., ability to specifically bind to the N-terminally modified target peptide. Examples of conservative amino acid changes are known in the art. Examples of non-conservative amino acid changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histidine, for (or by) an electronegative residue, e.g., glutamic acid or aspartic acid; or (d) a residue having a bulky side chain, e.g., phenylalanine, for (or by) one not having a side chain, e g., glycine. Methods of making targeted amino acid substitutions, deletions, truncations, and insertions are generally known in the art. For example, amino acid sequence variants can be prepared by mutations in the DNA. Methods for polynucleotide alterations are well known in the art, for example, Kunkel et al. (1987) Methods in Enzymol. 154:367-382; U.S. Pat. No. 4,873,192 and the references cited therein.

The term "sequence identity" is a measure of identity between polypeptides at the amino acid level, and a measure of identity between nucleic acids at nucleotide level. The polypeptide sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned. "Sequence identity" means the percentage of identical subunits at corresponding positions in two sequences when the two sequences are aligned to maximize subunit matching, e.g., taking into account gaps and insertions. For example, the BLAST algorithm (NCBI) calculates percent sequence identity and performs a statistical analysis of the similarity and identity between the two sequences. The software for performing BLAST analysis is publicly available through the National Center for Biotechnology Information (NCBI) website.

The term "sequence homology" as used herein refers to the sequence similarity between proteins at the amino acid level. "Sequence homology" is a measure of similarity between proteins at the amino acid level. The protein sequence homology may be determined by comparing the amino acid sequence in a given position in each sequence when the sequences are aligned. "Sequence homology" means the percentage of homologous subunits (e.g., amino acids) at corresponding positions in two sequences when the two sequences are aligned to maximize subunit matching, e.g., taking into account gaps which factor in insertions and deletions in the aligned sequences. Sequence homology is present when a subunit position in each of the two or more sequences is occupied by the identical amino acid or functionally similar amino acids (e.g., isosteric or isoelectric amino acid identities; amino acid residues that belong to the same functional class, such as e.g. positively charged residues, or small hydrophobic residues). Sequence homology is absent when a subunit position in each of the two or more sequences is occupied by a functionally different amino acid (e.g., lacking structural similarity). Methods for the alignment of sequences for comparison are well known in the art, such methods include the BLAST algorithm, which calculates percent sequence homology and performs a statistical analysis of the homology between the two sequences. The software for performing BLAST analysis is publicly available through the National Center for Biotechnology Information (NCBI) website.

The terms "corresponding to position(s)" or "position(s) . . . with reference to position(s)" of or within a peptide or a polynucleotide, such as recitation that nucleotides or amino acid positions "correspond to" nucleotides or amino acid positions of a disclosed sequence, such sequence set forth in the Sequence Listing, refers to nucleotides or amino acid positions identified in the polynucleotide or in the peptide upon alignment with the disclosed sequence using a standard alignment algorithm, such as the BLAST algorithm (NCBI). One skilled in the art can identify any given amino acid residue in a given peptide at a position corresponding to a particular position of a reference sequence, such as set forth in the Sequence Listing, by performing alignment of the peptide sequence with the reference sequence (for example, by using BLASTP publicly available through the NCBI website), matching the corresponding position of the reference sequence with the position in peptide sequence and thus identifying the amino acid residue within the peptide. Amino acid positions corresponding to the recited residues can be also determined by structural alignment to the experimentally-determined template structure in the PDB (as given by the PDB accession code after making structural truncations corresponding to the SEQ ID NO of interest), such as for each of the SEQ ID NOs: 7-59. The reference structures used in the structural alignment can be experimentally determined or generated by homology modeling using state of the art homology modeling methods such as Rosetta or PyRosetta macromolecular software suites, machine learning models such as AlphaFold2, or the like. Other useful structural alignment methods and/or programs include, but are not limited to, TM-align, PyMOL (superalign, cealign, and align methods), LSQMAN, Fr-TM-align, DALI, DaliLite, CE, CE-MC, and the like.

The term "peptide bond" as used herein refers to a chemical bond formed between two molecules (such as two amino acids) when the carboxyl group of one molecule reacts with the amino group of the other molecule, releasing a water molecule ($H_2O$).

The term "modified amino acid residue" as used herein refers to an amino acid residue within a peptide that comprises a modification that distinguish it from the corresponding original, or unmodified, amino acid residue. In some embodiments, the modification can be a naturally occurring post-translational modification of the amino acid residue. In other embodiments, the modification is a non-naturally occurring modification of the amino acid residue; such modified amino acid residue is not naturally present in peptides of living organisms (represents an unnatural amino acid residue). Such modified amino acid residue can be made by modifying a natural amino acid residue within the peptide by a modifying reagent, or can be chemically synthesized and incorporated into the peptide during peptide synthesis.

The term "joining" or "attaching" one substance to another substance means connecting or linking these substances together utilizing one or more covalent bond(s) and/or non-covalent interactions. Some examples of non-covalent interactions include hydrogen bonding, hydrophobic binding, and Van der Waals forces. Joining can be direct or indirect, such as via a linker or via another moiety. In preferred embodiments, joining two or more substances together would not impair structure or functional activities of the joined substances. The term "associated with" (e.g., one substance is associated with to another substance) means bringing two substances together, so they can coordinately participate in the methods described herein. In preferred embodiments, association of two substances preserves their structures and functional activities. Association can be direct or indirect. When one substance is directly associated with another substance, it is equivalent to one substance being joined or attached to another substance. Indirect association means that two substances are brought together by means other than direct joining or attachment. In some embodiments, indirect association implies that two substances are co-localized with each other, or located in a close proximity with each other.

The term "specific binding" as used herein refers to a binding reaction between an engineered binder and a cognate peptide (e.g., a peptide having a particular NTAA residue to which the binder binds) or a portion thereof, which occurs more readily than a similar reaction between the engineered binder and a random, non-cognate peptide. The term "specificity" is used herein to qualify the relative affinity by which an engineered binder binds to a cognate (e.g., suitable for binding based on the designed affinity) peptide. Specific binding typically means that an engineered binder binds to a cognate peptide at least twice more likely that to a random, non-cognate peptide (a 2:1 ratio of specific to non-specific binding). Specific binding to a particular modified NTAA residue of a peptide means that a binder binds to the modified NTAA residue with higher affinity compared to the same, but unmodified NTAA residue, and compared to other (structurally different) modified NTAA residues (modification of NTAA residue increases binding affinity between the binder and the peptide). In some embodiments, specific binding is not strictly selective, such as a binder specifically bind to two or more different modified NTAA residues compared to other modified NTAA residues. For example, a binder may specifically bind to both D and E modified NTAA residues compared to other modified NTAA residues (dual specificity). In another example, a binder may specifically bind to V, I and L modified NTAA residues compared to other modified NTAA residues (multi-specificity). Non-specific binding refers to background binding, and is the amount of signal that is produced in a binding assay between an engineered binder and an N-terminally modified peptide when the modified NTAA residue cognate for the engineered binder is not present at the N-terminus of the peptide. In some embodiments, specific binding refers to binding between an engineered metalloprotein binder and an N-terminally modified target peptide with a dissociation constant (Kd) of 500 nM or less.

In some embodiments, binding specificity between an engineered metalloprotein binder and an N-terminally modified target peptide is predominantly or substantially determined by interaction between the engineered metalloprotein binder and the modified NTAA residue of the N-terminally modified target peptide, which means that there is only minimal or no interaction between the engineered metalloprotein binder and the penultimate terminal amino acid residue (P2) of the target peptide, as well as other residues of the target peptide. In some embodiments, the engineered metalloprotein binder binds with at least 5-fold higher binding affinity to the modified NTAA residue of the target peptide than to any other region of the target peptide. In some embodiments, the engineered metalloprotein binder has a substrate binding pocket with certain size and/or geometry matching the size and/or geometry of the modified NTAA residue of the N-terminally modified target peptide, to which the engineered metalloprotein binder specifically binds to. In such embodiments, the modified NTAA residue occupies a volume encompassing a substrate binding pocket of the engineered metalloprotein binder that effectively precludes the P2 residue of the target peptide from entering into the substrate binding pocket or interacting with affinity-determining residues of the engineered metalloprotein binder. In some embodiments, the engineered metalloprotein binder specifically binds to N-terminally modified target peptides, wherein the target peptides share the same modified NTAA residue that interacts with the engineered metalloprotein binder, but have different P2 residues. In some embodiments, the engineered metalloprotein binder is capable of specifically binding to each N-terminally modified target peptide from a plurality of N-terminally modified target peptides, wherein the plurality of N-terminally modified target peptides contains at least 3, at least 5, or at least 10 N-terminally modified target peptides that were modified with the same N-terminal modifier agent, have the same modified NTAA residue, and have different P2 residues. Thus, in preferred embodiments, the engineered metalloprotein binder possesses binding affinity towards the modified NTAA residue of the N-terminally modified target peptide, but has little or no affinity towards P2 or other residues of the target peptide.

As used herein, the term “selectivity” refers to the ability of an engineered binder to preferentially bind to one or to several amino acid residues of a peptide, modified with a chemical modification. In preferred embodiments, “selectivity” describes preferential binding of a binder to a single N-terminal amino acid residue, or to a small group of NTAA residues (e.g., structurally related). In some embodiments, a binder may exhibit selective binding to a particular N-terminal amino acid residue. In some embodiments, a binder may exhibit selective binding to a particular class or type of amino acid residues. In some embodiments, a binder may exhibit particular binding kinetics (e.g., higher association rate constant and/or lower dissociation rate constant) to a particular class or type of amino acid residues or modified amino acid residues, compared to other amino acid residues or modified amino acid residues. In some embodiments, selectivity of each binder towards NTAA resides or NTAA resides of peptide analytes is determined in advance, before performing contacting steps of the disclosed methods.

As used herein, the term “heterocycle”, “heterocyclic”, or “heterocyclyl” refers to a saturated or an unsaturated nonaromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1(2H)-yl, and the like.

The term “substituted” means that the specified group or moiety bears one or more substituents in place of a hydrogen atom of the unsubstituted group, including, but not limited to, substituents such as alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocyclyl, aralkyl, aminosulfonyl, sulfonylamino, sulfonyl, oxo, carbonylalkylenealkoxy and the like. The term “unsubstituted” means that the specified group bears no substituents. The term “optionally substituted” means that the specified group is unsubstituted or substituted by one or more substituents and thus includes both substituted and unsubstituted versions of the group. Where the term “substituted” is used to describe a structural system, the substitution is meant to occur at any valency-allowed position on the system.

Use of ordinal terms such as “first”, “second”, “third”, etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

Throughout this disclosure, various embodiments of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

I. Binders for N-Terminally Modified Peptides

In one embodiment, provided herein is a metalloprotein binder that specifically binds to a N-terminally modified target peptide, wherein: said N-terminally modified target peptide is derived from a target peptide and said N-terminally modified target peptide has a formula: Z-P1-P2-peptide, said Z being a metal-binding N-terminal modification, said P1 being the N-terminal amino acid residue of said target peptide, and P2 being a penultimate terminal amino acid residue of said target peptide; and said binder specifically binds to said N-terminally modified target peptide through interaction between said binder and said Z and P1 of said N-terminally modified target peptide, wherein the binding specificity between said binder and said N-terminally modified target peptide is predominantly or substantially determined by said interaction between said binder and said P1 of said N-terminally modified target peptide.

The present binders can specifically bind to any suitable N-terminally modified target peptide. For example, the length of the target peptide and/or the N-terminally modified target peptide can be greater than 4 amino acids, greater than 5 amino acids, greater than 6 amino acids, greater than 7 amino acids, greater than 8 amino acids, greater than 9 amino acids, greater than 10 amino acids, greater than 11 amino acids, greater than 12 amino acids, greater than 13 amino acids, greater than 14 amino acids, greater than 15 amino acids, greater than 20 amino acids, greater than 25 amino acids, or greater than 30 amino acids.

The P1 or the N-terminal amino acid residue of a target peptide can be any suitable amino acid residue. In some embodiments, the P1 can comprise a naturally-occurring amino acid residue. In some embodiments, the P1 can comprise a modification, e.g., a naturally-occurring or a non-natural modification. In some embodiments, the P1 can comprise an amino acid with a post-translational modification. The P2 or the penultimate terminal amino acid residue of a target peptide can be any suitable amino acid residue. In some embodiments, the P2 can comprise a naturally-occurring amino acid residue. In some embodiments, the P2 can comprise a modification, e.g., a naturally-occurring or a non-natural modification. In some embodiments, the P2 can comprise an amino acid with a post-translational modification.

The Z can comprise any suitable metal-binding N-terminal modification. For example, the Z can comprise a synthetic N-terminal modification. In another example, the Z can comprise an amino acid moiety and/or has a size, e.g., length axis or volume, shape, and/or configuration similar to or exceeding a natural amino acid. In some embodiments, the Z can be a bipartite N-terminal modification (NTM) that comprises a natural or unnatural amino acid portion (AA) and a metal-binding group. The amino acid portion (AA) and the N-terminal metal-binding group can be connected or linked by any suitable bond or linkage. For example, the amino acid portion (AA) and the N-terminal metal-binding group can be connected with an amide bond. In some embodiments, the Z does not comprise an amino acid moiety. The Z can be a bipartite N-terminal modification (NTM) that comprises a small (or small molecule) chemical entity having a size, e.g., length axis or volume, shape, and/or configuration similar to or exceeding a natural amino acid, and a N-terminal metal-binding group. The small (or small molecule) chemical entity and the N-terminal metal-binding group can be connected or linked by any suitable bond or linkage, for example, an amide bond. Preferably, the Z can have a size, e.g., length axis of about 5-10 Å and volume of about 100-1000 $Å^3$. In some embodiments, the small (or small molecule) chemical entity has a length axis of about 5, 6, 7, 8, 9 or 10 Å, or any range thereof. In some embodiments, the small (or small molecule) chemical entity has a volume of about 100, 200, 300, 400, 500, 600, 700, 800, 900, 1000 $Å^3$ or any range thereof.

In some embodiments, the interaction between the binder and the Z has minimal or no impact or influence on the binding specificity between the binder and the N-terminally modified target peptide. In some embodiments, the interaction between the binder and the Z at least partially determines the binding strength or binding efficiency between the binder and the N-terminally modified target peptide.

In some embodiments, there is minimal or no interaction between the binder and the P2. In some embodiments, there is minimal interaction between the binder and the P2, and the minimal interaction between the binder and the P2 has minimal or no impact or influence on the binding specificity, strength and/or efficiency between the binder and the N-terminally modified target peptide; and/or P1-P2 occupies a volume or shape encompassing a cavity or pocket of the binder that effectively precludes the P2 from entering into or interacting with an affinity determining region of the binder. In some embodiments, the volume of the cavity or pocket is greater than the volume occupied by a glycine residue. In some embodiments, the volume of the pocket or cavity is less than about 1,000 $Å^3$.

In some embodiments, the present metalloprotein binders can specifically bind to N-terminally modified target peptide that contains a particular or specific N-terminal amino acid residue and have the ability to distinguish N-terminally modified target peptides that contain different N-terminal amino acid residues. In some embodiments, the present binders can also specifically bind to N-terminally modified target peptides that contain a group of N-terminal amino acid residues, and have the ability to distinguish such N-terminally modified target peptides from other N-terminally modified target peptides that contain N-terminal amino acid residue(s) outside the recognized group of the N-terminal amino acid residues. In some embodiments, the present binder specifically binds to multiple N-terminally modified target peptides that comprise the same P1 residue. In some embodiments, the present binder specifically binds to multiple N-terminally modified target peptides that comprise different P1 residues. For example, the present binder can specifically bind to multiple N-terminally modified target peptides that comprise 2, 3, 4, 5, 6, 7, 8, 9 or 10 different P1 residues.

The engineered metalloprotein binder can be derived or evolved from any suitable metalloenzyme. The engineered metalloprotein binder can have any suitable binding region, core or substrate pocket. For example, the engineered metalloprotein binder can comprise a b-barrel substrate pocket. In some embodiments, upon binding to a N-terminally modified target peptide, the Z-P1 group of the N-terminally modified target peptide occupy the metalloprotein binder substrate pocket. The pocket volume of the metalloenzyme from which the metalloprotein binder is derived can span volumes ranging from 200 $Å^3$-000 Å3 encompassing a range of Z-P1 sizes. For example, the pocket volume of the metalloenzyme from which the metalloprotein binder is derived can span volumes ranging from 200 $Å^3$-500 $Å^3$, 500 $Å^3$-1,000 $Å^3$ 1,000 $Å^3$-2100 $Å^3$, 2,000 $Å^3$-3,000 $Å^3$, or any subrange thereof, encompassing a range of Z-P1 sizes. The engineered metalloprotein binder can specifically binds to a N-terminally modified target peptide with any suitable P1 residue.

In some embodiments, the present metalloprotein binders can have a binding signal and/or affinity towards a modified target peptide comprising a specific P1 residue that is at least 2-fold or higher as compared to the binder's binding signal and/or affinity towards an otherwise identical modified target peptide but comprising a different P1 residue. In some embodiments, the present metalloprotein binders can have a binding signal and/or affinity towards a modified target peptide comprising a specific P1 residue that is at least 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1,000-fold, 1,500-fold, 2,000-fold, or higher, as compared to the binder's binding signal and/or affinity towards an otherwise identical modified target peptide but comprising a different P1 residue.

A nucleic acid encoding the above engineered metalloprotein binder is also provided herein. A vector, e.g., an expression vector, comprising the nucleic acid encoding the above engineered metalloprotein binder is also provided herein. A host cell comprising the above nucleic acid or the vector is further provided herein. The host cell can be any suitable type of cell. For example, the host cell can be a mammalian or human host cell.

In yet another embodiment, provided herein is a kit for obtaining an information regarding at least one amino acid residue of a peptide, the kit comprises:

a) a N-terminal modifier agent that is configured to contact a peptide to form a N-terminally modified peptide having a formula: Z-P1-P2-peptide, wherein P1 is a N-terminal amino acid residue of the peptide, P2 is a penultimate terminal amino acid residue of the peptide, and Z is an N-terminal modification capable of coordinating or chelating a metal ion M; and/or b) a metalloenzyme that binds to the metal ion M that is configured to specifically bind to the N-terminally modified peptide through interaction between the metalloenzyme, the metal ion M and the Z-P1-P2-peptide, wherein the binding specificity between the metalloenzyme and the Z1-P1-P2-peptide is predominantly or substantially determined by interaction between the metalloenzyme and a Z1-P1 group of the Z1-P1-P2-peptide.

II. Methods of Treating Target Peptides

In one embodiment, provided herein is a method of treating a target peptide, which method comprises: a) contacting a target peptide with a N-terminal modifier agent to form a N-terminally modified target peptide having a formula: Z-P1-P2-peptide, said Z being a metal-binding N-terminal modification, said P1 being the N-terminal amino acid residue of said target peptide, and P2 being a penultimate terminal amino acid residue of said target peptide; and b) contacting a metalloprotein binder with said N-terminally modified target peptide to allow said binder to specifically bind to said N-terminally modified target peptide through interaction between said binder and said Z and P1 of said N-terminally modified target peptide, wherein the binding specificity between said binder and said N-terminally modified target peptide is predominantly or substantially determined by said interaction between said binder and said P1 of said N-terminally modified target peptide.

In yet another embodiment, provided herein is a method for obtaining an information regarding at least one amino acid residue of a peptide, comprising the steps of: a) contacting a peptide with a first N-terminal modifier agent to form a N-terminally modified peptide having a formula: Z1-P1-P2-peptide, wherein P1 is a N-terminal amino acid residue of the peptide, P2 is a penultimate terminal amino acid residue of the peptide, and Z1 is an N-terminal modification capable of coordinating or chelating a metal ion M1; b) providing a first metalloenzyme that binds to the metal ion M1 and allowing specific binding between the Z1-P1-P2-peptide, the first metalloenzyme and the metal ion M1, wherein the binding specificity between the first metalloenzyme and the Z1-P1-P2-peptide is predominantly or substantially determined by interaction between the first metalloenzyme and a Z1-P1 group of the Z1-P1-P2-peptide; c) obtaining an information regarding the first metalloenzyme; and d) obtaining an information regarding the P1 amino acid residue of the peptide based on the obtained information regarding the first metalloenzyme.

In another embodiment, at step (b) of the method, a first set of metalloenzymes comprising the first metalloenzyme is provided, and each metalloenzyme from the first set of metalloenzymes binds to the metal ion M1.

In yet another embodiment, the method further comprises the following steps:

i) cleaving a peptide bond between P1 and P2 of the Z-P1-P2-peptide to form a second peptide having P2 as a new N-terminal amino acid residue;
ii) contacting the peptide with a second N-terminal modifier agent to form a N-terminally modified peptide having a formula: Z2-P2-peptide, wherein Z2 is an N-terminal modification capable of coordinating or chelating a metal ion M2;
iii) providing a second metalloenzyme that binds to the metal ion M2 and allowing specific binding between the Z2-P2-peptide, the second metalloenzyme and the metal ion M2, wherein the binding specificity between the second metalloenzyme and the Z2-P2-peptide is predominantly or substantially determined by interaction between the second metalloenzyme and a Z2-P2 group of the Z2-P2-peptide;
iv) obtaining an information regarding the second metalloenzyme; and
v) obtaining an information regarding the P2 amino acid residue of the peptide based on the obtained information regarding the second metalloenzyme.

The present methods can be used to treat any suitable target peptide or a target peptide with suitable length. For example, the length of the target peptide and/or the N-terminally modified target peptide can be greater than 4 amino acids, greater than 5 amino acids, greater than 6 amino acids, greater than 10 amino acids, greater than 15 amino acids, greater than 20 amino acids, or greater than 30 amino acids.

In some embodiments, the interaction between the binder and the Z has minimal or no impact or influence on the binding specificity between the binder and the N-terminally modified target peptide. In some embodiments, the interaction between the binder and the Z at least partially determines the binding strength or binding efficiency between the binder and the N-terminally modified target peptide.

In some embodiments, there is minimal or no interaction between the binder and the P2. In some embodiments, there is minimal interaction between the binder and the P2, and the minimal interaction between the binder and the P2 has minimal or no impact or influence on the binding specificity, strength and/or efficiency between the binder and the N-terminally modified target peptide; and/or P1-P2 occupies a volume or shape encompassing a cavity or pocket of the binder that effectively precludes the P2 from entering into or interacting with an affinity determining region of the binder.

The present binders used in the present methods can specifically bind to N-terminally modified target peptides that contain a particular or specific N-terminal amino acid residue, and they have the ability to distinguish N-terminally modified target peptides that contain different N-terminal amino acid residues. In other embodiments, the binders disclosed herein can specifically bind to N-terminally modified target peptides that contain a group of N-terminal amino acid residues, and they have the ability to distinguish such N-terminally modified target peptides from other N-terminally modified target peptides that contain N-terminal amino acid residue(s) outside the recognized group of the N-terminal amino acid residues. In some embodiments, the present binder used in the present methods specifically binds to multiple N-terminally modified target peptides that comprise the same P1 residue. In some embodiments, the present binder used in the present methods specifically binds to multiple N-terminally modified target peptides that comprise different P1 residues. For example, the present binder used in the present methods can specifically bind to multiple N-terminally modified target peptides that comprise 2, 3, 4, 5, 6, 7, 8, 9 or 10 different P1 residues.

In some embodiments, provided herein is a method of analyzing a plurality of peptides, the method comprising:

(a) modifying the plurality of peptides with an N-terminal modifier agent, thereby generating a modified N-terminal amino acid (NTAA) residue on each peptide of the plurality of peptides, wherein each peptide of the plurality of peptides is attached to a solid support, each modified NTAA residue is capable of coordinating or chelating a metal cation, and wherein the N-terminal modifier agent is selected from the group consisting of (6)

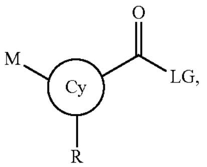

(7)

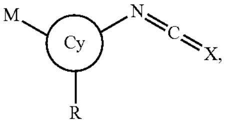

(8)

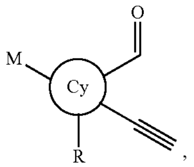

, and (9)

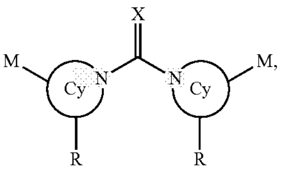

wherein M is a metal cation binding group that comprises sulfonamide, hydroxamic acid, sulfamate, or sulfamide; the group

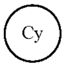

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, $OR^Q$, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH;

(b) contacting one or more peptides of the plurality of peptides with a set of engineered metalloprotein binders, wherein one or more engineered metalloprotein binders of the set specifically bind to a particular modified NTAA residue of the one or more peptides, wherein each engineered metalloprotein binder of the set comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp), and E (Glu); X1, X2, X3 and X4 are each any amino acid sequence independently comprising between 0 and 500 amino acid residues in length, and wherein the amino acid sequence X1-C/H/D/E-X2-C/H/D/E-X3-C/H/D/E-X4 chelates the metal cation; and (c) generating a signal indicative of the binding of the one or more engineered metalloprotein binders to the modified NTAA residue(s) of the one or more peptides, thereby analyzing the plurality of peptides.

In some embodiments, the disclosed method further comprises: (d) removing modified NTAA residues from peptides of the plurality of peptides by an agent configured to remove modified NTAA residues, thereby exposing a new NTAA residue in each of the peptides.

In some embodiments, the disclosed method further comprises: repeating steps (a)-(c) and, optionally, (d) for the new NTAA residues of the peptides.

In some embodiments, each engineered metalloprotein binder of the set is configured to specifically bind to a different modified NTAA residue of the one or more peptides.

In some embodiments, step (c) further comprises determining one or more characteristics of each peptide of the one or more peptides for which the signal was generated by using predetermined binding specificities of the engineered metalloprotein binders, thereby analyzing the plurality of peptides. In some embodiments, the disclosed method further comprises: determining at least partial sequence information of each peptide for which the signal was generated using the one or more determined characteristics. In some embodiments, the set of engineered metalloprotein binders comprises at least 3 structurally different engineered metalloprotein binders each having different binding specificities towards modified NTAA residues of the one or more peptides.

In some embodiments, each of the plurality of peptides is covalently attached to the solid support.

In some embodiments, the engineered metalloprotein binder further comprises a detectable label.

In some embodiments, the agent configured for removing modified NTAA residues comprises an engineered enzyme.

In some embodiments, the amino acid sequence X1-C/H/D/E-X2-C/H/D/E-X3-C/H/D/E-X4 further comprises one or more amino acid sequences selected from the group consisting of: (G/Q/R) (A/C/D/I/L)XX(C/F/I/V) H (F/I/L) H and H (C/L/V)X(C/D/H/L/V) (E/H/L/M/R/W/Y) N (A/N/P/S/T) (E/K/R/S/Y) (A/L/S/Y) SEQ ID NO: 102. In some embodiments, the amino acid sequence X1-C/H/D/E-X2-C/H/D/E-X3-C/H/D/E-X4 further comprises one or more amino acid sequences selected from the group consisting of: (A/C/D/I/S/V/Y)X(C/N)X(A/C/G/R/S/V)XX(C/F/I/L/T/V) X(C/G/K/N/V)X(F/I)(D/E/K/N/V)(D/E/F/N/Q) (A/S)XX (A/E/H/K/Q) (A/P/R/S/T)D(G/I/V)X(A/T/V) (I/L/M/N/R/V) and G(A/C/F/I/S)X(A/D/M/T)XPX(C/F/L)X(C/E/R)X (I/L/R/V).

In some embodiments, each engineered metalloprotein binder binds to a peptide modified with the N-terminal modifier agent with a thermodynamic dissociation constant ($K_d$) of 500 nM or less.

In some embodiments, the engineered metalloprotein binder is associated with a coding tag comprising identifying information regarding the engineered metalloprotein binder. In some of these embodiments, each of the plurality of peptides is associated with a recording tag comprising identifying information regarding the associated peptide or a protein from which the associated peptide is obtained from. In some of these embodiments, following binding of an engineered metalloprotein binder of the set to a modified NTAA residue of a peptide of the plurality, a nucleic acid molecule is generated, using a ligation or a primer extension, which comprises the identifying information regarding the engineered binder and the identifying information regarding the peptide or a protein from which the peptide is obtained from. In some embodiments, step (c) further comprises sequencing the nucleic acid molecule, and determining one or more characteristics of the peptide by using a predetermined binding specificity of the engineered metalloprotein binder.

The present methods can further comprise a step c) cleaving the peptide bond between the P1 and P2 to form a peptide wherein the P2 becomes N-terminal amino acid residue of the nascent peptide. The peptide bond between the P1 and P2 can be cleaved using any agent or reaction. For example, the peptide bond between the P1 and P2 can be cleaved using a chemical agent or reaction. In another example, the peptide bond between the P1 and P2 can be cleaved using a modified cleavase. In some embodiments, the peptide bond between the P1 and P2 is cleaved using an above descried modified or engineered cleavase described in U.S. published patent application US 2021/0214701 A1.

In some embodiments, the cleavage is conducted while the binder is bound with the N-terminally modified target peptide. In some embodiments, the cleavage is conducted after the binder is released and/or removed from the N-terminally modified target peptide.

In some embodiments, steps a)-c) can be repeated one or more times to form a peptide having a newly exposed N-terminal amino acid residue at the beginning of each cycle.

In the present methods, any suitable number of binder(s) can be used. In some embodiments, the binding step can comprise contacting a single binder with a collection of N-terminally modified target peptides to allow the binder to bind specifically to a subset of the N-terminally modified target peptides. In some embodiments, the binding step can comprise contacting a plurality of binders with N-terminally modified target peptides to allow the binders to specifically bind to at least one of the N-terminally modified target peptides.

In some embodiments, the binder used in the present methods can comprise a coding tag with identifying information regarding the binder. The coding tag can comprise any suitable type of molecule or composition. For example, the coding tag can comprise or can be a DNA molecule, an RNA molecule, a PNA molecule, a BNA molecule, an XNA, molecule, an LNA molecule, a γPNA molecule, or a combination thereof. In another example, the coding tag can comprise a unique molecular identifier (UMI) and/or a universal priming site. The binder and the coding tag can be joined or linked directly, or indirectly, e.g., via a linker.

The present methods can further comprise step d) transferring the identifying information of the coding tag to a recording tag attached to the N-terminally modified target peptide, thereby generating an extended recording tag on the N-terminally modified target peptide. Transferring the identifying information of the coding tag to the recording tag (or vice versa) can be effected using any agent or reaction. For example, transferring the identifying information of the coding tag to the recording tag (or vice versa) can be effected by primer extension or ligation.

In some embodiments, the steps of: a) contacting a target peptide with a N-terminal modifier agent; b) contacting a binder with the N-terminally modified target peptide; d) transferring the identifying information of the coding tag to a recording tag attached to the N-terminally modified target peptide; and c) cleaving the peptide bond between the P1 and P2 to form a peptide wherein the P2 becomes N-terminal amino acid residue of the nascent peptide, can be repeated in sequential order to generate one or more additional extended recording tags.

In some embodiments, the present methods can further comprise releasing the binder from the N-terminally modified target peptide and/or removing the released binder after step b) and before step c) or d). In some embodiments, the present methods can further comprise releasing the binder from the N-terminally modified target peptide and/or removing the released binder after step d) and before step c).

In some embodiments, the present methods can further comprise analyzing the one or more extended recording tag(s). The one or more extended recording tags can be amplified prior to analysis. The one or more extended recording tags can be analyzed using any suitable agent or reaction. For example, the one or more extended recording tags can be analyzed using a nucleic acid sequencing method. Any suitable nucleic acid sequencing method can be used. In some embodiments, the nucleic acid sequencing method can be sequencing by synthesis, sequencing by ligation, sequencing by hybridization, polony sequencing, ion semiconductor sequencing, or pyrosequencing. In some embodiments, the nucleic acid sequencing method can be single molecule real-time sequencing, nanopore-based sequencing, or direct imaging of DNA using advanced microscopy.

III. Modified or Engineered Cleavases

In another embodiment, provided herein is a modified or an engineered cleavase comprising a mutation, e.g., one or more amino acid modification(s), deletion(s), addition(s) or substitution(s), in an unmodified cleavase, wherein: said modified or engineered cleavase is derived from a dipeptidyl peptidase of *Thermomonas hydrothermalis* or *Caldithrix abyssii* and removes or is configured to remove a single N-terminally modified amino acid from a target peptide. In some embodiments, the present modified or engineered cleavase is configured to cleave the peptide bond between an N-terminally modified amino acid residue and a penultimate terminal amino acid residue of the target peptide.

The present modified or engineered cleavase can comprise any suitable active site. For example, the present modified or engineered cleavase can comprise an active site that interacts with the amide bond between the N-terminally modified amino acid residue and a penultimate terminal amino acid residue of the target peptide. The present modified or engineered cleavase can remove or can be configured to remove any suitable single N-terminally modified amino acid from a target peptide containing any suitable N-terminal modification.

The present modified or engineered cleavase can comprise any suitable amino acid sequence variation(s) as compared with the amino acid sequence of the unmodified cleavase. For example, the present modified or engineered cleavase can comprise an amino acid sequence that exhibits at least 50% identity, at least 60% identity, at least 70% identity, at least 80% identity, or at least 90%, or at least 95%, or more identity with the unmodified cleavase.

The present or engineered modified cleavase can comprise any suitable type of mutation(s). For example, wherein the mutation can comprise an amino acid substitution, deletion, addition, or a combination thereof.

In some embodiments, the present modified or engineered cleavase is derived from a dipeptidyl peptidase of *Thermomonas hydrothermalis* comprising an amino acid sequence set forth in SEQ ID NO:3 (WT sequence with the signal peptide) or SEQ ID NO:4 (WT sequence without the signal peptide).

The present modified or engineered cleavase can comprise any suitable amino acid sequence variations as compared with the amino acid sequence of the unmodified cleavase. For example, the present modified or engineered cleavase can comprise an amino acid sequence that exhibits at least 20% identity, at least 30% identity, at least 40% identity, at least 50% identity, at least 60% identity, at least 70% identity, at least 80% identity, at least 90% or more identity or at least 95% or more identity to the amino acid sequence set forth in SEQ ID NO:3 or SEQ ID NO:4, or a specific binding fragment thereof.

In some embodiments, the present modified or engineered cleavase has a mutation, with reference to numbering of SEQ ID NO: 3 or SEQ ID NO: 4, selected from the group consisting of N214X, W215X, R219X, N329X, N333X, A671X, D673X, G674X, N682X, M692X, I651X, and a combination thereof, X being one of the 20 naturally occurring amino acids other than the amino acid residue of the unmodified dipeptidyl peptidase at the mutated position. In some embodiments, the present modified or engineered cleavase has one or more amino acid modification(s) of N214M, W215G, R219T, N329R, D673A, and/or G674V.

In some embodiments, the present modified or engineered cleavase is derived from a dipeptidyl peptidase of *Caldithrix abyssii* comprising an amino acid sequence set forth in SEQ ID NO: 5 (WT sequence with the signal peptide) or SEQ ID NO: 6 (WT sequence without the signal peptide).

The present modified or engineered cleavase can comprise any suitable amino acid sequence variations as compared with the amino acid sequence of the unmodified cleavase. For example, the present modified or engineered cleavase can comprise an amino acid sequence that exhibits at least 20% identity, at least 30% identity, at least 40% identity, at least 50% identity, at least 60% identity, at least 70% identity, at least 80% identity, at least 90% or more identity or at least 95% or more identity to the amino acid sequence set forth in SEQ ID NO: 5 or SEQ ID NO: 6, or a specific binding fragment thereof.

In some embodiments, the present modified or engineered cleavase has a mutation, with reference to numbering of SEQ ID NO: 5 or SEQ ID NO: 6, selected from the group consisting of N207M, W208X, R212X, N322X, D663X, and a combination thereof, X being one of the 20 naturally occurring amino acids other than the amino acid residue of the unmodified dipeptidyl peptidase at the mutated position. In some embodiments, the present modified or engineered cleavase has one or more amino acid modification(s) of N207M, W208G, R212V, N322I, D663A, or a combination thereof.

In some embodiments, disclosed herein is a modified cleavase comprising a dipeptidyl aminopeptidase comprising at least two mutations in a substrate binding site, wherein the modified cleavase removes or is configured to remove a single labeled terminal amino acid from a peptide. In some embodiments, the single labeled terminal amino acid is an N-terminal labeled amino acid of the peptide, and the modified cleavase comprises at least two amino acid substitutions in an amine binding site.

In some embodiments, the modified cleavase does not remove an unlabeled terminal dipeptide from the peptide.

In some embodiments, a method of treating a peptide is provided, the method comprising the steps of: (a) contacting the peptide with a reagent for labeling a terminal amino acid of the peptide to produce a labeled peptide; and (b) contacting the labeled peptide with a modified cleavase, the modified cleavase comprising a dipeptidyl aminopeptidase comprising at least two mutations in a substrate binding site, wherein the modified cleavase removes or is configured to remove a single labeled terminal amino acid from a peptide.

In some embodiments, the substrate binding site of the modified cleavase is a Z-P1 binding site, wherein Z-P1 is a modified N-terminal amino acid (NTAA) residue of the target peptide.

IV. Kits of Treating Target Peptides

In yet another embodiment, provided herein is a kit of treating a target peptide, which kit comprises: a) a N-terminal modifier agent that is configured to contact a target peptide to form a N-terminally modified target peptide having a formula: Z-P1-P2-peptide, said Z being a N-terminal modification, said P1 being the N-terminal amino acid residue of said target peptide, and P2 being a penultimate terminal amino acid residue of said target peptide; and/or b) a binder that is configured to specifically bind to said N-terminally modified target peptide through interaction between said binder and said Z and P1 of said N-terminally modified target peptide, wherein the binding specificity between said binder and said N-terminally modified target peptide is predominantly or substantially determined by said interaction between said binder and said P1 of said N-terminally modified target peptide.

In some embodiments, the interaction between the binder and the Z has minimal or no impact or influence on the binding specificity between the binder and the N-terminally modified target peptide. In some embodiments, the interaction between the binder and the Z at least partially determines the binding strength or binding efficiency between the binder and the N-terminally modified target peptide.

In some embodiments, provided herein is also a kit for treating a target peptide, the kit comprising:

(a) an N-terminal modifier agent selected from the group consisting of:

(6)

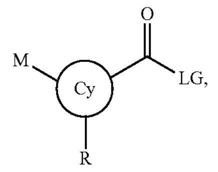

(7)

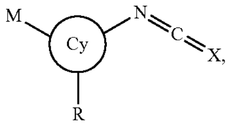

(8)

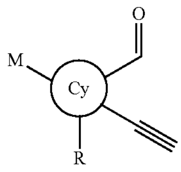

, and (9)

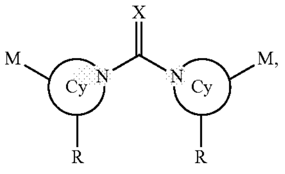

wherein M is a metal cation binding group that comprises sulfonamide, hydroxamic acid, sulfamate, or sulfamide; the group

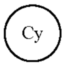

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, $OR^Q$, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH; and (b) an engineered metalloprotein binder that specifically binds to a modified N-terminal amino acid (NTAA) residue in a target peptide, wherein the modified NTAA residue is generated by modifying the target peptide with the N-terminal modifier agent, wherein the engineered metalloprotein binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates the metal cation; and (c) a solid support which is configured for attachment of the target peptide.

In some embodiments, the disclosed kit further comprises an agent configured to remove NTAA residues of peptides modified with the N-terminal modifier agent.

In some embodiments, the disclosed kit comprises at least 3 structurally different engineered metalloprotein binders each having different binding specificities towards NTAA residues of peptides modified with the N-terminal modifier agent.

In some embodiments, the engineered metalloprotein binder comprises a detectable label or a coding tag comprising identifying information regarding the engineered metalloprotein binder.

In some embodiments, the amino acid sequence X1-C/H/D/E-X2-C/H/D/E-X3-C/H/D/E-X4 further comprises one or more amino acid sequences selected from the group consisting of: E/F/N/Q), (G/Q/R) (A/C/D/I/L)XX(C/F/I/V) H (F/I/L) H, H (C/L/V)X(C/D/W/L/V) (E/H/L/M/R/W/Y) N (A/N/P/S/T) (E/K/R/S/Y) (A/L/S/Y) (A/S)XX(A/E/H/K/Q) (A/P/R/S/T)D(G/I/V)X(A/T/V) (I/L/M/N/R/V), and G(A/C/F/I/S)X(A/D/M/T)XPX(C/F/L)X(C/E/R)X(I/L/R/V).

In some embodiments, the engineered metalloprotein binder comprises an amino acid sequence having at least 40%, at least 50%, at least 60%, at least 70%, at least 80%, or at least 90% sequence identity to any one of the amino acid sequences selected from the group consisting of SEQ ID NO: 7-SEQ ID NO: 59, SEQ ID NO: 68-SEQ ID NO: 99 and SEQ ID NO: 105-SEQ ID NO: 135.

In preferred embodiments, in the N-terminally modified target peptide, the modified NTAA residue is connected to the target peptide via a covalent bond, such as an amide bond.

The present binders used in the present kits can specifically bind to N-terminally modified target peptide that contains a particular or specific N-terminal amino acid residue and have the ability to distinguish N-terminally modified target peptides that contain different N-terminal amino acid residues. The present binders used in the present kits can also specifically bind to N-terminally modified target peptides that contain a group of N-terminal amino acid residues, and have the ability to distinguish such N-terminally modified target peptides from other N-terminally modified target peptides that contain N-terminal amino acid residue(s) outside the recognized group of N-terminal amino acid residues. In some embodiments, the present binder used in the present kits specifically binds to multiple N-terminally modified target peptides that comprise the same P1 residue. In some embodiments, the present binder used in the present kits specifically binds to multiple N-terminally modified target peptides that comprise different P1 residues. For example, the present binder used in the present kits can specifically bind to multiple N-terminally modified target peptides that comprise 2, 3, 4, 5, 6, 7, 8, 9 or 10 different P1 residues.

In some embodiments, the present kits further comprise: c) an agent that is configured to cleave the peptide bond between the P1 and P2 to form a peptide wherein after cleavage, the P2 becomes N-terminal amino acid residue of the nascent peptide. The peptide bond between the P1 and P2 can be cleaved using any agent or reaction. In some embodiments, the peptide bond between the P1 and P2 is cleaved using a chemical agent or reaction. In another example, the present kits can comprise an enzyme for cleaving the peptide bond between the P1 and P2. In some embodiments, the present kits can comprise a modified or an engineered cleavase described in U.S. published patent application US 2021/0214701 A1.

In another embodiment, the present kits further comprise: c) a modified cleavase comprising a dipeptidyl aminopeptidase comprising at least two mutations in a substrate binding site, wherein the modified cleavase removes or is configured to remove a single labeled terminal amino acid from a peptide.

In some embodiments, the present modified cleavase provided herein is a modified or an engineered cleavase comprising a mutation, e.g., one or more amino acid modification(s), deletion(s), addition(s) or substitution(s), in an unmodified cleavase, wherein: said modified or engineered cleavase is derived from a dipeptidyl peptidase of *Thermomonas hydrothermalis* or *Caldithrix abyssii* and removes or is configured to remove a single N-terminally modified amino acid from a target peptide. The present modified cleavase is configured to cleave the peptide bond between an N-terminally modified amino acid residue and a penultimate terminal amino acid residue of the target peptide.

In some embodiments, the present kits can comprise a plurality of binders that are configured to specifically bind to the N-terminally modified target peptide.

In some embodiments, the binder used in the present kits can comprise a coding tag with identifying information regarding the binder. For example, the coding tag can comprise or can be a DNA molecule, an RNA molecule, a PNA molecule, a BNA molecule, an XNA, molecule, an LNA molecule, a γPNA molecule, or a combination thereof.

In some other embodiments, the engineered binder further comprises a detectable label.

In some embodiments, the present kits can further comprise: d) a reagent for transferring the identifying information of the coding tag to a recording tag attached to the N-terminally modified target peptide, thereby generating an extended recording tag on the N-terminally modified target peptide. For example, the present kits can further comprise a chemical ligation reagent or a biological ligation reagent for transferring the identifying information. In some embodiments, the present kits can further comprise a reagent for primer extension of single-stranded nucleic acid or double-stranded nucleic acid for transferring the identifying information.

In some embodiments, the present kits can further comprise a reagent for releasing the binder from the N-terminally modified target peptide and/or for removing the released binder.

In some embodiments, the present kits can further comprise an amplification reagent for amplifying the one or more extended recording tag(s). In some embodiments, the present kits can further comprise a solid support.

In any of the embodiments herein, a kit disclosed herein may further comprise one or more additional components necessary for carrying out a method described herein, such as sample preparation reagents, buffers, labels, and the like. As such, the kits may include one or more containers such as vials or bottles, with each container containing one or more separate components of the kit, and reagents for carrying out one or more steps of a method described herein. The kits may also include a denaturation reagent, buffers such as binding buffers and/or hybridization buffers, wash mediums, enzyme substrates, reagents for generating a labeled molecule, negative and positive controls, and/or written instructions for using the kit components for carrying out a method, for example, for analyzing a polypeptide as described herein. The instructions may be printed on a substrate, such as paper or plastic, etc. As such, the instructions may be present in the kits as a package insert, in the labeling of the container of the kit or components thereof (e.g., associated with the packaging or sub-packaging) etc. Any one or more of the kit components and instructions may be packaged, stored, and/or shipped separately from other kit components and instructions, or together with any one or more other kit components and instructions.

In some embodiments, disclosed herein is also a composition comprising:

(a) a solid support, wherein the solid support comprises a plurality of peptide molecules attached to the solid support, wherein each of the plurality of peptide molecules comprise a modified N-terminal amino acid (NTAA) residue generated by modifying a peptide molecule with an N-terminal modifier agent, wherein the modified NTAA residue is capable of coordinating or chelating a metal cation, and the N-terminal modifier agent is selected from the group consisting of:

(6)

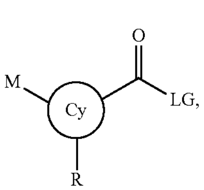

(7)

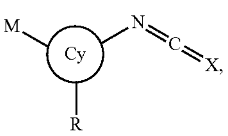

-continued (8)

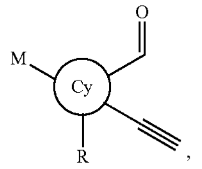

and (9)

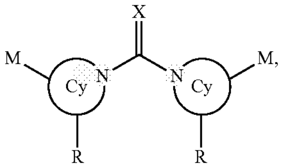

wherein M is a metal cation binding group that comprises sulfonamide, hydroxamic acid, sulfamate, or sulfamide; the group

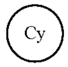

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, $OR^Q$, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH; and (b) an engineered metalloprotein binder that specifically binds to a peptide molecule of the plurality of peptide molecules, wherein the engineered metalloprotein binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates the metal cation.

In some embodiments, the disclosed composition comprises at least 3 structurally different engineered metalloprotein binders, wherein each engineered metalloprotein binder has different binding specificities towards NTAA residues of peptides modified with the N-terminal modifier agent.

In some embodiments of the composition, the engineered metalloprotein binder comprises a detectable label or a coding tag comprising identifying information regarding the engineered metalloprotein binder.

In some embodiments of the composition, each of the plurality of peptide molecules comprising the modified NTAA residue comprises any one of the structures selected from the group consisting of:

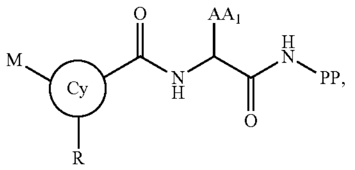

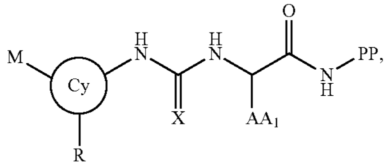

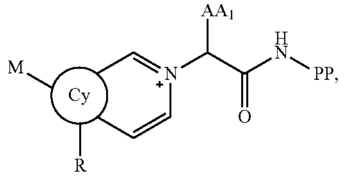

and

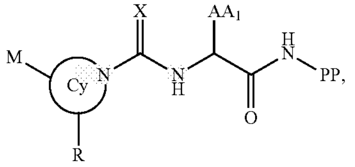

wherein AA is a side chain of the NTAA residue and PP is a peptide structure except for the modified NTAA residue.

In some embodiments of the composition, the amino acid sequence X1-C/H/D/E-X2-C/H/D/E-X3-C/H/D/E-X4 further comprises one or more amino acid sequences selected from the group consisting of:

(A/C/D/I/S/V/Y)X(C/N)X(A/C/G/R/S/V)XX(C/F/I/L/T/V)X(C/G/K/N/V)X(F/I)(D/E/K/N/V)(D/E/F/N/Q), (G/Q/R)(A/C/D/I/L)XX(C/F/I/V) H (F/I/L) H H (C/L/V)X(C/D/H/L/V) (E/H/L/M/R/W/Y) N (A/N/P/S/T) (E/K/R/S/Y) (A/L/S/Y) (A/S)XX(A/B/H/K/Q) (A/P/R/S/T)D(G/I/V)X(A/T/V) (I/L/M/N/R/V), and G(A/C/F/I/S)X(A/D/M/T)XPX(C/F/L) X(C/E/R)X(I/L/R/V).

In some embodiments of the composition, the engineered metalloprotein binder comprises an amino acid sequence having at least 40%, at least 50%, at least 60%, at least 70%, at least 80%, or at least 90% sequence identity to any one of the amino acid sequences selected from the group consisting of SEQ ID NO: 7-SEQ ID NO: 59, SEQ ID NO: 68-SEQ ID NO: 99 and SEQ ID NO: 105-SEQ ID NO: 135.

In some embodiments, the disclosed composition further comprises engineered metalloprotein binders and modified NTAA residues described in various embodiments above.

V. Peptide Assays

In some embodiments, the methods provided include using macromolecules, especially target peptide(s) associated with a recording tag, in a macromolecule analysis assay. In some particular embodiments, the macromolecules with associated and/or attached recording tags are subjected to a peptide analysis assay. In some embodiments, the macromolecule analysis assay is performed to assess the macromolecule, or to identify or determine at least a portion of the sequence of the peptide macromolecule, such as disclosed in earlier published applications US 2019/0145982 A1, US 2020/0348308 A1, US 2020/0348307 A1, US 2021/0208150 A1. In some embodiments, a plurality of macromolecules is analyzed using the described methods.

In some embodiments, the provided methods are for generating a nucleic acid encoded library representation of the binding history of the macromolecule. This nucleic acid encoded library can be amplified, and analyzed using high-throughput next generation digital sequencing methods, enabling millions to billions of molecules to be analyzed per run. The creation of a nucleic acid encoded library of binding information is useful in another way in that it enables enrichment, subtraction, and normalization by DNA-based techniques that make use of hybridization. These DNA-based methods are easily and rapidly scalable and customizable, and more cost-effective than those available for direct manipulation of other types of macromolecule libraries, such as protein libraries. Thus, nucleic acid encoded libraries of binding information can be processed prior to sequencing by one or more techniques to enrich and/or subtract and/or normalize the representation of sequences. This enables information of maximum interest to be extracted much more efficiently, rapidly and cost-effectively from very large libraries whose individual members may initially vary in abundance over many orders of magnitude.

In an exemplary workflow for analyzing peptides or peptides, the method generally includes contacting and binding of a binder comprising a coding tag to terminal amino acid (e.g., NTAA) of a peptide and transferring the binder's coding tag information to the recording tag associated with the peptide, thereby generating a first order extended recording tag. The terminal amino acid bound by the binder may be a chemically labeled or modified terminal amino acid. In some embodiments, the terminal amino acid (e.g., NTAA) is eliminated after the information from the coding tag is transferred. The terminal amino acid eliminated may be a chemically labeled or modified terminal amino acid. Removal of the NTAA by contacting with an enzyme or chemical reagents converts the penultimate amino acid of the peptide to a terminal amino acid. The peptide analysis may include one or more cycles of binding with additional binders to the terminal amino acid, transferring information from the additional binders to the extended nucleic acid thereby generating a higher order extended recording tag containing information from two or more coding tags, and eliminating the terminal amino acid in a cyclic manner. Additional binding, transfer, labeling, and removal, can occur as described above up to n amino acids to generate an $n^{th}$ order extended nucleic acid, which collectively represent the peptide. In some embodiments, the order of the steps in the process for a degradation-based peptide or peptide sequencing assay can be reversed or be performed in various orders. For example, in some embodiments, the terminal amino acid labeling can be conducted before and/or after the peptide is bound to the binder. In some embodiments, the workflow may include one or more wash steps before and/or after binding of the binders, transfer of information, labeling or modifying of the terminal amino acid, and/or removal of the terminal amino acid.

In some embodiments, the disclosed binders are used in the NGPS (next generation peptide sequencing) assay. The NGPS peptide sequencing assay comprises several chemical and enzymatic steps in a cyclical progression. The fact that NGPS sequencing is single molecule confers several key advantages to the process, including robustness to inefficiencies in the various cyclical chemical/enzymatic steps.

An exemplary NGPS method for analyzing a macromolecule (e.g., peptide) analyte comprises the following steps:

(a) providing the peptide analyte and an associated recording tag joined to a solid support;

(b) contacting the peptide analyte with a first binder capable of binding to the peptide analyte, wherein the first binder comprises a first coding tag that comprises identifying information regarding the first binder;

(c) following binding of the first binder to the peptide analyte, transferring the identifying information regarding the first binder from the first coding tag to the recording tag to generate a first order extended recording tag;

(d) contacting the peptide analyte with a second binder capable of binding to the peptide analyte, wherein the second binder comprises a second coding tag that comprises identifying information regarding the second binder;

(e) following binding of the second binder to the peptide analyte, transferring the identifying information regarding the second binder from the second coding tag to the first order extended recording tag to generate a second order extended recording tag; and (f) analyzing the second order extended recording tag, wherein analyzing comprises a sequencing method, and obtaining the identifying information regarding the first binder and the identifying information regarding the second binder to provide information regarding the peptide analyte, thereby analyzing the peptide analyte.

In preferred embodiments of the NGPS assay, binders are configured to recognize a modified NTAA on the immobilized peptide (NTAA-specific binders, FIG. 1). The steps of NGPS also include cleavage of the modified NTAA after binding and encoding steps. Then, the steps of binding, encoding, NTAA functionalization and cleavage are repeated n times to generate a DNA-encoded library on the recording tag associated with the immobilized peptide, representing identifying information at least for some amino acid residues of the immobilized peptide. Sequencing of the recording tag after completion of the n cycles provides the identifying information for these amino acid residues (both identities and order of the amino acid residues can be decoded from the sequence of the recording tag), which results in identification of the immobilized peptide.

Typically, for successful encoding (which comprises transferring the identifying information regarding the binder bound to the peptide from the coding tag of the binder to the recording tag), binders have affinity (Kd) to a component of the peptide of less than 500 nM, and preferably less than 100 nM; sometimes in the range of 10-100 nM, or in the range of 1-10 nM.

The described approach can be used to characterize and/or identify thousands, tens of thousands, or millions peptide analytes in parallel (in a single assay).

FIG. 1 depicts an exemplary degradation-like approach using a cyclic process including coding tag information transfer to a recording tag attached to the peptide, terminal amino acid elimination (e.g., NTAA elimination), and repeating the process in a cyclic manner. The peptide is attached, directly or indirectly, on a solid support. For example, the peptide can be immobilized on a solid support via a capture agent. Either the protein or capture agent may co-localize or be labeled with a recording tag, and proteins with associated recording tags are directly immobilized on a solid support. Information can be transferred from the coding tag on the bound binder to a proximal recording tag using any suitable means including by ligation or primer extension. In one embodiment as depicted, the coding tag includes spacer that is complementary to the spacer in the recording tag and can be used to initiate a primer extension reaction to transfer recording tag information to the coding tag. The final extended recording tag is optionally flanked by universal priming sites to facilitate downstream amplification and/or DNA sequencing. The forward universal priming site (e.g., Illumina's P5-SI sequence) can be part of the original recording tag design and the reverse universal priming site (e.g., Illumina's P7-S2' sequence) can be added (e.g., by extension) to the final extended recording tag. This final step may be done independently of a binder.

In the workflow as depicted in FIG. 1, the first step includes labeling or modifying the N-terminal amino acid (NTAA) with a functionalization reagent to enable removal of the NTAA in a later step; the functionalizing reagent generates an NTAA residue containing a functionalization moiety (e.g., a modification or label). A second step includes contacting the peptide with a binder that is attached to a DNA coding tag. In some embodiments, the labeling or modification of the NTAA may be performed prior to or after contacting the peptide with a binder. Upon binding of the binder to the NTAA of the peptide, information of the coding tag is transferred to the recording tag (e.g., via primer extension or ligation) to generate an extended recording tag. Lastly, the functionalized NTAA is eliminated via chemical or biological (e.g., enzymatic) means to expose a new NTAA.

As illustrated, the cycle is repeated "n" times to generate a final extended recording tag. In some embodiments, the order in the steps in the process for a degradation-based peptide sequencing assay can be reversed or moved around. In some embodiments, the terminal amino acid functionalization can be conducted after the peptide is bound to a support. In some embodiments, the analysis assay may include one or more additional steps, such as a wash step and/or treatment with other reagents. In some embodiments, the provided methods may be performed such that the C-terminal amino acid is modified, labeled, contacted by a binder, and/or eliminated from the peptide.

In some embodiments, the method includes obtaining and preparing macromolecules (e.g., peptides and proteins) from a single cell type or multiple cell types. In some embodiments, the sample comprises a population of cells. In some embodiments, the macromolecules (e.g., proteins, peptides, or peptides) are from a cellular or subcellular component, an extracellular vesicle, an organelle, or an organized subcomponent thereof. The macromolecules (e.g., proteins, peptides, or peptides) may be from organelles, for example, mitochondria, nuclei, or cellular vesicles.

In certain embodiments, a peptide, peptide, or protein can be fragmented before analyzing by the NGPS assay. For example, the fragmented peptide can be obtained by fragmenting a protein from a sample, such as a biological sample. The peptide, peptide, or protein can be fragmented by any means known in the art, including fragmentation by a protease or endopeptidase. In certain embodiments, a peptide, peptide, or protein is fragmented by proteinase K, or optionally, a thermolabile version of proteinase K to enable rapid inactivation. Protein and peptide fragmentation into peptides can be performed before or after attachment of a DNA recording tag. In certain embodiments, following enzymatic or chemical cleavage, the resulting peptide fragments are approximately the same desired length, e.g., from about 10 amino acids to about 70 amino acids, A cleavage reaction may be monitored, preferably in real time, by spiking the protein or peptide sample with a short test FRET (fluorescence resonance energy transfer) peptide comprising a peptide sequence containing a proteinase or endopeptidase cleavage site.

Various reactions may be used to attach the peptides to a solid support, or attach binders to corresponding coding tags. The peptides may be attached directly or indirectly to the solid support. In some cases, the peptide is attached to the solid support via a capture nucleic acid (capture DNA). Exemplary reactions include the copper catalyzed reaction of an azide and alkyne to form a triazole (Huisgen 1,3-dipolar cycloaddition), strain-promoted azide alkyne cycloaddition (SPAAC), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse electron demand Diels-Alder (IEDDA) reaction (e.g., m-tetrazine (mTet) or phenyl tetrazine (pTet) and trans-cyclooctene (TCO)); or pTet and an alkene), alkene and tetrazole photoreaction, Staudinger ligation of azides and phosphines, and various displacement reactions, such as displacement of a leaving group by nucleophilic attack on an electrophilic atom (Horisawa 2014, Knall, Hollauf et al. 2014). Exemplary displacement reactions include reaction of an amine with: an activated ester; an N-hydroxysuccinimide ester; an isocyanate; an isothioscyanate, an aldehyde, an epoxide, or the like. In some embodiments, iEDDA click chemistry is used for immobilizing peptides to a solid support since it is rapid and delivers high yields at low input concentrations. In another embodiment, m-tetrazine rather than tetrazine is used in an iEDDA click chemistry reaction, as m-tetrazine has improved bond stability. In another embodiment, phenyl tetrazine (pTet) is used in an iEDDA click chemistry reaction. In one case, a peptide is labeled with a bifunctional click chemistry reagent, such as alkyne-NHS ester (acetylene-PEG-NHS ester) reagent or alkyne-benzophenone to generate an alkyne-labeled peptide. In some embodiments, an alkyne can also be a strained alkyne, such as cyclooctynes including Dibenzocyclooctyl (DBCO), etc.

In certain embodiments where multiple proteins are immobilized on the same solid support, the proteins can be spaced appropriately to accommodate methods of analysis to be used to assess the proteins. For example, it may be advantageous to space the proteins that optimally to allow a nucleic acid-based method for assessing and sequencing the proteins to be performed. In some embodiments, the method for assessing and sequencing the proteins involve a binder which binds to the protein and the binder comprises a coding tag with information that is transferred to a nucleic acid attached to the proteins (e.g., recording tag). In some cases, information transfer from a coding tag of a binder bound to one protein may reach a neighboring protein.

In some embodiments, the surface of the solid support is passivated (blocked). A "passivated" surface refers to a surface that has been treated with outer layer of material. Methods of passivating surfaces include standard methods from the fluorescent single molecule analysis literature, including passivating surfaces with polymer like polyethylene glycol (PEG) (Pan et al., 2015, Phys. Biol. 12:045006), polysiloxane (e.g., Pluronic F-127), star polymers (e.g., star PEG) (Groll et al., 2010, Methods Enzymol. 472:1-18), hydrophobic dichlorodimethylsilane (DDS)+self-assembled Tween-20 (Hua et al., 2014, Nat. Methods 11:1233-1236), diamond-like carbon (DLC), DLC+PEG (Stavis et al., 2011, Proc. Natl. Acad. Sci. USA 108:983-988), and zwitterionic moiety (e.g., U.S. Patent Application Publication US 2006/0183863). In addition to covalent surface modifications, a number of passivating agents can be employed as well including surfactants like Tween-20, polysiloxane in solution (Pluronic series), poly vinyl alcohol (PVA), and proteins like BSA and casein. Alternatively, density of macromolecules (e.g., proteins, peptide, or peptides) can be titrated on the surface or within the volume of a solid substrate by spiking a competitor or "dummy" reactive molecule when immobilizing the proteins, peptides or peptides to the solid substrate.

To control protein spacing on the solid support, the density of functional coupling groups for attaching the protein (e.g., TCO or carboxyl groups (COOH)) may be titrated on the substrate surface. In some embodiments, multiple proteins are spaced apart on the surface or within the volume (e.g., porous supports) of a solid support such that adjacent proteins are spaced apart at a distance of about 50 nm to about 500 nm. In some embodiments, multiple a proteins are spaced apart on the surface of a solid support with an average distance of at least 50 nm, at least 60 nm, at least 70 nm, at least 80 nm, at least 90 nm, at least 100 nm, or at least 500 nm. In some embodiments, multiple a proteins are spaced apart on the surface of a solid support with an average distance of at least 50 nm. In some embodiments, proteins are spaced apart on the surface or within the volume of a solid support such that, empirically, the relative frequency of inter- to intra-molecular events (e.g. transfer of information) is <1:10; <1:100; <1:1,000; or <1:10,000.

In some embodiments, the provided methods includes an oligonucleotides that comprise hairpin structure and a restriction enzyme site (or portion thereof). In some embodiments, the methods include the use of a reaction system wherein mixed enzymes are provided to the reaction. For example, the activities of the polymerase, the nucleic acid joining reagent and the double strand nucleic acid cleaving reagent, are provided with suitable conditions, transferring information from a coding tag to the recording tag to generate an extended recording tag. In the provided methods, the recording tag used comprises at least a partially double stranded DNA structure. Some advantages using the described methods include high information transfer (encoding) success, simple design for a step-wise reaction, option to perform in a single step/as a single pot reaction, reducing the need for spacers or reducing spacer length, and/or minimizing DNA-DNA interactions in the system.

In one embodiment, the macromolecule (e.g., protein or peptide) is labeled with a DNA recording tag. In some embodiments, the sample is provided with a plurality of recording tags. In some embodiments, a plurality of macromolecules in the sample is provided with recording tags. The recording tags may be associated or attached, directly or indirectly to the macromolecules using any suitable means. In some embodiments, a macromolecule may be associated with one or more recording tags. In some embodiments, the recording tag may be any suitable sequenceable moiety to which identifying information can be transferred (e.g., information from one or more coding tags).

In some embodiments, the recording tag can include a sample identifying barcode. A sample barcode is useful in the multiplexed analysis of a set of samples in a single reaction vessel or immobilized to a single solid substrate or collection of solid substrates (e.g., a planar slide, population of beads contained in a single tube or vessel, etc.). For example, macromolecules from many different samples can be labeled with recording tags with sample-specific barcodes, and then all the samples pooled together prior to immobilization to a solid support, cyclic binding of the binder, and recording tag analysis. Alternatively, the samples can be kept separate until after creation of a DNA-encoded library, and sample barcodes attached during PCR amplification of the DNA-encoded library, and then mixed together prior to sequencing. This approach could be useful when assaying analytes (e.g., proteins) of different abundance classes.

In some embodiments, the recording tags associated with a library of peptides share a common spacer sequence. In other embodiments, the recording tags associated with a library of peptides have binding cycle specific spacer sequences that are complementary to the binding cycle specific spacer sequences of their cognate binders. In some embodiments, the spacer sequence in the recording tag is designed to have minimal complementarity to other regions in the recording tag; likewise, the spacer sequence in the coding tag should have minimal complementarity to other regions in the coding tag. In some cases, the spacer sequence of the recording tags and coding tags should have minimal sequence complementarity to components such unique molecular identifiers, barcodes (e.g., compartment, partition, sample, spatial location), universal primer sequences, encoder sequences, cycle specific sequences, etc. present in the recording tags or coding tags.

In certain embodiments, a recording tag comprises a universal priming site, e.g., a forward or 5' universal priming site. A universal priming site is a nucleic acid sequence that may be used for priming a library amplification reaction and/or for sequencing. A universal priming site may include, but is not limited to, a priming site for PCR amplification, flow cell adaptor sequences that anneal to complementary oligonucleotides on flow cell surfaces (e.g., Illumina next generation sequencing), a sequencing priming site, or a combination thereof. A universal priming site can be about 10 bases to about 60 bases. In some embodiments, a universal priming site comprises an Illumina P5 primer (5'-AATGATACGGCGACCACCGA-3'-SEQ ID NO:1) or an Illumina P7 primer (5'-CAAGCAGAAGACGGCATACGAGAT-3'-SEQ ID NO:2).

In some embodiments, the one or more tags or information of the one or more tags are transferred to the recording tag (e.g., via primer extension or ligation) to extend the recording tag. In some embodiments, one or more of the tags (e.g., compartment tag, a partition barcode, sample barcode, a fraction barcode, etc.) further comprise a functional moiety capable of reacting with an internal amino acid, the peptide backbone, or N-terminal amino acid on the plurality of protein complexes, proteins, or peptides. In some embodiments, the functional moiety is a click chemistry moiety, an aldehyde, an azide/alkyne, or a malemide/thiol, or an epoxide/nucleophile, an inverse electron demain Diels-Alder (iEDDA) group, or a moiety for a Staudinger reaction. In some specific embodiments, a plurality of compartment tags is formed by printing, spotting, ink-jetting the compartment tags into the compartment, or a combination thereof. In some embodiments, the tag is attached to a peptide to link the tag to the macromolecule via a peptide-peptide linkage. In some embodiments, the tag-attached peptide comprises a protein ligase recognition sequence.

In some embodiments, before providing the peptide analyte and the associated nucleic acid recording tag joined to the solid support, the provided methods further comprise attaching the peptide analyte to the nucleic acid recording tag optionally joined to the solid support. Various alternatives can be used during the attachment step. For example, the peptide analyte can first be attached to the nucleic acid recording tag forming a conjugate, and then the conjugate is attached to the solid support. Alternatively, the nucleic acid recording tag can be attached (immobilized) to the solid support, and then the peptide analyte is attached to the immobilized nucleic acid recording tag.

In certain embodiments, a peptide or peptide macromolecule can be immobilized to a solid support by an affinity capture reagent (and optionally covalently crosslinked), wherein the recording tag is associated with the affinity capture reagent directly, or alternatively, the macromolecule can be directly immobilized to the solid support with a recording tag. In one embodiment, the macromolecule is attached to a bait nucleic acid which hybridizes to a capture nucleic acid and is ligated to a capture nucleic acid which comprises a reactive coupling moiety for attaching to the solid support. In some embodiments, the bait or capture nucleic acid may serve as a recording tag to which information regarding the peptide can be transferred. In some embodiments, the macromolecule is attached to a bait nucleic acid to form a nucleic acid-macromolecule conjugate. In some embodiments, the immobilization methods comprise bringing the nucleic acid-macromolecule conjugate into proximity with a solid support by hybridizing the bait nucleic acid to a capture nucleic acid (e.g. capture hairpin DNA) attached to the solid support, and covalently coupling the nucleic acid-macromolecule conjugate to the solid support. In some cases, the nucleic acid-macromolecule conjugate is coupled indirectly to the solid support, such as via a linker. In some embodiments, a plurality of the nucleic acid-macromolecule conjugates is coupled on the solid support and any adjacently coupled nucleic acid-macromolecule conjugates are spaced apart from each other at an average distance of about 50 nm or greater.

In some embodiments, providing the peptide and an associated recording tag joined to a solid support comprises the following steps: attaching the peptide to the recording tag to generate a nucleic acid-peptide conjugate; bringing the nucleic acid-peptide conjugate into proximity with a solid support by hybridizing the recording tag in the nucleic acid-peptide conjugate to a capture nucleic acid attached to the solid support; and covalently coupling the nucleic acid-peptide conjugate to the solid support.

In some embodiments, providing the peptide and an associated recording tag joined to a solid support further comprises attaching the peptide analyte to the nucleic acid recording tag optionally joined to the solid support.

In some embodiments, the nucleic acid recording tag is associated directly or indirectly to the peptide analyte via a non-nucleotide chemical moiety.

In some embodiments, providing conditions to allow transfer of identifying information from a coding tag of the binder to a recording tag associated with the peptide comprises addition of an enzyme (such as DNA polymerase or DNA ligase) to the immobilized peptide, as well as an appropriate buffer for this enzyme (such as a buffer for DNA polymerase or DNA ligase). Standard buffers that provide functionality of DNA polymerase or DNA ligase are known in the art.

In preferred embodiments, to provide encoding reaction specificity, transfer of identifying information regarding a binder from a coding tag of the binder to a recording tag associated with an immobilized peptide occurs only following (or after) binding of the binder to the immobilized peptide. The binder binds specifically to a component of the immobilized peptide (in various embodiments, binds to a single NTAA residue, to a modified amino acid residue, such as post-translationally-modified residue, to an epitope, or to more than one epitopes simultaneously); and binding of the binder to the immobilized peptide does not depend on the presence of the recording tag associated with the immobilized peptide.

In the present invention, the nucleic acid recording tag associated with the peptide is an element of the disclosed analytical assay and is not a component of the peptide. Thus, binders of the present invention do not bind to the nucleic acid recording tag.

In some embodiments, the conjugation of the macromolecule with a recording tag is performed using standard amine coupling chemistries. For example, the e-amino group (e.g., of lysine residues) and the N-terminal amino group may be susceptible to labeling with amine-reactive coupling agents, depending on the pH of the reaction (Mendoza et al., Mass Spectrom Rev (2009) 28(5): 785-815).

In some embodiments, the recording tags may comprise a reactive moiety for a cognate reactive moiety present on the target macromolecule, e.g., the target protein, (e.g., click chemistry labeling, photoaffinity labeling). For example, recording tags may comprise an azide moiety for interacting with alkyne-derivatized proteins, or recording tags may comprise a benzophenone for interacting with native proteins, etc. Upon binding of the target protein by the target protein specific binder, the recording tag and target protein are coupled via their corresponding reactive moieties. After the target protein is labeled with the recording tag, the target-protein specific binder may be removed by digestion of the DNA capture probe linked to the target-protein specific binder. For example, the DNA capture probe may be designed to contain uracil bases, which are then targeted for digestion with a uracil-specific excision reagent (e.g., USER™), and the target-protein specific binder may be dissociated from the target protein. In some embodiments, other types of linkages besides hybridization can be used to link the recording tag to a macromolecule.

Coding tag information associated with a specific binder may be transferred to a recording tag using a variety of methods. In any of the preceding embodiments, the transfer of identifying information (e.g., from a coding tag to a recording tag) can be accomplished by ligation (e.g., an enzymatic or chemical ligation, a splint ligation, a sticky end ligation, a single-strand (ss) ligation such as a ssDNA ligation, or any combination thereof), a polymerase-mediated reaction (e.g., primer extension of single-stranded nucleic acid or double-stranded nucleic acid), or any combination thereof.

In some embodiments, a DNA polymerase that is used for primer extension possesses strand-displacement activity and has limited or is devoid of 3'-5 exonuclease activity. Several of many examples of such polymerases include Klenow exo- (Klenow fragment of DNA Pol 1), T4 DNA polymerase exo-, T7 DNA polymerase exo (Sequenase 2.0), Pfu exo-, Vent exo-, Deep Vent exo-, Bst DNA polymerase large fragment exo-, Bca Pol, and Phi29 Pol exo-. In a preferred embodiment, the DNA polymerase is active at room temperature and up to 45° C. In another embodiment, a "warm start" version of a thermophilic polymerase is employed such that the polymerase is activated and is used at about 40° C.-50° C. An exemplary warm start polymerase is Bst 2.0 Warm Start DNA Polymerase (New England Biolabs).

In some embodiments, various conditions for one or more steps of the method may be modified by one skilled in the art. For example, the temperature for contacting of the binders to the macromolecules or for hybridization of the spacer sequences on the recording tag and coding tag can be increased or decreased to modify specificity or stringency of the interactions. In some embodiments, to minimize non-specific interaction of the coding tag labeled binders in solution with the nucleic acids of immobilized proteins, competitor (also referred to as blocking) oligonucleotides complementary to nucleic acids containing spacer sequences (e.g., on the recording tag) can be added to binding reactions to minimize non-specific interactions. In some embodiments, the blocking oligonucleotides contain a sequence that is complementary to the coding tag or a portion thereof attached to the binder. In some embodiments, the coding tag comprises a hairpin nucleic acid, and the hairpin includes a sequence that is complementary to a spacer and/or barcode of the coding tag. Excess competitor oligonucleotides are washed from the binding reaction prior to primer extension, which effectively dissociates the annealed competitor oligonucleotides from the nucleic acids on the recording tag, especially when exposed to slightly elevated temperatures (e.g., 30-50° C.).

Coding tag information associated with a specific binder may be transferred to a nucleic acid on the recording tag associated with the immobilized peptide via ligation. Ligation may be a blunt end ligation or sticky end ligation. Ligation may be an enzymatic ligation reaction. Examples of ligases include, but are not limited to CV DNA ligase, T4 DNA ligase, T7 DNA ligase, T3 DNA ligase, Taq DNA ligase, *E. coli* DNA ligase. Alternatively, a ligation may be a chemical ligation reaction. In one embodiment, a spacer-less ligation is accomplished by using hybridization of a "recording helper" sequence with an arm on the coding tag. The annealed complement sequences are chemically ligated using standard chemical ligation or "click chemistry" (Gunderson et al., Genome Res (1998) 8(11): 1142-1153; Litovchick et al., Artif DNA PNA XNA (2014) 5(1): e27896; Roloff et al., Methods Mol Biol (2014) 1050:131-141).

Various aspects of coding tag and recording tag compositions, as well as aspects of transferring identifying information from a coding tag to a recording tag are disclosed in the earlier published application US 2019/0145982 A1, incorporated herein.

In another embodiment, transfer of PNAs can be accomplished with chemical ligation using published techniques. The structure of PNA is such that it has a 5' N-terminal amine group and an unreactive 3' C-terminal amide. Chemical ligation of PNA requires that the termini be modified to be chemically active. This is typically done by derivatizing the 5' N-terminus with a cysteinyl moiety and the 3' C-terminus with a thioester moiety. Such modified PNAs easily couple using standard native chemical ligation conditions (Roloff et al., (2013) Bioorgan. Med. Chem. 21:3458-3464).

In certain embodiments, an extended recording tag associated with the immobilized peptide may comprise information from multiple coding tags representing multiple, successive binding events. In these embodiments, a single, concatenated extended recording tag associated with the immobilized peptide can be representative of a single peptide. As referred to herein, transfer of coding tag information to the recording tag associated with the immobilized peptide also includes transfer to an extended recording tag as would occur in methods involving multiple, successive binding events. In certain embodiments, the binding event information is transferred from a coding tag to the recording tag associated with the immobilized peptide in a cyclic fashion. Cross-reactive binding events can be informatically filtered out after sequencing by requiring that at least two different coding tags, identifying two or more independent binding events, map to the same class of binders (cognate to a particular protein). The coding tag may contain an optional UMI sequence in addition to one or more spacer sequences.

In certain embodiments, a binder may be a selective binder. As used herein, selective binding refers to the ability of the binder to preferentially bind to a specific ligand (e.g., amino acid or class of amino acids) relative to binding to a different ligand (e.g., another amino acid or class of amino acids). Selectivity is commonly referred to as the equilibrium constant for the reaction of displacement of one ligand by another ligand in a complex with a binder. Typically, such selectivity is associated with the spatial geometry of the ligand and/or the manner and degree by which the ligand binds to a binder, such as by hydrogen bonding or Van der Waals forces (non-covalent interactions) or by reversible or non-reversible covalent attachment to the binder. It should also be understood that selectivity may be relative, and as opposed to absolute, and that different factors can affect the same, including ligand concentration. Thus, in one example, a binder selectively binds one of the twenty standard amino acids. In some embodiments, a binder may exhibit flexibility and variability in target binding preference in some or all of the positions of the targets. In some embodiments, a binder may have a preference for one or more specific target terminal amino acids and have a flexible preference for a target at the penultimate position. In some other examples, a binder may have a preference for one or more specific target amino acids in the penultimate amino acid position and have a flexible preference for a target at the terminal amino acid position. In some embodiments, a binder is selective for a target comprising a terminal amino acid and other components of a macromolecule. In some particular examples, a binder is selective for a target comprising a terminal amino acid and an amide peptide backbone.

In the practice of the methods disclosed herein, the ability of a binder to selectively bind a feature or component of a macromolecule, e.g., a peptide, need only be sufficient to allow transfer of its coding tag information to the recording tag associated with the peptide. Thus, selectively need only be relative to the other binders to which the peptide is exposed. It should also be understood that selectivity of a binder need not be absolute to a specific amino acid, but could be selective to a class of amino acids, such as amino acids with polar or non-polar side chains, or with electrically (positively or negatively) charged side chains, or with aromatic side chains, or some specific class or size of side chains, and the like. In some embodiments, the ability of a binder to selectively bind a feature or component of a macromolecule is characterized by comparing binding abilities of binders. For example, the binding ability of a binder to the target can be compared to the binding ability of a binder which binds to a different target, for example, comparing a binder selective for a class of amino acids to a binder selective for a different class of amino acids. In some embodiments, a binder selective for non-polar side chains is compared to a binder selective for polar side chains. In some embodiments, a binder selective for a feature, component of a peptide, or one or more amino acid exhibits at least 1×, at least 2×, at least 5×, at least 10×, at least 50×, at least 100×, or at least 500× more binding compared to a binder selective for a different feature, component of a peptide, or one or more amino acid.

In a particular embodiment, the binder has a high affinity and high selectivity for the macromolecule, e.g., the peptide, of interest. In particular, a high binding affinity with a low off-rate may be efficacious for information transfer between the coding tag and recording tag. In certain embodiments, a binder has a thermodynamic dissociation constant (Kd) of less than about 1000 nM, less than 500 nM, less than 200 nM, less than 100 nM, less than 50 nM, less than 10 nM, less than 5 nM, less than 1 nM, less than 0.5 nM, or less than 0.1 nM. Kd values of exemplary engineered metalloprotein binders are listed in Example 10 below. In a particular embodiment, the binder is added to the peptide at a concentration >1×, >5×, >10×, >100×, or >1000× its Kd to drive binding to completion. A binder may be engineered for high affinity for a modified NTAA, high specificity for a modified NTAA, or both. In some embodiments, binders can be developed through directed evolution of promising affinity scaffolds using phage display.

In certain embodiments, the binder further comprises one or more detectable labels such as fluorescent labels, in addition to the binding moiety. In some embodiments, the binder does not comprise a polynucleotide such as a coding tag. In some embodiments, the binder comprises an aptamer. In one embodiment, the binder comprises a peptide and a detectable label. In one embodiment, the detectable label is optically detectable. In some embodiments, the detectable label comprises a fluorescently moiety, a color-coded nanoparticle, a quantum dot or any combination thereof. In one embodiment the label comprises a polystyrene dye encompassing a core dye molecule such as a FluoSphere™, Nile Red, fluorescein, rhodamine, derivatized rhodamine dyes, such as TAMRA, phosphor, polymethadine dye, fluorescent phosphoramidite, TEXAS RED, green fluorescent protein, acridine, cyanine, cyanine 5 dye, cyanine 3 dye, 5-(2'-aminoethyl)-aminonaphthalene-1-sulfonic acid (EDANS), BODIPY, 120 ALEXA or a derivative or modification of any of the foregoing. In one embodiment, the detectable label is resistant to photobleaching while producing lots of signal (such as photons) at a unique and easily detectable wavelength, with high signal-to-noise ratio.

In certain embodiments, a macromolecule, e.g., a peptide, is also contacted with a non-cognate binder. As used herein, a non-cognate binder is referring to a binder that is selective for a different peptide feature or component than the particular peptide being considered. For example, if the n NTAA is phenylalanine, and the peptide is contacted with three binders selective for phenylalanine, tyrosine, and asparagine, respectively, the binder selective for phenylalanine would be first binder capable of selectively binding to the $n^h$ NTAA (e.g., phenylalanine), while the other two binders would be non-cognate binders for that peptide (since they are selective for NTAAs other than phenylalanine). The tyrosine and asparagine binders may, however, be cognate binders for other peptides in the sample. Thus, it should be understood that whether an agent is a binder or a non-cognate binder will depend on the nature of the particular peptide feature or component currently available for binding. Also, if multiple peptides are analyzed in a multiplexed reaction, a binder for one peptide may be a non-cognate binder for another, and vice versa.

In some embodiments, each unique binder within a library of binders has a unique barcode sequence. For example, 20 unique barcode sequences may be used for a library of 20 binders that bind to the 20 modified NTAA residues of immobilized peptides. In other embodiments, two or more different binders may share the same barcode sequence.

A coding tag may include a terminator nucleotide incorporated at the 3' end of the 3' spacer sequence. After a binder binds to a peptide and their corresponding coding tag and recording tags anneal via complementary spacer sequences, it is possible for primer extension to transfer information from the coding tag to the recording tag, or to transfer information from the recording tag to the coding tag. Addition of a terminator nucleotide on the 3' end of the coding tag prevents transfer of recording tag information to the coding tag. It is understood that for embodiments described herein involving generation of extended coding tags, it may be preferable to include a terminator nucleotide at the 3' end of the recording tag to prevent transfer of coding tag information to the recording tag.

A coding tag may be a single stranded molecule, a double stranded molecule, or a partially double stranded. A coding tag may comprise blunt ends, overhanging ends, or one of each. In some embodiments, a coding tag is partially double stranded, which prevents annealing of the coding tag to internal encoder and spacer sequences in a growing extended recording tag. In some embodiments, the coding tag comprises a hairpin. In certain embodiments, the hairpin comprises mutually complementary nucleic acid regions are connected through a nucleic acid strand. In some embodiments, the nucleic acid hairpin can also further comprise 3' and/or 5' single-stranded region(s) extending from the double-stranded stem segment. In some embodiments, the hairpin comprises a single strand of nucleic acid. In some embodiments, the coding tag sequence can be optimized for the particular sequencing analysis platform. For example, if the extended nucleic acid is to be analyzed using a nanopore sequencing instrument, the barcode sequences (e.g., sequences comprising identifying information from the coding tag) can be designed to be optimally electrically distinguishable in transit through a nanopore.

A coding tag is joined to a binder directly or indirectly, by any means known in the art, including covalent and non-covalent interactions. In some embodiments, a coding tag may be joined to binder enzymatically or chemically. In some embodiments, a coding tag may be joined to a binder via ligation. In other embodiments, a coding tag is joined to a binder via affinity binding pairs (e.g., biotin and streptavidin). In some cases, a coding tag may be joined to a binder to an unnatural amino acid, such as via a covalent interaction with an unnatural amino acid. In some particular embodiments, a binder is joined to a coding tag via a covalent linkage.

In some embodiments, a binder is joined to a coding tag via SpyCatcher-SpyTag interaction. The SpyTag peptide forms an irreversible covalent bond to the SpyCatcher protein via a spontaneous isopeptide linkage, thereby offering a genetically encoded way to create peptide interactions that resist force and harsh conditions (Zakeri et al., 2012, Proc. Natl. Acad. Sci. 109:E690-697; Li et al., 2014, J. Mol. Biol. 426:309-317). A binder may be expressed as a fusion protein comprising the SpyCatcher protein. In some embodiments, the SpyCatcher protein is appended on the N-terminus or C-terminus of the binder. The SpyTag peptide can be coupled to the coding tag using standard conjugation chemistries (Bioconjugate Techniques, G. T. Hermanson, Academic Press (2013)). In some particular embodiments, a binder is joined to a coding tag via methods, disclosed in the following published U.S. patents and patent applications: U.S. Pat. Nos. 9,547,003, 10,247,727, 10,527,609, 10,526,379, US 2016/272543 A1.

In some embodiments, an enzyme-based strategy is used to join the binder to a coding tag. For example, the binder may be joined to a coding tag using a formylglycine (FGly)-generating enzyme (FGE). In one example, a protein, e.g., SpyLigase, is used to join the binder to the coding tag (Fierer et al., Proc Natl Acad Sci USA. 2014 Apr. 1; 111(13): E1176-E1181).

In other embodiments, a binder is joined to a coding tag via SnoopTag-SnoopCatcher peptide-protein interaction. The SnoopTag peptide forms an isopeptide bond with the SnoopCatcher protein (Veggiani et al., Proc. Natl. Acad. Sci. USA, 2016, 113:1202-1207). A binder may be expressed as a fusion protein comprising the SnoopCatcher protein. In some embodiments, the SnoopCatcher protein is appended on the N-terminus or C-terminus of the binder. The SnoopTag peptide can be coupled to the coding tag using standard conjugation chemistries.

In yet other embodiments, a binder is joined to a coding tag via the HaloTag protein fusion tag and its chemical ligand. HaloTag is a modified haloalkane dehalogenase designed to covalently bind to synthetic ligands (HaloTag ligands) (Los et al., 2008, ACS Chem. Biol. 3:373-382). The synthetic ligands comprise a chloroalkane linker attached to a variety of useful molecules. A covalent bond forms between the HaloTag and the chloroalkane linker that is highly specific, occurs rapidly under physiological conditions, and is essentially irreversible.

In some embodiments, contacting of the first binder and second binder to the peptide, and optionally any further binders (e.g., third binder, fourth binder, fifth binder, and so on), are performed at the same time. For example, the first binder and second binder, and optionally any further order binders, can be pooled together, for example to form a library of binders. In another example, the first binder and second binder, and optionally any further order binders, rather than being pooled together, are added simultaneously to the peptide. In one embodiment, a library of binders comprises at least 20 binders that selectively bind to the 20 modified NTAA residues of immobilized peptides. In some embodiments, a library of binders comprises binders that selectively bind to the modified NTAA residues.

In other embodiments, the first binder and second binder, and optionally any further order binders, are each contacted with the peptide in separate binding cycles, added in sequential order. In certain embodiments, multiple binders are used at the same time in parallel. This parallel approach saves time and reduces non-specific binding by non-cognate binders to a site that is bound by a cognate binder (because the binders are in competition).

In certain embodiments, the concentration of the binders in a solution is controlled to reduce background and/or false positive results of the assay. In some embodiments, the concentration of a binder can be at any suitable concentration, e.g., at about 0.0001 nM, about 0.001 nM, about 0.01 nM, about 0.1 nM, about 1 nM, about 10 nM, about 100 nM, about 200 nM, about 500 nM, or about 1,000 nM.

In some embodiments, the ratio between the soluble binder molecules and the immobilized macromolecule, e.g., peptides, can be at any suitable range, e.g., at about 0.00001:1, about 0.0001:1, about 0.001:1, about 0.01:1, about 0.1:1, about 1:1, about 2:1, about 5:1, about 10:1, about 30:1, about 40:1, about 50:1, about 60:1, about 80:1, about 90:1, about 100:1, about $10^4$:1, about 105:1, about $10^6$:1, or higher, or any ratio in between the above listed ratios. Higher ratios between the soluble binder molecules and the immobilized peptide(s) and/or the nucleic acids can be used to drive the binding and/or the coding tag information transfer to completion. This may be particularly useful for detecting and/or analyzing low abundance peptides in a sample.

In some embodiments, following the transfer of identifying information from a coding tag to a recording tag, at least one terminal amino acid is removed, cleaved, or eliminated from the peptide. In some embodiments, the at least one removed terminal amino acid comprises a modified amino acid using any of the methods or reagents provided herein. In embodiments relating to methods of analyzing peptides or peptides using a degradation based approach, following contacting and binding of a first binder to an n terminal amino acid (e.g., NTAA) of a peptide of n amino acids and transfer of the first binder's coding tag information to a nucleic acid associated with the peptide, thereby generating a first order extended nucleic acid (e.g., on the recording tag), the n NTAA is eliminated as described herein. Removal of the n labeled NTAA by contacting with an enzyme or chemical reagents converts the n-1 amino acid of the peptide to an N-terminal amino acid, which is referred to herein as an n-1 NTAA. A second binder is contacted with the peptide and binds to the n-1 NTAA, and the second binder's coding tag information is transferred to the first order extended nucleic acid thereby generating a second order extended nucleic acid (e.g., for generating a concatenated $n^{th}$ order extended nucleic acid representing the peptide). Elimination of the n-1 labeled NTAA converts the n-2 amino acid of the peptide to an N-terminal amino acid, which is referred to herein as n-2 NTAA. Additional binding, transfer, labeling, and removal, can occur as described above up to n amino acids to generate an $n^{h}$ order extended nucleic acid or n separate extended nucleic acids, which collectively represent the peptide. As used herein, an n "order" when used in reference to a binder, coding tag, or extended nucleic acid, refers to the n binding cycle, wherein the binder and its associated coding tag is used or the n binding cycle where the extended nucleic acid recording tag is created.

In some embodiments, chemical methods to cleave a modified NTAA residue of an immobilized peptide are disclosed in the published applications U.S. 2022/0227889 A1 and U.S. 2020/0348307 A1.

In some embodiments, enzymatic methods to cleave a modified NTAA residue of an immobilized peptide are disclosed in the published applications US 2021/0214701 A1. In some particular embodiments, enzymatic methods include use of the modified or engineered cleavase that is derived from a dipeptidyl peptidase of *Thermomonas hydrothermalis* comprising an amino acid sequence set forth in SEQ ID NO:3 (WT sequence with the signal peptide) or SEQ ID NO:4 (WT sequence without the signal peptide). Some embodiments of enzymatic methods to cleave a modified NTAA residue of immobilized peptides are disclosed above in the section III (Modified or engineered cleavases).

The length of the final extended recording tags generated by the methods described herein is dependent upon multiple factors, including the length of the coding tag (e.g., barcode sequence and spacer) and the length of the starting recording tags (e.g., the recording tag may optionally include a unique molecular identifier, spacer, universal priming site, barcode(s), or combinations thereof), the number of transfer cycles performed, and whether coding tags from each binding cycle are transferred to the same extended recording tag or to multiple extended recording tags.

After the transfer of the final identifying information to the extended recording tag from a coding tag, the recording tag can be capped by addition of a universal reverse priming site via ligation, primer extension or other methods known in the art. In some embodiments, the universal forward priming site in the recording tag (e.g., on the recording tag) is compatible with the universal reverse priming site that is appended to the final extended recording tag. In some embodiments, a universal reverse priming site is an Illumina P7 primer (5'-CAAGCAGAAGACGGCATACGAGAT-3'-SEQ ID NO:2) or an Illumina P5 primer (5'-AATGATACGGCGACCACCGA-3'-SEQ ID NO:1). The sense or antisense P7 may be appended, depending on strand sense of the recording tag to which the identifying information from the coding tag is transferred to. An extended nucleic acid library can be cleaved or amplified directly from the solid support (e.g., beads) and used in traditional next generation sequencing assays and protocols.

In some embodiments, a primer extension reaction is performed on a library of single stranded extended recording tags to copy complementary strands thereof. Extended recording tags can be processed and analyzed using a variety of nucleic acid sequencing methods. In some embodiments, the collection of extended recording can be concatenated. In some embodiments, the extended recording tag can be amplified prior to determining the sequence. A library of recording tags may be amplified in a variety of ways. A library of recording tags (e.g., recording tags comprising identifying information from one or more coding tags) may undergo exponential amplification, e.g., via PCR or emulsion PCR. Emulsion PCR is known to produce more uniform amplification (Hori, Fukano et al., Biochem Biophys Res Commun (2007) 352(2): 323-328). Alternatively, a library of recording tags may undergo linear amplification, e.g., via in vitro transcription of template DNA using T7 RNA polymerase. The library of recording tags (e.g., extended nucleic acids) can be amplified using primers compatible with the universal forward priming site and universal reverse priming site contained therein. A library of recording tags can also be amplified using tailed primers to add sequence to either the 5'-end, 3'-end or both ends of the extended nucleic acids. Sequences that can be added to the termini of the extended nucleic acids include library specific index sequences to allow multiplexing of multiple libraries in a single sequencing run, adaptor sequences, read primer sequences, or any other sequences for making the library of extended nucleic acids compatible for a sequencing platform. An example of a library amplification in preparation for next generation sequencing is as follows: a 20 μl PCR reaction volume is set up using an extended nucleic acid library eluted from ~1 mg of beads (~10 ng), 200 pM dNTP, 1 pM of each forward and reverse amplification primers, 0.5 μl (1U) of Phusion Hot Start enzyme (New England Biolabs) and subjected to the following cycling conditions: 98° C. for 30 sec followed by 20 cycles of 98° C. for 10 sec, 60° C. for 30 sec, 72° C. for 30 sec, followed by 72° C. for 7 min, then hold at 4° C.

Examples of next generation sequencing methods that can be used for sequencing of the extended recording tags include sequencing by synthesis, sequencing by ligation, sequencing by hybridization, polony sequencing, ion semiconductor sequencing, and pyrosequencing. By attaching primers to a solid substrate and a complementary sequence to a nucleic acid molecule, a nucleic acid molecule can be hybridized to the solid substrate via the primer and then multiple copies can be generated in a discrete area on the solid substrate by using polymerase to amplify (these groupings are sometimes referred to as polymerase colonies or polonies). Consequently, during the sequencing process, a nucleotide at a particular position can be sequenced multiple times (e.g., hundreds or thousands of times)—this depth of coverage is referred to as "deep sequencing." Examples of high throughput nucleic acid sequencing technology include platforms provided by Illumina, BGI, Qiagen, Thermo-Fisher, and Roche, including formats such as parallel bead arrays, sequencing by synthesis, sequencing by ligation, capillary electrophoresis, electronic microchips, "biochips," microarrays, parallel microchips, and single-molecule arrays, as reviewed by Service (Science (2006) 311:1544-1546). Other approaches to sequencing of the extended recording tags can be used, such as described in U.S. Pat. Nos. 6,969,488, 6, 172,218, and 6,306,597, incorporated herein.

The sequencing methods described herein can be advantageously carried out in multiplex formats such that multiple different recording tags are manipulated simultaneously. In particular embodiments, different recording tags can be treated in a common reaction vessel or on a surface of a particular substrate. This allows convenient delivery of sequencing reagents, removal of unreacted reagents and detection of incorporation events in a multiplex manner.

In some embodiments, the information from analysis (e.g., sequencing) of at least a portion of the extended recording tag can be used to associate the sequences determined to corresponding a peptide and align to the proteome. In some cases, following sequencing of the extended recording tags, the resulting sequences can be collapsed by their UMIs and then associated to their corresponding peptides and aligned to the totality of the proteome. In some cases, resulting sequences can also be collapsed by their compartment tags and associated to their corresponding compartmental proteome, which in a particular embodiment contains only a single or a very limited number of protein molecules. In some embodiments, both protein identification and quantification can be derived from this digital peptide information.

The methods disclosed herein can be used for analysis, including detection, quantitation and/or sequencing, of a plurality of macromolecules simultaneously (multiplexing). Multiplexing as used herein refers to analysis of a plurality of macromolecules (e.g. peptides) in the same assay. The plurality of macromolecules can be derived from the same sample or different samples. The plurality of macromolecules can be derived from the same subject or different subjects. The plurality of macromolecules that are analyzed can be different macromolecules, or the same macromolecule derived from different samples. A plurality of macromolecules includes 2 or more macromolecules, 5 or more macromolecules, 10 or more macromolecules, 50 or more macromolecules, 100 or more macromolecules, 500 or more macromolecules, 1000 or more macromolecules, 5,000 or more macromolecules, 10,000 or more macromolecules, 50,000 or more macromolecules, 100,000 or more macromolecules, 500,000 or more macromolecules, or 1,000,000 or more macromolecules.

VI. Kits and Articles of Manufacture

Provided herein are kits and articles of manufacture comprising components for preparing and analyzing macromolecules (e.g., proteins, peptides, or peptides). The kits and articles of manufacture may include any one or more of the reagents and components used in the methods described above. In some embodiments, the kits optionally include instructions for use. In some embodiments, the kits comprise one or more of the following components: recoding tag(s), reagent(s) for attaching the recording tag, reagent(s) for transferring information from the probe tag to the recording tag, binder(s), reagent(s) for transferring identifying information from the coding tag to the recording tag, sequencing reagent(s), solid support(s), enzyme(s), buffer(s), and/or sample processing reagent(s) (e.g. fixation and permeabilization reagent(s).

In another embodiment, provided herein is a kit for obtaining an information regarding at least one amino acid residue of a peptide, the kit comprises:

a) a N-terminal modifier agent that is configured to contact a peptide to form a N-terminally modified peptide having a formula: Z-P1-P2-peptide, wherein P1 is a N-terminal amino acid residue of the peptide, P2 is a penultimate terminal amino acid residue of the peptide, and Z is an N-terminal modification capable of coordinating or chelating a metal ion M; and/or b) a metalloprotein binder that binds to the metal ion M that is configured to specifically bind to the N-terminally modified peptide through interaction between the metalloprotein binder, the metal ion M and the Z-P1-P2-peptide, wherein the binding specificity between the metalloprotein binder and the Z1-P1-P2-peptide is predominantly or substantially determined by interaction between the metalloprotein binder and a Z1-P1 group of the Z1-P1-P2-peptide.

In some embodiments, the kit comprises a plurality of metalloprotein binders.

In some embodiments, the kit further comprises reagents for treating the peptides. Any combination of fractionation, enrichment, and subtraction methods, of the macromolecules, e.g., the proteins, may be performed. For example, the reagent may be used to fragment or digest the macromolecules, e.g., the proteins. In some cases, the kit comprises reagents and components to fractionate, isolate, subtract, enrich the macromolecules, e.g., the proteins. In some embodiments, the kits further comprises a protease such as trypsin, LysN, or LysC.

In some embodiments, the kit also comprises one or more buffers or reaction fluids necessary for any of the desired reaction to occur. Buffers including wash buffers, reaction buffers, and binding buffers, elution buffers and the like are known to those or ordinary skill in the arts. In some embodiments, the kits further include buffers and other components to accompany other reagents described herein.

Reagents and kit components may be provided in any suitable container. In some embodiments, the kits further include buffers and other components to accompany other reagents described herein. The reagents, buffers, and other components may be provided in vials (such as sealed vials), vessels, ampules, bottles, jars, flexible packaging (e.g., sealed Mylar or plastic bags), and the like. Any of the components of the kits may be sterilized and/or sealed. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10.

In some embodiments, the kits or articles of manufacture may further comprise instruction(s) on the methods and uses described herein. In some embodiments, the instructions are directed to methods of analyzing the macromolecules (e.g., proteins, peptides, or peptides). The kits described herein may also include other materials desirable from a commercial and user standpoint, including other buffers, diluents, filters, syringes, and package inserts with instructions for performing any methods described herein. Any of the components of the kits may be sterilized and/or sealed.

Any of the above-mentioned kit and components, and any molecule, molecular complex or conjugate, reagent (e.g., chemical or biological reagents), agent, structure (e.g., support, surface, particle, or bead), reaction intermediate, reaction product, binding complex, or any other article of manufacture disclosed and/or used in the exemplary kits and methods, may be provided separately or in any suitable combination in order to form a kit.

Further aspects of the invention are discussed below.

In one embodiment, provided herein is an engineered metalloprotein binder that specifically binds to an N-terminally modified target peptide modified by an N-terminal modifier agent, wherein:

(a) the N-terminally modified target peptide has a formula: Z-P1-P2-peptide, wherein Z is an N-terminal modification capable of coordinating or chelating a metal cation, P1-P2-peptide is a target peptide before modification with the N-terminal modifier agent, Z-P1 is a modified N-terminal amino acid (NTAA) residue of the target peptide, and P2 is a penultimate terminal amino acid residue of the target peptide;

(b) the engineered metalloprotein binder specifically binds to the N-terminally modified target peptide through interaction between the engineered metalloprotein binder and the Z-P1 of the N-terminally modified target peptide; and (c) the engineered metalloprotein binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates a metal cation.

In another embodiment, provided herein is a kit for treating a target peptide, the kit comprising:

(a) an engineered binder that specifically binds to an N-terminally modified target peptide modified by an N-terminal modifier agent, wherein:

(i) the N-terminally modified target peptide has a formula: Z-P1-P2-peptide, wherein Z is an N-terminal modification capable of coordinating or chelating a metal cation, P1-P2-peptide is a target peptide before modification with the N-terminal modifier agent, Z-P1 is a modified N-terminal amino acid (NTAA) residue of the target peptide, and P2 is a penultimate terminal amino acid residue of the target peptide;

(ii) the engineered binder specifically binds to the N-terminally modified target peptide through interaction between the engineered binder and the Z-P1 of the N-terminally modified target peptide; and (iii) the engineered binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates a metal cation; and (b) the N-terminal modifier agent selected from the group consisting of compounds of the following Formula (6)-(9):

(6)

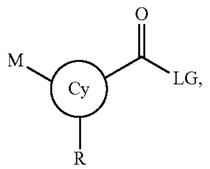

(7)

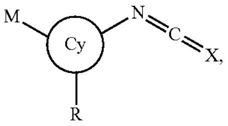

-continued (8)

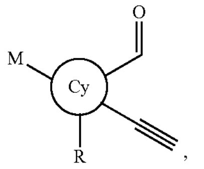

, and (9)

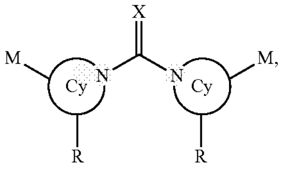

wherein M is a metal cation binding group that comprises sulfonamide, hydroxamic acid, sulfamate, or sulfamide; the group

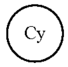

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, $OR^Q$, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH. In preferred embodiments, the metal cation binding group is a Zn cation binding group.

In another embodiment, provided herein is a method of treating a target peptide, the method comprises the following steps:

(a) contacting the target peptide with an N-terminal modifier agent to form an N-terminally modified peptide having a formula: Z-P1-P2-peptide, wherein Z is an N-terminal modification capable of coordinating or chelating a metal cation, P1-P2-peptide is a target peptide before modification with the N-terminal modifier agent, Z-P1 is a modified N-terminal amino acid (NTAA) residue of the target peptide, and P2 is a penultimate terminal amino acid residue of the target peptide; and (b) contacting an engineered metalloprotein binder with the N-terminally modified target peptide to allow the engineered binder to specifically bind to the N-terminally modified target peptide through interaction between the engineered binder and the modified NTAA residue of the N-terminally modified target peptide, wherein the engineered binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates a metal cation.

In some embodiments, the methods disclosed herein further comprise the step of removing the modified NTAA residue from the N-terminally modified target peptide, thereby exposing a new NTAA residue.

Disclosed herein is also a method of treating a plurality of peptides, the method comprising:

(a) contacting a catalyst of Formula (13):

(13)

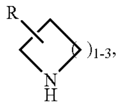

with a compound of Formula (8):

(8)

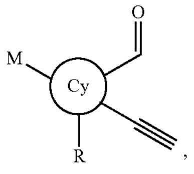

wherein M is a metal cation binding group that comprises sulfonamide, hydroxamic acid, sulfamate, or sulfamide; the group

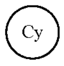

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, $OR^Q$, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH, under conditions to generate a catalytic intermediate of Formula (14):

(14)

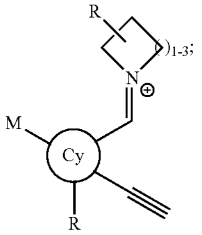

and (b) contacting a peptide of the plurality of peptides with the catalytic intermediate of Formula (14) to form an N-terminally modified peptide having a formula:

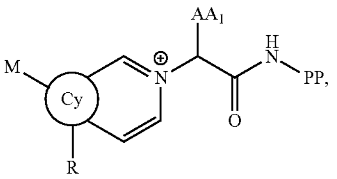

wherein AA1 is a side chain of an N-terminal amino acid (NTAA) residue of the peptide, and PP comprises amino acid residues of the peptide starting from a penultimate terminal amino acid residue of the peptide to a C-terminal amino acid (NTAA) residue of the peptide.

In some embodiments, the disclosed method further comprises the following step: (c) contacting the N-terminally modified peptide with a set of engineered binders, wherein at least one engineered binder of the set specifically binds to the modified NTAA residue of the N-terminally modified peptide, wherein each engineered binder of the set comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp), and E (Glu); X1, X2, X3 and X4 are each any amino acid sequence independently comprising between 0 and 500 amino acid residues in length, and wherein the amino acid sequence X1-C/H/D/E-X2-C/H/D/E-X3-C/H/D/E-X4 chelates the metal cation. In some embodiments, the disclosed method further comprises the following step: (d) detecting a signal indicative of the binding of the at least one engineered binder to the N-terminally modified peptide.

In some particular embodiments, the compound of Formula (8) comprises 4-(sulfamoyl)-2-ethynylbenzaldehyde. In some particular embodiments, the catalyst of Formula (13) comprises one of the compounds of Formula (10), Formula (11), or Formula (12):

(10)

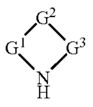

(11)

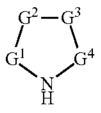

-continued (12)

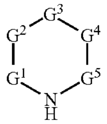

wherein:

$G^1$-$G^5$ are each independently selected from $CJ_2$, NH, S, and O provided not more than 1 of $G^1$-$G^5$ are NH, S, or O;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —$N(R^8)_2$, —$S(O)_nR^8$, —$NR^8SO_2R^8$, —$SO_2N(R^8)_2$, $SO_3R^8$, —$B(OR^8)_2$, $C(=O)R^8$, CN, $CON(R^8)_2$, —$COOR^8$, —C(═O) Ar, and tetrazole, where Ar represents a phenyl or 5-6 membered heteroaryl ring that is optionally substituted with one or two groups selected from halo, CN, $R^9$ and $OR^9$; each $R^8$ and each $R^9$ is independently selected from H, $C_1$-$C_2$ alkyl, and $C_1$-$C_2$ haloalkyl; n at each occurrence is independently 1 or 2.

Disclosed herein is also a method of treating a plurality of peptides, the method comprising:

(a) contacting a peptide of the plurality of peptides with an N-terminal modifier agent to form an N-terminally modified peptide having a formula: Z-P1-P2-peptide, wherein Z is an N-terminal modification capable of coordinating or chelating a metal cation, P1-P2-peptide is the peptide before modification with the N-terminal modifier agent, Z-P1 is a modified N-terminal amino acid (NTAA) residue of the peptide, and P2 is a penultimate terminal amino acid residue of the peptide;

(b) contacting the N-terminally modified peptide with a set of engineered binders, wherein at least one engineered binder of the set specifically binds to the modified NTAA residue of the N-terminally modified peptide, wherein each engineered binder of the set comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp), and E (Glu); X1, X2, X3 and X4 are each any amino acid sequence independently comprising between 0 and 500 amino acid residues in length, and wherein the amino acid sequence X1-C/H/D/E-X2-C/H/D/E-X3-C/H/D/E-X4 chelates the metal cation; (c) detecting a signal indicative of the binding of the at least one engineered binder to the N-terminally modified peptide; (d) optionally, dissociating the at least one engineered binder from the N-terminally modified peptide; (e) removing the modified NTAA residue from the N-terminally modified peptide by an agent configured for removing the modified NTAA residue, thereby exposing a new NTAA residue; and (f) optionally, repeating steps (a)-(e) one or more times for peptides of the plurality of peptides.

In some embodiments, steps of modifying NTAA residue of a peptide, contacting the modified NTAA residue with an engineered binder, and removing the modified NTAA residue in the methods disclosed herein are repeated sequentially at least one time. In each described modifying-binding-cleaving cycle, information regarding the (current)N-terminal amino acid of the target peptide can be obtained. Repeating this cycle more than one time can provide information regarding the amino acid sequence of the target peptide (both identity and order of the amino acid residues of the target peptide can be obtained).

In some embodiments, the step of detecting a signal indicative of the binding of the at least one engineered binder to the N-terminally modified peptide is postponed until one or more modifying-binding-cleaving cycles are completed (see, e.g., FIG. 1). In some of these embodiments, information regarding peptide binding events is accumulated in the nucleic acid tag associated with the analyzed peptide (e.g., accumulated in the extended recording tag, see also US 2019/0145982 A1 incorporated herein by reference and Example 7 below. In other embodiments, the step of detecting a signal indicative of the binding of the at least one engineered binder to the N-terminally modified peptide is performed after each binding step (e.g., when a fluorescent signal from a detectable label associated with the engineered binder is detected upon binding).

In some embodiments of the disclosed methods, each engineered binder of the set of engineered binders comprises a detectable label, and the detectable label is used to record binding between a polypeptide and the engineered binder. For example, the engineered binder binds to the polypeptide when the polypeptide has a cognate NTAA on its terminus; upon binding, by measuring fluorescent signal (e.g., intensity, lifetime, etc.) of the detectable label of the engineered binder on an integrated semiconductor chip, the identity of NTAA residue can be determined with certain probability. Further optical detection methods used for identification of terminal amino acid residues by binders conjugated with a detectable label are disclosed in US patent publications US 20210364527 A1, US 20210139973 A1, US 20200209257 A1, U.S. Ser. No. 11/549,942 B2, U.S. Ser. No. 11/282,586 B2, US 20210239705 A1 each of which are incorporated by reference in its entirety.

Engineered binders in the disclosed methods and compositions do not need to be strictly selective and may recognize, for example, functional classes of NTAA residues, such as negatively charged residues, positively charged residues, small hydrophobic residues, aromatic residues, and so on, or recognize other NTAA residue types. In some embodiments, at least some of engineered binders of the set of engineered binders are degenerate (each can bind more than one structure or more than one component of polypeptide). In some embodiments, degenerate engineered binders have specificity towards two or more NTAA residues. In some embodiments, specificity of each of engineered binders towards particular NTAA is not high. Use of degenerate engineered binders may reduce the overall number of engineered binders needed for successful polypeptide identification. In some embodiments, no more than 5, 6, 7, 8, 9 or 10 engineered binders having different NTAA specificities are needed for identification of at least 90% of polypeptides present in a sample.

In preferred embodiments, selectivity of each engineered binder used during the encoding assay towards NTAA resides of polypeptides is determined in advance, before performing contacting steps of the disclosed methods. Each engineered binder may be tested against a panel of peptides each having a different NTAA reside and an associated recording tag to characterize selectivity and, optionally, binding kinetics of the engineered binder for each of the 20 natural NTAA resides. When multiple alternative engineered binders exist, a set comprising minimum number of engineered binders may be selected that would cover all or a maximum number of the 20 natural NTAA resides.

In some embodiments, the methods provided herein include using a plurality of target polypeptides each associated with a recording tag in a polypeptide analysis assay. In some embodiments, the polypeptide analysis assay is performed to assess the polypeptide, or to identify or determine at least a portion of the sequence of the polypeptide macromolecule, such as disclosed in earlier published applications US 2019/0145982 A1, US 2020/0348308 A1, US 2020/0348307 A1, US 2021/0208150 A1, incorporated by reference herein.

In some embodiments, the provided methods are for generating a nucleic acid encoded library representation of the binding history of each polypeptide of the plurality of target polypeptides. This nucleic acid encoded library can be amplified, and analyzed using high-throughput next generation digital sequencing methods, enabling millions to billions of molecules to be analyzed per run. The creation of a nucleic acid encoded library of binding information is useful in another way in that it enables enrichment, subtraction, and normalization by DNA-based techniques that make use of hybridization. These DNA-based methods are easily and rapidly scalable and customizable, and more cost-effective than those available for direct manipulation of other types of macromolecule libraries, such as polypeptide libraries. Thus, nucleic acid encoded libraries of binding information can be processed prior to sequencing by one or more techniques to enrich and/or subtract and/or normalize the representation of sequences. This enables information of maximum interest to be extracted much more efficiently, rapidly and cost-effectively from very large libraries whose individual members may initially vary in abundance over many orders of magnitude.

In some embodiments, provided herein are methods for treating, analyzing and/or identifying a large plurality of polypeptides (e.g., at least 1000, 10000, 100000, 1000000 or more polypeptide molecules which comprise molecules of at least 100, 1000, 10000 or more different polypeptides) in a single assay. In some embodiments, methods provided herein comprise: providing a set of engineered binders none of which are specific for a single polypeptide or family of polypeptides, wherein each engineered binder of the set of engineered binders comprises a detectable label, a signal-generating moiety or a nucleic acid tag, and each engineered binder of the set of engineered binders have different cleavage specificities for NTAA residues; iteratively exposing the plurality of polypeptides to set of engineered binders and detecting signals generated upon binding of a engineered binder from the set to a polypeptide of the plurality of polypeptides, thereby determining a first group of the engineered binders which bind to each of the plurality of polypeptides, and, optionally, a second group of the engineered binders which do not bind to each of the plurality of polypeptides (e.g., for each polypeptides to be identified and for each binding cycle, one can determine both engineered binders that bind to the polypeptides and engineered binders that do not bind to the polypeptides). In some embodiments, it further allows to use one or more deconvolution methods based on the known binding properties of the engineered binders to match the group of the engineered binders to amino acid sequence of a polypeptide, thereby determining the identity of each of the plurality of polypeptides. In some embodiments, both known cleavage specificities of engineered binders for NTAA residues and their order of binding to the polypeptides are used to decode identify of the polypeptides.

In some embodiments, the methods provided herein are able to simultaneously identify multiple different polypeptides (such as at least 100, 1000, 10000 or more different polypeptides) within a single sample. In some embodiments, proteins from a sample can be fractionated into a plurality of fractions, and proteins in each plurality of fractions can be fragmented to polypeptides followed by barcoding of the polypeptides (e.g., by introducing a sample barcode into an associated recording tag for each polypeptide). Then, barcoded polypeptides from different fractions each conjugated to a recording tag can be pooled together and analyzed using methods and compositions disclosed herein. Fractionation, barcoding and pooling techniques are beneficial for analysis of complex biological samples, such as samples having proteins of vastly different abundances (e.g., plasma). Techniques for fractionation, barcoding and pooling are known in the art and disclosed, for example, in US 20190145982 A1, incorporated by reference herein.

In preferred embodiments of the disclosed methods, given that selectivities of each of the engineered binders towards NTAA residues are known, information regarding identity of the NTAA residue of the analyzed immobilized polypeptide is encoded in unique nucleic acid barcode present in the extended recording tag associated with each the plurality of polypeptides. This nucleic acid barcode may be used to decode the identity of the NTAA residue by using known information regarding binding kinetics and/or specificity of the engineered binders bound to the polypeptide at a given binding cycle. In some embodiments, the nucleic acid barcode may be used as an input to a probabilistic neural network which was trained to relate the sequence of the barcode to amino acid identity. Training can be performed by testing each engineered binder individually (optionally, conjugated to a coding tag) against a panel of peptides each having a different NTAA reside and an associated recording tag, collecting sequence information of the recording tags extended after the binding, and feeding the collected information to the probabilistic neural network. Alternatively, training can be performed by testing a set of engineered binders (optionally, each conjugated to a coding tag) against the panel of peptides, collecting sequence information of the recording tags extended after the binding, and feeding the collected information to the probabilistic neural network.

In some embodiments, during each encoding cycle, only single amino acid residue of the analyzed polypeptide gets encoded into the recording tag (each time it is a NTAA residue, which gets cleaved off at the end of each binding cycle). In other embodiments, a dipeptide gets encoded into the recording tag and dipeptides are cleaved between encoding cycles (e.g., by a dipeptidyl carboxypeptidase).

In some embodiments, after several cycles of contacting/transferring (also known as "encoding"), each immobilized polypeptide is back-translated into a series of unique nucleic acid barcodes on the corresponding recording tag associated with the immobilized peptide. During the analysis step, sequence of the extended recording tag can be analyzed to extract the abovementioned nucleic acid barcodes that correspond to each encoding cycle. Then, to associate the extracted nucleic acid barcodes with corresponding amino acid residues, an artificial intelligence (AI) model can be applied to calculate probabilities of occurrence of specific types of amino acid residues in corresponding places in amino acid sequence of the analyzed peptide. In preferred embodiments, the AI model can be trained using multiple known peptide sequences, which were used to generate encoding nucleic acid data on associated recording tags. Modeling encoding of multiple known peptides using known engineered binders allows for training the AI model to faithfully predict amino acid residues based on provided barcode nucleic acid sequences.

In some embodiments, the generated DNA barcodes on the extended recording tag of each polypeptides are input to a probabilistic neural network (PNN) which will learn to relate the sequence of a DNA barcode to an amino acid identity. Probabilistic neural networks (Mohebali, B., et al., Chapter 14—Probabilistic neural networks: a brief overview of theory, implementation, and application, in Handbook of Probabilistic Models, P. Samui, et al., Editors. 2020, Butterworth-Heinemann. p. 347-367) can approach Bayes optimal classification for multiclass problems such as amino acid identification from DNA barcodes (Klocker, J., et al., *Bayesian Neural Networks for Aroma Classification*. Journal of Chemical Information and Computer Sciences, 2002. 42(6): p. 1443-1449). A classifier based on PNN is guaranteed to learn and converge to an optimal classifier as the size of the representative data set increases. Probabilistic neural networks have parallel structure such that data from any amino acid residue are used to learn all other amino acid residues.

In some embodiments, the disclosed methods are used for peptide sequence determination based on probabilistic neural network ensembles. The machine learning method is characterized in that the sequence determination can be realized by the following steps: i) the peptide fragments of proteins are encoded using engineered binders into stretches of DNA sequences based on the physicochemical properties of amino acid residues; ii) a group of probabilistic neural network sub-classifiers are established, peptide fragments of proteins with known sequence are used to perform amino acid classification training and obtain a group of trained amino acid classification models; iii) the obtained models are utilized to determine peptide amino acid sequences in the test data sets; iv) the classification results output by the models are counted to generate amino acid candidate sets; v) the methods showing highest accuracy are combined to determine the amino acid sequence of protein peptide fragment; and vi) the algorithmic amino acid determination result is verified through k-fold cross-validation, where k is an integer.

In preferred embodiments of the disclosed methods and compositions, each engineered binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu), and each of the C/H/D/E amino acid residues is involved in chelation of a metal cation. In some embodiments, X1, X2, X3 and X4 sequences together comprise at least 30 amino acid residues in length, thereby allowing the combined X1-C/H/D/E-X2-C/H/D/E-X3-C/H/D/E-X4 sequence to form a 3D structure that chelates a metal cation and accommodates a modified N-terminal amino acid (NTAA) residue of the target peptide. Three indicated C/H/D/E residues form an active Zn(II) binding site within this 3D structure and each forms separate coordination bonds with the metal cation. The fourth coordination bond is formed between the metal cation and the NTM of the N-terminally modified peptide upon binding of the N-terminally modified peptide to the engineered metalloprotein binder.

In some embodiments, X1, X2, X3 and X4 together comprise at least 40, 50, 60, 70, 80, 90, 100, 150, 200 or 500 amino acid residues in length. In some embodiments, X1, X2, X3 and X4 are each any amino acid sequence comprising between 0 and 20, 0 and 50, 0 and 100, between 0 and 200, or between 0 and 500 amino acid residues in length. In some embodiments, X1, X2, X3 and X4 are each consists of an amino acid sequence comprising between 1 and 500, between 1 and 200, between 1 and 100, between 1 and 50, 1 and 20, between 2 and 100, between 3 and 100, between 5 and 100, between 5 and 200, between 10 and 200, or between 10 and 100 amino acid residues in length.

In some embodiments of the disclosed methods and compositions, each engineered binder comprises an amino acid sequence X1-H/C—X2-H/C—X3-H/C—X4, wherein H is a histidine (His) amino acid residue and C is a cysteine amino acid residue, wherein the amino acid sequence X1-H/C—X2-H/C—X3-H/C—X4 chelates a metal cation. In some embodiments of the disclosed methods and compositions, each engineered binder comprises an amino acid sequence X1-H—X2-H—X3-H—X4, wherein H is a histidine (His) amino acid residue, wherein the amino acid sequence X1-H—X2-H—X3-H—X4 chelates a metal cation (each of the three His amino acid residues is involved in chelation of a metal cation). In some embodiments of the disclosed methods and compositions, the metal cation is a zinc metal cation.

In some embodiments of the disclosed methods and compositions, the amino acid sequence X1-C/H/D/E-X2-C/H/D/E-X3-C/H/D/E-X4 comprises a metal-binding motif (e.g., a zinc-binding motif), such as one of the zinc-binding motifs known in the art. Exemplary zinc-binding motifs include (without limitation): X1-H—X2-H—X3-H—X4, X1-C—X2-C—X3-C—X4, X1-C—X2-C—X3-H—X4-C, X1-C—X2-C—X3-C—X4-C, X1-C—X2-C—X3-C—X4-H, X1-C—X2-C—X3-H-X4-H, X1-C—X2-C—X3-D-X4-C, X1-H—X2-H—X3-D-X4, X1-H—X2-H—X3-H—X4-H, X1-H—X2-H—X3-H—X4-D, X1-H—X2-H—X3-D-X4-D (see, for example, motifs recited in the known metalloprotein databases, such as Andreini C, Banci L, Bertini I, Rosato A. Zinc through the three domains of life. J Proteome Res. 2006 November; 5(11):3173-8; Putignano V, Rosato A, Banci L, Andreini C. MetalPDB in 2018: a database of metal sites in biological macromolecular structures. Nucleic Acids Res. 2018 Jan. 4; 46(D1):D459-D464; and Nakamura et al., MetalMine: a database of functional metal-binding sites in proteins, Plant Biotechnology 26, 517-521 (2009)).

In some embodiments, the amino acid sequence X1-C/H/D/E-X2-C/H/D/E-X3-C/H/D/E-X4 further comprises one or more of amino acid sequences selected from the group consisting of: one or more amino acid sequences selected from the group consisting of: (G/Q/R) (A/C/D/I/L)XX(C/F/I/V) H (F/I/L)H and H (C/L/V)X(C/D/H/L/V) (E/H/L/M/R/W/Y) N (A/N/P/S/T) (E/K/R/S/Y) (A/L/S/Y). In some embodiments, the amino acid sequence X1-C/H/D/E-X2-C/H/D/E-X3-C/H/D/E-X4 further comprises one or more amino acid sequences selected from the group consisting of: (A/C/D/I/S/V/Y)X(C/N)X(A/C/G/R/S/V)XX(C/F/I/L/T/V)X(C/G/K/N/V)X(F/I)(D/E/K/N/V) (D/E/F/N/Q), (A/S)XX(A/E/H/K/Q)(A/P/R/S/T)D(G/I/V)X(A/T/V) (I/L/M/N/R/V) and G(A/C/F/I/S)X(A/D/M/T)XPX(C/F/L)X(C/E/R)X(I/L/R/V). In some embodiments, the amino acid sequence X1-C/H/D/E-X2-C/H/D/E-X3-C/H/D/E-X4 further comprises one or more of amino acid sequences selected from the group consisting of: one or more amino acid sequences selected from the group consisting of: (A/C/D/I/S/V/Y)X(C/N)X(A/C/G/R/S/V)XX(C/F/I/L/T/V)X(C/G/K/N/V)X(F/I)(D/E/K/N/V)(D/E/F/N/Q), (G/Q/R) (A/C/D/I/L)XX(C/F/I/V) H (F/I/L) H, H (C/L/V)X(C/D/W/L/V) (E/H/L/M/R/W/Y) N (A/N/P/S/T) (E/K/R/S/Y) (A/L/S/Y), (A/S)XX(A/E/H/K/Q)

(A/P/R/S/T)D(G/I/V)X(A/T/V) (I/L/M/N/R/V) and G(A/C/F/I/S)X(A/D/M/T)XPX(C/F/L)X(C/E/R)X(I/L/R/V).

In some embodiments, the X1 amino acid sequence of the X1-C/H/D/E-X2-C/H/D/E-X3-C/H/D/E-X4 sequence comprises amino acid sequence (A/C/D/I/S/V/Y)X(C/N)X(A/C/G/R/S/V)XX(C/F/I/L/T/V)X(C/G/K/N/V)X(F/I)(D/E/K/N/V)(D/E/F/N/Q). In some embodiments, the X4 amino acid sequence of the X1-C/H/D/E-X2-C/H/D/E-X3-C/H/D/E-X4 sequence comprises amino acid sequences (A/S)XX(A/E/H/K/Q) (A/P/R/S/T)D(G/I/V)X(A/T/V) (I/L/M/N/R/V) and/or G(A/C/F/I/S)X(A/D/M/T)XPX(C/F/L)X(C/E/R)X(I/L/R/V).

In preferred embodiments, the engineered metalloprotein binder chelates a metal cation with a thermodynamic dissociation constant (Kd) of less than 1000 nM, less than 100 nM, less than 10 nM, less than 1 nM, less than 0.5 nM, less than 0.1 nM or less than 0.001 nM. In some embodiments of the disclosed methods and compositions, the metal cation is a zinc metal cation. Kd values for zinc metal cation vary greatly between different Zn-chelating proteins. For example, rhodopsin has a $Zn^{2+}$ affinity of 0.1 uM (Stojanovic, A., et al., Critical Role of Transmembrane Segment Zinc Binding in the Structure and Function of Rhodopsin. J. Biol. Chem. 279, 35932-35941 (2004)). In another example, the wild-type hCAII metalloenzyme binds Zn(II) with thermodynamic dissociation constant ($K_d$) of ~4 pM (Ippolito J A, et al., Structure-assisted redesign of a protein-zinc-binding site with femtomolar affinity. Proc Natl Acad Sci USA. 1995 May 23; 92(11):5017-21). Other natural and designed metalloproteins have zinc binding constants ($K_d$) ranging from fM to uM (Petros A K, et al., Femtomolar Zn(II) affinity in a peptide-based ligand designed to model thiolate-rich metalloprotein active sites. Inorg Chem. 2006 Dec. 11; 45(25):9941-58; Chan K L, et al., Characterization of the Zn(II) binding properties of the human Wilms' tumor suppressor protein C-terminal zinc finger peptide. Inorg Chem. 2014 Jun. 16; 53(12):6309-20). In some embodiments, the thermodynamic dissociation constant for zinc metal cation is predicted as described in Example 13. The affinity of $Zn^{2+}$ binding to proteins may depend on several factors beyond just Zn coordinating residues. For instance, the Zn binding affinity may either increase or decrease a function of pH. In addition, buffers, salts, and/or temperature can also contribute to differences in binding affinities. For the purpose of this disclosure, when it is referred to chelation of a zinc metal cation by an engineered metalloprotein binder with a thermodynamic dissociation constant (Kd), this constant is measured or predicted using conditions that are used during a binding reaction between the engineered metalloprotein binder and a target peptide having a modified NTAA residue (e.g., during calculation/measurement of the Zn Kd, pH, buffer, salt concentration, and/or temperature are set essentially the same as in the binding reaction).

In some embodiments, the engineered metalloprotein binder binds to the N-terminally modified target peptide with at least a 100-fold greater binding affinity than a model peptide that has at least 90% homology to the engineered binder over the entire sequence length, wherein the model peptide does not comprise the amino acid sequence X1-C/H/D/E-X2-C/H/D/E-X3-C/H/D/E-X4. For example, when at least one of the C/H/D/E residues of the engineered metalloprotein binder is mutated, the resulting motif is no longer capable of chelating a zinc metal cation with a thermodynamic dissociation constant (Kd) of 1000 nM or less. Such binder has a significantly reduced (such as at least 2, 5, 10, 100 or 1000 fold reduced) binding affinity towards the N-terminally modified target peptide. These reductions were calculated for exemplary binder scaffolds having sequences set forth in SEQ ID NO: 7-27 as shown in Tables 4-7 (the "Native Binder ΔKd" parameter).

In some embodiments, the engineered metalloprotein binder comprises an amino acid sequence having at least 40%, at least 50%, at least 60%, at least 70%, at least 80%, or at least 90% sequence homology to any one of the amino acid sequences selected from the group consisting of SEQ ID NO: 7-SEQ ID NO: 59, SEQ ID NO: 68-SEQ ID NO: 99 and SEQ ID NO: 105-SEQ ID NO: 135. In some embodiments, the engineered metalloprotein binder comprises an amino acid sequence having at least about 70, 75, 80, 85, 90, 95, 97, 98 or 99% sequence homology to any one of the amino acid sequences selected from the group consisting of SEQ ID NO: 7-SEQ ID NO: 59, SEQ ID NO: 68-SEQ ID NO: 99 and SEQ ID NO: 105-SEQ ID NO: 135.

In some embodiments, the engineered metalloprotein binder comprises an amino acid sequence having at least 40%, at least 50%, at least 60%, at least 70%, at least 80%, or at least 90% sequence identity to any one of the amino acid sequences selected from the group consisting of SEQ ID NO: 7-SEQ ID NO: 59, SEQ ID NO: 68-SEQ ID NO: 99 and SEQ ID NO: 105-SEQ ID NO: 135. In some embodiments, the engineered metalloprotein binder comprises an amino acid sequence having at least about 70, 75, 80, 85, 90, 95, 97, 98 or 99% sequence identity to any one of the amino acid sequences selected from the group consisting of SEQ ID NO: 7-SEQ ID NO: 59, SEQ ID NO: 68-SEQ ID NO: 99 and SEQ ID NO: 105-SEQ ID NO: 135.

In some embodiments, the engineered metalloprotein binder comprises an amino acid sequence, which differs from one of the amino acid sequences set forth in SEQ ID NO: 7, SEQ ID NO: 8, SEQ ID NO: 9, SEQ ID NO: 14, SEQ ID NO: 15, SEQ ID NO: 16, SEQ ID NO: 17, SEQ ID NO: 21, SEQ ID NO: 25, SEQ ID NO: 27, SEQ ID NO: 30, SEQ ID NO: 31, SEQ ID NO: 39, SEQ ID NO: 43 or SEQ ID NO: 68-SEQ ID NO: 74 by at least one amino acid residue in a Z-P1 binding site, or within 6 Å of the Z-P1 binding site of the engineered metalloprotein binder, wherein the Z-P1 binding site comprises one or more amino acid residues corresponding to amino acid positions 59, 64, 66, 88, 89, 91, 93, 103, 116, 118, 127, 128, 131, 137, 139, 193, 194, 195, 196, 198, 203, and 205 of SEQ ID NO: 7; or the Z-P1 binding site comprises one or more amino acid residues corresponding to amino acid positions 60, 63, 65, 68, 87, 88, 90, 92, 102, 115, 117, 127, 137, 139, 193, 194, 195, 196, 197, 198, 203, and 205 of SEQ ID NO: 8; or the Z-P1 binding site comprises one or more amino acid residues corresponding to amino acid positions 1, 2, 17, 59, 61, 64, 89, 91, 93, 103, 116, 118, 127, 131, 139, 193, 194, 195, 196, 197, 198, 199, 203, and 205 of SEQ ID NO: 9; or the Z-P1 binding site comprises one or more amino acid residues corresponding to amino acid positions 99, 100, 132-136, 190, 191, 194, 200, and 222 of SEQ ID NO: 14; or the Z-P1 binding site comprises one or more amino acid residues corresponding to amino acid positions 63-66, 83, 84, 86, 89, 92, 93, 96, 102, 149, 152-155, 158, and 175-177 of SEQ ID NO: 15; or the Z-P1 binding site comprises one or more amino acid residues corresponding to amino acid positions 117, 255, 256, 257, 258-260, 268, 270, 271, 290, 293, 294, 297, 315, 316, 377, 779, and 821 of SEQ ID NO: 16; or the Z-P1 binding site comprises one or more amino acid residues corresponding to amino acid positions 41, 58, 59, 60, 61, 62, 65, 77, 105, 107, 108, 109, 110-112, 147, 150, 151, 154, 155, 158, and 185 of SEQ ID NO: 17; or the Z-P1 binding site comprises one or more amino acid residues corresponding to amino acid positions 133-137, 153, 158, 160, 161, 169, 173, 176, 177, 180, 186, 191, 192, 209, 216, and 230 of SEQ ID NO: 21; or the Z-P1 binding site comprises one or more amino acid residues corresponding to amino acid positions 4-7, 9, 10, 14, 58, 90, 113, 134-138, 162, 181, 183-185, and 212 of SEQ ID NO: 25; or the Z-P1 binding site comprises one or more amino acid residues corresponding to amino acid positions 7, 9, 20, 104, 108, 139, 141, 164, 167, 169, 170, 171, 202, 204-210, 242, 245, and 248 of SEQ ID NO: 27; or the Z-P1 binding site comprises one or more amino acid residues corresponding to amino acid positions 90, 93, 96-99, 132, 133, 136, 142, 152, and 153 of SEQ ID NO: 30; or the Z-P1 binding site comprises one or more amino acid residues corresponding to amino acid positions 165, 166, 169, 227-230, 231, 235, 248, and 352 of SEQ ID NO: 31; or the Z-P1 binding site comprises one or more amino acid residues corresponding to amino acid positions 106-109, 141, 142, 145, 151, and 166-168 of SEQ ID NO: 39; or the Z-P1 binding site comprises one or more amino acid residues corresponding to amino acid positions 106, 107, 313-317, 325, 327, 379, 382-389, 448, 453, 506, and 564-566 of SEQ ID NO: 43; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 68; or the Z-P1 binding site comprises one or more amino acid residues corresponding to positions 62, 64, 65, 67, 88, 89, 118, 128, 129, 132, 138, 140, 196, 198, 200, 202, 204, and 205 of SEQ ID NO: 69; or the Z-P1 binding site comprises one or more amino acid residues corresponding to positions 60, 62, 63, 65, 89, 90, 119, 129, 130, 133, 134, 139, 141, 196, 198, 200, 202, 204, and 205 of SEQ ID NO: 70; or the Z-P1 binding site comprises one or more amino acid residues corresponding to positions 61, 63, 64, 66, 90, 91, 120, 130, 131, 134, 140, 197, 199, 201, 203, 205, and 206 of SEQ ID NO: 71; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 72; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 73; or the Z-P1 binding site comprises one or more amino acid residues corresponding to positions 61, 63, 64, 66, 90, 120, 129, 130, 133, 139, 141, 196, 198, 200, 202, 204, and 205 of SEQ ID NO: 74. To better accommodate Z-P1-P2-peptide in a substrate-binding pocket, the engineered metalloprotein binder can be mutated at one or more amino acid residues of the Z-P1 binding site, or at one or more amino acid residues within 6 Å of the Z-P1 binding site, which roughly corresponds to amino acid residues adjacent to the Z-P1 binding site. For example, any one amino acid residue within the Z-P1 binding site or having a Ca atom within 6 Å of the Z-P1 binding site could be mutated to any of the 20 amino acid residues. The Z-P1 binding site of the binder comprises amino acid residues that are involved in binding of the modified N-terminal amino acid (NTAA) residue of the target peptide.

In some embodiments, the engineered metalloprotein binder binds to the N-terminally modified target peptide with a thermodynamic dissociation constant (Kd) of 500 nM or less. In preferred embodiments, the engineered metalloprotein binder binds to the N-terminally modified target peptide with a thermodynamic dissociation constant (Kd) of less than 300 nM, less than 200 nM, less than 100 nM, less than 10 nM or less than 5 nM.

In some embodiments, the methods disclosed herein further comprise immobilizing the target peptide on a solid support before contacting the NTAA residue of a peptide with an engineered binder.

In some embodiments, the engineered binder comprises a detectable label or a nucleic acid tag, or a nucleic acid coding tag.

In some embodiments, the target peptide immobilized on a solid support is associated with a nucleic acid recording tag. In these embodiments, the engineered binder can comprise a nucleic acid coding tag that comprises identifying information regarding the engineered binder. Methods of encoding a history of binding events into nucleic acid sequence are disclosed in US published application US 2019/0145982 A1, and can be utilized with the methods disclosed herein.

In some embodiments, the N-terminal modifier agent is a compound of the following formula:

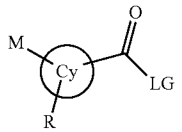

wherein:

M is a metal cation binding group that comprises sulfonamide, hydroxamic acid, sulfamate, or sulfamide;

the group

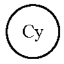

is a 5 or 6 membered aromatic ring which may contain up to three heteroatoms selected from N, O and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, and $CONHCH_3$; and LG is a leaving group. In preferred embodiments, the metal cation binding group is a Zn cation binding group (e.g., chelates $Zn^2$).

In some embodiments, LG is selected from the group consisting of N-succinimidyloxy, sulfo-N-succinimidyloxy, pentafluorophenoxy, tetrafluorophenoxy, 4-sulfo-phenoxy, and pyridinyl-2-oxy N-oxide.

Figure 6A:
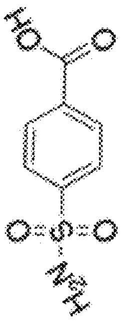
FIG. 6A-FIG. 6C. Structures of exemplary zinc-binding NTMs experimentally tested in this study. The tested NTMs are designated as M64-M98.
Figure 6A:
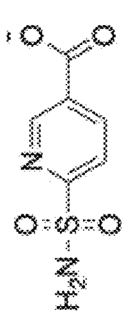
Figure 6A:
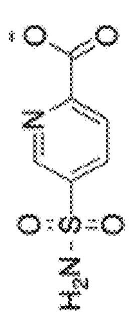
Figure 6A:
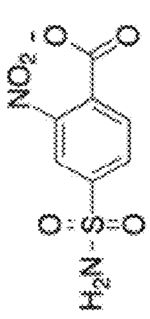
Figure 6A:
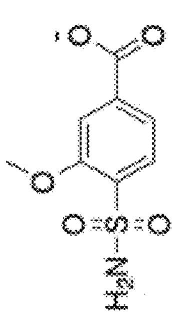
Figure 6A:
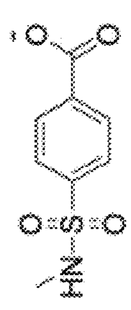
Figure 6A:
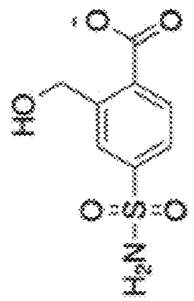
Figure 6A:
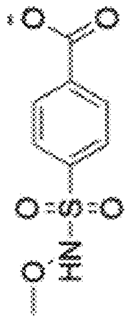
Figure 6A:
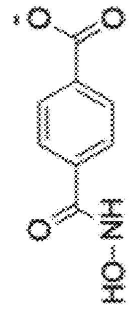
Figure 6A:
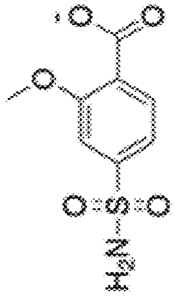
Figure 6A:
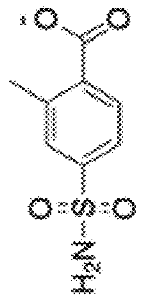
Figure 6A:
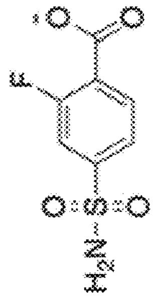
Figure 6B:
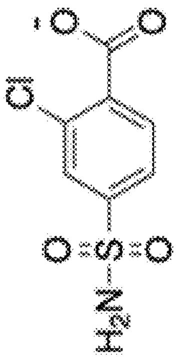
Figure 6B:
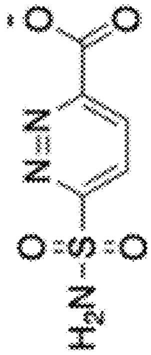
Figure 6B:
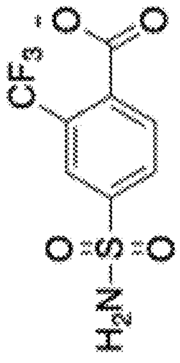
Figure 6B:
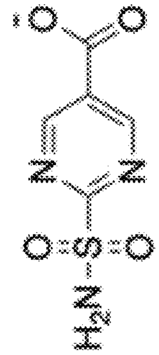
Figure 6B:
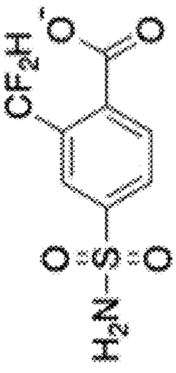
Figure 6B:
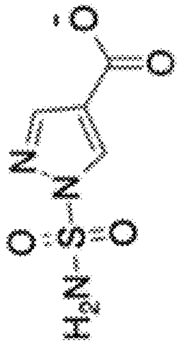
Figure 6B:
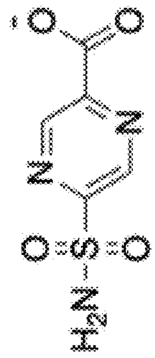
Figure 6B:
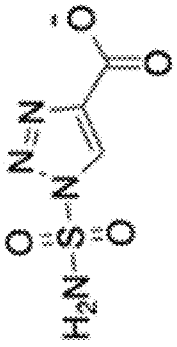
Figure 6B:
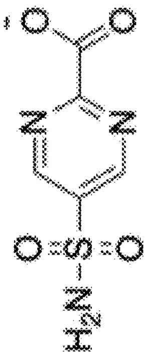
Figure 6B:
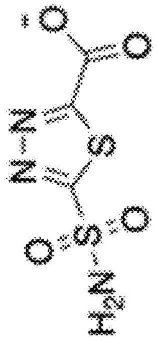
Figure 6C:
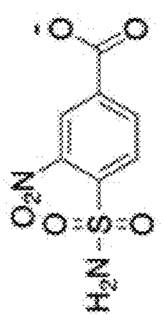
Figure 6C:
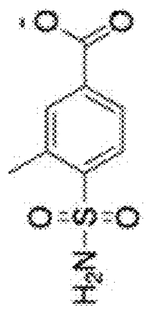
Figure 6C:
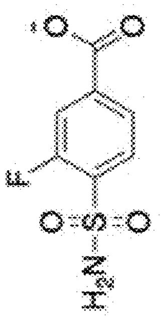
Figure 6C:
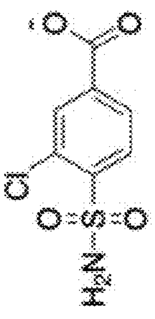
Figure 6C:
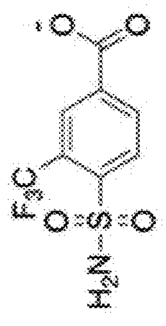
Figure 6C:
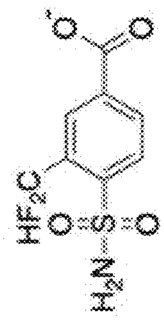
Figure 6C:
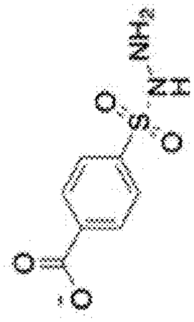
Figure 6C:
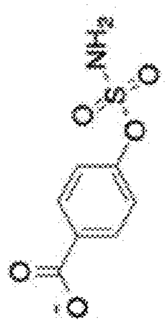
Figure 6C:
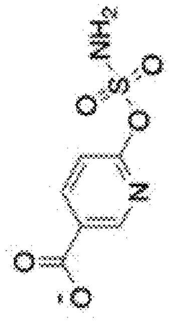
Figure 6C:
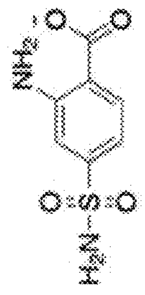
Figure 6C:
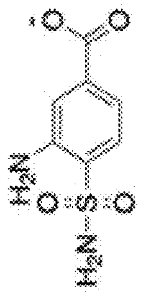
Figure 6C:
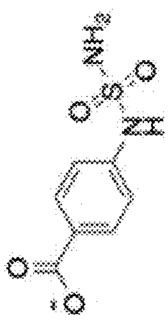

In some embodiments, the N-terminal modifier agent is one selected from the group consisting of NTM M64-NTM M98, the structures of which are shown in FIG. 6A-FIG. 6C.

In some embodiments, the N-terminal modifier agent further comprises a peptide coupling reagent.

Suitable reagents that are known in the art for performing the coupling reaction (amide bond formation) between the NTM and the NTAA include conventional peptide coupling reagents such as carbodiimides (e.g., dicyclohexyl carbodiimide (DCC), diisopropyl carbodiimide (DIPC), 1-ethyl-3-(3-dimethylaminopropyl)carbodiimide (EDC), 1-cyclohexyl-(2-morpholinoethyl)carbodiimide tosylate (CMCT), and the like), aminium/uronium salts (e.g., COMU, HATU, HBTU, TBTU, HCTU, and TSTU), phosphonium coupling reagents including PyBOP, PyAOP, PyOxim, and BOP, and phosphonate coupling reagents such as (3-(diethoxyphosphoryloxy)-1,2,3-benzotriazin-4(3H)-one)(DEPBT), and propylphosphonic anhydride (T3P). Suitable carbodiimide reagents include compounds of Formula (1) described below. Suitable aminium/uronium coupling reagents include compounds of Formula (2) described below.

In some embodiments, coupling conditions are used to minimize racemization of the NTMaa moiety of the N-terminal modifier agent during installation onto target peptides (Ramu, Vasanthakumar G., et al., "DEPBT as Coupling Reagent To Avoid Racemization in a Solution-Phase Synthesis of a Kyotorphin Derivative." 2014, Synthesis 46 (11): 1481-86).

In some embodiments, the N-terminal modifier agent comprises compound of Formula (1):

(1)

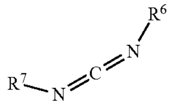

or a salt or conjugate thereof, wherein $R^6$ and $R^7$ are each independently $C_{1-6}$ alkyl, —$CO_2C_{1-4}$ alkyl, —$OR^k$, aryl, heteroaryl, cycloalkyl or heterocyclyl, wherein the $C_{1-6}$ alkyl, —$CO_2C_{1-4}$ alkyl, —$OR^k$, aryl, and cycloalkyl are each unsubstituted or substituted; and $R^k$ is H, $C_{1-6}$ alkyl, or heterocyclyl, wherein the $C_{1-6}$ alkyl and heterocyclyl are each unsubstituted or substituted; wherein heterocyclyl can be 5-8 membered ring comprising one or two heteroatoms selected from N, O and S as ring members, where the heteroaryl can be a 5-6 membered single ring or 8-10 membered bicyclic ring, each of which comprises one to three heteroatoms selected from N, O and S as ring members. Cycloalkyls include 3-7 membered carbocyclic rings, optionally substituted. Heterocyclyl can be 5-8 membered ring comprising one or two heteroatoms selected from N, O and S as ring members, and include tetrahydrofuranyl, piperidinyl, piperazinyl, dihydropyranyl, dioxanyl, and the like. Heteroaryl can be a 5-6 membered single ring or 8-10 membered bicyclic ring, each of which comprises one to three heteroatoms selected from N, O and S as ring members. Aryl includes phenyl, which can be substituted or unsubstituted. Heteroaryl includes pyridinyl, pyrimidinyl, or pyrazinyl; oxazolyl, isoxazolyl, thiazolyl, isothiazolyl, furanyl, thienyl, pyrrolidinyl, imidazolyl, pyrazolyl, and triazolyl, as well as a bicyclic group comprising any one of these fused to phenyl. Suitable substituents for the alkyl, cycloalkyl, heterocyclyl, aryl and heteroaryl groups include halo, hydroxy, amino, $C_1$-$C_2$ alkylamino, di-($C_1$-$C_2$ alkyl) amino, $C_1$-$C_2$ alkyl, $C_1$-$C_2$ alkoxy, $NO_2$, CN, $C_1$-$C_2$ haloalkyl, $C_1$-$C_2$ haloalkoxy, and halo, and for non-aromatic groups also oxo.

In some embodiments of Formula (1), $R^6$ and $R^7$ are each independently $C_{1-6}$ alkyl, 3-7 membered cycloalkyl, —$CO_2C_{1-4}$ alkyl, or aryl, especially phenyl. In some embodiments, $R^6$ and $R^7$ are each independently H, $C_{1-6}$ alkyl, phenyl, or cycloalkyl. In some embodiments, $R^6$ and $R^7$ are the same. In some embodiments, $R^6$ and $R^7$ are different.

In some embodiments, one of $R^6$ and $R^7$ is $C_{1-6}$ alkyl and the other is selected from the group consisting of $C_{1-6}$ alkyl, —$CO_2C_{1-4}$ alkyl, and —$OR^k$, wherein the $C_{1-6}$ alkyl, —$CO_2C_{1-4}$ alkyl, and —$OR^k$ are each unsubstituted or substituted. In some embodiments, one or both of $R^6$ and $R^7$ is $C_{1-6}$ alkyl, optionally substituted with aryl, such as phenyl. In some embodiments, one or both of $R^6$ and $R^7$ is $C_{1-6}$ alkyl, optionally substituted with heterocyclyl. In some embodiments, one of $R^6$ and $R^7$ is —$CO_2C_{1-4}$ alkyl and the other is selected from the group consisting of $C_{1-6}$ alkyl, —$CO_2C_{1-4}$ alkyl, and —$OR^k$, wherein the $C_{1-6}$ alkyl, —$CO_2C_{1-4}$ alkyl, and —$OR^k$ are each unsubstituted or substituted. In some embodiments, one of $R^6$ and $R^7$ is optionally substituted aryl and the other is selected from the group consisting of $C_{1-6}$ alkyl, —$CO_2C_{1-4}$ alkyl, —$OR^k$, aryl, heteroaryl, cycloalkyl and heterocyclyl, wherein the $C_{1-6}$ alkyl, —$CO_2C_{1-4}$ alkyl, —$OR^k$, aryl, and cycloalkyl are each unsubstituted or substituted. In some embodiments, one or both of $R^6$ and $R^7$ is aryl, optionally substituted with up to three groups selected from $C_{1-6}$ alkyl, halo, and $NO_2$.

In some embodiments, the N-terminal modifier agent comprises a compound of Formula (2):

(2)

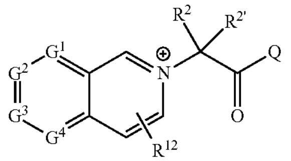

wherein Q is OH, $OR^Q$, or OM, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR;

M is a cationic counterion;

$G^1$-$G^5$ are each independently selected from CH, CJ, BN, BO, and N, provided not more than 3 of $G^1$-$G^5$ are N;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —$N(R^8)_2$, —$SR^8$, —$S(O)_nR^8$, —$NR^8SO_2R^8$, —$SO_2N(R^8)_2$, $SO_3R^8$, —$B(OR^8)_2$, $C(═O)R^8$, CN, $CON(R^8)_2$, —$COOR^B$, —C(—O)Ar, and tetrazole, where Ar represents a phenyl or 5-6 membered heteroaryl ring that is optionally substituted with one or two groups selected from halo, CN, $R^8$ and $OR^8$;

$R^2$ and $R^{2'}$ can each be the side chain of an amino acid, e.g. one of the side chains of the 20 common amino acid side chains, optionally protected amino acid side chains, post-translationally modified amino acid side chains, unnatural amino acid sidechains;

or $R^2$ and $R^{2'}$ can each be H or a group selected from aryl, heteroaryl, bicyclic aryl, bicyclic heteroaryl, and heterocyclyl, each of which is optionally substituted with one to six groups (or with one to four groups when $R^2$ or $R^{2'}$ is aromatic) selected from halo, CN, $NH_2$, $NH(CH_3)$, $N(CH_3)_2$, protected amine (e.g., N3, $NO_2$, NHFmoc, NHBoc), C(O)$NR_2$, NHC(O)R, $B(OR)_2$, aryl, heteroaryl, $C_1$-$C_2$ alkyl, $C_1$-$C_2$ haloalkyl, $C_1$-$C_2$ haloalkoxy, and —$OR^4$;

each R, $R^4$ and $R^8$ is independently selected at each occurrence from H, $C_1$-$C_2$ alkyl, and $C_1$-$C_2$ haloalkyl;

n at each occurrence is independently 1 or 2; and $R^{12}$ represents one or two optional substituents on the pyridinium ring, which are independently selected from $C_1$-$C_2$ alkyl, $C_1$-$C_2$ alkoxy, $C_1$-$C_2$ haloalkyl, $C_1$-$C_2$ haloalkoxy, and halo.

Compounds of Formula (2) also comprise an anionic counterion, typically an unreactive anionic counterion, such as halo, tetrafluoroborate, hexafluorophosphate, fluorosulfonate, trifluoromethylsulfonate, and the like.

In some embodiments, the N-terminal modifier agent comprises a compound of Formula (3):

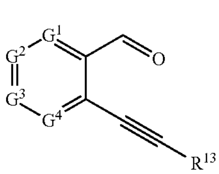

(3)

wherein:

$G^1$-$G^4$ are each independently selected from CH, CJ, and N, provided not more than 3 of $G^1$-$G^4$ are N;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —$N(R^8)_2$, —$SR^8$, —$S(O)_nR^8$, —$NR^8SO_2R^8$, —$SO_2N(R^8)_2$, $SO_3R^8$, —$B(OR^8)_2$, $C(=O)R^8$, CN, $CON(R^8)_2$, —$COOR^8$, —C(—O)Ar, and tetrazole, where Ar represents a phenyl or 5-6 membered heteroaryl ring that is optionally substituted with one or two groups selected from halo, CN, $R^8$ and $OR^8$;

each $R^8$ is independently selected from H, $C_1$-$C_2$ alkyl, and $C_1$-$C_2$ haloalkyl;

n at each occurrence is independently 1 or 2; and $R^{13}$ is selected from H, $C_1$-$C_2$ alkyl, $C_1$-$C_2$ alkoxy, $C_1$-$C_2$ haloalkyl, and $C_1$-$C_2$ haloalkoxy.

In some embodiments, the N-terminal modifier agent comprises a compound selected from the group consisting of compounds of the following formula:

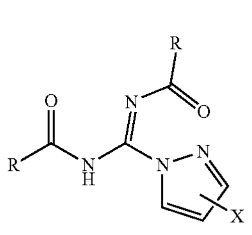

(A)

wherein R is $CH_3$, $CF_3$, $OC(CH_3)_3$, or $OCH_2C_6H_5$, and X is H, $CH_3$, $CF_3$, $CF_2H$, or $OCH_3$;

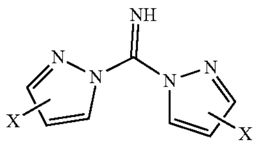

(B)

wherein X is H, $CH_3$, $CF_3$, $CF_2H$, $OCH_3$, or $SO_2NH_2$;

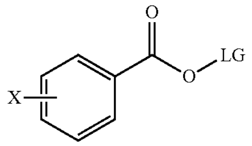

(C)

wherein X is H, F, Cl, $OCH_3$, $OCF_3$, CN, or $SO_2NH_2$, and LG is succinimide, pentafluorophenyl, or tetrafluorophenyl;

and

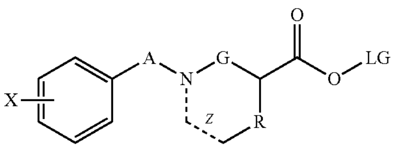

(D)

wherein X is H, F, Cl, $NH_2$, $OCH_3$, $OCF_3$, CN, or $SO_2NH_2$, A=CONH or $SO_2$, G=0 or 1 $CH_2$, R is any amino acid or unnatural amino acid, and Z ring=0 (not there), 1, 2, or 3 $CH_2$.

When a compound of Formula (3) reacts with a target polypeptide, it forms a bicyclic group of Formula 4:

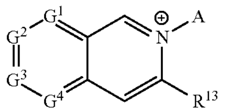

(4)

wherein A represents the point of attachment of the group to P1 of a target polypeptide;

$G^1$-$G^4$ are each independently selected from CH, CJ, and N, provided not more than 3 of $G^1$-$G^4$ are N;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —$N(R^8)_2$, —$SR^8$, —$S(O)_nR^8$, —$NR^8SO_2R^8$, —$SO_2N(R^8)_2$, $SO_3R^8$, —$B(OR^8)_2$, $C(=O)R^8$, CN, $CON(R^8)_2$, —$COOR^8$, —C(—O)Ar, and tetrazole, where Ar represents a phenyl or 5-6 membered heteroaryl ring that is optionally substituted with one or two groups selected from halo, CN, $R^9$ and $OR^9$;

each $R^8$ and each $R^9$ is independently selected from H, $C_1$-$C_2$ alkyl, and $C_1$-$C_2$ haloalkyl;

n at each occurrence is independently 1 or 2; and $R^{13}$ is selected from H, $C_1$-$C_2$ alkyl, $C_1$-$C_2$ alkoxy, $C_1$-$C_2$ haloalkyl, and $C_1$-$C_2$ haloalkoxy.

Therefore, in some embodiments, the modified target polypeptide is of Formula M-P1-P2-polypeptide, wherein M is the moiety of Formula (4). In some particular embodiments, the reagent of Formula (3) used to attach M to the target polypeptide's NTAA is 4-(sulfamoyl)-2-ethynylbenzaldehyde, and the group M in the modified target polypeptides of the Formula M-P1-P2-polypeptide is an 6-(sulfamoyl)isoquinolinium of Formula (4), where $G^1$, $G^2$, and $G^4$ are CH, $G^3$ is CJ, where J is comprised of —$SO_2(R^8)_2$ where $R^8$ is H.

Compounds of Formula (4) also comprise an anionic counterion, typically an unreactive anionic counterion, such as halo, tetrafluoroborate, hexafluorophosphate, fluorosulfonate, trifluoromethylsulfonate, and the like.

Unlike compounds of Formulas (1)-(2) where Q is OH or OM, which require a peptide coupling agent, when the NTM is a compound of Formula (3), no coupling agent is needed, as the ethynyl arylaldehyde reacts directly with the free amine of the NTAA.

$R^2$ for compounds of Formulas (1)-(2) can in particular be a side chain of an amino acid selected from alanine, aspartic acid, asparagine, glutamic acid, glutamine, glycine, (2-, 3-, or 4-pyridyl-)alanine, phenylglycine, 4-fluorophenylglycine, leucine, norleucine, isoleucine, cycloleucine, valine, dimethylglycine, methionine, methionine sulfoxide, phenylalanine, halophenylalanine, haloalkylphenylalanine, cyclopropylalanine, (2-thienyl)alanine, cyclopropylglycine, serine, phosphoserine, threonine, phosphothreonine, cysteine, carbamidomethylcysteine, trifluoromethylcysteine, tyrosine, phosphotyrosine, tryptophan, histidine, acetyllysine, proline, (2- or 3-)azetidine carboxylic acid, piperidine carboxylic acid, methylated lysine, citrulline, nitroarginine, and norvaline. In some embodiments, $R^{2'}$ is H.

Where Q is —$OR^Q$ in any of Formulas (1)-(2), RQ is typically an electron-deficient aryl or heteroaryl group. Suitable options include benzotriazolyl, halobenzotriazolyl, pyridinotriazolyl, benzotriazolyl-N-oxide, pyridinotriazolyl-N-oxide, —N-succinimide, 1-cyano-2-ethoxy-2-oxoethylideneamino, —N-phthalimide, 4-nitrophenyl, 2,4-dinitrophenyl, 4-fluorophenyl, 2,4-difluorophenyl, 2,3,4,5,6-pentafluorophenyl, 2,3,5,6-tetrafluorophenyl, and 4-sulfo-2,3,5,6,tetrafluorophenyl.

In compounds of Formula (3), each of $G^1$-$G^5$ is typically N or CJ, and preferably no more than two of them in any compound is N. In some embodiments, each J is selected from H, amino, halo, hydroxy, $CF_3$, $OCF_3$ $NO_2$, $SO_2Me$, $SO_2NR_2$, methoxy, methyl, phenyl, and —$B(OR)_2$ where each R is independently H or $C_{1-2}$ alkyl.

In yet another embodiment, provided herein is a method of treating a target peptide, the method comprises:

(a) contacting the target peptide with an N-terminal modifier agent to form an N-terminally modified peptide having a formula: Z-P1-P2-peptide, wherein Z is an N-terminal modification capable of coordinating or chelating a metal cation, P1-P2-peptide is a target peptide before modification with the N-terminal modifier agent, Z-P1 is a modified N-terminal amino acid (NTAA) residue of the target peptide, and P2 is a penultimate terminal amino acid residue of the target peptide; and (b) contacting an engineered metalloprotein binder with the N-terminally modified target peptide to allow the engineered binder to specifically bind to the N-terminally modified target peptide through interaction between the engineered binder and the modified NTAA residue of the N-terminally modified target peptide, wherein the engineered binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates a metal cation with a thermodynamic dissociation constant of 1000 nM or less.

In some embodiments, the engineered metalloprotein binder binds to the N-terminally modified target peptide with at least a 100-fold greater binding affinity than a model peptide that has at least 90% homology to the engineered binder over the entire sequence length, wherein the model peptide does not comprise the amino acid sequence X1-C/H/D/E-X2-C/H/D/E-X3-C/H/D/E-X4.

In some embodiments, the engineered metalloprotein binder comprises an amino acid sequence having at least 40%, at least 50%, at least 60%, at least 70%, at least 80%, or at least 90% sequence identity to any one of the amino acid sequences selected from the group consisting of SEQ ID NO: 7-SEQ ID NO: 59, SEQ ID NO: 68-SEQ ID NO: 99 and SEQ ID NO: 105-SEQ ID NO: 135.

In some embodiments, the engineered metalloprotein binder comprises an amino acid sequence, which differs from one of the amino acid sequences set forth in SEQ ID NO: 7, SEQ ID NO: 8, SEQ ID NO: 9, SEQ ID NO: 14, SEQ ID NO: 15, SEQ ID NO: 16, SEQ ID NO: 17, SEQ ID NO: 21, SEQ ID NO: 25, SEQ ID NO: 27, SEQ ID NO: 30, SEQ ID NO: 31, SEQ ID NO: 39, SEQ ID NO: 43 or SEQ ID NO: 68-SEQ ID NO: 74 by at least one amino acid residue in a Z-P1 binding site, or within 6 Å of the Z-P1 binding site of the engineered metalloprotein binder, wherein the Z-P1 binding site comprises one or more amino acid residues corresponding to amino acid positions 59, 64, 66, 88, 89, 91, 93, 103, 116, 118, 127, 128, 131, 137, 139, 193, 194, 195, 196, 198, 203, and 205 of SEQ ID NO: 7; or the Z-P1 binding site comprises one or more amino acid residues corresponding to amino acid positions 60, 63, 65, 68, 87, 88, 90, 92, 102, 115, 117, 127, 137, 139, 193, 194, 195, 196, 197, 198, 203, and 205 of SEQ ID NO: 8; or the Z-P1 binding site comprises one or more amino acid residues corresponding to amino acid positions 1, 2, 17, 59, 61, 64, 89, 91, 93, 103, 116, 118, 127, 131, 139, 193, 194, 195, 196, 197, 198, 199, 203, and 205 of SEQ ID NO: 9; or the Z-P1 binding site comprises one or more amino acid residues corresponding to amino acid positions 99, 100, 132-136, 190, 191, 194, 200, and 222 of SEQ ID NO: 14; or the Z-P1 binding site comprises one or more amino acid residues corresponding to amino acid positions 63-66, 83, 84, 86, 89, 92, 93, 96, 102, 149, 152-155, 158, and 175-177 of SEQ ID NO: 15; or the Z-P1 binding site comprises one or more amino acid residues corresponding to amino acid positions 117, 255, 256, 257, 258-260, 268, 270, 271, 290, 293, 294, 297, 315, 316, 377, 779, and 821 of SEQ ID NO: 16; or the Z-P1 binding site comprises one or more amino acid residues corresponding to amino acid positions 41, 58, 59, 60, 61, 62, 65, 77, 105, 107, 108, 109, 110-112, 147, 150, 151, 154, 155, 158, and 185 of SEQ ID NO: 17; or the Z-P1 binding site comprises one or more amino acid residues corresponding to amino acid positions 133-137, 153, 158, 160, 161, 169, 173, 176, 177, 180, 186, 191, 192, 209, 216, and 230 of SEQ ID NO: 21; or the Z-P1 binding site comprises one or more amino acid residues corresponding to amino acid positions 4-7, 9, 10, 14, 58, 90, 113, 134-138, 162, 181, 183-185, and 212 of SEQ ID NO: 25; or the Z-P1 binding site comprises one or more amino acid residues corresponding to amino acid positions 7, 9, 20, 104, 108, 139, 141, 164, 167, 169, 170, 171, 202, 204-210, 242, 245, and 248 of SEQ ID NO: 27; or the Z-P1 binding site comprises one or more amino acid residues corresponding to amino acid positions 90, 93, 96-99, 132, 133, 136, 142, 152, and 153 of SEQ ID NO: 30; or the Z-P1 binding site comprises one or more amino acid residues corresponding to amino acid positions 165, 166, 169, 227-230, 231, 235, 248, and 352 of SEQ ID NO: 31; or the Z-P1 binding site comprises one or more amino acid residues corresponding to amino acid positions 106-109, 141, 142, 145, 151, and 166-168 of SEQ ID NO: 39; or the Z-P1 binding site comprises one or more amino acid residues corresponding to amino acid positions 106, 107, 313-317, 325, 327, 379, 382-389, 448, 453, 506, and 564-566 of SEQ ID NO: 43; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 68; or the Z-P1 binding site comprises one or more amino acid residues corresponding to positions 62, 64, 65, 67, 88, 89, 118, 128, 129, 132, 138, 140, 196, 198, 200, 202, 204, and 205 of SEQ ID NO: 69; or the Z-P1 binding site comprises one or more amino acid residues corresponding to positions 60, 62, 63, 65, 89, 90, 119, 129, 130, 133, 134, 139, 141, 196, 198, 200, 202, 204, and 205 of SEQ ID NO: 70; or the Z-P1 binding site comprises one or more amino acid residues corresponding to positions 61, 63, 64, 66, 90, 91, 120, 130, 131, 134, 140, 197, 199, 201, 203, 205, and 206 of SEQ ID NO: 71; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 72; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 73; or the Z-P1 binding site comprises one or more amino acid residues corresponding to positions 61, 63, 64, 66, 90, 120, 129, 130, 133, 139, 141, 196, 198, 200, 202, 204, and 205 of SEQ ID NO: 74.

In some embodiments, the engineered metalloprotein binder binds to the N-terminally modified target peptide with a thermodynamic dissociation constant ($K_d$) of 500 nM or less.

In some embodiments, the engineered metalloprotein binder comprises a detectable label or a nucleic acid tag.

Exemplary Embodiments

The following enumerated embodiments represent certain embodiments and examples of the invention:

1. A method for obtaining an information regarding at least one amino acid residue of a peptide, comprising the steps of:
a) contacting a peptide with a first N-terminal modifier agent to form a N-terminally modified peptide having a formula:
Z1-P1-P2-peptide, wherein P1 is a N-terminal amino acid residue of the peptide, P2 is a penultimate terminal amino acid residue of the peptide, and Z1 is an N-terminal modification capable of coordinating or chelating a metal ion M1;
b) providing a first metalloprotein binder that binds to the metal ion M1 and allowing specific binding between the Z1-P1-P2-peptide, the first metalloprotein binder and the metal ion M1, wherein the binding specificity between the first metalloprotein binder and the Z1-P1-P2-peptide is predominantly or substantially determined by interaction between the first metalloprotein binder and a Z1-P1 group of the Z1-P1-P2-peptide;
c) obtaining an information regarding the first metalloprotein binder; and
d) obtaining an information regarding the P1 amino acid residue of the peptide based on the obtained information regarding the first metalloprotein binder.
2. The method of embodiment 1, wherein at step (b) a first set of metalloprotein binders comprising the first metalloprotein binder is provided, and each metalloprotein binder from the first set of metalloprotein binders binds to the metal ion M1.
3. The method of embodiment 1, further comprising the following steps:
i) cleaving a peptide bond between P1 and P2 of the Z-P1-P2-peptide to form a second peptide having P2 as a new N-terminal amino acid residue;
ii) contacting the peptide with a second N-terminal modifier agent to form a N-terminally modified peptide having a formula: Z2-P2-peptide, wherein Z2 is an N-terminal modification capable of coordinating or chelating a metal ion M2;
iii) providing a second metalloprotein binder that binds to the metal ion M2 and allowing specific binding between the Z2-P2-peptide, the second metalloprotein binder and the metal ion M2, wherein the binding specificity between the second metalloprotein binder and the Z2-P2-peptide is predominantly or substantially determined by interaction between the second metalloprotein binder and a Z2-P2 group of the Z2-P2-peptide;
iv) obtaining an information regarding the second metalloprotein binder; and
v) obtaining an information regarding the P2 amino acid residue of the peptide based on the obtained information regarding the second metalloprotein binder.
4. The method of embodiment 2, further comprising the following steps:
i) cleaving a peptide bond between P1 and P2 of the Z-P1-P2-peptide to form a second peptide having P2 as a new N-terminal amino acid residue;
ii) contacting the peptide with a second N-terminal modifier agent to form a N-terminally modified peptide having a formula: Z2-P2-peptide, wherein Z2 is an N-terminal modification capable of coordinating or chelating a metal ion M2;
iii) providing a second set of metalloprotein binders comprising a second metalloprotein binder, wherein each metalloprotein binder from the second set of metalloprotein binders binds to the metal ion M2, and allowing specific binding between the Z2-P2-peptide, the second metalloprotein binder and the metal ion M2, wherein the binding specificity between the second metalloprotein binder and the Z2-P2-peptide is predominantly or substantially determined by interaction between the second metalloprotein binder and a Z2-P2 group of the Z2-P2-peptide;
iv) obtaining an information regarding the second metalloprotein binder; and
v) obtaining an information regarding P2 amino acid residue of the peptide based on the obtained information regarding the second metalloprotein binder.
5. The method of embodiment 3 or 4, wherein the first N-terminal modifier agent is the same as the second N-terminal modifier agent, and Z1 is the same as Z2. 6. The method of any one of embodiments 3-5, wherein the first set of metalloprotein binders is the same as the second set of metalloprotein binders, and M1 is the same as M2. 7. The method of any one of embodiments 1-6, wherein the peptide is immobilized to a solid support.
8. The method of any one of embodiments 3-7, wherein the peptide bond between the P1 and P2 is cleaved using a chemical agent or an enzyme.
9. The method of any one of embodiments 1-6, wherein the metal ion M is Zn(II).

10. The method of any one of embodiments 3-9, wherein the first metalloprotein binder has an affinity for the Z1-P1 group of the Z1-P1-P2-peptide with a $K_d$ of less than 500 nM and the second metalloprotein binder has an affinity for the Z2-P2 group of the Z2-P2-peptide with a $K_d$ of less than 500 nM.

11. The method of any one of embodiments 1-10, wherein obtaining an information regarding P1 amino acid residue comprises identifying P1 amino acid residue.

12. The method of any one of embodiments 1-11, wherein providing the peptide comprises providing the peptide associated with a recording tag immobilized on a solid support;

the first metalloprotein binder is associated with a coding tag comprising identifying information regarding the first metalloprotein binder;

obtaining an information regarding the first metalloprotein binder comprises, upon binding of the first metalloprotein binder to the first N-terminally modified peptide, transferring identifying information from the coding tag to the recording tag associated with the immobilized peptide to generate an extended recording tag; and obtaining an information regarding P1 amino acid residue of the peptide comprises analyzing the extended recording tag by a sequencing method.

13. The method of any one of embodiments 1-17, wherein the first metalloprotein binder is fluorescently labeled; and identifying P1 amino acid residue of the peptide comprises detecting the fluorescence from the first metalloprotein binder.

14. A method of treating a target peptide, the method comprises the following steps:

(a) contacting the target peptide with an N-terminal modifier agent to form an N-terminally modified peptide having a formula: Z-P1-P2-peptide, wherein Z is an N-terminal modification capable of coordinating or chelating a metal cation, P1-P2-peptide is a target peptide before modification with the N-terminal modifier agent, Z-P1 is a modified N-terminal amino acid (NTAA) residue of the target peptide, and P2 is a penultimate terminal amino acid residue of the target peptide; and (b) contacting an engineered metalloprotein binder with the N-terminally modified target peptide to allow the engineered binder to specifically bind to the N-terminally modified target peptide through interaction between the engineered binder and the modified NTAA residue of the N-terminally modified target peptide, wherein the engineered binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates a metal cation with a thermodynamic dissociation constant of 1000 nM or less. In preferred embodiments, X1, X2, X3 and X4 together comprise at least 30 amino acid residues in length.

15. The method of embodiment 14, wherein the engineered metalloprotein binder binds to the N-terminally modified target peptide with at least a 100-fold greater binding affinity than a model peptide that has at least 90% homology to the engineered binder over the entire sequence length, wherein the model peptide does not comprise the amino acid sequence X1-C/H/D/E-X2-C/H/D/E-X3-C/H/D/E-X4.

16. The method of embodiment 14 or embodiment 15, wherein the engineered metalloprotein binder comprises an amino acid sequence having at least 40%, at least 50%, at least 60%, at least 70%, at least 80%, or at least 90% sequence identity to any one of the amino acid sequences selected from the group consisting of SEQ ID NO: 7-SEQ ID NO: 59, SEQ ID NO: 68-SEQ ID NO: 99 and SEQ ID NO: 105-SEQ ID NO: 135.

17. The method of any one of embodiments 14-16, wherein the engineered metalloprotein binder comprises an amino acid sequence, which differs from one of the amino acid sequences set forth in SEQ ID NO: 7, SEQ ID NO: 8, SEQ ID NO: 9, SEQ ID NO: 14, SEQ ID NO: 15, SEQ ID NO: 16, SEQ ID NO: 17, SEQ ID NO: 21, SEQ ID NO: 25, SEQ ID NO: 27, SEQ ID NO: 30, SEQ ID NO: 31, SEQ ID NO: 39, SEQ ID NO: 43 or SEQ ID NO: 68-SEQ ID NO: 74 by at least one amino acid residue in a Z-P1 binding site, or within 6 Å of the Z-P1 binding site of the engineered metalloprotein binder, wherein the Z-P1 binding site comprises one or more amino acid residues corresponding to amino acid positions 59, 64, 66, 88, 89, 91, 93, 103, 116, 118, 127, 128, 131, 137, 139, 193, 194, 195, 196, 198, 203, and 205 of SEQ ID NO: 7; or the Z-P1 binding site comprises one or more amino acid residues corresponding to amino acid positions 60, 63, 65, 68, 87, 88, 90, 92, 102, 115, 117, 127, 137, 139, 193, 194, 195, 196, 197, 198, 203, and 205 of SEQ ID NO: 8; or the Z-P1 binding site comprises one or more amino acid residues corresponding to amino acid positions 1, 2, 17, 59, 61, 64, 89, 91, 93, 103, 116, 118, 127, 131, 139, 193, 194, 195, 196, 197, 198, 199, 203, and 205 of SEQ ID NO: 9; or the Z-P1 binding site comprises one or more amino acid residues corresponding to amino acid positions 99, 100, 132-136, 190, 191, 194, 200, and 222 of SEQ ID NO: 14; or the Z-P1 binding site comprises one or more amino acid residues corresponding to amino acid positions 63-66, 83, 84, 86, 89, 92, 93, 96, 102, 149, 152-155, 158, and 175-177 of SEQ ID NO: 15; or the Z-P1 binding site comprises one or more amino acid residues corresponding to amino acid positions 117, 255, 256, 257, 258-260, 268, 270, 271, 290, 293, 294, 297, 315, 316, 377, 779, and 821 of SEQ ID NO: 16; or the Z-P1 binding site comprises one or more amino acid residues corresponding to amino acid positions 41, 58, 59, 60, 61, 62, 65, 77, 105, 107, 108, 109, 110-112, 147, 150, 151, 154, 155, 158, and 185 of SEQ ID NO: 17; or the Z-P1 binding site comprises one or more amino acid residues corresponding to amino acid positions 133-137, 153, 158, 160, 161, 169, 173, 176, 177, 180, 186, 191, 192, 209, 216, and 230 of SEQ ID NO: 21; or the Z-P1 binding site comprises one or more amino acid residues corresponding to amino acid positions 4-7, 9, 10, 14, 58, 90, 113, 134-138, 162, 181, 183-185, and 212 of SEQ ID NO: 25; or the Z-P1 binding site comprises one or more amino acid residues corresponding to amino acid positions 7, 9, 20, 104, 108, 139, 141, 164, 167, 169, 170, 171, 202, 204-210, 242, 245, and 248 of SEQ ID NO: 27; or the Z-P1 binding site comprises one or more amino acid residues corresponding to amino acid positions 90, 93, 96-99, 132, 133, 136, 142, 152, and 153 of SEQ ID NO: 30; or the Z-P1 binding site comprises one or more amino acid residues corresponding to amino acid positions 165, 166, 169, 227-230, 231, 235, 248, and 352 of SEQ ID NO: 31; or the Z-P1 binding site comprises one or more amino acid residues corresponding to amino acid positions 106-109, 141, 142, 145, 151, and 166-168 of SEQ ID NO: 39; or the Z-P1 binding site comprises one or more amino acid residues corresponding to amino acid positions 106, 107, 313-317, 325, 327, 379, 382-389, 448, 453, 506, and 564-566 of SEQ ID NO: 43; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 68; or the Z-P1 binding site comprises one or more amino acid residues corresponding to positions 62, 64, 65, 67, 88, 89, 118, 128, 129, 132, 138, 140, 196, 198, 200, 202, 204, and 205 of SEQ ID NO: 69; or the Z-P1 binding site comprises one or more amino acid residues corresponding to positions 60, 62, 63, 65, 89, 90, 119, 129, 130, 133, 134, 139, 141, 196, 198, 200, 202, 204, and 205 of SEQ ID NO: 70; or the Z-P1 binding site comprises one or more amino acid residues corresponding to positions 61, 63, 64, 66, 90, 91, 120, 130, 131, 134, 140, 197, 199, 201, 203, 205, and 206 of SEQ ID NO: 71; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 72; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 73; or the Z-P1 binding site comprises one or more amino acid residues corresponding to positions 61, 63, 64, 66, 90, 120, 129, 130, 133, 139, 141, 196, 198, 200, 202, 204, and 205 of SEQ ID NO: 74.

18. The method of any one of embodiments 14-17, wherein the N-terminal modifier agent is a compound of the following formula:

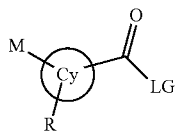

wherein:

M is a metal cation binding group that comprises sulfonamide, hydroxamic acid, sulfamate, or sulfamide;

the group

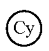

is a 5 or 6 membered aromatic ring which may contain up to three heteroatoms selected from N, O and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, and $CONHCH_3$; and LG is a leaving group.

19. The method of embodiment 18, wherein LG is selected from the group consisting of N-succinimidyloxy, sulfo-N-succinimidyloxy, pentafluorophenoxy, tetrafluorophenoxy, 4-sulfo-phenoxy, and pyridinyl-2-oxy N-oxide.

20. The method of any one of embodiments 14-19, wherein the engineered metalloprotein binder binds to the N-terminally modified target peptide with a thermodynamic dissociation constant ($K_d$) of 500 nM or less.

21. The method of any one of embodiments 14-20, further comprising step (c): removing the modified NTAA residue from the N-terminally modified target peptide, thereby exposing a new NTAA residue.

22. The method of embodiment 21, wherein steps (a), (b) and (c) are repeated sequentially at least one time.

23. The method of any one of embodiments 14-22, further comprising immobilizing the target peptide on a solid support before step (a).

24. The method of embodiment 23, wherein the target peptide immobilized on a solid support is associated with a nucleic acid recording tag.

25. The method of any one of embodiments 14-24, wherein the engineered binder comprises a detectable label or a nucleic acid tag or a nucleic acid coding tag.

26. The method of any one of embodiments 14-25, wherein the N-terminal modifier agent further comprises a peptide coupling reagent.

27. The method of embodiment 26, wherein the peptide coupling reagent is a compound of Formula (1) or (2), wherein:

Formula (1) is (1)

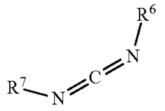

or a salt or conjugate thereof, wherein $R^6$ and $R^7$ are each independently $C_{1-6}$ alkyl, —$CO_2C_{1-4}$ alkyl, —ORk, aryl, heteroaryl, cycloalkyl or heterocyclyl, wherein the $C_{1-6}$ alkyl, —$CO_2C_{1-4}$ alkyl, —ORk, aryl, and cycloalkyl are each unsubstituted or substituted; and Rk is H, $C_{1-6}$ alkyl, or heterocyclyl, wherein the $C_{1-6}$ alkyl and heterocyclyl are each unsubstituted or substituted; wherein heterocyclyl can be 5-8 membered ring comprising one or two heteroatoms selected from N, O and S as ring members, where the heteroaryl can be a 5-6 membered single ring or 8-10 membered bicyclic ring, each of which comprises one to three heteroatoms selected from N, O and S as ring members; and Formula (2) is:

(2)

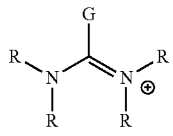

wherein:

each R is independently $C_{1-4}$ alkyl, optionally substituted with up to three groups selected from halo, $C_{1-2}$ alkoxy, $C_{1-2}$ haloalkyl, and $C_{1-2}$ haloalkoxy; and two R groups on the same N can optionally cyclize to form a 5-7 membered ring optionally containing an additional heteroatom selected from N, O and S as a ring member, and optionally substituted with one or two groups selected from oxo, $C_{1-2}$ alkyl, $C_{1-2}$ alkoxy, $C_{1-2}$ haloalkyl, and $C_{1-2}$ haloalkoxy; and G is selected from the group consisting of halo, benzotriazolyloxy, halobenzotriazolyloxy, pyridinotriazolyloxy, benzotriazolyl-N-oxide, pyridinotriazolyl-N-oxide, —O—(N-succinimide), 1-cyano-2-ethoxy-2-oxoethylideneaminooxy, and —O—(N-phthalimide).

28. The method of embodiment 26, wherein the peptide coupling reagent is selected from the group consisting of dicyclohexyl carbodiimide (DCC), diisopropyl carbodiimide (DIPC), 1-ethyl-3-(3-dimethylaminopropyl) carbodiimide (EDC), 1-cyclohexyl-(2-morpholinoethyl)carbodiimide tosylate (CMCT), COMU, HATU, HBTU, TBTU, HCTU, and TSTU, PyBOP, PyAOP, PyOxim, and BOP, and (3-(diethoxyphosphoryloxy)-1,2,3-benzotriazin-4(3H)-one)(DEPBT).

29. An engineered metalloprotein binder that specifically binds to an N-terminally modified target peptide modified by an N-terminal modifier agent, wherein:

a) the N-terminally modified target peptide has a formula: Z-P1-P2-peptide, wherein Z is an N-terminal modification capable of coordinating or chelating a metal cation, P1-P2-peptide is a target peptide before modification with the N-terminal modifier agent, Z-P1 is a modified N-terminal amino acid (NTAA) residue of the target peptide, and P2 is a penultimate terminal amino acid residue of the target peptide;

b) the engineered metalloprotein binder specifically binds to the N-terminally modified target peptide through interaction between the engineered metalloprotein binder and the Z-P1 of the N-terminally modified target peptide; and c) the engineered metalloprotein binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates a metal cation with a thermodynamic dissociation constant of 1000 nM or less. In preferred embodiments, X1, X2, X3 and X4 together comprise at least 30 amino acid residues in length.

30. The binder of embodiment 29, which binds to the N-terminally modified target peptide with at least a 100-fold greater binding affinity than a model peptide that has at least 90% homology to the engineered binder over the entire sequence length, wherein the model peptide does not comprise the amino acid sequence X1-C/H/D/E-X2-C/H/D/E-X3-C/H/D/E-X4.

31. The binder of embodiment 29 or embodiment 30, which comprises an amino acid sequence having at least 40%, at least 50%, at least 60%, at least 70%, at least 80%, or at least 90% sequence identity to any one of the amino acid sequences selected from the group consisting of SEQ ID NO: 7-SEQ ID NO: 59, SEQ ID NO: 68-SEQ ID NO: 99 and SEQ ID NO: 105-SEQ ID NO: 135.

32. The binder of any one of embodiments 29-31, which comprises an amino acid sequence, which differs from one of the amino acid sequences set forth in SEQ ID NO: 7, SEQ ID NO: 8, SEQ ID NO: 9, SEQ ID NO: 14, SEQ ID NO: 15, SEQ ID NO: 16, SEQ ID NO: 17, SEQ ID NO: 21, SEQ ID NO: 25, SEQ ID NO: 27, SEQ ID NO: 30, SEQ ID NO: 31, SEQ ID NO: 39, SEQ ID NO: 43 or SEQ ID NO: 68-SEQ ID NO: 74 by at least one amino acid residue in a Z-P1 binding site, or within 6 Å of the Z-P1 binding site of the engineered metalloprotein binder, wherein the Z-P1 binding site comprises one or more amino acid residues corresponding to amino acid positions 59, 64, 66, 88, 89, 91, 93, 103, 116, 118, 127, 128, 131, 137, 139, 193, 194, 195, 196, 198, 203, and 205 of SEQ ID NO: 7; or the Z-P1 binding site comprises one or more amino acid residues corresponding to amino acid positions 60, 63, 65, 68, 87, 88, 90, 92, 102, 115, 117, 127, 137, 139, 193, 194, 195, 196, 197, 198, 203, and 205 of SEQ ID NO: 8; or the Z-P1 binding site comprises one or more amino acid residues corresponding to amino acid positions 1, 2, 17, 59, 61, 64, 89, 91, 93, 103, 116, 118, 127, 131, 139, 193, 194, 195, 196, 197, 198, 199, 203, and 205 of SEQ ID NO: 9; or the Z-P1 binding site comprises one or more amino acid residues corresponding to amino acid positions 99, 100, 132-136, 190, 191, 194, 200, and 222 of SEQ ID NO: 14; or the Z-P1 binding site comprises one or more amino acid residues corresponding to amino acid positions 63-66, 83, 84, 86, 89, 92, 93, 96, 102, 149, 152-155, 158, and 175-177 of SEQ ID NO: 15; or the Z-P1 binding site comprises one or more amino acid residues corresponding to amino acid positions 117, 255, 256, 257, 258-260, 268, 270, 271, 290, 293, 294, 297, 315, 316, 377, 779, and 821 of SEQ ID NO: 16; or the Z-P1 binding site comprises one or more amino acid residues corresponding to amino acid positions 41, 58, 59, 60, 61, 62, 65, 77, 105, 107, 108, 109, 110-112, 147, 150, 151, 154, 155, 158, and 185 of SEQ ID NO: 17; or the Z-P1 binding site comprises one or more amino acid residues corresponding to amino acid positions 133-137, 153, 158, 160, 161, 169, 173, 176, 177, 180, 186, 191, 192, 209, 216, and 230 of SEQ ID NO: 21; or the Z-P1 binding site comprises one or more amino acid residues corresponding to amino acid positions 4-7, 9, 10, 14, 58, 90, 113, 134-138, 162, 181, 183-185, and 212 of SEQ ID NO: 25; or the Z-P1 binding site comprises one or more amino acid residues corresponding to amino acid positions 7, 9, 20, 104, 108, 139, 141, 164, 167, 169, 170, 171, 202, 204-210, 242, 245, and 248 of SEQ ID NO: 27; or the Z-P1 binding site comprises one or more amino acid residues corresponding to amino acid positions 90, 93, 96-99, 132, 133, 136, 142, 152, and 153 of SEQ ID NO: 30; or the Z-P1 binding site comprises one or more amino acid residues corresponding to amino acid positions 165, 166, 169, 227-230, 231, 235, 248, and 352 of SEQ ID NO: 31; or the Z-P1 binding site comprises one or more amino acid residues corresponding to amino acid positions 106-109, 141, 142, 145, 151, and 166-168 of SEQ ID NO: 39; or the Z-P1 binding site comprises one or more amino acid residues corresponding to amino acid positions 106, 107, 313-317, 325, 327, 379, 382-389, 448, 453, 506, and 564-566 of SEQ ID NO: 43; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 68; or the Z-P1 binding site comprises one or more amino acid residues corresponding to positions 62, 64, 65, 67, 88, 89, 118, 128, 129, 132, 138, 140, 196, 198, 200, 202, 204, and 205 of SEQ ID NO: 69; or the Z-P1 binding site comprises one or more amino acid residues corresponding to positions 60, 62, 63, 65, 89, 90, 119, 129, 130, 133, 134, 139, 141, 196, 198, 200, 202, 204, and 205 of SEQ ID NO: 70; or the Z-P1 binding site comprises one or more amino acid residues corresponding to positions 61, 63, 64, 66, 90, 91, 120, 130, 131, 134, 140, 197, 199, 201, 203, 205, and 206 of SEQ ID NO: 71; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 72; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 73; or the Z-P1 binding site comprises one or more amino acid residues corresponding to positions 61, 63, 64, 66, 90, 120, 129, 130, 133, 139, 141, 196, 198, 200, 202, 204, and 205 of SEQ ID NO: 74.

33. The binder of any one of embodiments 29-32, which binds to the N-terminally modified target peptide with a thermodynamic dissociation constant ($K_d$) of 500 nM or less.

34. The binder of any one of embodiments 29-33, which comprises a detectable label or a nucleic acid tag.

35. A kit for treating a target peptide, the kit comprises:

(a) an engineered metalloprotein binder of any of embodiments 29-34;

(b) one of more of the following:

1) an N-terminal modifier agent to form an N-terminally modified peptide having a formula: Z-P1-P2-peptide, wherein Z is an N-terminal modification capable of coordinating or chelating a metal cation, P1-P2-peptide is a target peptide before modification with the N-terminal modifier agent, Z-P1 is a modified N-terminal amino acid (NTAA) residue of the target peptide, and P2 is a penultimate terminal amino acid residue of the target peptide;

2) an agent configured for removing the modified NTAA residue from the N-terminally modified target peptide, thereby exposing a new NTAA residue;

3) an agent configured for immobilizing the target peptide on a solid support;

4) a solid support;

5) a nucleic acid recording tag;

6) a nucleic acid tag or a nucleic acid coding tag;

7) a detectable label; and/or 8) a peptide coupling reagent.

36. A kit for treating a target peptide, the kit comprising:

(a) an engineered binder that specifically binds to an N-terminally modified target peptide modified by an N-terminal modifier agent, wherein:

(i) the N-terminally modified target peptide has a formula: Z-P1-P2-peptide, wherein Z is an N-terminal modification capable of coordinating or chelating a metal cation, P1-P2-peptide is a target peptide before modification with the N-terminal modifier agent, Z-P1 is a modified N-terminal amino acid (NTAA) residue of the target peptide, and P2 is a penultimate terminal amino acid residue of the target peptide;

(ii) the engineered binder specifically binds to the N-terminally modified target peptide through interaction between the engineered binder and the Z-P1 of the N-terminally modified target peptide; and (iii) the engineered binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates a metal cation; and (b) the N-terminal modifier agent selected from the group consisting of (6)

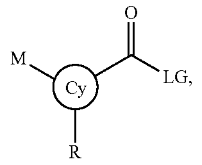

(7)

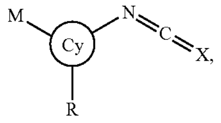

(8)

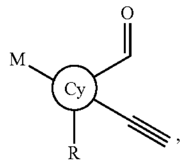

, and (9)

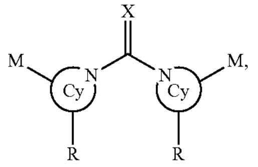

wherein M is a metal cation binding group that comprises sulfonamide, hydroxamic acid, sulfamate, or sulfamide; the group

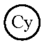

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, $OR^Q$, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH.

37. A kit for treating a target peptide, the kit comprising:

(a) an engineered binder that specifically binds to an N-terminally modified target peptide modified by an N-terminal modifier agent, wherein:

(i) the N-terminally modified target peptide has a formula: Z-P1-P2-peptide, wherein Z is an N-terminal modification capable of coordinating or chelating a metal cation, P1-P2-peptide is a target peptide before modification with the N-terminal modifier agent, Z-P1 is a modified N-terminal amino acid (NTAA) residue of the target peptide, and P2 is a penultimate terminal amino acid residue of the target peptide;

(ii) the engineered binder specifically binds to the N-terminally modified target peptide through interaction between the engineered binder and the Z-P1 of the N-terminally modified target peptide; and (iii) the engineered binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates a metal cation; and (b) an agent configured for removing the modified NTAA residue from the N-terminally modified target peptide, thereby exposing a new NTAA residue.

38. The kit of embodiment 37, wherein the kit further comprises the N-terminal modifier agent selected from the group consisting of:

(6)

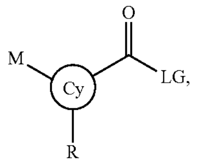

(7)

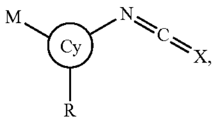

(8)

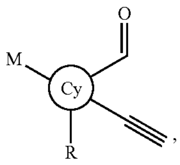

and (9)

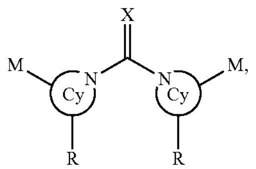

wherein M is a metal cation binding group that comprises sulfonamide, hydroxamic acid, sulfamate, or sulfamide; the group

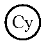

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, $OR^Q$, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH.

39. The kit of embodiment 36, wherein the kit further comprises an agent configured for removing the modified NTAA residue from the N-terminally modified target peptide, thereby exposing a new NTAA residue.

40. The kit of any one of embodiments 36-39, wherein the engineered binder is associated with a coding tag comprising identifying information regarding the engineered binder.

41. The kit of any one of embodiments 36-39, wherein the engineered binder further comprises a detectable label.

42. The kit of any one of embodiments 37 or 39-41, wherein the agent configured for removing the modified NTAA residue comprises an engineered enzyme.

43. The kit of embodiment 42, wherein the agent comprises a polypeptide comprising an amino acid sequence having at least about 90% sequence identity to SEQ ID NO: 67.

44. The kit of any one of embodiments 37 or 39-41, wherein the agent configured for removing the modified NTAA residue does not comprise an engineered enzyme.

45. The kit of any one of embodiments 36-44, wherein the amino acid sequence X1-C/H/D/E-X2-C/H/D/E-X3-C/H/D/E-X4 chelates the metal cation with a thermodynamic dissociation constant of 1000 nM or less.

46. The kit of any one of embodiments 36-45, wherein the engineered binder comprises an amino acid sequence having at least 40%, at least 50%, at least 60%, at least 70%, at least 80%, or at least 90% sequence identity to any one of the amino acid sequences selected from the group consisting of SEQ ID NO: 7-SEQ ID NO: 59, SEQ ID NO: 68-SEQ ID NO: 99 and SEQ ID NO: 105-SEQ ID NO: 135.

47. The kit of any one of embodiments 36-46, wherein the engineered binder comprises an amino acid sequence which differs from the amino acid sequence set forth in SEQ ID NO: 7, SEQ ID NO: 8, SEQ ID NO: 9, SEQ ID NO: 14, SEQ ID NO: 15, SEQ ID NO: 16, SEQ ID NO: 17, SEQ ID NO: 21, SEQ ID NO: 25, SEQ ID NO: 27, SEQ ID NO: 30, SEQ ID NO: 31, SEQ ID NO: 39, SEQ ID NO: 43 or SEQ ID NO: 68-SEQ ID NO: 74 by at least one amino acid residue within 6 Å of a Z-P1 binding site of the engineered binder, wherein:

the Z-P1 binding site comprises one or more amino acid residues corresponding to positions 59, 61, 63, 64, 66, 88, 89-91, 93, 103, 116, 118, 120, 127-131, 133, 137, 139, 141, 193-196, 198, 200, 202, and 203-205 of SEQ ID NO: 7; or the Z-P1 binding site comprises one or more amino acid residues corresponding to positions 60, 63, 65, 68, 87, 88, 90, 92, 102, 115, 117, 127, 137, 139, 193, 194, 195, 196, 197, 198, 203, and 205 of SEQ ID NO: 8; or the Z-P1 binding site comprises one or more amino acid residues corresponding to positions 1, 2, 17, 59, 61, 64, 89, 91, 93, 103, 116, 118, 127, 131, 139, 193, 194, 195, 196, 197, 198, 199, 203, and 205 of SEQ ID NO: 9; or the Z-P1 binding site comprises one or more amino acid residues corresponding to positions 99, 100, 132-136, 190, 191, 194, 200, and 222 of SEQ ID NO: 14; or the Z-P1 binding site comprises one or more amino acid residues corresponding to positions 63-66, 83, 84, 86, 89, 92, 93, 96, 102, 149, 152-155, 158, and 175-177 of SEQ ID NO: 15; or the Z-P1 binding site comprises one or more amino acid residues corresponding to positions 117, 255, 256, 257, 258-260, 268, 270, 271, 290, 293, 294, 297, 315, 316, 377, 779, and 821 of SEQ ID NO: 16; or the Z-P1 binding site comprises one or more amino acid residues corresponding to positions 41, 58, 59, 60, 61, 62, 65, 77, 105, 107, 108, 109, 110-112, 147, 150, 151, 154, 155, 158, and 185 of SEQ ID NO: 17; or the Z-P1 binding site comprises one or more amino acid residues corresponding to positions 133-137, 153, 158, 160, 161, 169, 173, 176, 177, 180, 186, 191, 192, 209, 216, and 230 of SEQ ID NO: 21; or the Z-P1 binding site comprises one or more amino acid residues corresponding to positions 4-7, 9, 10, 14, 58, 90, 113, 134-138, 162, 181, 183-185, and 212 of SEQ ID NO: 25; or the Z-P1 binding site comprises one or more amino acid residues corresponding to positions 7, 9, 20, 104, 108, 139, 141, 164, 167, 169, 170, 171, 202, 204-210, 242, 245, and 248 of SEQ ID NO: 27; or the Z-P1 binding site comprises one or more amino acid residues corresponding to positions 90, 93, 96-99, 132, 133, 136, 142, 152, and 153 of SEQ ID NO: 30; or the Z-P1 binding site comprises one or more amino acid residues corresponding to positions 165, 166, 169, 227-230, 231, 235, 248, and 352 of SEQ ID NO: 31; or the Z-P1 binding site comprises one or more amino acid residues corresponding to positions 106-109, 141, 142, 145, 151, and 166-168 of SEQ ID NO: 39; or the Z-P1 binding site comprises one or more amino acid residues corresponding to positions 106, 107, 313-317, 325, 327, 379, 382-389, 448, 453, 506, and 564-566 of SEQ ID NO: 43; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 68; or the Z-P1 binding site comprises one or more amino acid residues corresponding to positions 62, 64, 65, 67, 88, 89, 118, 128, 129, 132, 138, 140, 196, 198, 200, 202, 204, and 205 of SEQ ID NO: 69; or the Z-P1 binding site comprises one or more amino acid residues corresponding to positions 60, 62, 63, 65, 89, 90, 119, 129, 130, 133, 134, 139, 141, 196, 198, 200, 202, 204, and 205 of SEQ ID NO: 70; or the Z-P1 binding site comprises one or more amino acid residues corresponding to positions 61, 63, 64, 66, 90, 91, 120, 130, 131, 134, 140, 197, 199, 201, 203, 205, and 206 of SEQ ID NO: 71; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 72; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 73; or the Z-P1 binding site comprises one or more amino acid residues corresponding to positions 61, 63, 64, 66, 90, 120, 129, 130, 133, 139, 141, 196, 198, 200, 202, 204, and 205 of SEQ ID NO: 74.

48. The kit of any one of embodiments 36-47, wherein the N-terminal modifier agent is a compound of the following formula:

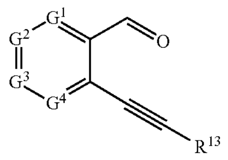

wherein:

$G^1$-$G^4$ are each independently selected from CH, CJ, and N, provided not more than 3 of $G^1$-$G^4$ are N;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —$N(R^8)_2$, —$SR^8$, —$S(O)_nR^8$, —$NR^8SO_2R^8$, —$SO_2N(R^8)_2$, $SO_3R^8$, —$B(OR^8)_2$, $C(=O)R^8$, CN, $CON(R^8)_2$, —$COOR^8$, —C(—O)Ar, and tetrazole, where Ar represents a phenyl or 5-6 membered heteroaryl ring that is optionally substituted with one or two groups selected from halo, CN, $R^8$ and $OR^8$;

each $R^8$ is independently selected from H, $C_1$-$C_2$ alkyl, and $C_1$-$C_2$ haloalkyl;

n at each occurrence is independently 1 or 2, and $R^{13}$ is selected from H, $C_1$-$C_2$ alkyl, $C_1$-$C_2$ alkoxy, $C_1$-$C_2$ haloalkyl, and $C_1$-$C_2$ haloalkoxy.

49. The kit of any one of embodiments 36-48, wherein the amino acid sequence X1-C/H/D/E-X2-C/H/D/E-X3-C/H/D/E-X4 further comprises one or more of amino acid sequences selected from the group consisting of: SEQ TD NO: 101 and SEQ TD NO: 102.

50. The kit of any one of embodiments 36-49, wherein the engineered binder binds to the N-terminally modified target peptide with a thermodynamic dissociation constant (Kd) of 500 nM or less.

51. The kit of any one of embodiments 36-50, further comprising: (i) an agent configured for immobilizing the target peptide on a solid support; and/or (ii) the solid support.

52. The kit of any one of embodiments 36-51, wherein the engineered binder binds to the N-terminally modified target peptide with at least a 100-fold greater binding affinity than a model polypeptide that has at least 90% identity to the engineered binder over the entire sequence length, wherein the model polypeptide does not comprise the amino acid sequence X1-C/H/D/E-X2-C/H/D/E-X3-C/H/D/E-X4.

53. A method of treating a plurality of peptides, the method comprising:

(a) contacting a peptide of the plurality of peptides with an N-terminal modifier agent to form an N-terminally modified peptide having a formula: Z-P1-P2-peptide, wherein Z is an N-terminal modification capable of coordinating or chelating a metal cation, P1-P2-peptide is the peptide before modification with the N-terminal modifier agent, Z-P1 is a modified N-terminal amino acid (NTAA) residue of the peptide, and P2 is a penultimate terminal amino acid residue of the peptide;

(b) contacting the N-terminally modified peptide with a set of engineered binders, wherein at least one engineered binder of the set specifically binds to the modified NTAA residue of the N-terminally modified peptide, wherein each engineered binder of the set comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp), and E (Glu); X1, X2, X3 and X4 are each any amino acid sequence independently comprising between 0 and 500 amino acid residues in length, and wherein the amino acid sequence X1-C/H/D/E-X2-C/H/D/E-X3-C/H/D/E-X4 chelates the metal cation;

(c) detecting a signal indicative of the binding of the at least one engineered binder to the N-terminally modified peptide;

(d) optionally, dissociating the at least one engineered binder from the N-terminally modified peptide;

(e) removing the modified NTAA residue from the N-terminally modified peptide by an agent configured for removing the modified NTAA residue, thereby exposing a new NTAA residue; and (f) optionally, repeating steps (a)-(e) one or more times for peptides of the plurality of peptides.

54. The method of embodiment 53, further comprising:

(g) determining one or more characteristics of each peptide for which the signal was detected in (c), thereby analyzing the plurality of peptides.

55. The method of embodiment 54, wherein for each peptide, the one or more characteristics is determined by matching known binding properties of one or more engineered binder bound to the peptide to characteristics of the peptide.

56. The method of any one of embodiments 53-55, wherein the amino acid sequence X1-C/H/D/E-X2-C/H/D/E-X3-C/H/D/E-X4 chelates the metal cation with a thermodynamic dissociation constant of 1000 nM or less.

57. The method of any one of embodiments 53-56, wherein the N-terminal modifier agent is a compound selected from the group consisting of:

(6)

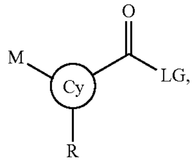

(7)

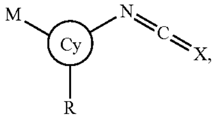

-continued (8)

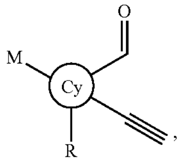

, and (9)

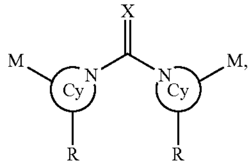

wherein M is a metal cation binding group that comprises sulfonamide, hydroxamic acid, sulfamate, or sulfamide; the group

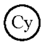

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, $OR^Q$, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH; and (ii) a compound of Formula (3):

(3)

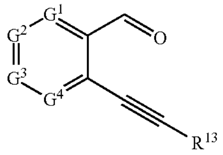

wherein:

$G^1$-$G^4$ are each independently selected from CH, CJ, and N, provided not more than 3 of $G^1$-$G^4$ are N;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —$N(R^8)_2$, —$SR^8$, —$S(O)_nR^8$, —$NR^8SO_2R^8$, —$SO_2N(R^8)_2$, $SO_3R^8$, —$B(OR^8)_2$, $C(═O)R^8$, CN, $CON(R^8)_2$, —$COOR^8$, —C(—O)Ar, and tetrazole, where Ar represents a phenyl or 5-6 membered heteroaryl ring that is optionally substituted with one or two groups selected from halo, CN, $R^8$ and $OR^8$;

each $R^8$ is independently selected from H, $C_1$-$C_2$ alkyl, and $C_1$-$C_2$ haloalkyl;

n at each occurrence is independently 1 or 2; and $R^{13}$ is selected from H, $C_1$-$C_2$ alkyl, $C_1$-$C_2$ alkoxy, $C_1$-$C_2$ haloalkyl, and $C_1$-$C_2$ haloalkoxy.

58. The method of any one of embodiments 53-57, wherein the engineered binder is associated with a coding tag comprising identifying information regarding the engineered binder.
59. The method of any one of embodiments 53-57, wherein the engineered binder further comprises a detectable label.
60. The method of any one of embodiments 53-59, wherein the agent configured for removing the modified NTAA residue comprises an engineered enzyme.
61. The method of any one of embodiments 53-59, wherein the agent configured for removing the modified NTAA residue does not comprise an engineered enzyme.
62. The method of any one of embodiments 53-61, wherein the amino acid sequence X1-C/H/D/E-X2-C/H/D/E-X3-C/H/D/E-X4 further comprises one or more of amino acid sequences selected from the group consisting of: SEQ ID NO: 101 and SEQ ID NO: 102.
63. The method of any one of embodiments 53-62, wherein the engineered binder comprises an amino acid sequence having at least 40%, at least 50%, at least 60%, at least 70%, at least 80%, or at least 90% sequence identity to any one of the amino acid sequences selected from the group consisting of SEQ ID NO: 7-SEQ ID NO: 59, SEQ ID NO: 68-SEQ ID NO: 99 and SEQ ID NO: 105-SEQ ID NO: 135.
64. The method of any one of embodiments 53-63, wherein the engineered binder binds to the N-terminally modified target peptide with a thermodynamic dissociation constant ($K_d$) of 500 nM or less.
65. A method of treating a plurality of peptides, the method comprising:
   (a) contacting a compound of Formula (13):

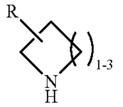

with a compound of Formula (8):

(8)

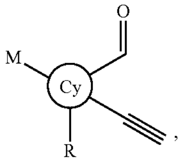

wherein M is a metal cation binding group that comprises sulfonamide, hydroxamic acid, sulfamate, or sulfamide; the group

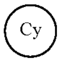

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, $OR^Q$, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH, under conditions to generate a catalytic intermediate of Formula (14):

(14)

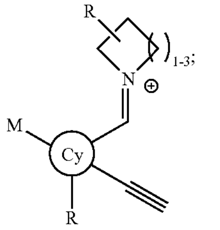

and (b) contacting a peptide of the plurality of peptides with the catalytic intermediate of Formula (14) to form an N-terminally modified peptide having a formula:

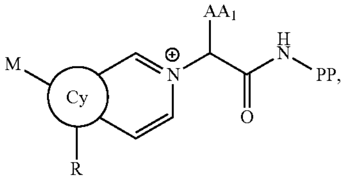

wherein AA1 is a side chain of an N-terminal amino acid (NTAA) residue of the peptide, and PP comprises amino acid residues of the peptide starting from a penultimate terminal amino acid residue of the peptide to a C-terminal amino acid (NTAA) residue of the peptide.
66. The method of embodiment 65, further comprising:
   (c) contacting the N-terminally modified peptide with a set of engineered binders, wherein at least one engineered binder of the set specifically binds to the modified NTAA residue of the N-terminally modified peptide, wherein each engineered binder of the set comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp), and E (Glu); X1, X2, X3 and X4 are each any amino acid sequence independently comprising between 0 and 500 amino acid residues in length, and wherein the amino acid sequence X1-C/H/D/E-X2-C/H/D/E-X3-C/H/D/E-X4 chelates the metal cation.
67. The method of embodiment 66, further comprising:
   (d) detecting a signal indicative of the binding of the at least one engineered binder to the N-terminally modified peptide.
68. A method of analyzing a plurality of peptides, the method comprising:

(a) modifying the plurality of peptides with an N-terminal modifier agent, thereby generating a modified N-terminal amino acid (NTAA) residue on each peptide of the plurality of peptides, wherein each peptide of the plurality of peptides is attached to a solid support, each modified NTAA residue is capable of coordinating or chelating a metal cation, and wherein the N-terminal modifier agent is selected from the group consisting of:

(6)

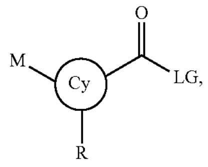

(7)

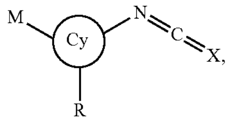

(8)

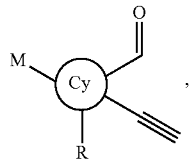

, and (9)

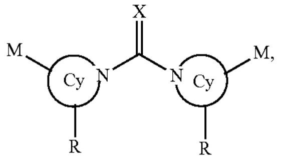

wherein M is a metal cation binding group that comprises sulfonamide, hydroxamic acid, sulfamate, or sulfamide; the group

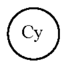

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, $OR^Q$, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH;

(b) contacting one or more peptides of the plurality of peptides with a set of engineered metalloprotein binders, wherein one or more engineered metalloprotein binders of the set specifically bind to a particular modified NTAA residue of the one or more peptides, wherein each engineered metalloprotein binder of the set comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp), and E (Glu); X1, X2, X3 and X4 are each any amino acid sequence independently comprising between 0 and 500 amino acid residues in length, and wherein the amino acid sequence X1-C/H/D/E-X2-C/H/D/E-X3-C/H/D/E-X4 chelates the metal cation; and (c) generating a signal indicative of the binding of the one or more engineered metalloprotein binders to the modified NTAA residue(s) of the one or more peptides, thereby analyzing the plurality of peptides.

69. The method of embodiment 68, further comprising:

(d) removing modified NTAA residues from peptides of the plurality of peptides by an agent configured to remove modified NTAA residues, thereby exposing a new NTAA residue in each of the peptides.

70. The method of embodiment 69, further comprising: repeating steps (a)-(c) and, optionally, (d) for the new NTAA residues of the peptides.

71. The method of any one of embodiments 68-70, wherein each engineered metalloprotein binder of the set is configured to specifically bind to a different modified NTAA residue of the one or more peptides.

72. The method of any one of embodiments 68-71, wherein (c) further comprises determining one or more characteristics of each peptide of the one or more peptides for which the signal was generated by using predetermined binding specificities of the engineered metalloprotein binders, thereby analyzing the plurality of peptides.

73. The method of embodiment 72, further comprising determining at least partial sequence information of each peptide for which the signal was generated using the one or more determined characteristics.

74. The method of embodiment 72, wherein the set of engineered metalloprotein binders comprises at least 3 structurally different engineered metalloprotein binders each having different binding specificities towards modified NTAA residues of the one or more peptides.

75. The method of any one of embodiments 68-74, wherein each of the plurality of peptides is covalently attached to the solid support.

76. The method of any one of embodiments 68-75, wherein the engineered metalloprotein binder further comprises a detectable label.

77. The method of any one of embodiments 69-76, wherein the agent configured for removing modified NTAA residues comprises an engineered enzyme.

78. The method of any one of embodiments 68-77, wherein the amino acid sequence X1-C/H/D/E-X2-C/H/D/E-X3-C/H/D/E-X4 further comprises one or more amino acid sequences selected from the group consisting of: SEQ TD NO: 101 and SEQ TD NO: 102.

79. The method of embodiment 78, wherein the amino acid sequence X1-C/H/D/E-X2-C/H/D/E-X3-C/H/D/E-X4 further comprises one or more amino acid sequences selected from the group consisting of: (A/C/D/I/S/V/Y)X(C/N)X(A/C/G/R/S/V)XX(C/F/I/L/T/V)X(C/G/K/N/V)X(F/I)(D/E/K/N/V)(D/E/F/N/Q), (A/S)

XX(A/E/H/K/Q) (A/P/R/S/T)D(G/I/V)X(A/T/V) (I/L/M/N/R/V) and G(A/C/F/I/S)X(A/D/M/T)XPX(C/F/L)X(C/E/R)X(I/L/R/V).

80. The method of any one of embodiments 68-79, wherein each engineered metalloprotein binder binds to a peptide modified with the N-terminal modifier agent with a thermodynamic dissociation constant (Kd) of 500 nM or less.

81. The method of any one of embodiments 68-80, wherein the engineered metalloprotein binder is associated with a coding tag comprising identifying information regarding the engineered metalloprotein binder.

82. The method of embodiment 81, wherein each of the plurality of peptides is associated with a recording tag comprising identifying information regarding the associated peptide or a protein from which the associated peptide is obtained from.

83. The method of embodiment 82, wherein following binding of an engineered metalloprotein binder of the set to a modified NTAA residue of a peptide of the plurality, a nucleic acid molecule is generated, using a ligation or a primer extension, which comprises the identifying information regarding the engineered binder and the identifying information regarding the peptide or a protein from which the peptide is obtained from.

84. The method of embodiment 83, wherein (c) further comprising sequencing the nucleic acid molecule, and determining one or more characteristics of the peptide by using a predetermined binding specificity of the engineered metalloprotein binder.

85. A kit for treating a target peptide, the kit comprising:

(a) an N-terminal modifier agent selected from the group consisting of:

(6)

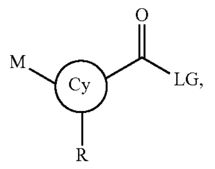

(7)

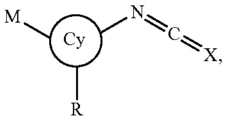

(8)

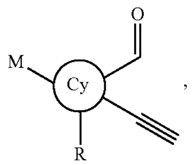

, and (9)

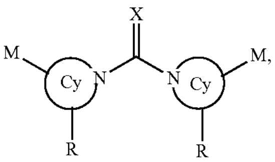

wherein M is a metal cation binding group that comprises sulfonamide, hydroxamic acid, sulfamate, or sulfamide; the group

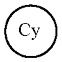

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, $OR^Q$, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH; and (b) an engineered metalloprotein binder that specifically binds to a modified N-terminal amino acid (NTAA) residue in a target peptide, wherein the modified NTAA residue is generated by modifying the target peptide with the N-terminal modifier agent, wherein the engineered metalloprotein binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates the metal cation; and (c) a solid support which is configured for attachment of the target peptide.

86. The kit of embodiment 85, further comprising an agent configured to remove NTAA residues of peptides modified with the N-terminal modifier agent.

87. The kit of embodiment 85 or embodiment 86, which comprises at least 3 structurally different engineered metalloprotein binders each having different binding specificities towards NTAA residues of peptides modified with the N-terminal modifier agent.

88. The kit of any one of embodiments 85-87, wherein the engineered metalloprotein binder comprises a detectable label or a coding tag comprising identifying information regarding the engineered metalloprotein binder.

89. The kit of any one of embodiments 85-88, wherein the amino acid sequence X1-C/H/D/E-X2-C/H/D/E-X3-C/H/D/E-X4 further comprises one or more amino acid sequences selected from the group consisting of SEQ ID NO: 101 and SEQ ID NO: 102.

90. A composition comprising:

(a) a solid support, wherein the solid support comprises a plurality of peptide molecules attached to the solid support; and (b) an engineered metalloprotein binder that specifically binds to a modified N-terminal amino acid (NTAA) residue of a peptide molecule of the plurality of peptide molecules, wherein (i) the modified NTAA residue is generated by modifying the peptide molecule with an N-terminal modifier agent, wherein the modified NTAA residue is capable of coordinating or chelating a metal cation;

(ii) the N-terminal modifier agent is selected from the group consisting of:

(6)

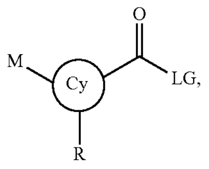

(7)

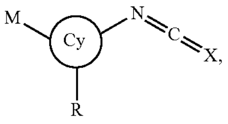

(8)

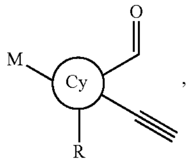

, and (9)

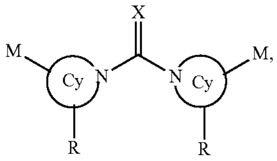

wherein M is a metal cation binding group that comprises sulfonamide, hydroxamic acid, sulfamate, or sulfamide; the group

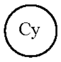

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, $OR^{Q}$, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH; and (iii) the engineered metalloprotein binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates the metal cation.

91. The composition of embodiment 90, which comprises at least 3 structurally different engineered metalloprotein binders, wherein each engineered metalloprotein binder has different binding specificities towards NTAA residues of peptides modified with the N-terminal modifier agent.

92. The composition of embodiment 90 or embodiment 91, wherein the engineered metalloprotein binder comprises a detectable label or a coding tag comprising identifying information regarding the engineered metalloprotein binder.

93. The composition of any one of embodiments 90-92, wherein the amino acid sequence X1-C/H/D/E-X2-C/H/D/E-X3-C/H/D/E-X4 further comprises one or more amino acid sequences selected from the group consisting of: SEQ ID NO: 101 and SEQ ID NO: 102.

94. The method, kit or composition of any one of embodiments 68-93, wherein the engineered metalloprotein binder comprises an amino acid sequence having at least 40%, at least 50%, at least 60%, at least 70%, at least 80%, or at least 90% sequence identity to any one of the amino acid sequences selected from the group consisting of SEQ ID NO: 7-SEQ ID NO: 59, SEQ ID NO: 68-SEQ ID NO: 99 and SEQ ID NO: 105-SEQ ID NO: 135.

95. The method, kit or composition of any one of the preceding embodiments, wherein each of the plurality of peptide molecules comprising the modified NTAA residue comprises one of the structures selected from the group consisting of:

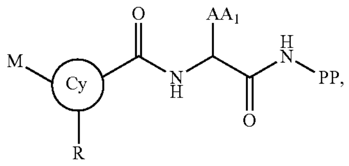

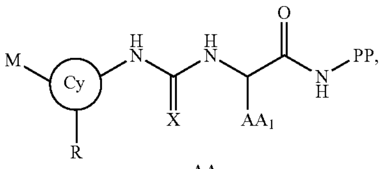

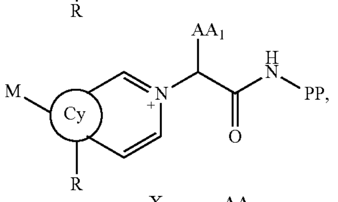

and

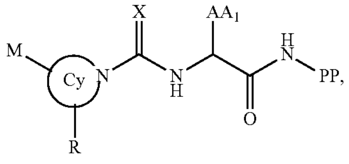

wherein AA1 is a side chain of the NTAA residue and PP is a peptide structure except for the modified NTAA residue.

96. The method, kit or composition of any one of the preceding embodiments, wherein in the N-terminally modified target peptide, the modified NTAA residue is connected to the target peptide via an amide bond.

Examples

The following examples are offered to illustrate but not to limit the methods, compositions, and uses provided herein.

Certain aspects of the present invention, including, but not limited to, embodiments for high-throughput peptide analysis, the Proteocode™ peptide assay, methods of generating specific binders recognizing modified NTAA residues of peptides, agents configured for removing modified NTAA residues from the N-terminally modified target peptides, information transfer between coding tags and recording tags, methods of making polynucleotide-peptide conjugates, methods for attachment of nucleotide-peptide conjugates to a support, methods of generating barcodes, methods for analyzing extended recording tags were disclosed in the earlier published applications US 2019/0145982 A1, US 2020/0348308 A1, US 2020/0348307 A1, US 2021/0208150 A1, US 2022/0049246 A1, US 2022/0283175 A1, US 2022/0144885 A1, US 2022/0227889 A1, US 2021/0214701 A1 and US 2023/0136966 A1, the contents of which are incorporated herein by reference in their entireties.

Example 1. Establishing Human Carbonic Anhydrase 2 (CA II) as Model Metalloprotein Binder for Modified Peptides Carbonic anhydrase is well known as one of the most efficient enzymes in nature. This zinc binding protein is expressed in nearly all forms of life, with numerous variants/isozymes that are distinct in protein sequence and structure, depending on the species of origin. The active site zinc ion is catalytic for the conversion of carbon dioxide and water to bicarbonate and is bound at the bottom of the 15 Å deep substrate binding pocket (for human carbonic anhydrase 2, SEQ ID NO: 7) characterized by hydrophobic walls and a hydrophilic cleft. Carbonic anhydrases have been pursued as drug targets for multiple indications, and numerous metal binding small molecule inhibitors have been identified along with corresponding crystal structures and SAR. Carbonic anhydrase is a small (~30 kD) monomeric protein (although some variants form dimers) with no appreciable post-translational modifications and a single cysteine (for human carbonic anhydrase 2, hCAII, SEQ ID NO: 7). It exhibits high structural stability, binding pocket evolvability using phage display and can be produced on a large scale. Genetic manipulation of carbonic anhydrase is well documented and many natural variants exist across organisms to provide a range of initial scaffolds for computational or practical evaluation. Further, phenylsulfonamide-modified peptides have been shown to bind to carbonic anhydrase with high affinity (Sigal and Whitesides, Benzenesulfonamide-peptide conjugates as probes for secondary binding sites near the active site of carbonic anhydrase, Bioorganic & Medicinal Chemistry letters, Vol. 6. No. 5, pp. 559-564, 1996). Thus, carbonic anhydrase is a promising candidate (binder scaffold) for a specific metalloprotein binder.

Figure 7A:
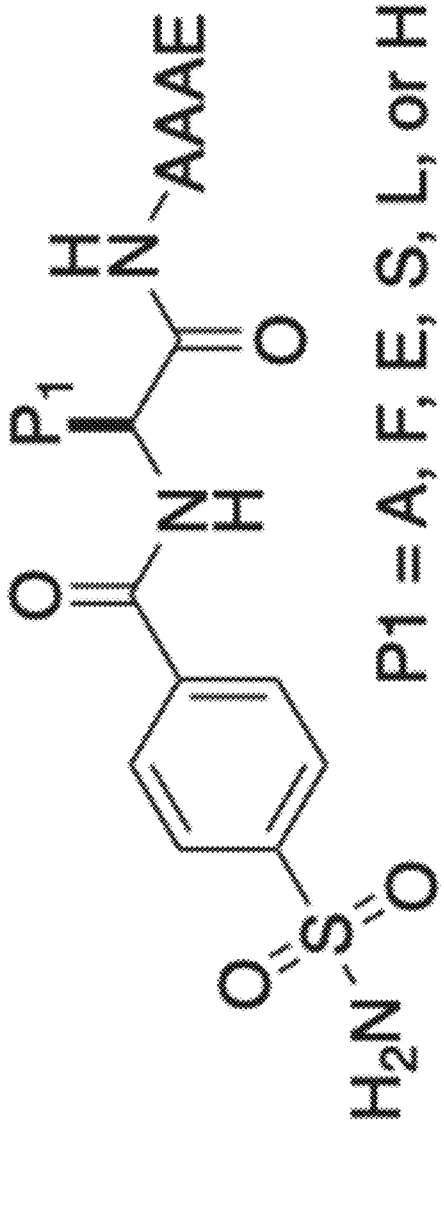
FIG. 7A. Structures of the SABA-modified XAAAE peptides.
Figure 7B:
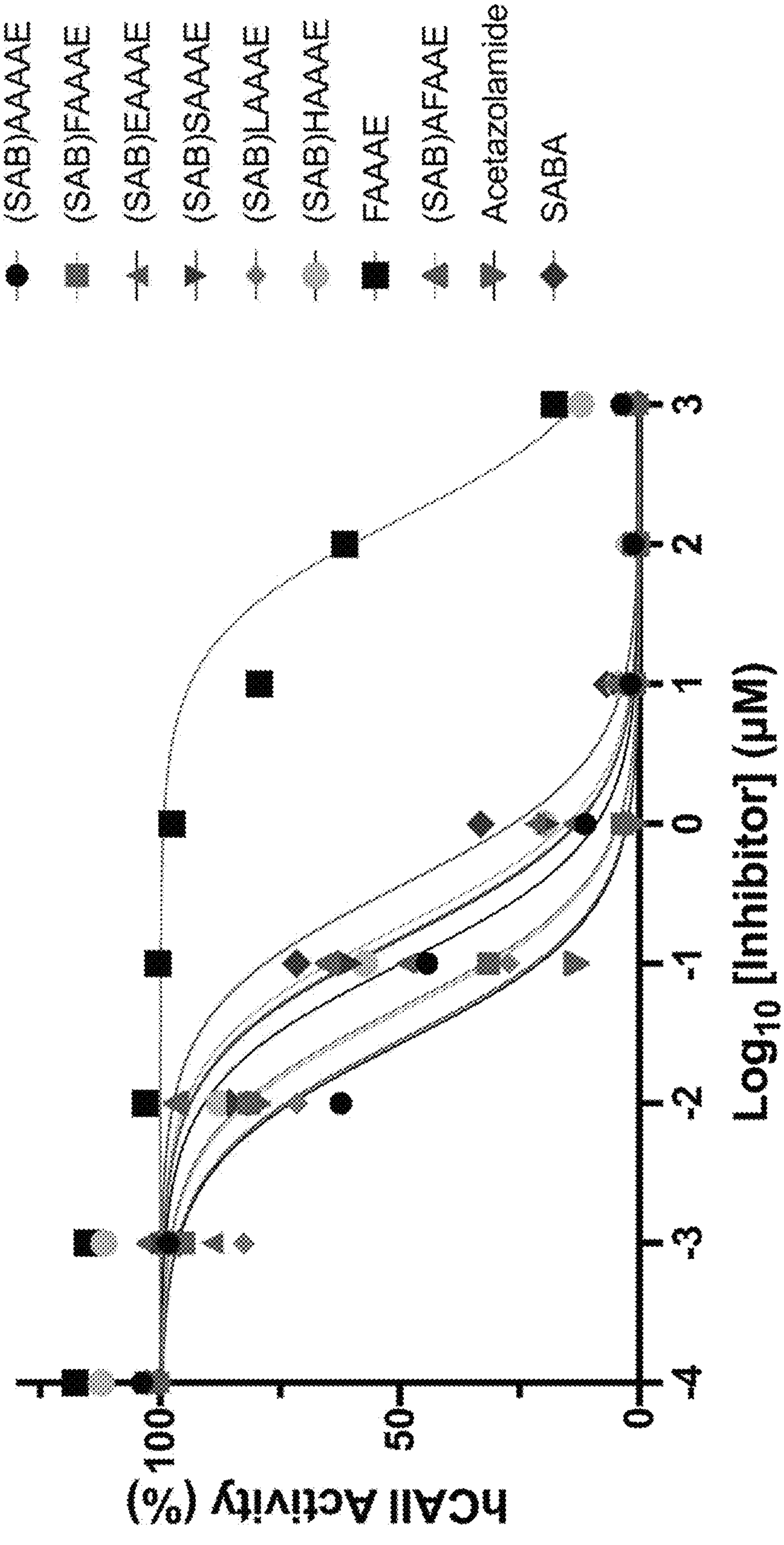
FIG. 7B. Inhibition of hCAII activity by the SABA-modified XAAAE peptides (IC50 values were determined).
Figures 8A, 8B:
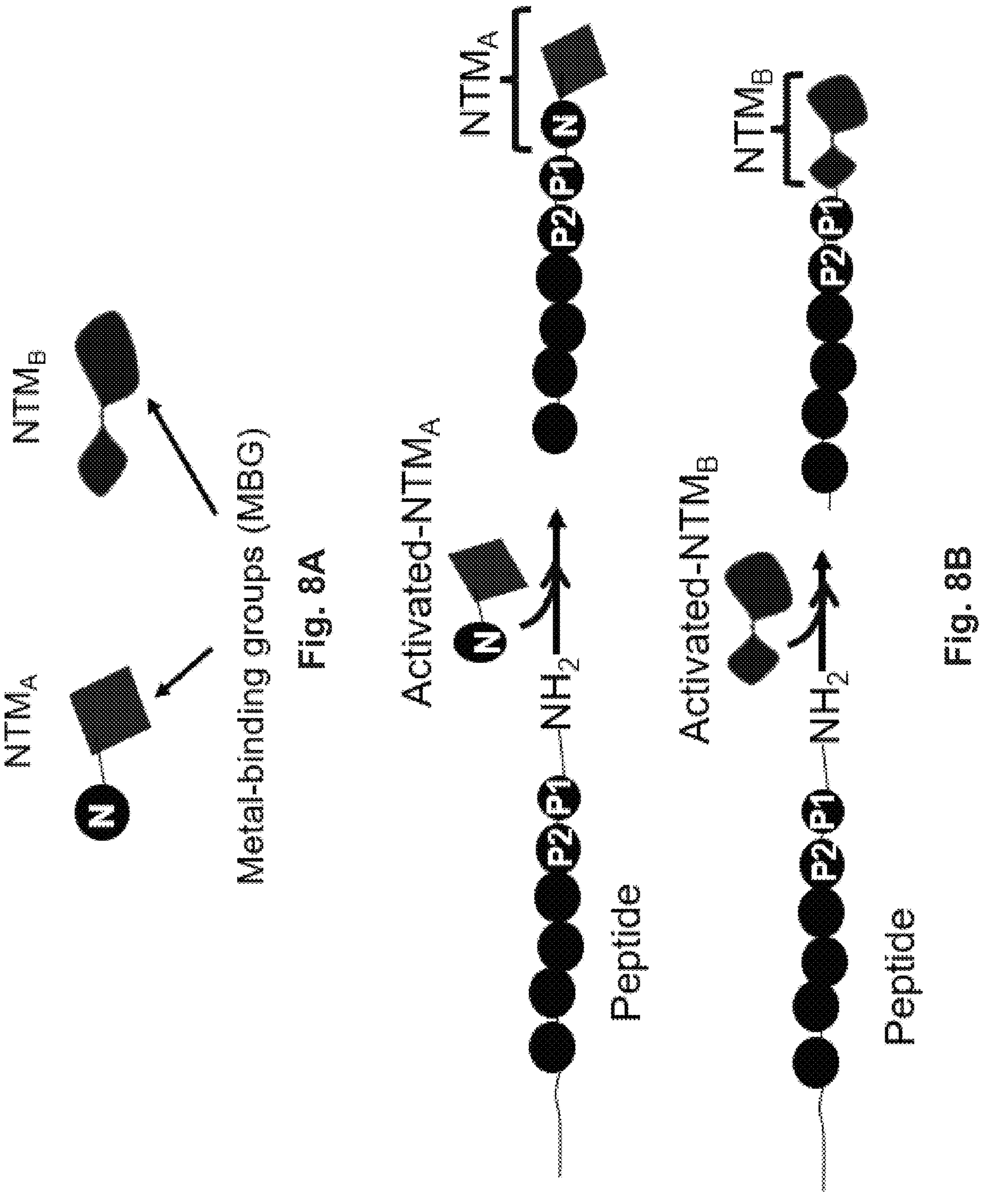
FIG. 8A-FIG. 8D. Exemplary design of N-terminal modifications (NTMs) to enable NTM-NTAA (NTM-P1) binding with minimal P2 bias. The size and shape of the NTM is designed to fill the metalloprotein binder substrate pocket such that only the P1 residue of the peptide makes substantial contact with the substrate pocket, but not P2 residue.
Figure 8C:
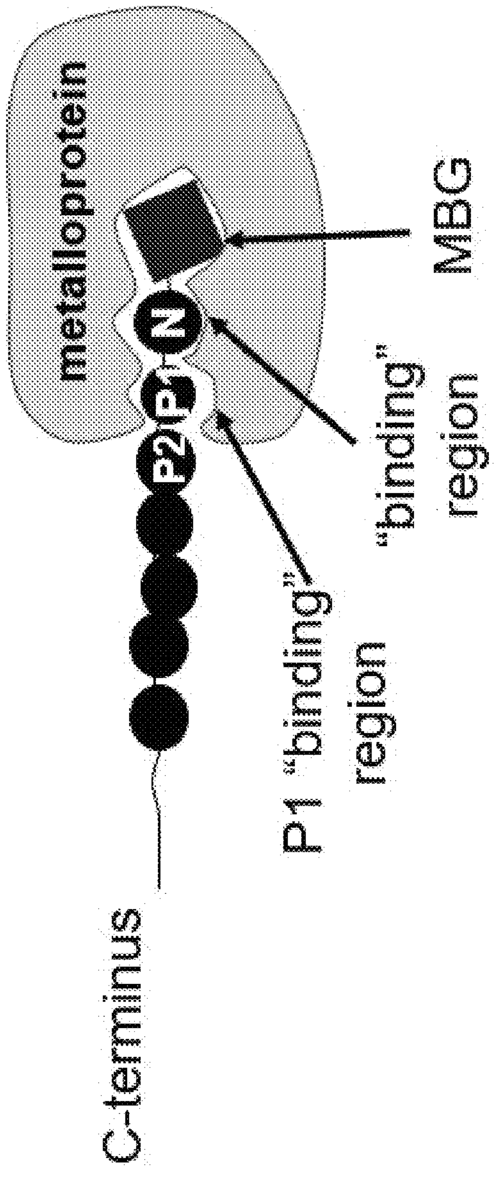
Figure 8D:
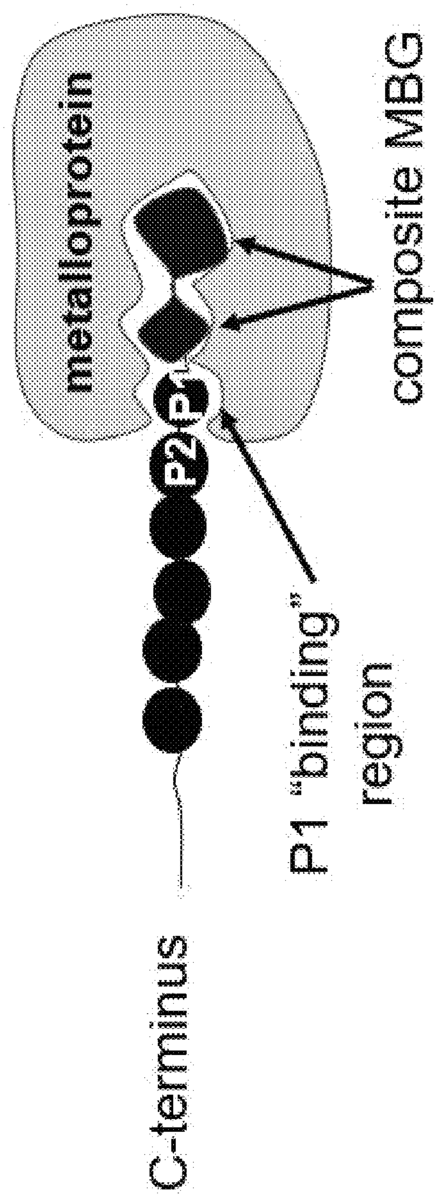

A functional assay for hCAII enzyme was set up. Carbonic anhydrase catalyzes the hydrolysis of 4-nitrophenyl acetate (4-NPA) to nitrophenol, which can be monitored by absorbance at 400 nm. The enzymatic carbonic anhydrase assay generally includes 0.2-1.0 μM enzyme and 10-500 μM 4-NPA in 20-200 μL in assay buffer. Assay buffer compositions can vary in buffer identity (Tris, phosphate, HEPES, etc.) and preferably do not precipitate required metal ions. Metal chelating agents (EDTA or EGTA), salt (NaCl, sulfate), detergent (Tween or Triton), and organic additives (acetonitrile, DMSO) may be employed to facilitate enzyme stability and reagent solubility. For the assay, 1 μM human carbonic anhydrase II, 50 mM MOPS (pH 7.6), 33 mM disodium sulfate, and 1 mM EDTA. To generate NTM-modified peptides, azide-derivatized peptides (via azide-PEG-amine and carbodiimide coupling to C-terminus of peptide) were conjugated to DBCO-coupled beads. As a metal-binding NTM that would possess high affinity binding to hCAII, 4-sulfamoylbenzoic acid (SABA) was employed as a metal binding pharmacophore to modify peptides at the N-terminus. To evaluate P1 dependence of the binding reaction, multiple P1 residues has been tested. SABA-XAAAE-$NH_2$ and SABA-AFAAE-$NH_2$ were obtained (FIG. 7A) by treating peptides immobilized on beads with SABA-NHS (X is a random amino acid residue). Binding affinities of the SABA-modified peptides to hCAII were estimated by calculating half-maximal inhibitory concentrations (IC50) of the peptides in the hCAII functional assay. 1 μM of hCAII in 50 mM MOPS (pH 7.6), 33 mM $Na_2SO_4$, 1 mM EDTA were mixed with different concentrations of the following compounds: SABA-XAAAE-$NH_2$, SABA-AFAAE-$NH_2$, FAAAE, SABA and acetazolamide (a control hCAII inhibitor). Effective dilution of each compound was from 1 mM to 0.1 nM, and DMSO was used as a vehicle; the mixtures were incubated for 10 minutes at 37° C. Thenp-Nitrophenylacetate (pNP-OAc) in DMSO was added to each well for an effective concentration of 500 μM, and inhibitory rates for each compound were determined by pNP release over 180 s (FIG. 7B). No significant binding/inhibition was observed with the native peptide, whereas SABA-modified peptides show efficient binding/inhibition with nM $K_d$ (assuming IC50≈$K_d$). Efficiencies of binding/inhibition vary depending on the P1 residue of the peptide (SABA-P1 binding efficiency: S<H<E<A<F<L) with IC50 ranging from 28 nM to 153 nM (Table 1). P2 dependence show ~4-fold difference, since IC50 are shown to be 48 nM, 183 nM, 45 nM for SABA-AA v. SABA-AF v. SABA-FA (SABA-P1-P2 groups).

Table 1. Half-maximal inhibitory concentrations ($IC_{50}$) of the SABA-modified peptides in the hCAII functional assay.

TABLE 1

Half-maximal inhibitory concentrations ($IC_{50}$) of the SABA-modified peptides in the hCAII functional assay.

| Compound | $IC_{50}$ (μM) |
|---|---|
| (SAB)AAAAE (SEQ ID NO: 143) | 0.0484 |
| (SAB)FAAAE (SEQ ID NO: 144) | 0.04498 |
| (SAB)EAAAE (SEQ ID NO: 145) | 0.0993 |
| (SAB)SAAAE (SEQ ID NO: 146) | 0.1534 |
| (SAB)LAAAE (SEQ ID NO: 147) | 0.02839 |
| (SAB)HAAAE (SEQ ID NO: 148) | 0.1485 |
| FAAAE (SEQ ID NO: 149) | 151.8 |
| (SAB)AFAAE (SEQ ID NO: 150) | 0.1827 |
| Acetazolamide | 0.02665 |
| SABA | 0.3594 |

Example 2. Selection and Design of Engineered Metalloprotein Binders Suitable for a Protein Binding (Such as NGPS) Assay and Capable of Binding NTM-P1 with Minimal P2 Bias Part I. Initial binder selection. To identify metalloproteins with potential utility as binders for the NGPS assay, zinc binding proteins with available crystal structures were reviewed from the literature in the Research Collaboratory for Structural Bioinformatics (RCSB) Protein Data Bank (PDB), and those with at least one accessible zinc ion, also referred to as Zn(II), binding site were identified as candidates for computational modeling studies. Accessible Zn(II) binding sites were defined as having trivalent Zn(II) coordination in PDB accession codes (also referred to as PDB IDs), in order to permit NTM-peptide coordination in the fourth Zn(II) coordination site, and binding pockets with either a conical or groove-shaped architecture near the Zn(II) binding site. Where Zn(II) binding sites had tetravalent Zn(II) coordination, one Zn(II)-chelating residue was mutated to either glycine or alanine to permit the fourth Zn(II) coordination site to be occupied by the NTM-peptide. Additionally, noncanonical amino acids were mutated to their canonical counterparts (e.g., cysteinesulfinic acid was mutated to cysteine). In effect, protein scaffolds where the Zn(II) ion is weakly bound and/or largely buried in the protein scaffold were excluded. Excessively large proteins (e.g., >100 kDa), those with numerous post-translational modifications (e.g., glycosylation), and oligomeric protein assemblies were also excluded. Crystal structures with small-molecule ligands coordinating the Zn(II) ion were given preference. A non-exhaustive list of PDB accession codes (PDB IDs) used for computational simulations is as follows: 5FCW, 2FV5, 2J83, 5E3C, 4Q4E, 5ELY, 1HEE, 4DJL, 1IAG, 1JAN, 1KAP, 1LML, 1OBR, 2CKI, 3P1V, 3UJZ, 4L63, 4LP6, 5K7J, 4DLM, 4YYT, 2CAB, 3P24, 5KZJ, 1JDO, 1Z97, 3ML5, 4KNM, 5JN8, 1AST, 1C7K, 2×7M, 3U7M, and 50D1.

Some scaffolds can be further optimized, such as reduced in size, by removing part(s) that form(s) a separate structure distant from a metal-binding portion of the scaffold. For example, 4Q4E scaffold (SEQ ID NO: 16) can be truncated to remove a separate domain which is structurally distinct from the metal-binding domain; the resulting truncated scaffold (SEQ ID NO: 59) has similar metal-binding properties to the original 4Q4E scaffold and similar relative Kd towards NTM-modified dipeptides.

Human carbonic anhydrases (hCA) were used as starting scaffolds for directed evolution toward binding modified NTAA residues of peptides.

Part II. NTM identification for the selected binders. Numerous small-molecule inhibitors of metalloproteins with enzymatic activity have precedence in the literature. In particular, arylsulfonamides and hydroxamic acids are well established Zn(II)-coordinating inhibitors of carbonic anhydrases and other metalloproteases. Additional established Zn(II)-coordinating ligand moieties include imidazoles, thiazoles, pyrazoles, thiols, hydrazides, N-hydroxyureas, squaric acids, carbamoylphosphonates, oxazolines, sulfamides, sulfamates, and quinolines. We designed N-terminal modifications (NTMs) to harbor these Zn(II)-coordinating moieties for high-affinity NTM binding to the Zn(II) ion in its respective metalloprotein. The NTMs were installed on a model dipeptide Ala-Ala (A-A) and used for in silico binding experiments and computational macromolecular modeling.

Based on internal data and computational modeling, metal-binding NTMs were designed such that when combined with the P1 amino acid residue (e.g., the N-terminal amino acid residue of the peptide), the NTM-P1 moiety occupies the hCA substrate pocket, with the P1 sidechain oriented closer to the molecular surface of the pocket. This design forces the P2 residue (penultimate residue) of the peptide to be located just outside the pocket or affinity determining region and contribute less Gibbs free energy to peptide binding. In particular, sulfamoyl benzene, pyrazolemethanimine (PMI), aminoguanidine and their chemical derivatives were evaluated.

Based on the data from Example 1, M64 NTM (FIG. 6A) has been initially selected. A 1.9 Å crystal structure of wild-type human carbonic anhydrase II (hCAII) protein (SEQ ID NO: 7) co-crystallized with M64-F group was obtained. Then, a set of Zn(II)-coordinating NTMs (e.g., derivatives of M64) was designed to provide enhanced binding affinity to the hCAII protein using structure-function analysis and crystal structure-based approach. The resulting NTMs (M64-M91 and M93-M98 (see FIG. 6A-6C)) were evaluated using a colorimetric IC50 assay to determine relative binding affinity of NTMs to the wild-type hCAII protein based on NTM inhibition capacity.

The colorimetric assay used 300 nM of wild-type carbonic anhydrase incubated in 45 μL of 50 mM MOPS (pH 7.5), 33 mM $Na_2SO_4$, and 1 mM EDTA aliquoted into a 96-well, clear, flat-bottom plate. To each column of the plate, a 1/10 dilution series from 1 mM to 0.1 nM of each NTM was added and incubated at 25° C. for 10 minutes to reach binding equilibrium. To this, 1 mM p-nitrophenylacetate (pNPA) was added to each well and screened on a plate reader at 405 nm wavelength. The initial rate of hydrolysis was observed over the first 60 seconds. The slopes versus the concentration of NTM were put into a non-linear regression equation to determine the IC50 of the NTM to the carbonic anhydrase.

Figure 9A:
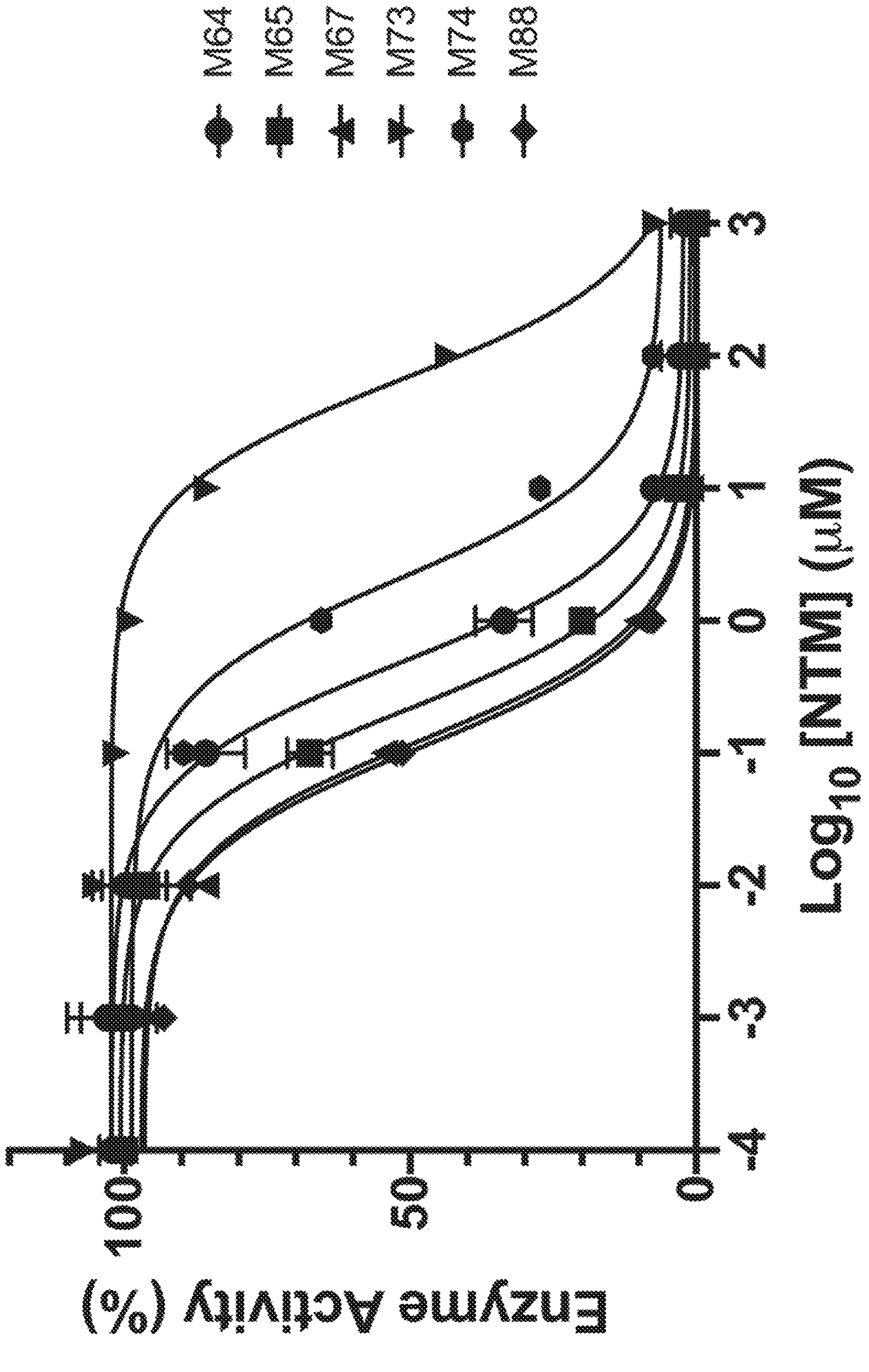
FIG. 9A-B.

12 M64 derivatives have been screened (Table 2; NTM structures are shown in FIG. 6A-6C). 6 tested NTMs provided ≥2-fold enhanced affinity over M64, as shown in FIG. 9A and Table 2.

Figure 9B:
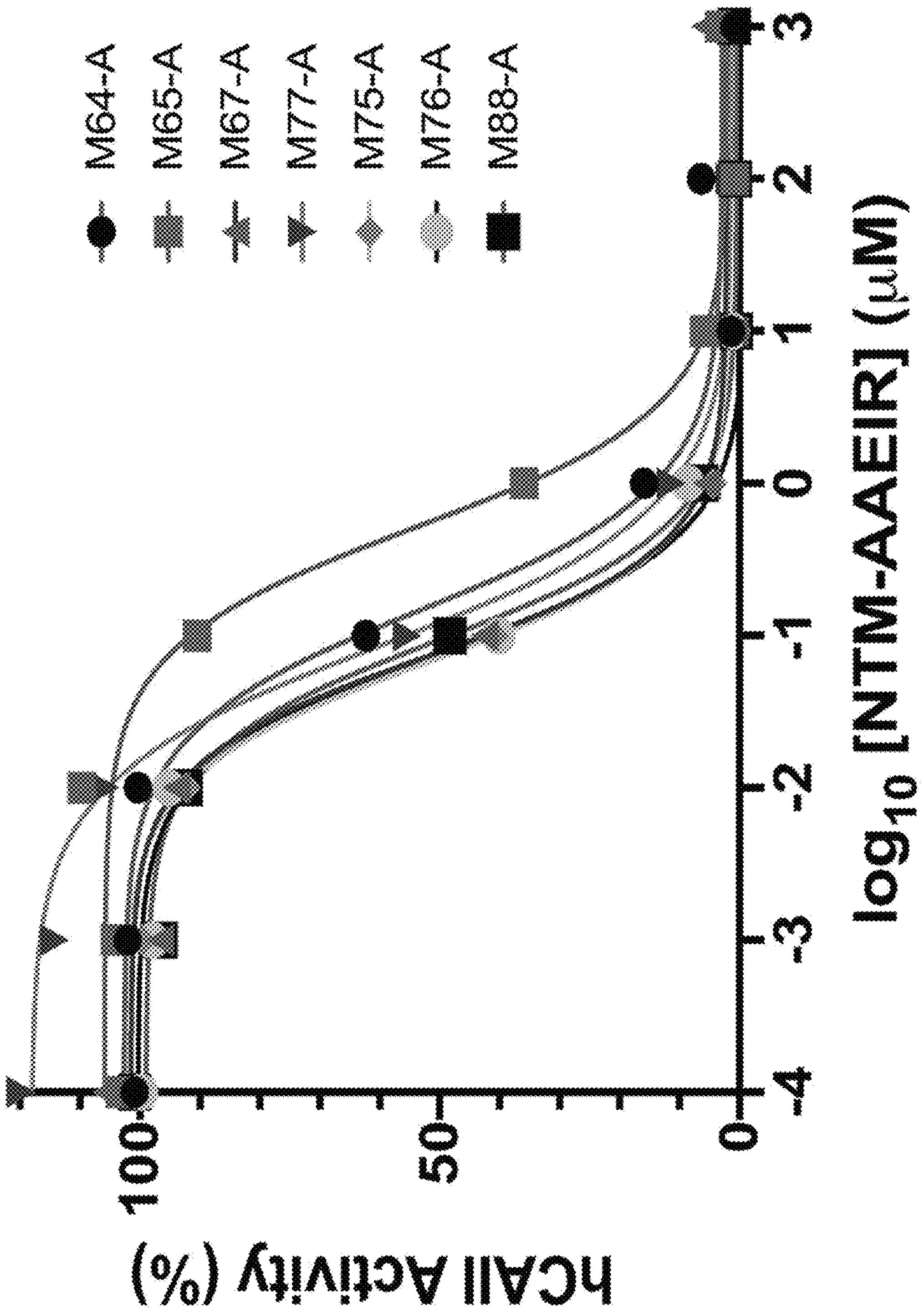

Next, the selected NTMs (derivatives of NTM M64) were installed on the N-terminus of a model peptide AAEIR by methods disclosed below. The N-terminally modified peptides were then evaluated using colorimetric IC50 assay to determine relative binding affinity of NTM-AAEIR to wild-type hCAII protein based on NTM-AAEIR inhibition capacity. The slopes versus the concentration of NTM-AAEIR were put into a non-linear regression equation to determine the IC50 of the selected NTM-AAEIR peptides to the wild-type hCAII. The results are shown in FIG. 9B and Table 2.

TABLE 2

Inhibition capacity of NTM M64 derivatives towards wild-type hCAII protein (relative to M64).

| NTM Substituent | NTM ID | IC50 (μM) | Fold Enhancement | NTM-AAEIR IC50 (μM) | Fold Enhancement |
|---|---|---|---|---|---|
| H | M64 | 0.473 | 1.0 | 0.150 | 1.0 |
| 3-endoN | M65 | 0.211 | 2.2 | 0.515 | 0.3 |
| 2-endoN | M66 | 0.992 | 0.5 | n.d. | n.d. |
| 2-NO2 | M67 | 0.124 | 3.8 | 0.073 | 2.0 |
| 3-OCH3 | M68 | n.d. | n.d. | n.d. | n.d. |
| 2-CH3 | M74 | 2.04 | 0.2 | n.d. | n.d. |
| 2-CF3 | M77 | 0.192 | 2.5 | 0.087 | 1.7 |

TABLE 2-continued

Inhibition capacity of NTM M64 derivatives towards wild-type hCAII protein (relative to M64).

| NTM Substituent | NTM ID | IC50 (μM) | Fold Enhancement | NTM-AAEIR IC50 (μM) | Fold Enhancement |
|---|---|---|---|---|---|
| 2-NH2 | — | 1.378 | 0.3 | n.d. | n.d. |
| 2-OCH3 | M73 | 65.43 | 0.0 | n.d. | n.d. |
| 2-F | M75 | 0.224 | 2.1 | 0.067 | 2.2 |
| 2-Cl | M76 | 0.180 | 2.6 | 0.077 | 1.9 |
| 3-F | M88 | 0.110 | 4.3 | 0.095 | 1.6 |

n.d.—not determined.
Fold enhancement is calculated relative to NTM M64.

Part III. NTM Parameterization. N-terminal modifications (NTMs), designated M64-M91 and M93-M97 (see FIG. 6A-6C), were parameterized for the Rosetta macromolecular modeling software suite by first generating conformer ensembles of each NTM using open-source RDKit software. For each NTM, each rotatable torsion angle sampled during conformer generation was clustered every 15°, from 0° to 360°, and the average torsion angle and standard deviation of the torsion angle was input to an Rosetta N-terminal modification parameterization patch file for sampling during NTM repacking in PyRosetta, a python-based interface to the Rosetta macromolecular modeling suite. For each atom of each NTM, partial charges were computed using the Amber antechamber software in a semi-empirical (AM1) with bond charge correction (BCC) model, AM1-BCC, which utilizes parameterization against the HF/6-31G* electrostatic potential of a training set of compounds with relevant functional groups. The partial charges of each atom type were also input into the Rosetta N-terminal modification parameterization patch file. NTMs were modeled onto the N-terminus of a dipeptide with amino acid sequence Ala-Ala (AA). The canonical C-terminus of each N-terminally modified dipeptide was computationally modeled with a dimethylamide moiety on the C-terminus.

Part IV. Computational modeling of potential binders. The three-dimensional coordinates of the metalloprotein binding residues and Zn(II) ion from PDB ID 4YYT, an X-ray diffraction crystal structure solved to 1.07 Å resolution of human carbonic anhydrase II in complex with a compound with a benzenesulfonamide moiety, 4-(2-hydroxyethyl)benzenesulfonamide, was used as a reference template for docking each NTM to the Zn(II) ion binding site in each PDB accession code (PDB ID) selected as binders (see "Part I. Initial binder selection" above). For each PDB ID, the residue number of the Zn(II) ion atom to be computationally modeled as binding the NTM-peptide was manually selected and cataloged in an input file. For each NTM (e.g., M64-M91 and M93-M97), an atom name map was manually generated between the atom names from the 4-(2-hydroxyethyl)benzenesulfonamide compound in PDB ID 4YYT to the structurally similar atom names in each NTM. Additionally, the interatomic distances between the Zn(II) ion atom and each of the three heavy polar atoms in the 4-(2-hydroxyethyl)benzenesulfonamide compound (e.g., the nitrogen and oxygen atoms of the sulfonamide moiety) in PDB ID 4YYT that are in close contact with the Zn(II) ion atom, respectively, were cataloged in an input file. The interatomic distances were applied as distance constraints (using a harmonic potential with 0.1 Å standard deviation) to the structurally similar polar heavy atoms in NTMs M64-M70, M73-M91, and M93-M97. Similarly, the interatomic distances between the Zn(II) ion atom and each of the three heavy polar atoms in the 4-naphthalen-1-yl-~{N}-oxidanyl-benzamide compound (e.g., the nitrogen and oxygen atoms of the hydroxamate moiety) in PDB ID 5FCW that are in close contact with the Zn(II) ion atom, respectively, were cataloged in an input file. Again, the interatomic distances were applied as applied as distance constraints (using a harmonic potential with 0.1 Å standard deviation) to the structurally similar polar heavy atoms in NTMs M71 and M72 (see below). Prior to computational simulations using the PyRosetta macromolecular design and modeling software suite, the following PDB IDs were prepared in Molecular Operating Environment (MOE) software to close bonds, correct hybridization and partial charges, and model loops that were missing in the protein scaffold deposited to the Protein Data Bank: 5K7J, 1LML, 5FCW, 3UJZ, 4L63, 4LP6, 5ELY, 1HEE, 2×7M, 1JAN, 3U7M, 2J83, 3P24, 5KZJ, 5JN8, and 4YYT. For each PDB ID and each NTM, one PyRosetta simulation was run to model the native protein scaffold ("native" binder), and one PyRosetta simulation was run to redesign the P1 pocket residues of the protein scaffold ("designed" binder).

For each PDB ID and NTM simulated using PyRosetta, the metal-chelating residues were algorithmically determined by finding the closest three residues in the protein scaffold containing the Zn(II) ion atom of interest, and for each of the metal-chelating residues algorithmically locating the closest polar heavy atom (of either nitrogen, oxygen, or sulfur atom types) on each metal-chelating residue to the Zn(II) ion atom of interest. Once the Zn(II) ion atom and the metal-binding atoms of each of the three metal-chelating residues were determined, the ordering of the metal-chelating atoms was permuted exhaustively, allowing for six different orderings of heavy polar atoms (3!=6 combinations). For each of the six different metal-chelating atom orderings, the three metal-chelating atoms along with the Zn(II) ion were superimposed onto the three metal-chelating atoms and Zn(II) ion atom in PDB ID 4YYT. In each of these six different superimpositions onto PDB ID 4YYT, the 4-(2-hydroxyethyl)benzenesulfonamide compound from PDB ID 4YYT was transferred to the binder using the PDB ID 4YYT crystal structure coordinates, and the protein scaffold from PDB ID 4YYT was deleted. Effectively at this stage, the 4-(2-hydroxyethyl)benzenesulfonamide compound acted as temporary surrogate for the NTM-dipeptide in the binder pocket. A clash score was calculated between the 4-(2-hydroxyethyl)benzenesulfonamide compound and the binder. The superimposition with the lowest clash score (fewest clashes) was selected as the most appropriate superimposition for further simulation. Subsequently, the NTM of the NTM-dipeptide was superimposed onto the 4-(2-hydroxyethyl)benzenesulfonamide compound in the binder using the aforementioned atom name map, and the 4-(2-hydroxyethyl)benzenesulfonamide compound was deleted. The torsion angle between the metal-binding atoms and the NTM aromatic ring was sampled at a torsion angle equal to the corresponding torsion angle in the 4-(2-hydroxyethyl) benzenesulfonamide compound, with and without adding 180°, and the NTM-dipeptide backbone torsion angles were randomized with bias toward Ramachandran torsion bins for the dipeptide amino acid identities (e.g., AA) a total of 100 times. For each NTM-dipeptide conformation, a clash score between the NTM-dipeptide and the binder was computed. The NTM-dipeptide conformation with the lowest clash score was selected for further simulation. Effectively at this stage, the NTM-dipeptide was docked into the binder and modeled as chelating the Zn(II) ion atom.

Subsequently, the metal-chelating residues and Zn(II) ion atomic 3-dimensional coordinates were constrained in place using a harmonic potential with 0.1 Å standard deviation. Furthermore, the aforementioned distance constraints between the Zn(II) ion atom and each of the three polar heavy atoms in close contact with the Zn(II) ion atom (e.g., as described above using interatomic distances derived from PDB ID 4YYT and PDB ID 5FCW) were applied using a harmonic potential with 0.1 Å standard deviation. Subsequently, P1 pocket residues were algorithmically determined as those on the binder within <4.5 Å from any atom in the NTM-dipeptide or those with Ca atoms within <6.0 Å of the P1 Ca atom, discounting the metal-chelating residues. For PyRosetta simulations maintaining the native amino acid sequence (discounting mutations to glycine or alanine of up to one residue in the Zn(II) ion binding site, as well as discounting mutations of noncanonical amino acids to their canonical counterparts [see "Binder Selection" above]; termed "native" binders), side-chain rotamers were permitted to repack with a fixed amino acid identity. For the PyRosetta simulations mutating the native amino acid sequence (again discounting mutations to glycine or alanine of up to one residue in the Zn(II) ion binding site, as well as discounting mutations of noncanonical amino acids to their canonical counterparts [see "Part I. Initial binder selection" above]; termed "designed" binders), side-chain rotamers were permitted to repack and/or design to the same or different amino acid identity. Side-chain rotamers and/or amino acid identities were sampled using a Monte Carlo Metropolis criterion algorithm, followed by minimization of protein backbone and side-chains in the full-atom Rosetta energy function "ref2015_cart". Side-chain repacking and backbone and side-chain minimization steps were iteratively processed in the PyRosetta algorithm FastRelax for the native binders, and the PyRosetta algorithm FastDesign for the designed binders. As such, new conformations of NTM-dipeptide in complex with the binders were algorithmically generated. Finally, biophysical metrics were computationally calculated as given in Tables 3-8.

The purpose of algorithmically mutating the native binders to generate the designed binders was to increase the binding affinity (e.g., decrease the thermodynamic dissociation constant) of the NTM-dipeptide for the native binder (e.g., equivalent to decreasing the change in Gibbs free energy upon NTM-dipeptide binding to the protein scaffold for the designed binder compared to the native binder). PyRosetta software employs a pseudorandom number generator (RNG) to generate a seed (e.g., an integer value) to initialize each PyRosetta simulation. As such, the input RNG-generated seed to the PyRosetta simulation results in a deterministic trajectory. Generally, each design simulation within PyRosetta software was expected to increase the affinity of the NTM-dipeptide for the native binder. As only one design simulation was run per PDB ID per NTM, it was expected that not all design simulations would result in increased affinity of the NTM-dipeptide for the native binder, as the FastDesign algorithm in the PyRosetta simulation could arrive in a local energetic minimum in sequence-structure space, rather than always arriving in the global energetic minimum in sequence-structure space. Therefore, by running the FastDesign algorithm in the PyRosetta simulation using a multitude of different RNG-generated seeds (on the order of using $10^3$ to $10^6$ unique RNG-generated seeds, with an upper-bound limited only by the practicality of procuring compute resources), it is expected that design simulations in PyRosetta software would result in designed binders with even higher ΔKd (native to designed) (e.g., overall a lower thermodynamic dissociation constant) of the NTM-dipeptide for the designed binder. Future computational protein modeling campaigns will employ multitudinous RNG-generated seeds to arrive in the global energetic minimum in sequence-structure space for each PDB ID and NTM combination. For each PDB ID and NTM combination, the designed binders with the highest ΔKd (native to designed) will be selected for experimental validation.

For each PDB ID, NTM, and either the native binder or designed binder, the following labels and/or biophysical metrics and their descriptions below were computed.

"PDB ID": the Protein Data Bank accession code for the selected binder.

"NTM": the N-terminal modification identifier.

"Metal Ion": the metal ion name and Roman numeral in parentheses representing the ionic charge or oxidation state of the metal ion.

"Metal-chelating Residues": a comma-separated list where each element represents the residue number followed by the one-letter amino acid identity. There are three metal-chelating residues per binder, and the NTM occupies the fourth metal ion coordination site.

"Native Binder ΔKd (Metal-chelating Residues to Gly)": for the native binder, the fold-change in the thermodynamic dissociation constant (Kd) of NTM-dipeptide binding upon mutation of the metal-chelating residues to glycine and translation of the metal ion from the interface, as given by the formula, $$\Delta K_d = e^{-\frac{\Delta\Delta G}{RT}},$$

where ΔΔG is the value given by "Native Binder ΔΔG (Metal-chelating Residues to Gly) (kcal/mol)" described below, R is the universal gas constant, and T is the temperature at 25° C.

"Designed Binder ΔKd (Metal-chelating Residues to Gly)": for the designed binder, the fold-change in the thermodynamic dissociation constant ($K_d$) of NTM-dipeptide binding upon mutation of the metal-chelating residues to glycine and translation of the metal ion from the interface, as given by the formula $$\Delta K_d = e^{-\frac{\Delta\Delta G}{RT}},$$

where ΔΔG is the value given by "Designed Binder ΔΔG (Metal-chelating Residues to Gly) (kcal/mol)" described below, R is the universal gas constant, and T is the temperature at 25° C.

"ΔKd (Native to Designed)": the fold-change improvement in the thermodynamic dissociation constant ($K_d$) of NTM-dipeptide binding upon designing the binder from the native binder sequence to the designed binder sequence, as given by the formula $$\Delta K_d = e^{-\frac{\Delta\Delta\Delta G}{RT}},$$

where $\Delta\Delta\Delta G = \Delta\Delta G^{designed} - \Delta\Delta G^{native}$, $\Delta\Delta G^{designed}$ is the value given by "Designed Binder ΔΔG (Metal-chelating Residues to Gly) (kcal/mol)", $\Delta\Delta G^{native}$ is the value given by "Native Binder ΔΔG (Metal-chelating Residues to Gly) (kcal/mol)", R is the universal gas constant, and T is the $\Delta K_d^{designed}$ temperature at 25° C. The value is tantamount to $$\Delta K_d = \frac{\Delta K_d^{designed}}{\Delta K_d^{native}}$$

where $\Delta K_d^{designed}$ is the value given by "Designed Binder ΔKd (Metal-chelating Residues to Gly)" and $\Delta K_d^{native}$ is the value given by "Native Binder ΔKd (Metal-chelating Residues to Gly)".

"P1 Pocket Residues": a comma-separated list where each element represents a residue number from the binder within ≤4.5 Å from any atom in the NTM-dipeptide or a residue with Cα atom within ≤6.0 Å of the P1 Cα atom, discounting metal-chelating residues as given in "Metal-chelating Residues". Each of these residues was permitted to repack to different rotamers in the native binder, and repack to different rotamers while updating amino acid identity in the designed binder.

"Mutations (Native to Designed)": a comma-separated list of mutations from the native binder to the designed binder, where each element represents the native binder amino acid identity followed by the residue number followed by the designed binder amino acid identity.

"Native Binder Sequence": the amino acid sequence of the native binder used in the computational simulation. "Designed Binder Sequence": the resulting amino acid sequence of the designed binder after the computational simulation.

Tables comprising data that evaluate relative binding affinities for metalloprotein binder scaffolds and exemplary designed binders are shown below.

TABLE 3

Estimated relative binding affinities for metalloprotein binder scaffolds using modeled M64-modified AA dipeptide as a substrate.

| PDB ID | Metal-chelating Residues | Native Binder ΔKd | Designed Binder ΔKd | ΔKd (Native to Designed) |
|---|---|---|---|---|
| 5ELY | 333D, 371E, 499H | 122.56 | 58.80 | 0.48 |
| 1C7K | 83H, 87H, 93D | 169.95 | 39933.41 | 234.97 |
| 2CAB | 90H, 92H, 115H | 1260.37 | 3025.70 | 2.40 |
| 3P24 | 162D, 316H, 320H | 1530.55 | 568.53 | 0.37 |
| 2X7M | 132H, 136H, 142H | 1917.26 | 83739.91 | 43.68 |
| 4DJL | 69H, 72E, 204H | 2064.17 | 3507.48 | 1.70 |
| 1AST | 92H, 96H, 102H | 3646.08 | 24966.00 | 6.85 |
| 2CKI | 168H, 172H, 178H | 3759.17 | 9048.85 | 2.41 |
| 5OD1 | 35H, 61H, 65H | 3802.74 | 936.01 | 0.25 |
| 1OBR | 69H, 72E, 204H | 4034.94 | 2502.52 | 0.62 |
| 1HEE | 69H, 72E, 196H | 4324.49 | 1649.98 | 0.38 |
| 4KNM | 92H, 94H, 117H | 4793.21 | 7027.04 | 1.47 |
| 4L63 | 160H, 164H, 170H | 5348.71 | 4895.40 | 0.92 |
| 4LP6 | 91H, 93H, 116H | 6154.33 | 5537.36 | 0.90 |
| 5JN8 | 97H, 99H, 122H | 6388.24 | 11297.01 | 1.77 |
| 1JAN | 119H, 123H, 129H | 7690.22 | 7237.69 | 0.94 |
| 3ML5 | 94H, 96H, 119H | 7730.89 | 2652.53 | 0.34 |
| 4Q4E | 293H, 297H, 316E | 8287.36 | 26716.71 | 3.22 |
| 2J83 | 166H, 170H, 176H | 9299.58 | 18565.42 | 2.00 |
| 2FV5 | 190H, 194H, 200H | 9776.33 | 21453.68 | 2.19 |
| 1LML | 165H, 169H, 235H | 9923.66 | 73906.30 | 7.45 |
| 4YYT | 91H, 93H, 116H | 10611.77 | 6598.19 | 0.62 |
| 1Z97 | 91H, 93H, 116H | 11600.71 | 18565.77 | 1.60 |
| 3UJZ | 408H, 412H, 418H | 12546.59 | 6165.14 | 0.49 |
| 1JD0 | 89H, 91H, 115H | 13497.78 | 5259.50 | 0.39 |
| 5E3C | 448H, 453H, 506E | 20466.38 | 26662.41 | 1.30 |
| 1KAP | 176H, 180H, 186H | 29950.61 | 176002.03 | 5.88 |
| 5K7J | 181H, 185H, 212H | 36645.34 | 45366.57 | 1.24 |
| 1IAG | 141H, 145H, 151H | 70228.70 | 30691.31 | 0.44 |
| 4DLM | 7H, 9H, 242D | 142141.47 | 818.42 | 0.01 |
| 3U7M | 111C, 154H, 158H | 541295.44 | 414363.56 | 0.77 |

Some of the tested scaffolds (e.g., 3U7M, 4DLM, 1IAG, 5K7J, 1KAP) show elevated "Native Binder ΔKd" parameter (calculated upon mutation of metal-chelating residues to Gly), indicating that metal-chelating residues and thus the metal ion significantly contribute to binding affinity for binding between the native binder and the M64-modified AA model peptide. Other tested scaffolds show significantly elevated "ΔKd (Native to Designed)" parameter (e.g., the fold-change improvement in Rd upon mutating the binder from the native binder sequence), indicating that the designed (modified) binders have improved binding affinities for binding between the designed binder and the M64-modified AA model peptide.

Examples of such designed binders having improved binding affinities include SEQ ID NOs: 28-31 based on the following scaffolds: 3U7M (having corresponding mutations: G58A, G60V, L61I, A62V, Q65M, 177L, TTO7D, ETO9L, G110Q, Y147L, V155L, E155A, and E185L); 1KAP (having corresponding mutations: A134L, A135V, A137V, Y158W, A1601, N161V, Y169R, T173L, E177M, N191H, A192P, R209L, and Y216L); 2X7M (having corresponding mutations: A901, L93V, G98L, Q991, E133A, F152P, and S153A); and 1LML (having corresponding mutations: E166V, A229E, S231Y, and F352L).

TABLE 4

Estimated relative binding affinities for metalloprotein binder scaffolds using modeled M65-modified AA dipeptide as a substrate.

| PDB ID | Metal-chelating Residues | Native Binder ΔKd | Designed Binder ΔKd | ΔKd (Native to Designed) |
|---|---|---|---|---|
| 1AST | 92H, 96H, 102H | 624.46 | 8647.93 | 13.85 |
| 1C7K | 83H, 87H, 93D | 32.38 | 3854.48 | 119.04 |
| 1HEE | 69H, 72E, 196H | 548.15 | 1705.60 | 3.11 |
| 1IAG | 141H, 145H, 151H | 38483.43 | 11906.58 | 0.31 |
| 1JAN | 119H, 123H, 129H | 12267.20 | 16932.23 | 1.38 |
| 1JD0 | 89H, 91H, 115H | 2074.28 | 2028.63 | 0.98 |
| 1KAP | 176H, 180H, 186H | 383.02 | 1905.54 | 4.97 |
| 1LML | 165H, 169H, 235H | 9543.07 | 11293.15 | 1.18 |
| 1OBR | 69H, 72E, 204H | 1737.31 | 1493.11 | 0.86 |
| 1Z97 | 91H, 93H, 116H | 5064.90 | 20860.11 | 4.12 |
| 2CAB | 90H, 92H, 115H | 504.50 | 985.06 | 1.95 |

TABLE 4-continued

Estimated relative binding affinities for metalloprotein binder scaffolds using modeled M65-modified AA dipeptide as a substrate.

| PDB ID | Metal-chelating Residues | Native Binder ΔKd | Designed Binder ΔKd | ΔKd (Native to Designed) |
|---|---|---|---|---|
| 2CKI | 168H, 172H, 178H | 10674.58 | 11152.29 | 1.04 |
| 2FV5 | 190H, 194H, 200H | 7606.85 | 4936.36 | 0.65 |
| 2J83 | 166H, 170H, 176H | 13645.70 | 26139.29 | 1.92 |
| 2X7M | 132H, 136H, 142H | 75987.80 | 33487.11 | 0.44 |
| 3ML5 | 94H, 96H, 119H | 1536.03 | 3717.35 | 2.42 |
| 3P24 | 162D, 316H, 320H | 20.48 | 4.07 | 0.20 |
| 3U7M | 111C, 154H, 158H | 114409.43 | 352385.06 | 3.08 |
| 3UJZ | 408H, 412H, 418H | 18043.30 | 13734.32 | 0.76 |
| 4DJL | 69H, 72E, 204H | 2083.30 | 1521.04 | 0.73 |
| 4DLM | 7H, 9H, 242D | 16141.45 | 2301.79 | 0.14 |
| 4KNM | 92H, 94H, 117H | 7450.23 | 9396.54 | 1.26 |
| 4L63 | 160H, 164H, 170H | 1775.95 | 23991.78 | 13.51 |
| 4LP6 | 91H, 93H, 116H | 6288.96 | 10964.18 | 1.74 |
| 4Q4E | 293H, 297H, 316E | 47969.63 | 650053.88 | 13.55 |
| 4YYT | 91H, 93H, 116H | 3347.82 | 10851.54 | 3.24 |
| 5E3C | 448H, 453H, 506E | 298.39 | 12151.96 | 40.73 |
| 5ELY | 333D, 371E, 499H | 14.12 | 27.22 | 1.93 |
| 5JN8 | 97H, 99H, 122H | 2959.72 | 6101.65 | 2.06 |
| 5K7J | 181H, 185H, 212H | 53027.31 | 46548.05 | 0.88 |
| 5OD1 | 35H, 61H, 65H | 43.77 | 135.18 | 3.09 |

Some of the tested scaffolds (e.g., 3U7M, 2×7M, 5K7J, and 4Q4E) show elevated "Native Binder ΔKd" parameter (calculated upon mutation of metal-chelating residue to Gly), indicating that metal-chelating residues significantly contribute to binding affinity for binding between the unmodified binder and the M65-modified AA model peptide. Other tested scaffolds show significantly elevated "ΔKd (Native to Designed)" parameter (the fold-change improvement in $K_d$ upon mutating the binder from the native binder sequence), indicating that the designed (modified) binders have improved binding affinities for binding between the designed binder and the M65-modified AA model peptide.

Examples of such designed binders having improved binding affinities include SEQ ID NOs: 32-34 based on the following scaffolds: 4Q4E (having corresponding mutations: E117L, F254L, M256T, A258V, M259V, E260P, K270A, Y271L, D286E, R289A, E294V, K3151, V320L, D3231, Y372F, Y377L, and E378W); 3U7M (having corresponding mutations: G58L, V59A, G60M, A62V, Q65L, A74V, E109F, G110Q, L112I, S113A, R124L,Y147L, I150L, V151I, E155A, and E185L); 1Z97 (having corresponding mutations: N59D, K61L, R64L, R88L, Q89F, E103L, F127Y, L131Q, V1391, S193A, L194M, T195A, T196V, C199L, and 1203V).

TABLE 5

Estimated relative binding affinities for metalloprotein binder scaffolds using modeled M72-modified AA dipeptide as a substrate.

| PDB ID | Metal-chelating Residues | Native Binder ΔKd | Designed Binder ΔKd | ΔKd (Native to Designed) |
|---|---|---|---|---|
| 1AST | 92H, 96H, 102H | 63722.81 | 153194.55 | 2.40 |
| 1C7K | 83H, 87H, 93D | 3619.15 | 55440.38 | 15.32 |
| 1HEE | 69H, 72E, 196H | 4872.80 | 10558.65 | 2.17 |
| 1IAG | 141H, 145H, 151H | 272387.13 | 117757.55 | 0.43 |
| 1JAN | 119H, 123H, 129H | 86651.15 | 60249.68 | 0.70 |
| 1JD0 | 89H, 91H, 115H | 57701.91 | 74639.14 | 1.29 |
| 1KAP | 176H, 180H, 186H | 607558.25 | 24239.16 | 0.04 |
| 1LML | 165H, 169H, 235H | 373307.00 | 883379.63 | 2.37 |
| 1OBR | 69H, 72E, 204H | 5899.94 | 63562.03 | 10.77 |
| 1Z97 | 91H, 93H, 116H | 137532.61 | 56436.28 | 0.41 |

TABLE 5-continued

Estimated relative binding affinities for metalloprotein binder scaffolds using modeled M72-modified AA dipeptide as a substrate.

| PDB ID | Metal-chelating Residues | Native Binder ΔKd | Designed Binder ΔKd | ΔKd (Native to Designed) |
|---|---|---|---|---|
| 2CAB | 90H, 92H, 115H | 25980.07 | 26741.91 | 1.03 |
| 2CKI | 168H, 172H, 178H | 49689.99 | 325644.06 | 6.55 |
| 2FV5 | 190H, 194H, 200H | 84020.88 | 121252.92 | 1.44 |
| 2J83 | 166H, 170H, 176H | 393620.22 | 764526.31 | 1.94 |
| 2X7M | 132H, 136H, 142H | 25480.32 | 221792.09 | 8.70 |
| 3ML5 | 94H, 96H, 119H | 24181.60 | 75366.99 | 3.12 |
| 3P1V | 292H, 296H, 303D | 1044.22 | 14978.47 | 14.34 |
| 3P24 | 162D, 316H, 320H | 1033.65 | 321.75 | 0.31 |
| 3U7M | 111C, 154H, 158H | 1734168.13 | 3053128.50 | 1.76 |
| 3UJZ | 408H, 412H, 418H | 21819.33 | 649907.44 | 29.79 |
| 4DJL | 69H, 72E, 204H | 4125.50 | 6537.24 | 1.58 |
| 4DLM | 7H, 9H, 242D | 6191.26 | 8855.59 | 1.43 |
| 4KNM | 92H, 94H, 117H | 16386.69 | 39221.91 | 2.39 |
| 4L63 | 160H, 164H, 170H | 414865.09 | 706820.19 | 1.70 |
| 4LP6 | 91H, 93H, 116H | 41791.11 | 127011.07 | 3.04 |
| 4Q4E | 293H, 297H, 316E | 550570.81 | 1051209.63 | 1.91 |
| 4YYT | 91H, 93H, 116H | 5946.47 | 119100.20 | 20.03 |
| 5E3C | 448H, 453H, 506E | 36406.44 | 321.92 | 0.01 |
| 5ELY | 333D, 371E, 499H | 3.40 | 193.01 | 56.78 |
| 5JN8 | 97H, 99H, 122H | 105169.23 | 158107.19 | 1.50 |
| 5K7J | 181H, 185H, 212H | 531165.69 | 275995.47 | 0.52 |
| 5OD1 | 35H, 61H, 65H | 57407.41 | 105279.06 | 1.83 |

Some of the tested scaffolds (e.g., 3U7M, 1KAP, 4Q4E, 5K17J) show elevated "Native Binder ΔKd" parameter (calculated upon mutation of metal-chelating residue to Gly), indicating that metal-chelating residues significantly contribute to binding affinity for binding between the unmodified binder and the M72-modified AA model peptide. Other tested scaffolds show significantly elevated "ΔKd (Native to Designed)" parameter (the fold-change improvement in Rd upon mutating the binder from the native binder sequence), indicating that the designed (modified) binders have improved binding affinities for binding between the designed binder and the M72-modified AA model peptide.

Examples of such designed binders having improved binding affinities include SEQ ID NOs: 35-38 based on the following scaffolds: 4Q4E (having corresponding mutations: E117V, F254L, M256T, A258M, E260V, F267V, N268H, K(2701, Y2711A, V2721, V290L, E294A, K3151, Y377L, N7761, and R779L); 3U7M (having corresponding mutations: Q45L, G58A, V59G, G60M, A62V, Q65M, A74V, V75M, Y86W, G110E, Y147L, P148A, V15TIA, F152M, E155A, and E185L); 1LML (having corresponding mutations: E121H, V124I, E166A, G230K, S2311, A249K, and F352L); 3UJZ (having corresponding mutations: W328E, $H_{329}$T, G389K1, and D409A).

TABLE 6

Estimated relative binding affinities for metalloprotein binder scaffolds using modeled M83-modified AA dipeptide as a substrate.

| PDB ID | Metal-chelating Residues | Native Binder ΔKd | Designed Binder ΔKd | ΔKd (Native to Designed) |
|---|---|---|---|---|
| 1AST | 92H, 96H, 102H | 2157.53 | 643.78 | 0.30 |
| 1C7K | 83H, 87H, 93D | 3.87 | 757.14 | 195.71 |
| 1HEE | 69H, 72E, 196H | 101.78 | 447.93 | 4.40 |
| 1IAG | 141H, 145H, 151H | 18156.32 | 32811.39 | 1.81 |
| 1JAN | 119H, 123H, 129H | 3457.45 | 4324.86 | 1.25 |
| 1JD0 | 89H, 91H, 115H | 366.58 | 7387.84 | 20.15 |
| 1KAP | 176H, 180H, 186H | 210.29 | 1934.99 | 9.20 |
| 1LML | 165H, 169H, 235H | 7425.52 | 16438.11 | 2.21 |

TABLE 6-continued

Estimated relative binding affinities for metalloprotein binder scaffolds using modeled M83-modified AA dipeptide as a substrate.

| PDB ID | Metal-chelating Residues | Native Binder ΔKd | Designed Binder ΔKd | ΔKd (Native to Designed) |
|---|---|---|---|---|
| 1OBR | 69H, 72E, 204H | 400.06 | 178.40 | 0.45 |
| 1Z97 | 91H, 93H, 116H | 1553.89 | 3533.71 | 2.27 |
| 2CAB | 90H, 92H, 115H | 218.38 | 155.09 | 0.71 |
| 2CKI | 168H, 172H, 178H | 2304.49 | 6260.11 | 2.72 |
| 2FV5 | 190H, 194H, 200H | 7887.99 | 6212.09 | 0.79 |
| 2J83 | 166H, 170H, 176H | 3303.57 | 5819.76 | 1.76 |
| 2X7M | 132H, 136H, 142H | 2178.02 | 2675.89 | 1.23 |
| 3ML5 | 94H, 96H, 119H | 437.21 | 854.57 | 1.95 |
| 3P24 | 162D, 316H, 320H | 90.89 | 116.58 | 1.28 |
| 3UJZ | 408H, 412H, 418H | 1463.70 | 3880.85 | 2.65 |
| 4DJL | 69H, 72E, 204H | 148.21 | 317.72 | 2.14 |
| 4DLM | 7H, 9H, 242D | 1581.41 | 826.23 | 0.52 |
| 4KNM | 92H, 94H, 117H | 227.25 | 397.20 | 1.75 |
| 4L63 | 160H, 164H, 170H | 4040.53 | 2388.26 | 0.59 |
| 4LP6 | 91H, 93H, 116H | 496.85 | 622.44 | 1.25 |
| 4Q4E | 293H, 297H, 316E | 17175.40 | 29270.72 | 1.70 |
| 4YYT | 91H, 93H, 116H | 2614.89 | 1839.03 | 0.70 |
| 5E3C | 448H, 453H, 506E | 551.44 | 2259.82 | 4.10 |
| 5JN8 | 97H, 99H, 122H | 917.74 | 1065.74 | 1.16 |
| 5K7J | 181H, 185H, 212H | 21430.29 | 45.75 | 0.00 |
| 5OD1 | 35H, 61H, 65H | 1673.40 | 3711.28 | 2.22 |

Some of the tested scaffolds (e.g., 5K7J, 1IAG, 4Q4E, 2FV5) show elevated "Native Binder ΔKd" parameter (calculated upon mutation of metal-chelating residue to Gly), indicating that metal-chelating residues significantly contribute to binding affinity for binding between the unmodified binder and the M83-modified AA model peptide. Other tested scaffolds show significantly elevated "ΔKd (Native to Designed)" parameter (the fold-change improvement in $K_d$ upon mutating the binder from the native binder sequence), indicating that the designed (modified) binders have improved binding affinities for binding between the designed binder and the M83-modified AA model peptide.

Examples of such designed binders having improved binding affinities include SEQ ID NOs: 39-41 based on the following scaffolds: 1IAG (having corresponding mutations: G108L, K109L, E142L, K154P, R166L, and G168E); 4Q4E (having corresponding mutations: E117M, M256T, G257L, A258L, M2591, E260P, Y271L, K282E, D286R, R289A, V290A, E2941, T3431, Y377L, and E378Y); 1LML (having corresponding mutations: E166A, G227A, G230K, S23TA, and F352R).

TABLE 7

Estimated relative binding affinities for metalloprotein binder scaffolds using modeled M86-modified AA dipeptide as a substrate.

| PDB ID | Metal-chelating Residues | Native Binder ΔKd | Designed Binder ΔKd | ΔKd (Native to Designed) |
|---|---|---|---|---|
| 4Q4E | 293H, 297H, 316E | 94.46 | 9912.31 | 104.94 |
| 3P24 | 162D, 316H, 320H | 5.96 | 546.35 | 91.74 |
| 1LML | 165H, 169H, 235H | 2377.73 | 56506.00 | 23.76 |
| 2J83 | 166H, 170H, 176H | 1399.24 | 17083.00 | 12.21 |
| 2X7M | 132H, 136H, 142H | 400.13 | 4735.54 | 11.84 |
| 5E3C | 448H, 453H, 506E | 3361.75 | 24206.04 | 7.20 |
| 2FV5 | 190H, 194H, 200H | 5330.16 | 22997.28 | 4.31 |
| 1AST | 92H, 96H, 102H | 599.93 | 2454.49 | 4.09 |
| 1HEE | 69H, 72E, 196H | 175.26 | 520.44 | 2.97 |
| 1C7K | 83H, 87H, 93D | 9608.85 | 21262.48 | 2.21 |
| 2CAB | 90H, 92H, 115H | 1604.91 | 3465.38 | 2.16 |
| 3UJZ | 408H, 412H, 418H | 2939.88 | 5962.35 | 2.03 |
| 5K7J | 181H, 185H, 212H | 3518.29 | 6266.39 | 1.78 |

TABLE 7-continued

Estimated relative binding affinities for metalloprotein binder scaffolds using modeled M86-modified AA dipeptide as a substrate.

| PDB ID | Metal-chelating Residues | Native Binder ΔKd | Designed Binder ΔKd | ΔKd (Native to Designed) |
|---|---|---|---|---|
| 1IAG | 141H, 145H, 151H | 11713.26 | 18621.20 | 1.59 |
| 1Z97 | 91H, 93H, 116H | 10557.23 | 11990.08 | 1.14 |
| 1JAN | 119H, 123H, 129H | 1591.16 | 1676.96 | 1.05 |
| 1OBR | 69H, 72E, 204H | 1811.64 | 1899.29 | 1.05 |
| 4DJL | 69H, 72E, 204H | 2206.03 | 2311.16 | 1.05 |
| 4YYT | 91H, 93H, 116H | 3987.37 | 3931.71 | 0.99 |
| 1KAP | 176H, 180H, 186H | 1030.36 | 988.12 | 0.96 |
| 2CKI | 168H, 172H, 178H | 2761.10 | 2629.84 | 0.95 |
| 4L63 | 160H, 164H, 170H | 5922.17 | 4017.96 | 0.68 |
| 4KNM | 92H, 94H, 117H | 1591.47 | 979.08 | 0.62 |
| 3P1V | 292H, 296H, 303D | 74.18 | 43.77 | 0.59 |
| 1JD0 | 89H, 91H, 115H | 2021.82 | 1153.22 | 0.57 |
| 5JN8 | 97H, 99H, 122H | 5808.72 | 2999.19 | 0.52 |
| 4LP6 | 91H, 93H, 116H | 4784.62 | 2140.14 | 0.45 |
| 3ML5 | 94H, 96H, 119H | 5293.72 | 1478.20 | 0.28 |
| 5OD1 | 35H, 61H, 65H | 4392.91 | 357.91 | 0.08 |
| 5ELY | 333D, 371E, 499H | 28.58 | 0.22 | 0.01 |
| 4DLM | 7H, 9H, 242D | 49820.61 | 324.14 | 0.01 |
| 3U7M | 111C, 154H, 158H | 47436.00 | 28.83 | 0.00 |

Some of the tested scaffolds (e.g., 4DLM, 3U7M, 1IAG) show elevated "Native Binder ΔKd" parameter (calculated upon mutation of metal-chelating residue to Gly), indicating that metal-chelating residues significantly contribute to binding affinity for binding between the unmodified binder and the M86-modified AA model peptide. Other tested scaffolds show significantly elevated "ΔKd (Native to Designed)" parameter (the fold-change improvement in $K_d$ upon mutating the binder from the native binder sequence), indicating that the designed (modified) binders have improved binding affinities for binding between the designed binder and the M86-modified AA model peptide.

Examples of such designed binders having improved binding affinities include SEQ ID NOs: 42-44 based on the following scaffolds: 1LML (having corresponding mutations: E121H, E166V, A229R, S231V, A249D, and F352L); 5E3C (having corresponding mutations: S106A, F107W, E314W, Y316V, R317F, E325M, E327F, F379M, S382L, A386L, G387M, I388M, N389V, Q564D, A565V, and $H_{566}L$); 2FV5 (having corresponding mutations: V99L, T132R, G134L, L135I, A136V, R142H, and E191A).

TABLE 8

Estimated relative binding affinities for metalloprotein binder scaffolds using modeled M93-modified AA dipeptide as a substrate.

| PDB ID | Metal-chelating Residues | Native Binder ΔKd | Designed Binder ΔKd | ΔKd (Native to Designed) |
|---|---|---|---|---|
| 1AST | 92H, 96H, 102H | 88.28 | 604.55 | 6.85 |
| 1C7K | 83H, 87H, 93D | 36.94 | 135.29 | 3.66 |
| 1HEE | 69H, 72E, 196H | 42.01 | 13279.05 | 316.11 |
| 1IAG | 141H, 145H, 151H | 449733.69 | 761383.69 | 1.69 |
| 1JAN | 119H, 123H, 129H | 5577.24 | 2358.56 | 0.42 |
| 1JD0 | 89H, 91H, 115H | 13848.33 | 8220.91 | 0.59 |
| 1KAP | 176H, 180H, 186H | 16227.89 | 9729.70 | 0.60 |
| 1LML | 165H, 169H, 235H | 462.30 | 1269.72 | 2.75 |
| 1OBR | 69H, 72E, 204H | 292.25 | 457.65 | 1.57 |
| 1Z97 | 91H, 93H, 116H | 7690.77 | 9501.19 | 1.24 |
| 2CAB | 90H, 92H, 115H | 1985.88 | 3837.03 | 1.93 |
| 2CKI | 168H, 172H, 178H | 214.61 | 627.69 | 2.92 |
| 2FV5 | 190H, 194H, 200H | 74857.21 | 63626.83 | 0.85 |
| 2J83 | 166H, 170H, 176H | 2659.17 | 6651.53 | 2.50 |
| 2X7M | 132H, 136H, 142H | 1640.68 | 7633.48 | 4.65 |

TABLE 8-continued

Estimated relative binding affinities for metalloprotein binder scaffolds using modeled M93-modified AA dipeptide as a substrate.

| PDB ID | Metal-chelating Residues | Native Binder ΔKd | Designed Binder ΔKd | ΔKd (Native to Designed) |
|---|---|---|---|---|
| 3ML5 | 94H, 96H, 119H | 2038.30 | 3126.74 | 1.53 |
| 3P1V | 292H, 296H, 303D | 0.79 | 6813.98 | 8619.65 |
| 3P24 | 162D, 316H, 320H | 216.76 | 100.03 | 0.46 |
| 3U7M | 111C, 154H, 158H | 9019.96 | 38102.75 | 4.22 |
| 3UJZ | 408H, 412H, 418H | 3886.24 | 1106.90 | 0.28 |
| 4DJL | 69H, 72E, 204H | 476.38 | 412.89 | 0.87 |
| 4DLM | 7H, 9H, 242D | 1196381.63 | 236.72 | 0.00 |
| 4KNM | 92H, 94H, 117H | 327.86 | 2651.61 | 8.09 |
| 4L63 | 160H, 164H, 170H | 268.50 | 4128.77 | 15.38 |
| 4LP6 | 91H, 93H, 116H | 2863.43 | 2057.83 | 0.72 |
| 4Q4E | 293H, 297H, 316E | 71632.62 | 201534.89 | 2.81 |
| 4YYT | 91H, 93H, 116H | 2612.60 | 5526.18 | 2.12 |
| 5JN8 | 97H, 99H, 122H | 6403.97 | 15281.48 | 2.39 |
| 5K7J | 181H, 185H, 212H | 186244.88 | 5069823.00 | 27.22 |
| 5OD1 | 35H, 61H, 65H | 217.69 | 1749.32 | 8.04 |

Some of the tested scaffolds (e.g., 4DLM, 1IAG, 5K7J, 2FV5, 4Q4E) show elevated "Native Binder ΔKd" parameter (calculated upon mutation of metal-chelating residue to Gly), indicating that metal-chelating residues significantly contribute to binding affinity for binding between the unmodified binder and the M93-modified AA model peptide. Other tested scaffolds show significantly elevated "ΔKd (Native to Designed)" parameter (the fold-change improvement in Kd upon mutating the binder from the native binder sequence), indicating that the designed (modified) binders have improved binding affinities for binding between the designed binder and the M93-modified AA model peptide.

Examples of such designed binders having improved binding affinities include SEQ ID NOs: 45-47 based on the following scaffolds: 5K7J (having corresponding mutations: K7D, P58V, 1134L, K136M, L1581, G160M, 1161V, N162L, D166M, G179V, 1180L, A183K, D184S, A210M, A211V, and L2321); 1IAG (having corresponding mutations: G108M, K109L, E142L, R166L, and G168D); 4Q4E (having corresponding mutations: E117L, G2571, A258V, M2591, E260P, K282E, D286K, R289Q, V2901, E294A, K3151, V320L, D323V, T3431, Y372F, Y377M, and E378W).

Further, in silico tested scaffolds selected based on high Native Binder ΔKd or high Designed Binder ΔKd (e.g., 3U7M, 4Q4E and 1AST) were further evaluated against a panel of NTMs (M64-M91 and M93-M98). All three scaffolds shared M72 as one of the two NTMs that provide highest relative binding affinity (see Tables 9 and 10).

TABLE 9

Estimated relative binding affinities for PDB ID 3U7M metalloprotein binder scaffold tested against different modeled NTM-modified AA dipeptides as substrates.

| NTM | Metal-chelating Residues | Native Binder ΔKd | Designed Binder ΔKd | ΔKd (Native to Designed) |
|---|---|---|---|---|
| M71 | 111C, 154H, 158H | 3501028.50 | 2207561.25 | 0.63 |
| M72 | 111C, 154H, 158H | 1734168.13 | 3053128.50 | 1.76 |
| M89 | 111C, 154H, 158H | 1031853.69 | 40826.33 | 0.04 |
| M96 | 111C, 154H, 158H | 976407.19 | 18512.25 | 0.02 |
| M64 | 111C, 154H, 158H | 541295.44 | 414363.56 | 0.77 |
| M69 | 111C, 154H, 158H | 482314.28 | 230.61 | 0.00 |
| M79 | 111C, 154H, 158H | 351483.22 | 164567.31 | 0.47 |
| M74 | 111C, 154H, 158H | 320104.91 | 154488.63 | 0.48 |

TABLE 9-continued

Estimated relative binding affinities for PDB ID 3U7M metalloprotein binder scaffold tested against different modeled NTM-modified AA dipeptides as substrates.

| NTM | Metal-chelating Residues | Native Binder ΔKd | Designed Binder ΔKd | ΔKd (Native to Designed) |
|---|---|---|---|---|
| M77 | 111C, 154H, 158H | 211693.53 | 8780.37 | 0.04 |
| M87 | 111C, 154H, 158H | 188750.83 | 33779.50 | 0.18 |
| M73 | 111C, 154H, 158H | 164210.64 | 1355697.25 | 8.26 |
| M65 | 111C, 154H, 158H | 114409.43 | 352385.06 | 3.08 |
| M68 | 111C, 154H, 158H | 112102.16 | 125073.30 | 1.12 |
| M85 | 111C, 154H, 158H | 103877.56 | 14651.04 | 0.14 |
| M95 | 111C, 154H, 158H | 60689.87 | 77287.09 | 1.27 |
| M70 | 111C, 154H, 158H | 47725.49 | 54078.62 | 1.13 |
| M86 | 111C, 154H, 158H | 47436.00 | 28.83 | 0.00 |
| M76 | 111C, 154H, 158H | 46162.30 | 42348.16 | 0.92 |
| M75 | 111C, 154H, 158H | 29492.38 | 161397.19 | 5.47 |
| M88 | 111C, 154H, 158H | 28316.23 | 83574.75 | 2.95 |
| M66 | 111C, 154H, 158H | 26813.67 | 41052.95 | 1.53 |
| M94 | 111C, 154H, 158H | 21822.65 | 7226.57 | 0.33 |
| M93 | 111C, 154H, 158H | 9019.96 | 38102.75 | 4.22 |
| M67 | 111C, 154H, 158H | 8874.03 | 2196.70 | 0.25 |
| M82 | 111C, 154H, 158H | 5851.96 | 70393.65 | 12.03 |
| M84 | 111C, 154H, 158H | 5279.65 | 13634.45 | 2.58 |
| M97 | 111C, 154H, 158H | 4746.72 | 233747.84 | 49.24 |
| M91 | 111C, 154H, 158H | 4423.19 | 170669.83 | 38.59 |
| M80 | 111C, 154H, 158H | 3808.76 | 6704.17 | 1.76 |
| M81 | 111C, 154H, 158H | 3596.61 | 2829.83 | 0.79 |
| M78 | 111C, 154H, 158H | 2998.50 | 8125.12 | 2.71 |
| M83 | 111C, 154H, 158H | 2515.06 | 0.00 | 0.00 |
| M90 | 111C, 154H, 158H | 231.28 | 1522.03 | 6.58 |

TABLE 10

Estimated relative binding affinities for 4Q4E metalloprotein binder scaffold tested against different modeled NTM-modified AA dipeptides as substrates.

| NTM | Metal-chelating Residues | Native Binder ΔKd | Designed Binder ΔKd | ΔKd (Native to Designed) |
|---|---|---|---|---|
| M72 | 293H, 297H, 316E | 550570.81 | 1051209.63 | 1.91 |
| M93 | 293H, 297H, 316E | 71632.62 | 201534.89 | 2.81 |
| M75 | 293H, 297H, 316E | 63327.81 | 1008.73 | 0.02 |
| M69 | 293H, 297H, 316E | 57445.40 | 44320.43 | 0.77 |
| M65 | 293H, 297H, 316E | 47969.63 | 650053.88 | 13.55 |
| M71 | 293H, 297H, 316E | 40402.22 | 31.60 | 0.00 |
| M70 | 293H, 297H, 316E | 25470.41 | 30806.31 | 1.21 |
| M68 | 293H, 297H, 316E | 21628.25 | 4221563.00 | 195.19 |
| M96 | 293H, 297H, 316E | 20559.98 | 11119.35 | 0.54 |
| M73 | 293H, 297H, 316E | 20422.63 | 139066.25 | 6.81 |
| M83 | 293H, 297H, 316E | 17175.40 | 29270.72 | 1.70 |
| M78 | 293H, 297H, 316E | 14846.99 | 401.02 | 0.03 |
| M95 | 293H, 297H, 316E | 13913.03 | 152.32 | 0.01 |
| M66 | 293H, 297H, 316E | 12065.32 | 17295.57 | 1.43 |
| M85 | 293H, 297H, 316E | 10439.38 | 70105.59 | 6.72 |
| M76 | 293H, 297H, 316E | 8862.41 | 19224.22 | 2.17 |
| M74 | 293H, 297H, 316E | 8742.56 | 4372.22 | 0.50 |
| M64 | 293H, 297H, 316E | 8287.36 | 26716.71 | 3.22 |
| M81 | 293H, 297H, 316E | 7297.53 | 186.28 | 0.03 |
| M87 | 293H, 297H, 316E | 4935.47 | 1178.78 | 0.24 |
| M97 | 293H, 297H, 316E | 4349.30 | 404.36 | 0.09 |
| M67 | 293H, 297H, 316E | 3731.95 | 2670.95 | 0.72 |
| M77 | 293H, 297H, 316E | 3045.48 | 31041.90 | 10.19 |
| M79 | 293H, 297H, 316E | 2489.93 | 2661.60 | 1.07 |
| M88 | 293H, 297H, 316E | 2231.58 | 26357.38 | 11.81 |
| M89 | 293H, 297H, 316E | 1534.39 | 805.60 | 0.53 |
| M91 | 293H, 297H, 316E | 1369.91 | 4103.11 | 3.00 |
| M80 | 293H, 297H, 316E | 916.31 | 684.38 | 0.75 |
| M90 | 293H, 297H, 316E | 547.45 | 497.67 | 0.91 |

TABLE 10-continued

Estimated relative binding affinities for 4Q4E metalloprotein binder scaffold tested against different modeled NTM-modified AA dipeptides as substrates.

| NTM | Metal-chelating Residues | Native Binder ΔKd | Designed Binder ΔKd | ΔKd (Native to Designed) |
|---|---|---|---|---|
| M82 | 293H, 297H, 316E | 401.61 | 3249.67 | 8.09 |
| M94 | 293H, 297H, 316E | 217.74 | 391455.53 | 1797.83 |
| M84 | 293H, 297H, 316E | 217.11 | 274.43 | 1.26 |
| M86 | 293H, 297H, 316E | 94.46 | 9912.31 | 104.94 |

Next, using the modelling methods described in this Example, multiple homologs of human carbonic anhydrases belonging to alpha-carbonic anhydrase family were explored, and their metal-chelating residues as well as residues that form the NTM-P1 binding pocket were determined. Members of alpha-carbonic anhydrase family share the same structural fold (e.g., Manyumwa C V, et al., Alpha-Carbonic Anhydrases from Hydrothermal Vent Sources as Potential Carbon Dioxide Sequestration Agents: In Silico Sequence, Structure and Dynamics Analyses. Int J Mol Sci. 2020 Oct. 29; 21(21):8066; Rains, et al., (2019). Bicarbonate Inhibition of Carbonic Anhydrase Mimics Hinders Catalytic Efficiency: Elucidating the Mechanism and Gaining Insight toward Improving Speed and Efficiency. ACS Catalysis. 9.10.1021/acscatal.8b04077) despite having relatively low present sequence identity between different members (e.g., 40-70% sequence identity). Exemplary members studied in this disclosure include scaffolds having amino acid sequences set forth in SEQ ID NO: 7-SEQ ID NO: 9 and SEQ ID NO: 68-SEQ ID NO: 74, which include carbonic anhydrase enzymes from the following species: *Homo sapiens, Echinops telfairi, Crassostrea gigas, Calypte anna, Acipenser ruthenus, Thalassophryne amazonica, Manis javanica*, and *Mauremys reevesii*. Table 11 below shows results of the modeling of exemplary alpha-carbonic anhydrase enzymes, indicating residues comprising Z-P1 (e.g., NTM-P1) binding site of each scaffold determined based on modeling of the crystal structure of the corresponding scaffold; % sequence identity to human carbonic anhydrase II scaffold (SEQ ID NO:7), as well as original P1 target residues determined by performing encoding assays with the corresponding scaffolds (as described in Example 7 below).

TABLE 11

Structural and functional characteristics of different alpha-carbonic anhydrase-based binder scaffolds.

| SEQ ID NO: | Residues comprising Z-P1 binding site of the scaffold | Sequence Identity to SEQ ID NO: 7 (%) | Source | Original P1 target residues |
|---|---|---|---|---|
| 68 | 61, 63, 64, 66, 90, 91, 120, 129, 130, 133, 139, 141, 196, 198, 200, 202, 204, 205 | 81.853 | *Echinops telfairi* | LIV |
| 69 | 62, 64, 65, 67, 88, 89, 118, 128, 129, 132, 138, 140, 196, 198, 200, 202, 204, 205 | 23.228 | *Crassostrea gigas* | V |
| 70 | 60, 62, 63, 65, 89, 90, 119, 129, 130, 133, 134, 139, 141, 196, 198, 200, 202, 204, 205 | 61.719 | *Calypte anna* | VIL |

TABLE 11-continued

Structural and functional characteristics of different alpha-carbonic anhydrase-based binder scaffolds.

| SEQ ID NO: | Residues comprising Z-P1 binding site of the scaffold | Sequence Identity to SEQ ID NO: 7 (%) | Source | Original P1 target residues |
|---|---|---|---|---|
| 71 | 61, 63, 64, 66, 90, 91, 120, 130, 131, 134, 140, 197, 199, 201, 203, 205, 206 | 64.093 | *Acipenser ruthenus* | LIV |
| 72 | 61, 63, 64, 66, 90, 91, 120, 129, 130, 133, 139, 141, 196, 198, 200, 202, 204, 205 | 60.232 | *Thalassophryne amazonica* | VILF |
| 73 | 61, 63, 64, 66, 90, 91, 120, 129, 130, 133, 139, 141, 196, 198, 200, 202, 204, 205 | 84.17 | *Manis javanica* | VIL |
| 74 | 61, 63, 64, 66, 90, 120, 129, 130, 133, 139, 141, 196, 198, 200, 202, 204, 205 | 69.498 | *Mauremys reevesii* | LIV |

In view of the conservation of the structural fold within alpha-carbonic anhydrase family, using methods described in this Example and Examples 4-6 below, a high affinity binder may be constructed using a starting scaffold comprising amino acid sequence that is at least 70%, at least 80%, at least 90% or more identity to any one of SEQ ID NO: 7-SEQ ID NO: 9 and SEQ ID NO: 68-SEQ ID NO: 74. Table 11 further provides guidance on particular amino acid residues within Z-P1 binding site of each scaffold that may be mutated to accommodate particular NTM and P1 (NTAA) residue, providing selectivity for the engineered binder. These include not only residues that are predicted to form Z-P1 binding site, but also neighboring residues (within 6 Å from any residue of the Z-P1 binding site, which is based on analysis of crystal structures of multiple generated binders) that may also be important for the interaction between the binder and a target peptide. For example, an engineered binder may comprise an amino acid sequence which differs from the amino acid sequence set forth in SEQ ID NO: 68-SEQ ID NO: 74 by at least one amino acid residue within 6 Å of a Z-P1 binding site of the engineered binder, wherein:

the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 68; or the Z-P1 binding site comprises one or more amino acid residues corresponding to positions 62, 64, 65, 67, 88, 89, 118, 128, 129, 132, 138, 140, 196, 198, 200, 202, 204, and 205 of SEQ ID NO: 69; or the Z-P1 binding site comprises one or more amino acid residues corresponding to positions 60, 62, 63, 65, 89, 90, 119, 129, 130, 133, 134, 139, 141, 196, 198, 200, 202, 204, and 205 of SEQ ID NO: 70; or the Z-P1 binding site comprises one or more amino acid residues corresponding to positions 61, 63, 64, 66, 90, 91, 120, 130, 131, 134, 140, 197, 199, 201, 203, 205, and 206 of SEQ ID NO: 71; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 72; or the Z-P1 binding site comprises one or more amino acid residues corresponding to positions 61, 63, 64, 66, 90, 91, 120, 129, 130, 133, 139, 141, 196, 198, 200, 202, 204, and 205 of SEQ ID NO: 73; or the Z-P1 binding site comprises one or more amino acid residues corresponding to positions 61, 63, 64, 66, 90, 120, 129, 130, 133, 139, 141, 196, 198, 200, 202, 204, and 205 of SEQ ID NO: 74.

Example 3. Exemplary Origin, Synthesis and Installation of NTMs on NTAA Residues of Peptides by N-Terminal Modifier Agents Structures, origin and installation methods for exemplary N-terminal modifier agents used for modification of NTAA residues of peptides are shown below.

N-terminal modifier agent for M=M64 (in the ester form).

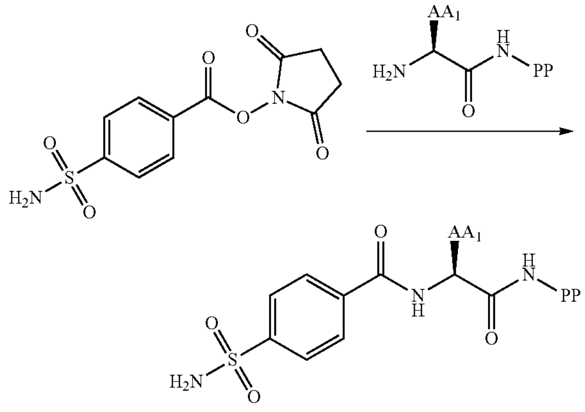

Exemplary method of installing M64 onto N-terminal amino acid of a peptide, shown as NTAA-PP. Peptides, in solution or on solid-support, were dissolved in 25 μL of 0.4 M MOPS buffer, pH=7.6 and 25 μL of acetonitrile (ACN). Separately, the active ester reagent was prepared from M64 and dissolved in 25 uL DMA and 25 uL ACN to a concentration of 0.05 M stock solution. Then, 50 μL of the active ester stock solution was added to the peptide-ACN:MOPS solution and incubated at 65° C. for 60 minutes. Upon completion, the peptides were functionalized with the respective modification as shown in the above schemes.

Alternatively, a surfactant-aqueous coupled system can be employed to install NTM (M64) onto the N-terminal amino acid of peptides. Using a 10 mM solution of 5% DMSO in 2% TGPS-750-M in water containing 1% 2,6-lutidine, the peptides are modified to completion in 20 minutes at 40° C.

M65-M91 and M93-M97 NTMs have been similarly installed on N-terminal amino acids of peptides.

Exemplary NTM Materials and Syntheses.

A. Commercial sources of 4-carboxybenzenesulfonamide and substituted 4-carboxybenzenesulfonamides:

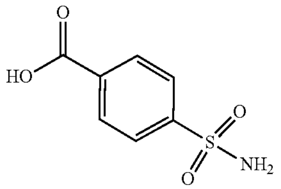 [SMILES: NS(=O)(=O)c1ccc(C(=O)O)cc1]

4-Carboxybenzenesulfonamide; vendor: Combi-Blocks; Item #: QA-8702; MW 201.2; CAS 138-41-0

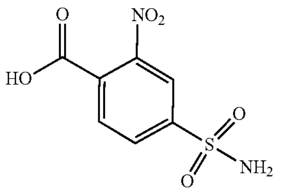 [SMILES: NS(=O)(=O)c1ccc(C(=O)O)c([N+](=O)[O-])c1]

2Nitro-4-sulfamoylbenzoic acid; vendor: Combi-Blocks; Item #: WZ-9277; MW 246.2; CAS 29092-31-7

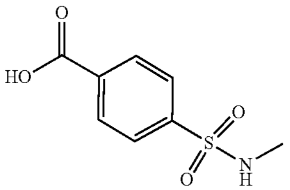

4-[(Methylamino)sulfonyl]benzoic acid; vendor: Combi-Blocks; Item #: ST-1977; MW 215.2; CAS 10252-63-8

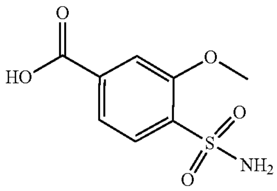

3-Methoxy-4-sulfamoylbenzoic acid; vendor: Enamine; Item #: EN300-189718; MW 231.2; CAS 860562-94-3

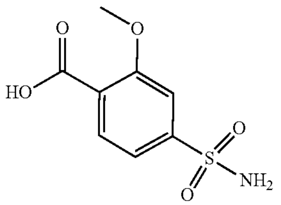

2-Methoxy-4-sulfarnoylbenzoic acid; vendor: Fisher Scientific; Item #: BB016296; MW 231.2; CAS 481-28

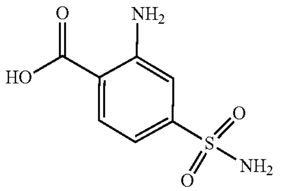

2-Amino-4-sulfamoylbenzoic acid; vendor: Enamine; Item #: EN300-263098; MW 216.2; CAS 25096-72-4

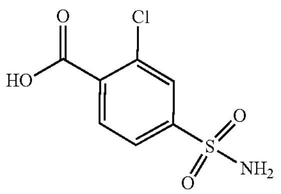 [SMILES: NS(=O)(=O)c1ccc(C(=O)O)c(Cl)c1]

2-Chloro-4-sulfamoylbenzoic acid; vendor: Enamine; Item #: EN300-147322; MW 235.6; CAS 53250-84-3

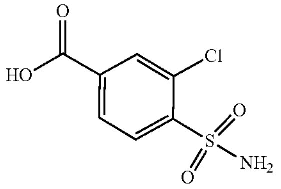 [SMILES: NS(=O)(=O)c1ccc(C(=O)O)cc1Cl]

3-Chloro-4-sulfamoylbenzoic acid; vendor: Enamine; Item #: EN300-64348; MW 235.6; CAS 34263-53-1

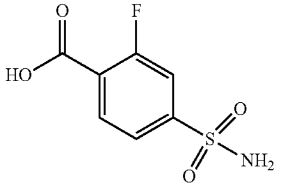 [SMILES: NS(=O)(=O)c1ccc(C(=O)O)c(F)c1]

2-Fluoro-4-sulfamoylbenzoic acid; vendor: Enamine; Item #: EN300-123320; MW 219.2; CAS 714968-42-0

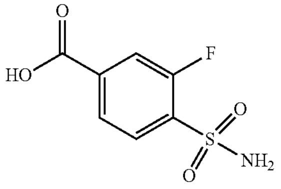 [SMILES: NS(=O)(=O)c1ccc(C(=O)O)cc1F]

3-Fluoro-4-sulfamoylbenzoic acid; vendor: Enamine; Item #: EN300-97835; MW 219.2; CAS 244606-37-9.

B. Commercial Sources of Sulfamoylpyridine Carboxylic Acids:

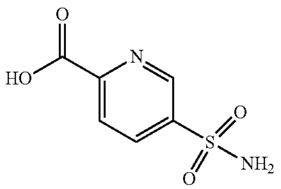 [SMILES: NS(=O)(=O)c1ccc(C(=O)O)nc1]

5-Sulfamoylpyridine-3-carboxylic acid; vendor: Enamine; Item #: EN300-124374; MW 202.2; CAS 1308677-67-9

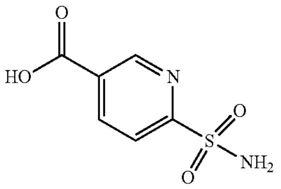 [SMILES: NS(=O)(=O)c1ccc(C(=O)O)cn1]

6-Sulfamoylpyridine-3-carboxylic acid; vendor: Enamine; Item #: EN300~120480; MW 202.2; CAS 285135-56-0.

C. Substituted 4-Carboxybenzenesulfonamides Prepared in Step(s) from Commercial Materials:

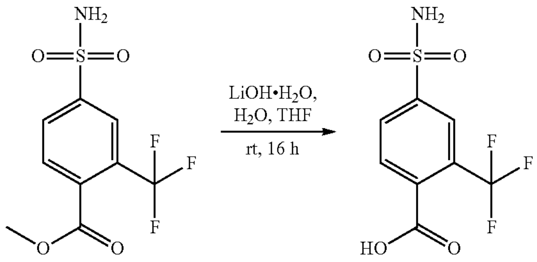 [SMILES: COC(=O)c1ccc(S(N)(=O)=O)cc1C(F)(F)F ; NS(=O)(=O)c1ccc(C(=O)O)c(C(F)(F)F)c1]

To a solution of commercially available methyl 4-sulfamoyl-2-(trifluoromethyl)benzoate (250 mg, 0.88 mmol) in THF (5 mL) a premixture of LiOH·H2O (111 mg, 2.65 mmol) in $H_2O$ (2 mL) was added, and the resulting solution was stirred for 16 h at room temperature. The reaction mixture was quenched with 4 eq. of conc. HCl and the solvents were removed in vacuo. The white residue was suspended in $H_2O$, sonicated, stirred for 2 h, and the solids were collected by filtration to give the desired 2-trifluoro-4-sulfamoylbenzoic acid as a pure white solid. MS (ESI) 267 ($M^-$–H).

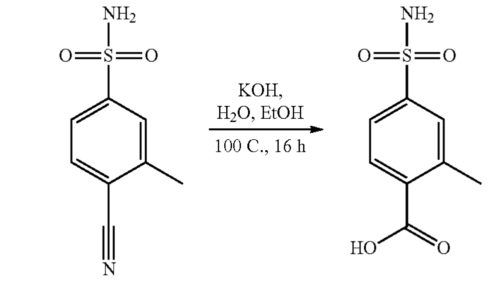

To a solution of commercially available 4-cyano-3-methylbenzene-1-sulfonamide (250 mg, 1.27 mmol) in EtOH (6 mL) $H_2O$ (6 mL) and pulverized KOH (572 mg, 10.19 mmol) were added. The resulting solution was stirred for 16 h at 100° C. The reaction mixture was quenched with 9 eq. of conc. HCl and the solvents were removed in vacuo. The white residue was purified by flash column chromatography ($SiO_2$) eluting with EtOAc (spiked with 5% AcOH) and heptane using a 10% to 100% gradient to give the desired 2-methyl-4 sulfamoylbenzoic acid as a pure white solid. MS (ESI) 214 ($M^-$–H).

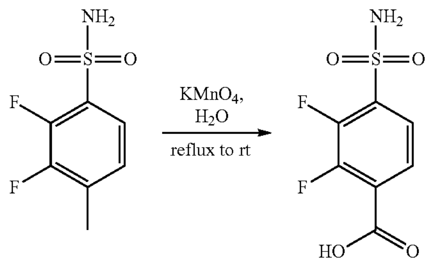

Commercially available 2,3-difluoro-4-methyl-1benzene-1-sulfonamide was suspended in $H_2O$ (13 mL) and stirred to reflux after which $KMnO_4$ (858 mg, 5.43 mmol) was added in portions over 50 min. The resulting solution was stirred for an additional 30 min at reflux, then stirred at room temperature for 16 h. The reaction mixture was filtered through a frit and the filtrate was adjusted to pH=1 with conc. HCl. The low pH filtrate was then extracted twice with EtOAc, and the organics were dried ($Na_2SO_4$), filtered, and evaporated in vacuo. The mostly pure white residue was further triturated in a 1% MeOH/DCM solvent system and filtered to give the desired 2,3-difluoro-4-sulfamoylbenzoic acid as a white solid. MS (ESI) 236 ($M^-$–H).

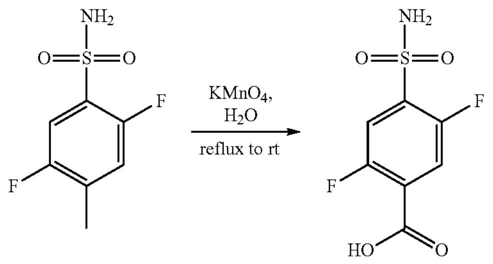

Commercially available 2,5-difluoro-4-methylbenzene-1-sulfonamide was suspended in $H_2O$ (13 mL) and stirred to reflux after which $KMnO_4$ (858 mg, 5.43 mmol) was added in portions over 50 min. The resulting solution was stirred for an additional 30 min at reflux, then stirred at room temperature for 16 h. The reaction mixture was filtered through a frit and the filtrate was adjusted to pH=1 with conc. HCl. The low pH filtrate was then extracted twice with EtOAc and the organics were dried ($Na_2SO_4$), filtered, and evaporated in vacuo. The mostly pure white residue was further triturated in a 1% MeOH/DCM solvent system and filtered to give the desired 25-difluoro-4-sulfamoylbenzoic acid as a white solid. MS (ESI) 236 ($M^-$–H).

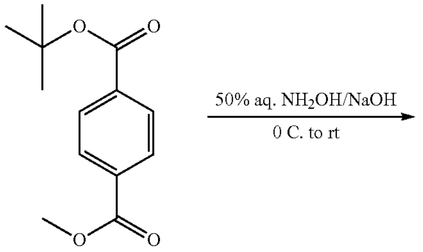

-continued

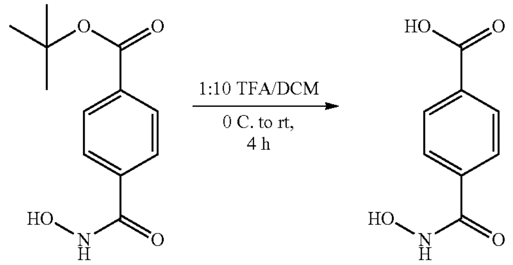

Step 1:

Pulverized NaOH (424 mg, 10.60 mmol) was dissolved in a 0° C. solution of hydroxylamine in water (50% wt, 2.50 mL, 42.40 mmol) which was followed by dropwise addition of commercially available tert-butyl methyl terephthalate (250 mg, 1.06 mmol) premixed with THF/MeOH (15/15 mL). The resulting reaction mixture was allowed to warm to room temperature and stirred for 45 min before acetic acid (0.66 mL, 11.66 mmol) was added to quench. The solvents were removed by evaporation under reduced pressure. The resulting crude was treated with saturated aqueous $NaHCO_3$ (pH adjusted to ~9) and diluted with ethyl acetate. The organic phase was washed with brine, dried over anhydrous $Na_2SO_4$, filtered, and concentrated under vacuum to afford the 4-tert-butylcarboxy-benzenehydroxamic acid as a white, crystalline powder. MS (ESI) 238 ($M^-$–H).

Step 2:

To a 0° C. solution of 4-tert-butylcarboxy-benzenehydroxamic acid (100 mg, 0.42 mmol) in DCM (5 mL) was added TFA (0.5 mL). The resulting reaction mixture was allowed to warm to room temperature and stirred for 4 h at which time the product was a thick suspension in the reaction mixture. The solids were filtered off and rinsed with DCM to afford 4-carboxybenzenehydroxamic acid as a white powder. MS (ESI) 181 ($M^-$–H).

D. Alternative synthesis of sulfamoylpyridine carboxylic acid prepared from commercial materials:

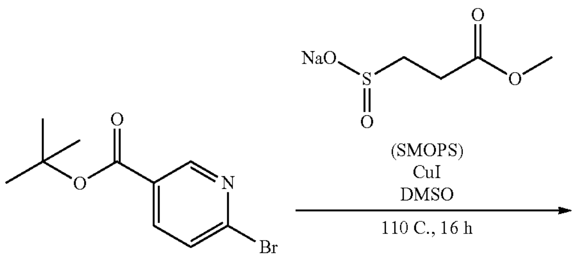

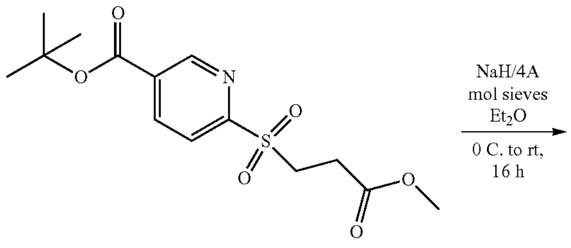

-continued

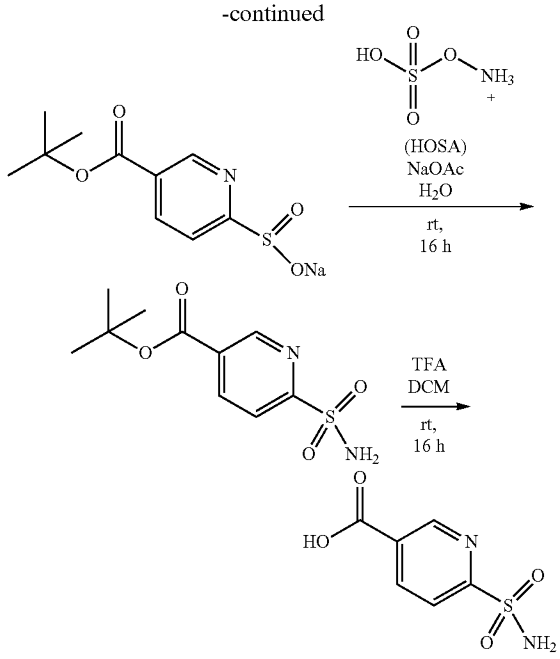

Step 1:

To tert-butyl 6-bromonicotinate (0.5 g, 1.94 mmol) in DMSO (10 mL) SMOPS (1.01 g, 5.82 mmol) and CuI (1.11 g, 5.82 mmol) were added. The reaction was stirred under a natural atmosphere at 110° C. for 16 hours. The mixture was cooled to room temperature, diluted with excess ethyl acetate and filtered through a pad of celite. The filtrate was washed 2× with water, 2× with brine, dried ($Na_2SO_4$), filtered, and evaporated in vacuo. The residue was purified by flash column chromatography ($SiO_2$) eluting with EtOAc and heptane using a 20% to 100% gradient to give the desired methyl 3-((5-tert-butylcarboxypyridin-2-yl)sulfonyl)propanoate. MS (ESI) 330 ($M^+$+H).

Step 2:

Under an argon atmosphere at 0° C. sodium hydride (22 mg, 0.55 mmol) and activated 4 Å molecular sieves (1.42 g, 2.58 g per mmol of starting material) were combined. To the stirring solids methyl 3-((5-ter-butylcarboxypyridin-2-yl) sulfonyl)propanoate (0.18 g, 0.55 mmol) premixed with dry $Et_2O$ (15 mL) was slowly added. After 5 minutes, the ice bath was removed and the reaction was sealed and stirred at room temperature for 16 hours. The mixture was cooled to 0 C, diluted with excess MeOH, and filtered through a pad of celite. The filtrate was evaporated in vacuo, dissolved in water and washed 3× with DCM. The aqueous layer was evaporated in vacuo and coevaporated once with heptane and once with $CH_3CN$. The white solid residue was the desired and pure 5-tert-butylcarboxy pyridin-2-yl-sodium sulfinate. MS (ESI) 245 ($M^+$+H).

Step 3:

To 5-tert-butylcarboxypyridin-2-yl)sodium sulfinate (0.15 g, 0.57 mmol) in $H_2O$ (5 mL) sodium acetate (0.057 g, 0.68 mmol) and hydroxylamine-O-sulfonic acid (0.077 g, 0.68 mmol) were added. The reaction was stirred at room temperature for 16 hours and filtered to give pure 5-tert-butylcarboxypyridin-2-yl-sulfonamide. MS (ESI) 259 ($M^+$+H).

Step 4:

To a 0° C. solution of 5-tert-butylcarboxypyridin-2-yl-sulfonamide (0.15 g, 0.58 mmol) in DCM (6 mL) was added TFA (0.6 mL). The resulting reaction mixture was allowed to warm to room temperature and stirred for 16 h. The solvents were evaporated to dryness and coevaporated 2× with heptane to afford 6-sulfamoylpyridine-3-carboxylic acid as a white powder. MS (ESI) 201 ($M^-$−H).

Exemplary structures of N-terminal modifier agents as well as corresponding installation reactions on NTAA residues of peptides are shown in FIG. 14.

Example 4. Binder Engineering from the Metalloenzyme Scaffolds

Binder engineering involves improving affinities of potential binding sites through rational, structure-based approaches on a parental scaffold and generating libraries that contain degenerate NNK codons at multiple, defined positions using Kunkel mutagenesis and phage display selection. Kunkel mutagenesis is a known site-directed mutagenesis strategy that introduces point mutations by annealing mutation-containing oligonucleotides to single-stranded uracil-containing single strand DNA (dU-ssDNA) templates. Exemplary Kunkel mutagenesis and phage display selection methods are described in U.S. Pat. No. 9,102,711 B2; U.S. Ser. No. 10/906,968 B2; and Kunkel, Proc. Natl. Acad. Sci. USA, 1985, 83(2):488-492.

In this example, high diversity (~$10^{10}$) phage libraries using NNK variant site encoding were constructed targeting residues positions within the substrate-binding pockets of the selected metalloenzymes. Phosphorylated primers were obtained that possess degenerate codons at intended positions and were annealed to uracilated ssDNA containing the parental sequence of the same binder of interest with introduced SacII sites. After polymerase extension and ligation, the heteroduplex DNA was transformed into custom TG1RM cells (Lucigen TG1 Electrocompetent Cells containing a pCDF-lb plasmid expressing SacII enzyme), which removed undesired template DNA with SacII sites resulting in $10^9$-$10^{10}$ libraries. Monovalent phage libraries were packaged using standard helper phage and precipitated using PEG/NaCl solution. Using standard protocols, phage libraries were panned against different N-terminally modified target peptides. NTAA modification was applied to target peptides during binder screening and maturation to increase substrate surface available for interaction with the binder, which would result in selection of binders with higher affinity and P1 specificity.

For each round of phage display selection, precipitated phage in the presence of peptide and protein competitors were first depleted against beads coated with off-target peptides for 1 hour at 24° C. and then panned against beads coated with target peptides for 1 hour at 24° C. After washing 6 times with PBST, beads-bound phages were eluted using 0.2 M pH=2.2 glycine for 10 min at 24° C. and then subsequently used to infect mid-log phase TG1 cells. Once the final round of selection was complete, the output was profiled in a phage-based, multiplexed binding assay (Luminex, DiaSorin, USA) against a panel of N-terminally modified target peptides and underwent next-generation sequencing to obtain clone enrichment sequence information. Luminex enables analysis of binding of phage libraries against multiple peptide targets immobilized on beads in a single assay well. This is accomplished by spatially separating immunoassays performed on beads that contain unique fluorophore cores that exhibit distinct excitation/emission profiles. Multiple target peptide-specific beads are combined in a single well of a multi-well microplate to detect and quantify multiple targets simultaneously. Specific binders were isolated against a variety of N-terminally modified target peptides. Based on the sequence identities after enrichment, consensus mutations or mutational hotspots were identified and binders were expressed and purified for testing in the encoding assay.

Example 5. Binder Maturation

Binder maturation for affinity and specificity involved multiple cycles of error prone PCR prior to library construction via Kunkel mutagenesis and phage display selection, performed essentially as described in Example 4. Briefly, 60-90 cycles of error prone PCR on a parental binder generated PCR amplicons with an average of 4-6 random amino acid mutations per 100 amino acids. The dsDNA amplicon was digested by lambda exonuclease into “megaprimer” ssDNA, which was used to generate heteroduplex DNA by annealing to uracilated ssDNA of the vector containing the parental sequence of the same binder of interest with introduced SacII sites. After polymerase extension and ligation, the heteroduplex DNA was transformed into custom TG1RM cells (Lucigen TG1 Electrocompetent Cells containing a pCDF-lb plasmid expressing SacII enzyme), which removed undesired template DNA with SacII sites resulting in 109-1010 libraries. Monovalent phage libraries were packaged using standard helper phage and precipitated using PEG/NaCl solution. For each round of phage display selection, precipitated phage in the presence of peptide and protein competitors were first depleted against beads coated with off-target peptides for 1 hour at 24° C. and then panned against beads coated with target peptides for 1 hour at 24° C. After washing 6 times with PBST, beads-bound phages were eluted using 0.2 M pH=2.2 glycine for 10 min at 24° C. and then subsequently used to infect mid-log phase TG1 cells. Once the final round of selection was completed, the output was profiled in a phage-based, multiplexed binding assay (Luminex, DiaSorin, USA) against a panel of N-terminally modified target peptides and underwent next-generation sequencing to obtain clone enrichment sequence information. Based on the sequence identities after enrichment, consensus mutations or mutational hotspots were identified and binders were expressed and purified for testing in the encoding assay.

Example 6. Binder Expression and Purification

Plasmid DNA was received from a vendor generated source containing the identified engineered binder conjugated with an N-terminal hexa-histidine tag and a C-terminal SpyCatcher domain. Plasmids were transformed into chemically competent *E. coli* cells using standard methods. Recovery was done by adding 150 ul of warm SOC and incubation for 1 hour at 30° C. After recovery, 80 ul of transformed culture was added to 1 ml 2YT containing corresponding antibiotic. The culture was grown overnight and then used to generate stock in glycerol. The stock was then used to inoculate an overnight culture of 2YT containing corresponding antibiotic, and the culture was grown overnight for ~20 hours at 37° C. This culture was subsequently used to inoculate another larger volume culture of 2YT containing corresponding antibiotic at a 100-fold dilution. The culture was then left at 37° C. for 3-4 hours until an optical density of 0.6 was reached. Temperature was then lowered to 15° C. and protein expression was induced with a final concentration of 0.5 mM IPTG. The cultures were grown for an additional 16-20 hours and the cells were harvested by centrifugation at 4,000 rpm for 20 min. The cellular pellets were stored at −80° C. until ready for use.

Stored cellular pellets were resuspend in 25 mM Tris pH=7.9, 500 mM NaCl, and 10 mM imidazole with included protease inhibitor and were lysed by sonication. The clarified lysate was loaded onto an AKTA FPLC using a tandem purification method of nickel affinity and size-exclusion chromatography. The retained protein was eluted from the nickel affinity column using 25 mM Tris pH 7.9, 500 mM NaCl, 300 mM imidazole directly onto the size-exclusion column. The size-exclusion buffer was 25 mM P04 pH 7.4 with 150 mM NaCl, and after elution and concentration, glycerol was added to final concentration of 10%. Proteins were aliquoted, frozen, and stored at −80° C.

Example 7. Evaluation of Binding Efficiencies of Binders Via the Multiplex Encoding Assay To evaluate binding efficiencies of selected purified binders, a previously developed ProteoCode™ assay (disclosed in detail in US 20190145982 A1, incorporated herein) was used. This variant of the ProteoCode™ assay comprises contacting binder-coding tag conjugates with the N-terminally modified immobilized peptides associated with the recording tags. If affinity of the binder to the modified NTAA of the immobilized peptides is strong enough (typically, Kd should be less than 500 nM, and preferably, less than 200 nM), the coding tag and the recording tag form hybridization complex via hybridization of the corresponding spacer regions to allow transfer of barcode information from the coding tag to the recording tag via a primer extension reaction (the encoding reaction), generating extended recording tag. Sequencing of extended recording tags after the encoding cycle may be used to identify binder(s) that was(were) bound to the immobilized peptide. At the same time, estimating fractions of the recording tags being extended (encoded) during primer extension reaction provides estimate of efficiency of the encoding reaction, which directly correlates with binding affinity of the binder to the particular modified NTAA.

The described encoding assay was used to generate binding profiles for the selected binders across a set of 288 peptides (17×17 combination of different P1 and P2 residues) modified with a specific N-terminal modifier agent. For the encoding assay, selected binders engineered from metalloenzyme scaffolds as described in the previous Examples 4-6 were used. Each binder was conjugated to a corresponding nucleic acid coding tag comprising barcode with identifying information regarding the binder. The coding tag specific for the binder was attached to SpyTag via a PEG linker, and the resulting fusions were reacted with binder-SpyCatcher fusion protein via SpyTag-SpyCatcher interaction, essentially as described in US 2021/0208150 A1. Briefly, amine-functionalized oligonucleotide coding tags were conjugated to a heterobifunctional linker containing an NHS ester, PEG24 linker and maleimide. Excess linker was removed by acetone purification, and excess linker in solution was removed by centrifugation. Purified oligonucleotide-PEG24-maleimide was incubated overnight with SpyTag peptide forming a conjugate via a cysteine residue. The sample was spun down to remove precipitate and the supernatant was transferred to a 10k molecular weight filter to remove excess SpyTag peptide. After multiple washes, the final bioconjugate of SpyTag peptide containing a PEG24 linker and coding tag oligonucleotide was obtained and subsequently combined with the binder/

SpyCatcher fusion protein spontaneously forming the final binder-fused coding tag conjugate.

An array of target peptide-recording tag conjugates having a variety of different NTAAs was generated (17×17 combination of different P1 and P2 residues). The peptides containing C-terminally attached 6-Azido-L-lysine were reacted with DBCO-C2-modified 17 nt oligonucleotides in 100 mM HEPES, pH=7.0 at 60° C. for 1 hour. Each NTAA peptide-oligonucleotide conjugate was ligated to two different 15 nt DNA fragments containing a 7 nt barcode and an 8 nt spacer sequence using splint DNA and T4 DNA ligase to generate a peptide-recording tag conjugate with two different barcodes. A total of 576 peptide-recording tag conjugates were prepared and pooled for ligation and immobilization on short hairpin capture DNAs attached to the beads (NHS-Activated Sepharose High Performance, Cytiva, USA).

The capture DNAs were attached to the beads using trans-cyclooctene (TCO) and methyltetrazine (mTet)-based click chemistry. TCO-modified short hairpin capture DNAs (16 basepair stem, 4 base loop, 17 base 5' overhang) were reacted with mTet-coated beads. The peptide-recording tag pools (20 nM) were annealed to the hairpin capture DNAs attached to the beads in 0.5 M NaCl, 50 mM sodium citrate, 0.02% SDS, pH 7.0, and incubated for 30 minutes at 37° C. The beads were washed once with 1× phosphate buffer, 0.1% Tween 20 and resuspended in 1× Quick ligation solution (New England Biolabs, USA) with T4 DNA ligase. After a 30 min incubation at 25° C., the beads were washed once with 1× phosphate buffer, 0.1% Tween 20, three times with 0.1 M NaOH, 0.1% Tween 20, three times with 1× phosphate buffer, 0.10% Tween 20, and resuspended in 50 μL of PBST.

Before the encoding assay, the beads with immobilized target peptide-recording tag conjugates were treated with an N-terminal modifier agent by methods disclosed in Example 3 above to modify the N-terminal of the immobilized peptides. The modified beads with peptide conjugates were washed once with 70% Ethanol, washed once with water and resuspended in PBST. The coding tags attached to the binders form a loop with 12 bp duplex and 9 nt spacer at the 3', which is complementary to the 3' spacer of the recording tag on the beads.

The cycle of the encoding assay described in this example consists of contacting the immobilized peptides with a metalloenzyme binder-coding tag conjugate. For this, each binder (50 nM) was incubated with the recording tag-peptide conjugates immobilized on the beads for 30 min at 25° C., followed by washing twice with 1× phosphate buffer, pH 7.3, 500 mM NaCl, 0.10% Tween 20. This was followed by transferring information of the coding tag to the recording tags associated with the target peptides by a primer extension reaction after partial hybridization between the coding tag and the recording tag through a shared spacer region using a DNA polymerase having 5'-to-3' polymerization activity and having substantially reduced 3'-to-5' exonuclease activity. Extension was performed by addition of 50 mM Tris-HCl, pH 7.5, 2 mM $MgSO_4$, 50 mM NaCl, 1 mM DTT, 0.1 mg/mL BSA, 0.1% Tween 20, dNTP mixture (125 uM of each) and 0.125 U/uL of Klenow fragment (3'->5' exo-) (MCLAB, USA) at 25° C. for 15 min, followed by one wash of 1× phosphate buffer, 0.10% Tween 20, twice with 0.1 M NaOH+0.1% Tween 20, and twice with 1× phosphate buffer, 0.1% Tween 20. After the recording tag extension, the binder-coding tag conjugate was washed away, and the sample was capped by introducing with primer binding site for PCR and NGS with incubation of 400 nM of an end capping oligo with 0.125 U/uL of WT Klenow fragment (3'->5' exo-), dNTPs (each at 125 uM), 50 mM Tris-HCl (pH, 7.5), 2 mM $MgSO_4$, 50 mM NaCl, 1 mM DTT, 0.1% Tween 20, and 0.1 mg/mL BSA at 25° C. for 10 min. The beads were washed once with 1× phosphate buffer, 0.1% Tween 20, twice with 0.1 M NaOH+0.1% Tween 20, and twice with 1× phosphate buffer, 0.1% Tween 20. Then, the extended recording tags were amplified and analyzed by nucleic acid sequencing.

Sequencing of recording tags after the encoding cycle was used to estimate fractions of the recording tags being extended (encoded) during primer extension reactions. The efficiencies of the encoding reactions were evaluated based on yield (based on fractions of recording tag reads contained barcode information of the coding tag (encoded)) and background signal (fractions of recording tag reads contained barcode information that are associated with a non-cognate peptide).

Example 8. High Specificity Binders Against Modified N-Terminal Amino Acid (NTAA) Residues of Target Peptides Generated from the Metalloenzyme Scaffold An exemplary metalloenzyme scaffold (sequence set forth in SEQ ID NO: 7) was used to generate a panel of binders specific for selected modified N-terminal amino acid (NTAA) residues (Z-P1) of target peptides.

Binder engineering and maturation from the metalloenzyme scaffold were performed essentially as described in Examples 4 and 5. The crystal structures of the scaffold were retrieved from the PDB database (4LP6, 4YYT), and used to guide selection of key residues in the structure for modification during engineering and maturation. M64 N-terminal modification (NTM) that coordinates zinc (ZnII) ion was installed on target peptides to provide more binding surface and achieve better specificity during engineering. Specific binders were successfully selected against modified D, F, H, E, T, A, G, V, S, I, Y, S, and N NTAA residues of peptides. Exemplary carbonic anhydrase-based binders are disclosed in SEQ ID NO: 48-SEQ ID NO: 57 and SEQ ID NO: 75-SEQ ID NO: 82. Exemplary non-carbonic anhydrase-based binders are disclosed in SEQ ID NO: 28-SEQ ID NO: 47.

Engineered binders presented in the Sequence Listing (SEQ ID NOs: 28-57 and 75-82 show binding diversity across different tested NTMs. By using the described modeling methods, metalloprotein binders can be engineered to recognize a diverse set of Z-P1s on target peptides. Sequences of engineered binders differ significantly from corresponding starting metalloenzyme scaffolds, and each of the engineered binders designed to have an improve binding affinity and having sequences as set forth in SEQ ID NOs: 28-57 and 75-82 contains 5-20 amino acid substitutions from the corresponding starting scaffold. Since most amino acid substitutions were designed to be on the substrate-interaction region of the binders, geometry of substrate-binding pockets of the scaffolds and atomic interactions within them were significantly changed during modelling process.

Engineered binders set forth in SEQ ID NOs: 28-57 and 75-82 typically have about 90-98% sequence identity with corresponding starting scaffolds. Additionally, these binders may be further processed for improving their characteristics, such as Z-P1 affinity, P1 selectivity and/or P2 tolerance. Moreover, conservative amino acid substitutions can be made in the binder's sequence that would improve its characteristics unrelated to the Z-P1 binding, such as improve binder's stability or increase expression level of the binder in bacterial cells. Such conservative amino acid substitutions are known to skilled in the art, and the updated binder's sequence may have less than about 90% sequence identity with the corresponding starting scaffolds (for example, may have about 80% or 85% sequence identity with the corresponding starting scaffolds).

The N-terminal modifications were chosen based on size (having a volume, preferably, from about 100 Å$^3$ to about 500 Å$^3$), and also based on ability to coordinate Zn(II) ion and also to interact with substrate binding pockets of metalloenzyme scaffolds, forming hydrogen bond-based, hydrophobic or other non-covalent interactions. The aim for an engineered metalloenzyme-based binder is to specifically bind to the N-terminally modified target peptide through interaction between the engineered binder and the Z-P1 of the N-terminally modified target peptide, so that, preferably, binding specificity between the engineered binder and the N-terminally modified target peptide is predominantly or substantially determined by interaction between the engineered binder and the Z-P1 of the N-terminally modified target peptide. It can be achieved with a proper geometry of substrate binding pocket of the engineered metalloprotein binder, when there is minimal or no interaction between the binder and the P2 residue of the target peptide. When P1-P2 part occupies a volume encompassing the substrate binding pocket of the engineered binder, and P1 residues is modified with an NTM having a volume similar to a volume of an amino acid residue, it would effectively preclude the P2 residue from entering into or interacting with an affinity determining region of the engineered binder interacting with the N-terminally modified target peptide (FIG. 8A-8D).

Thus, an engineered binder should have relatively high selectivity towards a modified P1 (Z-P1) residue and broad tolerance for different P2 residues. To evaluate whether the engineered binders selected from different metalloenzyme-based scaffolds possess these features, heatmap arrays were generated, where each cell of the array represents an encoding efficiency of the given binder that binds to a specific combination of P1-P2 residues of the target peptide. To generate such heatmap arrays, encoding data (fractions of the recording tags being encoded) were collected in parallel as described in Example 7 for an immobilized set of 288 peptides (17×17 combination of different P1 and P2 residues) and plotted as two-dimensional matrix for diverse P1-P2 combinations (see e.g., FIG. 10-FIG. 13). Encoding efficiencies are shown as black/white gradient, wherein the more intense white color represents higher encoding efficiency (FIG. 10-FIG. 13).

Figure 10:
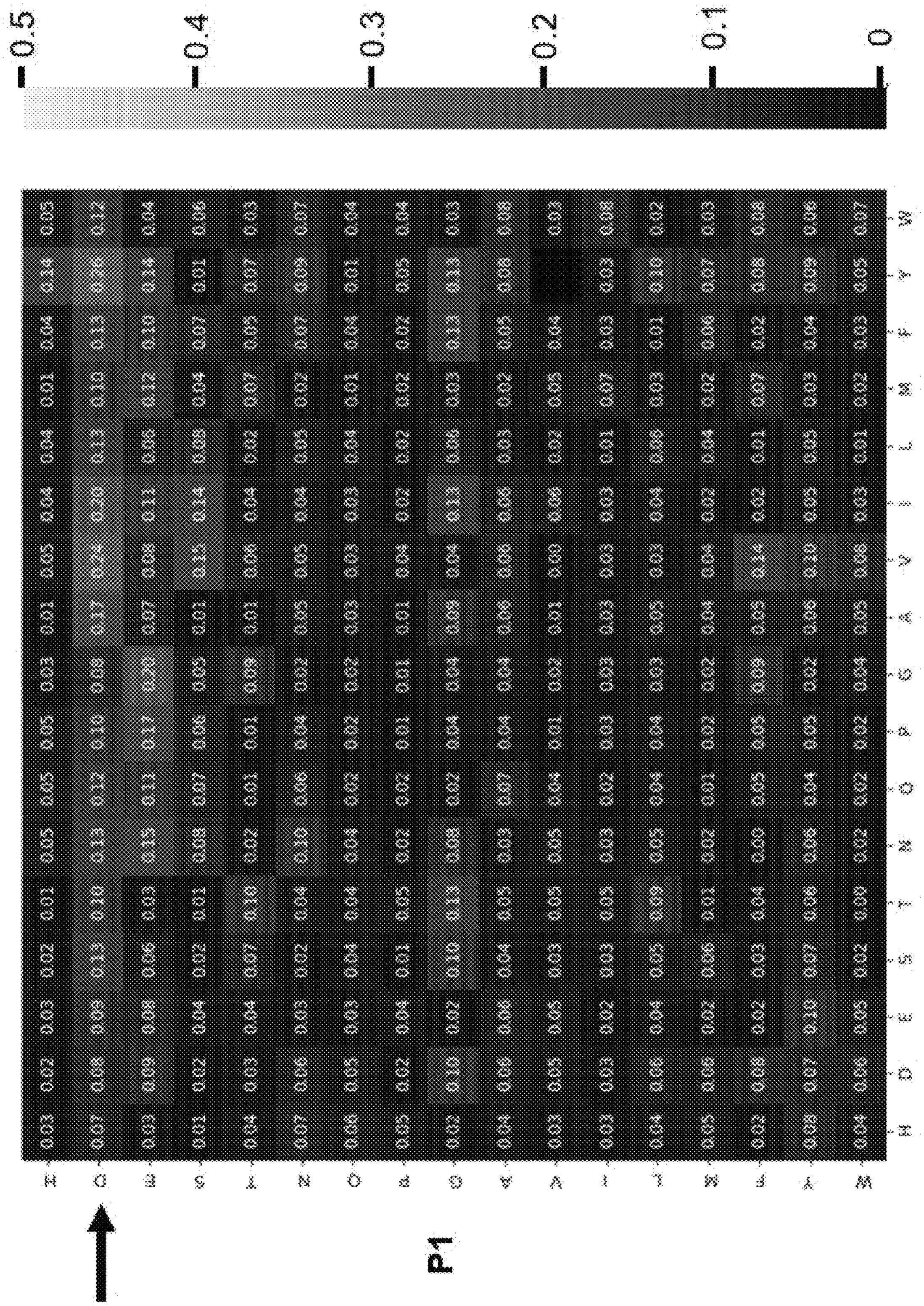
FIG. 10 illustrates exemplary heatmap data showing encoding efficiency (calculated as fraction of recording tags encoded) for the engineered M64-D binder (SEQ ID NO: 48) in the multiplex encoding assay on immobilized set of 288 peptides (17×17 combination of different P1 and P2 residues). Arrow on the left shows primary binder's specificity. The more intense white color of a cell representing a particular P1-P2 combination indicates higher encoding efficiency, and the number in the cell indicates encoding yield for peptide with the P1-P2 combination (fraction of recording tags encoded).

An example of heatmap data for a representative M64-D-specific binder is shown on FIG. 10. FIG. 10 shows results of multiple parallel encoding reactions for the binder engineered from the scaffold having sequence as set forth in SEQ ID NO: 7 to specifically recognize M64-modified D NTAA residue of target peptides, and the binder's sequence is as set forth in SEQ ID NO: 48.

Figure 11:
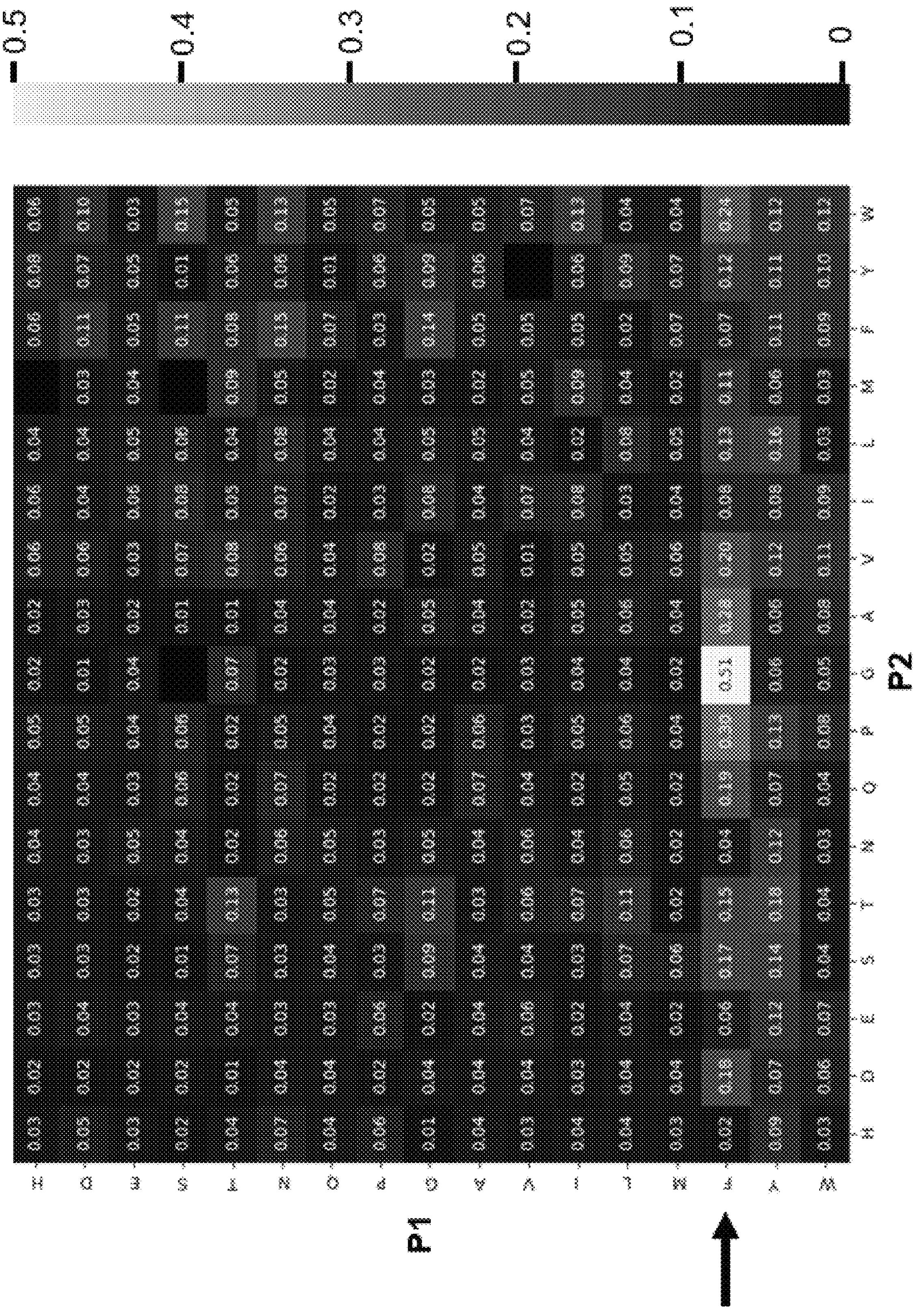
FIG. 11 illustrates exemplary heatmap data showing encoding efficiency (calculated as fraction of recording tags encoded) for the engineered M64-F binder (SEQ ID NO: 51) in the multiplex encoding assay on immobilized set of 288 peptides (17×17 combination of different P1 and P2 residues). Arrow on the left shows primary binder's specificity. The more intense white color of a cell representing a particular P1-P2 combination indicates higher encoding efficiency, and the number in the cell indicates encoding yield for peptide with the P1-P2 combination (fraction of recording tags encoded).

Another example of heatmap data for a representative M64-F-specific binder is shown on FIG. 11. FIG. 11 shows results of multiple parallel encoding reactions for the binder engineered from the scaffold having sequence as set forth in SEQ ID NO: 7 to specifically recognize M64-modified F NTAA residue of target peptides, and the binder's sequence is as set forth in SEQ ID NO: 51.

Figure 12:
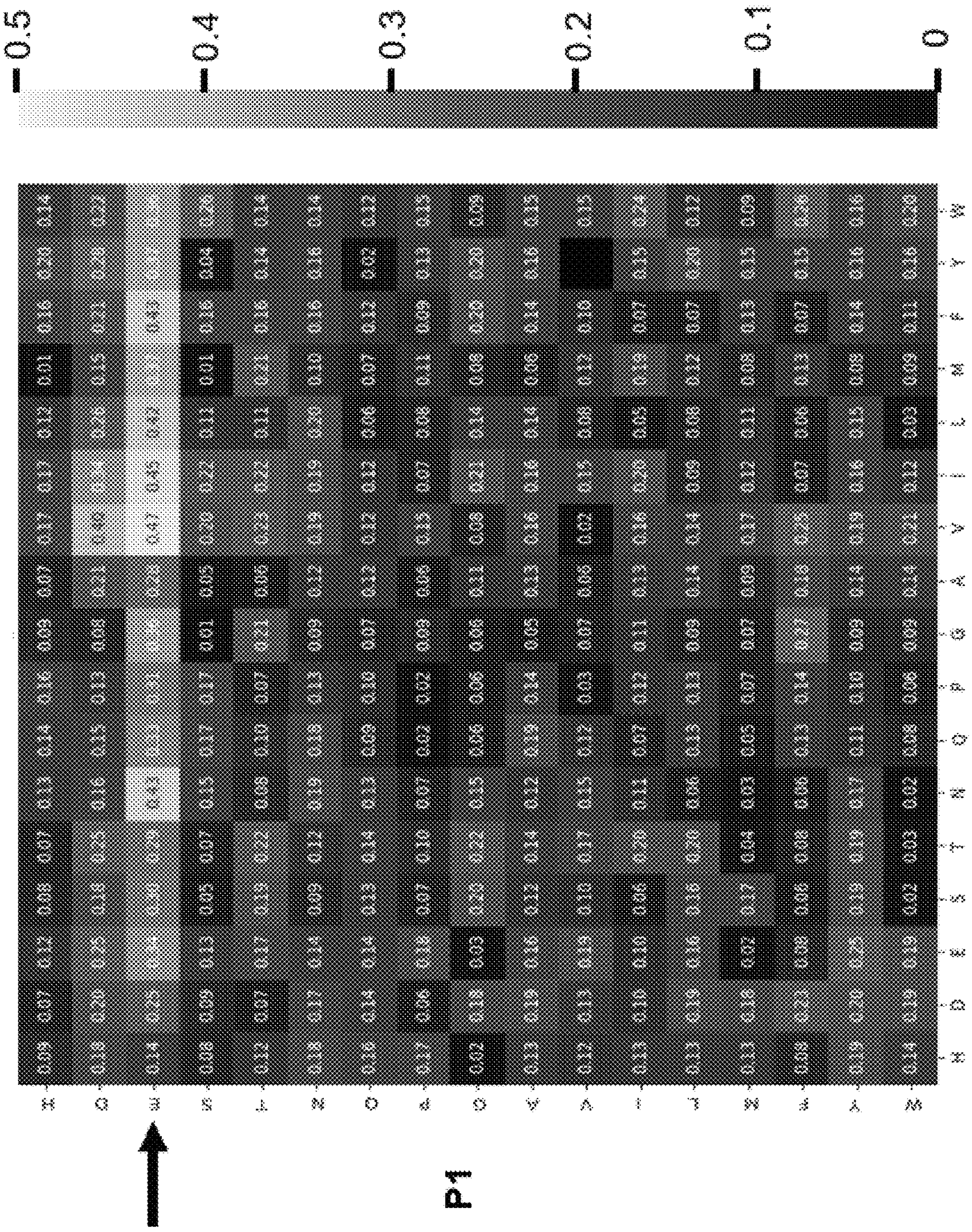
FIG. 12 illustrates exemplary heatmap data showing encoding efficiency (calculated as fraction of recording tags encoded) for the engineered M64-E binder (SEQ ID NO: 55) in the multiplex encoding assay on immobilized set of 288 peptides (17×17 combination of different P1 and P2 residues). Arrow on the left shows primary binder's specificity. The more intense white color of a cell representing a particular P1-P2 combination indicates higher encoding efficiency, and the number in the cell indicates encoding yield for peptide with the P1-P2 combination (fraction of recording tags encoded).

Another example of heatmap data for a representative M64-E-specific binder is shown on FIG. 12. FIG. 12 shows results of multiple parallel encoding reactions for the binder engineered from the scaffold having sequence as set forth in SEQ ID NO: 7 to specifically recognize M64-modified E NTAA residue of target peptides, and the binder's sequence is as set forth in SEQ ID NO: 55.

Figure 13:
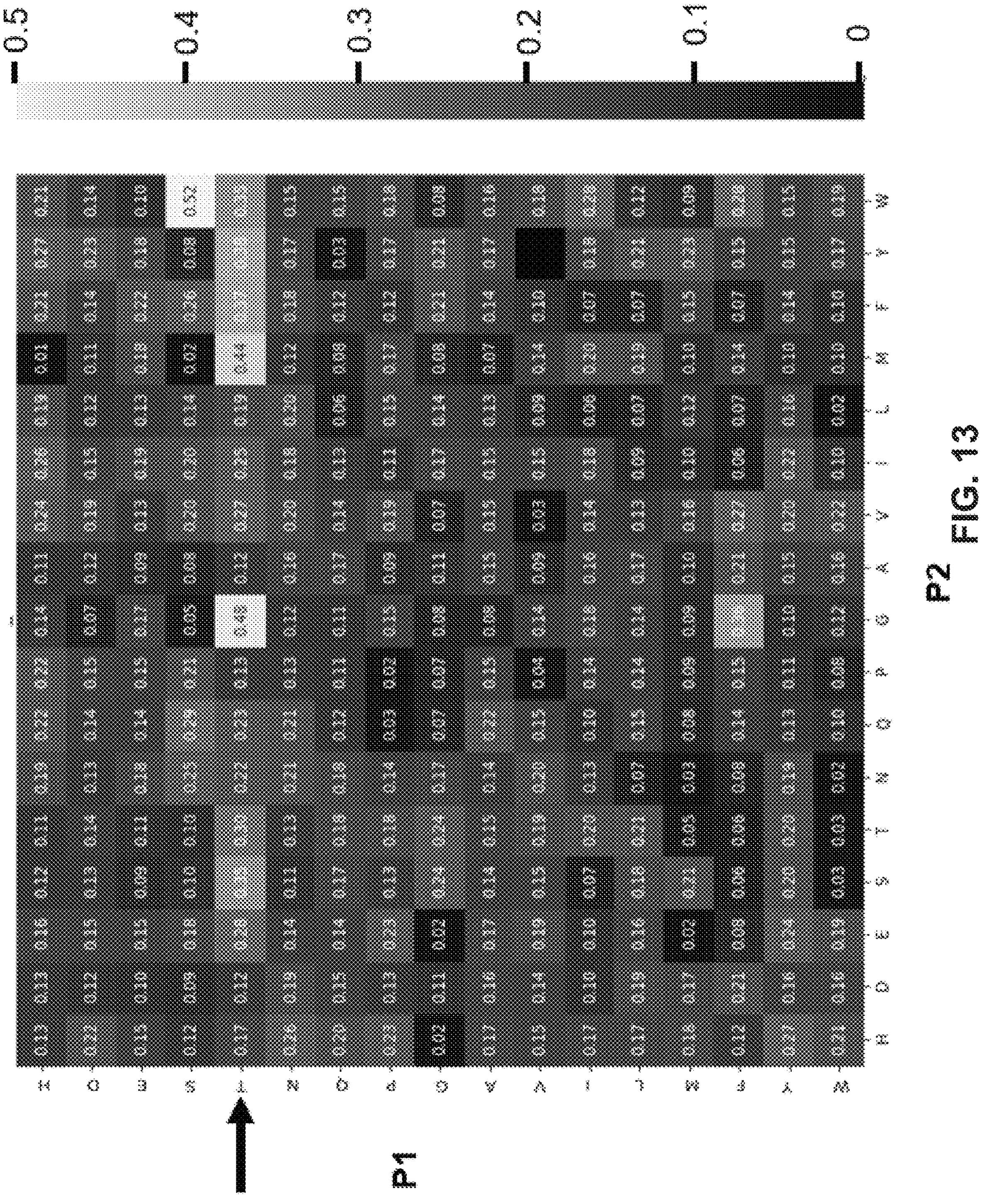
FIG. 13 illustrates exemplary heatmap data showing encoding efficiency (calculated as fraction of recording tags encoded) for the engineered M64-T binder (SEQ ID NO: 57) in the multiplex encoding assay on immobilized set of 288 peptides (17×17 combination of different P1 and P2 residues). Arrow on the left shows primary binder's specificity. The more intense white color of a cell representing a particular P1-P2 combination indicates higher encoding efficiency, and the number in the cell indicates encoding yield for peptide with the P1-P2 combination (fraction of recording tags encoded).

Another example of heatmap data for a representative M64-T-specific binder is shown on FIG. 13. FIG. 13 shows results of multiple parallel encoding reactions for the binder engineered from the scaffold having sequence as set forth in SEQ ID NO: 7 to specifically recognize M64-modified T NTAA residue of target peptides, and the binder's sequence is as set forth in SEQ ID NO: 57.

Such binders can be used in combination with each other and other metalloprotein binders to identify different modified NTAA residues of target peptides.

Kd values for the selected engineered hCAII binders were obtained using the colorimetric assay similar to described in Example 2.

In the colorimetric assay, 300 nM of wild-type carbonic anhydrase or engineered hCAII binders were aliquoted into a 96-well, clear, flat-bottom plate in 45 μL of 50 mM MOPS (pH7.5), 33 mM $Na_2SO_4$, 1 mM EDTA and 0.1% Tween 20. To each column of the plate, a 1/10 dilution series from 1 mM to 0.1 nM of each NTM-derivatized peptide was added and incubated at 25 C for 30 minutes to reach binding equilibrium. To this, 1 mM p-nitrophenylacetate (pNPA) was added to each well and screened on a plate reader at 405 nm. The initial rate of hydrolysis was observed over the first 60 seconds. The slopes versus the concentration of NTM-derivatized peptide were put into a non-linear regression equation to determine the IC50 (50% inhibitory concentration) of the NTM-derivatized peptide to the wild-type hCAII or engineered hCAII binders. The IC50 value measured in this experiment (see Table 12) provided relative binding affinities of the binders ($K_d$ values).

TABLE 12

IC50 values (μM) for wild-type hCAII, wild-type hCAI and two engineered hCAII binders tested against five M64-derivatized model peptides.

| SEQ ID NO: | Specificity | M64-DAEIR | M64-EAEIR | M64-AAEIR | M64-FAEIR | M64-LAEIR |
|---|---|---|---|---|---|---|
| 7 | N/A | 0.089 ± 0.020 | 0.630 ± 0.098 | 0.020 ± 0.004 | 0.018 ± 0.003 | 0.028 ± 0.008 |
| 58 | Hydrophobics | 0.136 ± 0.038 | 1.088 ± 0.360 | 0.109 ± 0.034 | 0.012 ± 0.001 | 0.016 ± 0.004 |
| 48 | D | 0.101 ± 0.021 | 9.476 ± 2.676 | 8.334 ± 1.767 | 10.04 ± 5.519 | 162.8 ± 124.0 |

TABLE 12-continued

IC50 values (μM) for wild-type hCAII, wild-type hCAI and two engineered hCAII binders tested against five M64-derivatized model peptides.

| SEQ ID NO: | Specificity | M64-DAEIR | M64-EAEIR | M64-AAEIR | M64-FAEIR | M64-LAEIR |
|---|---|---|---|---|---|---|
| 51 | F | 7.191 ± 2.740 | 193.3 ± 96.32 | 3.239 ± 1.134 | 0.310 ± 0.112 | 6.907 ± 2.184 |

Example 9. Quantification of Engineered Binder's P1 Selectivity and P2 Tolerability Based on Calculating Corresponding P1 and P2 Gini Scores To quantify engineered binder's P1 selectivity and P2 tolerance, relative P1 selectivity towards a modified P1 (Z-P1) residue and relative P2 tolerance for different P2 residues were calculated as corresponding Gini coefficients. The Gini coefficient is a single number that demonstrates a degree of inequality in a distribution (a measure of inequality). It is used to estimate how far a given distribution deviates from a totally equal distribution. The Gini coefficient is defined as follows.

For a population uniform on the values $y_i$, i=1 to n, indexed in non-decreasing order ($y_i \leq y_{i+1}$):

$$G = \frac{1}{n}\left(n + 1 - 2\left(\frac{\sum_{i=1}^{n}(n + 1 - i)y_i}{\sum_{i=1}^{n} y_i}\right)\right)$$

This may be simplified to:

$$G = \frac{2\sum_{i=1}^{n} i y_i}{n\sum_{i=1}^{n} yi} - \frac{n+1}{n}. \qquad \text{(Equation 1)}$$

This formula applies to any population, since each member can be assigned its own y (Damgaard, Christian. "Gini Coefficient." From MathWorld—A Wolfram Web Resource). To calculate Gini coefficient for engineered binder's P1 selectivity based on heatmap data, the above formula was used, where n represents number of P1 residues (n=17), and $y_i$ represent fractions of recording tags encoded on the ith most encoding P1. Similarly, to calculate Gini coefficient for engineered binder's P2 tolerance based on heatmap data, the above formula was used, where n represents number of P2 residues (n=17), and $y_i$ represent fractions of recording tags encoded on the ith most encoding P2. Higher P1 indicates more selectivity towards the particular Z-P1 residue the binders specifically binds to, whereas lower P2 score indicates less selectivity towards particular P2 residue (and higher tolerance). These scores provide only relative estimation of selectivity, and they were arbitrary set to be: P1 score more than 0.15 for a binder to be considered as specific; and P2 score less than 0.4 for a binder to be considered P2-independent. It should be noted that the scores may be further improved through further binder selection and maturation process.

For preferred engineered binders to be used in the ProteoCode™ assay or in another high throughput peptide analysis assay, binding specificity between the engineered binder and the N-terminally modified target peptide is predominantly or substantially determined by interaction between the engineered binder and the Z-P1 of the N-terminally modified target peptide. It implies or indicates that such engineered binder has a high P1 score (for example, more than 0.25) and will have a low P2 score (for example, less than 0.3). Depending on particular assay, more or less specific binders can be employed. Alternative measurements of binder's P1 selectivity and P2 tolerance can be utilized, and different threshold values for P1 selectivity and P2 tolerance can be set.

To evaluate Z-P1 specificity (via P1 selectivity and P2 tolerance) of selected binders engineered by the methods described in Example 4 and 5, P1 and P2 scores were calculated for the binders based on multiplex encoding data (heatmap data) and shown in Table 13. Corresponding binder sequences (based on SEQ ID NOs) are as set forth in the Sequence Listing. Starting scaffolds for the binders are shown in the second column of Table 13 (based on SEQ ID NOs) together with the NTM used to modify P1 residue.

TABLE 13

Z-P1 specificity, P1 selectivity and P2 tolerance of selected engineered binders.

| SEQ ID NO of the binder | SEQ ID NO of the scaffold and NTM | Specificity towards P1 | P1 score | P2 score |
|---|---|---|---|---|
| 48 | 7, M = M64 | D | 0.293762153 | 0.194449 |
| 49 | 7, M = M64 | D | 0.369155476 | 0.19823689 |
| 50 | 7, M = M64 | D | 0.248650734 | 0.25259301 |
| 51 | 7, M = M64 | F | 0.321647176 | 0.35559918 |
| 53 | 7, M = M64 | F | 0.232907355 | 0.242115 |
| 55 | 7, M = M64 | E | 0.292695353 | 0.19862444 |
| 56 | 7, M = M64 | E | 0.278916867 | 0.24028269 |
| 57 | 7, M = M64 | T | 0.278718119 | 0.21382942 |
| 7 | 7, M = M64 | — | 0.941176471 | 0.94117647 |
| 58 | 58, M = M64 | Small hydrophobic | 0.337689944 | 0.23579931 |

Engineered binders presented in the Sequence Listing and in Table 13 show diversity across Z-P1 specificity, since D, E, T and F represent amino acid residues having different biochemical properties (charged, polar uncharged and hydrophobic). Thus, by using the described methods, metalloprotein binders can be engineered to recognize a diverse set of Z-P1s on target peptides.

Sequences of engineered binders differ significantly from corresponding starting metalloenzyme scaffolds, and each of the engineered binders with sequences as set forth in SEQ ID NOs: 48-57 contains 3-10 amino acid substitutions from the corresponding starting scaffold. Since most amino acid substitutions were designed to be on the substrate-interaction region of the binders, geometry of substrate-binding pockets of the scaffolds and atomic interactions within them were significantly changed during engineering and maturation process.

Engineered binders shown in Table 13 typically have about 97-98% sequence identity with corresponding starting scaffold. Additionally, these binders may be further processed through another maturation round for improving their characteristics, such as Z-P1 affinity, P1 selectivity and/or P2 tolerance. In the next maturation round new amino acid substitutions will likely be introduced, and the updated binder's sequence may be further away from the sequence of the corresponding starting scaffold, such that it will have about 90 or 95% sequence identity with the corresponding starting scaffold. Moreover, conservative amino acid substitutions can be made in the binder's sequence that would improve its characteristics unrelated to the Z-P1 binding, such as improve binder's stability or increase expression level of the binder in bacterial cells. Such conservative amino acid substitutions are known to skilled in the art, and the updated binder's sequence may have less than about 90% sequence identity with the corresponding starting scaffold (for example, may have about 80% or 85% sequence identity with the corresponding starting scaffold).

Example 10. Affinity Characterization of Exemplary Generated Binders by Bio-Layer Interferometry (BLI)

Bio-layer interferometry (BLI) is an optical analytical and label-free method to directly measure kinetics between two biomolecules. In this technology, one biomolecule is immobilized on a surface in the form of a small tip, this tip is then dipped in a microplate containing the second biomolecule of interest. White light is directed down the tip to the tip surface where the binding is measured as a shift in wavelength that is caused as a result of the interference between incident and reflected light. More specifically, there are two surfaces at the tip, a reference layer and the experiment layer, the latter is where the biomolecules immobilize and bind. As the distance between these two layers increases due to biomolecules binding and immobilizing, the shift between incident and reflected wavelengths increases as caused by the light waves interfering at the two layers. Therefore, the size and the number of biomolecules that bind onto the surface is proportional to the shift measured. This shift is plotted against time to give a sensogram from which $k_{on}$, $k_{off}$ and ultimately KD can be calculated.

All binding experiments were carried out on an 8-channel Gator Prime (Gator Bio) instrument. To measure the affinity of each binder-peptide pair, biotinylated peptides were immobilized on Streptavidin coated biosensor tips (Gator Bio), which were dipped in six binder concentrations and two controls. All binding assays were performed at 22° C. in 96 well polypropylene plates (Gator Bio) and carried out in triplicates with a well volume of 200 uL. Streptavidin coated biosensors were hydrated in the baseline buffer for 10 mins before each assay. All binding experiments used biotinylated peptides with the following sequence construct, M64-P1-P2-ΔK-(PEG9)(PEG9)-K(Biotin) and all peptides were diluted in the baseline buffer. Binders having sequences set forth in SEQ ID NO: 75-SEQ ID NO: 82 were tested. The binders originated from three different metalloenzyme scaffolds and were engineered according to the methods disclosed in Examples 4-6. KD values were generated from at least three independent experiments performed on different protein concentration ranged from 100 to 10000 nM. All binders were serially diluted using the baseline buffer either by 2- or 3-fold. Baseline buffer consisted of 50 mM MOPS pH 7.5, 33 mM $NaSO_4$, 1 mM EDTA and 0.1% Tween-20. The following protocol was used for each binding assay under shaker speed of 1000 rpm, which generated the best quality binding with minimal sensor to sensor variation and baseline drift (Table 14).

TABLE 14

BLI binding assay protocol.

| Step | Sample | Time (seconds) | Shaking (RPM) |
|---|---|---|---|
| Baseline | Baseline buffer | 200 | 1000 |
| Loading (immobilizing peptides on tips) | 500 nM biotinylated peptide | 30 | 500 |
| Baseline | Baseline buffer | 200 | 1000 |
| Association (binder to immobilized peptides) | 2-3X serial dilution of binders | 500 | 1000 |
| Dissociation | Baseline buffer | 500 | 1000 |

Between each binding assay, if biosensors were used more than once, the following protocol was used to regenerate the biosensor for subsequent binding assays (Table 15). Regeneration buffer consisted of 150 nM NaCl and 10 mM Glycine pH 2.0.

TABLE 15

BLI biosensor regeneration protocol.

| Step | Sample | Time (seconds) | Shaking (RPM) |
|---|---|---|---|
| Regenerate | Regeneration buffer | 5 | 1000 |
| Neutralize | Baseline buffer | 5 | 1000 |
| Regenerate | Regeneration buffer | 5 | 1000 |
| Neutralize | Baseline buffer | 5 | 1000 |
| Regenerate | Regeneration buffer | 5 | 1000 |
| Neutralize | Baseline buffer | 5 | 1000 |

Analysis of binding curves. Negative control did not show any response and the curve went to the baseline level. Binding curves were aligned to the association step and subtracted using the reference curve. Each set of processed curves were then fit locally and inspected. The residual plot, R2 and Chi2 were examined to be <0.1 nm, >0.95 nm and <3 nm respectively. If any curves did not fit these criteria, they were removed from the analysis. Next, the qualifying curves were filled globally and the kinetic parameters kobs, kon, koff and KD were calculated along with their errors. The errors were inspected to be less than 1000 of its calculated value. Finally, the theoretical shift at equilibrium from the qualifying curves were filled on a steady state plot, and the KD and Rmax (theoretical maximum binding capacity in nm) were calculated from that curve. The kinetic parameters of exemplary generated binders (having sequences set forth in SEQ ID NO: 75-SEQ ID NO: 82) with their respective targets (indicated as P1 residue of immobilized peptides) are shown in Table 16.

TABLE 16

Kinetic parameters of exemplary generated binders.

| SEQ ID NO: | P1 | koff(1/s) | kon(1/Ms) | KD(M) |
|---|---|---|---|---|
| 75 | T | 1.11E−02 | 2.33E+04 | 4.88E−07 |
| 75 | V | 4.73E−04 | 2.37E+04 | 2.00E−08 |
| 76 | E | 1.31E−03 | 7.59E+03 | 1.73E−07 |
| 77 | S | 1.03E−02 | 1.03E+04 | 3.48E−06 |
| 78 | N | 1.84E−03 | 2.10E+04 | 8.74E−08 |
| 79 | F | 2.98E−03 | 2.66E+04 | 1.12E−07 |
| 80 | Y | 4.15E−03 | 2.22E+04 | 1.87E−07 |
| 81 | G | 2.50E−03 | 2.01E+04 | 1.25E−07 |
| 82 | D | 1.19E−04 | 4.17E+03 | 2.87E−08 |

Most of the tested engineered binders as shown above have a very similar kon around the 10e+4 M-1s-1 magnitude, except for the two negative charged residue binders (SEQ ID NO: 76 and SEQ ID NO: 82), which have $k_{on}$ about 0.5-1 order of magnitude less. All of the tested engineered binders have a thermodynamic dissociation constant (Kd) of 350 nM or less.

Other methods for measurement of thermodynamic dissociation constant (Kd) for engineered binders can be employed. The described BLI-based method provides conservative (higher) Kd estimates for engineered binders compared to in-solution techniques (e.g., when target peptides are in solution, and not immobilized on a solid support), which may show lower Kd values due to absence of support-related steric constrains.

Example 11. Determination of Conserved Sequence Motifs in Alpha-Carbonic Anhydrase-Based Binders Considering the conserved structural fold of the carbonic anhydrase scaffolds (see Example 2 and Table 11), as well as binders produced from different alpha-carbonic anhydrase scaffolds (see Examples 7, 8, and 10), conserved sequence motifs shared within the generated group of binders were identified based on multiple sequence alignments. Clustal Omega multiple sequence alignment web form (version 1.2.4) was used to generate a multiple sequence alignment using native and engineered alpha-carbonic anhydrase protein sequences (Sievers F, et al., Fast, scalable generation of high-quality protein multiple sequence alignments using Clustal Omega. Mol Syst Biol. 2011 Oct. 11; 7:539). Regions of alpha-carbonic anhydrase involved in binding the NTAA of the NTM-NTAA polypeptide and binding the Zn (II) ion were structurally analyzed using PyMOL software (Schrödinger, L., & DeLano, W, (2020), PyMOL) of RCSB PDB accession number 4YYT. In particular, 1,488 experimentally characterized sequences of alpha-carbonic anhydrase binders and corresponding starting sequences (natural alpha-carbonic anhydrase proteins), including at least the amino acid sequences set forth in SEQ ID NO: 7-SEQ ID NO: 9, SEQ ID NO: 48-SEQ ID NO: 52, SEQ ID NO: 54-SEQ ID NO: 57, SEQ ID NO: 68-SEQ ID NO: 99 and SEQ ID NO: 105-SEQ ID NO: 135 were used to generate conserved sequence motifs present in substrate binding (e.g., NTM-P1 and the Zn (II) ion) pockets. For each sequence set forth in SEQ ID NO: 7-SEQ ID NO: 9, SEQ ID NO: 48-SEQ ID NO: 52, SEQ ID NO: 54-SEQ ID NO: 57, SEQ ID NO: 68-SEQ ID NO: 99 and SEQ ID NO: 105-SEQ ID NO: 135, the NTM-P1 pocket was determined as disclosed in Example 2. The sequence set forth in SEQ ID NO: 7 was used as the reference sequence, with residues 56-69, 86-93, 116-139, and 192-203 comprising the NTM-NTAA binding pocket and the Zn (II) ion binding site. As a result, the following conserved amino acid sequences were identified: (A/C/D/I/S/V/Y)X(C/N)X(A/C/G/R/S/V)XX(C/F/I/L/T/V)X(C/G/K/N/V)X(F/I)(D/E/K/N/V)(D/E/F/N/Q), (G/Q/R) (A/C/D/I/L)XX(C/F/I/V) H (F/I/L)H, H (C/L/V)X(C/D/H/L/V) (E/H/L/M/R/W/Y) N (A/N/P/S/T) (E/K/R/S/Y) (A/L/S/Y), (A/S)XX(A/E/H/K/Q) (A/P/R/S/T)D(G/I/V)X (A/T/V) (I/L/M/N/R/V), and G(A/C/F/I/S)X(A/D/M/T) XPX(C/F/L)X(C/E/R)X(I/L/R/V). In these sequences, X corresponds to any one of the 20 standard amino acids; and other positions are either exactly determined or chosen from indicated amino acid residues (e.g., "(I/V)" means I or V in this position). The Zn (II)-chelating histidine residues are residues 91, 93, and 116 in SEQ ID NO: 7, and they correspond to residue 6 in (G/Q/R) (A/C/D/I/L)XX(C/F/I/V) H (F/I/L) H, residue 8 in (G/Q/R) (A/C/D/I/L)XX(C/F/I/V) H (F/I/L)H, and residue 1 in H (C/L/V)X(C/D/H/L/V) (E/H/L/M/R/W/Y) N (A/N/P/S/T) (E/K/R/S/Y) (A/L/S/Y), respectively.

Example 12. Functionalization of a N-Terminal Amino Acid (NTAA) Residue of a Polypeptide with a Sulfonamide-Containing 2-Ethynylbenzaldehyde as the N-Terminal Modifier Agent Functionalization of a N-terminal amino acid with a sulfonamide-containing 2-ethynylbenzaldehyde can be achieved through both aqueous and non-aqueous (organic) environments.

In aqueous environments, buffer composition, pH, the N-terminal modifier agent concentration, and temperature are the most critical components. In preferred embodiments, the reaction buffer does not contain primary amine ($R—NH_2$, $R—NH_3^+$)-containing components: Tris, ammonium, glycine, and so on. In preferred embodiments, the reaction buffer (10-500 mM) has the pH within range of 5.5-11. In preferred embodiments, the installation reaction is catalyzed through a transient iminium intermediate by use of secondary amine-containing small molecules as buffer additives in a 0.1-10% range (see FIG. 15A-FIG. 15B), which increases the rate of the reaction by at least 2-fold (see FIG. 15C). Examples of secondary amines are L-/D-proline, azetidine, pyrrolidine, morpholine, piperidine, piperazine, and their optionally substituted analogs. Shown in FIG. 15B is the particular installation reaction comprising modification of the N-terminal modifier agent (left) with L-proline, creating the catalytic intermediate (middle), which reacts with the peptide generating the peptide modified with M103 NTM. The explored temperature range of this reaction was 20-80° C., and a time course of this reaction from 0-60 minutes. The explored M103 concentrations of this reaction were 0.1-50 mM.

Exemplary reaction conditions for the reaction shown in FIG. 15B and FIG. 15C were as follows. M103 installation was performed on a P1-F peptide (1 eq.) using 2 eq. of M103 in the presence and absence of the catalyst (1% (w/v) proline) with 25% DMSO as the M103 vehicle. Buffer conditions were 0.1M potassium phosphate (KPhos) buffer, pH=8, with and without the catalyst. The reactions were incubated 0-60 minutes at 60° C., and aliquots were taken in 15-minute intervals, quenched with 1% formic acid in water, and injected into an Agilent single-quad LC-MS instrument for further analysis. The conversion was monitored using the 216 nm wavelength channel, and the comparison of conversion rates is shown in FIG. 15C. In FIG. 15C, SM indicates starting material peptide and Prod indicates the product peptide (M103-peptide)); KPhos indicates the reaction condition without the catalyst, and 1% proline indicates the reaction condition with the catalyst (proline). FIG. 15C demonstrates significant increase in efficiency of the M103 installation in the presence of the catalyst.

In organic conditions, similar considerations were valid for the M103 installation. Organic solvents tested were DMSO, DMF, DMA, $CH_3CN$, and a combination thereof (5-95%). The temperature ranges of the installation reaction remained 20-80° C., with M103 concentrations ranged from 0.1-50 mM. The pH of the installation reaction was not adjusted or monitored due to the pure organic nature of the reaction. Aside from the aforementioned secondary amine catalyst (0.1-10%), no additional base was added to the reaction mixture.

Exemplary N-terminal modifier agents of Formula (8), wherein one example of such agents is shown in FIG. 15A, provide certain advantages compared to N-terminal modifier agents, such as agents of Formula (6). N-terminal modifier agents of Formula (8) have a non-NHS reaction mechanism that is mostly N-terminus specific, so they provide with increased specificity towards primary amine groups present in peptide backbones (in the N-terminus and side chains of Lys residues) in comparison with other N-terminal modifier agents, which may also react with hydroxyl groups (such as side chains of Ser or Thr residues) (data not shown). The increased specificity towards primary amine groups allows to lower background in the binding and encoding reactions described herein. Thus, N-terminal modifier agents of Formula (8) are preferred over N-terminal modifier agents of Formula (6) for peptide modification.

Exemplary N-terminal modifier agent shown in FIG. 15A can be generalized as a compound of Formula (8):

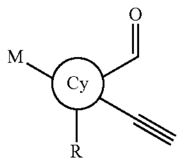

(8), wherein M is a metal cation binding group that comprises sulfonamide, hydroxamic acid, sulfamate, or sulfamide; the group

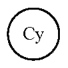

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, $OR^Q$, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH.

FIG. 15D shows generic scheme for synthesis of compounds of Formula (8), wherein X═F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, CN, or $CONH_2$. The process comprises steps 1-6 as described below.

Step 1: Commercially available or synthesized 3-bromo-4-methyl-5-H(X)-6H(X)-benzenesulfonamide was oxidized using standard literature procedures to afford the desired 3-bromo-4-carboxy-5-H(X)-6H(X)-benzenesulfonamide.

Step 2: 3-bromo-4-carboxy-5-H(X)-6H(X)-benzenesulfonamide was esterified using standard literature procedures to afford the desired methyl 2-bromo-4-sulfamoyl-5-H(X)-6H(X)-benzoate.

Step 3: methyl 2-bromo-4-sulfamoyl-5-H(X)-6H(X)-benzoate was reduced using standard literature procedures to afford the desired 3-bromo-4-hydroxymethyl-5-H(X)-6H(X)-benzenesulfonamide.

Step 4: 3-bromo-4-hydroxymethyl-5-H(X)-6H(X)-benzenesulfonamide was transformed with palladium catalysis using standard literature procedures to afford the desired 3-(triisopropylsilyl)ethynyl-4-hydroxymethyl-5-H(X)-6H(X)-benzenesulfonamide.

Steps 5 and 6: 3-(triisopropylsilyl)ethynyl-4-hydroxymethyl-5-H(X)-6H(X)-benzenesulfonamide was transformed to the final desired compound using standard literature procedures to afford the desired 3-H-ethynyl-4-formyl-5-H(X)-6H(X)-benzenesulfonamide.

FIG. 15E shows exemplary synthesis of 3-H-ethynyl-4-formylbenzenesulfonamide (an exemplary compound of Formula (8)), which is suitable for N-terminal modification of peptides. The process comprises steps 1-6 as described below.

Step 1: To a refluxing and stirring suspension of 3-bromo-4-methylbenzenesulfonamide (7.3 g, 29.19 mmol) in DI $H_2O$ (200 mL) was added potassium permanganate (18.45 g, 116.75 mmol) in 8 portions over 2 h (2.31 g every 15 min). After addition, the reaction was stirred at reflux for 2 additional hours then at room temperature overnight. The mixture was sonicated and filtered through a pad of celite, rinsing with $H_2O$ until the filtrate was colorless. The filtrate was acidified with 6 M aqueous HCl (pH ~1), diluted with EtOAc and the layers were separated. The aqueous layer was extracted one additional time EtOAc, the organics were combined, washed with brine, dried ($Na_2SO_4$), filtered, and evaporated in vacuo. The white solid residue afforded the desired 3-bromo-4-carboxybenzenesulfonamide (6.45 g, 79%). MS (ESI) 280,282 (doublet) ($M^-$–H). TLC vs SM in 60% EtOAc/Heptane w/3% AcOH is useful to see conversion.

Step 2: Combined 3-bromo-4-carboxybenzenesulfonamide (6.45 g, 23.03 mmol), MeOH (150 mL), $H_2SO_4$ (1.85 mL, 34.54 mmol) and stirred at reflux 16 h under N2 atmosphere. The TLC (60% EtOAc/Heptane w/3% AcOH) at this point showed full conversion. The volume of MeOH was reduced by one-half via roto-evaporation and the reaction mixture was poured into ~500 mL of ice water. The white slurry was stirred cold for 1 h and filtered off, rinsing with minimal ice water. The resulting white solid was air dried for 1 h (under vacuum) then dried on house vac overnight to afford the desired methyl 2-bromo-4-sulfamoylbenzoate (6.1 g, 90%). MS (ESI) 294,296 (doublet) ($M^-$–H).

Step 3: Combined methyl 2-bromo-4-sulfamoylbenzoate (6.1 g, 20.74 mmol) with THF (150 mL) and stirred at 0° C. under N2 atmosphere. $LiBH_4$ (51.85 mL, 103.69 mmol, 2.0 M solution in THF) was added in rapid drops, the ice bath was removed upon completing the addition, and the resulting mixture was stirred at 45° C. for 16 h. The reaction was cooled to 0° C. and 4 M aqueous HCl (130 mL, 518.45 mmol) was slowly added. The volume of THF was reduced by one-half via roto-evaporation and the mixture was diluted with 2-methyl THF and brine. The TLC (70% EtOAc/Heptane) at this point showed full conversion. The aqueous layer was extracted one additional time with 2-methyl THF, the organics were combined, washed with brine, dried ($Na_2SO_4$), filtered, evaporated in vacuo and kept on vacuum overnight. The resulting white solid afforded the desired 3-bromo-4-hydroxymethyl-benzenesulfonamide (5.7 g, 103%). MS (ESI) 266,288 (doublet) ($M^-$−H).

Step 4: Under an argon atmosphere was combined 3-bromo-4-hydroxymethyl-benzenesulfonamide (2.00 g, 7.52 mmol), $Pd(PPh_3)_4$ (0.13 g, 0.113 mmol) and 4-methylpiperidine (20 mL). The stirring mixture was subsurface purged with argon gas for 5 min, then triisopropylsilylacetylene (1.94 mL, 9.02 mmol) was added. The combined mixture was subsurface purged again with argon gas for 5 min then heated to 120° C. for 24 h under argon atmosphere. The reaction was cooled to rt and diluted with EtOAc and saturated aqueous $NH_4Cl$. The organic layer was extracted one additional time with saturated aqueous $NH_4Cl$, dried ($Na_2SO_4$), filtered, and evaporated in vacuo. The crude residue was purified by flash column chromatography ($SiO_2$) eluting with EtOAc and heptane using a 5% to 85% gradient to give the desired 3-(triisopropylsilyl)ethynyl-4-hydroxymethyl-benzenesulfonamide as a pure white solid (2.4 g, 87%). MS (ESI) 366 ($M^-$−H).

Steps 5 and 6: Under a nitrogen atmosphere was combined 3-(triisopropylsilyl)ethynyl-4-hydroxymethyl-benzenesulfonamide (2.4 g, 6.53 mmol) with 1,4-dioxane (40 mL) and the mixture was stirred at 0° C. To the stirring solution was added TBAF (7.18 mL, 7.18 mmol, 1.0 M solution in THF). The ice bath was removed and the reaction was stirred at rt for 1.5 h at which time the TLC (60% EtOAc/Heptane) indicated complete conversion. The reaction mixture was cooled to 0° C. once more and DCM (40 mL) was added followed by Dess-Martin periodinane (5.54 g, 13.06 mmol). The ice bath was removed, and the reaction was stirred at room temperature for 16 h. The mixture was cooled to 0° C. and 200 mL of a 1:1 solution of saturated aqueous $NaHCO_3$/1.5M $Na_2S203.5H_2O$ was added in quick drops from an addition funnel. The ice bath was removed and the solution was stirred at rt for 30 min then diluted with DCM and brine. The aqueous layer was extracted one additional time with DCM. The organics were combined, washed with brine, dried ($Na_2SO_4$), filtered, and evaporated in vacuo. The crude residue was purified by flash column chromatography ($SiO_2$) eluting with EtOAc and heptane using a 5% to 80% gradient to give the desired 3-H-ethynyl-4-formylbenzenesulfonamide as a pure white solid (1.15 g, 84%, two steps). MS (ESI) 208 ($M^-$−H).

In some embodiments of the described NTM installation reaction, the catalyst for installation of the N-terminal modifier agent shown in FIG. 15A comprises a compound of Formula (10), Formula (11), or Formula (12):

(10)

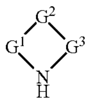

(11)

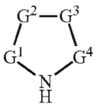

-continued (12)

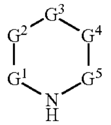

wherein:

G1-G5 are each independently selected from $CJ_2$, NH, S, and O provided not more than 1 of G1-G5 are NH, S, or O;

J at each occurrence is independently selected from H, $C_1$-$C_2$ alkyl, $NO_2$, $C_1$-$C_2$ haloalkyl, $C_1$-$C_2$ haloalkoxy, halo, —$OR^8$, —N(R8)$_2$, —$S(O)_nR^8$, —$NR^8SO_2R^8$, —$SO_2N(R^8)_2$, $SO_3R^8$, —$B(OR^8)_2$, C(═O)$R^8$, CN, CON$(R^8)_2$, —$COOR^8$, —C(—O)Ar, and tetrazole, where Ar represents a phenyl or 5-6 membered heteroaryl ring that is optionally substituted with one or two groups selected from halo, CN, $R^9$ and $OR^9$;

each $R^8$ and each $R^9$ is independently selected from H, $C_1$-$C_2$ alkyl, and $C_1$-$C_2$ haloalkyl;

n at each occurrence is independently 1 or 2.

Example 13. De Novo Design of Engineered Binders Based on Zinc Metal Cation Chelation Motifs and Estimation of a Thermodynamic Dissociation Constant of Zinc Metal Cation for Engineered Binders In this example, in silico modeling of de novo designed binding agents having amino acid sequences unrelated to any known natural sequence is disclosed. The goal of this example is to demonstrate the ability of generating engineered binding agents from non-natural sequences. To generate binding agents that are independent of the carbonic anhydrase fold, or any other natural fold, state-of-the-art de novo protein design methodologies were implemented as described below. Utilization of a combination of state-of-the-art de novo protein design methodologies including but not limited to PyRosetta macromolecular design and modeling software (S. Chaudhury, S. Lyskov & J. J. Gray, "PyRosetta: a script-based interface for implementing molecular modeling algorithms using Rosetta," Bioinformatics, 26(5), 689-691 (2010)), DiffDock and DiffDock-L molecular docking software (Corso, et al. "Diffdock: Diffusion steps, twists, and turns for molecular docking," (2022)), RFdiffusion software (Watson, et al., De novo design of protein structure and function with RFdiffusion. Nature. 2023 August; 620(7976):1089-1100) involving denoising diffusion generative models, RFdiffusion All-Atom software (Krishna, Rohith et al. "Generalized biomolecular modeling and design with RoseTTAFoid All-Atom." *Science* (New York N.Y.) vol. 384,6693 (2024): eadl2528) for building protein structures around small molecules using denoising diffusion generative models, RFdesign software (Wang, Jue et al. "Scaffolding protein functional sites using deep learning." *Science* (New York, N.Y.) vol. 377,6604 (2022): 387-394) involving constrained hallucination and protein inpainting, ProteinMPNN software (Dauparas J, et al., Robust deep learning-based protein sequence design using ProteinMPNN. Science. 2022; 378(6615):49-56) involving message passing neural networks, LigandMPNN (Dauparas, J., Lee, G. R., Pecoraro, R., An, L., Anishchenko, I., Glasscock, C., & Baker, D. (2023). Atomic context-conditioned protein sequence design using LigandMPNN. Biorxiv, 2023-12) involving explicit modeling of the non-protein components of biomolecular systems using message passing neural networks, and deep learning-based structure prediction software including but not limited to ESMFold software (Zeming Lin, et al., Evolutionary-scale prediction of atomic level protein structure with a language model. Science 379, 6637 (2023)), AlphaFold2 software (Jumper, J., et al., Highly accurate protein structure prediction with AlphaFold. Nature 596, 583-589 (2021)), OpenFold software (Ahdritz, Gustaf et al. "OpenFold: retraining AlphaFold2 yields new insights into its learning mechanisms and capacity for generalization." Nature nme/hods, 10.1038/s41592-024-02272-z. 14 May. 2024), RoseTTAFold All-Atom software (Krishna, Rohith et al. "Generalized biomolecular modeling and design with RoseTTAFold All-Atom." Science (New York, N.Y.) vol. 384,6693 (2024): eadl2528), and RoseTTAFold2 software (Minkyung Baek, et al., Efficient and accurate prediction of protein structure using RoseTTAFold2. bioRxiv 2023.05.24.542179), were sufficient to develop novel binding agents to both metal ions and N-terminally modified polypeptide sequences.

Briefly, the 3-dimensional Cartesian coordinates of a minimal metal ion-binding polypeptide motif was extracted from the crystal coordinates of a protein of interest; for example, the human carbonic anhydrase isoform II (hCAII) enzyme bound to a Zn(II) metal ion was used having the Research Collaboratory for Structural Bioinformatics (RCSB) Protein Data Bank (PDB) accession number 4YYT. In another embodiment, a minimal metal ion-binding polypeptide motif was extracted from a variant of the hCAII enzyme (e.g. a binding agent) bound to a Zn(II) metal ion and optionally bound to a NTM-NTAA molecule as a co-crystal structure.

For 4YYT, the 3-dimensional Cartesian coordinates of at least the three histidine residues responsible for chelating the Zn(II) ion, and optionally additional polypeptide residues covalently attached to the three histidine residues that are responsible for chelating the Zn(II) ion, were extracted into a separate PDB file using PyMOL software (Schr6dinger, L., & DeLano, W. (2020). PyMOL) or PyRosetta software. In another embodiment, one or optionally more than one residue forming intermolecular interactions (including but not limited to hydrogen bond interactions, dipole-dipole interactions, pi-pi interactions, cation-pi interactions, van der Waals interactions, and salt bridges) to the N-terminally modified polypeptide in the co-crystal structure may be extracted as a motif into a separate PDB file using PyMOL software or PyRosetta software. In the case of starting with a crystal structure without a N-terminally modified polypeptide bound in the pocket of the enzyme or binding agent, DiffDock (or optionally DiffDock-L or similar software) molecular docking software may also be used to model the N-terminally modified polypeptide into the hCAII binding pocket, and the N-terminally modified polypeptide optionally extracted with the minimal metal ion-binding polypeptide motif, as well as optionally the N-terminally modified polypeptide binding motif, into the separate PDB file. RFdiffusion (or RFdiffusion All-Atom) software was then run using the generated separate PDB file as input, as well as a 'contigs' string defining the scaffold lengths and positions with respect to the continuous or disjointed minimal metal ion-binding motif polypeptide residues; for example, a 'contigs' string may indicate an insertion of 5-150 residues between the first and second Zn(II)-chelating histidine residues, another insertion of 10-200 residues between the second and third Zn(II)-chelating histidine residues, and flanking insertions of 5-40 residues on the N-terminus of the first Zn(II)-chelating histidine residue and the C-terminus of the third Zn(II)-chelating histidine residue. In the case of running RFdiffusion All-Atom, the N-terminally modified polypeptide in the input PDB file was used as the ligand, such that the protein structure was built around the N-terminally modified polypeptide. Running RFdiffusion (or RFdiffusion All-Atom) software over multiple replicates produces highly structurally diverse, covalently bonded backbone coordinates representing protein folds not discovered in nature and representing novel folds unrelated to the hCAII enzyme, yet still harboring the Zn(II) binding motif and optionally the N-terminally modified polypeptide binding motifs.

Once many protein backbones have been generated in high-throughput using graphical processing unit (GPU) or central processing unit (CPU) hardware, the amino acid sequence was designed onto the protein backbones using ProteinMPNN (and/or LigandMPNN) software(s), excluding design of residues involved in chelating the Zn(II) ion and optionally residues involved in binding the N-terminally modified polypeptide. The designed sequence was threaded on the protein backbone, as well as the Zn(II) ion itself superimposed into the Zn(II) ion binding motif in the protein backbone, and optionally the N-terminally modified polypeptide was also superimposed into the designed pocket, using PyRosetta macromolecular design and modeling software. In the embodiment of using RFdiffusion All-Atom software and LigandMPNN software, the N-terminally modified polypeptide was already included in the output PDB file and did not require superimposing into the designed binding pocket. Subsequently, relaxation of the structure in the Rosetta energy function (Alford R F, et al., The Rosetta All-Atom Energy Function for Macromolecular Modeling and Design J Chem Theory Comput. 2017; 13(6): 3031-3048) was performed, which involves iterating between sidechain repacking with fixed backbone coordinates in a Markov Chain Monte Carlo trajectory, and minimization of the system energy by modifying the degrees of freedom including backbone phi and psi dihedral angles, sidechain chi dihedral angles, bond lengths, and geometries between the Zn(II) ion and Zn(II)-chelating residues, and between the binder and the N-terminally modified polypeptide.

At this stage, biochemically plausible de novo designed Zn(II)-binding polypeptides have been developed based on scaffolding of extracted Zn(II)-binding motifs and optionally the extracted N-terminally modified polypeptide binding motifs as described above, but still need to be filtered and ranked on biophysical and deep learning-based metrics to achieve a reasonable number of designs to experimentally validate.

A number of structure prediction softwares, including ESMFold, AlphaFold2, ColabFold, OpenFold, RoseTTAFold All-Atom, or RoseTTAFold2, were implemented to predict the structure of the binding agent from the designed amino acid sequence. The root-mean-squared distances (RMSD) of the backbone atoms (N, Ca, C, and O) between the designed protein model and the predicted structure were calculated, wherein the lower the RMSD between the two structures, the higher is the confidence that the designed protein folds into a correct shape. The utilized structure prediction softwares also report the predicted local distance difference test (pLDDT), which is a per-residue confidence metric that was utilized to filter out designed binders with low predicted per-residue confidence from the structure prediction model(s). The RMSD between the structure prediction model created using ESMFold software and the design model generated using the aforementioned de novo design protocol were calculated, in addition to the average pLDDT across all residues in the binding agent as reported by ESMFold software (Zeming Lin, et al., Evolutionary-scale prediction of atomic level protein structure with a language model. Science 379, 6637 (2023), see Table 17). Additionally, the average pLDDT across all residues in the binding agent as reported by ColabFold software are reported in Table 19. NTM-dipeptide sequence of M64-AA, wherein M64 is the NTM, was used in all metric calculations for Table 17 and Table 18, which show calculated metrics for exemplary de novo generated binding agents comprising amino acid sequences set forth in SEQ ID NO: 83-SEQ ID NO: 99. Additionally, the NTM-dipeptide sequence of M103-AA, wherein M103 is the N-terminal modification (NTM), was used in all metrics calculations for Table 19 and Table 20, which show calculated metrics for exemplary de novo generated binding agents comprising amino acid sequences set forth in SEQ ID NO: 105-SEQ ID NO: 123.

TABLE 17

Computed foldability metrics for de novo designed Zn(II)-binding proteins based on scaffolding extracted Zn(II)-binding motifs.

| SEQ ID NO: | Average pLDDT | RMSD, Backbone Atoms of Structure Prediction Model to Design Model (Å) | Soluble Aggregation Propensity | Percent Loops (%) | Percent β-sheets (%) | Percent α-helices (%) | Total Score Per Residue (kcal/mol) | Buried Hydrophobic Surface Area (Å$^2$) |
|---|---|---|---|---|---|---|---|---|
| 83 | 86.2 | 0.764 | 48.1 | 16.9 | 0.0 | 83.1 | −4.426 | 22056.4 |
| 84 | 85.1 | 0.833 | 37.5 | 19.1 | 0.0 | 80.9 | −4.573 | 16005.4 |
| 85 | 84.8 | 0.885 | 41.7 | 16.2 | 0.0 | 83.8 | −4.570 | 18353.4 |
| 86 | 84.3 | 0.806 | 119.1 | 13.0 | 0.0 | 87.0 | −4.474 | 24337.1 |
| 87 | 85.5 | 0.872 | 41.2 | 17.8 | 0.0 | 82.2 | −4.402 | 13927.8 |
| 88 | 85.6 | 0.819 | 57.5 | 13.4 | 0.0 | 86.6 | −4.517 | 25431.1 |
| 89 | 85.9 | 0.742 | 70.7 | 15.7 | 0.0 | 84.3 | −4.544 | 20698.3 |
| 90 | 86.3 | 0.765 | 82.1 | 20.9 | 22.3 | 56.8 | −4.354 | 27173.1 |
| 91 | 76.9 | 1.246 | 47.2 | 21.5 | 21.9 | 56.7 | −4.567 | 20053.6 |
| 92 | 78.3 | 1.032 | 48.1 | 26.0 | 21.0 | 53.0 | −4.427 | 17361.5 |
| 93 | 74.7 | 1.724 | 76.4 | 23.8 | 21.2 | 55.0 | −3.990 | 29833.5 |
| 94 | 73.9 | 1.527 | 84.7 | 30.1 | 17.8 | 52.1 | −3.951 | 29589.7 |
| 95 | 61.4 | 2.801 | 79.2 | 34.9 | 40.7 | 24.4 | −3.522 | 13077.7 |
| 96 | 68.1 | 2.818 | 71.9 | 25.4 | 22.6 | 52.0 | −3.861 | 20789.3 |
| 97 | 69.4 | 2.712 | 107.5 | 32.1 | 27.2 | 40.6 | −3.878 | 35363.8 |
| 98 | 63.8 | 3.777 | 106.8 | 26.2 | 11.7 | 62.2 | −3.880 | 30860.3 |
| 99 | 62.2 | 3.436 | 77.5 | 25.3 | 29.3 | 45.4 | −3.684 | 18354.5 |

TABLE 18

Computed NTM-dipeptide binding metrics for de novo designed Zn(II)-binding proteins based on scaffolding extracted Zn(II)-binding motifs.

| SEQ ID NO: | ΔΔG (kcal/mol) | NTM- NTAA Internal Energy (kcal/mol) | Shape Complementarity, Binding Agent to NTM-dipeptide | SASA, NTM-NTAA (Å$^2$) | SASA, P2 dimethylamide (Å$^2$) |
|---|---|---|---|---|---|
| 83 | −22.091 | −10.339 | 0.74 | 124.21 | 4.23 |
| 84 | −27.625 | −7.295 | 0.75 | 171.56 | 3.08 |
| 85 | −31.647 | −15.078 | 0.85 | 115.56 | 0.0 |
| 86 | −41.507 | −13.465 | 0.74 | 83.20 | 12.32 |
| 87 | −39.448 | −11.641 | 0.77 | 130.79 | 0.38 |
| 88 | −28.333 | −11.198 | 0.84 | 144.82 | 0.77 |
| 89 | −31.079 | −11.404 | 0.80 | 113.23 | 0.38 |
| 90 | −37.477 | −16.190 | 0.86 | 3.46 | 2.31 |
| 91 | −0.082 | −17.992 | 0.83 | 0.0 | 6.93 |
| 92 | −29.298 | −13.849 | 0.81 | 65.77 | 4.62 |
| 93 | −30.938 | −9.937 | 0.81 | 65.5 | 4.62 |
| 94 | −34.430 | −8.562 | 0.76 | 99.85 | 0.0 |
| 95 | −27.276 | −6.712 | 0.70 | 54.07 | 5.77 |
| 96 | −26.184 | −6.044 | 0.79 | 54.83 | 4.62 |
| 97 | −3.734 | −2.028 | 0.79 | 11.53 | 3.08 |
| 98 | −37.909 | −8.890 | 0.75 | 41.87 | 5.39 |
| 99 | −30.728 | 4.379 | 0.59 | 38.60 | 5.77 |

Additional biophysical metrics were calculated in PyRosetta software to predict the foldability of the de novo designed binding agents as well as the binding propensity of the N-terminally modified dipeptide (NTM-dipeptide) used in the design calculations (see Table 17, Table 18, Table 19 and Table 20). Computational metrics involved in predicting the foldability of the designed polypeptide sequences include: the soluble aggregation propensity of the binding agent, also known as the developability index (Lauer™, et al., Developability index: a rapid in silico tool for the screening of antibody aggregation propensity. J Pharm Sci. 2012; 101(1):102-115), wherein lower soluble aggregation propensity values correlate with lower propensities of the binding agent to aggregate upon expression in *E. coli*; the percent loops, percent β-sheets, and percent α-helices based on the Dictionary of Secondary Structure in Proteins (DSSP) algorithm (Kdbsch W, Sander C. Dictionary of protein secondary structure: pattern recognition of hydrogen-bonded and geometrical features. Biopolymers. 1983; 22(12):2577-2637), which computes the secondary structure of proteins based on atomic coordinates, wherein the lower percentage of loops and higher percentage of P-sheets and α-helices that form well-defined and ordered structures correlates with a higher propensity for a well-folded and ordered binder upon expression; the total energy of the binder-NTM-dipeptide complex normalized by the number of residues in the complex (e.g., total score per residue) as computed by the Rosetta energy function “ref2015”, wherein lower total score per residue values indicate more energetically favorable intramolecular and intermolecular interactions in the complex, which correlates with a higher propensity for the designed complex adopting the desired structure in vitro; and the buried hydrophobic (e.g., nonpolar) surface area (Rocklin G J, et al., Global analysis of protein folding using massively parallel design, synthesis, and testing. Science. 2017; 357(6347):168-175) (computed for Phe, Ala, Met, Ile, Leu, Tyr, Val, and Trp residues) of each binder, wherein the higher the buried hydrophobic surface area in the binder, the higher the propensity for the binder to be well-folded (see Table 16, Table 17, and Table 19). Computationally-derived biophysical metrics involved in predicting the binding propensity of NTM-dipeptide to the designed binder include: difference in the change of Gibbs free energy of the system with the NTM-dipeptide in the bound state to the change in Gibbs free energy of the system with the NTM-dipeptide in the unbound state (e.g., after translating it 250 Å from the binder, including relaxation of the binder and NTM-dipeptide in the bound and unbound states) using the Rosetta energy function “ref2015” (e.g., ΔΔG), wherein the lower the ΔΔG of binding of the NTM-dipeptide, the more favorable intermolecular interactions there are in the binder-NTM-dipeptide complex; the NTM-NTAA internal energy as evaluated by the Rosetta energy function “ref2015”, wherein the lower the NTM-NTAA internal energy, the more favorable intramolecular and intermolecular interactions are present in the NTM-NTAA in the binder-NTM-dipeptide complex; the shape complementarity (Lawrence M C, Colman P M. Shape complementarity at protein/protein interfaces. J Mol Biol. 1993; 234(4):946-950) between the binder and NTM-dipeptide, wherein the higher the shape complementarity value, the better the NTM-dipeptide fits into the designed binding pocket of the binder; the solvent accessible surface area (SASA) (Adolf-Bryfogle J, et al. Growing Glycans in Rosetta: Accurate de novo glycan modeling, density fitting, and rational sequon design. PLoS Comput Biol. 2024 Jun. 24; 20(6): e1011895) of the NTM-NTAA, wherein the lower the SASA of the NTM-NTAA, the more buried the NTM-NTAA is in the binder-NTM-dipeptide complex; and the average SASA of the two carbon atoms of the methyl groups on the dimethylamide moiety that was modeled onto the C-terminus of the NTM-dipeptide (e.g., the second residue of the dipeptide; P2) used in the computational protein design simulations, wherein the higher the average SASA of the P2 dimethylamide moiety, the more solvent-exposed is the P2 dimethylamide moiety indicating that the NTM-dipeptide can enter and exit the designed NTM-NTAA binding pocket in solution (see Table 17, Table 18, Table 19, and Table 20).

Figure 16:
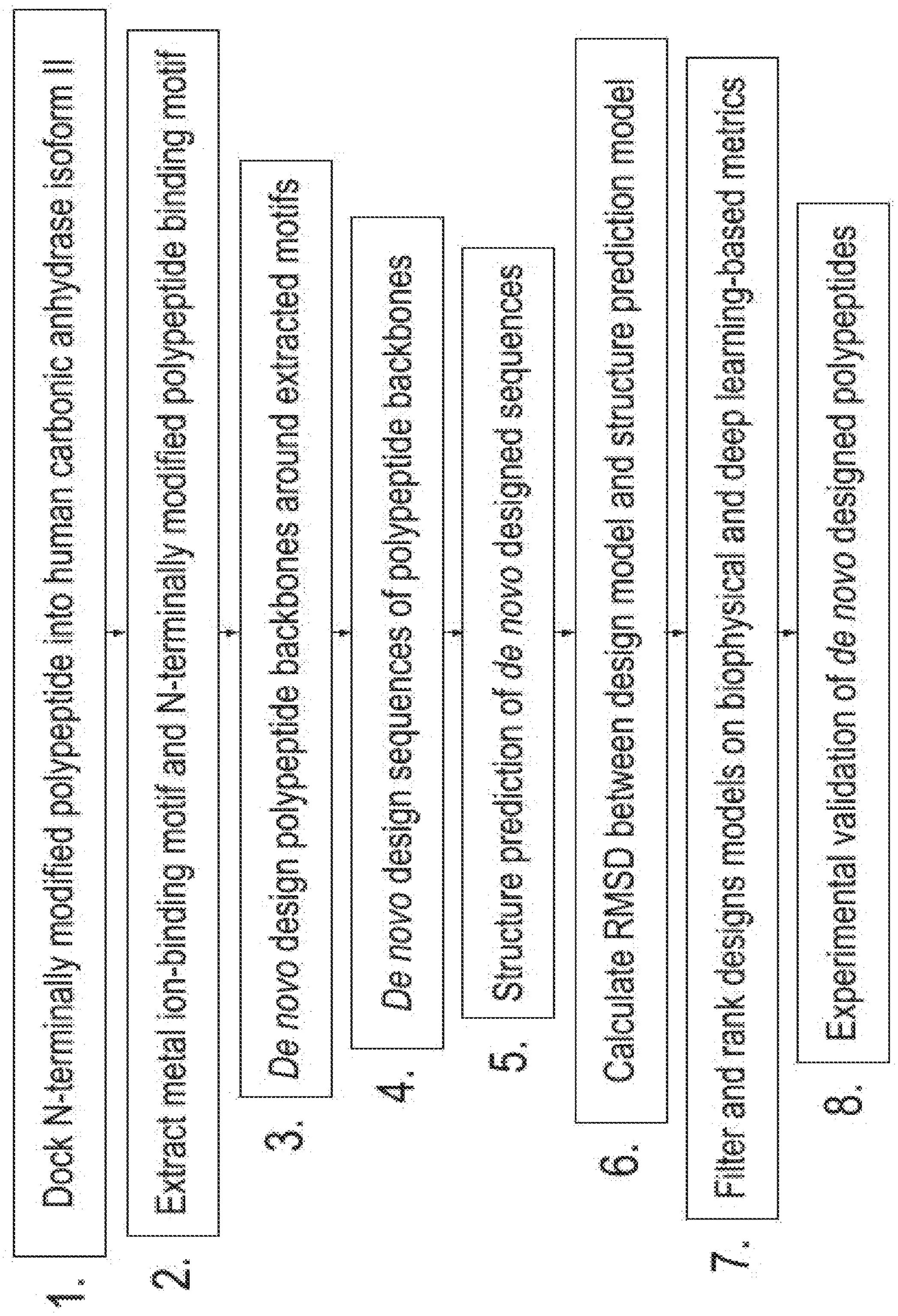
FIG. 16 illustrates exemplary schematic workflow for de novo designing of engineered binders based on metal ion-binding motifs. Example 13 provides further description.

In summary, a number of biophysical metrics were calculated and used for filtering and ranking the binders, in order to select engineered binders that are most likely to be well-expressed and exhibit high affinity toward both the metal ion and the N-terminally modified polypeptide (Table 16, Table 17, Table 18, Table 19, and Table 20). In addition, other known metrics can be calculated for further binder characterization and ranking (see, e.g., Watson, et al., De novo design of protein structure and function with RFdiffusion. Nature. 2023 August; 620(7976):1089-1100; Rocklin G J, et al., Global analysis of protein folding using massively parallel design, synthesis, and testing. Science. 2017; 357(6347):168-175; Dou J, et al., De novo design of a fluorescence-activating P-barrel. Nature. 2018; 561(7724): 485-491; Yeh A H, et al., De novo design of luciferases using deep learning. Nature. 2023; 614(7949):774-780; Motmaen A, et al., Peptide-binding specificity prediction using fine-tuned protein structure prediction networks. Proc Natl Acad Sci USA. 2023, 120(9):e2216697120; Chidyausiku™, et al., De novo design of immunoglobulin-like domains. Nat Commun. 2022; 13(1):5661; Wang J, et al., Scaffolding protein functional sites using deep learning. Science. 2022, 377 (6604):387-394; Wu K, et al., De novo design of modular peptide-binding proteins by superhelical matching. Nature. 2023; 616(7957):581-589). The schematic workflow of the described modeling process is shown in FIG. 16. By the process described in this Example, several binders having affinity toward Zn(II) metal ion and N-terminally modified polypeptides with diverse shapes and sizes were successfully engineered, with representative examples shown herein as comprising amino acid sequences set forth in SEQ ID NO: 83-SEQ ID NO: 99, as well as the sequences set forth in SEQ ID NO: 105-SEQ ID NO: 123.

TABLE 19

Computed foldability metrics for de novo designed Zn(II)-binding proteins based on scaffolding extracted Zn(II)-binding motifs.

| SEQ ID NO: | Average pLDDT | RMSD, Backbone Atoms of Structure Prediction Model to Design Model (Å) | Soluble Aggregation Propensity | Percent Loops (%) | Percent β-sheets (%) | Percent α-helices (%) | Total Score Per Residue (kcal/mol) | Buried Hydrophobic Surface Area (Å$^2$) |
|---|---|---|---|---|---|---|---|---|
| 105 | 66.5 | 6.273 | 98.6 | 38.9 | 19.1 | 42.4 | −0.82 | 18925.9 |
| 106 | 55.8 | 9.424 | 100.7 | 37.3 | 9.1 | 54 | −0.298 | 19677.9 |
| 107 | 73.8 | 3.3 | 81.6 | 37.4 | 30.9 | 32.1 | −1.378 | 19533.7 |
| 108 | 65.9 | 4.236 | 68.3 | 36.3 | 32.4 | 31.7 | −2.418 | 19200.3 |
| 109 | 64 | 8.676 | 76.6 | 39 | 30.5 | 31.1 | −2.104 | 12079.6 |
| 110 | 73.7 | 4.012 | 91.3 | 35 | 16.7 | 48.7 | −3.039 | 21078.1 |
| 111 | 69.6 | 2.886 | 85.3 | 34.6 | 17.5 | 48.3 | −2.478 | 19950.3 |
| 112 | 75.7 | 3.162 | 48.8 | 34 | 14.3 | 52.1 | −1.976 | 17851.4 |
| 113 | 76.1 | 3.786 | 83.6 | 35.7 | 16.7 | 47.9 | −2.179 | 20578 |
| 114 | 76.1 | 5.35 | 63 | 34.3 | 13.6 | 52.5 | −2.593 | 19351.4 |
| 115 | 60.5 | 4.908 | 65.2 | 35.1 | 13.2 | 52.1 | −2.258 | 18434.9 |
| 116 | 70.1 | 3.369 | 63.1 | 34.7 | 13.2 | 52.5 | −2.444 | 18711.8 |
| 117 | 72.9 | 3.835 | 43.3 | 33.6 | 15.5 | 51.3 | −2.563 | 17598.4 |
| 118 | 74.5 | 6.12 | 82.6 | 36.9 | 16 | 47.5 | −2.481 | 19738.3 |
| 119 | 64.8 | 2.77 | 86.8 | 37.6 | 15.2 | 47.5 | −2.364 | 20646.7 |
| 120 | 73 | 3.811 | 97.2 | 36.1 | 16.7 | 47.5 | −1.768 | 21547.7 |
| 121 | 61.3 | 4.601 | 93.6 | 37 | 26 | 37.4 | −1.063 | 18907.9 |
| 122 | 72.2 | 4.577 | 120.8 | 37.4 | 25.6 | 37.4 | −2.279 | 20502 |
| 123 | 64.8 | 11.722 | 113.4 | 37 | 25.6 | 37.8 | −1.817 | 20678.6 |

TABLE 20

Computed NTM-dipeptide binding metrics for de novo designed Zn(II)-binding proteins based on scaffolding extracted Zn(II)-binding motifs. N/D indicates "not determined".

| SEQ ID NO: | Target | ΔΔG (kcal/mol) | NTM-NTAA Internal Energy (kcal/mol) | Shape Complementarity, Binding Agent to NTM-dipeptid | Buried Surface Area of NTM-NTAA (Å$^2$) | SASA, NTM-NTAA (Å$^2$) | SASA, P2 dimethylamide (Å$^2$) |
|---|---|---|---|---|---|---|---|
| 105 | M103-YV | −33.058 | −6.742 | 0.52 | 395.73 | 22.02 | 0.38 |
| 106 | M103-FG | −23.669 | 4.218 | 0.81 | 253.72 | 85 | 4.62 |
| 107 | M103-FG | −29.018 | −10.904 | 0.74 | 257.76 | 66.98 | 4.23 |
| 108 | M103-FG | −23.939 | −3.917 | 0.57 | 255.92 | 57.91 | 5.39 |
| 109 | M103-YV | −31.692 | −7.886 | 0.67 | 271.4 | 59.18 | 6.54 |
| 110 | M103-YV | −34.656 | −8.129 | 0.68 | 299.39 | 52.67 | 6.16 |
| 111 | M103-YV | −30.347 | −4.531 | 0.68 | 257.45 | 73.65 | 6.93 |
| 112 | M103-YV | −26.835 | −4.633 | 0.67 | 298.67 | 55.11 | 5 |
| 113 | M103-YV | −29.041 | −3.576 | N/D | 259.52 | 92.24 | 6.16 |
| 114 | M103-YV | −24.072 | −4.295 | 0.69 | 278.57 | 79.64 | 5 |
| 115 | M103-YV | −27.36 | −4.869 | 0.71 | 255.75 | 81.92 | 6.93 |
| 116 | M103-YV | −30.227 | −6.29 | 0.71 | 279.1 | 86.68 | 3.46 |
| 117 | M103-YV | −30.004 | −5.521 | 0.7 | 292.66 | 61.18 | 5.39 |
| 118 | M103-YV | −30.585 | −5.793 | 0.72 | 268.2 | 75.19 | 4.23 |
| 119 | M103-YV | −30.157 | −6.804 | 0.7 | 284.11 | 62.75 | 8.08 |
| 120 | M103-YV | −31.313 | −6.984 | 0.73 | 290.43 | 54.78 | 7.31 |
| 121 | M103-YV | −40.059 | −11.241 | 0.68 | 414.11 | 14.35 | 0 |
| 122 | M103-YV | −39.56 | −5.758 | N/D | 410.15 | 2.43 | 0 |
| 123 | M103-YV | −44.902 | −11.829 | 0.68 | 416.83 | 10.86 | 0 |

Next, thermodynamic dissociation constant (Kd) values for the engineered and de novo designed Zn(II)-binding proteins were computed. In order to estimate the Kd values for the Zn(II) ion bound in human alpha-carbonic anhydrase II homologs and de novo designed Zn(II)-binding proteins based on scaffolding the Zn(II)-binding motif from native Zn(II)-binding proteins, experimentally determined Kd values for the Zn(II) ion bound in human alpha-carbonic anhydrase isoform II (hCAII) mutants were obtained from Table 7 of the following reference: Krishnamurthy V M, et al., Carbonic anhydrase as a model for biophysical and physical-organic studies of proteins and protein-ligand binding. Chem Rev. 2008; 108(3):946-1051). For example, Kd value for Zn(II) for wild-type hCAII is 0.004 nM. In addition, Kd values for the following hCAII mutants were incorporated: H94A, H94D, H94C, H94E, H96A, H96C, H119C, H119D, T198C, T198D, T198E, T198H, Q92A, Q92L, Q92N, Q92E, E117A, E117Q, Q92A/E117A, T198 Å. Computational models of the 3-dimensional Cartesian coordinates of the single and double mutants of hCAII with the Zn(II) ion bound were generated by first predicting the structure of the wild-type hCAII using ESMFold (Zeming Lin, et al., Evolutionary-scale prediction of atomic level protein structure with a language model. Science 379, 6637

Figure 17:
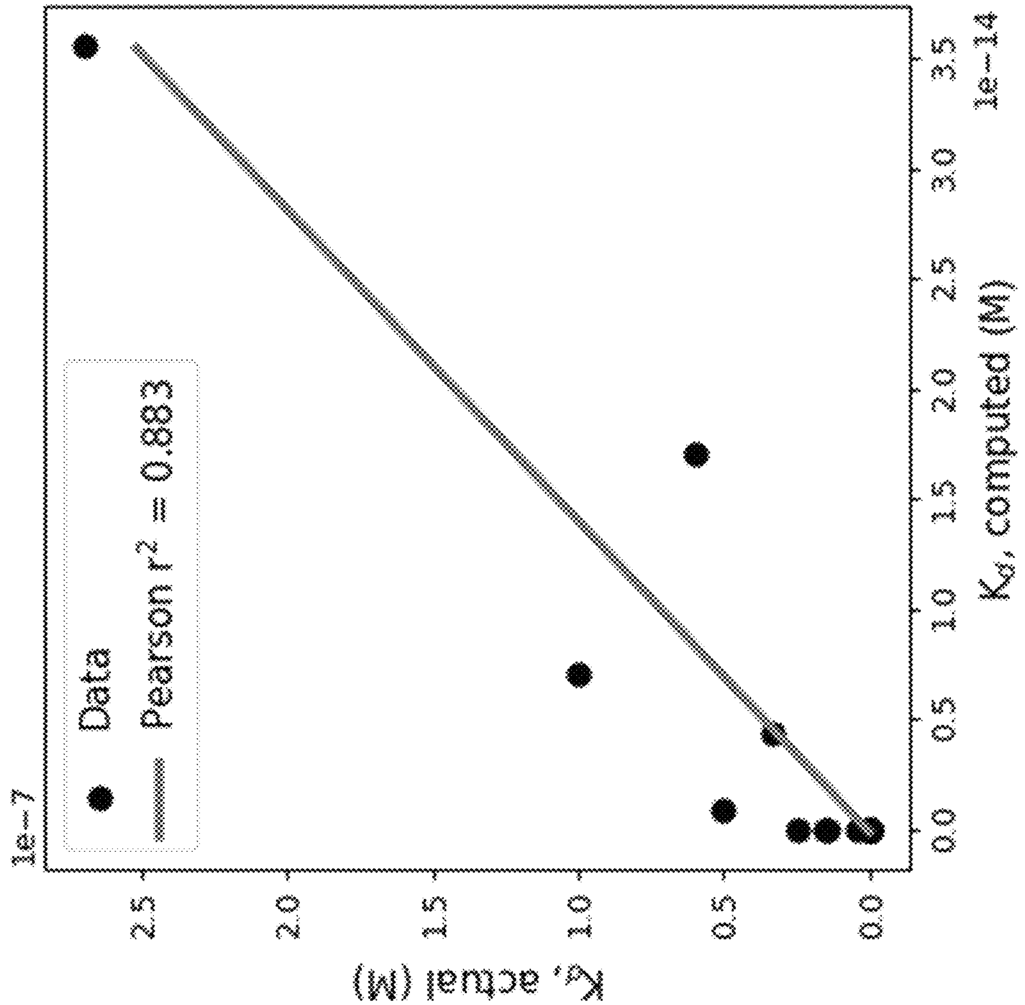
FIG. 17. Exemplary correlation between in silico (computed) and in vitro (actual) thermodynamic dissociation constant ($K_d$) values of the Zn(II) ion bound in human alpha-carbonic anhydrase isoform II variants (black circles). The computed and actual $K_d$ values were fit to a linear model using non-linear least squares regression (grey line), and the squared Pearson correlation coefficient ($r^2$) of the fit to the actual $K_d$ values is shown.

(2023)), and explicitly setting the 3-dimensional Cartesian coordinates of the three Zn(II)-chelating histidine residues resolved from the X-ray diffraction crystal structure of hCAII from RCSB PDB accession number 4YYT, after superimposing the structure prediction model onto the crystal coordinates of RCSB PDB accession number 4YYT using the heavy atom (e.g., non-hydrogen atoms) coordinates of the three Zn(II)-chelating histidine residues between the two models. The 3-dimensional Cartesian coordinates of the Zn(II) ion from the crystal structure were used to concatenate the Zn(II) ion into the structure prediction model, followed by constrained Cartesian minimization in the Rosetta energy function (Alford R F, et al., The Rosetta All-Atom Energy Function for Macromolecular Modeling and Design, J Chem Theory Comput. 2017; 13(6):3031-3048) of the backbone and sidechain atoms of all residues in the system after placing coordinate constraints onto the Zn(II) ion and the three Zn(II)-chelating histidine residues, which resulted in the computational model of wild-type hCAII bound to the Zn(II) ion. Using this model of wild-type hCAII bound to the Zn(II) ion, the remaining hCAII single and double mutants described above were generated one at a time in PyRosetta macromolecular modeling and design software by repacking the mutated residue(s) to generate the mutations, followed by constrained Cartesian minimization of backbone atoms in the system with minimization of the sidechain(s) of the mutated residue(s) with coordinate constraints enabled on the Zn(II) ion to preserved the crystal structure coordinates of the Zn(II) ion. For the wild-type hCAII and hCAII variants, the ΔΔG of binding of the Zn(II) ion was evaluated in PyRosetta software using the Ddg filter, in which the difference between the change in Gibbs free energy of the system in the Zn(II)-bound state and the change in Gibbs free energy of the system after the Zn(II) ion had been translated by 250 Å away from the Zn(II)-binding site was evaluated without repacking of sidechains (e.g., ΔΔG). For the wild-type hCAII and hCAII variants, the computed ΔΔG values were used to compute the $K_d$ values using the formula K_d (computed)=e^(ΔΔG/(R·T)), wherein R=1.987203611·10^(−3) kcal/(mol·K) and T=295.15 K was used for modeling purposes, resulting in the computed $K_d$ values presented in FIG. 17 as plotted against the actual $K_d$ values presented below. In order to calibrate the computed $K_d$ values to the actual $K_d$ values, the computed and actual $K_d$ values were fit to a linear equation, K_d (actual)=m·K_d (computed)+b, where b=0.0 M, using non-linear least squares regression, resulting in a slope of m=7.083·10^6 and a squared Pearson correlation coefficient r^2 =0.883 of the linear fit to the actual $K_d$ data. The computational protocol of evaluating ΔΔG values followed by $K_d$ calculation and extrapolation of the computed $K_d$ values to actual $K_d$ values using the linear fit was repeated for the hCAII homologs presented in Table 21 (left columns) and the de novo designed Zn(II)-binding proteins based on scaffolding the Zn(II)-binding motifs as described above and presented in Table 21 (right columns), wherein estimated Kd values for the Zn(II) ion below the minimum Kd value in the training data (data of hCAII wild-type mutants adopted from Krishnamurthy V M, et al., 2008 as described above) are demarked as <0.0002 nM, as values below this threshold Kd value may be inaccurate as they were not represented in the training data. By these methodologies, the thermodynamic dissociation constants of the Zn(II) ion in hCAII homologs and de novo designed Zn(II)-binding proteins were estimated (Table 21).

TABLE 21

Estimations of thermodynamic dissociation constant (Ka) values for the Zn(II) ion bound in human alpha-carbonic anhydrase isoform II homologs and in de novo designed Zn(II)-binding proteins based on scaffolding extracted Zn(II)-binding motifs (e.g., binders).

| SEQ ID NO: | Estimated $K_d$ for Zn(II) (nM) |
|---|---|
| 68 | <0.0002 |
| 69 | 0.0004 |
| 70 | <0.0002 |
| 71 | 0.0004 |
| 72 | <0.0002 |
| 73 | 0.0006 |
| 74 | 0.0055 |
| 83 | 0.0032 |
| 84 | 0.0093 |
| 85 | 0.0581 |
| 86 | 0.0521 |
| 87 | 0.0027 |
| 88 | 0.0032 |
| 89 | 0.0472 |
| 90 | <0.0002 |
| 91 | <0.0002 |
| 92 | <0.0002 |
| 93 | <0.0002 |
| 94 | <0.0002 |
| 95 | 71.3788 |
| 96 | 25.5079 |
| 97 | 91.2243 |
| 98 | 4.8675 |
| 99 | 51.0271 |

Figure 18:
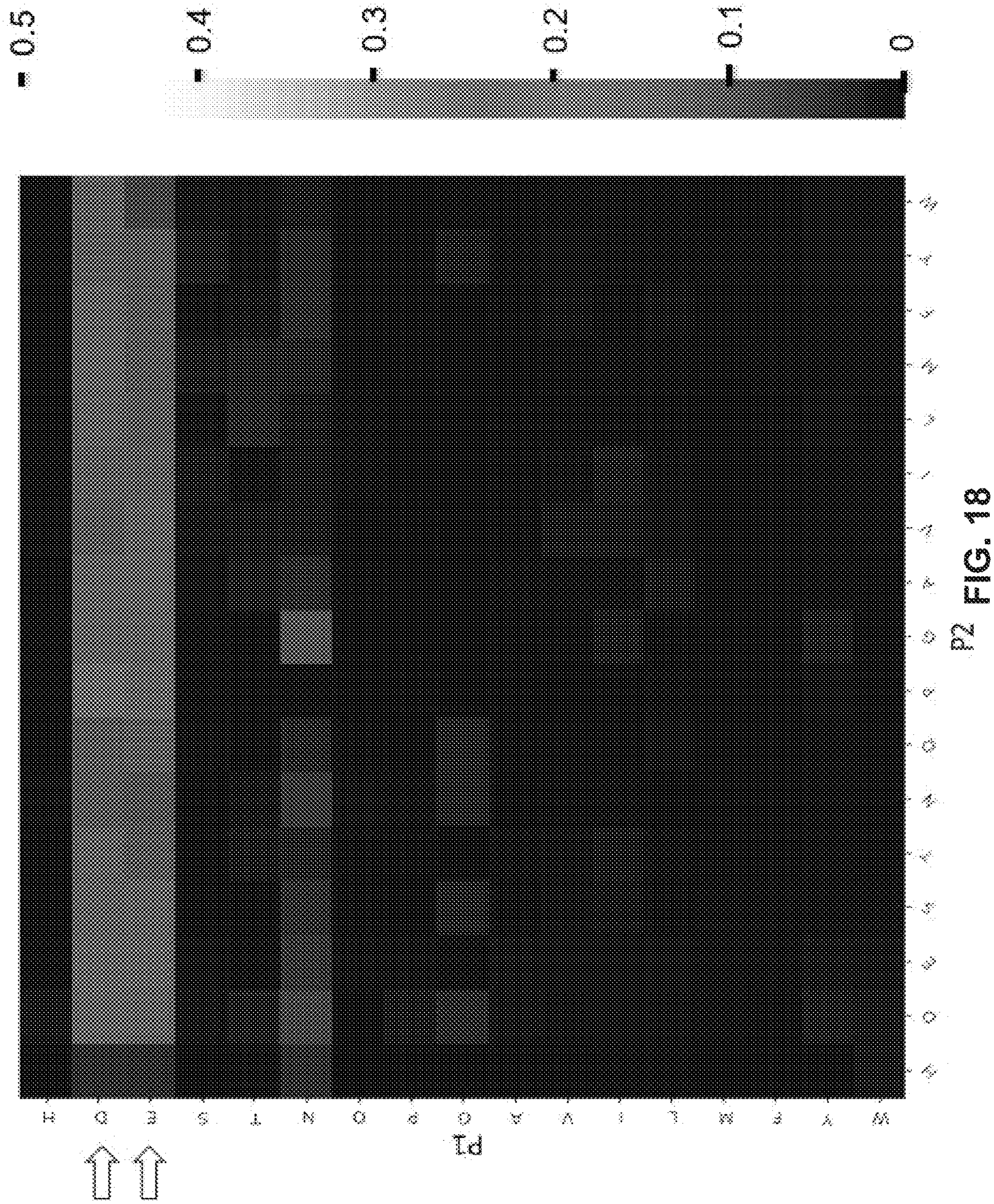
FIG. 18 illustrates exemplary heatmap data showing encoding efficiency (calculated as fraction of recording tags encoded) for the engineered M103-E/D binder (SEQ ID NO: 125) in the multiplex encoding assay on immobilized set of 289 peptides (17×17 combination of different P1 and P2 residues). Arrows on the left show primary binder's specificity. The more intense white color of a cell representing a particular P1-P2 combination indicates higher encoding efficiency.
Figure 19:
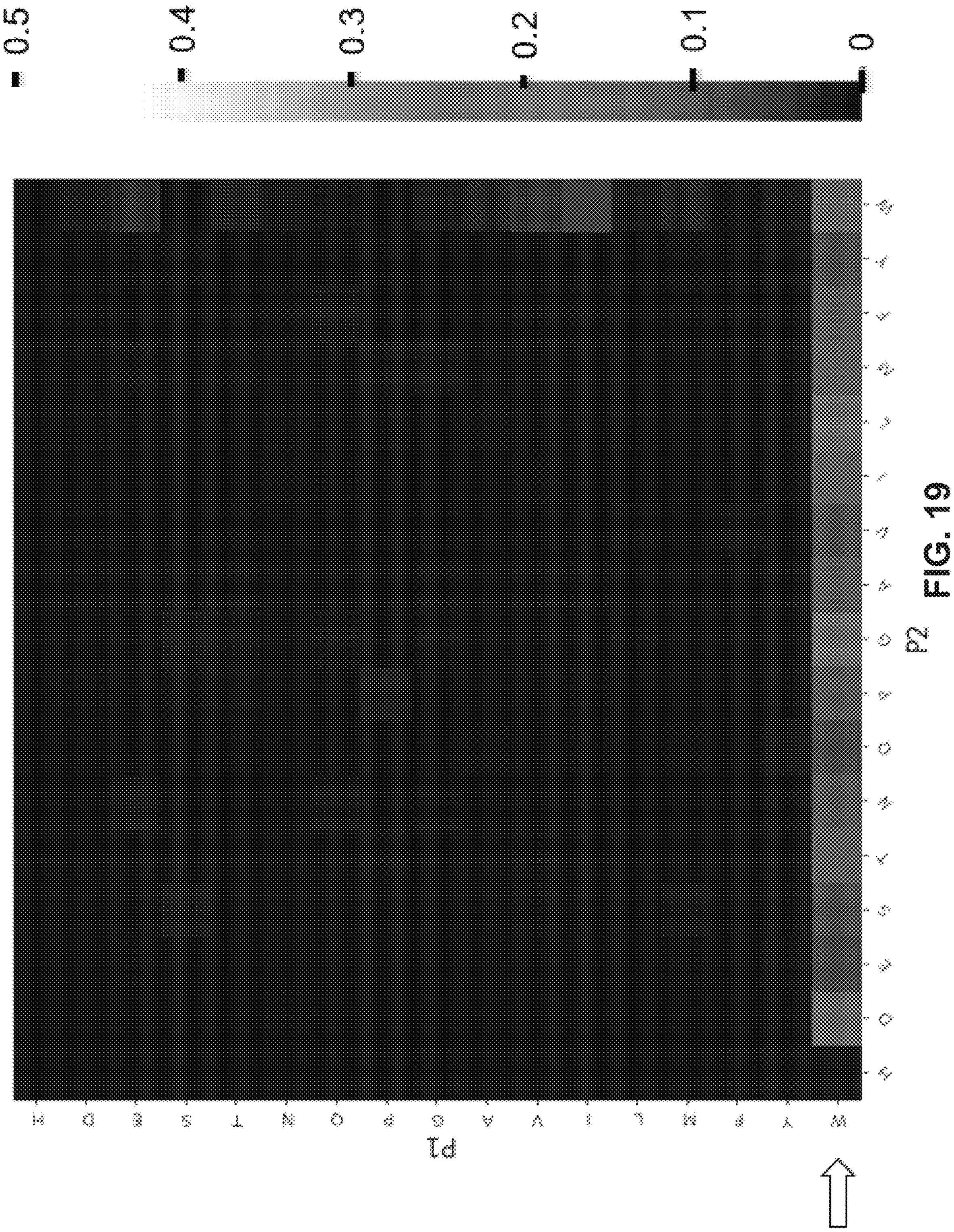
FIG. 19 illustrates exemplary heatmap data showing encoding efficiency (calculated as fraction of recording tags encoded) for the engineered M103-W binder (SEQ ID NO: 126) in the multiplex encoding assay on immobilized set of 289 peptides (17×17 combination of different P1 and P2 residues). Arrow on the left shows primary binder's specificity. The more intense white color of a cell representing a particular P1-P2 combination indicates higher encoding efficiency.
Figure 20:
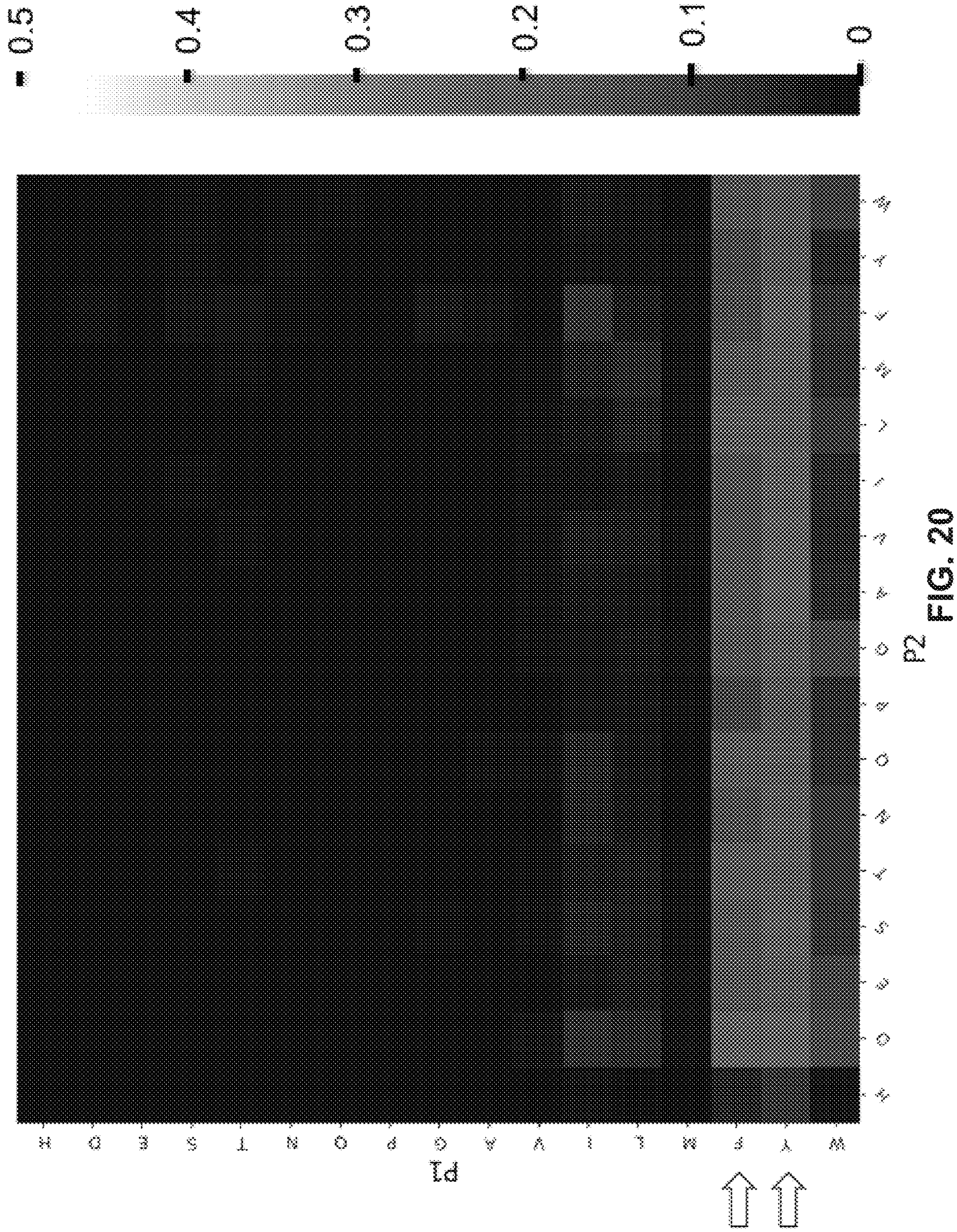
FIG. 20 illustrates exemplary heatmap data showing encoding efficiency (calculated as fraction of recording tags encoded) for the engineered M103-Y/F binder (SEQ ID NO: 127) in the multiplex encoding assay on immobilized set of 289 peptides (17×17 combination of different P1 and P2 residues). Arrows on the left show primary binder's specificity. The more intense white color of a cell representing a particular P1-P2 combination indicates higher encoding efficiency.

Example 14. LigandMPNN-Redesign of S222 Binders for Sequence Diversity and Thermostability In this Example, binding agents based on carbonic anhydrase scaffolds were redesigned using the LigandMPNN software to generate binding agents that have only 30-40% sequence identity to the parent binders. The sequences of three different parent binding agents with known M103-P1-P2 binding affinities were changed to achieve higher thermostability and sequence diversity than 14 carbonic anhydrase homologs. The following binding agents were used, each based on the hCAII scaffold: S222_1333 which binds the M103-EA peptide (SEQ ID NO: 125), S222_1519 which binds the M103-WA peptide (SEQ ID NO: 126), and S222_1581 which binds the M103-YA peptide (SEQ ID NO: 127). Installation of the M103 modification was described above. Exemplary heatmap data for the corresponding binders are shown on FIG. 18-FIG. 20, indicating the specificity of the binders towards particular M103-modified P1P2 peptides. The heatmaps on FIG. 18-FIG. 20 were generated as described in Example 8, showing results of multiple parallel encoding reactions for the binders having sequences as set forth in SEQ ID NO: 125-127, respectively.

Starting from a co-crystal structure of a human carbonic anhydrase isoform II (hCAII) variant bound to a Zn(II) ion and M103-YV peptide (generated in-house; data not shown), structural models of each of the three binding agents were generated using PyRosetta macromolecular modeling software (Chaudhury S, Lyskov S, Gray J J. PyRosetta: a script-based interface for implementing molecular modeling algorithms using Rosetta. Bioinformatics. 2010 Mar. 1; 26(5):689-91; Le K H, et al., PyRosetta Jupyter Notebooks Teach Biomolecular Structure Prediction and Design. Biophysicist (Rockv). 2021 April; 2(1):108-122) to model the lowest energy bound state of the binding agent with a Zn(II) ion and its M103-P1-P2 target. Subsequently, the message passing neural network LigandMPNN (Dauparas, J., et al., Atomic context-conditioned protein sequence design using LigandMPNN, (2023), Biorxiv, 2023-12; Dauparas, et al., (2022). Robust deep learning-based protein sequence design using ProteinMPNN. Science, 378(6615), 49-56) was used to generate novel sequence variants of each of the three binding agents bound to their respective targets. The structurally modeled Zn(II) ion and M103-dipeptide (with a dimethylamide C-terminus) were used as ligands for LigandMPNN. The following residues surrounding the target binding site were prevented from redesign during sequence design with LigandMPNN: for SEQ ID NO: 125, residues 62, 67, 91, 92, 94, 96, 106, 119, 121, 130, 134, 140, 197, 198, and 199 remained fixed; for SEQ ID NO: 126, residues 62, 67, 91, 92, 94, 96, 106, 119, 121, 130, 134, 140, 142, 197, 198, and 199 remained fixed; and for SEQ ID NO: 127, residues 65, 67, 91, 92, 94, 96, 106, 119, 121, 130, 134, 140, 142, 197, 198, and 199 remained fixed. For each of the parent binding agent models bound to a Zn(II) ion and their respective target, inferences on four different LigandMPNN pretrained models were run (e.g., LigandMPNN software is released with several different pretrained model weights, in which the weights are trained by modifying the training dataset by adding 0.05, 0.10, 0.20, or 0.30 Å standard deviation Gaussian noise to the protein and context atoms prior to training), and each of those models were run at five different temperatures (0.1, 0.2, 0.3, 0.4, and 0.5; wherein higher temperatures result in sampling higher sequence diversities), and each of those temperatures were run with a batch size of 16 and for each of those batch sizes the number of batches was set to 16, totaling 5, 120 sequences generated per parent binding agent.

Figure 21A:
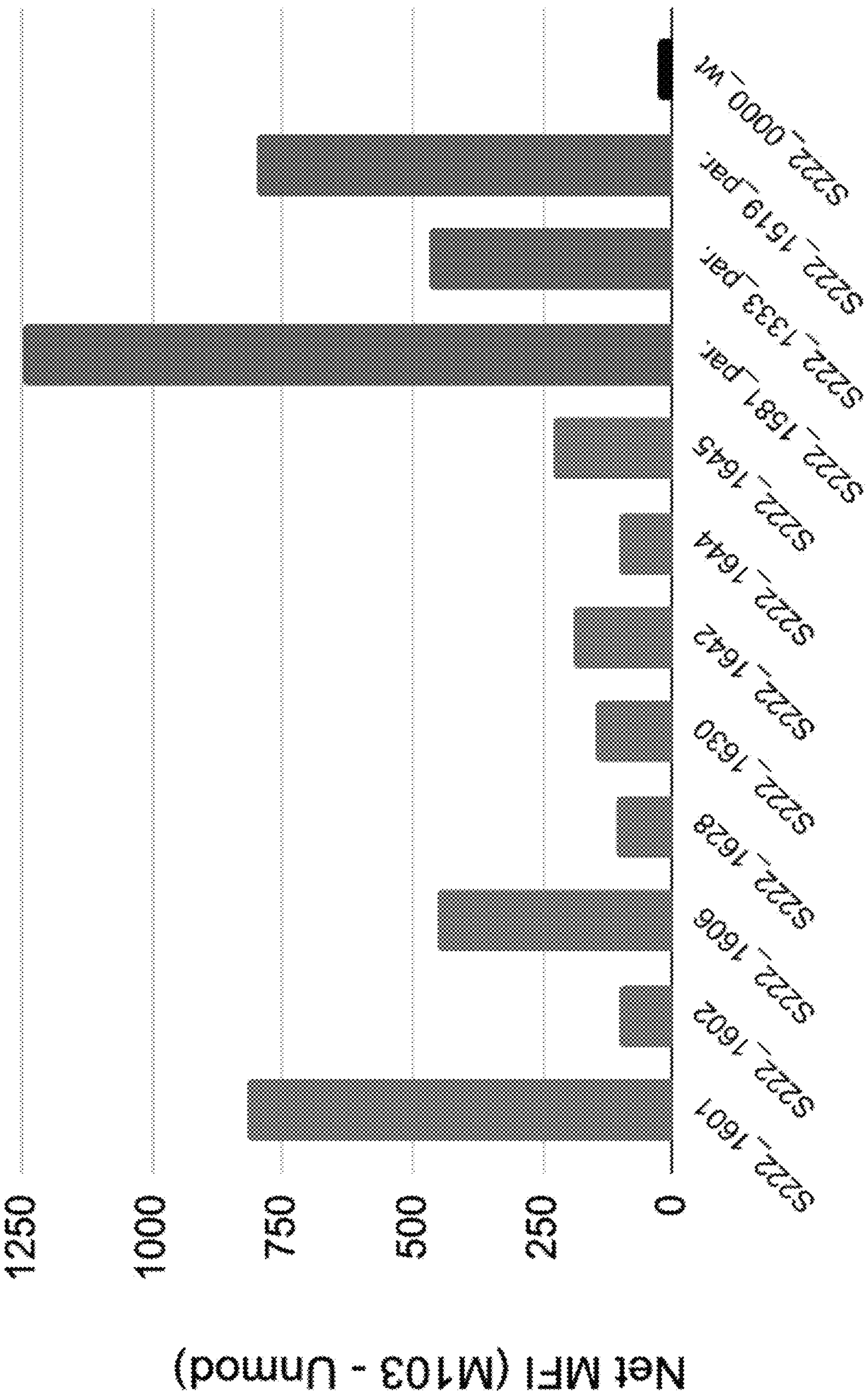
FIG. 21A-B.
Figure 21B:
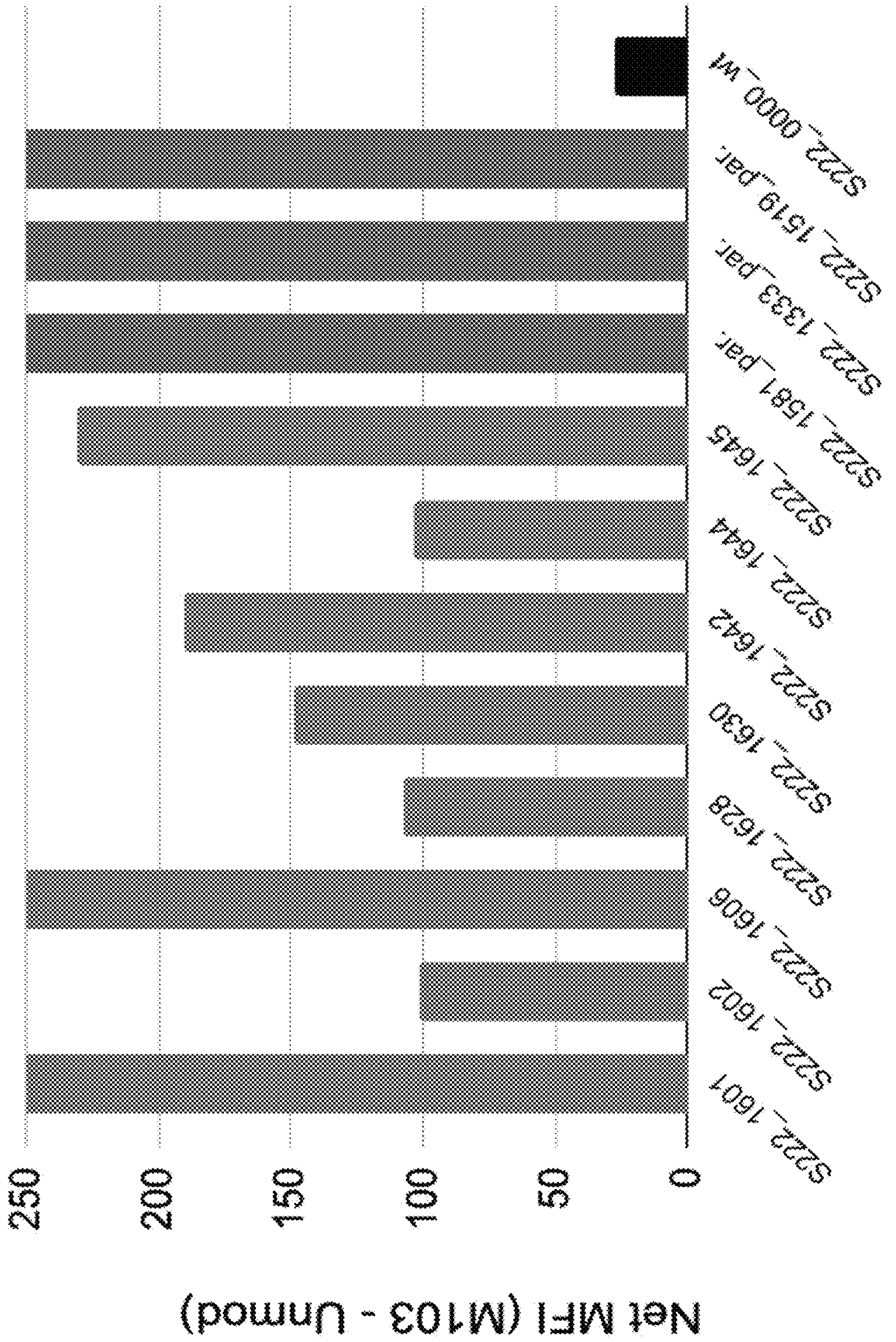

Each of the 5, 120 sequences generated per parent binding agent bound to a Zn(II) ion and their respective target was aligned to the amino acid sequences of 14 different carbonic anhydrase homologs using a global pairwise sequence alignment algorithm, where identical characters are given 1 point, 0 points are given/deducted for each non-identical character, 1 point is deducted when opening a gap, and 0.1 points are deducted when extending a gap. The 14 different carbonic anhydrase homologs that were aligned are provided in SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 68, SEQ ID NO: 69, SEQ ID NO: 70, SEQ ID NO: 71, SEQ ID NO: 72, SEQ ID NO: 73, and SEQ ID NO: 74. For each global pairwise sequence alignment, the percent sequence identity of the designed binding agent amino acid sequence to the carbonic anhydrase homolog amino acid sequence was calculated as the number positions with matched identities over the total number of positions in the longer of the two aligned sequences. For each designed binding agent amino acid sequence, the average percent identity to the 14 carbonic anhydrase homologs was calculated using the aforementioned calculated percent sequence identities. For each parent binding agent bound to a Zn(II) ion and their respective target, the 5, 120 designed amino acid sequences generated were sorted by average percent identity to the 14 carbonic anhydrase homologs in ascending order, and top generated unique sequences with the lowest average percent sequence identity to the 14 carbonic anhydrase homologs were selected (Table 24) for structure prediction (see Table 23), macromolecular modeling (see Table 22), and experimental confirmation of the binding (see FIG. 21A-21B) to the modified NTAA residue.

For the unique sequences selected with the lowest average percent sequence identity to the 14 carbonic anhydrase homologs per parent binding agent, the three-dimensional structure that the binding agent will adopt upon folding was predicted using ColabFold (Mirdita M, et al., ColabFold: making protein folding accessible to all. Nat Methods. 2022 June; 19(6):679-682; Jumper J, et al., Highly accurate protein structure prediction with AlphaFold. Nature. 2021 August; 596(7873):583-589) using three recycles per sequence, five AlphaFold2 models per sequence, and a recycle early stop tolerance set to 0. For each designed binding agent sequence, the predicted local difference distance test (pLDDT) was averaged over all residues in each AlphaFold2 model, and the average pLDDT per AlphaFold2 model was averaged over all five AlphaFold2 models, yielding a ColabFold Average pLDDT (5 models) score (Table 23). Similarly, for each designed binding agent sequence, the predicted aligned error (PAE) was averaged over all residue pairs in each AlphaFold2 model, and the average PAE per AlphaFold2 model was averaged over all five AlphaFold2 models, yielding a ColabFold Average PAE (5 models) score (Table 23). It is known that the ColabFold Average pLDDT (5 models) score is a measure of average local confidence scaled from 0 to 100 where scores closer to 100 indicate higher confidence in the three-dimensional structure prediction models and generally more accurate structural predictions. It is also known that the ColabFold Average PAE (5 models) score is a measure of how much average error AlphaFold2 places on the relative orientations between all pairs of residues within the predicted structures, where scores closer to 0 indicate lower error in the orientations of residues in the structure prediction models and generally more accurate structural predictions. The ColabFold Average pLDDT (5 models) scores and ColabFold Average PAE (5 models) scores for the novel binding agent sequences suggest that AlphaFold2 predicts the three-dimensional structures of their sequences with high accuracy (Table 23).

For each of the novel binding agent sequences, the C-alpha atoms of the AlphaFold2 model with the highest pLDDT were superimposed onto the C-alpha atoms of the initial macromolecular structural model of the parent binding agent bound to a Zn(II) ion and its M103-P1-P2 target that was previously generated using PyRosetta macromolecular modeling software, the three-dimensional Cartesian coordinates of the Zn(II) ion and the bound M103-P1-P2 target were transferred onto the AlphaFold2 model, and a macromolecular structural model of the novel binding agent in complex with the Zn(II) ion and M103-P1-P2 target was generated using PyRosetta software with the FastRelax protocol (Maguire J B, et al., Perturbing the energy landscape for improved packing during computational protein design. Proteins. 2021 April; 89(4):436-449). Subsequently, the macromolecular model of the complex structure was scored in PyRosetta with biophysical metrics that report on expression, folding, and target binding propensities (Table 22). For comparison, the initial macromolecular structural model of the parent binding agent bound to a Zn(II) ion and its M103-PT-P2 target was scored in PyRosetta similarly.

The following relationships were taken into consideration during modeling and analysis: the higher the buried hydrophobic surface area of the binding agent, the higher the thermostability of the binding agent upon folding in aqueous environments; the higher the shape complementarity between the binding agent and its target, the higher the binding affinity (e.g., the lower the thermodynamic dissociation constant) of the binding agent for its target; the higher the contact molecular surface area between the binding agent and its target, the higher the binding affinity (e.g., the lower the thermodynamic dissociation constant) of the binding agent for its target; the lower the net charge of the binding agent, the higher the probability that the binding agent expresses soluble in *E. coli* due to the decreasing aggregation propensity with negatively charged nucleic acid molecules; the lower the soluble aggregation propensity of the binding agent, the higher the probability that the binding agent expresses soluble in *E. coli* without aggregation; the lower the number of buried unsatisfied hydrogen bonds within 5.5 Å of the surface of the binding agent as calculated in the macromolecular model of the binding agent, the higher the probability of the binding agent sequence folding into the modeled structure upon expression in *E. coli*; the lower the number of very buried unsatisfied hydrogen bonds below 5.5 Å of the surface of the binding agent as calculated in the macromolecular model of the binding agent, the higher the probability of the binding agent sequence folding into the modeled structure upon expression in *E. coli*; the in the complex and the higher the probability the binding agent is to exhibit binding specificity toward that P1 identity over different P identities; the higher the solvent accessible surface area of the P2 residue in the complex, the lower the degree of burial of the P2 residue in the complex and the higher the probability the binding agent is to exhibit binding promiscuity toward different P2 identities. The calculated biophysical metrics for the designed binding agents were similar in magnitude to the calculated biophysical metrics for their respective parent binding agents (see Table 22) that have experimentally characterized binding activity, and therefore, the computationally derived biophysical metrics suggest that the designed binding agents warrant experimental binding measurements, further described below.

TABLE 22

Calculated biophysical metrics of parent binding agents (SEQ ID NO: 125-127) and designed binding agents from macromolecular modeling that report on expression, folding, and target binding propensities.

| SEQ ID NO: | Target | Buried Hydrophobic Surface Area of Binding Agent (Å$^2$) | Shape Complementarity, Target and Binding Agent | Contact Molecular Surface Area, Target and Binding Agent (Å$^2$) | Net Charge of Binding Agent | Soluble Aggregation Propensity of Binding Agent | Number of Surface Unsatisfied Hydrogen Bonds | Number of Buried Unsatisfied Hydrogen Bonds | Cavity Volume (Å$^3$) | ΔΔG of Target Binding (kcal/mol) | ΔG of Binding Agent (kcal/mol) | P1 Solvent Accessible Surface Area (Å$^2$) | P2 Solvent Accessible Surface Area (Å$^2$) |
|---|---|---|---|---|---|---|---|---|---|---|---|---|---|
| 125 | M103-EA | 17855.041 | 0.648 | 197.511 | 0 | 77.586 | 19 | 5 | 147.755 | −23.799 | −836.892 | 36.182 | 113.042 |
| 126 | M103-WA | 18078.967 | 0.741 | 196.821 | −2 | 78.759 | 15 | 6 | 115.007 | −32.52 | −950.871 | 110.502 | 116.193 |
| 127 | M103-YA | 17334.311 | 0.799 | 229.378 | −1 | 71.972 | 17 | 4 | 86.859 | −37.501 | −938.188 | 57.216 | 116.653 |
| 128 | M103-YA | 17837.469 | 0.759 | 239.06 | −10 | 75.909 | 11 | 14 | 218.114 | −42.942 | −959.013 | 36.32 | 111.206 |
| 129 | M103-YA | 17820.529 | 0.768 | 226.977 | −8 | 96.304 | 16 | 10 | 133.505 | −40.259 | −951.108 | 53.137 | 108.259 |
| 130 | M103-YA | 18987.123 | 0.754 | 221.49 | −10 | 81.595 | 10 | 13 | 138.796 | −38.664 | −979.076 | 49.622 | 114.334 |
| 131 | M103-EA | 19154.254 | 0.673 | 192.026 | −4 | 94.57 | 22 | 9 | 188.093 | −27.128 | −1001.682 | 52.995 | 111.28 |
| 132 | M103-EA | 19477.172 | 0.568 | 168.535 | −3 | 84.898 | 22 | 11 | 226.132 | −24.334 | −979.847 | 52.893 | 123.832 |
| 133 | M103-WA | 19206.479 | 0.741 | 203.04 | −8 | 101.199 | 17 | 10 | 69.065 | −36.313 | −990.594 | 95.905 | 108.793 |
| 134 | M103-WA | 18403.41 | 0.766 | 204.471 | −14 | 78.966 | 12 | 10 | 182.916 | −36.036 | −965.504 | 104.587 | 130.799 |
| 135 | M103-WA | 18666.48 | 0.699 | 194.053 | −8 | 93.319 | 19 | 6 | 189.099 | −32.687 | −950.163 | 93.167 | 118.04 |

lower the cavity volume (e.g., total intra-protein voids) of the binding agent as calculated in the macromolecular model of the binding agent, the higher the probability of the binding agent sequence folding into the modeled structure upon expression in *E. coli*; the lower the difference in the change of Gibbs free energy of the binding agent in complex with its target and the change of Gibbs free energy of the binding agent and target separated after translating the target 250 Å from the binding agent without relaxation of the binding agent and target in the bound and unbound states (e.g., the ΔΔG of target binding), the higher the binding affinity (e.g., the lower the thermodynamic dissociation constant) of the binding agent for its target; the lower the change in Gibbs free energy of the binding agent (e.g. the ΔG of the binding agent), the higher the thermostability of the binding agent upon folding in aqueous environments; the lower the solvent accessible surface area of the P1 residue in the complex, the higher the degree of burial of the P residue

TABLE 23

The average predicted local difference distance test (pLDDT) and average predicted aligned error (PAE) for the designed binding agents from ColabFold, indicating the three-dimensional structure predictions are on average high confidence across residues and on average low error in relative residue orientation.

| SEQ ID NO: | ColabFold Average pLDDT (5 models) | ColabFold Average PAE (5 models) |
|---|---|---|
| 128 | 92.808 | 4.018 |
| 129 | 93.939 | 3.572 |
| 130 | 91.095 | 4.021 |
| 131 | 90.689 | 4.639 |
| 132 | 93.445 | 3.714 |
| 133 | 92.776 | 4.01 |
| 134 | 93.076 | 4.032 |
| 135 | 93.104 | 3.849 |

TABLE 24

Global pairwise sequence alignments between each of the designed binding agents and each of the 14 carbonic anhydrase homologs were performed, and the percent sequence identity of each designed binding agent amino acid sequence to each carbonic anhydrase homolog amino acid sequence is reported here. Additionally, for each designed binding agent the average percent sequence identity to the 14 carbonic anhydrase homologs is reported.

| SEQ ID NO: | Average Percent Identity to Carbonic Anhydrase Homologs | Percent Identity to SEQ ID NO: 7 | Percent Identity to SEQ ID NO: 8 | Percent Identity to SEQ ID NO: 9 | Percent Identity to SEQ ID NO: 10 | Percent Identity to SEQ ID NO: 11 | Percent Identity to SEQ ID NO: 12 | Percent Identity to SEQ ID NO: 13 |
|---|---|---|---|---|---|---|---|---|
| 128 | 37.531 | 44.231 | 36.122 | 37.405 | 29.818 | 37.262 | 34.201 | 38.783 |
| 129 | 38.328 | 45 | 36.398 | 37.308 | 29.304 | 39.544 | 32.463 | 41.509 |
| 130 | 38.91 | 47.126 | 36.122 | 36.538 | 27.437 | 40.076 | 34.328 | 39.695 |
| 131 | 39.926 | 45.769 | 38.168 | 39.773 | 26.838 | 40.84 | 33.704 | 42.146 |
| 132 | 40.078 | 46.923 | 40.076 | 39.313 | 29.304 | 41.132 | 35.531 | 42.205 |
| 133 | 39.103 | 45.769 | 41.065 | 38.577 | 27.574 | 36.641 | 34.328 | 39.773 |
| 134 | 39.325 | 48.462 | 39.847 | 42.529 | 28.47 | 38.55 | 33.088 | 39.313 |
| 135 | 39.326 | 46.923 | 39.163 | 35.385 | 31.273 | 39.163 | 32.09 | 40.684 |

| SEQ ID NO: | Percent Identity to SEQ ID NO: 68 | Percent Identity to SEQ ID NO: 69 | Percent Identity to SEQ ID NO: 70 | Percent Identity to SEQ ID NO: 71 | Percent Identity to SEQ ID NO: 72 | Percent Identity to SEQ ID NO: 73 | Percent Identity to SEQ ID NO: 74 |
|---|---|---|---|---|---|---|---|
| 128 | 39.231 | 36.466 | 39.847 | 38.403 | 36.641 | 39.615 | 37.405 |
| 129 | 41.923 | 34.601 | 40.996 | 37.931 | 38.462 | 42.692 | 38.462 |
| 130 | 42.308 | 38.29 | 42.205 | 40.84 | 37.023 | 42.366 | 40.385 |
| 131 | 44.615 | 37.5 | 41.573 | 41.887 | 41.923 | 43.462 | 40.769 |
| 132 | 42.692 | 37.828 | 41.573 | 40.909 | 41.985 | 41.923 | 39.695 |
| 133 | 40.996 | 34.717 | 41.603 | 41.985 | 40.385 | 41.923 | 42.105 |
| 134 | 43.846 | 36.981 | 40.076 | 38.314 | 36.154 | 44.231 | 40.684 |
| 135 | 42.692 | 37.218 | 40.996 | 41.288 | 42.146 | 43.077 | 38.462 |

Eight designed binding agents (SEQ ID NO: 128-135) with the calculated characteristics disclosed in Tables 22-23 and each having sequence that has only ~35-40% sequence identity to parent proteins (SEQ ID NO: 125-127) and carbonic anhydrase homologs from different organisms were expressed in *E. coli* (alongside their parent binding agents) essentially as disclosed in Example 6. Each protein was purified by immobilized metal affinity chromatography (IMAC) using Ni-NTA beads.

Each purified protein was prepared in a buffered solution (50 mM MOPS, 33 mM $Na_2SO_4$, 0.1% BSA, 0.02% Tween-20, 0.05% sodium azide—pH 7.4) to a final concentration of 500 nM. Separately, 16 populations of pre-dyed avidin beads were coated with biotinylated peptides bearing the following M103-P1 residues, where P1 denotes H, E, D, N, S, T, G, A, C(Cm) (Cm=carboxymethyl group), M, I, L, V, F, Y or W, and where x denotes a mixture of A, D, E, F, G, H, I, L, M, N, P, Q, R, S, T, V, W, and Y, alongside an additional 17th bead population lacking M103 ("G-peptide loaded") on either PEG9 or $(G3S)_4$ flexible linkers for bead attachment (Table 25). The linkers were chosen to address peptide stability issues, and the nature of the linker does not affect the binding (data not shown).

TABLE 25

Model peptides used for the binding experiment.

| Target | Linker for attachment to beads | Peptide |
|---|---|---|
| M103-HX | $PEG_9$ | M103-HXG[$PEG_9$]K(Biotin)-$NH_2$ |
| M103-EX | $PEG_9$ | M103-EXG[$PEG_9$]K(Biotin)-$NH_2$ |
| M103-DX | $PEG_9$ | M103-DXG[$PEG_9$]K(Biotin)-$NH_2$ |
| M103-NX | $PEG_9$ | M103-NXG[$PEG_9$]K(Biotin)-$NH_2$ |
| M103-SX | $(G_3S)_4$ | M103-SXGGGGSGGGSGGGSK(Biotin)-$NH_2$ (SEQ ID NO: 136) |
| M103-TX | $(G_3S)_4$ | M103-TXGGGGSGGGSGGGSK(Biotin)-$NH_2$ (SEQ ID NO: 137) |
| M103-GX | $PEG_9$ | M103-GXG[$PEG_9$]K(Biotin)-$NH_2$ |
| M103-AX | $PEG_9$ | M103-AXG[$PEG_9$]K(Biotin)-$NH_2$ |

TABLE 25-continued

| Model peptides used for the binding experiment. | | |
|---|---|---|
| Target | Linker for attachment to beads | Peptide |
| M103-C(Cm) | $(G_3S)_4$ | M103-C(CM)XGGGGSGGGSGGGSK(Biotin)-$NH_2$ (SEQ ID NO: 138) |
| M103-MX | $PEG_9$ | M103-MXG[$PEG_9$]K(Biotin)-$NH_2$ |
| M103-IX | $PEG_9$ | M103-IXG[$PEG_9$]K(Biotin)-$NH_2$ |
| M103-LX | $PEG_9$ | M103-LXG[$PEG_9$]K(Biotin)-$NH_2$ |
| M103-VX | $PEG_9$ | M103-VXG[$PEG_9$]K(Biotin)-$NH_2$ |
| M103-FX | $PEG_9$ | M103-FXG[$PEG_9$]K(Biotin)-$NH_2$ |
| M103-WX | $PEG_9$ | M103-WXG[$PEG_9$]K(Biotin)-$NH_2$ |
| M103-YX | $(G_3S)_4$ | M103-YXGGGGSGGGSGGGSK(Biotin)-$NH_2$ (SEQ ID NO: 139) |
| G | $PEG_9$ | G[$PEG_9$]K(Biotin)-$NH_2$ |

The 17 bead populations were combined and incubated with protein samples by mechanical agitation with a magnetic tip (Kingfisher). Beads were then treated with an Phycoerythrin-labeled Anti-6His antibody, and assayed on a Luminex MAGPIX instrument to determine the mean fluorescence intensity (MFI) of each binder for each bead population as a method of determining the binder's propensity to bind to the peptide N-terminally modified with M103 on each bead population. The Luminex beads are pre-dyed in a way that allows the bead populations to be differentiated, so the binding signal against particular immobilized peptide may be obtained. Signal associated with peptide-free beads (blank), and the G-peptide bead (the last row in Table 25; non-specific binding) was subtracted to determine the net MFI of each binder-peptide combination. The highest observed net MFI for each binder is summarized against the carbonic anhydrase-based binder parents (S222_1333, S222_1519, S222_1581, which correspond to SEQ ID NOs: 127-127) and the wild-type carbonic anhydrase "grandparent" (S222_0000, SEQ ID NO: 7) (see FIG. 21A-B). The results demonstrate that the designed binding agents (SEQ ID NO: 128-135) with the calculated ~35-40% sequence identity to parent proteins (SEQ ID NO: 125-127) and to the other carbonic anhydrase homologs retain ability to bind N-terminally modified peptides over unmodified peptides, in particular in comparison with the unmodified (wild-type) carbonic anhydrase "grandparent" (SEQ ID NO: 7). The strength and specificity of the binding can be further adjusted by additional binder affinity maturation methods, as described above (see, e.g., Examples 4 and 5).

The present disclosure is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure. These and other changes can be made to the embodiments in light of the above detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

| SEQUENCE TABLE | | |
|---|---|---|
| SEQ ID No. | Sequence (5'→3' for DNA sequences, N-terminus to C-terminus for amino acid sequences) | Description |
| 1 | AATGATACGGCGACCACCGA | P5 primer |
| 2 | CAAGCAGAAGACGGCATACGAGAT | P7 primer |
| 3 | MHKTRLVAALAAALATLAPAAWADEGMWVPQQLPEIAGALKKAGLKL DPKQLSDLTGDPMGAVVSLGGCTGSFVSPQGLVATNHHCAYGAIQLNSTP EKNLIKDGFNAPTQADELSAGPNARIYVLEGITDVTAQAKAAMAAAGND PVARANALEAFEKKITSDCEAEPGYRCRVYSFMGGITYRLFKNLEIKDVRL VYAPPSSVGKFGGDIDNWMWPRHTGDFSFYRAYVGKDGKPAPYSKDNV PYRPKHWLKIADTPLGEGDFVMVAGYPGRTDRYALVAEFENTQNWLYP AISKAYKDQIALVEAAAKDNPEIAVKYAAALAGWNNTSKNFDGQLEGFK RNDVLAIKRREEAAVLEWLRARGKAGTPALEAHAALVKLVADTARTQER DLVLGSFNRTGIIGVAVNLYRLAIERQKPDAEREPGYQQRDLPVIEGSLKQ MERRYVPAMDRQLRAYWLDRYVALPAAQHVAAVDAWLGGSDKAAAE AALARLDQSRLGSLEERLKWFNADRAAFEASTDPAIQYAVAVMPTLLAM | Dipeptidyl peptidase from *Thermomonas hydrothermalis* (with the signal peptide) Peptidase S46 [*Thermomonas hydrothermalis*] |

-continued

SEQUENCE TABLE

| SEQ ID No. | Sequence (5'→3' for DNA sequences, N-terminus to C-terminus for amino acid sequences) | Description |
|---|---|---|
| | EQQAKTRYGVALEARPRYLQAVVDYKKSKGQAVYPDANSTLRITYGHV<br>KGYTGLNGKVYTPFTTLEEVAAKETGVEPFDNPKALLEAVAAKRYAGLA<br>DARLGTVPVNFLADLDITGGNSGSPVLDANGRLVGLAFDGTLESVASNW<br>VFDPVLTRMISVDQRYMRWIMQEVMPAPQLLEELGVPPRQ | |
| 4 | DEGMWVPQQLPEIAGALKKAGLKLDPKQLSDLTGDPMGAVVSLGGCTGS<br>FVSPQGLVATNHHCAYGAIQLNSTPEKNLIKDGFNAPTQADELSAGPNARI<br>YVLEGITDVTAQAKAAMAAAGNDPVARANALEAFEKKITSDCEAEPGYR<br>CRVYSFMGGITYRLFKNLEIKDVRLVYAPPSSVGKFGGDIDNWMWPRHT<br>GDFSFYRAYVGKDGKPAPYSKDNVPYRPKHWLKIADTPLGEGDFVMVA<br>GYPGRTDRYALVAEFENTQNWLYPAISKAYKDQIALVEAAAKDNPEIAV<br>KYAAALAGWNNTSKNFDGQLEGFKRNDVLAIKRREEAAVLEWLRARGK<br>AGTPALEAHAALVKLVADTARTQERDLVLGSFNRTGIIGVAVNLYRLAIE<br>RQKPDAEREPGYQQRDLPVIEGSLKQMERRYVPAMDRQLRAYWLDRYV<br>ALPAAQHVAAVDAWLGGSDKAAAEAALARLDQSRLGSLEERLKWFNAD<br>RAAFEASTDPAIQYAVAVMPTLLAMEQQAKTRYGVALEARPRYLQAVV<br>DYKKSKGQAVYPDANSTLRITYGHVKGYTGLNGKVYTPFTTLEEVAAKE<br>TGVEPFDNPKALLEAVAAKRYAGLADARLGTVPVNFLADLDITGGNSGSP<br>VLDANGRLVGLAFDGTLESVASNWVFDPVLTRMISVDQRYMRWIMQEV<br>MPAPQLLEELGVPPRQ | Dipeptidyl peptidase from *Thermomonas hydrothermalis* (without the signal peptide) Peptidase S46 [*Thermomonas hydrothermalis*] |
| 5 | MKIRLFGVLLLFTFSLFAEEGMYPITEIHKLNLKKLGIELSADQIFSENEVSL<br>SDAIVQIGGCTGSFISPEGLILTNHHCAFRAIQNISSTENDYLTNGFVAHTLQ<br>EERPAKGYTVRITERVEDVSQRVLNAVKHIEDPIEREKAIEKITKQIVKEQE<br>QKHPGKRAAVSEMFPGKTYYLFIYTYLKDVRLVYAPPRSIGEFGGEFDNW<br>EWPRHTGDFTLMRAYVAPDGSPSDYSEENVPYRPKSYLKVAAKGVEEGD<br>RVFILGYPGRTYRHRTSAFLAFEYEFRMPFVVDWYQWQIDLLTTLGKDDA<br>DRSLKFSSWIKGLANTEKNYRGKLQGIRRIGLLEQKKNEEEKIQVFIAENN<br>LKKYQHVLTEIKQIYHTYRQSAVREMLLSYFGRSPVLPAVARTLVLAAEE<br>RQKEDLERERAFMDRNFKRTQTYTLLRLKNFDSQADQLILQELLKKAAAL<br>PEDQRISALRSIFKLDDAAETRQVISEAYRKTRLSDPEFVKTCFAKTPDELK<br>ALNDPLINWMLALKEDYETLKNIRKERNGKLRRLRALWLEAKQAYLKTD<br>FIPDANGTYRMTFGFIEGYAPADAVYKAPITTGRGILEKHTGKSPFDTPEK<br>LLALLKAKQFGPFVSKTVGTLPVGILYSCDTTGGNSGSPVLNARGQLVGL<br>NFDRAFEATINDYAWNHQYSRSIGVDIRYILFLLKYFSGAEHLLEEMGVQ | Dipeptidyl peptidase from *Caldithrix abyssii* (with the signal peptide) S46 family peptidase [*Caldithrix abyssi*] |
| 6 | EEGMYPITEIHKLNLKKLGIELSADQIFSENEVSLSDAIVQIGGCTGSFISPE<br>GLILTNHHCAFRAIQNISSTENDYLTNGFVAHTLQEERPAKGYTVRITERV<br>EDVSQRVLNAVKHIEDPIEREKAIEKITKQIVKEQEQKHPGKRAAVSEMFP<br>GKTYYLFIYTYLKDVRLVYAPPRSIGEFGGEFDNWEWPRHTGDFTLMRA<br>YVAPDGSPSDYSEENVPYRPKSYLKVAAKGVEEGDRVFILGYPGRTYRHR<br>TSAFLAFEYEFRMPFVVDWYQWQIDLLTTLGKDDADRSLKFSSWIKGLA<br>NTEKNYRGKLQGIRRIGLLEQKKNEEEKIQVFIAENNLKKYQHVLTEIKQI<br>YHTYRQSAVREMLLSYFGRSPVLPAVARTLVLAAEERQKEDLERERAFM<br>DRNFKRTQTYTLLRLKNFDSQADQLILQELLKKAAALPEDQRISALRSIFK<br>LDDAAETRQVISEAYRKTRLSDPEFVKTCFAKTPDELKALNDPLINWMLA<br>LKEDYETLKNIRKERNGKLRRLRALWLEAKQAYLKTDFIPDANGTYRMT<br>FGFIEGYAPADAVYKAPITTGRGILEKHTGKSPFDTPEKLLALLKAKQFGP<br>FVSKTVGTLPVGILYSCDTTGGNSGSPVLNARGQLVGLNFDRAFEATIND<br>YAWNHQYSRSIGVDIRYILFLLKYFSGAEHLLEEMGVQ | Dipeptidyl peptidase from *Caldithrix abyssii* (without the signal peptide) S46 family peptidase [*Caldithrix abyssi*] |
| 7 | HWGYGKHNGPEHWHKDFPIAKGERQSPVDIDTHTAKYDPSLKPLSVSYD<br>QATSLRILNNGHAFNVEFDDSQDKAVLKGGPLDGTYRLIQFHFHWGSLDG<br>QGSEHTVDKKKYAAELHLVHWNTKYGDFGKAVQQPDGLAVLGIFLKVG<br>SAKPGLQKVVDVLDSIKTKGKSADFTNFDPRGLLPESLDYWTYPGSLTTPP<br>LLECVTWIVLKEPISVSSEQVLKFRKLNFNGEGEPEELMVDNWRPAQPLK<br>NRQIKASF | Carbonic anhydrase II, *Homo sapiens* (scaffold); PDB ID: 4LP6 |
| 8 | WGYDDKNGPEQWSKLYPIANGNNQSPVDIKTSETKHDTSLKPISVSYNPA<br>TAKEIINVGHSFHVNFEDNQDRSVLKGGPFSDSYRLFQFHFHWGSTNEHG<br>SEHTVDGVKYSAELHVAHWNSAKYSSLAEAASKADGLAVIGVLMKVGE<br>ANPKLQKVLDALQAIKTKGKRAPFTNFDPSTLLPSSLDFWTYPGSLTHPPL<br>YESVTWIICKESISVSSEQLAQFRSLLSNVEGDNAVPMQHNNRPTQPLKGR<br>TVRASF | Carbonic anhydrase I, *Homo sapiens* (scaffold); PDB ID: 2CAB |
| 9 | EWGYASHNGPDHWHELFPNAKGENQSPIELHTKDIRHDPSLQPWSVSYD<br>GGSAKTILNNGKTCRVVFDDTYDRSMLRGGPLPGPYRLRQFHLHWGSSD<br>DHGSEHTVDGVKYAAELHLVHWNPKYNTFKEALKQRDGIAVIGIFLKIGH<br>ENGEFQIFLDALDKIKTKGKEAPFTKFDPSSLFPASRDYWTYQGSLTTPPCE<br>ECIVWLLLKEPMTVSSDQMAKLRSLLSSAENEPPVPLVSNWRPPQPINNRV<br>VRASF | Carbonic anhydrase III, *Homo sapiens* (scaffold); PDB ID: 1Z97 |

-continued

SEQUENCE TABLE

| SEQ ID No. | Sequence (5'→3' for DNA sequences, N-terminus to C-terminus for amino acid sequences) | Description |
|---|---|---|
| 10 | AESHWCYEVQAESSNYPCLVPVKWGGNCQKDRQSPINIVTTKAKVDKKL<br>GRFFFSGYDKKQTWTVQNNGHSVMMLLENKASISGGGLPAPYQAKQLHL<br>HWSDLPYKGSEHSLDGEHFAMEMHIVHEKEKGTSRNVKEAQDPEDEIAV<br>LAFLVEAGTQVNEGFQPLVEALSNIPKPEMSTTMAESSLLDLLPKEEKLRH<br>YFRYLGSLTTPTCDEKVVWTVFREPIQLHREQILAFSQKLYYDKEQTVSM<br>KDNVRPLQQLGQRTVIKS | Carbonic anhydrase IV, *Homo sapiens* (scaffold); PDB ID: 5JN8 |
| 11 | GHHGWGYGQDDGPSHWHKLYPIAQGDRQSPINIISSQAVYSPSLQPLELSY<br>EACMSLSITNNGHSVQVDFNDSDDRTVVTGGPLEGPYRLKQFHFHWGKK<br>HDVGSEHTVDGKSFPSELHLVHWNAKKYSTFGEAASAPDGLAVVGVFLE<br>TGDEHPSMNRLTDALYMVRFKGTKAQFSCFNPKSLLPASRHYWTYPGSL<br>TTPPLSESVTWIVLREPISISERQMGKFRSLLFTSEDDERIHMVNNFRPPQPL<br>KGRVVKASFRA | Carbonic anhydrase VII (C183S/C217S), *Homo sapiens* (scaffold); PDB ID: 3ML5 |
| 12 | KWTYFGPDGENSWSKKYPSCGGLLQSPIDLHSDILQYDASLTPLEFQGYN<br>LSANKQFLLTNNGHSVKLNLPSDMHIQGLQSRYSATQLHLHWGNPNDPH<br>GSEHTVSGQHFAAELHIVHYNSDLYPDASTASNKSEGLAVLAVLIEMGSF<br>NPSYDKIFSHLQHVKYKGQEAFVPGFNIEELLPERTAEYYRYRGSLTTPPC<br>NPTVLWTVFRNPVQISQEQLLALETALYCTHMDDPSPREMINNFRQVQKF<br>DERLVYTSFS | Carbonic anhydrase XII, *Homo sapiens* (scaffold); PDB ID: 1JD0 |
| 13 | LSWGYREHNGPIHWKEFFPIADGDQQSPIEIKTKEVKYDSSLRPLSIKYDPS<br>SAKIISNSGHSFNVDFDDTENKSVLRGGPLTGSYRLRQVHLHWGSADDHG<br>SEHIVDGVSYAAELHVVHWNSDKYPSFVEAAHEPDGLAVLGVFLQIGEPN<br>SQLQKITDTLDSIKEKGKQTRFTNFDLLSLLPPSWDYWTYPGSLTVPPLLES<br>VTWIVLKQPINISSQQLAKFRSLLCTAEGEAAAFLVSNHRPPQPLKGRKVR<br>ASFH | Carbonic anhydrase XIII, *Homo sapiens* (scaffold); PDB ID: 4KNM |
| 14 | ADPDPMKNTCKLLVVADHRFYRYMGRGEESTTTNYLIELIDRVDDIYRNT<br>AWDNAGFKGYGIQIEQIRILKSPQEVKPGEKHYNMAKSYPNEEKDAWDV<br>KMLLEQFSFDIAEEASKVCLAHLFTYQDFDMGTLGLAYGGSPRANSHGG<br>VCPKAYYSPVGKKNIYLNSGLTSTKNYGKTILTKEADLVTTHELGHNFGA<br>EHDPDGLAECAPNEDQGGKYVMYPIAVSGDHENNKMFSQCSKQSIYKTIE<br>SKAQECFQERSNA | ADAM17 (aka TACE), *Homo sapiens* (scaffold); PDB ID: 2FV5 |
| 15 | AAILGDEYLWSGGVIPYTFAGVSGADQSAILSGMQELEEKTCIRFVPRTTE<br>SDYVEIFTSGSGCWSYVGRISGAQQVSLQANGCVYHGTIIHELMHAIGFYH<br>EHTRMDRDNYVTINYQNVDPSMTSNFDIDTYSRYVGEDYQYYSIMHYGK<br>YSFSIQWGVLETIVPLQNGIDLTDPYDKAHMLQTDANQINNLYTNECSL | Astacin, *Astacus astacus*, (scaffold); PDB ID: 1AST |
| 16 | PQAKYRHDYRAPDYQITDIDLTFDLDAQKTVVTAVSQAVRHGASDAPLR<br>LNGEDLKLVSVHINDEPWTAWKEEEGALVISNLPERFTLKIINEISPAANTA<br>LEGLYQSGDALCTQCEAEGFRHITYYLDRPDVLARFTTKIIADKIKYPFLLS<br>NGNRVAQGELENGRHWVQWQDPFPKPCYLFALVAGDFDVLRDTFTTRS<br>GREVALELYVDRGNLDRAPWAMTSLKNSMKWDEERFGLEYDLDIYMIV<br>AVDFFNMGAMENKGLNIFNSKYVLARTDTATDKDYLDIERVIGHEYFHN<br>WTGNRVTCRDWFQLSLKEGLTVFRDQEFSSDLGSRAVNRINNVRTMRGL<br>QFAEDASPMAHPIRPDMVIEMNNFYTLTVYEKGAEVIRMIHTLLGEENFQ<br>KGMQLYFERHDGSAATCDDFVQAMEDASNVDLSHFRRWYSQSGTPIVTV<br>KDDYNPETEQYTLTISQRTPATPDQAEKQPLHIPFAIELYDNEGKVIPLQKG<br>GHPVNSVLNVTQAEQTFVFDNVYFQPVPALLCEFSAPVKLEYKWSDQQL<br>TFLMRHARNDFSRWDAAQSLLATYIKLNVARHQQGQPLSLPVHVADAFR<br>AVLLDEKIDPALAAEILTLPSVNEMAELFDIIDPIAIAEVREALTRTLATELA<br>DELLAIYNANYQSEYRVEHEDIAKRTLRNACLRFLAFGETHLADVLVSKQ<br>FHEANNMTDALAALSAAVAAQLPCRDALMQEYDDKWHQNGLVMDKW<br>FILQATSPAANVLETVRGLLQHRSFTMSNPNRIRSLIGAFAGSNPAAFHAE<br>DGSGYLFLVEMLTDLNSRNPQVASRLIEPLIRLKRYDAKRQEKMRAALEQ<br>LKGLENLSGDLYEKITKALA | Aminopeptidase N, *Escherichia coli* (scaffold); PDB ID: 4Q4E |
| 17 | MLTMKDIIRDGHPTLRQKAAELELPLTKEEKETLIAMREFLVNSQDEEIAK<br>RYGLRSGVGLAAPQINISKRMIAVLIPDDGSGKSYDYMLVNPKIVSHSVQE<br>AYLPTGEGCLSVDDNVAGLVHRHNRITIKAKDIEGNDIQLRLKGYPAIVFQ<br>HEIDHLNGVMFYDHIDKDHPLQPHTDAVEVLE | Peptide deformylase, *Staphylococcus aureus* (scaffold); PDB ID: 3U7M |
| 18 | KHNMKAFLDELKAENIKKFLYNFTQIPHLAGTEQNFQLAKQIQSQWKEFG<br>LDSVELAHYDVLLSYPNKTHPNYISIINEDGNEIFNTSLFEPPPPGYENVSDI<br>VPPFSAFSPQGMPEGDLVYVNYARTEDFFKLERDMKINCSGKIVIARYGK<br>VFRGNKVKNAQLAGAKGVILYSDPADYFAPGVKSYPDGWNLPGGVQR<br>GNILNLNGAGDPLTPGYPANEYAYRRGIAEAVGLPSIPVHPIGYYDAQKLL | Glutamate carboxypeptidase II, *Homo sapiens* (scaffold); PDB ID: 5ELY |

-continued

SEQUENCE TABLE

| SEQ ID No. | Sequence (5'→3' for DNA sequences, N-terminus to C-terminus for amino acid sequences) | Description |
|---|---|---|
| | EKMGGSAPPDSSWRGSLKVPYNVGPGFTGNFSTQKVKMHIHSTNEVTRIY NVIGTLRGAVEPDRYVILGGHRDSWVFGGIDPQSGAAVVHEIVRSFGTLK KEGWRPRRTILFASWDAEEFGLLGSTEWAEENSRLLQERGVAYINADSSIE GNYTLRVDCTPLMYSLVHNLTKELKSPDEGFEGKSLYESWTKKSPSPEFS GMPRISKLGSGNDFEVFFQRLGIASGRARYTKNWETNKFSGYPLYHSVYE TYELVEKFYDPMFKYHLTVAQVRGGMVFELANSIVLPFDCRDYAVVLRK YADKIYSISMKHPQEMKTYSVSFDSLFSAVKNFTEIASKFSERLQDFDKSN PIVLRMMNDQLMFLERAFIDPLGLPDRPFYRHVIYAPSSHNKYAGESFPGI YDALFDIESKVDPSKAWGEVKRQIYVAAFTVQAAAETLSEVA | |
| 19 | ARSTNTFNYATYHTLDEIYDFMDLLVAQHPELVSKLQIGRSYEGRPIYVLK FSTGGSNRPAIWIDLGIHSREWITQATGVWFAKKFTENYGQNPSFTAILDS MDIFLEIVTNPNGFAFTHSENRLWRKTRSVTSSSLCVGVDANRNWDAGFG KAGASSSPCSETYHGKYANSEVEVKSIVDFVKNHGNFKAFLSIHSYSQLLL YPYGYTTQSIPDKTELNQVAKSAVAALKSLYGTSYKYGSIITTIYQASGGSI DWSYNQGIKYSFTFELRDTGRYGFLLPASQIIPTAQETWLGVLTIMEHTVN N | Carboxypeptidase A, *Bos taurus* (scaffold); PDB ID: 1HEE |
| 20 | DFPSYDSGYHNYNEMVNKINTVASNYPNIVKKFSIGKSYEGRELWAVKIS DNVGTDENEPEVLYTALHHAREHLTVEMALYTLDLFTQNYNLDSRITNL VNNREIYIVFNINPDGGEYDISSGSYKSWRKNRQPNSGSSYVGTDLNRNY GYKWGCCGGSSGSPSSETYRGRSAFSAPETAAMRDFINSRVVGGKQQIKT LITFHTYSELILYPYGYTYTDVPSDMTQDDFNVFKTMANTMAQTNGYTPQ QASDLYITDGDMTDWAYGQHKIFAFTFEMYPTSYNPGFYPPDEVIGRETS RNKEAVLYVAEKADCPYSVIGKSC | Carboxypeptidase T, *Bos taurus* (scaffold); PDB ID: 4DJL |
| 21 | GRSDAYTQVDNFLHAYARGGDELVNGHPSYTVDQAAEQILREQASWQK APGDSVLTLSYSFLTKPNDFFNTPWKYVSDIYSLGKFSAFSAQQQAQAKLS LQSWSDVTNIHFVDAGQGDQGDLTFGNFSSSVGGAAFAFLPDVPDALKG QSWYLINSSYSANVNPANGNYGRQTLTHEIGHTLGLSHPGDYNAGEGDPT YADATYAEDTRAYSVMSYWEEQNTGQDFKGAYSSAPLLDDIAAIQKLYG ANLTTRTGDTVYGFNSNTERDFYSATSSSSKLVFSVWDAGGNDTLDFSGF SQNQKINLNEKALSDVGGLKGNVSIAAGVTVENAIGGSGSDLLIGNDVAN VLKGGAGNDILYGGLGADQLWGGAGADTFVYGDIAESSAAAPDTLRDFV SGQDKIDLSGLDAFVNGGLVLQYVDAFAGKAGQAILSYDAASKAGSLAID FSGDAHADFAINLIGQATQADIVV | Alkaline protease, *Pseudomonas aeruginosa* PAO1 (scaffold); PDB ID: 1KAP |
| 22 | DFPSYDSGYHNYNEMVNKINTVASNYPNIVKKFSIGKSYEGRELWAVKIS DNVGTDENEPEVLYTALHHAREHLTVEMALYTLDLFTQNYNLDSRITNL VNNREIYIVFNINPDGGEYDISSGSYKSWRKNRQPNSGSSYVGTDLNRNY GYKWGCCGGSSGSPSSETYRGRSAFSAPETAAMRDFINSRVVGGKQQIKT LITFHTYSELILYPYGYTYTDVPSDMTQDDFNVFKTMANTMAQTNGYTPQ QASDLYITDGDMTDWAYGQHKIFAFTFEMYPTSYNPGFYPPDEVIGRETS RNKEAVLYVAEKADCPYSVIGKSC | Carboxypeptidase T, *Thermoactinomyces vulgaris* (scaffold); PDB ID: 1OBR |
| 23 | NSAIYFNTSQPINDLQGSLAAEVKFAQSQILPAHPKEGDSQPHLTSLRKSLL LVRPVKADDKTPVQVEARDDNNKILGTLTLYPPSSLPDTIYHLDGVPEGGI DFTPHNGTKKIINTVAEVNKLSDASGSSIHSHLTNNALVEIHTANGRWVRD IYLPQGPDLEGKMVRFVSSAGYSSTVFYGDRKVTLSVGNTLLFKYVNGQ WFRSGELENNRITYAQHIWSAELPAHWIVPGLNLVIKQGNLSGRLNDIKIG APGELLLHTIDIGMLTTPRDRFDFAADAAAHREYFQTIPVSRMIVNNYAPL HLKEVMLPTGELLTDMDPGNGGWHSGTMRQRIGKELVSHGIDNANYGL NSTAGLGENSHPYVVAQLAAHNSRGNYANGIQVHGGSGGGGIVTLDSTL GNEFSHDVGHNYGLGHYVDGFKGSVHRSAENNNSTWGWDGDKKRFIPN FYPSQTNEKSCLNNQCQEPFDGHKFGFDAMAGGSPFSAANRFTMYTPNSS AIIQRFFENKAVFDSRSSTGFSKWNADTQEMEPYEHTIDRAEQITASVNEL SESKMAELMAEYAVVKVHMWNGNWTRNIYIPTASADNRGSILTINHEAG YNSYLFINGDEKVVSQGYKKSFVSDGQFWKERDVVDTREARKPEQFGVP VTTLVGYYDPEGTLSSYIYPAMYGAYGFTYSDDSQNLSDNDCQLQVDTK EGQLRFRLANHRANNTVMNKFHINVPTESQPTQATLVCNNKILDTKSLTP APEGLTYTVNGQALPAKENEGCIVSVNSGKRYCLPVGQRSGYSLPDWIVG QEVYVDSGAKAKVLLSDWDNLSYNRIGEFVGNVNPADMKKVKAWNGQ YLDFSKPRSMRVVYK | StcE, *Escherichia coli* (scaffold); PDB ID: 3UJZ |
| 24 | MAERTPNEEKKVIGYADHNGQLYNITSIYGPVINYTVPDENITINTINSTGE RTQLTINYSDYVREAFNEWAPSGIRVQQVSSSGAEARVVSFSTTNYADNS LGSTIFDPSGNSRTRIDIGSFNRIVMNNFEKLKSRGAIPANMSPEEYIKLKLR ITIKHEIGHILGLLHNNEGGSYFPHGVGLEVARCRLLNQAPSIMLNGSNYD YIDRLSHYLERPVTETDIGPSRNDIEGVRVMRRGGSGNSFTNRFSCLGLGL AF | AB5 holotoxin, *Escherichia coli* (scaffold); PDB ID: 4L63 |
| 25 | GSPRYLKGWLKDVVQLSLRRPSFRASRQRPIISLNERILEFNKRNITAIIAEY KRKSPSGLDVERDPIEYSKFMERYAVGLSILTEEKYFNGSYETLRKIASSVS IPILMADFIVKESQIDDAYNLGADTVLLIVKILTERELESLLEYARSYGMEP | ZE2 (TIM barrel), *Saccharolobus* |

-continued

SEQUENCE TABLE

| SEQ ID No. | Sequence (5'→3' for DNA sequences, N-terminus to C-terminus for amino acid sequences) | Description |
|---|---|---|
| | LIGINDENDLDIALRIGARFIGIHSADHETLEINKENQRKLISMIPSNVVKVA AHGISERNEIEELRKLGVNAFLIGSSLMRNPEKIKEFIL | *solfataricus* P2 (scaffold); PDB ID: 5K7J |
| 26 | GSPLAQQIKNTLTFIGQANAAGRMDEVRTLQQNLHPLWAEYFQQTEGSG GSPLAQQIQYGHVLIHQARAAGRMDEVRRLSENTLQLMKEYFQQS | MID1 sc10 (de novo helical bundle), artificial sequence (scaffold); PDB ID: 5OD1 |
| 27 | ALRIDSHQHFWRYRAADYPWIGAGMGVLARDYLPDALHPLMHAQALGA SIAVQARAGRDETAFLLELACDEARIAAVVGWEDLRAPQLAERVAEWRG TKLRGFRHQLQDEADVRAFVDDADFARGVAWLQANDYVYDVLVFERQL PDVQAFCARHDAHWLVLDHAGKPALAEFDRDDTALARWRAALRELAAL PHVVCKLSGLVTEADWRRGLRASDLRHIEQCLDAALDAFGPQRLMFGSD WPVCLLAASYDEVASLVERWAESRLSAAERSALWGGTAARCYALP | Amidohydrolase, *Burkholderia multivorans* ATCC 17616 (scaffold); PDB ID: 4DLM |
| 28 | MLTMKDIIRDGHPTLRQKAAELELPLTKEEKETLIAMREFLVNSQDEEIAK RYGLRSAVVIVAPMINISKRMIAVLLPDDGSGKSYDYMLVNPKIVSHSVQ EAYLPDGLQCLSVDDNVAGLVHRHNRITIKAKDIEGNDIQLRLKGLPAILF QHAIDHLNGVMFYDHIDKDHPLQPHTDAVEVLL | PDB ID: 3U7M; mutant; M64 |
| 29 | GRSDAYTQVDNFLHAYARGGDELVNGHPSYTVDQAAEQILREQASWQK APGDSVLTLSYSFLTKPNDFFNTPWKYVSDIYSLGKFSAFSAQQQAQAKLS LQSWSDVTNIHFVDAGQGDQGDLTFGNFSSSVGGLVFVFLPDVPDALKG QSWYLINSSWSIVVNPANGNRGRQLLTHMIGHTLGLSHPGDYHPGEGDPT YADATYAEDTLAYSVMSLWEEQNTGQDFKGAYSSAPLLDDIAAIQKLYG ANLTTRTGDTVYGFNSNTERDFYSATSSSSKLVFSVWDAGGNDTLDFSGF SQNQKINLNEKALSDVGGLKGNVSIAAGVTVENAIGGSGSDLLIGNDVAN VLKGGAGNDILYGGLGADQLWGGAGADTFVYGDIAESSAAAPDTLRDFV SGQDKIDLSGLDAFVNGGLVLQYVDAFAGKAGQAILSYDAASKAGSLAID FSGDAHADFAINLIGQATQADIVV | PDB ID: 1KAP; mutant; M64 |
| 30 | LVPRGSHMKLCLVAFDGRIPMLSSIVDRFEEHVSEYLGEVKVKKKRAKLP EHAYSKVRGQYLARALLDTLRGMKGEYDRVLGLTSEDLYIPGVNFVFLIA RCPGREAVVSVARLLDPDPELYLERVVKELTHALGHTFGLGHCPDRNCV MSPASSLLEVDRKSPNFCRRCTELLQRNLKRGG | PDB ID: 2X7M; mutant; M64 |
| 31 | VVRDVNWGALRIAVSTEDLTDPAYHCARVGQHVKDHAGAIVTCTAEDIL TNEKRDILVKHLIPQAVQLHTERLKVQQVQGKWKVTDMVGDICGDFKVP QAHITEGFSNTDFVMYVASVPSEEGVLAWATTCQTFSDGHPAVGVINIPA ANIASRYDQLVTRVVTHVMAHALGFSGPFFEDARIVANVPNVRGKNFDV PVINSSTAVAKAREQYGCDTLEYLEVEDQGGEGYAGSHIKMRNAQDELM APAAAAGYYTALTMAIFQDLGFYQADFSKAEVMPWGQNAGCAFLTNKC MEQSVTQWPAMFCNESEDAIRCPTSRLSLGACGVTRHPGLPPYWQYFTDP SLAGVSALMDYCPVVVPYSDGSCTQRASEAHASLLPFNVFSDAARCIDGA FRPKATDGIVKSYAGLCANVQCDTATRTYSVQVHGSNDYTNCTPGLRVE LSTVSNAFEGGGYITCPPYVEVCQGNVQAAKDGGN | PDB ID: 1LML; mutant; M64 |
| 32 | PQAKYRHDYRAPDYQITDIDLTFDLDAQKTVVTAVSQAVRHGASDAPLR LNGEDLKLVSVHINDEPWTAWKEEEGALVISNLPERFTLKIINEISPAANTA LEGLYQSGDALCTQCLAEGFRHITYYLDRPDVLARFTTKIIADKIKYPFLLS NGNRVAQGELENGRHWVQWQDPFPKPCYLFALVAGDFDVLRDTFTTRS GREVALELYVDRGNLDRAPWAMTSLKNSMKWDEERFGLEYDLDIYMIV AVDFLNTGVVPNKGLNIFNSALVLARTDTATDKDYLEIEAVIGHVYFHNW TGNRVTCRDWFQLSLIEGLTLFRIQEFSSDLGSRAVNRINNVRTMRGLQFA EDASPMAHPIRPDMVIEMNNFFTLTVLWKGAEVIRMIHTLLGEENFQKGM QLYFERHDGSAATCDDFVQAMEDASNVDLSHFRRWYSQSGTPIVTVKDD YNPETEQYTLTISQRTPATPDQAEKQPLHIPFAIELYDNEGKVIPLQKGGHP VNSVLNVTQAEQTFVFDNVYFQPVPALLCEFSAPVKLEYKWSDQQLTFL MRHARNDFSRWDAAQSLLATYIKLNVARHQQGQPLSLPVHVADAFRAV LLDEKIDPALAAEILTLPSVNEMAELFDIIDPIAIAEVREALTRTLATELADE LLAIYNANYQSEYRVEHEDIAKRTLRNACLRFLAFGETHLADVLVSKQFH EANNMTDALAALSAAVAAQLPCRDALMQEYDDKWHQNGLVMDKWFIL QATSPAANVLETVRGLLQHRSFTMSNPNRIRSLIGAFAGSNPAAFHAEDGS GYLFLVEMLTDLNSRNPQVASRLIEPLIRLKRYDAKRQEKMRAALEQLKG LENLSGDLYEKITKALA | PDB ID: 4Q4E; mutant; M65 |
| 33 | MLTMKDIIRDGHPTLRQKAAELELPLTKEEKETLIAMREFLVNSQDEEIAK RYGLRSLAMLVAPLINISKRMIVVLIPDDGSGKSYDYMLVNPKIVSHSVQE AYLPTGFQCIAVDDNVAGLVHLHNRITIKAKDIEGNDIQLRLKGLPALIFQ HAIDHLNGVMFYDHIDKDHPLQPHTDAVEVLL | PDB ID: 3U7M; mutant; M65 |

-continued

SEQUENCE TABLE

| SEQ ID No. | Sequence (5'→3' for DNA sequences, N-terminus to C-terminus for amino acid sequences) | Description |
|---|---|---|
| 34 | EWGYASHNGPDHWHELFPNAKGENQSPIELHTKDIRHDPSLQPWSVSYD GGSAKTILNDGLTCLVVFDDTYDRSMLRGGPLPGPYRLLFFHLHWGSSDD HGSLHTVDGVKYAAELHLVHWNPKYNTYKEAQKQRDGIAIIGIFLKIGHE NGEFQIFLDALDKIKTKGKEAPFTKFDPSSLFPASRDYWTYQGAMAVPPLE ECVVWLLLKEPMTVSSDQMAKLRSLLSSAENEPPVPLVSNWRPPQPINNR VVRASFK | PDB ID: 1Z97; mutant; M65 |
| 35 | MLTMKDIIRDGHPTLRQKAAELELPLTKEEKETLIAMREFLVNSLDEEIAK RYGLRSAGMLVAPMINISKRMIVMLIPDDGSGKSWDYMLVNPKIVSHSVQ EAYLPTGEECLSVDDNVAGLVHRHNRITIKAKDIEGNDIQLRLKGLAAIA MQHAIDHLNGVMFYDHIDKDHPLQPHTDAVEVLL | PDB ID: 3U7M; mutant; M72 |
| 36 | PQAKYRHDYRAPDYQITDIDLTFDLDAQKTVVTAVSQAVRHGASDAPLR LNGEDLKLVSVHINDEPWTAWKEEEGALVISNLPERFTLKIINEISPAANTA LEGLYQSGDALCTQCVAEGFRHITYYLDRPDVLARFTTKIIADKIKYPFLLS NGNRVAQGELENGRHWVQWQDPFPKPCYLFALVAGDFDVLRDTFTTRS GREVALELYVDRGNLDRAPWAMTSLKNSMKWDEERFGLEYDLDIYMIV AVDFLNTGMMVNKGLNIVHSIAILARTDTATDKDYLDIERLIGHAYFHNW TGNRVTCRDWFQLSLIEGLTVFRDQEFSSDLGSRAVNRINNVRTMRGLQF AEDASPMAHPIRPDMVIEMNNFYTLTVLEKGAEVIRMIHTLLGEENFQKG MQLYFERHDGSAATCDDFVQAMEDASNVDLSHFRRWYSQSGTPIVTVKD DYNPETEQYTLTISQRTPATPDQAEKQPLHIPFAIELYDNEGKVIPLQKGGH PVNSVLNVTQAEQTFVFDNVYFQPVPALLCEFSAPVKLEYKWSDQQLTFL MRHARNDFSRWDAAQSLLATYIKLNVARHQQGQPLSLPVHVADAFRAV LLDEKIDPALAAEILTLPSVNEMAELFDIIDPIAIAEVREALTRTLATELADE LLAIYNANYQSEYRVEHEDIAKRTLRNACLRFLAFGETHLADVLVSKQFH EANNMTDALAALSAAVAAQLPCRDALMQEYDDKWHQNGLVMDKWFIL QATSPAANVLETVRGLLQHRSFTMSNPIRILSLIGAFAGSNPAAFHAEDGS GYLFLVEMLTDLNSRNPQVASRLIEPLIRLKRYDAKRQEKMRAALEQLKG LENLSGDLYEKITKALA | PDB ID: 4Q4E; mutant; M72 |
| 37 | VVRDVNWGALRIAVSTEDLTDPAYHCARVGQHVKDHAGAIVTCTAEDIL TNEKRDILVKHLIPQAVQLHTERLKVQQVQGKWKVTDMVGDICGDFKVP QAHITEGFSNTDFVMYVASVPSHEGILAWATTCQTFSDGHPAVGVINIPAA NIASRYDQLVTRVVTHAMAHALGFSGPFFEDARIVANVPNVRGKNFDVP VINSSTAVAKAREQYGCDTLEYLEVEDQGGAKIAGSHIKMRNAQDELMA PKAAAGYYTALTMAIFQDLGFYQADFSKAEVMPWGQNAGCAFLTNKCM EQSVTQWPAMFCNESEDAIRCPTSRLSLGACGVTRHPGLPPYWQYFTDPS LAGVSALMDYCPVVVPYSDGSCTQRASEAHASLLPFNVFSDAARCIDGAF RPKATDGIVKSYAGLCANVQCDTATRTYSVQVHGSNDYTNCTPGLRVEL STVSNAFEGGGYITCPPYVEVCQGNVQAAKDGGN | PDB ID: 1LML; mutant; M72 |
| 38 | NSAIYFNTSQPINDLQGSLAAEVKFAQSQILPAHPKEGDSQPHLTSLRKSLL LVRPVKADDKTPVQVEARDDNNKILGTLTLYPPSSLPDTIYHLDGVPEGGI DFTPHNGTKKIINTVAEVNKLSDASGSSIHSHLTNNALVEIHTANGRWVRD IYLPQGPDLEGKMVRFVSSAGYSSTVFYGDRKVTLSVGNTLLFKYVNGQ WFRSGELENNRITYAQHIWSAELPAHWIVPGLNLVIKQGNLSGRLNDIKIG APGELLLHTIDIGMLTTPRDRFDFAADAAAHREYFQTIPVSRMIVNNYAPL HLKEVMLPTGELLTDMDPGNGGETSGTMRQRIGKELVSHGIDNANYGLN STAGLGENSHPYVVAQLAAHNSRGNYANGIQVHGKSGGGGIVTLDSTLG NEFSHAVGHNYGLGHYVDGFKGSVHRSAENNNSTWGWDGDKKRFIPNF YPSQTNEKSCLNNQCQEPFDGHKFGFDAMAGGSPFSAANRFTMYTPNSSA IIQRFFENKAVFDSRSSTGFSKWNADTQEMEPYEHTIDRAEQITASVNELSE SKMAELMAEYAVVKVHMWNGNWTRNIYIPTASADNRGSILTINHEAGYN SYLFINGDEKVVSQGYKKSFVSDGQFWKERDVVDTREARKPEQFGVPVT TLVGYYDPEGTLSSYIYPAMYGAYGFTYSDDSQNLSDNDCQLQVDTKEG QLRFRLANHRANNTVMNKFHINVPTESQPTQATLVCNNKILDTKSLTPAP EGLTYTVNGQALPAKENEGCIVSVNSGKRYCLPVGQRSGYSLPDWIVGQE VYVDSGAKAKVLLSDWDNLSYNRIGEFVGNVNPADMKKVKAWNGQYL DFSKPRSMRVVYK | 3UJZ; mutant; M72 |
| 39 | NLPQRYIELVVVADRRVFMKYNSDLNIIRTRVHEIVNIINKFYRSLNIRVSL TDLEIWSGQDFITIQSSSSNTLNSFGEWRERVLLIWKRHDNAQLLTAINFEG KIILLAYTSSMCNPRSSVGIVKDHSPINLLVAVTMAHLLGHNLGMEHDGP DCLRGASLCIMLPELTPGRSYEFSDDSMGYYQKFLNQYKPQCILNKP | PDB ID: 1IAG; mutant; M83 |
| 40 | PQAKYRHDYRAPDYQITDIDLTFDLDAQKTVVTAVSQAVRHGASDAPLR LNGEDLKLVSVHINDEPWTAWKEEEGALVISNLPERFTLKIINEISPAANTA LEGLYQSGDALCTQCMAEGFRHITYYLDRPDVLARFTTKIIADKIKYPFLL SNGNRVAQGELENGRHWVQWQDPFPKPCYLFALVAGDFDVLRDTFTTRS GREVALELYVDRGNLDRAPWAMTSLKNSMKWDEERFGLEYDLDIYMIV AVDFFNTLLIPNKGLNIFNSKLVLARTDTATDEDYLRIEAAIGHIYFHNWT GNRVTCRDWFQLSLKEGLTVFRDQEFSSDLGSRAVNRINNVRIMRGLQFA | PDB ID: 4Q4E; mutant; M83 |

-continued

SEQUENCE TABLE

| SEQ ID No. | Sequence (5'→3' for DNA sequences, N-terminus to C-terminus for amino acid sequences) | Description |
|---|---|---|
| | EDASPMAHPIRPDMVIEMNNFYTLTVLYKGAEVIRMIHTLLGEENFQKGM QLYFERHDGSAATCDDFVQAMEDASNVDLSHFRRWYSQSGTPIVTVKDD YNPETEQYTLTISQRTPATPDQAEKQPLHIPFAIELYDNEGKVIPLQKGGHP VNSVLNVTQAEQTFVFDNVYFQPVPALLCEFSAPVKLEYKWSDQQLTFL MRHARNDFSRWDAAQSLLATYIKLNVARHQQGQPLSLPVHVADAFRAV LLDEKIDPALAAEILTLPSVNEMAELFDIIDPIAIAEVREALTRTLATELADE LLAIYNANYQSEYRVEHEDIAKRTLRNACLRFLAFGETHLADVLVSKQFH EANNMTDALAALSAAVAAQLPCRDALMQEYDDKWHQNGLVMDKWFIL QATSPAANVLETVRGLLQHRSFTMSNPNRIRSLIGAFAGSNPAAFHAEDGS GYLFLVEMLTDLNSRNPQVASRLIEPLIRLKRYDAKRQEKMRAALEQLKG LENLSGDLYEKITKALA | |
| 41 | VVRDVNWGALRIAVSTEDLTDPAYHCARVGQHVKDHAGAIVTCTAEDIL TNEKRDILVKHLIPQAVQLHTERLKVQQVQGKWKVTDMVGDICGDFKVP QAHITEGFSNTDFVMYVASVPSEEGVLAWATTCQTFSDGHPAVGVINIPA ANIASRYDQLVTRVVTHAMAHALGFSGPFFEDARIVANVPNVRGKNFDV PVINSSTAVAKAREQYGCDTLEYLEVEDQAGAKAAGSHIKMRNAQDELM APAAAAGYYTALTMAIFQDLGFYQADFSKAEVMPWGQNAGCAFLTNKC MEQSVTQWPAMFCNESEDAIRCPTSRLSLGACGVTRHPGLPPYWQYFTDP SLAGVSARMDYCPVVVPYSDGSCTQRASEAHASLLPFNVFSDAARCIDGA FRPKATDGIVKSYAGLCANVQCDTATRTYSVQVHGSNDYTNCTPGLRVE LSTVSNAFEGGGYITCPPYVEVCQGNVQAAKDGGN | PDB ID: 1LML; mutant; M83 |
| 42 | VVRDVNWGALRIAVSTEDLTDPAYHCARVGQHVKDHAGAIVTCTAEDIL TNEKRDILVKHLIPQAVQLHTERLKVQQVQGKWKVTDMVGDICGDFKVP QAHITEGFSNTDFVMYVASVPSHEGVLAWATTCQTFSDGHPAVGVINIPA ANIASRYDQLVTRVVTHVMAHALGFSGPFFEDARIVANVPNVRGKNFDV PVINSSTAVAKAREQYGCDTLEYLEVEDQGGRGVAGSHIKMRNAQDELM APDAAAGYYTALTMAIFQDLGFYQADFSKAEVMPWGQNAGCAFLTNKC MEQSVTQWPAMFCNESEDAIRCPTSRLSLGACGVTRHPGLPPYWQYFTDP SLAGVSALMDYCPVVVPYSDGSCTQRASEAHASLLPFNVFSDAARCIDGA FRPKATDGIVKSYAGLCANVQCDTATRTYSVQVHGSNDYTNCTPGLRVE LSTVSNAFEGGGYITCPPYVEVCQGNVQAAKDGGN | PDB ID: 1LML; mutant; M86 |
| 43 | DTQYILPNDIGVSSLDSREAFRLLSPTERLYAYHLSRAAWYGGLAVLLQTS PEAPYIYALLSRLFRAQDPDQLRQHALAEGLTEEEYQAFLVYAAGVYSNM GNYKAWGDTKFVPNLPKEKLERVILGSEAAQQHPEEVRGLWQTCGELMF SLEPRLRHLGLGKEGITTYFSGNCTMEDAKLAQDFLDSQNLSAYNTRLFK EVDGCGKPYYEVRLASVLGSEPSLDSEVTSKLKSYEFRGSPFQVTRGDYA PILQKVVEQLEKAKAYAANSHQGQMLAQYIESFTQGSIEAHKRGSRFWIQ DKGPIVESYIGFIWSVFDPFGSRGMFFGFVAVVNKAMSAKFERLVASAEQ LLKELPWPPTFEKDKFLTPDFTSLDVLTMAGLGIPLMMVIPNYDDLRQTE GFKNVSLGNVLAVAYATQREKLTFLEEDDKDLYILWKGPSFDVQVGLHA LLGHGSGKLFVQDEKGAFNFDQETVINPETGEQIQSWYRCGETWDSKFST IASSYEECRAESVGLYLSLHPQVLEIFGFEGADAEDVIYVNWLNMVRAGL LALEFYTPEAFNWRDVLMQARFVILRVLLEAGEGLVTITPTTGSDGRPDA RVRLDRSKIRSVGKPALERFLRRLQVLKSTGDVAGGRALYEGYATVTDAP PESFLTLRDTVLLRKESRKLIVQPNTRLEGSDVQLLEYEASAAGLIRSFSER FPEDGPELEEILTQLATADARFW | PDB ID: 5E3C; mutant; M86 |
| 44 | ADPDPMKNTCKLLVVADHRFYRYMGRGEESTTTNYLIELIDRVDDIYRNT AWDNAGFKGYGIQIEQIRILKSPQEVKPGEKHYNMAKSYPNEEKDAWDL KMLLEQFSFDIAEEASKVCLAHLFTYQDFDMGRLLIVYGGSPHANSHGGV CPKAYYSPVGKKNIYLNSGLTSTKNYGKTILTKEADLVTTHALGHNFGAE HDPDGLAECAPNEDQGGKYVMYPIAVSGDHENNKMFSQCSKQSIYKTIES KAQECFQERSNA | PDB ID: 2FV5; mutant; M86 |
| 45 | GSPRYLDGWLKDVVQLSLRRPSFRASRQRPIISLNERILEFNKRNITAIIAEY KRKSVSGLDVERDPIEYSKFMERYAVGLSILTEEKYFNGSYETLRKIASSV SIPILMADFIVKESQIDDAYNLGADTVLLLVMILTERELESLLEYARSYGME PIIMVLDENMLDIALRIGARFIVLHSKSHETLEINKENQRKLISMIPSNVVKV MVHGISERNEIEELRKLGVNAFIIGSSLMRNPEKIKEFIL | PDB ID: 5K7J; mutant; M93 |
| 46 | NLPQRYIELVVVADRRVFMKYNSDLNIIRTRVHEIVNIINKFYRSLNIRVSL TDLEIWSGQDFITIQSSSSNTLNSFGEWRERVLLIWKRHDNAQLLTAINFEG KIIMLAYTSSMCNPRSSVGIVKDHSPINLLVAVTMAHLLGHNLGMEHDGK DCLRGASLCIMLPDLTPGRSYEFSDDSMGYYQKFLNQYKPQCILNKP | PDB ID: 1IAG; mutant; M93 |
| 47 | PQAKYRHDYRAPDYQITDIDLTFDLDAQKTVVTAVSQAVRHGASDAPLR LNGEDLKLVSVHINDEPWTAWKEEEGALVISNLPERFTLKIINEISPAANTA LEGLYQSGDALCTQCLAEGFRHITYYLDRPDVLARFTTKIIADKIKYPFLLS NGNRVAQGELENGRHWVQWQDPFPKPCYLFALVAGDFDVLRDTFTTRS GREVALELYVDRGNLDRAPWAMTSLKNSMKWDEERFGLEYDLDIYMIV AVDFFNMIVIPNKGLNIFNSKYVLARTDTATDEDYLKIEQIIGHAYFHNWT | PDB ID: 4Q4E; mutant; M93 |

-continued

SEQUENCE TABLE

| SEQ ID No. | Sequence (5'→3' for DNA sequences, N-terminus to C-terminus for amino acid sequences) | Description |
|---|---|---|
| | GNRVTCRDWFQLSLIEGLTLFRVQEFSSDLGSRAVNRINNVRIMRGLQFAE DASPMAHPIRPDMVIEMNNFFTLTVMWKGAEVIRMIHTLLGEENFQKGM QLYFERHDGSAATCDDFVQAMEDASNVDLSHFRRWYSQSGTPIVTVKDD YNPETEQYTLTISQRTPATPDQAEKQPLHIPFAIELYDNEGKVIPLQKGGHP VNSVLNVTQAEQTFVFDNVYFQPVPALLCEFSAPVKLEYKWSDQQLTFL MRHARNDFSRWDAAQSLLATYIKLNVARHQQGQPLSLPVHVADAFRAV LLDEKIDPALAAEILTLPSVNEMAELFDIIDPIAIAEVREALTRTLATELADE LLAIYNANYQSEYRVEHEDIAKRTLRNACLRFLAFGETHLADVLVSKQFH EANNMTDALAALSAAVAAQLPCRDALMQEYDDKWHQNGLVMDKWFIL QATSPAANVLETVRGLLQHRSFTMSNPNRIRSLIGAFAGSNPAAFHAEDGS GYLFLVEMLTDLNSRNPQVASRLIEPLIRLKRYDAKRQEKMRAALEQLKG LENLSGDLYEKITKALA | |
| 48 | HWGYGKHNGPEHWHKDFPIAKGERQSPVDIDTHTAKYDPSLKPLSVSYD QATSLRILNNGHAFNVEFDDSQDKAVLKGGPLDGTYRLIQFHFHWGSLDG QGSEHTVDKKKYAAELHLVHWNTKYGDFGKAVQHPDGLAVLGIFLKVG SAKPGLQKVVDVLDSIKTKGKSADFTNFDPRGLLPESLDYWTYPGSRTTP PLLESVTWIVLKEPISVSSEQVLKFRKLNFNGEGEPEELMVDNWRPAQPLK NRQIKASF | Carbonic anhydrase II mutant, M = M64 |
| 49 | HWGYGKHNGPEHWHKDFPIAKGERQSPVDIDTHTAKYDPSLKPLSVSYD QATSLRILNNGHAFNVEFDDSQDKAVLKGGPLDGTYRLIQFHFHWGSLDG QGSEHTVDKKKYAAELHLVHWNTKYGDFDKAVRQPDGLAVLGIFLKVG SAKPGLQKVVDVLDSIKTKGKSADFTNFDPRGLLPESLDYWTYPGSRTTP PLLESVTWIVLKEPISVSSEQVLKFRKLNFNGEGEPEELMVDNWRPAQPLK NRQIKASF | Carbonic anhydrase II mutant, M = M64 |
| 50 | HWGYGKHNGPEHWHKDFPIAKGERQSPVDIDTHTAKYDPSLKPLSVSYD QATSLRILNNGHAFNVEFDDSQDKAVLKGGPLDGTYRLIQFHFHWGSLDG QGSEHTVDKKKYAAELHLVHWNTKYGDFDKAVQQPDGLAVLGIFLNVG SARPGLQKVVDVLDSIKTKGKSAYFTNFDPRGLLPESLDYWTYPGSRTTPP LLESVTWIVLKEPISVSSEQILKFRKLNFNREGEPEELMVDNWRPTQPLKN RQIKASF | Carbonic anhydrase II mutant, M = M64 |
| 51 | HWGYGKHNGPEHWHKDFPIAKGERQSPVDIDTHTAKYDPSLKPLSVSYD QATSLRILNNGHAFEVEFDDSQDKAVLKGGPLDGTYRLVQFHFHWGSLD GQGSEHTVDKKKYAAELHLVHWNTKYGDYGKAMQQPDGLAVLGIFLK VGSAKPGLQKVVDVLDSIKTKGKSADFTNFDPRGLLPESLDYWTYPGSGT VPPLLESVTWIVLKEPISVSSEQVLKFRKLNFNGEGEPEELMVDNWRPAQP LKNRQIKASF | Carbonic anhydrase II mutant, M = M06, P1 = F |
| 52 | HWGYGKHNGPEHWHKDFPIAKGERQSPVDIDTHTAKYDPSLKPLSVSYD QATSLRILNDGHAFQVEFDDSQDKAVLKGGPLDGTYRLVQFHFHWGSLD GQGSEHTVDKKKYAAELHLVHWNTKYGDYGKAMQQPDGLAVLGIFLK VGSAKPGLQKVVDVLDSIKTKGKSADFTNFDPRGLLPESLDYWTYPGSGT VPPLLESVTWIVLKEPISVSSEQVLKFRKLNFNGEGEPEELMVDNWRPAQP LKNRQIKASF | Carbonic anhydrase II mutant, M = M06, P1 = F |
| 53 | HWGYGKHNGPEHWHKDFPIAKGERQSPVDIDTHTAKYDPSLKPLSVSYD QATSLRILNNGHAFNVEFDDSQDKAVLKGGPLDGTYRLIQFHFHWGSLDG QGSEHTVDKKKYAAELHLVHWNTKYGDFGKAMQQPDGLAVLGIFLKVG SAKPGLQKVVDVLDSIKTKGKSADFTNFDPRGLLPESLDYWTYPGSGTVP PLLESVTWIVLKEPISVSSEQVLKFRKLNFNGEGEPEELMVDNWRPAQPLK NRQIKASF | Carbonic anhydrase II mutant, M = M06, P1 = F |
| 54 | HWGYGKHNGPEHWHKDFPIAKGERQSPVDIDTHTAKYDPSLKPLSVSYD QATSLRILNDGHAFEVEFDDSQDKAVLKGGPLDGTYRLIQFHFHWGSLDG QGSEHTVDKKKYAAELHLVHWNTKYGDFGKALQQPDGMAILGIFLKVG SAKPGLQKVVDVLDSIKTKGKSADFTNFDPRGLLPESLDYWTYPGSQTIPP LLESVTWIVLKEPISVSSEQVLKFRKLNFNGEGEPEELMVDNWRPAQPLK NRQIKASF | Carbonic anhydrase II mutant, M = M06, P1 = H |
| 55 | HWGYGKHNGPEHWHKDFPIAKGERQSPVDIDTHTAKYDPSLKPLSVSYD QATSLRILNNGHAFLVEFDDSQDKAVLKGGPLDGTYRLKQFHFHWGSLD GQGSEHTVDKKKYAAELHLVHWNTKYGDYGKALQQPDGIAVLGIFLKV GSAKPGLQKVVDVLDSIKTKGKSADFTNFDPRGLLPESLDYWTYPGSRTIP PLLESVTWIVLKEPISVSSEQVLKFRKLNFNGEGEPEELMVDNWRPAQPLK NRQIKASF | Carbonic anhydrase II mutant, M = M06, P1 = E |

-continued

SEQUENCE TABLE

| SEQ ID No. | Sequence (5'→3' for DNA sequences, N-terminus to C-terminus for amino acid sequences) | Description |
|---|---|---|
| 56 | HWGYGKHNGPEHWHKDFPIAKGERQSPVDIDTHTAKYDPSLKPLSVSYD<br>QATSLRILNNGHAFLVEFDDSQDKAVLKGGPLDGTYRLIQFHFHWGSLDG<br>QGSEHTVDKKKYAAELHLVHWNTKYGDYGKALQQPDGIAVLGIFLKVG<br>SAKPGLQKVVDVLDSIKTKGKSADFTNFDPRGLLPESLDYWTYPGSRTIPP<br>LLESVTWIVLKEPISVSSEQVLKFRKLNFNGEGEPEELMVDNWRPAQPLK<br>NRQIKASF | Carbonic anhydrase II mutant, M = M64, P1 = E |
| 57 | HWGYGKHNGPEHWHKDFPIAKGERQSPVDIDTHTAKYDPSLKPLSVSYD<br>QATSLRILNDGHAFRVEFDDSQDKAVLKGGPLDGTYRLKQFHFHWGSLD<br>GQGSEHTVDKKKYAAELHLVHWNTKYGDFGKAGQQPDGIAILGIFLKVG<br>SAKPGLQKVVDVLDSIKTKGKSADFTNFDPRGLLPESLDYWTYPGSETIPP<br>LLESVTWIVLKEPISVSSEQVLKFRKLNFNGEGEPEELMVDNWRPAQPLK<br>NRQIKASF | Carbonic anhydrase II mutant, M = M06, P1 = T |
| 58 | DWGYDDKNGPEQWSKLYPIANGNNQSPVDIKTSETKHDTSLKPISVSYNP<br>ATAKEIINVGHSFHVNFEDNDNRSVLKGGPFSDSYRLFQFHFHWGSTNEH<br>GSEHTVDGVKYSAELHVAHWNSAKYSSLAEAASKADGLAVIGVLMKVG<br>EANPKLQKVLDALQAIKTKGKRAPFTNFDPSTLLPSSLDFWTYPGSLTHPP<br>LYESVTWIICKESISVSSEQLAQFRSLLSNVEGDNAVPMQHNNRPTQPLKG<br>RTVRASF | Carbonic anhydrase I, *Homo sapiens* (scaffold); |
| 59 | PQAKYRHDYRAPDYQITDIDLTFDLDAQKTVVTAVSQAVRHGASDAPLR<br>LNGEDLKLVSVHINDEPWTAWKEEEGALVISNLPERFTLKIINEISPAANTA<br>LEGLYQSGDALCTQCEAEGFRHITYYLDRPDVLARFTTKIIADKIKYPFLLS<br>NGNRVAQGELENGRHWVQWQDPFPKPCYLFALVAGDFDVLRDTFTTRS<br>GREVALELYVDRGNLDRAPWAMTSLKNSMKWDEERFGLEYDLDIYMIV<br>AVDFFNMGAMENKGLNIFNSKYVLARTDTATDKDYLDIERVIGHEYFHN<br>WTGNRVTCRDWFQLSLKEGLTVFRDQEFSSDLGSRAVNRINNVRTMRGL<br>QFAEDASPMAHPIRPDMVIEMNNFYTLTVYEKGAEVIRMIHTLLGEENFQ<br>KGMQLYFERHDGSAATCDDFVQAMEDASNVDLSHFRRWYSQSGTPIVTV<br>KDDYNPETEQYTLTISQRTPATPDQAEKQPLHIPFAIELYDNEGKVIPLQKG<br>GHPVNSVLNVTQAEQTFVFDNVYFQPVPALLCEFSAPVKLEYKWSDQQL<br>TFLMRHARNDFSRWDAAQSLLATYIKLNVARHQQGQPLSLPVHVADAFR<br>AVLLDEKIDPALAAEILTLPSVNEMAELFDIIDPIAIAEVREALTRTLATELA<br>DELLAIYNANYQSEYRVEHEDIAKRTLRNACLRFLAFGETHLADVLVSKQ<br>FHEANNMTDALAALSAAVAAQLP | Artificial (4Q4E reduced) |
| 60 | AFAAE | model peptide |
| 61 | XAAAE | model peptide |
| 62 | DAEIR | model peptide |
| 63 | EAEIR | model peptide |
| 64 | AAEIR | model peptide |
| 65 | FAEIR | model peptide |
| 66 | LAEIR | model peptide |
| 67 | MHKTRLVAALAAALATLAPAAWADEGMWVPQQLPEIAGALKKAGLKL<br>DPKQLSDLTGDPMGAVVSLGGCTGSFVSPQGLVATNHHCAYGAIQLNSTP<br>EKNLIKDGFNAPTQADELSAGPNARIYVLEGITDVTAQAKAAMAAAGND<br>PVARANALEAFEKKITSDCEAEPGYRCRVYSFMGGITYRLFKNLEIKDVRL<br>VYAPPSSVGKFGGDIDMGMWPTHTGDFSFYRAYVGKDGKPAPY<br>SKDNVPYRPKHWLKIADTPLGEGDFVMVAGYPGRTDRYALVAEFENTQN<br>WLYPAISKAYKDQIALVEAAAKDNPEIAVKYAAALAGWNRTSKNFDGQL<br>EGFKRNDVLAIKRREEAAVLEWLRARGKAGTPALEAHAALVKLVADTAR<br>TQERDLVLGSFNRTGIIGVAVNLYRLAIERQKPDAEREPGYQQRDLPVIEG<br>SLKQMERRYVPAMDRQLRAYWLDRYVALPAAQHVAAVDAWLG<br>GSDKAAAEAALARLDQSRLGSLEERLKWFNADRAAFEASTDPAIQYAVA<br>VMPTLLAMEQQAKTRYGVALEARPRYLQAVVDYKKSKGQAVYPDANST<br>LRITYGHVKGYTGLNGKVYTPFTTLEEVAAKETGVEPFDNPKALLEAVAA<br>KRYAGLADARLGTVPVNFLADLDITGGNSGSPVLDANGRLVGLAFAGTL<br>ESVASNWVFDPVLTRMISVDQRYMRWIMQEVMPAPQLLEELGVP<br>PRQ | engineered cleavase |

-continued

SEQUENCE TABLE

| SEQ ID No. | Sequence (5'→3' for DNA sequences, N-terminus to C-terminus for amino acid sequences) | Description |
|---|---|---|
| 68 | SHHWGYAKHNGPDSWHENFPIAKGERQSPVNIDSRSAKHDPALKPLSINY EQATSRKILNNGHSFNVEFDDSQDKAVLKGGPLDGTYRLIQFHFHWGSSD EQGSEHTVDKKMYPAELHLVHWNTKYADFGQAVQHPDGLAVLGIFLKIG SAKPDLQRVLDILDSIKTKGKSAEFKNFDPRGLLPNSLDYWTYPGSLTTPP LLECVTWIVLREPISVSSEQIKKFRSLSINGDNEPEEPMVINFRPPQPLKSRQI RASFK | S320_0000-XP_004697542.1_ carbonic_ anhydrase_2_ [*Echinops_telfairi*] |
| 69 | MSWGYEKNNGPALWHENFPVAKGNRQSPIDISTKACQVDNQLCSKPFQI NYSTEKNAEVSNTGSSIKVQIKEVSEIKGGPLEGTWRLEQFHLHWGSSND RGSEHTIDGKTYAAELHLVHWNAKKYASFGEAADKPDGLAVLGFMVNV GKEHAGFKTITDVCSKIQEAGSSVKLDKDFNPSCMLGKLDHYWTYLGSLT TPPLFESVTWTLFSDVIEISQAQMDALRSLKFNNGKCMMDNYRPPCALCG RSVKASK | S325_0000-carbonic_ anhydrase_2_ isoform_X2 [*Crassostrea_gigas* |
| 70 | LHWGYDEHNGPAHWKEVFPVANGDRQSPIDIKTEETKYDPSLRPLNPNY DPASAKIILNNGHSTSVEFDDTVNKSVLTGGPLSGTYRLRQIHFHWGSNDE AGSEHAVDGMKYAAELHVVHWNAEKYSSFVEAARQSDGLAVMAVFLKI GECNPQLKKITDRLDTIRIKGKKALFTNFDPSCLLPKSLDYWTYFGSLTVPP LLESVIWIVLREPISVCSEQLAKFRSLLSTAEDEVACCLLRNFRPPQPLKGR EVRRN | S334_0000-XP_030300927.1_ carbonic_ anhydrase_13-like_ [*Calypte_anna*] |
| 71 | AHSWGYDVENGPDKWGDHFPIANGPRQSPIDVVPSQAQYDASLAPLSIQY DPATAKGILNNGHSFQVDFVDSEDRSVLKGGPVSGTYRLRQFHFHWGSSD EHGSEHTVQGVKYPAELHLVHWNSGKYPSFGESAAQPDGLAVVGVFLKI GNANPYLQKIIDAFDAIKEKGKQTSFSDFNPATLLPGSLDFWTYDGSLTTP PLLESVTWIVLKETISVSAEQMARFRSLLFTGDGEAPCHMVDNYRPPQPLK QRSVRASFK | S336_0000-_ carbonic_ anhydrase-like [*Acipenser_ruthenus*] |
| 72 | SHAWGYGAANGPHKWAEDFPVANGSRQSPINIVTSDTLYDPTLKPVKLTF DPSTCTGILNNGHSIQVDFEDDTSSSTLTGGPVSGTYQLRQFHFHWGAADE RGSEHTINNFSFPCELHLVHWNNKYPSFGEAVTKPDGLAVLGVFLKIGPA NPRLQKLLDLLDAVKTKGKQTDLSFFDPKTLLPNSQHFWTYDGSLTTPPL LESVTWIILKEPISVSPAQMRKFRSLLFSGEGEAPLCMVDNYRPPQPLKGR KVRATFK | S337_0000-_ carbonic_ anhydrase [*Thalassophryne_ amazonica*] |
| 73 | SHHWGYGKHNGPENWHKDFPIAKGERQSPIDIDSKAANYDPSLKPLHISY QQAASRRIINNGHSFNVEFDDSQNKAVLEGGPLTGPYRLIQFHFHWGSSD GLGSEHTVDKKRFPAELHLVHWNTRYGDFGKAVQHTDGLAVLGIFLKIG GAKPDLQKVIDVLDSIKTKGQSADFPNFDPRGLLPESLDYWTYPGSLTTPP LLECVTWIVLKEPISVSSEQILKFRNLHFNKEGDPDEVMVDNWRPVQPLK NRQIKASFQ | S340_0000-_ carbonic_ anhydrase_2_ [*Manis_javanica*] |
| 74 | SRHWGYASHNGPAHWHENFPIANGEHQSPIDINTESAQYDFSLKPLHFSY DPSTAKNIVNNGHSFNVEFDDSADKSVLRGGALEGTYRLIQFHIHWGSCE GQGSEHTVDGVQYDAELHLVHWNTKYGRFGEAVKHPDGLTVVGVFLQV GSDRPGIQKIIDALDSIQTKGKQASFTNFDPKNLLPTSLDYWTYQGSLTTPP LLECVIWHVLREPISVSSEQLCKLRGLCFSAENETPYHMMDNWRPCQPLK GREVRASFQ | S344_0000-_ carbonic_ anhydrase_2-like_isoform_ X1_ [*Mauremys_reevesii*] |
| 75 | EWGYASHNGPDHWHELFPNAKGENQSPIELHTKDIRHDPSLQPWSVSYD GGSAKTILNNGKTLGVVFDDTYDRSMLRGGPLPGPYRLREFHLHWGSSD DHGSEHTVDGVKYAAELHLLHWNPKYNTFKEALKQRDGLAVIGIFLKIG HENGEFQIFLDALDKIKTKGKEAPFTKFDPSSLFPASRDYWTYQGSMTIPP LMEAVVWLLLKEPMTVSSDQMAKLRSLLSSAENEPPVPLVSNWRPPQPIN NRVVRASFK | Synthetic binder, S279_0004 |
| 76 | SHHWGYGKHNGPEHWHKDFPIAKGERQSPVDIDTHTAKYDPSLKPLSVS YDQATSLRILNNGHTFLVEFDDSQDKAVLKGGPLDGTYRLRQFHFHWGS LDGQGSEHTVDKKKYAAELHLLHWNTKYGDYGKAKQQPDGIAILGIFLK VGSAKPGLQKVVDVLDSIKTKGKSADFTNFDPRGLLPESLDYWTYPGSMT IPPLLESVTWIVLKEPISVSSEQVLKFRKLNFNGEGEPEELMVDNWRPAQP LKNRQIKASFK | Synthetic binder, S222_0431 |
| 77 | SHHWGYGKHNGPEHWHKDFPIAKGERQSPVDIDTHTAKYDPSLKPLSVS YDQATSLRILNNGHAFDVEFDDSQDKAVLKGGPLDGTYRLHQFHFHWGS LDGQGSEHTVDKKKYAAELHLVHWNTKYGDYGKAAQQPDGLAILGIFL KVGSAKPGLQKVVDVLDSIKTKGKSADFTNFDPRGLLPESLDYWTYPGS MTIPPLLESVTWIVLKEPISVSSEQVLKFRKLNFNGEGEPEELMVDNWRPA QPLKNRQIKASFK | Synthetic binder, S222_0882 |
| 78 | SHHWGYGKHNGPEHWHKDFPIAKGERQSPVDIDTHTAKYDPSLKPLSVS YDQATSLRILNDGHAFAVEFDDSQDKAVLKGGPLDGTYRLFQFHFHWGS LDGQGSEHTVDKKKYAAELHLVHWNTKYGDFGKAKQQPDGLAVLGIFL | Synthetic binder, S222_0397 |

-continued

SEQUENCE TABLE

| SEQ ID No. | Sequence (5'→3' for DNA sequences, N-terminus to C-terminus for amino acid sequences) | Description |
|---|---|---|
| | KVGSAKPGLQKVVDVLDSIKTKGKSADFTNFDPRGLLPESLDYWTYPGSQ TVPPLLESVTWIVLKEPISVSSEQVLKFRKLNFNGEGEPEELMVDNWRPAQ PLKNRQIKASFK | |
| 79 | SHHWGYGKHNGPEHWHKDFPIAKGERQSPVDIDTHTAKYDPSLKPLSVS YDQATSLRILNNGHTFIVEFDDSQDKAVLKGGPLDGTYRLVQFHFHWGSL DGQGSEHTVDKKKYAAELHLVHWNTKYGDLGKALQQPDGLAILGIFLKV GSAKPGLQKVVDVLDSIKTKGKSADFTNFDPRGLLPESLDYWTYPGSWT VPPLLESVTWIVLKEPISVSSEQVLKFRKLNFNGEGEPEELMVDNWRPAQP LKNRQIKASFK | Synthetic binder, S222_0903 |
| 80 | SHHWGYGKHNGPEHWHKDFPIAKGERQSPVDIDTHTAKYDPSLKPLSVS YDQATSLRILNDGHAFKVEFDDSQDKAVLKGGPLDGTYRLEQFHFHWGS LDGQGSEHTVDKKKYAAELHLVHWNTKYGDLGKAMQQPDGLAILGIFL KVGSAKPGLQKVVDVLDSIKTKGKSADFTNFDPRGLLPESLDYWTYPGSQ TIPPLIESVTWIVLKEPISVSSEQVLKFRKLNFNGEGEPEELMVDNWRPAQP LKNRQIKASFK | Synthetic binder, S222_0395 |
| 81 | SHHWGYGKHNGPEHWHKDFPIAKGERQSPVDIDTHTAKYDPSLKPLSVS YDQATSLRILNNGHAFRVEFDDSQDKAVLKGGPLDGTYRLHQFHFHWGS LDGQGSEHTVDKKKYAAELHLVHWNTKYGDFGKAEQQPDGLAILGIFLK VGSAKPGLQKVVDVLDSIKTKGKSADFTNFDPRGLLPESLDYWTYPGSMT VPPLLESVTWIVLKEPISVSSEQVLKFRKLNFNGEGEPEELMVDNWRPAQP LKNRQIKASFK | Synthetic binder, S222_0913 |
| 82 | ASPDWGYDDKNGPEQWSKLYPIANGNNQSPVDIKTSETKHDTSLKPISVS YNPATAKEIINVGHSFRVNFEDNDNRSVLKGGPFSDSYRLYQFHFHWGST NEHGSEHTVDGVKYSAELHVVHWNSAKYSSLAEALSKADGIAVIGVLMK VGEANPKLQKVLDALQAIKTKGKRAPFTNFDPSTLLPSSLDFWTYPGSWT APPLYEIVTWIILKESISVSSEQLAQFRSLLSNVEGDNAVPMQHNNRPTQPL KGRTVRASF | Synthetic binder, S254_0083 |
| 83 | DARVEEIVALLEGDVADAEERLARIIELIGEMTPEEQRALAERVRESGELA ENLLRLLEATSDEFVRTELAALIKKLTTAGKAALVEMLVEMLLRNPDVSR DVIRKIHELMHAIGFYHSSENPAGFVRTLGELLAELATPELAPFVRELFDK VVEKVEAAIKAGKSTEEIQKLMAEALSEAFLEFAKRGDPRLTVRMISITAL VHTIMHYPEDAELVKEFAEAMLETLDEIAERTPELREEILRERELLKKTIEN ILKT | Synthetic binder, S396_0000 |
| 84 | MEEEKRELLKKALEAFEKFEAEKDEEEKIRLAVIALAYLQALKALEDGDE EKAKLFKEFAEKAKTATEEEAMKILHELMHAIGFYHAEEEKESDEEFLAR VRAILEDTLLSFAEVKGRELGLDPEEARAIAREVFAELPEEAWRTWAKMV RLIMHYGYDREELRKLLLEASESLAAAVRRLLARLEA | Synthetic binder, S397_0000 |
| 85 | SALEEEYARLRAAVEARATRLAERLAARAEDPRVRAAIADLLARLRAAL AAGPTRVRLLTALLALIIAEAILEDPELAAKIIHEIMHYTTPEEYVALIDKIF KLAGLDIEATDEDKRKAWQALHELMHAIGFYHDTPYEEILKYLKENGWR IAAALMAGAVVYLEEGLEAALEAARATLEAMAAAEEELAKEREEAA | Synthetic binder, S398_0000 |
| 86 | MEEEERRRRRERLEEAAEAVAETLRRLIFARAFFGPAAALAIAEEALAAA KASGDEEVEELFRLLLLQVRGNVGLRAALALPLFRDVLERILAEMVSVIM HYGSVEELVAAFIALLVRLAIELLLLLARYRAEISPAERVAILIAAVSAVVT AYLIATEATPWTRRLVLQILHELMHAIGFYHDTSTEEVLAFMRERPEEFLL ALDALGLLGVASLRLGTLYERAGFREEAERIARRLAEVTVAALKEALKLR | Synthetic binder, S399_0000 |
| 87 | AAERREEVRREVEEILEELEKRVEEAKAAKEWTEAQKLVAIAAAFLEALA RLADLIAERGDVPLELVLKAYQKLHELMHAIGFYHAEKAKEILEKKFSIIK GISEETKKTVTEAVLFIMHYWDSSPEEMAREYRAWLLARRPEIRKAAEEL KALLKAMEAAA | Synthetic binder, S400_0000 |
| 88 | SRLRELQARARARLLALSVADLRALAAAAKNPAMALMLAELARARELLA ASEEALREDVLAAAEAARARLAELSRDEAIAIMFRLALYLALFPDLSEEER RRLLEVMHELMHAIGFYHAEENPKKNIEVAAELAKEFLLDVDMFLDIRA REGWPQEKLDAVREETRRILEEMKEKAKTATLEEYEEIMKKAAEEIAKRL EEAGFREGAEIMKLAFEHEIQATRAAYLIMHYPKSEEDRERTLEAIVEHVL LFLELLAALVAAARRAAARAAARAA | Synthetic binder, S401_0000 |
| 89 | TAELEELLAQAAELLRALEEGDLERADELFAELGEAGLELLRLYALVNRT LAVAEIMHYYETEEELLERLERLKGILRRAAYALERTGLDPELLELFKRLL EALEDPSLTDEELIEIWKEAHELMHAIGFYHADEYIEKLTQAFYEASVADV ETLARGAAAMLYAGRGEEALARLRALALAAFPELAPLVDRAVELAAENP VLAITLLLLLLRVAQ | Synthetic binder, S402_0000 |

-continued

SEQUENCE TABLE

| SEQ ID No. | Sequence (5'→3' for DNA sequences, N-terminus to C-terminus for amino acid sequences) | Description |
|---|---|---|
| 90 | MIIFAIADFDATERVAAFVREKLREGKVRTVIIVAFFAGSPEAALAALALFA<br>ETVKAVVLTIKEVTKGKSIGLLLVFDLGIHSREAEAAAAVLEAALPVIARA<br>VAEAKDAGAIEEVELVITSFNNAALLERVVAHARALFEREVAGAKVHGIN<br>TAPDEAGQEALVEYIAELAKELAERTDYLVVALASIHTTRPDSRVVKLMT<br>RLILAIIERLDSPVLIIGLAGTPIVLAAMVYIMLTLQEAKGLEVENLLSPEGA<br>ALLAAIRAAEAAARLAAALAA | Synthetic binder, S403_0000 |
| 91 | MKAMVGVIFVLVGGASPEEQKEAHEKFREIIDILKEVLGVDKVFYGMFIL<br>DASVSIEEFKKQVKELKEKFKKWAEAIKKELKEKYKVDELVVSVSIHVVE<br>PKDKSEEEKEEYEKLVKELAEEFAVQMAKLSEGFKKRIFYFDLGIHSRESI<br>EKQAKLLKSAIEAMLKYLEEKEKEKKEEIEVYIGVRYVASTSEEELKKLKE<br>IFEKEAEELKKLAEEYGVKFFAGFGTSSREDLEKIFNKFKEAID | Synthetic binder, S404_0000 |
| 92 | MLIVHVLLNLSGSIEESVERAKTILEAVFEVTAGKKILLISIHLGLGIELKDS<br>AREALKRLEAFAKELAKKYGSELTIRFVYVDDSLEEAHARAVARTREILE<br>RAVEEEGVDVIVTDLGIHSREVELAGPMYAAILETMKELADREGGTLIGV<br>AVGTPEANARFAAMLEAVGARVLVASEEDSLEEIRARVRAALEAAL | Synthetic binder, S405_0000 |
| 93 | MKAGLVVAALLDEENKEAQEEQLKKLKEFLKENYPKLDMVIVVTPVGSE<br>ATAASAARIMREIRELFPEDFDAAIAGENISDTRLLEQIAREAGLPLAGTLY<br>SDDEPRGREAVERLAAELGRPIVNAGGSAYNAGVLIELAIKRGSKLLVLAT<br>HGAGFFAIIGEAINALLREADEVEIGVFVSASPRVTFIAYSLAIAAALLENGL<br>DAARARLEILETEYGFPRALTLHASMRPEDAKRAVEALADEIDYVNIVMD<br>PHVADNAEELVKVVVEEAAKKGLKKIRFWFLGGESGAERALRVAKVLFE<br>EAKKYGIEVEIEFFTDSPKAKELIEEIEKLKKELE | Synthetic binder, S406_0000 |
| 94 | MGKITFLAGATTEDVAALLAEELRRIRERYGIRGAIAGENISDTRLLEQIAR<br>EAGLPLAGTLYSDLGPEYLPLALARTDALLERWADYEGVWFSANNRVAI<br>RALELAAERGLRVVVLSSGAPTIALALRAAELSPRFEEIIFSSHGLNLAMGA<br>AALYLIAREKGIEFELRLRNASDRTLVALAGAKAVWEDLEAYAKEEGVEL<br>KVVAFETTGTEEEAKARKEELIKKAKEEGALAFLIGGDPHGLMSPETAAAI<br>ATELIEAMADIGVKHIIVILGDEPNTRVMVEAIMAKIKEVIKEKGIEKVYVF<br>GDSPFVAALAAELAELANATLWRGA | Synthetic binder, S407_0000 |
| 95 | SLLTSFHETLKNLLEVMKDLGFEYLTAHLHFGEEGGTLHLLFYNPAHGTP<br>EAAREAPPRGIPLVSKTFPDGSTISTTAATTGSDGGFAEVTIGLKEGDGPDQ<br>VLSLPKNQTLDVSEGGFTGDLESLKSEKELENYLKGKEIANQIVEGKYKT<br>VGFRSLPGKVEIIGTNLDGTTETVTIDKLEFDPEKLSRRGVTHLTLANAAV<br>GVPLP | Synthetic binder, S408_0000 |
| 96 | MEALLERARRRIRERQEREVLDGLIALARATAEEAGFRFVDEHEHRSPGP<br>AVLNGLRHLLFYNPAFGTEAAARKARLGPGGAPRAVRVTPEELAAALRE<br>ALAAVRDTAGFAVVTLPLVDPSLLSPHVRAVFASLGARGGARLIVLGVAS<br>LASSFTHDEDGGANEAEFALHNRVWEHLLAALETVRDEADLRAAADAAL<br>AKWLELVPELEAALAGRPRNVAHLVLGYLLYVEVSEEAVAAELARLAAE<br>AAAA | Synthetic binder, S409_0000 |
| 97 | SNREAVLRRLLERALAALEAAGFRVLGVHLHFGYKEEMAKDPSGKKIVL<br>PYGHLHILAWNPAFGTLEAALKARVAERPAIIEAAYISPRESDIERLIELVR<br>TEPVARLSIMFLNVTPESIKGLIRLLEALAERPDIKVKLFVTKSADVSELLK<br>KAKELGIEVKEVDLSEWKLLWEAIEEGYAAVYVANIPEEDPLALKILEEFA<br>ERALARALASLAGAPLVEVEIDLNPTDPLNYGFRTRAGRLTHGFKFPLPV<br>MMAFFDYSGSREVVKKSAELFKEDVLTLARLGFIEDVVVALAAGGAATR<br>AKLAESADIIVEMLRELAEALAALGKRFRVAVVAARDPADTAALLALLA<br>RLPELEVEVVREDRDVGRNVALIELDVSLNVGKVKV | Synthetic binder, S410_0000 |
| 98 | MVEELMAVLEYWVETLKKAVSPVTGYKFVRSHIHSEPGGEAEGHVHLVF<br>YNPKYGTLEAALKHGKDVKAPVRVHVEPLTPEQAALRRKGMLYVLGSEE<br>AQRRLPWYRTVALAYAEALRDLAEAAGAPLLPDSMLNPEAILATIDEAVA<br>AVKEEGKLITEPPSPEELKLVEADAANVVKFIKEEVAEDLQKFGILVVELP<br>LMPLDSFLYYLGPQNGVLSYSGGLTFPPEEMAAALLPQYEHYEKLRKKAE<br>EILKEARKLIKEAKKKEGEDKEKVEELKKKVREKIKEYMELEKERARLGF<br>SPGYEIAFRLEELLEEEGVDEEFKEEVRERIREFIYEAVKENFARELAKEGN<br>VFRIKVFTGVPFFATPETRPAIEARMEEDAARVRA | Synthetic binder, S411_0000 |
| 99 | SAARRAALAARARERLEEAIKAVKEILEKNKEKIGYELLDYHLHAEPREP<br>VDDDPSLPRLVGIVHFTLYNKEFGTPEAALKANGGKAPGFLVFSVLLLSRR<br>PEYESTFSTGVLSYLGNPTTPDGHGGMPFDLAQKLLGKTSLAKIKEYYTK<br>NYYYIEGPDYTGPLEEQISYLKEVLETAVENMPAIKAAVMASGDGSGNVL<br>WVILLAGVVVDDEAADAWLAELAAARA | Synthetic binder, S412_0000 |
| 100 | (A/C/D/I/S/V/Y)X(C/N)X(A/C/G/R/S/V)XX(C/F/I/L/T/V)X<br>(C/G/K/N/V)X(F/I)(D/E/K/N/V)(D/E/F/N/Q) | Conserved motif |

-continued

SEQUENCE TABLE

| SEQ ID No. | Sequence (5'→3' for DNA sequences, N-terminus to C-terminus for amino acid sequences) | Description |
|---|---|---|
| 101 | (G/Q/R)(A/C/D/I/L)XX(C/F/I/V)H(F/I/L)H | Conserved motif |
| 102 | H(C/L/V)X(C/D)/H/L/V)(E/H/L/M/R/W/Y)N(A/N/P/S/T)(E/K/R/S/Y)(A/L/S/Y) | Conserved motif |
| 103 | (A/S)XX(A/E/H/K/Q)(A/P/R/S/T)D(G/I/V)X(A/T/V)(I/L/M/N/R/V) | Conserved motif |
| 104 | G(A/C/F/I/S)X(A/D/M/T)XPX(C/F/L)X(C/E/R)X(I/L/R/V) | Conserved motif |
| 105 | KKQHVVLVLLPESKVGGSPAAEAILEGVKEALEEANSPEVKGRLYRTTILPEQAREAARYGRDVQNSLGAGVVLFYASPPGESGAPAQPFTREAVLAQVRAALAADTRETPGPKAAQAHVHADGVEHRALNVVDGRVDEASLEAVKEVEGATAWEVHVLLGRLAPFRTPSPNYAVAKPPEERAAALAAVAAALAQAIPGISVLLVGEDSTERATAAARAAVAAAGATPVVRGLDIGEITDESDLERIKEAAKEAVREAIAER | Synthetic binder, S508_0000 |
| 106 | AGGAAGLAPLVGVGEEQRPELERALREALERLGLPLPPEDLPPGTRVELHILSRDGNLAVLAPPGLEAARAIADWLVAQGLVSQYHLHISGPEPEAEKVAKEIIKAFGGDESVLVAPELRHGGVAPGVPRETYEEVAELLPEEGRAFLLYLIATLSRGTNLGLRSDPAALDAAEHTRGSGLRWYGESLRLAGRVLSEELLAAARAVVDRIFGKVRGASEERLEEAARELVEALVELLEEERREEVREGAERAAERLLRLGLAR | Synthetic binder, S509_0000 |
| 107 | ATEWAVSLSLGGDGEIRPLAGPVDSPESRARIAAATRVGVHLYPLPENYRTGEESFADARAAFAALRARFADTATLFPFGIIGTLFVFTAVGDRAAIRALIDATVELFGHRVSFSGPSQVHTHGPGDIRARTLGDVSTAELPAVAEAELARARPDEEVHALDASGAAVYLGGRETGAQGIKAPYRVATVSLNRSTDEALAAVDAALAAGADEITALGFAETAEENARVRANLEALLARFPDAVAEERANADGQYLLARVRLR | Synthetic binder, S510_0000 |
| 108 | ATEWGVTLSLGAGGELRPLAGPVDSPESQARIAAATRVGAHVYPLPLNVRTGEESFADARAAFDELKARFADTVDLFSLGIIGTLFVFVGTGDAAGVAALIRAIVERFGQRVSFSGKSQVHTHGPGDIRSRALGEVKTEELEAVARAELKNARPDEEVHALDADGAAVYLGGAETGAQGIKAPFRAATVSLGRSTDEALAAVDRLRALGADEILALGFATTEEENARVRANLEALRARFPDAEAWEEANADGRNLLARIRLR | Synthetic binder, S511_0000 |
| 109 | APAVGVAALRKGREEGNVITPEGRALAEALAAADPRIRVEGTVLSVTAATEAELEAAVARLAAAFRARGYTVVIVGPADLPALAHADVAVVPSEPGAALEAEAQAHPDHEITEVHLVRPGRVETLPLRPEELRALDPRLAAEGSQWHAHGVAPDSPLRGYGEHGPRPPLGPFSSILA | Synthetic binder, S512_0000 |
| 110 | KTALQVWVDAEKALIDELLERDPRVSAEQAALARELLDLRAAESKTSNVATPEYFAFLEAHAEELAALREAPLGHLVGVYPVGTTLANLTIFPRVDPERHPLEALVRVFNALPGFAPNELHVVRPDGSVQRVRGAEGIERVTGAPLPPLKGKYAEHSEPGAEEVTLEPGSQVHFHGDYALTPEQFKAFVRRLNEEAGPAVWGLTVVDAPAEFAPLALARVRLAIEFGLDVEVTLTGAAFAAELAAALRAAAAEAGVRATVTIR | Synthetic binder, S513_0000 |
| 111 | KTALQLHIDHLLALIDRLIEEDPRVDRELAELAKELLRAYGELAKTGNVRTPEFVALEKEHAEKLKEAEKALVGKALNVVPVGTVFANLTIFPFVDPSKTKLKDLVDVFNSIPGFNPGELHVVHPDGTVQRVRSKEQIERVLGAKLPEGEAKYPEHSEPGAEEVTLRPGSQVHFHGDTSLTPEQFKAFVKLANEKAGPVVAGITLVDVPAEYAPLALERARFWIDFGVDVELTAVGTAFAPELEAAVRAAGAEAGVRVTVTIR | Synthetic binder, S514_0000 |
| 112 | AEARRELVDLLIERIRRFAKLGDEEDQKHAELAIKSLELEAELSKTSNIATKEYFDFEEENKEEWEKLKKSRIGKVHGLYPSGTTSAALSISLTVGASPEHLKAGFAALNALPGFAPGELHVVRPDKSVSRVVGREGIERVTGAQVSPLTATAAEHSDAGEEEVTAQPGDQFHVHGDKSLTREEFIALNRRVHEAGGRVRRGVVAAAGSEEEADATLELIRFYLELNLEVRLTVSGDEAAGERIREEARRLAEERAAEAVPGRAL | Synthetic binder, S515_0000 |
| 113 | KTALQVWIDAELALIDRLVREDPSVSPEQADLARELLRARGAEAATGNVATPALRALEAAHAEALAALREAPLGKLLNVYPVGTTFANLTIFIYVDPAKTKLEDLFAVYNSIPGFAPAELHVVHPDGSVQRVRTPEQIERVTGAKTPPSRAAWAEHDEPGAEEVTLEPGSQVHFHGPHSLTVEEFKEFVKLANEKAGPVRWGLTLVDAPASFAPLALERVRLAIDFGLDVEITLRGTAFAPELEAAARAAGAAAGVAVTVTIE | Synthetic binder, S516_0000 |

-continued

SEQUENCE TABLE

| SEQ ID No. | Sequence (5'→3' for DNA sequences, N-terminus to C-terminus for amino acid sequences) | Description |
|---|---|---|
| 114 | AEARGAIIDFLIELIKEVAEREDEETKKFAELSIKLLEKERELSKTGNYATQ EYFNFIEENREAFEKLKKSKIGRLLALYPRGTTLAATTISLGGAAVDRSKL KAFFEVLNAVPGFAPGELHVVRPDGSTSYVVGKENIEKVTGAKTPPLEAK RAEHSKEGDKVVEVQPGDQAHVHGDHSFTIEEFIAAARRAREAGSVPLVG LTVDAGTEEEAELSLRRIAFYLELGFDVTFTTSGDAEASERIRERALALGA EAAARFGVRVL | Synthetic binder, S517_0000 |
| 115 | AEARRDLIDFLLEEVDELAKTLDEEGREHAEKAKEILRLEAELSREGDYAT QEYFDFLEEHKEFLEKLKKSLIGKNLGLTPQGTTLAATTVSFGGGGLQSQA KAWFEAFRAIPGFAISELHVVYPDGSTSYVRGRENIERVTGAETTPLRGRR AEHSGEGEKEVVAKPGSQLHAHGDHGLTREEFIAAARRNAEAGGPVSVG LQVSASSGASAELALRRARRFAELGLVVSYTTTGDAEAGARLRAAVDAV LAEAAARFGIGGLA | Synthetic binder, S518_0000 |
| 116 | AEAVQEHAELLIKDLKEFAEIEKSEEVKEDTELAIELIKKYAELSKTSNVAT KEFFEFIEKNKEKLEKLKKSLVGRVHGLTPRGTILANLSRGTAVGAVGPER KKAAVEVLNSVPNFAPSELHVVRADGTVSYIVGQEGIEKATGAKVSDLKG DFAEHDKEGEKEVEVRPGDQFHFHGTHALTREEQIAFNRLAAEAGVRPRV GLVASGGREEHAELALRRARFYLELGFAVEVELLDGEAGERLREAVEAA AAERAAEFGVAGL | Synthetic binder, S519_0000 |
| 117 | AEARGDLIDLLIKRVERLKEREDEETKKDADLAIELLEKERELSKEGNYAT DEYREFLEKNKEWLEKLKKSRIGKKLGLYPRGTTLAATTITLGGGAVDRS KLKAFFAVINAQPNFAPGELHVVRPDGSVSRVRGREGIERVTGATTPPLTA KRAEHSGPGDERVEVRPGDQAHVHGDHSLTREEFIALNRRAREAGAEPW VGLTVDAGTRWEAEEALELAEYYLDLGLNVSVTTSGDEEASRYIRERLEA AAAERAAEYGVRGL | Synthetic binder, S520_0000 |
| 118 | KTALQLHIDFEIALIRRLLEEFPEVDKELAELAIEALRKEGELAKEGNVTTP EYRAFLEEHKETWEKLKEALIGKAVNAYPVGTHLANLVITVFVDPSKTKV EDLVDVFNSIPGFNPAELHVVHPDGSVQSVISPEKIEKVTGAKLPPGKAKY PEHSEPGAENVTLEEGSQLHFHGPHSLTPEEFKEFVKLAKEKAGPVRKGLT LVDVPAEFAPLALERARFFIDFGLDVELTATNTAFAPELEAAVRAAAAEK GVTATVTIV | Synthetic binder, S521_0000 |
| 119 | KTALQVLIDFELALIDRLTREEPRVDPALADLAKEILRAEGELAKTGNVAT PEYFALLDARAAELAALKKALLGKAVNVYPVGTHLANLTIPFVDPSKVK LEDLVAVYRAIPGFAPGELHVVYPDGSVQRVRTPEQIRRVTGAELPPERAP WPEHSEPGAERVELKEGSQVHFHGPHSLTPEEFKAFVKRANEVAGPVRVG ITLVDVPAEFAPLALERVRLYIDFGLSVEITLRNTAFAPELEREARAAGAA AGVDVTVTIE | Synthetic binder, S522_0000 |
| 120 | KTALQVWIDFTKALIRRLIEEDPEVDRELAETAIELLDKRGELAKTGNVAT PEYFAALEKLKETLEKLKEALLGKAVNVYPVGTHFANLVIFIYVDPSKTSL EDLVAVYRAIPGFAPAELHVVRPDGSVDAVRSKEQIERVLGAPLPEADAP WPEHSEPGAEEVTLVEGSQVHFHGPHSLTLEEFKAFVKRANELAGPVVAG LTAVDVPASYAPLLLERARLYIDFGLDVRVTLTGTAFAPELEAALRAAAA EAGVRATVTIR | Synthetic binder, S523_0000 |
| 121 | ATPTPEEEVAVLREAGRRLAARLRAAGLTVRVRELTAAPGAVVTVEGTV LVFHGEVTPELQRLLPQTLLTLVRPGPDTSNSEFGNGVATPEDVDTVEAAI REVVEEAAPRGVTVRAQWHFHSEPVDTIWGGYTDGKRGPNVDTARAAW RAGGGGELHAVVGTAEAPSIVAPNRATPEQLAAAVAAARAAYEAARAR GDPVLGVLVVLPGVGLGQPPSETARAIAERLLALLAPLGLLGRAEVLTEG APGEGPALVLLLRSAA | Synthetic binder, S524_0000 |
| 122 | AAPTDEEVVAVLRRTGRDIAERLRAAGHRVRVVELTAAPGEVVTVEGTV LVFVGELDPALIRLLPQTLLTLEAPGPDTSNSEYGRGVATPADVDTVEAAI REAVEAAAPVGVPVRVQWHFHAEPADTIWGGYTNGKPGPNLDAARAAW AAAGPGELHVVVGTVDAPSIVAPNRATPEQLAAARALAEALYAAARAEG LPVLGVLVVLPGVGLGQPPSAAAEAIARGLLALLAPLGIAGEARILTEGAP GEGPAAVLLLRAAA | Synthetic binder, S525_0000 |
| 123 | SAPTPEEVVAVLLAVGRRIEARLRAAGLRVRAQFLTAAPGAVTTVVGTVL VFVGELTPELQRDLPVTLLTLVREGPDTSNSEFGRGVATLEDVETVIEVAR AAVEEAAPVGVPVRVQFHFHAEPADTIWGGFVNGEEGPNLDKAIAAWKA AGPGELHLVVGTREAPSIVAPNYATPEQLAAAVAQAEALYAAARAEGLP VLGVLVVLPGLGLGKPPSETAAAIGEELLARLAPLGVAGRVEVLTEGAPG EGPAAVLLLRAAA | Synthetic binder, S526_0000 |
| 124 | MSHHWGYGKHNGPEHWHKDFPIAKGERQSPVDIDTHTAKYDPSLKPLSV SYDQATSLRILNNGHTFDVEFDDSQDKAVLKGGPLDGTYRLHQFHFHWG SLDGQGSEHTVDKKKYAAELHLVHWNTKYGDPGKASQQPDGLAILGIFL KVGSAKPGLQKVVDVLDSIKTKGKSADFTNFDPRGLLPESLDYWTYPGSS | S222_1589, M103-I binder |

-continued

SEQUENCE TABLE

| SEQ ID No. | Sequence (5'→3' for DNA sequences, N-terminus to C-terminus for amino acid sequences) | Description |
|---|---|---|
| | TVPPLMESVTWIVLKEPISVSSEQVLKFRKLNFNGEGEPEELMVDNWRPA QPLKNRQIKASFK | |
| 125 | MSHHWGYGKHNGPEHWHKDFPIAKGERQSPVDIDTHTAKYDPSLKPLSV SYDQATSLRILNDGHAFKVEFDDSQDKAVLKGGPLDGTYRLRQFHFHWG SLDGQGSEHTVDKKKYAAELHLLHWNTKYGDYGKAAQQPDGLAVLGIF LKVGSAKPGLQKVVDVLDSIKTKGKSADFTNFDPRGLLPESLDYWTYPGS MTVPPLLESVTWIVLKEPISVSSEQVLKFRKLNFNGEGEPEELMVDNWRP AQPLKNRQIKASFK | S222_1333, M103-E binder |
| 126 | MSHHWGYGKHNGPEHWHKDFPIAKGERQSPVDIDTHTAKYDPSLKPLSV SYDQATSLRILNDGHAFAVEFDDSQDKAVLKGGPLDGTYRLFQFHFHWG SLDGQGSEHTVDKKKYAAELHLAHWNTKYGDLGKASQQPDGIAILGIFL KVGSAKPGLQKVVDVLDSIKTKGKSADFTNFDPRGLLPESLDYWTYPGSF TVPPLLESVTWIVLKEPISVSSEQVLKFRKLNFNGEGEPEELMVDNWRPAQ PLKNRQIKASFK | S222_1519, M103-W binder |
| 127 | MSHHWGYGKHNGPEHWHKDFPIAKGERQSPVDIDTHTAKYDPSLKPLSV SYDQATSLRILNNGHTFSVEFDDSQDKAVLKGGPLDGTYRLGQFHFHWG SLDGQGSEHTVDKKKYAAELHLVHWNTKYGDPGKATQQPDGLAILGIFL KVGSAKPGLQKVVDVLDSIKTKGKSADFTNFDPRGLLPESLDYWTYPGSA TVPPLLESVTWIVLKEPISVSSEQVLKFRKLNFNGEGEPEELMVDNWRPAQ PLKNRQIKASFK | S222_1581, M103-Y binder |
| 128 | NTEKPGFGPHNGDEHWHQKYPVWLGPRRSPVDVDTERAVYDPSLSPLQV DFSKAVSLYMENTGLTWSLYFDNTAPTAAITGGPLDGEYIVGQLHTHTGS QDDKGSEFTVNGKEYAGELHFVSFNSKYGNPSVATKDETGLAILTVPIDV GADNAGLTPLVAKLPNIRYKGEKTDAKNINPAGLLPAGLDFYYYPGSATV PPYEESVLHLLLREAVDASRAQLDAFRSLYRTKRGEPEMKLVDNYVEPKP LGDRTILSSTQ | Synthetic binder, S222_1601 |
| 129 | SSGKPGFGPDNGPDHWAQTYPQFNGDRTTPVDIDSKKAKYNPALQPLKV DLSKVVSLHLENLGLTFSLFFDDTTESGTITGGPLTGTYRVGQVHIHIGSTP DSGSEYTFDGRRYAGELHIVAYNVRYGNPAVATLKEDGLAILTVPLVVGD TNPGFVPLAELLPQIRYRNDSADATGINPLGLLPDRLDHYYVKGSATVPPY LESVMHLVLKEPVTVSEEQLEAFRSLQRTSRGEPFEPLVDNYVPPKPLGNR EILSSFK | Synthetic binder, S222_1602 |
| 130 | TRNTPGFGPDNGYDHWKDVYPVVAGNRVGPVDIDSEKAIYDASLQPLQV DLRNAVSLHLENTGFTFSLHFDFSNESGTIRGGPLRGTYRLGQFHIHVGSD YSSGSEYTIDGKTYAGELHFVAFNVKYGNPEVATQQPDGLAILVVPLVVG ETNPGFVVIAEKLPEVRYRGDSVDATGINPAGLLPASLAYYYFPSSATVPP FNQAVRHLVLREPVTISEEQLEAFRSLQLTGAGEPHQALVDNYAPPKPLG NREILASFK | Synthetic binder, S222_1606 |
| 131 | GRNKPGYGDDNGFDKWHEKYPNVLGEKRSPVNIDSKKAEYDESLKPLEL DLSDYRSLELLNDGLTPKLLFDDSALLGTIRGGPLTGTYILRQIHIHVGASD DRGSEYTFDGRNYPAELHFLFFHAGYGNYAAAALQPDGLVILSIPVEVGD PNPGLAPIVDLLPQVRYRGDRVAAKGFDPRGLLPKSLEFYYYQGSMTVPP FLESVTHIVLKEPVPISQAQLDAWRQLQRTAAGEPVVPLVDNYAPPKPLK NRKILSSFK | Synthetic binder, S222_1628 |
| 132 | GENKPGFGPDNGPEHWSELYPNWNGDLRAPVDVNTDKAVYDPTLKPLVI DLSKAVSLRLENDGYHWKLYFDYSADRATLTGGPLKGVYRLRQLHIHVG ATDDEGSEYTINGEKYAAELHFLFFNVQFGNYEEAAQKPDGLAALTVPVR VGKTNSGFTPLVDKLPQVRYKGDSVEAKDFDPRDLLPKSLKYYYYPGSM TVPPFLESVLHILLKEPVELSKAQLDAFRQLYRNRAGEARELLVNNFVPPK PLGNRTIYSSFK | Synthetic binder, S222_1630 |
| 133 | GRDTPGFDSTNGWEHWQDRFPNVNGALRSPVDINTQEAVYDPSLKPLKID LSNAKSLYMFNDGLFPALYFDNSTPSATLSGGPLDGTYRLFQAHVHVGAD DEHGSEHTINGKYFAGELHFAFFNEKYGNLDKASLQKNGIAIFSVYIEVGD AQPGLLPWAELLPQIRYKGDWVDASGINPLGLLPKSLDFYYYKGSFTVPP FNESVIHIVSKEPVTASQAQLDAFRALQKTGKGEPYQPLIDNYVPPKPLGN RTILSSFQ | Synthetic binder, S222_1642 |
| 134 | NENVPGFDEETGFEKWHEIYPEVLGPRVSPVDIDTKRAVYDPSLKPLEVDF SDARSLKLYNDGLFPALYFDDSTDTATLRGGPLDGVYRVFQIHIHIGSSDD EGSEFTIDGKRYAGELHFAAYNQQYGNLGKASQQENGIAILTIPIEVGAAT AGFAPFADRLPDIRYKGEEVDFTGFDPRGLLPASLKHYYYPGSFTVPPFSQ SVTHLLLRERVTLSEAQLAALRSLSRTEEGEPYVPLQDNYRPARDLGDRTI KTSFK | Synthetic binder, S222_1644 |

-continued

SEQUENCE TABLE

| SEQ ID No. | Sequence (5'→3' for DNA sequences, N-terminus to C-terminus for amino acid sequences) | Description |
|---|---|---|
| 135 | QSFKPGFTADNGFDHWAERYPQVDGPRQSPVDINSDKAVYDPTLKELKV NLSDAVSLHLHNDGLFAALYFDNSTLSGTIEGGPLKGTYVLFQIHIHVGST DDTGSEYTFDGEAFAGEIHFAAYNTEYGNLAAASQQPDGIAILTVPVSVG DTNPGLVPLAERLPRIRYRGETTDATGYNPKGLLPKSLDFYYYPGSFTVPP FLESVTHLVLKEPITASAAQLAAFRALRRTGRGEPMELLVDNYRPPLPLGN RTIKSSVK | Synthetic binder, S222_1645 |
| 136 | M103-SXGGGGSGGGSGGGSK(Biotin)-$NH_2$ | Model peptide; N-terminally modified with M103; X-any amino acid |
| 137 | M103-TXGGGGSGGGSGGGSK(Biotin)-$NH_2$ | Model peptide; N-terminally modified with M103; X-any amino acid |
| 138 | M103-C(Cm)XGGGGSGGGSGGGSK(Biotin)-$NH_2$ | Model peptide; N-terminally modified with M103; Cm = carboxymethyl group |
| 139 | M103-YXGGGGSGGGSGGGSK(Biotin)-$NH_2$ | Model peptide; N-terminally modified with M103; X-any amino acid |

SEQUENCE LISTING

```
Sequence total quantity: 150
SEQ ID NO: 1            moltype = DNA  length = 20
FEATURE                 Location/Qualifiers
misc_feature            1..20
                        note = P5 primer
source                  1..20
                        mol_type = other DNA
                        organism = synthetic construct
SEQUENCE: 1
aatgatacgg cgaccaccga                                              20

SEQ ID NO: 2            moltype = DNA  length = 24
FEATURE                 Location/Qualifiers
misc_feature            1..24
                        note = P7 primer
source                  1..24
                        mol_type = other DNA
                        organism = synthetic construct
SEQUENCE: 2
caagcagaag acggcatacg agat                                         24

SEQ ID NO: 3            moltype = AA  length = 723
FEATURE                 Location/Qualifiers
REGION                  1..723
                        note = Dipeptidyl peptidase from Thermomonas hydrothermalis
                         (with the signal peptide)
source                  1..723
                        mol_type = protein
                        organism = Thermomonas hydrothermalis
SEQUENCE: 3
MHKTRLVAAL AAALATLAPA AWADEGMWVP QQLPEIAGAL KKAGLKLDPK QLSDLTGDPM  60
GAVVSLGGCT GSFVSPQGLV ATNHHCAYGA IQLNSTPEKN LIKDGFNAPT QADELSAGPN  120
ARIYVLEGIT DVTAQAKAAM AAAGNDPVAR ANALEAFEKK ITSDCEAEPG YRCRVYSFMG  180
GITYRLFKNL EIKDVRLVYA PPSSVGKFGG DIDNWMWPRH TGDFSFYRAY VGKDGKPAPY  240
SKDNVPYRPK HWLKIADTPL GEGDFVMVAG YPGRTDRYAL VAEFENTQNW LYPAISKAYK  300
```

-continued

```
DQIALVEAAA KDNPEIAVKY AAALAGWNNT SKNFDGQLEG FKRNDVLAIK RREEAAVLEW  360
LRARGKAGTP ALEAHAALVK LVADTARTQE RDLVLGSFNR TGIIGVAVNL YRLAIERQKP  420
DAEREPGYQQ RDLPVIEGSL KQMERRYVPA MDRQLRAYWL DRYVALPAAQ HVAAVDAWLG  480
GSDKAAAEAA LARLDQSRLG SLEERLKWFN ADRAAFEAST DPAIQYAVAV MPTLLAMEQQ  540
AKTRYGVALE ARPRYLQAVV DYKKSKGQAV YPDANSTLRI TYGHVKGYTG LNGKVYTPFT  600
TLEEVAAKET GVEPFDNPKA LLEAVAAKRY AGLADARLGT VPVNFLADLD ITGGNSGSPV  660
LDANGRLVGL AFDGTLESVA SNWVFDPVLT RMISVDQRYM RWIMQEVMPA PQLLEELGVP  720
PRQ                                                                723

SEQ ID NO: 4            moltype = AA  length = 700
FEATURE                 Location/Qualifiers
REGION                  1..700
                        note = Dipeptidyl peptidase from Thermomonas hydrothermalis
                         (without the signal peptide)
source                  1..700
                        mol_type = protein
                        organism = Thermomonas hydrothermalis
SEQUENCE: 4
DEGMWVPQQL PEIAGALKKA GLKLDPKQLS DLTGDPMGAV VSLGGCTGSF VSPQGLVATN  60
HHCAYGAIQL NSTPEKNLIK DGFNAPTQAD ELSAGPNARI YVLEGITDVT AQAKAAMAAA  120
GNDPVARANA LEAFEKKITS DCEAEPGYRC RVYSFMGGIT YRLFKNLEIK DVRLVYAPPS  180
SVGKFGGDID NWMWPRHTGD FSFYRAYVGK DGKPAPYSKD NVPYRPKHWL KIADTPLGEG  240
DFVMVAGYPG RTDRYALVAE FENTQNWLYP AISKAYKDQI ALVEAAAKDN PEIAVKYAAA  300
LAGWNNTSKN FDGQLEGFKR NDVLAIKRRE EAAVLEWLRA RGKAGTPALE AHAALVKLVA  360
DTARTQERDL VLGSFNRTGI IGVAVNLYRL AIERQKPDAE REPGYQQRDL PVIEGSLKQM  420
ERRYVPAMDR QLRAYWLDRY VALPAAQHVA AVDAWLGGSD KAAAEAALAR LDQSRLGSLE  480
ERLKWFNADR AAFEASTDPA IQYAVAVMPT LLAMEQQAKT RYGVALEARP RYLQAVVDYK  540
KSKGQAVYPD ANSTLRITYG HVKGYTGLNG KVYTPFTTLE EVAAKETGVE PFDNPKALLE  600
AVAAKRYAGL ADARLGTVPV NFLADLDITG GNSGSPVLDA NGRLVGLAFD GTLESVASNW  660
VFDPVLTRMI SVDQRYMRWI MQEVMPAPQL LEELGVPPRQ                        700

SEQ ID NO: 5            moltype = AA  length = 710
FEATURE                 Location/Qualifiers
REGION                  1..710
                        note = Dipeptidyl peptidase from Caldithrix abyssi (with
                         the signal peptide)
source                  1..710
                        mol_type = protein
                        organism = Caldithrix abyssi
SEQUENCE: 5
MKIRLFGVLL LFTFSLFAEE GMYPITEIHK LNLKKLGIEL SADQIFSENE VSLSDAIVQI  60
GGCTGSFISP EGLILTNHHC AFRAIQNISS TENDYLTNGF VAHTLQEERP AKGYTVRITE  120
RVEDVSQRVL NAVKHIEDPI EREKAIEKIT KQIVKEQEQK HPGKRAAVSE MFPGKTYYLF  180
IYTYLKDVRL VYAPPRSIGE FGGEFDNWEW PRHTGDFTLM RAYVAPDGSP SDYSEENVPY  240
RPKSYLKVAA KGVEEGDRVF ILGYPGRTYR HRTSAFLAFE YEFRMPFVVD WYQWQIDLLT  300
TLGKDDADRS LKFSSWIKGL ANTEKNYRGK LQGIRRIGLL EQKKNEEEKI QVFIAENNLK  360
KYQHVLTEIK QIYHTYRQSA VREMLLSYFG RSPVLPAVAR TLVLAAEERQ KEDLERERAF  420
MDRNFKRTQT YTLLRLKNFD SQADQLILQE LLKKAAALPE DQRISALRSI FKLDDAAETR  480
QVISEAYRKT RLSDPEFVKT CFAKTPDELK ALNDPLINWM LALKEDYETL KNIRKERNGK  540
LRRLRALWLE AKQAYLKTDF IPDANGTYRM TFGFIEGYAP ADAVYKAPIT TGRGILEKHT  600
GKSPFDTPEK LLALLKAKQF GPFVSKTVGT LPVGILYSCD TTGGNSGSPV LNARGQLVGL  660
NFDRAFEATI NDYAWNHQYS RSIGVDIRYI LFLLKYFSGA EHLLEEMGVQ              710

SEQ ID NO: 6            moltype = AA  length = 692
FEATURE                 Location/Qualifiers
REGION                  1..692
                        note = Dipeptidyl peptidase from Caldithrix abyssi (without
                         the signal peptide)
source                  1..692
                        mol_type = protein
                        organism = Caldithrix abyssi
SEQUENCE: 6
EEGMYPITEI HKLNLKKLGI ELSADQIFSE NEVSLSDAIV QIGGCTGSFI SPEGLILTNH  60
HCAFRAIQNI SSTENDYLTN GFVAHTLQEE RPAKGYTVRI TERVEDVSQR VLNAVKHIED  120
PIEREKAIEK ITKQIVKEQE QKHPGKRAAV SEMFPGKTYY LFIYTYLKDV RLVYAPPRSI  180
GEFGGEFDNW EWPRHTGDFT LMRAYVAPDG SPSDYSEENV PYRPKSYLKV AAKGVEEGDR  240
VFILGYPGRT YRHRTSAFLA FEYEFRMPFV VDWYQWQIDL LTTLGKDDAD RSLKFSSWIK  300
GLANTEKNYR GKLQGIRRIG LLEQKKNEEE KIQVFIAENN LKKYQHVLTE IKQIYHTYRQ  360
SAVREMLLSY FGRSPVLPAV ARTLVLAAEE RQKEDLERER AFMDRNFKRT QTYTLLRLKN  420
FDSQADQLIL QELLKKAAAL PEDQRISALR SIFKLDDAAE TRQVISEAYR KTRLSDPEFV  480
KTCFAKTPDE LKALNDPLIN WMLALKEDYE TLKNIRKERN GKLRRLRALW LEAKQAYLKT  540
DFIPDANGTY RMTFGFIEGY APADAVYKAP ITTGRGILEK HTGKSPFDTP EKLLALLKAK  600
QFGPFVSKTV GTLPVGILYS CDTTGGNSGS PVLNARGQLV GLNFDRAFEA TINDYAWNHQ  660
YSRSIGVDIR YILFLLKYFS GAEHLLEEMG VQ                                692

SEQ ID NO: 7            moltype = AA  length = 256
FEATURE                 Location/Qualifiers
REGION                  1..256
                        note = Carbonic anhydrase II scaffold
```

-continued

```
source                  1..256
                        mol_type = protein
                        organism = Homo sapiens
SEQUENCE: 7
HWGYGKHNGP EHWHKDFPIA KGERQSPVDI DTHTAKYDPS LKPLSVSYDQ ATSLRILNNG  60
HAFNVEFDDS QDKAVLKGGP LDGTYRLIQF HFHWGSLDGQ GSEHTVDKKK YAAELHLVHW  120
NTKYGDFGKA VQQPDGLAVL GIFLKVGSAK PGLQKVVDVL DSIKTKGKSA DFTNFDPRGL  180
LPESLDYWTY PGSLTTPPLL ECVTWIVLKE PISVSSEQVL KFRKLNFNGE GEPEELMVDN  240
WRPAQPLKNR QIKASF                                                256

SEQ ID NO: 8            moltype = AA  length = 256
FEATURE                 Location/Qualifiers
REGION                  1..256
                        note = Carbonic anhydrase I scaffold
source                  1..256
                        mol_type = protein
                        organism = Homo sapiens
SEQUENCE: 8
WGYDDKNGPE QWSKLYPIAN GNNQSPVDIK TSETKHDTSL KPISVSYNPA TAKEIINVGH  60
SFHVNFEDNQ DRSVLKGGPF SDSYRLFQFH FHWGSTNEHG SEHTVDGVKY SAELHVAHWN  120
SAKYSSLAEA ASKADGLAVI GVLMKVGEAN PKLQKVLDAL QAIKTKGKRA PFTNFDPSTL  180
LPSSLDFWTY PGSLTHPPLY ESVTWIICKE SISVSSEQLA QFRSLLSNVE GDNAVPMQHN  240
NRPTQPLKGR TVRASF                                                256

SEQ ID NO: 9            moltype = AA  length = 256
FEATURE                 Location/Qualifiers
REGION                  1..256
                        note = Carbonic anhydrase III scaffold
source                  1..256
                        mol_type = protein
                        organism = Homo sapiens
SEQUENCE: 9
EWGYASHNGP DHWHELFPNA KGENQSPIEL HTKDIRHDPS LQPWSVSYDG GSAKTILNNG  60
KTCRVVFDDT YDRSMLRGGP LPGPYRLRQF HLHWGSSDDH GSEHTVDGVK YAAELHLVHW  120
NPKYNTFKEA LKQRDGIAVI GIFLKIGHEN GEFQIFLDAL DKIKTKGKEA PFTKFDPSSL  180
FPASRDYWTY QGSLTTPPCE ECIVWLLLKE PMTVSSDQMA KLRSLLSSAE NEPPVPLVSN  240
WRPPQPINNR VVRASF                                                256

SEQ ID NO: 10           moltype = AA  length = 266
FEATURE                 Location/Qualifiers
REGION                  1..266
                        note = Carbonic anhydrase IV scaffold
source                  1..266
                        mol_type = protein
                        organism = Homo sapiens
SEQUENCE: 10
AESHWCYEVQ AESSNYPCLV PVKWGGNCQK DRQSPINIVT TKAKVDKKLG RFFFSGYDKK  60
QTWTVQNNGH SVMMLLENKA SISGGGLPAP YQAKQLHLHW SDLPYKGSEH SLDGEHFAME  120
MHIVHEKEKG TSRNVKEAQD PEDEIAVLAF LVEAGTQVNE GFQPLVEALS NIPKPEMSTT  180
MAESSLLDLL PKEEKLRHYF RYLGSLTTPT CDEKVVWTVF REPIQLHREQ ILAFSQKLYY  240
DKEQTVSMKD NVRPLQQLGQ RTVIKS                                     266

SEQ ID NO: 11           moltype = AA  length = 262
FEATURE                 Location/Qualifiers
REGION                  1..262
                        note = Carbonic anhydrase VII scaffold
source                  1..262
                        mol_type = protein
                        organism = Homo sapiens
SEQUENCE: 11
GHHGWGYGQD DGPSHWHKLY PIAQGDRQSP INIISSQAVY SPSLQPLELS YEACMSLSIT  60
NNGHSVQVDF NDSDDRTVVT GGPLEGPYRL KQFHFHWGKK HDVGSEHTVD GKSFPSELHL  120
VHWNAKKYST FGEAASAPDG LAVVGVFLET GDEHPSMNRL TDALYMVRFK GTKAQFSCFN  180
PKSLLPASRH YWTYPGSLTT PPLSESVTWI VLREPISISE RQMGKFRSLL FTSEDDERIH  240
MVNNFRPPQP LKGRVVKASF RA                                         262

SEQ ID NO: 12           moltype = AA  length = 260
FEATURE                 Location/Qualifiers
REGION                  1..260
                        note = Carbonic anhydrase XII scaffold
source                  1..260
                        mol_type = protein
                        organism = Homo sapiens
SEQUENCE: 12
KWTYFGPDGE NSWSKKYPSC GGLLQSPIDL HSDILQYDAS LTPLEFQGYN LSANKQFLLT  60
NNGHSVKLNL PSDMHIQGLQ SRYSATQLHL HWGNPNDPHG SEHTVSGQHF AAELHIVHYN  120
SDLYPDASTA SNKSEGLAVL AVLIEMGSFN PSYDKIFSHL QHVKYKGQEA FVPGFNIEEL  180
LPERTAEYYR YRGSLTTPPC NPTVLWTVFR NPVQISQEQL LALETALYCT HMDDPSPREM  240
INNFRQVQKF DERLVYTSFS                                            260
```

```
SEQ ID NO: 13          moltype = AA  length = 259
FEATURE                Location/Qualifiers
REGION                 1..259
                       note = Carbonic anhydrase XIII scaffold
source                 1..259
                       mol_type = protein
                       organism = Homo sapiens
SEQUENCE: 13
LSWGYREHNG PIHWKEFFPI ADGDQQSPIE IKTKEVKYDS SLRPLSIKYD PSSAKIISNS  60
GHSFNVDFDD TENKSVLRGG PLTGSYRLRQ VHLHWGSADD HGSEHIVDGV SYAAELHVVH  120
WNSDKYPSFV EAAHEPDGLA VLGVFLQIGE PNSQLQKITD TLDSIKEKGK QTRFTNFDLL  180
SLLPPSWDYW TYPGSLTVPP LLESVTWIVL KQPINISSQQ LAKFRSLLCT AEGEAAAFLV  240
SNHRPPQPLK GRKVRASFH                                            259

SEQ ID NO: 14          moltype = AA  length = 261
FEATURE                Location/Qualifiers
REGION                 1..261
                       note = ADAM17 (aka TACE) scaffold
source                 1..261
                       mol_type = protein
                       organism = Homo sapiens
SEQUENCE: 14
ADPDPMKNTC KLLVVADHRF YRYMGRGEES TTTNYLIELI DRVDDIYRNT AWDNAGFKGY  60
GIQIEQIRIL KSPQEVKPGE KHYNMAKSYP NEEKDAWDVK MLLEQFSFDI AEEASKVCLA  120
HLFTYQDFDM GTLGLAYGGS PRANSHGGVC PKAYYSPVGK KNIYLNSGLT STKNYGKTIL  180
TKEADLVTTH ELGHNFGAEH DPDGLAECAP NEDQGGKYVM YPIAVSGDHE NNKMFSQCSK  240
QSIYKTIESK AQECFQERSN A                                         261

SEQ ID NO: 15          moltype = AA  length = 200
FEATURE                Location/Qualifiers
REGION                 1..200
                       note = Astacin, scaffold
source                 1..200
                       mol_type = protein
                       organism = Astacus astacus
SEQUENCE: 15
AAILGDEYLW SGGVIPYTFA GVSGADQSAI LSGMQELEEK TCIRFVPRTT ESDYVEIFTS  60
GSGCWSYVGR ISGAQQVSLQ ANGCVYHGTI IHELMHAIGF YHEHTRMDRD NYVTINYQNV  120
DPSMTSNFDI DTYSRYVGED YQYYSIMHYG KYSFSIQWGV LETIVPLQNG IDLTDPYDKA  180
HMLQTDANQI NNLYTNECSL                                           200

SEQ ID NO: 16          moltype = AA  length = 866
FEATURE                Location/Qualifiers
REGION                 1..866
                       note = Aminopeptidase N, scaffold
source                 1..866
                       mol_type = protein
                       organism = Escherichia coli
SEQUENCE: 16
PQAKYRHDYR APDYQITDID LTFDLDAQKT VVTAVSQAVR HGASDAPLRL NGEDLKLVSV  60
HINDEPWTAW KEEEGALVIS NLPERFTLKI INEISPAANT ALEGLYQSGD ALCTQCEAEG  120
FRHITYYLDR PDVLARFTTK IIADKIKYPF LLSNGNRVAQ GELENGRHWV QWQDPFPKPC  180
YLFALVAGDF DVLRDTFTTR SGREVALELY VDRGNLDRAP WAMTSLKNSM KWDEERFGLE  240
YDLDIYMIVA VDFFNMGAME NKGLNIFNSK YVLARTDTAT DKDYLDIERV IGHEYFHNWT  300
GNRVTCRDWF QLSLKEGLTV FRDQEFSSDL GSRAVNRINN VRTMRGLQFA EDASPMAHPI  360
RPDMVIEMNN FYTLTVYEKG AEVIRMIHTL LGEENFQKGM QLYFERHDGS AATCDDFVQA  420
MEDASNVDLS HFRRWYSQSG TPIVTVKDDY NPETEQYTLT ISQRTPATPD QAEKQPLHIP  480
FAIELYDNEG KVIPLQKGGH PVNSVLNVTQ AEQTFVFDNV YFQPVPALLC EFSAPVKLEY  540
KWSDQQLTFL MRHARNDFSR WDAAQSLLAT YIKLNVARHQ QGQPLSLPVH VADAFRAVLL  600
DEKIDPALAA EILTLPSVNE MAELFDIIDP IAIAEVREAL TRTLATELAD ELLAIYNANY  660
QSEYRVEHED IAKRTLRNAC LRFLAFGETH LADVLVSKQF HEANNMTDAL AALSAAVAAQ  720
LPCRDALMQE YDDKWHQNGL VMDKWFILQA TSPAANVLET VRGLLQHRSF TMSNPNRIRS  780
LIGAFAGSNP AAFHAEDGSG YLFLVEMLTD LNSRNPQVAS RLIEPLIRLK RYDAKRQEKM  840
RAALEQLKGL ENLSGDLYEK ITKALA                                    866

SEQ ID NO: 17          moltype = AA  length = 185
FEATURE                Location/Qualifiers
REGION                 1..185
                       note = Peptide deformylase, scaffold
source                 1..185
                       mol_type = protein
                       organism = Staphylococcus aureus
SEQUENCE: 17
MLTMKDIIRD GHPTLRQKAA ELELPLTKEE KETLIAMREF LVNSQDEEIA KRYGLRSGVG  60
LAAPQINISK RMIAVLIPDD GSGKSYDYML VNPKIVSHSV QEAYLPTGEG CLSVDDNVAG  120
LVHRHNRITI KAKDIEGNDI QLRLKGYPAI VFQHEIDHLN GVMFYDHIDK DHPLQPHTDA  180
VEVLE                                                           185
```

```
SEQ ID NO: 18          moltype = AA  length = 696
FEATURE                Location/Qualifiers
REGION                 1..696
                       note = Glutamate carboxypeptidase II, scaffold
source                 1..696
                       mol_type = protein
                       organism = Homo sapiens
SEQUENCE: 18
KHNMKAFLDE LKAENIKKFL YNFTQIPHLA GTEQNFQLAK QIQSQWKEFG LDSVELAHYD  60
VLLSYPNKTH PNYISIINED GNEIFNTSLF EPPPPGYENV SDIVPPFSAF SPQGMPEGDL  120
VYVNYARTED FFKLERDMKI NCSGKIVIAR YGKVFRGNKV KNAQLAGAKG VILYSDPADY  180
FAPGVKSYPD GWNLPGGGVQ RGNILNLNGA GDPLTPGYPA NEYAYRRGIA EAVGLPSIPV  240
HPIGYYDAQK LLEKMGGSAP PDSSWRGSLK VPYNVGPGFT GNFSTQKVKM HIHSTNEVTR  300
IYNVIGTLRG AVEPDRYVIL GGHRDSWVFG GIDPQSGAAV VHEIVRSFGT LKKEGWRPRR  360
TILFASWDAE EFGLLGSTEW AEENSRLLQE RGVAYINADS SIEGNYTLRV DCTPLMYSLV  420
HNLTKELKSP DEGFEGKSLY ESWTKKSPSP EFSGMPRISK LGSGNDFEVF FQRLGIASGR  480
ARYTKNWETN KFSGYPLYHS VYETYELVEK FYDPMFKYHL TVAQVRGGMV FELANSIVLP  540
FDCRDYAVVL RKYADKIYSI SMKHPQEMKT YSVSFDSLFS AVKNFTEIAS KFSERLQDFD  600
KSNPIVLRMM NDQLMFLERA FIDPLGLPDR PFYRHVIYAP SSHNKYAGES FPGIYDALFD  660
IESKVDPSKA WGEVKRQIYV AAFTVQAAAE TLSEVA                          696

SEQ ID NO: 19          moltype = AA  length = 307
FEATURE                Location/Qualifiers
REGION                 1..307
                       note = Carboxypeptidase A, scaffold
source                 1..307
                       mol_type = protein
                       organism = Bos taurus
SEQUENCE: 19
ARSTNTFNYA TYHTLDEIYD FMDLLVAQHP ELVSKLQIGR SYEGRPIYVL KFSTGGSNRP  60
AIWIDLGIHS REWITQATGV WFAKKFTENY GQNPSFTAIL DSMDIFLEIV TNPNGFAFTH  120
SENRLWRKTR SVTSSSLCVG VDANRNWDAG FGKAGASSSP CSETYHGKYA NSEVEVKSIV  180
DFVKNHGNFK AFLSIHSYSQ LLLYPYGYTT QSIPDKTELN QVAKSAVAAL KSLYGTSYKY  240
GSIITTIYQA SGGSIDWSYN QGIKYSFTFE LRDTGRYGFL LPASQIIPTA QETWLGVLTI  300
MEHTVNN                                                          307

SEQ ID NO: 20          moltype = AA  length = 323
FEATURE                Location/Qualifiers
REGION                 1..323
                       note = Carboxypeptidase T, scaffold
source                 1..323
                       mol_type = protein
                       organism = Bos taurus
SEQUENCE: 20
DFPSYDSGYH NYNEMVNKIN TVASNYPNIV KKFSIGKSYE GRELWAVKIS DNVGTDENEP  60
EVLYTALHHA REHLTVEMAL YTLDLFTQNY NLDSRITNLV NNREIYIVFN INPDGGEYDI  120
SSGSYKSWRK NRQPNSGSSY VGTDLNRNYG YKWGCCGGSS GSPSSETYRG RSAFSAPETA  180
AMRDFINSRV VGGKQQIKTL ITFHTYSELI LYPYGYTYTD VPSDMTQDDF NVFKTMANTM  240
AQTNGYTPQQ ASDLYITDGD MTDWAYGQHK IFAFTFEMYP TSYNPGFYPP DEVIGRETSR  300
NKEAVLYVAE KADCPYSVIG KSC                                        323

SEQ ID NO: 21          moltype = AA  length = 470
FEATURE                Location/Qualifiers
REGION                 1..470
                       note = Alkaline protease, PAO1, scaffold
source                 1..470
                       mol_type = protein
                       organism = Pseudomonas aeruginosa
SEQUENCE: 21
GRSDAYTQVD NFLHAYARGG DELVNGHPSY TVDQAAEQIL REQASWQKAP GDSVLTLSYS  60
FLTKPNDFFN TPWKYVSDIY SLGKFSAFSA QQQAQAKLSL QSWSDVTNIH FVDAGQGDQG  120
DLTFGNFSSS VGGAAFAFLP DVPDALKGQS WYLINSSYSA NVNPANGNYG RQTLTHEIGH  180
TLGLSHPGDY NAGEGDPTYA DATYAEDTRA YSVMSYWEEQ NTGQDFKGAY SSAPLLDDIA  240
AIQKLYGANL TTRTGDTVYG FNSNTERDFY SATSSSSKLV FSVWDAGGND TLDFSGFSQN  300
QKINLNEKAL SDVGGLKGNV SIAAGVTVEN AIGGSGSDLL IGNDVANVLK GGAGNDILYG  360
GLGADQLWGG AGADTFVYGD IAESSAAAPD TLRDFVSGQD KIDLSGLDAF VNGGLVLQYV  420
DAFAGKAGQA ILSYDAASKA GSLAIDFSGD AHADFAINLI GQATQADIVV           470

SEQ ID NO: 22          moltype = AA  length = 323
FEATURE                Location/Qualifiers
REGION                 1..323
                       note = Carboxypeptidase T, scaffold
source                 1..323
                       mol_type = protein
                       organism = Thermoactinomyces vulgaris
SEQUENCE: 22
DFPSYDSGYH NYNEMVNKIN TVASNYPNIV KKFSIGKSYE GRELWAVKIS DNVGTDENEP  60
EVLYTALHHA REHLTVEMAL YTLDLFTQNY NLDSRITNLV NNREIYIVFN INPDGGEYDI  120
SSGSYKSWRK NRQPNSGSSY VGTDLNRNYG YKWGCCGGSS GSPSSETYRG RSAFSAPETA  180
```

```
AMRDFINSRV VGGKQQIKTL ITFHTYSELI LYPYGYTYTD VPSDMTQDDF NVFKTMANTM  240
AQTNGYTPQQ ASDLYITDGD MTDWAYGQHK IFAFTFEMYP TSYNPGFYPP DEVIGRETSR  300
NKEAVLYVAE KADCPYSVIG KSC                                          323

SEQ ID NO: 23          moltype = AA  length = 860
FEATURE                Location/Qualifiers
REGION                 1..860
                       note = StcE, scaffold
source                 1..860
                       mol_type = protein
                       organism = Escherichia coli
SEQUENCE: 23
NSAIYFNTSQ PINDLQGSLA AEVKFAQSQI LPAHPKEGDS QPHLTSLRKS LLLVRPVKAD  60
DKTPVQVEAR DDNNKILGTL TLYPPSSLPD TIYHLDGVPE GGIDFTPHNG TKKIINTVAE  120
VNKLSDASGS SIHSHLTNNA LVEIHTANGR WVRDIYLPQG PDLEGKMVRF VSSAGYSSTV  180
FYGDRKVTLS VGNTLLFKYV NGQWFRSGEL ENNRITYAQH IWSAELPAHW IVPGLNLVIK  240
QGNLSGRLND IKIGAPGELL LHTIDIGMLT TPRDRFDFAA DAAAHREYFQ TIPVSRMIVN  300
NYAPLHLKEV MLPTGELLTD MDPGNGGWHS GTMRQRIGKE LVSHGIDNAN YGLNSTAGLG  360
ENSHPYVVAQ LAAHNSRGNY ANGIQVHGGS GGGGIVTLDS TLGNEFSHDV GHNYGLGHYV  420
DGFKGSVHRS AENNNSTWGW DGDKKRFIPN FYPSQTNEKS CLNNQCQEPF DGHKFGFDAM  480
AGGSPFSAAN RFTMYTPNSS AIIQRFFENK AVFDSRSSTG FSKWNADTQE MEPYEHTIDR  540
AEQITASVNE LSESKMAELM AEYAVVKVHM WNGNWTRNIY IPTASADNRG SILTINHEAG  600
YNSYLFINGD EKVVSQGYKK SFVSDGQFWK ERDVVDTREA RKPEQFGVPV TTLVGYYDPE  660
GTLSSYIYPA MYGAYGFTYS DDSQNLSDND CQLQVDTKEG QLRFRLANHR ANNTVMNKFH  720
INVPTESQPT QATLVCNNKI LDTKSLTPAP EGLTYTVNGQ ALPAKENEGC IVSVNSGKRY  780
CLPVGQRSGY SLPDWIVGQE VYVDSGAKAK VLLSDWDNLS YNRIGEFVGN VNPADMKKVK  840
AWNGQYLDFS KPRSMRVVYK                                              860

SEQ ID NO: 24          moltype = AA  length = 259
FEATURE                Location/Qualifiers
REGION                 1..259
                       note = AB5 holotoxin, scaffold
source                 1..259
                       mol_type = protein
                       organism = Escherichia coli
SEQUENCE: 24
MAERTPNEEK KVIGYADHNG QLYNITSIYG PVINYTVPDE NITINTINST GERTQLTINY  60
SDYVREAFNE WAPSGIRVQQ VSSSGAEARV VSFSTTNYAD NSLGSTIFDP SGNSRTRIDI  120
GSFNRIVMNN FEKLKSRGAI PANMSPEEYI KLKLRITIKH EIGHILGLLH NNEGGSYFPH  180
GVGLEVARCR LLNQAPSIML NGSNYDYIDR LSHYLERPVT ETDIGPSRND IEGVRVMRRG  240
GSGNSFTNRF SCLGLGLAF                                               259

SEQ ID NO: 25          moltype = AA  length = 249
FEATURE                Location/Qualifiers
REGION                 1..249
                       note = ZE2 (TIM barrel), scaffold
source                 1..249
                       mol_type = protein
                       organism = Saccharopolyspora sp.
SEQUENCE: 25
GSPRYLKGWL KDVVQLSLRR PSFRASRQRP IISLNERILE FNKRNITAII AEYKRKSPSG  60
LDVERDPIEY SKFMERYAVG LSILTEEKYF NGSYETLRKI ASSVSIPILM ADFIVKESQI  120
DDAYNLGADT VLLIVKILTE RELESLLEYA RSYGMEPLIG INDENDLDIA LRIGARFIGI  180
HSADHETLEI NKENQRKLIS MIPSNVVKVA AHGISERNEI EELRKLGVNA FLIGSSLMRN  240
PEKIKEFIL                                                          249

SEQ ID NO: 26          moltype = AA  length = 94
FEATURE                Location/Qualifiers
REGION                 1..94
                       note = MID1sc10 (de novo helical bundle), scaffold
source                 1..94
                       mol_type = protein
                       organism = synthetic construct
SEQUENCE: 26
GSPLAQQIKN TLTFIGQANA AGRMDEVRTL QQNLHPLWAE YFQQTEGSGG SPLAQQIQYG  60
HVLIHQARAA GRMDEVRRLS ENTLQLMKEY FQQS                              94

SEQ ID NO: 27          moltype = AA  length = 287
FEATURE                Location/Qualifiers
REGION                 1..287
                       note = Amidohydrolase, scaffold
source                 1..287
                       mol_type = protein
                       note = ATCC 17616
                       organism = Burkholderia multivorans
SEQUENCE: 27
ALRIDSHQHF WRYRAADYPW IGAGMGVLAR DYLPDALHPL MHAQALGASI AVQARAGRDE  60
TAFLLELACD EARIAAVVGW EDLRAPQLAE RVAEWRGTKL RGFRHQLQDE ADVRAFVDDA  120
DFARGVAWLQ ANDYVYDVLV FERQLPDVQA FCARHDAHWL VLDHAGKPAL AEFDRDDTAL  180
```

```
ARWRAALREL AALPHVVCKL SGLVTEADWR RGLRASDLRH IEQCLDAALD AFGPQRLMFG  240
SDWPVCLLAA SYDEVASLVE RWAESRLSAA ERSALWGGTA ARCYALP                287

SEQ ID NO: 28          moltype = AA  length = 185
FEATURE                Location/Qualifiers
REGION                 1..185
                       note = PDB ID: 3U7M; mutant; M64
source                 1..185
                       mol_type = protein
                       organism = synthetic construct
SEQUENCE: 28
MLTMKDIIRD GHPTLRQKAA ELELPLTKEE KETLIAMREF LVNSQDEEIA KRYGLRSAVV  60
IVAPMINISK RMIAVLLPDD GSGKSYDYML VNPKIVSHSV QEAYLPDGLQ CLSVDDNVAG  120
LVHRHNRITI KAKDIEGNDI QLRLKGLPAI LFQHAIDHLN GVMFYDHIDK DHPLQPHTDA  180
VEVLL                                                              185

SEQ ID NO: 29          moltype = AA  length = 470
FEATURE                Location/Qualifiers
REGION                 1..470
                       note = PDB ID: 1KAP; mutant; M64
source                 1..470
                       mol_type = protein
                       organism = synthetic construct
SEQUENCE: 29
GRSDAYTQVD NFLHAYARGG DELVNGHPSY TVDQAAEQIL REQASWQKAP GDSVLTLSYS  60
FLTKPNDFFN TPWKYVSDIY SLGKFSAFSA QQQAQAKLSL QSWSDVTNIH FVDAGQGDQG  120
DLTFGNFSSS VGGLVFVFLP DVPDALKGQS WYLINSSWSI VVNPANGNRG RQLLTHMIGH  180
TLGLSHPGDY HPGEGDPTYA DATYAEDTLA YSVMSLWEEQ NTGQDFKGAY SSAPLLDDIA  240
AIQKLYGANL TTRTGDTVYG FNSNTERDFY SATSSSSKLV FSVWDAGGND TLDFSGFSQN  300
QKINLNEKAL SDVGGLKGNV SIAAGVTVEN AIGGSGSDLL IGNDVANVLK GGAGNDILYG  360
GLGADQLWGG AGADTFVYGD IAESSAAAPD TLRDFVSGQD KIDLSGLDAF VNGGLVLQYV  420
DAFAGKAGQA ILSYDAASKA GSLAIDFSGD AHADFAINLI GQATQADIVV             470

SEQ ID NO: 30          moltype = AA  length = 182
FEATURE                Location/Qualifiers
REGION                 1..182
                       note = PDB ID: 2X7M; mutant; M64
source                 1..182
                       mol_type = protein
                       organism = synthetic construct
SEQUENCE: 30
LVPRGSHMKL CLVAFDGRIP MLSSIVDRFE EHVSEYLGEV KVKKKRAKLP EHAYSKVRGQ  60
YLARALLDTL RGMKGEYDRV LGLTSEDLYI PGVNFVFLIA RCPGREAVVS VARLLDPDPE  120
LYLERVVKEL THALGHTFGL GHCPDRNCVM SPASSLLEVD RKSPNFCRRC TELLQRNLKR  180
GG                                                                 182

SEQ ID NO: 31          moltype = AA  length = 478
FEATURE                Location/Qualifiers
REGION                 1..478
                       note = PDB ID: 1LML; mutant; M64
source                 1..478
                       mol_type = protein
                       organism = synthetic construct
SEQUENCE: 31
VVRDVNWGAL RIAVSTEDLT DPAYHCARVG QHVKDHAGAI VTCTAEDILT NEKRDILVKH  60
LIPQAVQLHT ERLKVQQVQG KWKVTDMVGD ICGDFKVPQA HITEGFSNTD FVMYVASVPS  120
EEGVLAWATT CQTFSDGHPA VGVINIPAAN IASRYDQLVT RVVTHVMAHA LGFSGPFFED  180
ARIVANVPNV RGKNFDVPVI NSSTAVAKAR EQYGCDTLEY LEVEDQGGEG YAGSHIKMRN  240
AQDELMAPAA AAGYYTALTM AIFQDLGFYQ ADFSKAEVMP WGQNAGCAFL TNKCMEQSVT  300
QWPAMFCNES EDAIRCPTSR LSLGACGVTR HPGLPPYWQY FTDPSLAGVS ALMDYCPVVV  360
PYSDGSCTQR ASEAHASLLP FNVFSDAARC IDGAFRPKAT DGIVKSYAGL CANVQCDTAT  420
RTYSVQVHGS NDYTNCTPGL RVELSTVSNA FEGGGYITCP PYVEVCQGNV QAAKDGGN    478

SEQ ID NO: 32          moltype = AA  length = 866
FEATURE                Location/Qualifiers
REGION                 1..866
                       note = PDB ID: 4Q4E; mutant; M65
source                 1..866
                       mol_type = protein
                       organism = synthetic construct
SEQUENCE: 32
PQAKYRHDYR APDYQITDID LTFDLDAQKT VVTAVSQAVR HGASDAPLRL NGEDLKLVSV  60
HINDEPWTAW KEEEGALVIS NLPERFTLKI INEISPAANT ALEGLYQSGD ALCTQCLAEG  120
FRHITYYLDR PDVLARFTTK IIADKIKYPF LLSNGNRVAQ GELENGRHWV QWQDPFPKPC  180
YLFALVAGDF DVLRDTFTTR SGREVALELY VDRGNLDRAP WAMTSLKNSM KWDEERFGLE  240
YDLDIYMIVA VDFLNTGVVP NKGLNIFNSA LVLARTDTAT DKDYLEIEAV IGHVYFHNWT  300
GNRVTCRDWF QLSLIEGLTL FRIQEFSSDL GSRAVNRINN VRTMRGLQFA EDASPMAHPI  360
RPDMVIEMNN FFTLTVLWKG AEVIRMIHTL LGEENFQKGM QLYFERHDGS AATCDDFVQA  420
MEDASNVDLS HFRRWYSQSG TPIVTVKDDY NPETEQYTLT ISQRTPATPD QAEKQPLHIP  480
```

-continued

```
FAIELYDNEG KVIPLQKGGH PVNSVLNVTQ AEQTFVFDNV YFQPVPALLC EFSAPVKLEY  540
KWSDQQLTFL MRHARNDFSR WDAAQSLLAT YIKLNVARHQ QGQPLSLPVH VADAFRAVLL  600
DEKIDPALAA EILTLPSVNE MAELFDIIDP IAIAEVREAL TRTLATELAD ELLAIYNANY  660
QSEYRVEHED IAKRTLRNAC LRFLAFGETH LADVLVSKQF HEANNMTDAL AALSAAVAAQ  720
LPCRDALMQE YDDKWHQNGL VMDKWFILQA TSPAANVLET VRGLLQHRSF TMSNPNRIRS  780
LIGAFAGSNP AAFHAEDGSG YLFLVEMLTD LNSRNPQVAS RLIEPLIRLK RYDAKRQEKM  840
RAALEQLKGL ENLSGDLYEK ITKALA                                       866

SEQ ID NO: 33          moltype = AA  length = 185
FEATURE                Location/Qualifiers
REGION                 1..185
                       note = PDB ID: 3U7M; mutant; M65
source                 1..185
                       mol_type = protein
                       organism = synthetic construct
SEQUENCE: 33
MLTMKDIIRD GHPTLRQKAA ELELPLTKEE KETLIAMREF LVNSQDEEIA KRYGLRSLAM  60
LVAPLINISK RMIVVLIPDD GSGKSYDYML VNPKIVSHSV QEAYLPTGFQ CIAVDDNVAG  120
LVHLHNRITI KAKDIEGNDI QLRLKGLPAL IFQHAIDHLN GVMFYDHIDK DHPLQPHTDA  180
VEVLL                                                              185

SEQ ID NO: 34          moltype = AA  length = 257
FEATURE                Location/Qualifiers
REGION                 1..257
                       note = PDB ID: 1Z97; mutant; M65
source                 1..257
                       mol_type = protein
                       organism = synthetic construct
SEQUENCE: 34
EWGYASHNGP DHWHELFPNA KGENQSPIEL HTKDIRHDPS LQPWSVSYDG GSAKTILNDG  60
LTCLVVFDDT YDRSMLRGGP LPGPYRLLFF HLHWGSSDDH GSLHTVDGVK YAAELHLVHW  120
NPKYNTYKEA QKQRDGIAII GIFLKIGHEN GEFQIFLDAL DKIKTKGKEA PFTKFDPSSL  180
FPASRDYWTY QGAMAVPPLE ECVVWLLLKE PMTVSSDQMA KLRSLLSSAE NEPPVPLVSN  240
WRPPQPINNR VVRASFK                                                 257

SEQ ID NO: 35          moltype = AA  length = 185
FEATURE                Location/Qualifiers
REGION                 1..185
                       note = PDB ID: 3U7M; mutant; M72
source                 1..185
                       mol_type = protein
                       organism = synthetic construct
SEQUENCE: 35
MLTMKDIIRD GHPTLRQKAA ELELPLTKEE KETLIAMREF LVNSLDEEIA KRYGLRSAGM  60
LVAPMINISK RMIVMLIPDD GSGKSWDYML VNPKIVSHSV QEAYLPTGEE CLSVDDNVAG  120
LVHRHNRITI KAKDIEGNDI QLRLKGLAAI AMQHAIDHLN GVMFYDHIDK DHPLQPHTDA  180
VEVLL                                                              185

SEQ ID NO: 36          moltype = AA  length = 866
FEATURE                Location/Qualifiers
REGION                 1..866
                       note = PDB ID: 4Q4E; mutant; M72
source                 1..866
                       mol_type = protein
                       organism = synthetic construct
SEQUENCE: 36
PQAKYRHDYR APDYQITDID LTFDLDAQKT VVTAVSQAVR HGASDAPLRL NGEDLKLVSV  60
HINDEPWTAW KEEEGALVIS NLPERFTLKI INEISPAANT ALEGLYQSGD ALCTQCVAEG  120
FRHITYYLDR PDVLARFTTK IIADKIKYPF LLSNGNRVAQ GELENGRHWV QWQDPFPKPC  180
YLFALVAGDF DVLRDTFTTR SGREVALELY VDRGNLDRAP WAMTSLKNSM KWDEERFGLE  240
YDLDIYMIVA VDFLNTGMMV NKGLNIVHSI AILARTDTAT DKDYLDIERL IGHAYFHNWT  300
GNRVTCRDWF QLSLIEGLTV FRDQEFSSDL GSRAVNRINN VRTMRGLQFA EDASPMAHPI  360
RPDMVIEMNN FYTLTVLEKG AEVIRMIHTL LGEENFQKGM QLYFERHDGS AATCDDFVQA  420
MEDASNVDLS HFRRWYSQSG TPIVTVKDDY NPETEQYTLT ISQRTPATPD QAEKQPLHIP  480
FAIELYDNEG KVIPLQKGGH PVNSVLNVTQ AEQTFVFDNV YFQPVPALLC EFSAPVKLEY  540
KWSDQQLTFL MRHARNDFSR WDAAQSLLAT YIKLNVARHQ QGQPLSLPVH VADAFRAVLL  600
DEKIDPALAA EILTLPSVNE MAELFDIIDP IAIAEVREAL TRTLATELAD ELLAIYNANY  660
QSEYRVEHED IAKRTLRNAC LRFLAFGETH LADVLVSKQF HEANNMTDAL AALSAAVAAQ  720
LPCRDALMQE YDDKWHQNGL VMDKWFILQA TSPAANVLET VRGLLQHRSF TMSNPIRILS  780
LIGAFAGSNP AAFHAEDGSG YLFLVEMLTD LNSRNPQVAS RLIEPLIRLK RYDAKRQEKM  840
RAALEQLKGL ENLSGDLYEK ITKALA                                       866

SEQ ID NO: 37          moltype = AA  length = 478
FEATURE                Location/Qualifiers
REGION                 1..478
                       note = PDB ID: 1LML; mutant; M72
source                 1..478
                       mol_type = protein
                       organism = synthetic construct
```

-continued

```
SEQUENCE: 37
VVRDVNWGAL RIAVSTEDLT DPAYHCARVG QHVKDHAGAI VTCTAEDILT NEKRDILVKH  60
LIPQAVQLHT ERLKVQQVQG KWKVTDMVGD ICGDFKVPQA HITEGFSNTD FVMYVASVPS  120
HEGILAWATT CQTFSDGHPA VGVINIPAAN IASRYDQLVT RVVTHAMAHA LGFSGPFFED  180
ARIVANVPNV RGKNFDVPVI NSSTAVAKAR EQYGCDTLEY LEVEDQGGAK IAGSHIKMRN  240
AQDELMAPKA AAGYYTALTM AIFQDLGFYQ ADFSKAEVMP WGQNAGCAFL TNKCMEQSVT  300
QWPAMFCNES EDAIRCPTSR LSLGACGVTR HPGLPPYWQY FTDPSLAGVS ALMDYCPVVV  360
PYSDGSCTQR ASEAHASLLP FNVFSDAARC IDGAFRPKAT DGIVKSYAGL CANVQCDTAT  420
RTYSVQVHGS NDYTNCTPGL RVELSTVSNA FEGGGYITCP PYVEVCQGNV QAAKDGGN    478

SEQ ID NO: 38           moltype = AA  length = 860
FEATURE                 Location/Qualifiers
REGION                  1..860
                        note = 3UJZ; mutant, M72
source                  1..860
                        mol_type = protein
                        organism = synthetic construct
SEQUENCE: 38
NSAIYFNTSQ PINDLQGSLA AEVKFAQSQI LPAHPKEGDS QPHLTSLRKS LLLVRPVKAD  60
DKTPVQVEAR DDNNKILGTL TLYPPSSLPD TIYHLDGVPE GGIDFTPHNG TKKIINTVAE  120
VNKLSDASGS SIHSHLTNNA LVEIHTANGR WVRDIYLPQG PDLEGKMVRF VSSAGYSSTV  180
FYGDRKVTLS VGNTLLFKYV NGQWFRSGEL ENNRITYAQH IWSAELPAHW IVPGLNLVIK  240
QGNLSGRLND IKIGAPGELL LHTIDIGMLT TPRDRFDFAA DAAAHREYFQ TIPVSRMIVN  300
NYAPLHLKEV MLPTGELLTD MDPGNGGETS GTMRQRIGKE LVSHGIDNAN YGLNSTAGLG  360
ENSHPYVVAQ LAAHNSRGNY ANGIQVHGKS GGGGIVTLDS TLGNEFSHAV GHNYGLGHYV  420
DGFKGSVHRS AENNNSTWGW DGDKKRFIPN FYPSQTNEKS CLNNQCQEPF DGHKFGFDAM  480
AGGSPFSAAN RFTMYTPNSS AIIQRFFENK AVFDSRSSTG FSKWNADTQE MEPYEHTIDR  540
AEQITASVNE LSESKMAELM AEYAVVKVHM WNGNWTRNIY IPTASADNRG SILTINHEAG  600
YNSYLFINGD EKVVSQGYKK SFVSDGQFWK ERDVVDTREA RKPEQFGVPV TTLVGYYDPE  660
GTLSSYIYPA MYGAYGFTYS DDSQNLSDND CQLQVDTKEG QLRFRLANHR ANNTVMNKFH  720
INVPTESQPT QATLVCNNKI LDTKSLTPAP EGLTYTVNGQ ALPAKENEGC IVSVNSGKRY  780
CLPVGQRSGY SLPDWIVGQE VYVDSGAKAK VLLSDWDNLS YNRIGEFVGN VNPADMKKVK  840
AWNGQYLDFS KPRSMRVVYK                                             860

SEQ ID NO: 39           moltype = AA  length = 201
FEATURE                 Location/Qualifiers
REGION                  1..201
                        note = PDB ID: 1IAG; M83
source                  1..201
                        mol_type = protein
                        organism = synthetic construct
SEQUENCE: 39
NLPQRYIELV VVADRRVFMK YNSDLNIIRT RVHEIVNIIN KFYRSLNIRV SLTDLEIWSG  60
QDFITIQSSS SNTLNSFGEW RERVLLIWKR HDNAQLLTAI NFEGKIILLA YTSSMCNPRS  120
SVGIVKDHSP INLLVAVTMA HLLGHNLGME HDGPDCLRGA SLCIMLPELT PGRSYEFSDD  180
SMGYYQKFLN QYKPQCILNK P                                           201

SEQ ID NO: 40           moltype = AA  length = 866
FEATURE                 Location/Qualifiers
REGION                  1..866
                        note = PDB ID: 4Q4E; mutant; M83
source                  1..866
                        mol_type = protein
                        organism = synthetic construct
SEQUENCE: 40
PQAKYRHDYR APDYQITDID LTFDLDAQKT VVTAVSQAVR HGASDAPLRL NGEDLKLVSV  60
HINDEPWTAW KEEEGALVIS NLPERFTLKI INEISPAANT ALEGLYQSGD ALCTQCMAEG  120
FRHITYYLDR PDVLARFTTK IIADKIKYPF LLSNGNRVAQ GELENGRHWV QWQDPFPKPC  180
YLFALVAGDF DVLRDTFTTR SGREVALELY VDRGNLDRAP WAMTSLKNSM KWDEERFGLE  240
YDLDIYMIVA VDFFNTLLIP NKGLNIFNSK LVLARTDTAT DEDYLRIEAA IGHIYFHNWT  300
GNRVTCRDWF QLSLKEGLTV FRDQEFSSDL GSRAVNRINN VRIMRGLQFA EDASPMAHPI  360
RPDMVIEMNN FYTLTVLYKG AEVIRMIHTL LGEENFQKGM QLYFERHDGS AATCDDFVQA  420
MEDASNVDLS HFRRWYSQSG TPIVTVKDDY NPETEQYTLT ISQRTPATPD QAEKQPLHIP  480
FAIELYDNEG KVIPLQKGGH PVNSVLNVTQ AEQTFVFDNV YFQPVPALLC EFSAPVKLEY  540
KWSDQQLTFL MRHARNDFSR WDAAQSLLAT YIKLNVARHQ QGQPLSLPVH VADAFRAVLL  600
DEKIDPALAA EILTLPSVNE MAELFDIIDP IAIAEVREAL TRTLATELAD ELLAIYNANY  660
QSEYRVEHED IAKRTLRNAC LRFLAFGETH LADVLVSKQF HEANNMTDAL AALSAAVAAQ  720
LPCRDALMQE YDDKWHQNGL VMDKWFILQA TSPAANVLET VRGLLQHRSF TMSNPNRIRS  780
LIGAFAGSNP AAFHAEDGSG YLFLVEMLTD LNSRNPQVAS RLIEPLIRLK RYDAKRQEKM  840
RAALEQLKGL ENLSGDLYEK ITKALA                                      866

SEQ ID NO: 41           moltype = AA  length = 478
FEATURE                 Location/Qualifiers
REGION                  1..478
                        note = PDB ID: 1LML; mutant; M83
source                  1..478
                        mol_type = protein
                        organism = synthetic construct
SEQUENCE: 41
```

-continued

```
VVRDVNWGAL RIAVSTEDLT DPAYHCARVG QHVKDHAGAI VTCTAEDILT NEKRDILVKH  60
LIPQAVQLHT ERLKVQQVQG KWKVTDMVGD ICGDFKVPQA HITEGFSNTD FVMYVASVPS  120
EEGVLAWATT CQTFSDGHPA VGVINIPAAN IASRYDQLVT RVVTHAMAHA LGFSGPFFED  180
ARIVANVPNV RGKNFDVPVI NSSTAVAKAR EQYGCDTLEY LEVEDQAGAK AAGSHIKMRN  240
AQDELMAPAA AAGYYTALTM AIFQDLGFYQ ADFSKAEVMP WGQNAGCAFL TNKCMEQSVT  300
QWPAMFCNES EDAIRCPTSR LSLGACGVTR HPGLPPYWQY FTDPSLAGVS ARMDYCPVVV  360
PYSDGSCTQR ASEAHASLLP FNVFSDAARC IDGAFRPKAT DGIVKSYAGL CANVQCDTAT  420
RTYSVQVHGS NDYTNCTPGL RVELSTVSNA FEGGGYITCP PYVEVCQGNV QAAKDGGN    478

SEQ ID NO: 42          moltype = AA  length = 478
FEATURE                Location/Qualifiers
REGION                 1..478
                       note = PDB ID: 1LML; mutant; M86
source                 1..478
                       mol_type = protein
                       organism = synthetic construct
SEQUENCE: 42
VVRDVNWGAL RIAVSTEDLT DPAYHCARVG QHVKDHAGAI VTCTAEDILT NEKRDILVKH  60
LIPQAVQLHT ERLKVQQVQG KWKVTDMVGD ICGDFKVPQA HITEGFSNTD FVMYVASVPS  120
HEGVLAWATT CQTFSDGHPA VGVINIPAAN IASRYDQLVT RVVTHVMAHA LGFSGPFFED  180
ARIVANVPNV RGKNFDVPVI NSSTAVAKAR EQYGCDTLEY LEVEDQGGRG VAGSHIKMRN  240
AQDELMAPDA AAGYYTALTM AIFQDLGFYQ ADFSKAEVMP WGQNAGCAFL TNKCMEQSVT  300
QWPAMFCNES EDAIRCPTSR LSLGACGVTR HPGLPPYWQY FTDPSLAGVS ALMDYCPVVV  360
PYSDGSCTQR ASEAHASLLP FNVFSDAARC IDGAFRPKAT DGIVKSYAGL CANVQCDTAT  420
RTYSVQVHGS NDYTNCTPGL RVELSTVSNA FEGGGYITCP PYVEVCQGNV QAAKDGGN    478

SEQ ID NO: 43          moltype = AA  length = 724
FEATURE                Location/Qualifiers
REGION                 1..724
                       note = PDB ID: 5E3C; mutant; M86
source                 1..724
                       mol_type = protein
                       organism = synthetic construct
SEQUENCE: 43
DTQYILPNDI GVSSLDSREA FRLLSPTERL YAYHLSRAAW YGGLAVLLQT SPEAPYIYAL  60
LSRLFRAQDP DQLRQHALAE GLTEEEYQAF LVYAAGVYSN MGNYKAWGDT KFVPNLPKEK  120
LERVILGSEA AQQHPEEVRG LWQTCGELMF SLEPRLRHLG LGKEGITTYF SGNCTMEDAK  180
LAQDFLDSQN LSAYNTRLFK EVDGCGKPYY EVRLASVLGS EPSLDSEVTS KLKSYEFRGS  240
PFQVTRGDYA PILQKVVEQL EKAKAYAANS HQGQMLAQYI ESFTQGSIEA HKRGSRFWIQ  300
DKGPIVESYI GFIWSVFDPF GSRGMFFGFV AVVNKAMSAK FERLVASAEQ LLKELPWPPT  360
FEKDKFLTPD FTSLDVLTMA GLGIPLMMVI PNYDDLRQTE GFKNVSLGNV LAVAYATQRE  420
KLTFLEEDDK DLYILWKGPS FDVQVGLHAL LGHGSGKLFV QDEKGAFNFD QETVINPETG  480
EQIQSWYRCG ETWDSKFSTI ASSYEECRAE SVGLYLSLHP QVLEIFGFEG ADAEDVIYVN  540
WLNMVRAGLL ALEFYTPEAF NWRDVLMQAR FVILRVLLEA GEGLVTITPT TGSDGRPDAR  600
VRLDRSKIRS VGKPALERFL RRLQVLKSTG DVAGGRALYE GYATVTDAPP ESFLTLRDTV  660
LLRKESRKLI VQPNTRLEGS DVQLLEYEAS AAGLIRSFSE RFPEDGPELE EILTQLATAD  720
ARFW                                                               724

SEQ ID NO: 44          moltype = AA  length = 261
FEATURE                Location/Qualifiers
REGION                 1..261
                       note = PDB ID: 2FV5; mutant; M86
source                 1..261
                       mol_type = protein
                       organism = synthetic construct
SEQUENCE: 44
ADPDPMKNTC KLLVVADHRF YRYMGRGEES TTTNYLIELI DRVDDIYRNT AWDNAGFKGY  60
GIQIEQIRIL KSPQEVKPGE KHYNMAKSYP NEEKDAWDLK MLLEQFSFDI AEEASKVCLA  120
HLFTYQDFDM GRLLIVYGGS PHANSHGGVC PKAYYSPVGK KNIYLNSGLT STKNYGKTIL  180
TKEADLVTTH ALGHNFGAEH DPDGLAECAP NEDQGGKYVM YPIAVSGDHE NNKMFSQCSK  240
QSIYKTIESK AQECFQERSN A                                            261

SEQ ID NO: 45          moltype = AA  length = 249
FEATURE                Location/Qualifiers
REGION                 1..249
                       note = PDB ID: 5K7J; mutant; M93
source                 1..249
                       mol_type = protein
                       organism = synthetic construct
SEQUENCE: 45
GSPRYLDGWL KDVVQLSLRR PSFRASRQRP IISLNERILE FNKRNITAII AEYKRKSVSG  60
LDVERDPIEY SKFMERYAVG LSILTEEKYF NGSYETLRKI ASSVSIPILM ADFIVKESQI  120
DDAYNLGADT VLLLVMILTE RELESLLEYA RSYGMEPIIM VLDENMLDIA LRIGARFIVL  180
HSKSHETLEI NKENQRKLIS MIPSNVVKVM VHGISERNEI EELRKLGVNA FIIGSSLMRN  240
PEKIKEFIL                                                          249

SEQ ID NO: 46          moltype = AA  length = 201
FEATURE                Location/Qualifiers
REGION                 1..201
```

```
                      note = PDB ID: 1IAG; mutant; M93
source                1..201
                      mol_type = protein
                      organism = synthetic construct
SEQUENCE: 46
NLPQRYIELV VVADRRVFMK YNSDLNIIRT RVHEIVNIIN KFYRSLNIRV SLTDLEIWSG  60
QDFITIQSSS SNTLNSFGEW RERVLLIWKR HDNAQLLTAI NFEGKIIMLA YTSSMCNPRS  120
SVGIVKDHSP INLLVAVTMA HLLGHNLGME HDGKDCLRGA SLCIMLPDLT PGRSYEFSDD  180
SMGYYQKFLN QYKPQCILNK P                                           201

SEQ ID NO: 47         moltype = AA  length = 866
FEATURE               Location/Qualifiers
REGION                1..866
                      note = PDB ID: 4Q4E; mutant; M93
source                1..866
                      mol_type = protein
                      organism = synthetic construct
SEQUENCE: 47
PQAKYRHDYR APDYQITDID LTFDLDAQKT VVTAVSQAVR HGASDAPLRL NGEDLKLVSV  60
HINDEPWTAW KEEEGALVIS NLPERFTLKI INEISPAANT ALEGLYQSGD ALCTQCLAEG  120
FRHITYYLDR PDVLARFTTK IIADKIKYPF LLSNGNRVAQ GELENGRHWV QWQDPFPKPC  180
YLFALVAGDF DVLRDTFTTR SGREVALELY VDRGNLDRAP WAMTSLKNSM KWDEERFGLE  240
YDLDIYMIVA VDFFNMIVIP NKGLNIFNSK YVLARTDTAT DEDYLKIEQI IGHAYFHNWT  300
GNRVTCRDWF QLSLIEGLTL FRVQEFSSDL GSRAVNRINN VRIMRGLQFA EDASPMAHPI  360
RPDMVIEMNN FFTLTVMWKG AEVIRMIHTL LGEENFQKGM QLYFERHDGS AATCDDFVQA  420
MEDASNVDLS HFRRWYSQSG TPIVTVKDDY NPETEQYTLT ISQRTPATPD QAEKQPLHIP  480
FAIELYDNEG KVIPLQKGGH PVNSVLNVTQ AEQTFVFDNV YFQPVPALLC EFSAPVKLEY  540
KWSDQQLTFL MRHARNDFSR WDAAQSLLAT YIKLNVARHQ QGQPLSLPVH VADAFRAVLL  600
DEKIDPALAA EILTLPSVNE MAELFDIIDP IAIAEVREAL TRTLATELAD ELLAIYNANY  660
QSEYRVEHED IAKRTLRNAC LRFLAFGETH LADVLVSKQF HEANNMTDAL AALSAAVAAQ  720
LPCRDALMQE YDDKWHQNGL VMDKWFILQA TSPAANVLET VRGLLQHRSF TMSNPNRIRS  780
LIGAFAGSNP AAFHAEDGSG YLFLVEMLTD LNSRNPQVAS RLIEPLIRLK RYDAKRQEKM  840
RAALEQLKGL ENLSGDLYEK ITKALA                                      866

SEQ ID NO: 48         moltype = AA  length = 256
FEATURE               Location/Qualifiers
REGION                1..256
                      note = Carbonic anhydrase II mutant, M=M64
source                1..256
                      mol_type = protein
                      organism = synthetic construct
SEQUENCE: 48
HWGYGKHNGP EHWHKDFPIA KGERQSPVDI DTHTAKYDPS LKPLSVSYDQ ATSLRILNNG  60
HAFNVEFDDS QDKAVLKGGP LDGTYRLIQF HFHWGSLDGQ GSEHTVDKKK YAAELHLVHW  120
NTKYGDFGKA VQHPDGLAVL GIFLKVGSAK PGLQKVVDVL DSIKTKGKSA DFTNFDPRGL  180
LPESLDYWTY PGSRTTPPLL ESVTWIVLKE PISVSSEQVL KFRKLNFNGE GEPEELMVDN  240
WRPAQPLKNR QIKASF                                                 256

SEQ ID NO: 49         moltype = AA  length = 256
FEATURE               Location/Qualifiers
REGION                1..256
                      note = Carbonic anhydrase II mutant, M=M64
source                1..256
                      mol_type = protein
                      organism = synthetic construct
SEQUENCE: 49
HWGYGKHNGP EHWHKDFPIA KGERQSPVDI DTHTAKYDPS LKPLSVSYDQ ATSLRILNNG  60
HAFNVEFDDS QDKAVLKGGP LDGTYRLIQF HFHWGSLDGQ GSEHTVDKKK YAAELHLVHW  120
NTKYGDFDKA VRQPDGLAVL GIFLKVGSAK PGLQKVVDVL DSIKTKGKSA DFTNFDPRGL  180
LPESLDYWTY PGSRTTPPLL ESVTWIVLKE PISVSSEQVL KFRKLNFNGE GEPEELMVDN  240
WRPAQPLKNR QIKASF                                                 256

SEQ ID NO: 50         moltype = AA  length = 256
FEATURE               Location/Qualifiers
REGION                1..256
                      note = Carbonic anhydrase II mutant, M=M64
source                1..256
                      mol_type = protein
                      organism = synthetic construct
SEQUENCE: 50
HWGYGKHNGP EHWHKDFPIA KGERQSPVDI DTHTAKYDPS LKPLSVSYDQ ATSLRILNNG  60
HAFNVEFDDS QDKAVLKGGP LDGTYRLIQF HFHWGSLDGQ GSEHTVDKKK YAAELHLVHW  120
NTKYGDFDKA VQQPDGLAVL GIFLNVGSAR PGLQKVVDVL DSIKTKGKSA YFTNFDPRGL  180
LPESLDYWTY PGSRTTPPLL ESVTWIVLKE PISVSSEQIL KFRKLNFNRE GEPEELMVDN  240
WRPTQPLKNR QIKASF                                                 256

SEQ ID NO: 51         moltype = AA  length = 256
FEATURE               Location/Qualifiers
REGION                1..256
```

```
                         note = Carbonic anhydrase II mutant, M=M64
source                   1..256
                         mol_type = protein
                         organism = synthetic construct
SEQUENCE: 51
HWGYGKHNGP EHWHKDFPIA KGERQSPVDI DTHTAKYDPS LKPLSVSYDQ ATSLRILNNG  60
HAFEVEFDDS QDKAVLKGGP LDGTYRLVQF HFHWGSLDGQ GSEHTVDKKK YAAELHLVHW  120
NTKYGDYGKA MQQPDGLAVL GIFLKVGSAK PGLQKVVDVL DSIKTKGKSA DFTNFDPRGL  180
LPESLDYWTY PGSGTVPPLL ESVTWIVLKE PISVSSEQVL KFRKLNFNGE GEPEELMVDN  240
WRPAQPLKNR QIKASF                                                256

SEQ ID NO: 52            moltype = AA  length = 256
FEATURE                  Location/Qualifiers
REGION                   1..256
                         note = Carbonic anhydrase II mutant, M=M64
source                   1..256
                         mol_type = protein
                         organism = synthetic construct
SEQUENCE: 52
HWGYGKHNGP EHWHKDFPIA KGERQSPVDI DTHTAKYDPS LKPLSVSYDQ ATSLRILNDG  60
HAFQVEFDDS QDKAVLKGGP LDGTYRLVQF HFHWGSLDGQ GSEHTVDKKK YAAELHLVHW  120
NTKYGDYGKA MQQPDGLAVL GIFLKVGSAK PGLQKVVDVL DSIKTKGKSA DFTNFDPRGL  180
LPESLDYWTY PGSGTVPPLL ESVTWIVLKE PISVSSEQVL KFRKLNFNGE GEPEELMVDN  240
WRPAQPLKNR QIKASF                                                256

SEQ ID NO: 53            moltype = AA  length = 256
FEATURE                  Location/Qualifiers
REGION                   1..256
                         note = Carbonic anhydrase II mutant, M=M64
source                   1..256
                         mol_type = protein
                         organism = synthetic construct
SEQUENCE: 53
HWGYGKHNGP EHWHKDFPIA KGERQSPVDI DTHTAKYDPS LKPLSVSYDQ ATSLRILNNG  60
HAFNVEFDDS QDKAVLKGGP LDGTYRLIQF HFHWGSLDGQ GSEHTVDKKK YAAELHLVHW  120
NTKYGDFGKA MQQPDGLAVL GIFLKVGSAK PGLQKVVDVL DSIKTKGKSA DFTNFDPRGL  180
LPESLDYWTY PGSGTVPPLL ESVTWIVLKE PISVSSEQVL KFRKLNFNGE GEPEELMVDN  240
WRPAQPLKNR QIKASF                                                256

SEQ ID NO: 54            moltype = AA  length = 256
FEATURE                  Location/Qualifiers
REGION                   1..256
                         note = Carbonic anhydrase II mutant, M=M64
source                   1..256
                         mol_type = protein
                         organism = synthetic construct
SEQUENCE: 54
HWGYGKHNGP EHWHKDFPIA KGERQSPVDI DTHTAKYDPS LKPLSVSYDQ ATSLRILNDG  60
HAFEVEFDDS QDKAVLKGGP LDGTYRLIQF HFHWGSLDGQ GSEHTVDKKK YAAELHLVHW  120
NTKYGDFGKA LQQPDGMAIL GIFLKVGSAK PGLQKVVDVL DSIKTKGKSA DFTNFDPRGL  180
LPESLDYWTY PGSQTIPPLL ESVTWIVLKE PISVSSEQVL KFRKLNFNGE GEPEELMVDN  240
WRPAQPLKNR QIKASF                                                256

SEQ ID NO: 55            moltype = AA  length = 256
FEATURE                  Location/Qualifiers
REGION                   1..256
                         note = Carbonic anhydrase II mutant, M=M64
source                   1..256
                         mol_type = protein
                         organism = synthetic construct
SEQUENCE: 55
HWGYGKHNGP EHWHKDFPIA KGERQSPVDI DTHTAKYDPS LKPLSVSYDQ ATSLRILNNG  60
HAFLVEFDDS QDKAVLKGGP LDGTYRLKQF HFHWGSLDGQ GSEHTVDKKK YAAELHLVHW  120
NTKYGDYGKA LQQPDGIAVL GIFLKVGSAK PGLQKVVDVL DSIKTKGKSA DFTNFDPRGL  180
LPESLDYWTY PGSRTIPPLL ESVTWIVLKE PISVSSEQVL KFRKLNFNGE GEPEELMVDN  240
WRPAQPLKNR QIKASF                                                256

SEQ ID NO: 56            moltype = AA  length = 256
FEATURE                  Location/Qualifiers
REGION                   1..256
                         note = Carbonic anhydrase II mutant, M=M64
source                   1..256
                         mol_type = protein
                         organism = synthetic construct
SEQUENCE: 56
HWGYGKHNGP EHWHKDFPIA KGERQSPVDI DTHTAKYDPS LKPLSVSYDQ ATSLRILNNG  60
HAFLVEFDDS QDKAVLKGGP LDGTYRLIQF HFHWGSLDGQ GSEHTVDKKK YAAELHLVHW  120
NTKYGDYGKA LQQPDGIAVL GIFLKVGSAK PGLQKVVDVL DSIKTKGKSA DFTNFDPRGL  180
LPESLDYWTY PGSRTIPPLL ESVTWIVLKE PISVSSEQVL KFRKLNFNGE GEPEELMVDN  240
```

```
WRPAQPLKNR QIKASF                                                    256

SEQ ID NO: 57          moltype = AA  length = 256
FEATURE                Location/Qualifiers
REGION                 1..256
                       note = Carbonic anhydrase II mutant, M=M64
source                 1..256
                       mol_type = protein
                       organism = synthetic construct
SEQUENCE: 57
HWGYGKHNGP EHWHKDFPIA KGERQSPVDI DTHTAKYDPS LKPLSVSYDQ ATSLRILNDG  60
HAFRVEFDDS QDKAVLKGGP LDGTYRLKQF HFHWGSLDGQ GSEHTVDKKK YAAELHLVHW  120
NTKYGDFGKA GQQPDGIAIL GIFLKVGSAK PGLQKVVDVL DSIKTKGKSA DFTNFDPRGL  180
LPESLDYWTY PGSETIPPLL ESVTWIVLKE PISVSSEQVL KFRKLNFNGE GEPEELMVDN  240
WRPAQPLKNR QIKASF                                                    256

SEQ ID NO: 58          moltype = AA  length = 257
FEATURE                Location/Qualifiers
REGION                 1..257
                       note = Carbonic anhydrase I, M=M64
source                 1..257
                       mol_type = protein
                       organism = synthetic construct
SEQUENCE: 58
DWGYDDKNGP EQWSKLYPIA NGNNQSPVDI KTSETKHDTS LKPISVSYNP ATAKEIINVG  60
HSFHVNFEDN DNRSVLKGGP FSDSYRLFQF HFHWGSTNEH GSEHTVDGVK YSAELHVAHW  120
NSAKYSSLAE AASKADGLAV IGVLMKVGEA NPKLQKVLDA LQAIKTKGKR APFTNFDPST  180
LLPSSLDFWT YPGSLTHPPL YESVTWIICK ESISVSSEQL AQFRSLLSNV EGDNAVPMQH  240
NNRPTQPLKG RTVRASF                                                   257

SEQ ID NO: 59          moltype = AA  length = 722
FEATURE                Location/Qualifiers
REGION                 1..722
                       note = truncated 4Q4E scaffold
source                 1..722
                       mol_type = protein
                       organism = synthetic construct
SEQUENCE: 59
PQAKYRHDYR APDYQITDID LTFDLDAQKT VVTAVSQAVR HGASDAPLRL NGEDLKLVSV  60
HINDEPWTAW KEEEGALVIS NLPERFTLKI INEISPAANT ALEGLYQSGD ALCTQCEAEG  120
FRHITYYLDR PDVLARFTTK IIADKIKYPF LLSNGNRVAQ GELENGRHWV QWQDPFPKPC  180
YLFALVAGDF DVLRDTFTTR SGREVALELY VDRGNLDRAP WAMTSLKNSM KWDEERFGLE  240
YDLDIYMIVA VDFFNMGAME NKGLNIFNSK YVLARTDTAT DKDYLDIERV IGHEYFHNWT  300
GNRVTCRDWF QLSLKEGLTV FRDQEFSSDL GSRAVNRINN VRTMRGLQFA EDASPMAHPI  360
RPDMVIEMNN FYTLTVYEKG AEVIRMIHTL LGEENFQKGM QLYFERHDGS AATCDDFVQA  420
MEDASNVDLS HFRRWYSQSG TPIVTVKDDY NPETEQYTLT ISQRTPATPD QAEKQPLHIP  480
FAIELYDNEG KVIPLQKGGH PVNSVLNVTQ AEQTFVFDNV YFQPVPALLC EFSAPVKLEY  540
KWSDQQLTFL MRHARNDFSR WDAAQSLLAT YIKLNVARHQ QGQPLSLPVH VADAFRAVLL  600
DEKIDPALAA EILTLPSVNE MAELFDIIDP IAIAEVREAL TRTLATELAD ELLAIYNANY  660
QSEYRVEHED IAKRTLRNAC LRFLAFGETH LADVLVSKQF HEANNMTDAL AALSAAVAAQ  720
LP                                                                   722

SEQ ID NO: 60          moltype = AA  length = 5
FEATURE                Location/Qualifiers
REGION                 1..5
                       note = model peptide
source                 1..5
                       mol_type = protein
                       organism = synthetic construct
SEQUENCE: 60
AFAAE                                                                5

SEQ ID NO: 61          moltype = AA  length = 5
FEATURE                Location/Qualifiers
REGION                 1..5
                       note = model peptide
VARIANT                1
                       note = Xaa is any standard L-amino acid residue
source                 1..5
                       mol_type = protein
                       organism = synthetic construct
SEQUENCE: 61
XAAAE                                                                5

SEQ ID NO: 62          moltype = AA  length = 5
FEATURE                Location/Qualifiers
REGION                 1..5
                       note = model peptide
source                 1..5
```

```
                        mol_type = protein
                        organism = synthetic construct
SEQUENCE: 62
DAERIR                                                       5

SEQ ID NO: 63           moltype = AA  length = 5
FEATURE                 Location/Qualifiers
REGION                  1..5
                        note = model peptide
source                  1..5
                        mol_type = protein
                        organism = synthetic construct
SEQUENCE: 63
EAEIR                                                        5

SEQ ID NO: 64           moltype = AA  length = 5
FEATURE                 Location/Qualifiers
REGION                  1..5
                        note = model peptide
source                  1..5
                        mol_type = protein
                        organism = synthetic construct
SEQUENCE: 64
AAEIR                                                        5

SEQ ID NO: 65           moltype = AA  length = 5
FEATURE                 Location/Qualifiers
REGION                  1..5
                        note = model peptide
source                  1..5
                        mol_type = protein
                        organism = synthetic construct
SEQUENCE: 65
FAEIR                                                        5

SEQ ID NO: 66           moltype = AA  length = 5
FEATURE                 Location/Qualifiers
REGION                  1..5
                        note = model peptide
source                  1..5
                        mol_type = protein
                        organism = synthetic construct
SEQUENCE: 66
LAEIR                                                        5

SEQ ID NO: 67           moltype = AA  length = 723
FEATURE                 Location/Qualifiers
REGION                  1..723
                        note = engineered cleavase
source                  1..723
                        mol_type = protein
                        organism = synthetic construct
SEQUENCE: 67
MHKTRLVAAL AAALATLAPA AWADEGMWVP QQLPEIAGAL KKAGLKLDPK QLSDLTGDPM  60
GAVVSLGGCT GSFVSPQGLV ATNHHCAYGA IQLNSTPEKN LIKDGFNAPT QADELSAGPN  120
ARIYVLEGIT DVTAQAKAAM AAAGNDPVAR ANALEAFEKK ITSDCEAEPG YRCRVYSFMG  180
GITYRLFKNL EIKDVRLVYA PPSSVGKFGG DIDMGMWPTH TGDFSFYRAY VGKDGKPAPY  240
SKDNVPYRPK HWLKIADTPL GEGDFVMVAG YPGRTDRYAL VAEFENTQNW LYPAISKAYK  300
DQIALVEAAA KDNPEIAVKY AAALAGWNRT SKNFDGQLEG FKRNDVLAIK RREEAAVLEW  360
LRARGKAGTP ALEAHAALVK LVADTARTQE RDLVLGSFNR TGIIGVAVNL YRLAIERQKP  420
DAEREPGYQQ RDLPVIEGSL KQMERRYVPA MDRQLRAYWL DRYVALPAAQ HVAAVDAWLG  480
GSDKAAAEAA LARLDQSRLG SLEERLKWFN ADRAAFEAST DPAIQYAVAV MPTLLAMEQQ  540
AKTRYGVALE ARPRYLQAVV DYKKSKGQAV YPDANSTLRI TYGHVKGYTG LNGKVYTPFT  600
TLEEVAAKET GVEPFDNPKA LLEAVAAKRY AGLADARLGT VPVNFLADLD ITGGNSGSPV  660
LDANGRLVGL AFAGTLESVA SNWVFDPVLT RMISVDQRYM RWIMQEVMPA PQLLEELGVP  720
PRQ                                                          723

SEQ ID NO: 68           moltype = AA  length = 259
FEATURE                 Location/Qualifiers
REGION                  1..259
                        note = S320_0000 - XP_004697542.1_carbonic_anhydrase_2_
source                  1..259
                        mol_type = protein
                        organism = Echinops telfairi
SEQUENCE: 68
SHHWGYAKHN GPDSWHENFP IAKGERQSPV NIDSRSAKHD PALKPLSINY EQATSRKILN  60
NGHSFNVEFD DSQDKAVLKG GPLDGTYRLI QFHFHWGSSD EQGSEHTVDK KMYPAELHLV  120
HWNTKYADFG QAVQHPDGLA VLGIFLKIGS AKPDLQRVLD ILDSIKTKGK SAEFKNFDPR  180
GLLPNSLDYW TYPGSLTTPP LLECVTWIVL REPISVSSEQ IKKFRSLSIN GDNEPEEPMV  240
```

```
INFRPPQPLK SRQIRASFK                                        259

SEQ ID NO: 69          moltype = AA  length = 254
FEATURE                Location/Qualifiers
REGION                 1..254
                       note = S325_0000 - _carbonic_anhydrase_2_isoform_X2_
source                 1..254
                       mol_type = protein
                       organism = Crassostrea gigas
SEQUENCE: 69
MSWGYEKNNG PALWHENFPV AKGNRQSPID ISTKACQVDN QLCSKPFQIN YSTEKNAEVS  60
NTGSSIKVQI KEVSEIKGGP LEGTWRLEQF HLHWGSSNDR GSEHTIDGKT YAAELHLVHW  120
NAKKYASFGE AADKPDGLAV LGFMVNVGKE HAGFKTITDV CSKIQEAGSS VKLDKDFNPS  180
CMLGKLDHYW TYLGSLTTPP LFESVTWTLF SDVIEISQAQ MDALRSLKFN NGKCMMDNYR  240
PPCALCGRSV KASK                                             254

SEQ ID NO: 70          moltype = AA  length = 257
FEATURE                Location/Qualifiers
REGION                 1..257
                       note = S334_0000 -
                        XP_030300927.1_carbonic_anhydrase_13-like_
source                 1..257
                       mol_type = protein
                       organism = Calypte anna
SEQUENCE: 70
LHWGYDEHNG PAHWKEVFPV ANGDRQSPID IKTEETKYDP SLRPLNPNYD PASAKIILNN  60
GHSTSVEFDD TVNKSVLTGG PLSGTYRLRQ IHFHWGSNDE AGSEHAVDGM KYAAELHVVH  120
WNAEKYSSFV EAARQSDGLA VMAVFLKIGE CNPQLKKITD RLDTIRIKGK KALFTNFDPS  180
CLLPKSLDYW TYFGSLTVPP LLESVIWIVL REPISVCSEQ LAKFRSLLST AEDEVACCLL  240
RNFRPPQPLK GREVRRN                                          257

SEQ ID NO: 71          moltype = AA  length = 260
FEATURE                Location/Qualifiers
REGION                 1..260
                       note = S336_0000 - _carbonic_anhydrase-like_
source                 1..260
                       mol_type = protein
                       organism = Acipenser ruthenus
SEQUENCE: 71
AHSWGYDVEN GPDKWGDHFP IANGPRQSPI DVVPSQAQYD ASLAPLSIQY DPATAKGILN  60
NGHSFQVDFV DSEDRSVLKG GPVSGTYRLR QFHFHWGSSD EHGSEHTVQG VKYPAELHLV  120
HWNSGKYPSF GESAAQPDGL AVVGVFLKIG NANPYLQKII DAFDAIKEKG KQTSFSDFNP  180
ATLLPGSLDF WTYDGSLTTP PLLESVTWIV LKETISVSAE QMARFRSLLF TGDGEAPCHM  240
VDNYRPPQPL KQRSVRASFK                                       260

SEQ ID NO: 72          moltype = AA  length = 259
FEATURE                Location/Qualifiers
REGION                 1..259
                       note = S337_0000 - _carbonic_anhydrase_
source                 1..259
                       mol_type = protein
                       organism = Thalassophryne amazonica
SEQUENCE: 72
SHAWGYGAAN GPHKWAEDFP VANGSRQSPI NIVTSDTLYD PTLKPVKLTF DPSTCTGILN  60
NGHSIQVDFE DDTSSSTLTG GPVSGTYQLR QFHFHWGAAD ERGSEHTINN FSFPCELHLV  120
HWNNKYPSFG EAVTKPDGLA VLGVFLKIGP ANPRLQKLLD LLDAVKTKGK QTDLSFFDPK  180
TLLPNSQHFW TYDGSLTTPP LLESVTWIIL KEPISVSPAQ MRKFRSLLFS GEGEAPLCMV  240
DNYRPPQPLK GRKVRATFK                                        259

SEQ ID NO: 73          moltype = AA  length = 259
FEATURE                Location/Qualifiers
REGION                 1..259
                       note = S340_0000 -_carbonic_anhydrase_2_
source                 1..259
                       mol_type = protein
                       organism = Manis javanica
SEQUENCE: 73
SHHWGYGKHN GPENWHKDFP IAKGERQSPI DIDSKAANYD PSLKPLHISY QQAASRRIIN  60
NGHSFNVEFD DSQNKAVLEG GPLTGPYRLI QFHFHWGSSD GLGSEHTVDK KRFPAELHLV  120
HWNTRYGDFG KAVQHTDGLA VLGIFLKIGG AKPDLQKVID VLDSIKTKGQ SADFPNFDPR  180
GLLPESLDYW TYPGSLTTPP LLECVTWIVL KEPISVSSEQ ILKFRNLHFN KEGDPDEVMV  240
DNWRPVQPLK NRQIKASFQ                                        259

SEQ ID NO: 74          moltype = AA  length = 259
FEATURE                Location/Qualifiers
REGION                 1..259
                       note = S344_0000 - carbonic_anhydrase_2-like_isoform_X1_
source                 1..259
                       mol_type = protein
```

```
                         organism = Mauremys reevesii
SEQUENCE: 74
SRHWGYASHN GPAHWHENFP IANGEHQSPI DINTESAQYD FSLKPLHFSY DPSTAKNIVN  60
NGHSFNVEFD DSADKSVLRG GALEGTYRLI QFHIHWGSCE GQGSEHTVDG VQYDAELHLV  120
HWNTKYGRFG EAVKHPDGLT VVGVFLQVGS DRPGIQKIID ALDSIQTKGK QASFTNFDPK  180
NLLPTSLDYW TYQGSLTTPP LLECVIWHVL REPISVSSEQ LCKLRGLCFS AENETPYHMM  240
DNWRPCQPLK GREVRASFQ                                              259

SEQ ID NO: 75            moltype = AA  length = 257
FEATURE                  Location/Qualifiers
REGION                   1..257
                         note = Synthetic binder, S279_0004
source                   1..257
                         mol_type = protein
                         organism = synthetic construct
SEQUENCE: 75
EWGYASHNGP DHWHELFPNA KGENQSPIEL HTKDIRHDPS LQPWSVSYDG GSAKTILNNG  60
KTLGVVFDDT YDRSMLRGGP LPGPYRLREF HLHWGSSDDH GSEHTVDGVK YAAELHLLHW  120
NPKYNTFKEA LKQRDGLAVI GIFLKIGHEN GEFQIFLDAL DKIKTKGKEA PFTKFDPSSL  180
FPASRDYWTY QGSMTIPPLM EAVVWLLLKE PMTVSSDQMA KLRSLLSSAE NEPPVPLVSN  240
WRPPQPINNR VVRASFK                                                257

SEQ ID NO: 76            moltype = AA  length = 259
FEATURE                  Location/Qualifiers
REGION                   1..259
                         note = Synthetic binder, S222_0431
source                   1..259
                         mol_type = protein
                         organism = synthetic construct
SEQUENCE: 76
SHHWGYGKHN GPEHWHKDFP IAKGERQSPV DIDTHTAKYD PSLKPLSVSY DQATSLRILN  60
NGHTFLVEFD DSQDKAVLKG GPLDGTYRLR QFHFHWGSLD GQGSEHTVDK KKYAAELHLL  120
HWNTKYGDYG KAKQQPDGIA ILGIFLKVGS AKPGLQKVVD VLDSIKTKGK SADFTNFDPR  180
GLLPESLDYW TYPGSMTIPP LLESVTWIVL KEPISVSSEQ VLKFRKLNFN GEGEPEELMV  240
DNWRPAQPLK NRQIKASFK                                              259

SEQ ID NO: 77            moltype = AA  length = 259
FEATURE                  Location/Qualifiers
REGION                   1..259
                         note = Synthetic binder, S222_0882
source                   1..259
                         mol_type = protein
                         organism = synthetic construct
SEQUENCE: 77
SHHWGYGKHN GPEHWHKDFP IAKGERQSPV DIDTHTAKYD PSLKPLSVSY DQATSLRILN  60
NGHAFDVEFD DSQDKAVLKG GPLDGTYRLH QFHFHWGSLD GQGSEHTVDK KKYAAELHLV  120
HWNTKYGDYG KAAQQPDGLA ILGIFLKVGS AKPGLQKVVD VLDSIKTKGK SADFTNFDPR  180
GLLPESLDYW TYPGSMTIPP LLESVTWIVL KEPISVSSEQ VLKFRKLNFN GEGEPEELMV  240
DNWRPAQPLK NRQIKASFK                                              259

SEQ ID NO: 78            moltype = AA  length = 259
FEATURE                  Location/Qualifiers
REGION                   1..259
                         note = Synthetic binder, S222_0397
source                   1..259
                         mol_type = protein
                         organism = synthetic construct
SEQUENCE: 78
SHHWGYGKHN GPEHWHKDFP IAKGERQSPV DIDTHTAKYD PSLKPLSVSY DQATSLRILN  60
DGHAFAVEFD DSQDKAVLKG GPLDGTYRLF QFHFHWGSLD GQGSEHTVDK KKYAAELHLV  120
HWNTKYGDFG KAKQQPDGLA VLGIFLKVGS AKPGLQKVVD VLDSIKTKGK SADFTNFDPR  180
GLLPESLDYW TYPGSQTVPP LLESVTWIVL KEPISVSSEQ VLKFRKLNFN GEGEPEELMV  240
DNWRPAQPLK NRQIKASFK                                              259

SEQ ID NO: 79            moltype = AA  length = 259
FEATURE                  Location/Qualifiers
REGION                   1..259
                         note = Synthetic binder, S222_0903
source                   1..259
                         mol_type = protein
                         organism = synthetic construct
SEQUENCE: 79
SHHWGYGKHN GPEHWHKDFP IAKGERQSPV DIDTHTAKYD PSLKPLSVSY DQATSLRILN  60
NGHTFIVEFD DSQDKAVLKG GPLDGTYRLV QFHFHWGSLD GQGSEHTVDK KKYAAELHLV  120
HWNTKYGDLG KALQQPDGLA ILGIFLKVGS AKPGLQKVVD VLDSIKTKGK SADFTNFDPR  180
GLLPESLDYW TYPGSWTVPP LLESVTWIVL KEPISVSSEQ VLKFRKLNFN GEGEPEELMV  240
DNWRPAQPLK NRQIKASFK                                              259

SEQ ID NO: 80            moltype = AA  length = 259
```

-continued

```
FEATURE                Location/Qualifiers
REGION                 1..259
                       note = Synthetic binder, S222_0395
source                 1..259
                       mol_type = protein
                       organism = synthetic construct
SEQUENCE: 80
SHHWGYGKHN GPEHWHKDFP IAKGERQSPV DIDTHTAKYD PSLKPLSVSY DQATSLRILN  60
DGHAFKVEFD DSQDKAVLKG GPLDGTYRLE QFHFHWGSLD GQGSEHTVDK KKYAAELHLV  120
HWNTKYGDLG KAMQQPDGLA ILGIFLKVGS AKPGLQKVVD VLDSIKTKGK SADFTNFDPR  180
GLLPESLDYW TYPGSQTIPP LIESVTWIVL KEPISVSSEQ VLKFRKLNFN GEGEPEELMV  240
DNWRPAQPLK NRQIKASFK                                                259

SEQ ID NO: 81          moltype = AA  length = 259
FEATURE                Location/Qualifiers
REGION                 1..259
                       note = Synthetic binder, S222_0913
source                 1..259
                       mol_type = protein
                       organism = synthetic construct
SEQUENCE: 81
SHHWGYGKHN GPEHWHKDFP IAKGERQSPV DIDTHTAKYD PSLKPLSVSY DQATSLRILN  60
NGHAFRVEFD DSQDKAVLKG GPLDGTYRLH QFHFHWGSLD GQGSEHTVDK KKYAAELHLV  120
HWNTKYGDFG KAEQQPDGLA ILGIFLKVGS AKPGLQKVVD VLDSIKTKGK SADFTNFDPR  180
GLLPESLDYW TYPGSMTVPP LLESVTWIVL KEPISVSSEQ VLKFRKLNFN GEGEPEELMV  240
DNWRPAQPLK NRQIKASFK                                                259

SEQ ID NO: 82          moltype = AA  length = 260
FEATURE                Location/Qualifiers
REGION                 1..260
                       note = Synthetic binder, S254_0083
source                 1..260
                       mol_type = protein
                       organism = synthetic construct
SEQUENCE: 82
ASPDWGYDDK NGPEQWSKLY PIANGNNQSP VDIKTSETKH DTSLKPISVS YNPATAKEII  60
NVGHSFRVNF EDNDNRSVLK GGPFSDSYRL YQFHFHWGST NEHGSEHTVD GVKYSAELHV  120
VHWNSAKYSS LAEALSKADG IAVIGVLMKV GEANPKLQKV LDALQAIKTK GKRAPFTNFD  180
PSTLLPSSLD FWTYPGSWTA PPLYEIVTWI ILKESISVSS EQLAQFRSLL SNVEGDNAVP  240
MQHNNRPTQP LKGRTVRASF                                               260

SEQ ID NO: 83          moltype = AA  length = 259
FEATURE                Location/Qualifiers
REGION                 1..259
                       note = Synthetic binder, S396_0000
source                 1..259
                       mol_type = protein
                       organism = synthetic construct
SEQUENCE: 83
DARVEEIVAL LEGDVADAEE RLARIIELIG EMTPEEQRAL AERVRESGEL AENLLRLLEA  60
TSDEFVRTEL AALIKKLTTA GKAALVEMLV EMLLRNPDVS RDVIRKIHEL MHAIGFYHSS  120
ENPAGFVRTL GELLAELATP ELAPFVRELF DKVVEKVEAA IKAGKSTEEI QKLMAEALSE  180
AFLEFAKRGD PRLTVRMISI TALVHTIMHY PEDAELVKEF AEAMLETLDE IAERTPELRE  240
EILRERELLK KTIENILKT                                                259

SEQ ID NO: 84          moltype = AA  length = 187
FEATURE                Location/Qualifiers
REGION                 1..187
                       note = Synthetic binder, S397_0000
source                 1..187
                       mol_type = protein
                       organism = synthetic construct
SEQUENCE: 84
MEEEKRELLK KALEAFEKFE AEKDEEEKIR LAVIALAYLQ ALKALEDGDE EKAKLFKEFA  60
EKAKTATEEE AMKILHELMH AIGFYHAEEE KESDEEFLAR VRAILEDTLL SFAEVKGREL  120
GLDPEEARAI AREVFAELPE EAWRTWAKMV RLIMHYGYDR EELRKLLLEA SESLAAAVRR  180
LLARLEA                                                             187

SEQ ID NO: 85          moltype = AA  length = 197
FEATURE                Location/Qualifiers
REGION                 1..197
                       note = Synthetic binder, S398_0000
source                 1..197
                       mol_type = protein
                       organism = synthetic construct
SEQUENCE: 85
SALEEEYARL RAAVEARATR LAERLAARAE DPRVRAAIAD LLARLRAALA AGPTRVRLLT  60
ALLALIIAEA ILEDPELAAK IIHEIMHYTT PEEYVALIDK IFKLAGLDIE ATDEDKRKAW  120
QALHELMHAI GFYHDTPYEE ILKYLKENGW RIAAALMAGA VVYLEEGLEA ALEAARATLE  180
```

```
AMAAAEEELA KEREEAA                                               197

SEQ ID NO: 86          moltype = AA  length = 253
FEATURE                Location/Qualifiers
REGION                 1..253
                       note = Synthetic binder, S399_0000
source                 1..253
                       mol_type = protein
                       organism = synthetic construct
SEQUENCE: 86
MEEEERRRRR ERLEEAAEAV AETLRRLIFA RAFFGPAAAL AIAEEALAAA KASGDEEVEE  60
LFRLLLLQVR GNVGLRAALA LPLFRDVLER ILAEMVSVIM HYGSVEELVA AFIALLVRLA  120
IELLLLLARY RAEISPAERV AILIAAVSAV VTAYLIATEA TPWTRRLVLQ ILHELMHAIG  180
FYHDTSTEEV LAFMRERPEE FLLALDALGL LGVASLRLGT LYERAGFREE AERIARRLAE  240
VTVAALKEAL KLR                                                   253

SEQ ID NO: 87          moltype = AA  length = 162
FEATURE                Location/Qualifiers
REGION                 1..162
                       note = Synthetic binder, S400_0000
source                 1..162
                       mol_type = protein
                       organism = synthetic construct
SEQUENCE: 87
AAERREEVRR EVEEILEELE KRVEEAKAAK EWTEAQKLVA IAAAFLEALA RLADLIAERG  60
DVPLELVLKA YQKLHELMHA IGFYHAEKAK EILEKKFSII KGISEETKKT VTEAVLFIMH  120
YWDSSPEEMA REYRAWLLAR RPEIRKAAEE LKALLKAMEA AA                   162

SEQ ID NO: 88          moltype = AA  length = 276
FEATURE                Location/Qualifiers
REGION                 1..276
                       note = Synthetic binder, S401_0000
source                 1..276
                       mol_type = protein
                       organism = synthetic construct
SEQUENCE: 88
SRLRELQARA RARLLALSVA DLRALAAAAK NPAMALMLAE LARARELLAA SEEALREDVL  60
AAAEAARARL AELSRDEAIA IMFRLALYLA LFPDLSEEER RRLLEVMHEL MHAIGFYHAE  120
ENPKKNIEVA AELAKEFLLD VVDMFLDIRA REGWPQEKLD AVREETRRIL EEMKEKAKTA  180
TLEEYEEIMK KAAEEIAKRL EEAGFREGAE IMKLAFEHEI QATRAAYLIM HYPKSEEDRE  240
RTLEAIVEHV LLFLELLAAL VAAARRAAAR AAARAA                           276

SEQ ID NO: 89          moltype = AA  length = 216
FEATURE                Location/Qualifiers
REGION                 1..216
                       note = Synthetic binder, S402_0000
source                 1..216
                       mol_type = protein
                       organism = synthetic construct
SEQUENCE: 89
TAELEELLAQ AAELLRALEE GDLERADELF AELGEAGLEL LRLYALVNRT LAVAEIMHYY  60
ETEEELLERL ERLKGILRRA AYALERTGLD PELLELFKRL LEALEDPSLT DEELIEIWKE  120
AHELMHAIGF YHADEYIEKL TQAFYEASVA DVETLARGAA AMLYAGRGEE ALARLRALAL  180
AAFPELAPLV DRAVELAAEN PVLAITLLLL LLRVAQ                           216

SEQ ID NO: 90          moltype = AA  length = 277
FEATURE                Location/Qualifiers
REGION                 1..277
                       note = Synthetic binder, S403_0000
source                 1..277
                       mol_type = protein
                       organism = synthetic construct
SEQUENCE: 90
MIIFAIADFD ATERVAAFVR EKLREGKVRT VIIVAFFAGS PEAALAALAL FAETVKAVVL  60
TIKEVTKGKS IGLLLVFDLG IHSREAEAAA AVLEAALPVI ARAVAEAKDA GAIEEVELVI  120
TSFNNAALLE RVVAHARALF EREVAGAKVH GINTAPDEAG QEALVEYIAE LAKELAERTD  180
YLVVALASIH TTRPDSRVVK LMTRLILAII ERLDSPVLII GLAGTPIVLA AMVYIMLTLQ  240
EAKGLEVENL LSPEGAALLA AIRAAEAAAR LAAALAA                          277

SEQ ID NO: 91          moltype = AA  length = 246
FEATURE                Location/Qualifiers
REGION                 1..246
                       note = Synthetic binder, S404_0000
source                 1..246
                       mol_type = protein
                       organism = synthetic construct
SEQUENCE: 91
MKAMVGVIFV LVGGASPEEQ KEAHEKFREI IDILKEVLGV DKVFYGMFIL DASVSIEEFK  60
KQVKELKEKF KKWAEAIKKE LKEKYKVDEL VVSVSIHVVE PKDKSEEEKE EYEKLVKELA  120
```

```
EEFAVQMAKL SEGFKKRIFY FDLGIHSRES IEKQAKLLKS AIEAMLKYLE EKEKEKKEEI  180
EVYIGVRYVA STSEEELKKL KEIFEKEAEE LKKLAEEYGV KFFAGFGTSS REDLEKIFNK  240
FKEAID                                                            246

SEQ ID NO: 92          moltype = AA  length = 199
FEATURE                Location/Qualifiers
REGION                 1..199
                       note = Synthetic binder, S405_0000
source                 1..199
                       mol_type = protein
                       organism = synthetic construct
SEQUENCE: 92
MLIVHVLLNL SGSIEESVER AKTILEAVFE VTAGKKILLI SIHLGLGIEL KDSAREALKR  60
LEAFAKELAK KYGSELTIRF VYVDDSLEEA HARAVARTRE ILERAVEEEG VDVIVTDLGI  120
HSREVELAGP MYAAILETMK ELADREGGTL IGVAVGTPEA NARFAAMLEA VGARVLVASE  180
EDSLEEIRAR VRAALEAAL                                              199

SEQ ID NO: 93          moltype = AA  length = 339
FEATURE                Location/Qualifiers
REGION                 1..339
                       note = Synthetic binder, S406_0000
source                 1..339
                       mol_type = protein
                       organism = synthetic construct
SEQUENCE: 93
MKAGLVVAAL LDEENKEAQE EQLKKLKEFL KENYPKLDMV IVVTPVGSEA TAASAARIMR  60
EIRELFPEDF DAAIAGENIS DTRLLEQIAR EAGLPLAGTL YSDDEPRGRE AVERLAAELG  120
RPIVNAGGSA YNAGVLIELA IKRGSKLLVL ATHGAGFFAI IGEAINALLR EADEVEIGVF  180
VSASPRVTFI AYSLAIAAAL LFNGLDAARA RLEILETEYG FPRALTLHAS MRPEDAKRAV  240
EALADEIDYV NIVMDPHVAD NAEELVKVVV EEAAKKGLKK IRFWFLGGES GAERALRVAK  300
VLFEEAKKYG IEVEIEFFTD SPKAKELIEE IEKLKKELE                        339

SEQ ID NO: 94          moltype = AA  length = 331
FEATURE                Location/Qualifiers
REGION                 1..331
                       note = Synthetic binder, S407_0000
source                 1..331
                       mol_type = protein
                       organism = synthetic construct
SEQUENCE: 94
MGKITFLAGA TTEDVAALLA EELRRIRERY GIRGAIAGEN ISDTRLLEQI AREAGLPLAG  60
TLYSDLGPEY LPLALARTDA LLERWADYEG VWFSANNRVA IRALELAAER GLRVVVLSSG  120
APTIALALRA AELSPRFEEI IFSSHGLNLA MGAAALYLIA REKGIEFELR LRNASDRTLV  180
ALAGAKAVWE DLEAYAKEEG VELKVVAFET TGTEEEAKAR KEELIKKAKE EGALAFLIGG  240
DPHGLMSPET AAAIATELIE AMADIGVKHI IVILGDEPNT RVMVEAIMAK IKEVIKEKGI  300
EKVYVFGDSP FVAALAAELA ELANATLWRG A                                331

SEQ ID NO: 95          moltype = AA  length = 208
FEATURE                Location/Qualifiers
REGION                 1..208
                       note = Synthetic binder, S408_0000
source                 1..208
                       mol_type = protein
                       organism = synthetic construct
SEQUENCE: 95
SLLTSFHETL KNLLEVMKDL GFEYLTAHLH FGEEGGTLHL LFYNPAHGTP EAAREAPPRG  60
IPLVSKTFPD GSTISTTAAT TGSDGGFAEV TIGLKEGDGP DQVLSLPKNQ TLDVSEGGFT  120
GDLESLKSEK ELENYLKGKE IANQIVEGKY KTVGFRSLPG KVEIIGTNLD GTTETVTIDK  180
LEFDPEKLSR RGVTHLTLAN AAVGVPLP                                    208

SEQ ID NO: 96          moltype = AA  length = 251
FEATURE                Location/Qualifiers
REGION                 1..251
                       note = Synthetic binder, S409_0000
source                 1..251
                       mol_type = protein
                       organism = synthetic construct
SEQUENCE: 96
MEALLERARR RIRERQEREV LDGLIALARA TAEEAGFRFV DEHEHRSPGP AVLNGLRHLL  60
FYNPAFGTEA AARKARLGPG GAPRAVRVTP EELAAALREA LAAVRDTAGF AVVTLPLVDP  120
SLLSPHVRAV FASLGARGGA RLIVLGVASL ASSFTHDEDG GANEAEFALH NRVWEHLLAA  180
LETVRDEADL RAAADAALAK WLELVPELEA ALAGRPRNVA HLVLGYLLYV EVSEEAVAAE  240
LARLAAEAAA A                                                      251

SEQ ID NO: 97          moltype = AA  length = 388
FEATURE                Location/Qualifiers
REGION                 1..388
                       note = Synthetic binder, S410_0000
source                 1..388
```

```
                        mol_type = protein
                        organism = synthetic construct
SEQUENCE: 97
SNREAVLRRL LERALAALEA AGFRVLGVHL HFGYKEEMAK DPSGKKIVLP YGHLHILAWN  60
PAFGTLEAAL KARVAERPAI IEAAYISPRE SDIERLIELV RTEPVARLSI MFLNVTPESI  120
KGLIRLLEAL AERPDIKVKL FVTKSADVSE LLKKAKELGI EVKEVDLSEW KLLWEAIEEG  180
YAAVYVANIP EEDPLALKIL EEFAERALAR ALASLAGAPL VEVEIDLNPT DPLNYGFRTR  240
AGRLTHGFKF PLPVMMAFFD YSGSREVVKK SAELFKEDVL TLARLGFIED VVVALAAGGA  300
ATRAKLAESA DIIVEMLREL AEALAALGKR FRVAVVAARD PADTAALLAL LARLPELEVE  360
VVREDRDVGR NVALIELDVS LNVGKVKV                                    388

SEQ ID NO: 98           moltype = AA  length = 385
FEATURE                 Location/Qualifiers
REGION                  1..385
                        note = Synthetic binder, S411_0000
source                  1..385
                        mol_type = protein
                        organism = synthetic construct
SEQUENCE: 98
MVEELMAVLE YWVETLKKAV SPVTGYKFVR SHIHSEPGGE AEGHVHLVFY NPKYGTLEAA  60
LKHGKDVKAP VRVHVEPLTP EQAALRRKGM LYVLGSEEAQ RRLPWYRTVA LAYAEALRDL  120
AEAAGAPLLP DSMLNPEAIL ATIDEAVAAV KEEGKLITEP PSPEELKLVE ADAANVVKFI  180
KEEVAEDLQK FGILVVELPL MPLDSFLYYL GPQNGVLSYS GGLTFPPEEM AAALLPQYEH  240
YEKLRKKAEE ILKEARKLIK EAKKKEGEDK EKVEELKKKV REKIKEYMEL EKERARLGFS  300
PGYEIAFRLE ELLEEEGVDE EFKEEVRERI REFIYEAVKE NFARELAKEG NVFRIKVFTG  360
VPFATPETRP AIEARMEEDA ARVRA                                       385

SEQ ID NO: 99           moltype = AA  length = 228
FEATURE                 Location/Qualifiers
REGION                  1..228
                        note = Synthetic binder, S412_0000
source                  1..228
                        mol_type = protein
                        organism = synthetic construct
SEQUENCE: 99
SAARRAALAA RARERLEEAI KAVKEILEKN KEKIGYELLD YHLHAEPREP VDDDPSLPRL  60
VGIVHFTLYN KEFGTPEAAL KANGGKAPGF LVFSVLLLSR RPEYESTFST GVLSYLGNPT  120
TPDGHGGMPF DLAQKLLGKT SLAKIKEYYT KNYYYIEGPD YTGPLEEQIS YLKEVLETAV  180
ENMPAIKAAV MASGDGSGNV LWVILLAGVV VDDEAADAWL AELAAARA              228

SEQ ID NO: 100          moltype =   length =
SEQUENCE: 100
000

SEQ ID NO: 101          moltype =   length =
SEQUENCE: 101
000

SEQ ID NO: 102          moltype =   length =
SEQUENCE: 102
000

SEQ ID NO: 103          moltype =   length =
SEQUENCE: 103
000

SEQ ID NO: 104          moltype =   length =
SEQUENCE: 104
000

SEQ ID NO: 105          moltype = AA  length = 262
FEATURE                 Location/Qualifiers
REGION                  1..262
                        note = Synthetic binder, S508_0000
source                  1..262
                        mol_type = protein
                        organism = synthetic construct
SEQUENCE: 105
KKQHVVLVLL PESKVGGSPA AEAILEGVKE ALEEANSPEV KGRLYRTTIL PEQAREAARY  60
GRDVQNSLGA GVVLFYASPP GESGAPAQPF TREAVLAQVR AALAADTRET PGPKAAQAHV  120
HADGVEHRAL NVVDGRVDEA SLEAVKEVEG ATAWEVHVLL GRLAPFRTPS PNYAVAKPPE  180
ERAAALAAVA AALAQAIPGI SVLLVGEDST ERATAAARAA VAAAGATPVV RGLDIGEITD  240
ESDLERIKEA AKEAVREAIA ER                                          262

SEQ ID NO: 106          moltype = AA  length = 263
FEATURE                 Location/Qualifiers
REGION                  1..263
                        note = Synthetic binder, S509_0000
source                  1..263
```

```
                        mol_type = protein
                        organism = synthetic construct
SEQUENCE: 106
AGGAAGLAPL VGVGEEQRPE LERALREALE RLGLPLPPED LPPGTRVELH ILSRDGNLAV  60
LAPPGLEAAR AIADWLVAQG LVSQYHLHIS GPEPEAEKVA KEIIKAFGGD ESVLVAPELR  120
HGGVAPGVPR ETYEEVAELL PEEGRAFLLY LIATLSRGTN LGLRSDPAAL DAAEHTRGSG  180
LRWYGESLRL AGRVLSEELL AAARAVVDRI FGKVRGASEE RLEEAARELV EALVELLEEE  240
RREEVREGAE RAAERLLRLG LAR                                          263

SEQ ID NO: 107          moltype = AA  length = 262
FEATURE                 Location/Qualifiers
REGION                  1..262
                        note = Synthetic binder, S510_0000
source                  1..262
                        mol_type = protein
                        organism = synthetic construct
SEQUENCE: 107
ATEWAVSLSL GGDGEIRPLA GPVDSPESRA RIAAATRVGV HLYPLPENYR TGEESFADAR  60
AAFAALRARF ADTATLFPFG IIGTLFVFTA VGDRAAIRAL IDATVELFGH RVSFSGPSQV  120
HTHGPGDIRA RTLGDVSTAE LPAVAEAELA RARPDEEVHA LDASGAAVYL GGRETGAQGI  180
KAPYRVATVS LNRSTDEALA AVDAALAAGA DEITALGFAE TAEENARVRA NLEALLARFP  240
DAVAEERANA DGQYLLARVR LR                                           262

SEQ ID NO: 108          moltype = AA  length = 262
FEATURE                 Location/Qualifiers
REGION                  1..262
                        note = Synthetic binder, S511_0000
source                  1..262
                        mol_type = protein
                        organism = synthetic construct
SEQUENCE: 108
ATEWGVTLSL GAGGELRPLA GPVDSPESQA RIAAATRVGA HVYPLPLNVR TGEESFADAR  60
AAFDELKARF ADTVDLFSLG IIGTLFVFVG TGDAAGVAAL IRAIVERFGQ RVSFSGKSQV  120
HTHGPGDIRS RALGEVKTEE LEAVARAELK NARPDEEVHA LDADGAAVYL GGAETGAQGI  180
KAPFRAATVS LGRSTDEALA AVDRLRALGA DEILALGFAT TEEENARVRA NLEALRARFP  240
DAEAWEEANA DGRNLLARIR LR                                           262

SEQ ID NO: 109          moltype = AA  length = 177
FEATURE                 Location/Qualifiers
REGION                  1..177
                        note = Synthetic binder, S512_0000
source                  1..177
                        mol_type = protein
                        organism = synthetic construct
SEQUENCE: 109
APAVGVAALR KGREEGNVIT PEGRALAEAL AAADPRIRVE GTVLSVTAAT EAELEAAVAR  60
LAAAFRARGY TVVIVGPADL PALAHADVAV VPSEPGAALE AEAQAHPDHE ITEVHLVRPG  120
RVETLPLRPE ELRALDPRLA AEGSQWHAHG VAPDSPLRGY GEHGPRPPLG PFSSILA     177

SEQ ID NO: 110          moltype = AA  length = 263
FEATURE                 Location/Qualifiers
REGION                  1..263
                        note = Synthetic binder, S513_0000
source                  1..263
                        mol_type = protein
                        organism = synthetic construct
SEQUENCE: 110
KTALQVWVDA EKALIDELLE RDPRVSAEQA ALARELLDLR AAESKTSNVA TPEYFAFLEA  60
HAEELAALRE APLGHLVGVY PVGTTLANLT IFPRVDPERH PLEALVRVFN ALPGFAPNEL  120
HVVRPDGSVQ RVRGAEGIER VTGAPLPPLK GKYAEHSEPG AEEVTLEPGS QVHFHGDYAL  180
TPEQFKAFVR RLNEEAGPAV WGLTVVDAPA EFAPLALARV RLAIEFGLDV EVTLTGAAFA  240
AELAAALRAA AAEAGVRATV TIR                                          263

SEQ ID NO: 111          moltype = AA  length = 263
FEATURE                 Location/Qualifiers
REGION                  1..263
                        note = Synthetic binder, S514_0000
source                  1..263
                        mol_type = protein
                        organism = synthetic construct
SEQUENCE: 111
KTALQLHIDH LLALIDRLIE EDPRVDRELA ELAKELLRAY GELAKTGNVR TPEFVALEKE  60
HAEKLKEAEK ALVGKALNVV PVGTVFANLT IFPFVDPSKT KLKDLVDVFN SIPGFNPGEL  120
HVVHPDGTVQ RVRSKEQIER VLGAKLPEGE AKYPEHSEPG AEEVTLRPGS QVHFHGDTSL  180
TPEQFKAFVK LANEKAGPVV AGITLVDVPA EYAPLALERA RFWIDFGVDV ELTAVGTAFA  240
PELEAAVRAA GAEAGVRVTV TIR                                          263

SEQ ID NO: 112          moltype = AA  length = 265
FEATURE                 Location/Qualifiers
```

```
REGION                  1..265
                        note = Synthetic binder, S515_0000
source                  1..265
                        mol_type = protein
                        organism = synthetic construct
SEQUENCE: 112
AEARRELVDL LIERIRRFAK LGDEEDQKHA ELAIKSLELE AELSKTSNIA TKEYFDFEEE  60
NKEEWEKLKK SRIGKVHGLY PSGTTSAALS ISLTVGASPE HLKAGFAALN ALPGFAPGEL  120
HVVRPDKSVS RVVGREGIER VTGAQVSPLT ATAAEHSDAG EEEVTAQPGD QFHVHGDKSL  180
TREEFIALNR RVHEAGGRVR RGVVAAAGSE EEADATLELI RFYLELNLEV RLTVSGDEAA  240
GERIREEARR LAEERAAEAV PGRAL                                       265

SEQ ID NO: 113          moltype = AA  length = 263
FEATURE                 Location/Qualifiers
REGION                  1..263
                        note = Synthetic binder, S516_0000
source                  1..263
                        mol_type = protein
                        organism = synthetic construct
SEQUENCE: 113
KTALQVWIDA ELALIDRLVR EDPSVSPEQA DLARELLRAR GAEAATGNVA TPALRALEAA  60
HAEALAALRE APLGKLLNVY PVGTTFANLT IFIYVDPAKT KLEDLFAVYN SIPGFAPAEL  120
HVVHPDGSVQ RVRTPEQIER VTGAKTPPSR AAWAEHDEPG AEEVTLEPGS QVHFHGPHSL  180
TVEEFKEFVK LANEKAGPVR WGLTLVDAPA SFAPLALERV RLAIDFGLDV EITLRGTAFA  240
PELEAAARAA GAAAGVAVTV TIE                                         263

SEQ ID NO: 114          moltype = AA  length = 265
FEATURE                 Location/Qualifiers
REGION                  1..265
                        note = Synthetic binder, S517_0000
source                  1..265
                        mol_type = protein
                        organism = synthetic construct
SEQUENCE: 114
AEARGAIIDF LIELIKEVAE REDEETKKFA ELSIKLLEKE RELSKTGNYA TQEYFNFIEE  60
NREAFEKLKK SKIGRLLALY PRGTTLAATT ISLGGAAVDR SKLKAFFEVL NAVPGFAPGE  120
LHVVRPDGST SYVVGKENIE KVTGAKTPPL EAKRAEHSKE GDKVVEVQPG DQAHVHGDHS  180
FTIEEFIAAA RRAREAGSVP LVGLTVDAGT EEEAELSLRR IAFYLELGFD VTFTTSGDAE  240
ASERIRERAL ALGAEAAARF GVRVL                                       265

SEQ ID NO: 115          moltype = AA  length = 265
FEATURE                 Location/Qualifiers
REGION                  1..265
                        note = Synthetic binder, S518_0000
source                  1..265
                        mol_type = protein
                        organism = synthetic construct
SEQUENCE: 115
AEARRDLIDF LLEEVDELAK TLDEEGREHA EKAKEILRLE AELSREGDYA TQEYFDFLEE  60
HKEFLEKLKK SLIGKNLGLT PQGTTLAATT VSFGGGGLQS QAKAWFEAFR AIPGFAISEL  120
HVVYPDGSTS YVRGRENIER VTGAETTPLR GRRAEHSGEG EKEVVAKPGS QLHAHGDHGL  180
TREEFIAAAR RNAEAGGPVS VGLQVSASSG ASAELALRRA RRFAELGLVV SYTTTGDAEA  240
GARLRAAVDA VLAEAAARFG IGGLA                                       265

SEQ ID NO: 116          moltype = AA  length = 265
FEATURE                 Location/Qualifiers
REGION                  1..265
                        note = Synthetic binder, S519_0000
source                  1..265
                        mol_type = protein
                        organism = synthetic construct
SEQUENCE: 116
AEAVQEHAEL LIKDLKEFAE IEKSEEVKED TELAIELIKK YAELSKTSNV ATKEFFEFIE  60
KNKEKLEKLK KSLVGRVHGL TPRGTILANL SRGTAVGAVG PERKKAAVEV LNSVPNFAPS  120
ELHVVRADGT VSYIVGQEGI EKATGAKVSD LKGDFAEHDK EGEKEVEVRP GDQFHFHGTH  180
ALTREEQIAF NRLAAEAGVR PRVGLVASGG REEHAELALR RARFYLELGF AVEVELLDGE  240
AGERLREAVE AAAAERAAEF GVAGL                                       265

SEQ ID NO: 117          moltype = AA  length = 265
FEATURE                 Location/Qualifiers
REGION                  1..265
                        note = Synthetic binder, S520_0000
source                  1..265
                        mol_type = protein
                        organism = synthetic construct
SEQUENCE: 117
AEARGDLIDL LIKRVERLKE REDEETKKDA DLAIELLEKE RELSKEGNYA TDEYREFLEK  60
NKEWLEKLKK SRIGKKLGLY PRGTTLAATT ITLGGGAVDR SKLKAFFAVI NAQPNFAPGE  120
LHVVRPDGSV SRVRGREGIE RVTGATTPPL TAKRAEHSGP GDERVEVRPG DQAHVHGDHS  180
```

```
LTREEFIALN RRAREAGAEP WVGLTVDAGT RWEAEEALEL AEYYLDLGLN VSVTTSGDEE  240
ASRYIRERLE AAAAERAAEY GVRGL                                        265

SEQ ID NO: 118          moltype = AA  length = 263
FEATURE                 Location/Qualifiers
REGION                  1..263
                        note = Synthetic binder, S521_0000
source                  1..263
                        mol_type = protein
                        organism = synthetic construct
SEQUENCE: 118
KTALQLHIDF EIALIRRLLE EFPEVDKELA ELAIEALRKE GELAKEGNVT TPEYRAFLEE  60
HKETWEKLKE ALIGKAVNAY PVGTHLANLV ITVFVDPSKT KVEDLVDVFN SIPGFNPAEL  120
HVVHPDGSVQ SVISPEKIEK VTGAKLPPGK AKYPEHSEPG AENVTLEEGS QLHFHGPHSL  180
TPEEFKEFVK LAKEKAGPVR KGLTLVDVPA EFAPLALERA RFFIDFGLDV ELTATNTAFA  240
PELEAAVRAA AAEKGVTATV TIV                                          263

SEQ ID NO: 119          moltype = AA  length = 263
FEATURE                 Location/Qualifiers
REGION                  1..263
                        note = Synthetic binder, S522_0000
source                  1..263
                        mol_type = protein
                        organism = synthetic construct
SEQUENCE: 119
KTALQVLIDF ELALIDRLTR EEPRVDPALA DLAKEILRAE GELAKTGNVA TPEYFALLDA  60
RAAELAALKK ALLGKAVNVY PVGTHLANLT IFPFVDPSKV KLEDLVAVYR AIPGFAPGEL  120
HVVYPDGSVQ RVRTPEQIRR VTGAELPPER APWPEHSEPG AERVELKEGS QVHFHGPHSL  180
TPEEFKAFVK RANEVAGPVR VGITLVDVPA EFAPLALERV RLYIDFGLSV EITLRNTAFA  240
PELEREARAA GAAAGVDVTV TIE                                          263

SEQ ID NO: 120          moltype = AA  length = 263
FEATURE                 Location/Qualifiers
REGION                  1..263
                        note = Synthetic binder, S523_0000
source                  1..263
                        mol_type = protein
                        organism = synthetic construct
SEQUENCE: 120
KTALQVWIDF TKALIRRLIE EDPEVDRELA ETAIELLDKR GELAKTGNVA TPEYFAALEK  60
LKETLEKLKE ALLGKAVNVY PVGTHFANLV IFIYVDPSKT SLEDLVAVYR AIPGFAPAEL  120
HVVRPDGSVD AVRSKEQIER VLGAPLPEAD APWPEHSEPG AEEVTLVEGS QVHFHGPHSL  180
TLEEFKAFVK RANELAGPVV AGLTAVDVPA SYAPLLLERA RLYIDFGLDV RVTLTGTAFA  240
PELEAALRAA AAEAGVRATV TIR                                          263

SEQ ID NO: 121          moltype = AA  length = 262
FEATURE                 Location/Qualifiers
REGION                  1..262
                        note = Synthetic binder, S524_0000
source                  1..262
                        mol_type = protein
                        organism = synthetic construct
SEQUENCE: 121
ATPTPEEEVA VLREAGRRLA ARLRAAGLTV RVRELTAAPG AVVTVEGTVL VFHGEVTPEL  60
QRLLPQTLLT LVRPGPDTSN SEFGNGVATP EDVDTVEAAI REVVEEAAPR GVTVRAQWHF  120
HSEPVDTIWG GYTDGKRGPN VDTARAAWRA GGGGELHAVV GTAEAPSIVA PNRATPEQLA  180
AAVAAARAAY EAARARGDPV LGVLVVLPGV GLGQPPSETA RAIAERLLAL LAPLGLLGRA  240
EVLTEGAPGE GPALVLLLRS AA                                           262

SEQ ID NO: 122          moltype = AA  length = 262
FEATURE                 Location/Qualifiers
REGION                  1..262
                        note = Synthetic binder, S525_0000
source                  1..262
                        mol_type = protein
                        organism = synthetic construct
SEQUENCE: 122
AAPTDEEVVA VLRRTGRDIA ERLRAAGHRV RVVELTAAPG EVVTVEGTVL VFVGELDPAL  60
IRLLPQTLLT LEAPGPDTSN SEYGRGVATP ADVDTVEAAI REAVEAAAPV GVPVRVQWHF  120
HAEPADTIWG GYTNGKPGPN LDAARAAWAA AGPGELHVVV GTVDAPSIVA PNRATPEQLA  180
AARALAEALY AAARAEGLPV LGVLVVLPGV GLGQPPSAAA EAIARGLLAL LAPLGIAGEA  240
RILTEGAPGE GPAAVLLLRA AA                                           262

SEQ ID NO: 123          moltype = AA  length = 262
FEATURE                 Location/Qualifiers
REGION                  1..262
                        note = Synthetic binder, S526_0000
source                  1..262
                        mol_type = protein
```

```
                         organism = synthetic construct
SEQUENCE: 123
SAPTPEEVVA VLLAVGRRIE ARLRAAGLRV RAQFLTAAPG AVTTVVGTVL VFVGELTPEL  60
QRDLPVTLLT LVREGPDTSN SEFGRGVATL EDVETVIEVA RAAVEEAAPV GVPVRVQFHF  120
HAEPADTIWG GFVNGEEGPN LDKAIAAWKA AGPGELHLVV GTREAPSIVA PNYATPEQLA  180
AAVAQAEALY AAARAEGLPV LGVLVVLPGL GLGKPPSETA AAIGEELLAR LAPLGVAGRV  240
EVLTEGAPGE GPAAVLLLRA AA                                          262

SEQ ID NO: 124           moltype = AA  length = 260
FEATURE                  Location/Qualifiers
REGION                   1..260
                         note = S222_1589, M103-I binder
source                   1..260
                         mol_type = protein
                         organism = synthetic construct
SEQUENCE: 124
MSHHWGYGKH NGPEHWHKDF PIAKGERQSP VDIDTHTAKY DPSLKPLSVS YDQATSLRIL  60
NNGHTFDVEF DDSQDKAVLK GGPLDGTYRL HQFHFHWGSL DGQGSEHTVD KKKYAAELHL  120
VHWNTKYGDP GKASQQPDGL AILGIFLKVG SAKPGLQKVV DVLDSIKTKG KSADFTNFDP  180
RGLLPESLDY WTYPGSSTVP PLMESVTWIV LKEPISVSSE QVLKFRKLNF NGEGEPEELM  240
VDNWRPAQPL KNRQIKASFK                                             260

SEQ ID NO: 125           moltype = AA  length = 260
FEATURE                  Location/Qualifiers
REGION                   1..260
                         note = S222_1333, M103-E binder
source                   1..260
                         mol_type = protein
                         organism = synthetic construct
SEQUENCE: 125
MSHHWGYGKH NGPEHWHKDF PIAKGERQSP VDIDTHTAKY DPSLKPLSVS YDQATSLRIL  60
NDGHAFKVEF DDSQDKAVLK GGPLDGTYRL RQFHFHWGSL DGQGSEHTVD KKKYAAELHL  120
LHWNTKYGDY GKAAQQPDGL AVLGIFLKVG SAKPGLQKVV DVLDSIKTKG KSADFTNFDP  180
RGLLPESLDY WTYPGSMTVP PLLESVTWIV LKEPISVSSE QVLKFRKLNF NGEGEPEELM  240
VDNWRPAQPL KNRQIKASFK                                             260

SEQ ID NO: 126           moltype = AA  length = 260
FEATURE                  Location/Qualifiers
REGION                   1..260
                         note = S222_1519, M103-W binder
source                   1..260
                         mol_type = protein
                         organism = synthetic construct
SEQUENCE: 126
MSHHWGYGKH NGPEHWHKDF PIAKGERQSP VDIDTHTAKY DPSLKPLSVS YDQATSLRIL  60
NDGHAFAVEF DDSQDKAVLK GGPLDGTYRL FQFHFHWGSL DGQGSEHTVD KKKYAAELHL  120
AHWNTKYGDL GKASQQPDGI AILGIFLKVG SAKPGLQKVV DVLDSIKTKG KSADFTNFDP  180
RGLLPESLDY WTYPGSFTVP PLLESVTWIV LKEPISVSSE QVLKFRKLNF NGEGEPEELM  240
VDNWRPAQPL KNRQIKASFK                                             260

SEQ ID NO: 127           moltype = AA  length = 260
FEATURE                  Location/Qualifiers
REGION                   1..260
                         note = S222_1581, M103-Y binder
source                   1..260
                         mol_type = protein
                         organism = synthetic construct
SEQUENCE: 127
MSHHWGYGKH NGPEHWHKDF PIAKGERQSP VDIDTHTAKY DPSLKPLSVS YDQATSLRIL  60
NNGHTFSVEF DDSQDKAVLK GGPLDGTYRL GQFHFHWGSL DGQGSEHTVD KKKYAAELHL  120
VHWNTKYGDP GKATQQPDGL AILGIFLKVG SAKPGLQKVV DVLDSIKTKG KSADFTNFDP  180
RGLLPESLDY WTYPGSATVP PLLESVTWIV LKEPISVSSE QVLKFRKLNF NGEGEPEELM  240
VDNWRPAQPL KNRQIKASFK                                             260

SEQ ID NO: 128           moltype = AA  length = 260
FEATURE                  Location/Qualifiers
REGION                   1..260
                         note = Synthetic binder, S222_1601
source                   1..260
                         mol_type = protein
                         organism = synthetic construct
SEQUENCE: 128
NTEKPGFGPH NGDEHWHQKY PVWLGPRRSP VDVDTERAVY DPSLSPLQVD FSKAVSLYME  60
NTGLTWSLYF DNTAPTAAIT GGPLDGEYIV GQLHTHTGSQ DDKGSEFTVN GKEYAGELHF  120
VSFNSKYGNP SVATKDETGL AILTVPIDVG ADNAGLTPLV AKLPNIRYKG EKTDAKNINP  180
AGLLPAGLDF YYYPGSATVP PYEESVLHLL LREAVDASRA QLDAFRSLYR TKRGEPEMKL  240
VDNYVEPKPL GDRTILSSTQ                                             260

SEQ ID NO: 129           moltype = AA  length = 260
```

```
FEATURE                Location/Qualifiers
REGION                 1..260
                       note = Synthetic binder, S222_1602
source                 1..260
                       mol_type = protein
                       organism = synthetic construct
SEQUENCE: 129
SSGKPGFGPD NGPDHWAQTY PQFNGDRTTP VDIDSKKAKY NPALQPLKVD LSKVVSLHLE  60
NLGLTFSLFF DDTTESGTIT GGPLTGTYRV GQVHIHIGST PDSGSEYTFD GRRYAGELHI  120
VAYNVRYGNP AVATLKEDGL AILTVPLVVG DTNPGFVPLA ELLPQIRYRN DSADATGINP  180
LGLLPDRLDH YYVKGSATVP PYLESVMHLV LKEPVTVSEE QLEAFRSLQR TSRGEPFEPL  240
VDNYVPPKPL GNREILSSFK                                              260

SEQ ID NO: 130         moltype = AA  length = 260
FEATURE                Location/Qualifiers
REGION                 1..260
                       note = Synthetic binder, S222_1606
source                 1..260
                       mol_type = protein
                       organism = synthetic construct
SEQUENCE: 130
TRNTPGFGPD NGYDHWKDVY PVVAGNRVGP VDIDSEKAIY DASLQPLQVD LRNAVSLHLE  60
NTGFTFSLHF DFSNESGTIR GGPLRGTYRL GQFHIHVGSD YSSGSEYTID GKTYAGELHF  120
VAFNVKYGNP EVATQQPDGL AILVVPLVVG ETNPGFVVIA EKLPEVRYRG DSVDATGINP  180
AGLLPASLAY YYFPSSATVP PFNQAVRHLV LREPVTISEE QLEAFRSLQL TGAGEPHQAL  240
VDNYAPPKPL GNREILASFK                                              260

SEQ ID NO: 131         moltype = AA  length = 260
FEATURE                Location/Qualifiers
REGION                 1..260
                       note = Synthetic binder, S222_1628
source                 1..260
                       mol_type = protein
                       organism = synthetic construct
SEQUENCE: 131
GRNKPGYGDD NGFDKWHEKY PNVLGEKRSP VNIDSKKAEY DESLKPLELD LSDYRSLELL  60
NDGLTPKLLF DDSALLGTIR GGPLTGTYIL RQIHIHVGAS DDRGSEYTFD GRNYPAELHF  120
LFFHAGYGNY AAAALQPDGL VILSIPVEVG DPNPGLAPIV DLLPQVRYRG DRVAAKGFDP  180
RGLLPKSLEF YYYQGSMTVP PFLESVTHIV LKEPVPISQA QLDAWRQLQR TAAGEPVVPL  240
VDNYAPPKPL KNRKILSSFK                                              260

SEQ ID NO: 132         moltype = AA  length = 260
FEATURE                Location/Qualifiers
REGION                 1..260
                       note = Synthetic binder, S222_1630
source                 1..260
                       mol_type = protein
                       organism = synthetic construct
SEQUENCE: 132
GENKPGFGPD NGPEHWSELY PNWNGDLRAP VDVNTDKAVY DPTLKPLVID LSKAVSLRLE  60
NDGYHWKLYF DYSADRATLT GGPLKGVYRL RQLHIHVGAT DDEGSEYTIN GEKYAAELHF  120
LFFNVQFGNY EEAAQKPDGL AALTVPVRVG KTNSGFTPLV DKLPQVRYKG DSVEAKDFDP  180
RDLLPKSLKY YYYPGSMTVP PFLESVLHIL LKEPVELSKA QLDAFRQLYR NRAGEARELL  240
VNNFVPPKPL GNRTIYSSFK                                              260

SEQ ID NO: 133         moltype = AA  length = 260
FEATURE                Location/Qualifiers
REGION                 1..260
                       note = Synthetic binder, S222_1642
source                 1..260
                       mol_type = protein
                       organism = synthetic construct
SEQUENCE: 133
GRDTPGFDST NGWEHWQDRF PNVNGALRSP VDINTQEAVY DPSLKPLKID LSNAKSLYMF  60
NDGLFPALYF DNSTPSATLS GGPLDGTYRL FQAHVHVGAD DEHGSEHTIN GKYFAGELHF  120
AFFNEKYGNL DKASLQKNGI AIFSVYIEVG DAQPGLLPWA ELLPQIRYKG DWVDASGINP  180
LGLLPKSLDF YYYKGSFTVP PFNESVIHIV SKEPVTASQA QLDAFRALQK TGKGEPYQPL  240
IDNYVPPKPL GNRTILSSFQ                                              260

SEQ ID NO: 134         moltype = AA  length = 260
FEATURE                Location/Qualifiers
REGION                 1..260
                       note = Synthetic binder, S222_1644
source                 1..260
                       mol_type = protein
                       organism = synthetic construct
SEQUENCE: 134
NENVPGFDEE TGFEKWHEIY PEVLGPRVSP VDIDTKRAVY DPSLKPLEVD FSDARSLKLY  60
NDGLFPALYF DDSTDTATLR GGPLDGVYRV FQIHIHIGSS DDEGSEFTID GKRYAGELHF  120
```

-continued

```
AAYNQQYGNL GKASQQENGI AILTIPIEVG AATAGFAPFA DRLPDIRYKG EEVDFTGFDP  180
RGLLPASLKH YYYPGSFTVP PFSQSVTHLL LRERVTLSEA QLAALRSLSR TEEGEPYVPL  240
QDNYRPARDL GDRTIKTSFK                                             260

SEQ ID NO: 135         moltype = AA  length = 260
FEATURE                Location/Qualifiers
REGION                 1..260
                       note = Synthetic binder, S222_1645
source                 1..260
                       mol_type = protein
                       organism = synthetic construct
SEQUENCE: 135
QSFKPGFTAD NGFDHWAERY PQVDGPRQSP VDINSDKAVY DPTLKELKVN LSDAVSLHLH  60
NDGLFAALYF DNSTLSGTIE GGPLKGTYVL FQIHIHVGST DDTGSEYTFD GEAFAGEIHF  120
AAYNTEYGNL AAASQQPDGI AILTVPVSVG DTNPGLVPLA ERLPRIRYRG ETTDATGYNP  180
KGLLPKSLDF YYYPGSFTVP PFLESVTHLV LKEPITASAA QLAAFRALRR TGRGEPMELL  240
VDNYRPPLPL GNRTIKSSVK                                             260

SEQ ID NO: 136         moltype = AA  length = 16
FEATURE                Location/Qualifiers
REGION                 1..16
                       note = Model peptide
SITE                   1
                       note = N-terminally modified with 6-sulfamoylisoquinolinium
VARIANT                2
                       note = Any Amino Acid
SITE                   16
                       note = biotin
source                 1..16
                       mol_type = protein
                       organism = synthetic construct
SEQUENCE: 136
SXGGGGSGGG SGGGSK                                                 16

SEQ ID NO: 137         moltype = AA  length = 16
FEATURE                Location/Qualifiers
REGION                 1..16
                       note = Model peptide
SITE                   1
                       note = N-terminally modified with 6-sulfamoylisoquinolinium
VARIANT                2
                       note = Any Amino Acid
SITE                   16
                       note = biotin
source                 1..16
                       mol_type = protein
                       organism = synthetic construct
SEQUENCE: 137
TXGGGGSGGG SGGGSK                                                 16

SEQ ID NO: 138         moltype = AA  length = 16
FEATURE                Location/Qualifiers
REGION                 1..16
                       note = Model peptide
SITE                   1
                       note = N-terminally modified with 6-sulfamoylisoquinolinium
VARIANT                2
                       note = Any Amino Acid
SITE                   16
                       note = biotin
source                 1..16
                       mol_type = protein
                       organism = synthetic construct
SEQUENCE: 138
CXGGGGSGGG SGGGSK                                                 16

SEQ ID NO: 139         moltype = AA  length = 16
FEATURE                Location/Qualifiers
REGION                 1..16
                       note = Model peptide
SITE                   1
                       note = N-terminally modified with 6-sulfamoylisoquinolinium
VARIANT                2
                       note = Any Amino Acid
SITE                   16
                       note = biotin
source                 1..16
                       mol_type = protein
                       organism = synthetic construct
```

```
SEQUENCE: 139
YXGGGGSGGG SGGGSK                                                  16

SEQ ID NO: 140          moltype = AA  length = 7
FEATURE                 Location/Qualifiers
source                  1..7
                        mol_type = protein
                        organism = synthetic construct
SEQUENCE: 140
FARDCSN                                                            7

SEQ ID NO: 141          moltype = AA  length = 6
FEATURE                 Location/Qualifiers
source                  1..6
                        mol_type = protein
                        organism = synthetic construct
SEQUENCE: 141
ARDCSN                                                             6

SEQ ID NO: 142          moltype = AA  length = 11
FEATURE                 Location/Qualifiers
source                  1..11
                        mol_type = protein
                        organism = synthetic construct
SEQUENCE: 142
HEXGHXXGXX H                                                       11

SEQ ID NO: 143          moltype = AA  length = 5
FEATURE                 Location/Qualifiers
source                  1..5
                        mol_type = protein
                        organism = synthetic construct
MOD_RES                 1
                        note = N-terminal 4-sulfamoylbenzoic acid
SEQUENCE: 143
AAAAE                                                              5

SEQ ID NO: 144          moltype = AA  length = 5
FEATURE                 Location/Qualifiers
source                  1..5
                        mol_type = protein
                        organism = synthetic construct
MOD_RES                 1
                        note = N-terminal 4-sulfamoylbenzoic acid
SEQUENCE: 144
FAAAE                                                              5

SEQ ID NO: 145          moltype = AA  length = 5
FEATURE                 Location/Qualifiers
source                  1..5
                        mol_type = protein
                        organism = synthetic construct
MOD_RES                 1
                        note = N-terminal 4-sulfamoylbenzoic acid
SEQUENCE: 145
EAAAE                                                              5

SEQ ID NO: 146          moltype = AA  length = 5
FEATURE                 Location/Qualifiers
source                  1..5
                        mol_type = protein
                        organism = synthetic construct
MOD_RES                 1
                        note = N-terminal 4-sulfamoylbenzoic acid
SEQUENCE: 146
SAAAE                                                              5

SEQ ID NO: 147          moltype = AA  length = 5
FEATURE                 Location/Qualifiers
source                  1..5
                        mol_type = protein
                        organism = synthetic construct
MOD_RES                 1
                        note = N-terminal 4-sulfamoylbenzoic acid
SEQUENCE: 147
LAAAE                                                              5

SEQ ID NO: 148          moltype = AA  length = 5
FEATURE                 Location/Qualifiers
```

-continued

```
source                1..5
                      mol_type = protein
                      organism = synthetic construct
MOD_RES               1
                      note = N-terminal 4-sulfamoylbenzoic acid
SEQUENCE: 148
HAAAE                                                                   5

SEQ ID NO: 149        moltype = AA  length = 5
FEATURE               Location/Qualifiers
source                1..5
                      mol_type = protein
                      organism = synthetic construct
SEQUENCE: 149
FAAAE                                                                   5

SEQ ID NO: 150        moltype = AA  length = 5
FEATURE               Location/Qualifiers
source                1..5
                      mol_type = protein
                      organism = synthetic construct
MOD_RES               1
                      note = N-terminal 4-sulfamoylbenzoic acid
SEQUENCE: 150
AFAAE                                                                   5
```

What is claimed is:

1. A method of analyzing a plurality of peptides, the method comprising:

(a) modifying the plurality of peptides with an N-terminal modifier agent, thereby generating a modified N-terminal amino acid (NTAA) residue on each peptide of the plurality of peptides, wherein each peptide of the plurality of peptides is attached to a solid support, each modified NTAA residue is capable of coordinating or chelating a metal cation, and wherein the N-terminal modifier agent is selected from the group consisting of:

(8)

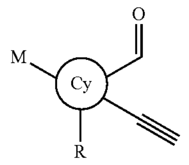

and (9)

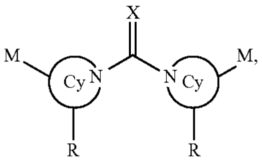

wherein M is a metal cation binding group that comprises sulfonamide, hydroxamic acid, sulfamate, or sulfamide; the group

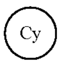

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, ORQ, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O) R or —C(═O)—OR; CC is a cationic counterion; X is one of the following: O, S, Se, or NH, and wherein the modified NTAA residue on each peptide comprises one of the structures selected from the group consisting of:

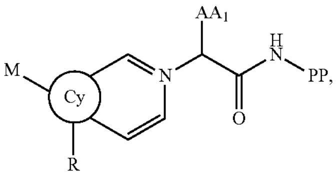

and

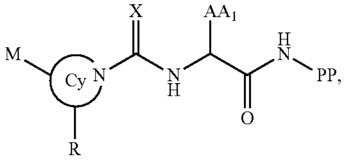

wherein AA1 is a side chain of the modified NTAA residue and PP is a peptide structure except for the modified NTAA residue;

(b) contacting one or more peptides of the plurality of peptides with a set of engineered metalloprotein binders, wherein one or more engineered metalloprotein binders of the set specifically bind to a particular modified NTAA residue of the one or more peptides, wherein each engineered metalloprotein binder of the set comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp), and E (Glu); X1, X2, X3 and X4 are each any amino acid sequence independently comprising between 0 and 500 amino acid residues in length, and wherein the amino acid sequence X1-C/H/D/E-X2-C/H/D/E-X3-C/H/D/E-X4 chelates the metal cation; and (c) generating a signal indicative of the binding of the one or more engineered metalloprotein binders to the modified NTAA residue(s) of the one or more peptides, thereby analyzing the plurality of peptides.

2. The method of claim 1, further comprising:

(d) removing modified NTAA residues from peptides of the plurality of peptides by an agent configured to remove modified NTAA residues, thereby exposing a new NTAA residue in each of the peptides.

3. The method of claim 2, further comprising: repeating steps (a)-(c) and, optionally, (d) for the new NTAA residues of the peptides.

4. The method of claim 1, wherein each engineered metalloprotein binder of the set is configured to specifically bind to a different modified NTAA residue of the one or more peptides.

5. The method of claim 1, wherein (c) further comprises determining one or more characteristics of each peptide of the one or more peptides for which the signal was generated by using predetermined binding specificities of the engineered metalloprotein binders, thereby analyzing the plurality of peptides.

6. The method of claim 5, further comprising determining at least partial sequence information of each peptide for which the signal was generated using the one or more determined characteristics.

7. The method of claim 5, wherein the set of engineered metalloprotein binders comprises at least 3 structurally different engineered metalloprotein binders each having different binding specificities towards modified NTAA residues of the one or more peptides.

8. The method of claim 1, wherein the engineered metalloprotein binder further comprises a detectable label.

9. The method of claim 2, wherein the agent configured for removing modified NTAA residues comprises an engineered enzyme.

10. The method of claim 1, wherein the amino acid sequence X1-C/H/D/E-X2-C/H/D/E-X3-C/H/D/E-X4 further comprises one or more amino acid sequences selected from the group consisting of: SEQ ID NO: 101 and SEQ ID NO: 102.

11. The method of claim 10, wherein the amino acid sequence X1-C/H/D/E-X2-C/H/D/E-X3-C/H/D/E-X4 further comprises one or more amino acid sequences selected from the group consisting of:

(A/C/D/I/S/V/Y)X(C/N)X(A/C/G/R/S/V)XX(C/F/I/L/T/V)X(C/G/K/N/V)X(F/I)(D/E/K/N/V)(D/E/F/N/Q), (A/S)XX(A/E/H/K/Q) (A/P/R/S/T)D(G/I/V)X(A/T/V)(I/L/M/N/R/V) and G(A/C/F/I/S)X(A/D/M/T)XPX(C/F/L)X(C/E/R)X(I/L/R/V), wherein X corresponds to any one of the 20 standard amino acids.

12. The method of claim 1, wherein each engineered metalloprotein binder comprises an amino acid sequence having at least 40% sequence identity to any one of the amino acid sequences selected from the group consisting of SEQ ID NO: 7-SEQ ID NO: 59, SEQ ID NO: 68-SEQ ID NO: 99 and SEQ ID NO: 105-SEQ ID NO: 135.

13. The method of claim 1, wherein the engineered metalloprotein binder is associated with a coding tag comprising identifying information regarding the engineered metalloprotein binder.

14. The method of claim 13, wherein each of the plurality of peptides is associated with a recording tag comprising identifying information regarding the associated peptide or a protein from which the associated peptide is obtained from.

15. The method of claim 14, wherein following binding of an engineered metalloprotein binder of the set to a modified NTAA residue of a peptide of the plurality, a nucleic acid molecule is generated, using a ligation or a primer extension, which comprises the identifying information regarding the engineered binder and the identifying information regarding the peptide or a protein from which the peptide is obtained from.

16. The method of claim 15, wherein (c) further comprising sequencing the nucleic acid molecule, and determining one or more characteristics of the peptide by using a predetermined binding specificity of the engineered metalloprotein binder.

17. A kit for treating a target peptide, the kit comprising:

(a) an N-terminal modifier agent selected from the group consisting of:

(8)

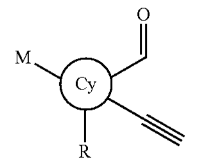

and (9)

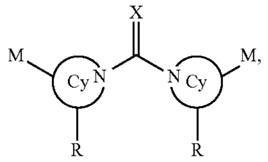

wherein M is a metal cation binding group that comprises sulfonamide, hydroxamic acid, sulfamate, or sulfamide; the group

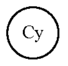

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, N $(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, ORQ, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O) R or —C(═O)—OR; CC is a cationic counterion; X is one of the following: O, S, Se, or NH; and (b) an engineered metalloprotein binder that specifically binds to a modified N-terminal amino acid (NTAA) residue in a target peptide, wherein the modified NTAA residue comprises one of the structures selected from the group consisting of:

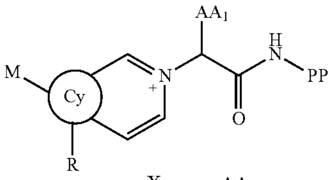

and

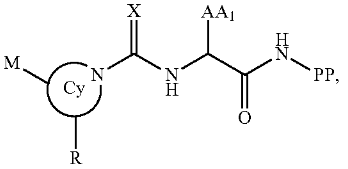

wherein AA1 is a side chain of the modified NTAA residue and PP is a peptide structure except for the modified NTAA residue; wherein the modified NTAA residue is generated by modifying the target peptide with the N-terminal modifier agent, wherein the engineered metalloprotein binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates the metal cation; and (c) a solid support which is configured for attachment of the target peptide.

18. The kit of claim 17, further comprising an agent configured to remove NTAA residues of peptides modified with the N-terminal modifier agent.

19. The kit of claim 17, which comprises at least 3 structurally different engineered metalloprotein binders each having different binding specificities towards modified NTAA residues of peptides modified with the N-terminal modifier agent.

20. The kit of claim 17, wherein the engineered metalloprotein binder comprises a coding tag comprising identifying information regarding the engineered metalloprotein binder.

21. The kit of claim 17, wherein the amino acid sequence X1-C/H/D/E-X2-C/H/D/E-X3-C/H/D/E-X4 further comprises one or more amino acid sequences selected from the group consisting of: SEQ ID NO: 101 and SEQ ID NO: 102.

22. A composition comprising:

(a) a solid support, wherein the solid support comprises a plurality of peptide molecules attached to the solid support, wherein each of the plurality of peptide molecules comprise a modified N-terminal amino acid (NTAA) residue generated by modifying a peptide molecule with an N-terminal modifier agent, wherein the modified NTAA residue is capable of coordinating or chelating a metal cation, and the N-terminal modifier agent is selected from the group consisting of:

(8)

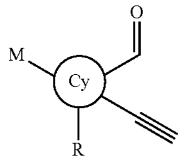

and

-continued (9)

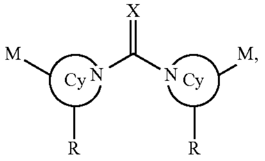

wherein M is a metal cation binding group that comprises sulfonamide, hydroxamic acid, sulfamate, or sulfamide; the group

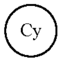

is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, $N(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, ORQ, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O)R or —C(═O)—OR; CC is a cationic counterion; X is one of the following: O, S, Se, or NH, wherein the modified NTAA residue of each of the plurality of peptide molecules comprises one of the structures selected from the group consisting of:

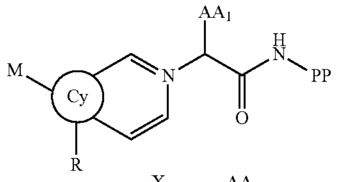

and

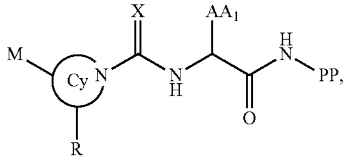

wherein AA1 is a side chain of the modified NTAA residue and PP is a peptide structure except for the modified NTAA residue; and (b) an engineered metalloprotein binder that specifically binds to the modified NTAA residue of a peptide molecule of the plurality of peptide molecules, wherein the engineered metalloprotein binder comprises an amino acid sequence X1-C/H/D/E-X2-C/H/D/E-X3-C/H/D/E-X4, wherein C/H/D/E is any single amino acid residue independently selected from the group consisting of amino acid residues C (Cys), H (His), D (Asp) and E (Glu); X1, X2, X3 and X4 are each any amino acid sequence comprising between 0 and 500 amino acid residues in length, and wherein the amino acid sequence X1-C/H/D/E-X2-C/H/D/E-X3-C/H/D/E-X4 chelates the metal cation.

23. The composition of claim 22, which comprises at least 3 structurally different engineered metalloprotein binders, wherein each engineered metalloprotein binder has different binding specificities towards modified NTAA residues of peptides.

24. The composition of claim 22, wherein the engineered metalloprotein binder comprises a coding tag comprising identifying information regarding the engineered metalloprotein binder.

25. The composition of claim 22, wherein the amino acid sequence X1-C/H/D/E-X2-C/H/D/E-X3-C/H/D/E-X4 further comprises one or more amino acid sequences selected from the group consisting of: SEQ ID NO: 101 and SEQ ID NO: 102.

26. The composition of claim 22, wherein the engineered metalloprotein binder comprises an amino acid sequence having at least 40% sequence identity to any one of the amino acid sequences selected from the group consisting of SEQ ID NO: 7-SEQ ID NO: 59, SEQ ID NO: 68-SEQ ID NO: 99 and SEQ ID NO: 105-SEQ ID NO: 135.

27. The kit of claim 17, wherein the N-terminal modifier agent has a structure of Formula (8):

(8)

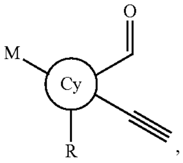, wherein M is a metal cation binding group that comprises sulfonamide, hydroxamic acid, sulfamate, or sulfamide; the group 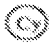 is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, N $(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, ORQ, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O) R or —C(═O)—OR; CC is a cationic counterion; X is one of the following: O, S, Se, or NH.

28. The composition of claim 22, wherein the N-terminal modifier agent has a structure of Formula (8):

(8)

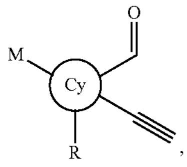, wherein M is a metal cation binding group that comprises sulfonamide, hydroxamic acid, sulfamate, or sulfamide; the group 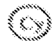 is a 5 or 6 membered aromatic ring containing up to three heteroatoms selected from N, O, and S as ring members, and is optionally substituted by R; R represents one or two optional substituents selected from the group consisting of F, Cl, $CH_3$, $CF_2H$, $CF_3$, OH, $OCH_3$, $OCF_3$, $NH_2$, N $(CH_3)_2$, $NO_2$, $SCH_3$, $SO_2CH_3$, $CH_2OH$, $B(OH)_2$, CN, $CONH_2$, $CO_2H$, and $CONHCH_3$; LG is OH, ORQ, or OCC, each RQ is independently aryl or heteroaryl, each of which is optionally substituted with one or more groups selected from halo, nitro, cyano, sulfonate, carboxylate, alkylsulfonyl, and N of heteroaryl is optionally oxidized; or RQ can be —C(═O) R or —C(═O)—OR; CC is a cationic counterion; X is one of the following: O, S, Se, or NH.

* * * * *